US006897220B2

(12) United States Patent
Delorme et al.

(10) Patent No.: US 6,897,220 B2
(45) **Date of Patent: *May 24, 2005**

(54) INHIBITORS OF HISTONE DEACETYLASE

(75) Inventors: Daniel Delorme, St-Lazare (CA); Zhihong Zhou, Kirkland (CA)

(73) Assignee: MethylGene, Inc., Quebec (CA)

( * ) Notice: Subject to any disclaimer, the term of this patent is extended or adjusted under 35 U.S.C. 154(b) by 8 days.

This patent is subject to a terminal disclaimer.

(21) Appl. No.: 10/358,556

(22) Filed: Feb. 4, 2003

(65) Prior Publication Data

US 2004/0142953 A1 Jul. 22, 2004

Related U.S. Application Data

(63) Continuation-in-part of application No. 10/242,304, filed on Sep. 12, 2002.

(60) Provisional application No. 60/391,728, filed on Jun. 26, 2002, and provisional application No. 60/322,402, filed on Sep. 14, 2001.

(51) Int. Cl.[7] .................... C07D 239/42; A61K 31/506; A61P 35/00

(52) U.S. Cl. ....................................... 514/275; 544/331

(58) Field of Search ........................... 544/331; 514/275

(56) References Cited

U.S. PATENT DOCUMENTS

| | | | | |
|---|---|---|---|---|
| 5,332,750 | A | 7/1994 | Mederski et al. | 514/340 |
| 5,945,450 | A | 8/1999 | Takeenouchi et al. | 514/535 |
| 6,034,251 | A | 3/2000 | Aslanian et al. | 548/338 |
| 6,174,905 | B1 | 1/2001 | Suzuki et al. | 514/346 |
| 6,376,515 | B2 | 4/2002 | Zhu et al. | 514/318 |
| 2002/0061860 | A1 | 5/2002 | Li et al. | 514/44 |

FOREIGN PATENT DOCUMENTS

| | | | |
|---|---|---|---|
| CA | 2136288 | 11/1994 | 487/4 |
| EP | 0 657 454 | 11/1994 | 487/4 |
| EP | 0 847 992 | 9/1997 | 213/30 |
| EP | 1 256 341 | 11/2002 | 31/196 |
| JP | 1999269146 | 10/1999 | 213/30 |
| JP | 1999302173 | 11/1999 | 31/44 |
| JP | 2003137866 | 5/2003 | 209/90 |
| WO | WO 98/45252 | 10/1998 | 233/65 |
| WO | WO 00/03704 | 1/2000 | 31/165 |
| WO | WO 01/16106 | 3/2001 | 213/30 |
| WO | WO 01/38322 | 5/2001 | 333/38 |
| WO | WO 01/60354 | 8/2001 | 31/196 |
| WO | WO 01/68585 | 9/2001 | 233/75 |
| WO | WO 02/069947 | 9/2002 | |
| WO | WO2001068585 | 8/2003 | 257/18 |

OTHER PUBLICATIONS

Suzuki, et al., "Synthesis and Histone Deacetylase Inhibitory Activity of New Benzamide Derivatives," Journal of Medicinal Chemistry, American Chemical Society, Washington U.S., vol. 42, No. 15, 1999, pp. 3001–3003.

Database Crossfire Beilstein (Online) Beilstein Institut zur Förderung der Chemischen Wissenschaftern, Frankfurt am Main, DE, N,N[1]–di (o–aminophenyl) terephthalamide, Database accession No. 5619310 XP–002229372, Third invention abstract & Indian J. Chem. Sect. B., vol. 25, 1986, pp. 1146–1149.

Database Crossfire Beilstein (Online) Beilstein Institut zur Förerung der Chemischen Wissenschaften, Frankfurt am Main, DE, Database accession No. 3016237 XP–002229373, 4, 6–dimino–N, N[1]–bis–(2–amino–phebyl)–isoph thalamide. Third invention abstract & Chem. Heterocycl. Compd. vol. 13, 1977, pp. 1029–1032.

Database Crossfire Beilstein (Online) Beilstein Institut zur Förerung der Chemischen Wissenschaften, Frankfurt am Main, DE, Database accession No. 3458834 XP 002229374 4, 6–dimino–N, N[1]–bis–(2–amino–phenyl)–phtha lamide. Third invention abstract & Justus Liebigs Ann. Chem., vol. 347, 1906, p. 116.

Picard et al., "Desymmetrization Reactions: A Convenient Synthesis of Aromatic Diamide Diamines" Synthesis vol. 10, 2001, pp. 1471–1478.

Rabilloud G et al., "Réactions de condensation de 1 'o–phénediamine avec les benzoxazin–3, 1–ones–4 substituées en position 2" Bull. Soc. Chim. Fr., 1975, pp. 2682–2686.

*Primary Examiner*—Venkataraman Balasubramanian
(74) *Attorney, Agent, or Firm*—McDonnell Boehnen Hulbert & Berghoff LLP

(57) ABSTRACT

The invention relates to the inhibition of histone deacetylase. The invention provides compounds and methods for inhibiting histone deacetylase enzymatic activity. The invention also provides compositions and methods for treating cell proliferative diseases and conditions.

4 Claims, 11 Drawing Sheets

Inhibition of Panc-1 Human Pancreatic Cancer Tumor Growth by Compound 376 After Oral Administration

INHIBITORS OF HISTONE DEACETYLASE

BACKGROUND OF THE INVENTION

1. Field of the Invention

This invention relates to the inhibition of histone deacetylase. More particularly, the invention relates to compounds and methods for inhibiting histone deacetylase enzymatic activity.

2. Summary of the Related Art

In eukaryotic cells, nuclear DNA associates with histones to form a compact complex called chromatin. The histones constitute a family of basic proteins which are generally highly conserved across eukaryotic species. The core histones, termed H2A, H28, H3, and H4, associate to form a protein core. DNA winds around this protein core, with the basic amino acids of the histones interacting with the negatively charged phosphate groups of the DNA. Approximately 146 base pairs of DNA wrap around a histone core to make up a nucleosome particle, the repeating structural motif of chromatin.

Csordas, *Biochem. J.,* 286: 23–38 (1990) teaches that histones are subject to posttranslational acetylation of the α,ε-amino groups of N-terminal lysine residues, a reaction that is catalyzed by histone acetyl transferase (HAT1). Acetylation neutralizes the positive charge of the lysine side chain, and is thought to impact chromatin structure. Indeed, Taunton et al., *Science,* 272: 408–411 (1996), teaches that access of transcription factors to chromatin templates is enhanced by histone hyperacetylation. Taunton et al. further teaches that an enrichment in underacetylated histone H4 has been found in transcriptionally silent regions of the genome.

Histone acetylation is a reversible modification, with deacetylation being catalyzed by a family of enzymes termed histone deacetylases (HDACs). Grozinger et al., *Proc. Natl. Acad. Sci. USA,* 96: 4868–4873 (1999), teaches that HDACs is divided into two classes, the first represented by yeast Rpd3-like proteins, and the second represented by yeast Hda1-like proteins. Grozinger et al. also teaches that the human HDAC1, HDAC2, and HDAC3 proteins are members of the first class of HDACs, and discloses new proteins, named HDAC4, HDAC5, and HDAC6, which are members of the second class of HDACs. Kao et al., *Genes & Dev.,* 14: 55–66 (2000), discloses HDAC7, a new member of the second class of HDACs. Van den Wyngaert, *FEBS,* 478: 77–83 (2000) discloses HDAC8, a new member of the first class of HDACs.

Richon et al., *Proc. Natl. Acad. Sci. USA,* 95: 3003–3007 (1998), discloses that HDAC activity is inhibited by trichostabn A (TSA), a natural product isolated from *Streptomyces hygroscopicus*, and by a synthetic compound, suberoylanilide hydroxamic acid (SAHA). Yoshida and Beppu, *Exper. Cell Res.,* 177: 122–131 (1988), teaches that TSA causes arrest of rat fibroblasts at the $G_1$ and $G_2$ phases of the cell cycle, implicating HDAC in cell cycle regulation. Indeed, Finnin et al., *Nature,* 401: 188–193 (1999), teaches that TSA and SAHA inhibit cell growth, induce terminal differentiation, and prevent the formation of tumors in mice. Suzuki et al., U.S. Pat. No. 6,174,905, EP 0847992, JP 258863/96, and Japanese Application No. 10138957, disclose benzamide derivatives that induce cell differentiation and inhibit HDAC. Delorme et al., WO 01/38322 and PCT IB01/00683, disclose additional compounds that serve as HDAC inhibitors.

The molecular cloning of gene sequences encoding proteins with HDAC activity has established the existence of a set of discrete HDAC enzyme isoforms. Grozinger et al., *Proc. Natl. Acad. Sci. USA,* 96:4868–4873 (1999), teaches that HDACs may be divided into two classes, the first represented by yeast Rpd3-like proteins, and the second represented by yeast Hda1-like proteins. Grozinger et al. also teaches that the human HDAC-1, HDAC-2, and HDAC-3 proteins are members of the first class of HDACs, and discloses new proteins, named HDAC4, HDAC-5, and HDAC-6, which are members of the second class of HDACs. Kao et al., *Gene & Development* 14:55–66 (2000), discloses an additional member of this second class, called HDAC-7. More recently, Hu, E. et al. J. Bio. Chem. 275:15254–13264 (2000) discloses the newest member of the first class of histone deacetylases, HDAC-8. It has been unclear what roles these individual HDAC enzymes play.

These findings suggest that inhibition of HDAC activity represents a novel approach for intervening in cell cycle regulation and that HDAC inhibitors have great therapeutic potential in the treatment of cell proliferative diseases or conditions. To date, few inhibitors of histone deacetylase are known in the art. There is thus a need to identify additional HDAC inhibitors and to identify the structural features required for potent HDAC inhibitory activity.

BRIEF SUMMARY OF THE INVENTION

The invention provides compounds and methods for treating cell proliferative diseases. The invention provides new inhibitors of histone deacetylase enzymatic activity.

In a first aspect, the invention provides compounds that are useful as inhibitors of histone deacetylase.

In a second aspect, the invention provides a composition comprising an inhibitor of histone deacetylase according to the invention and a pharmaceutically acceptable carrier, excipient, or diluent.

In a third aspect, the invention provides a method of inhibiting histone deacetylase in a cell, comprising contacting a cell in which inhibition of histone deacetylase is desired with an inhibitor of histone deacetylase of the invention.

The foregoing merely summarizes certain aspects of the invention and is not intended to be limiting in nature. These aspects and other aspects and embodiments are described more fully below.

DETAILED DESCRIPTION OF THE PREFERRED EMBODIMENTS

Figure 1:
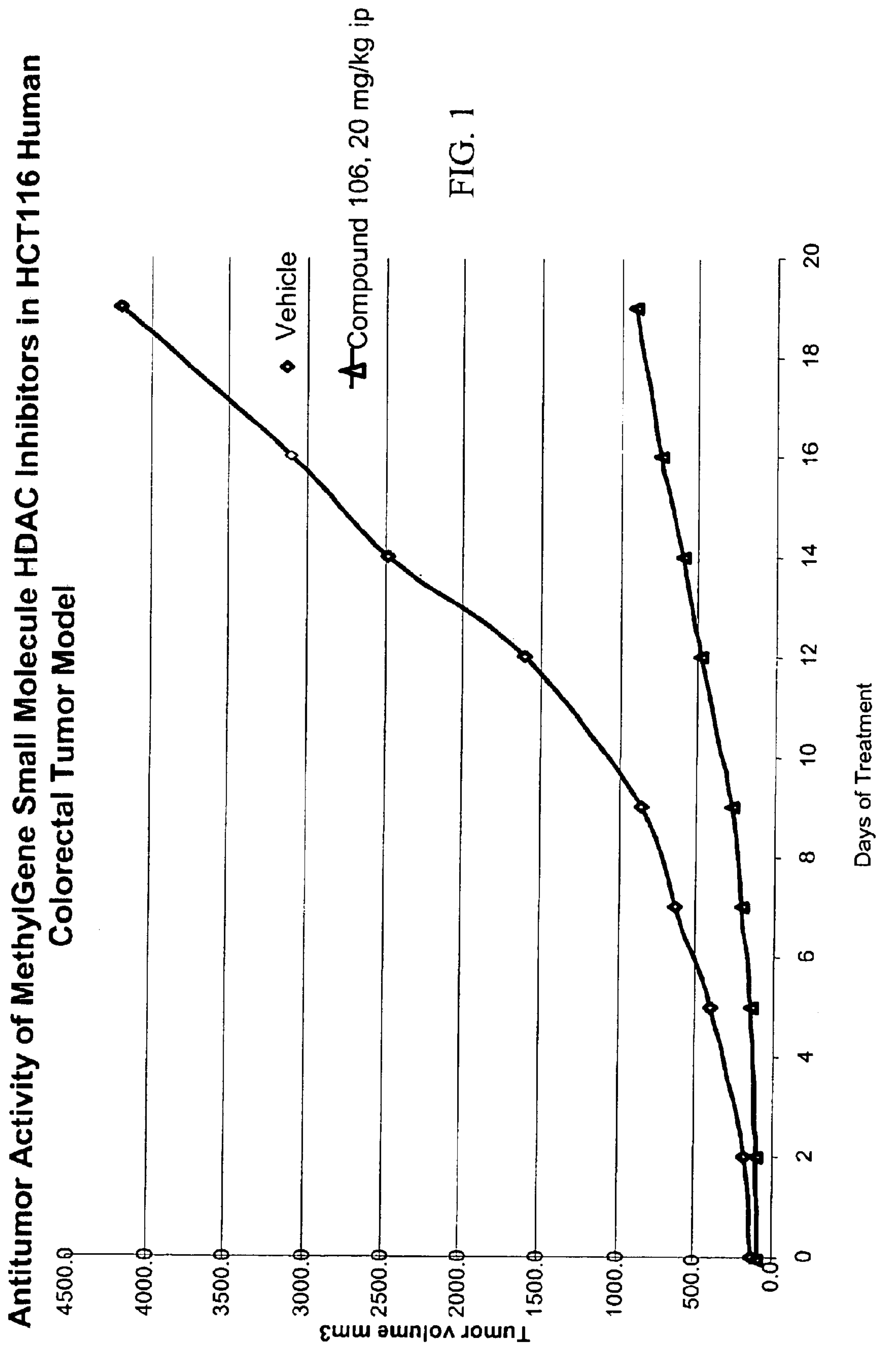
FIG. 1 is a graph showing the antitumor activity of compound 106 in an HCT 116 human colorectal tumor model.
Figure 2:
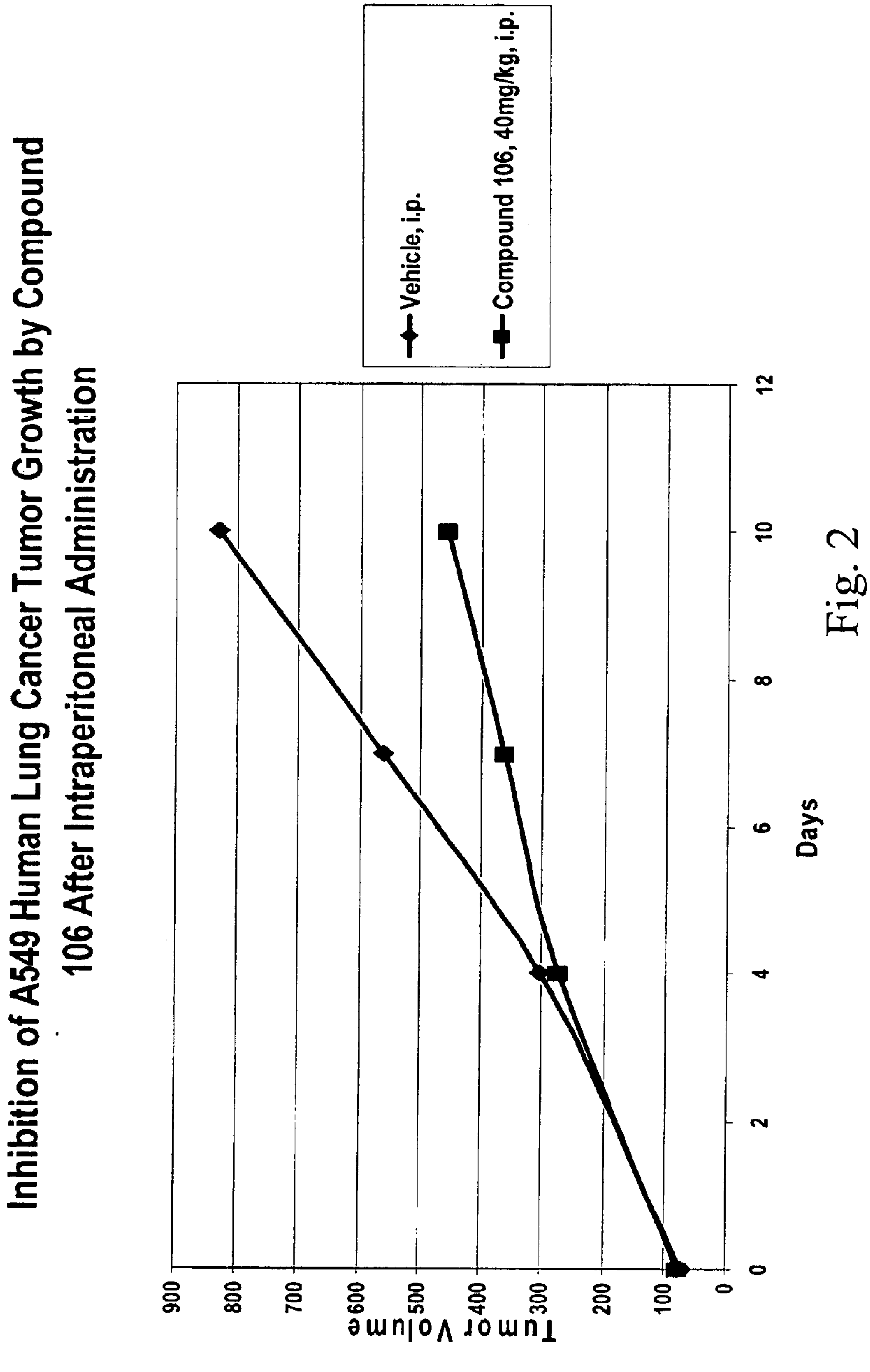
FIGS. 2–11 show additional data for other compounds used in the in vivo experiment described in Assay Example 2.
Figure 3:
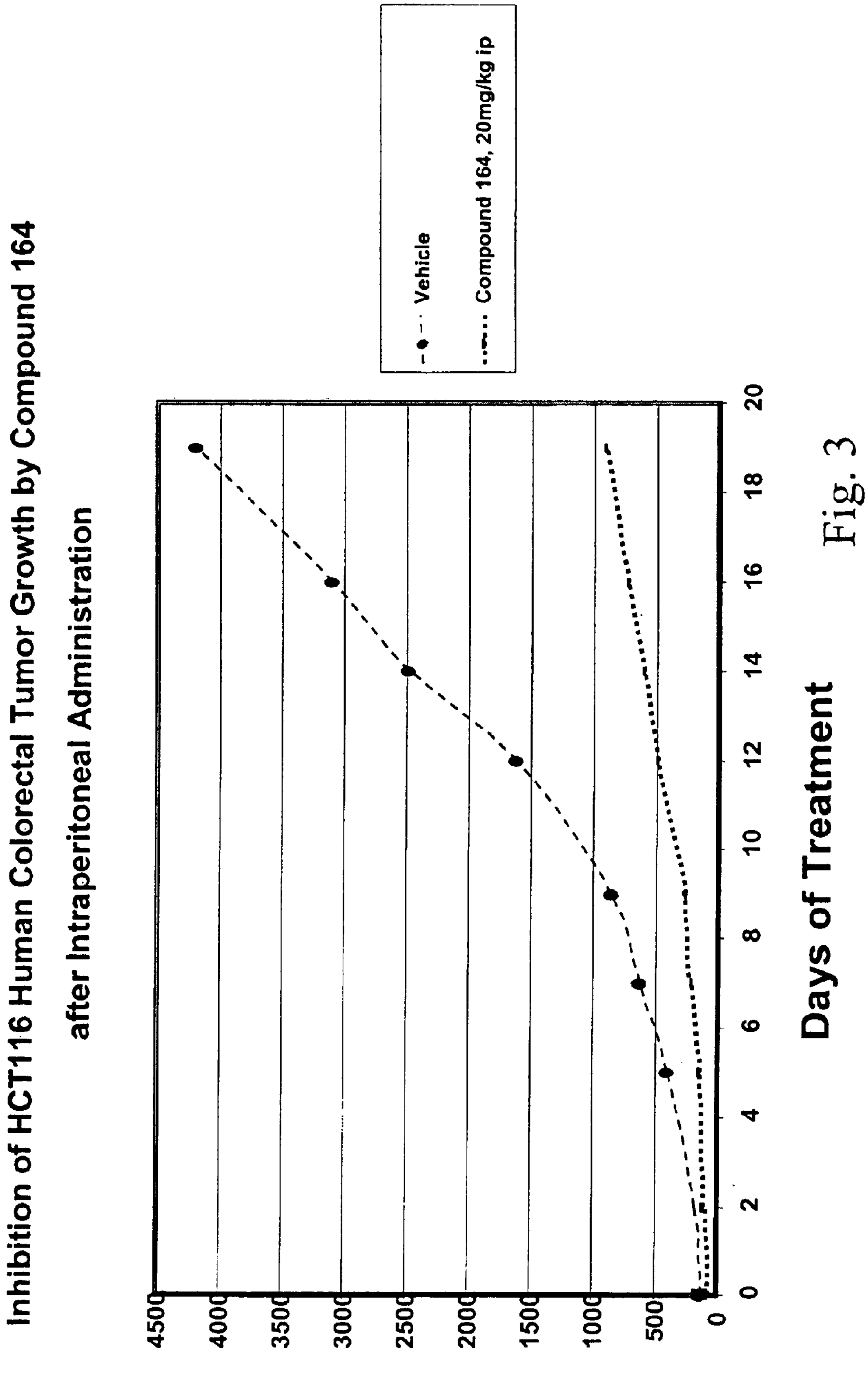
Figure 4:
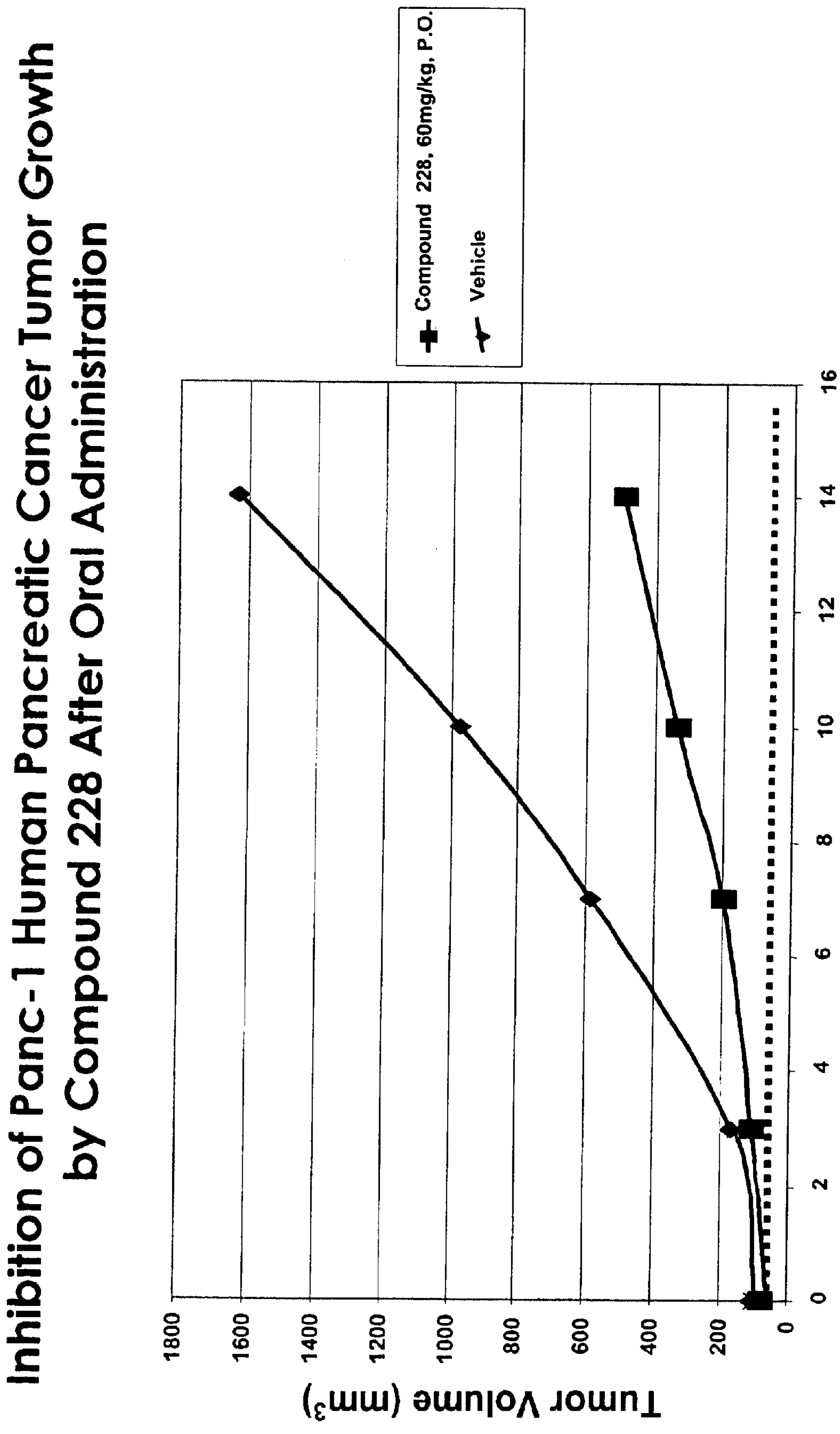
Figure 5:
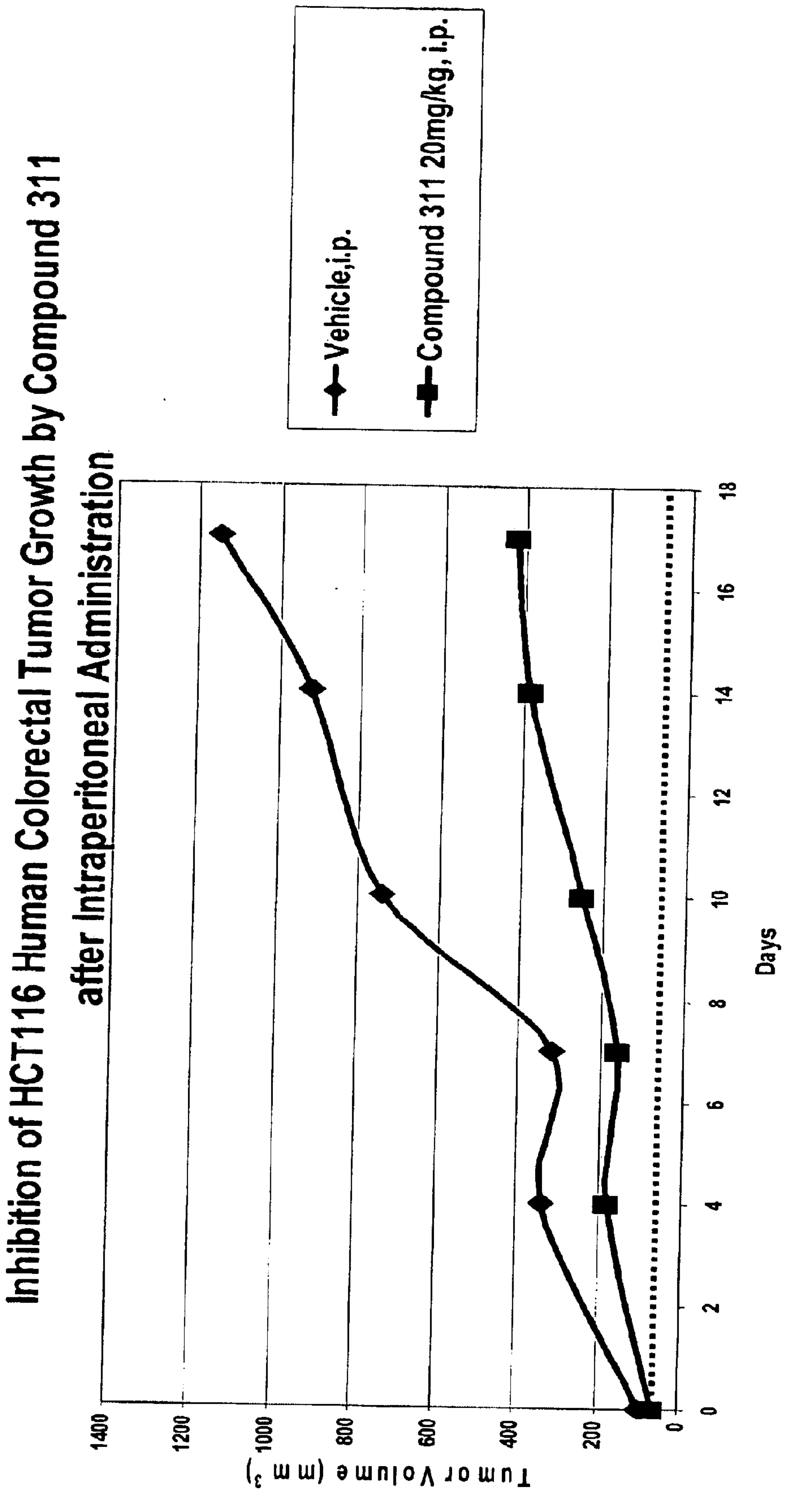
Figure 6:
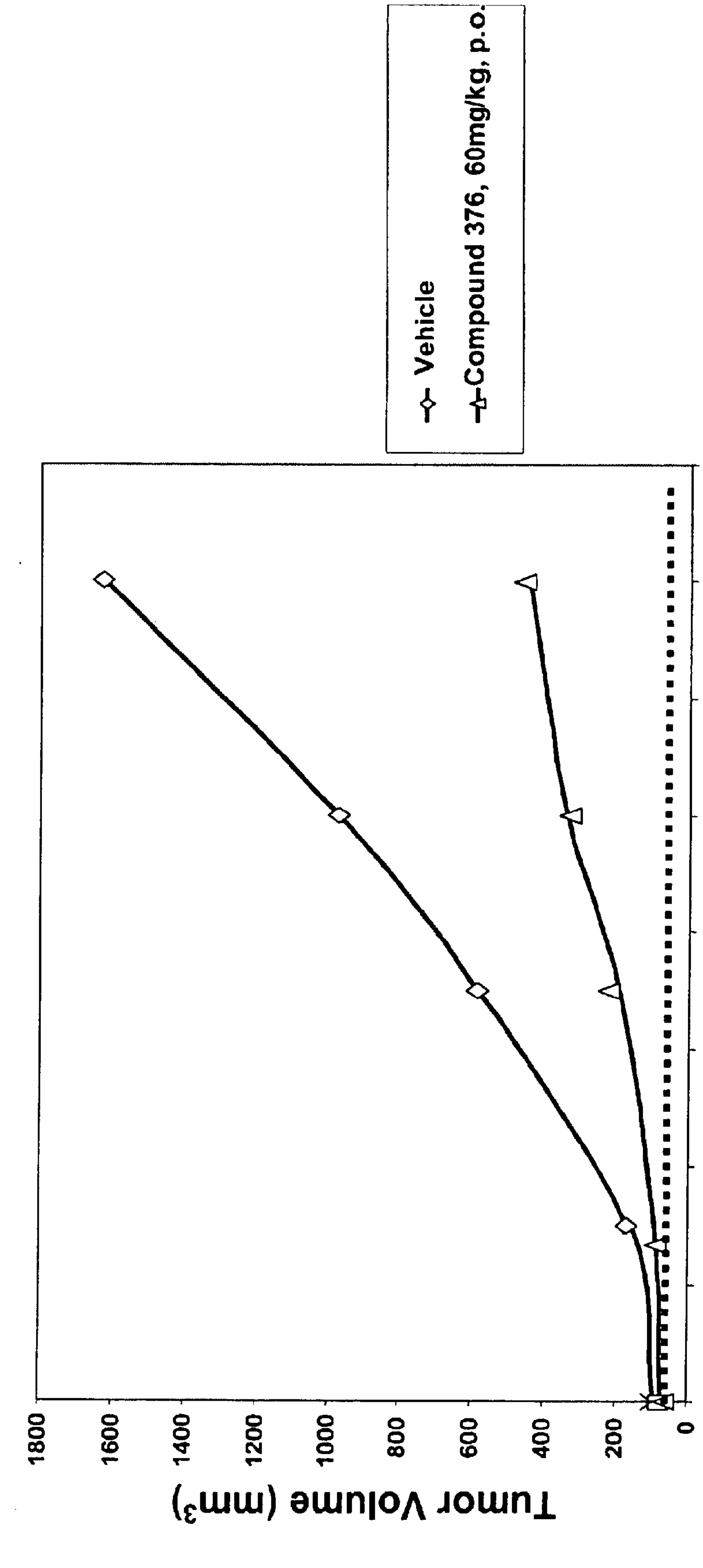
Figure 7:
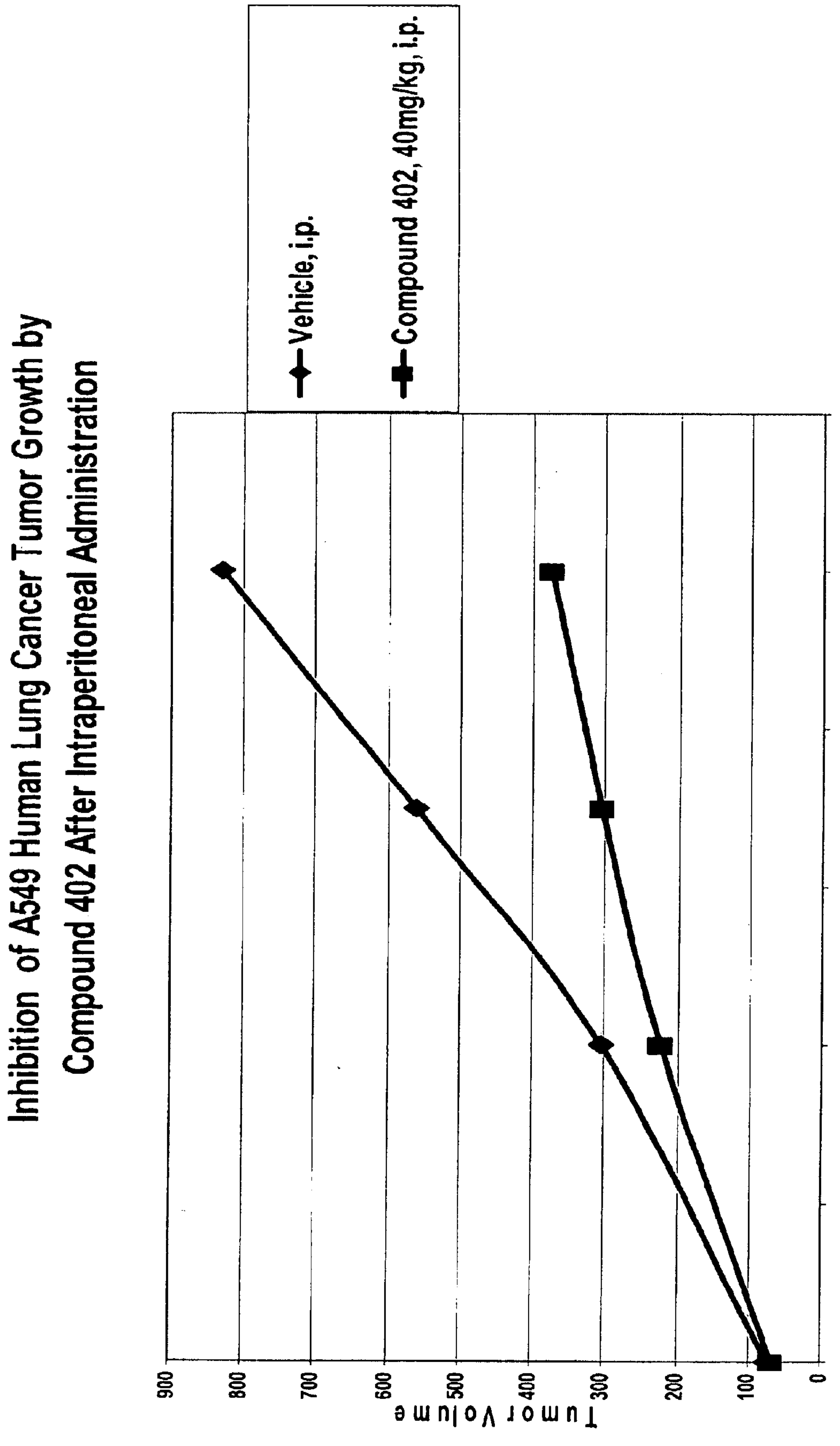
Figure 8:
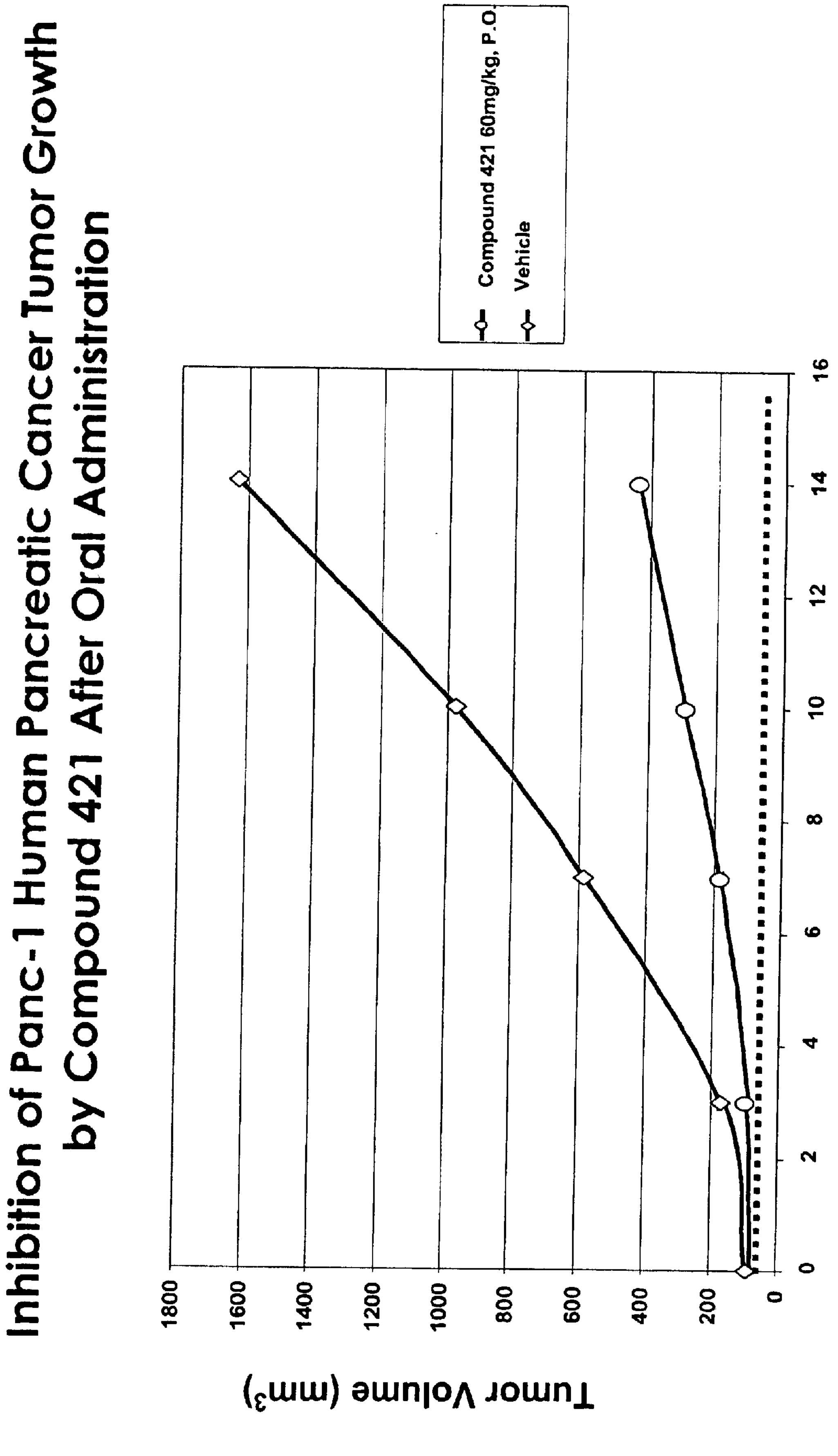
Figure 9:
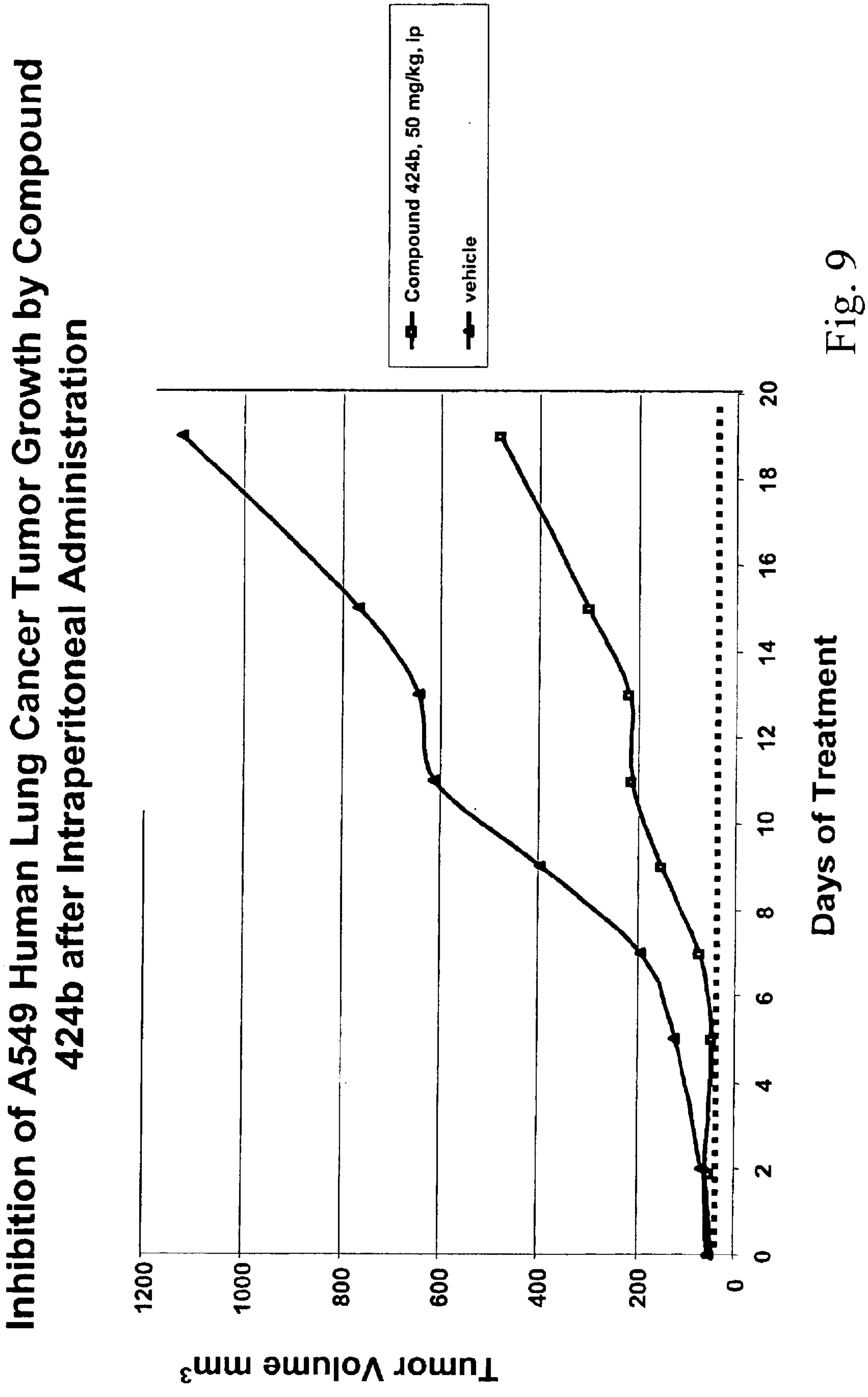
Figure 10:
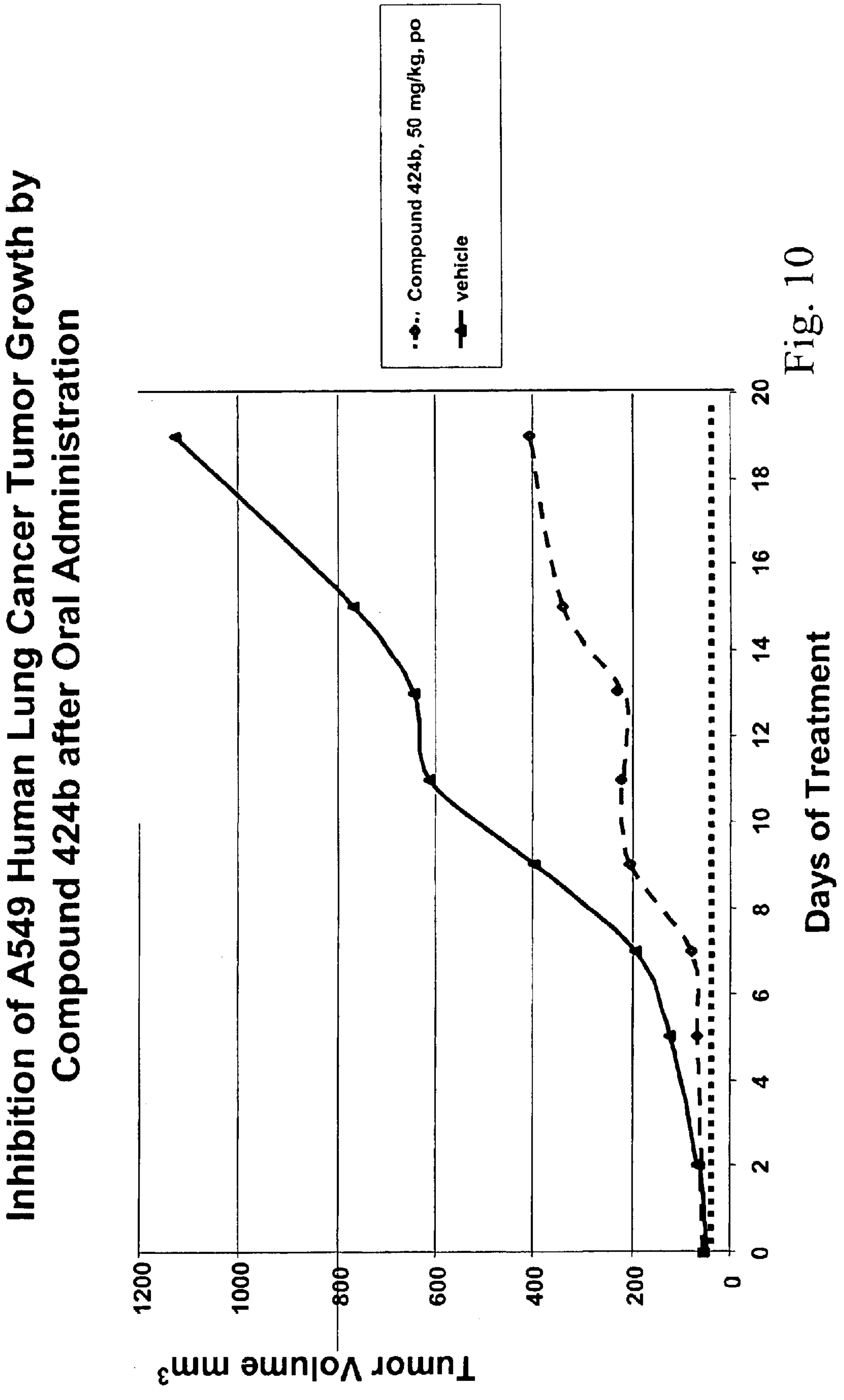
Figure 11:
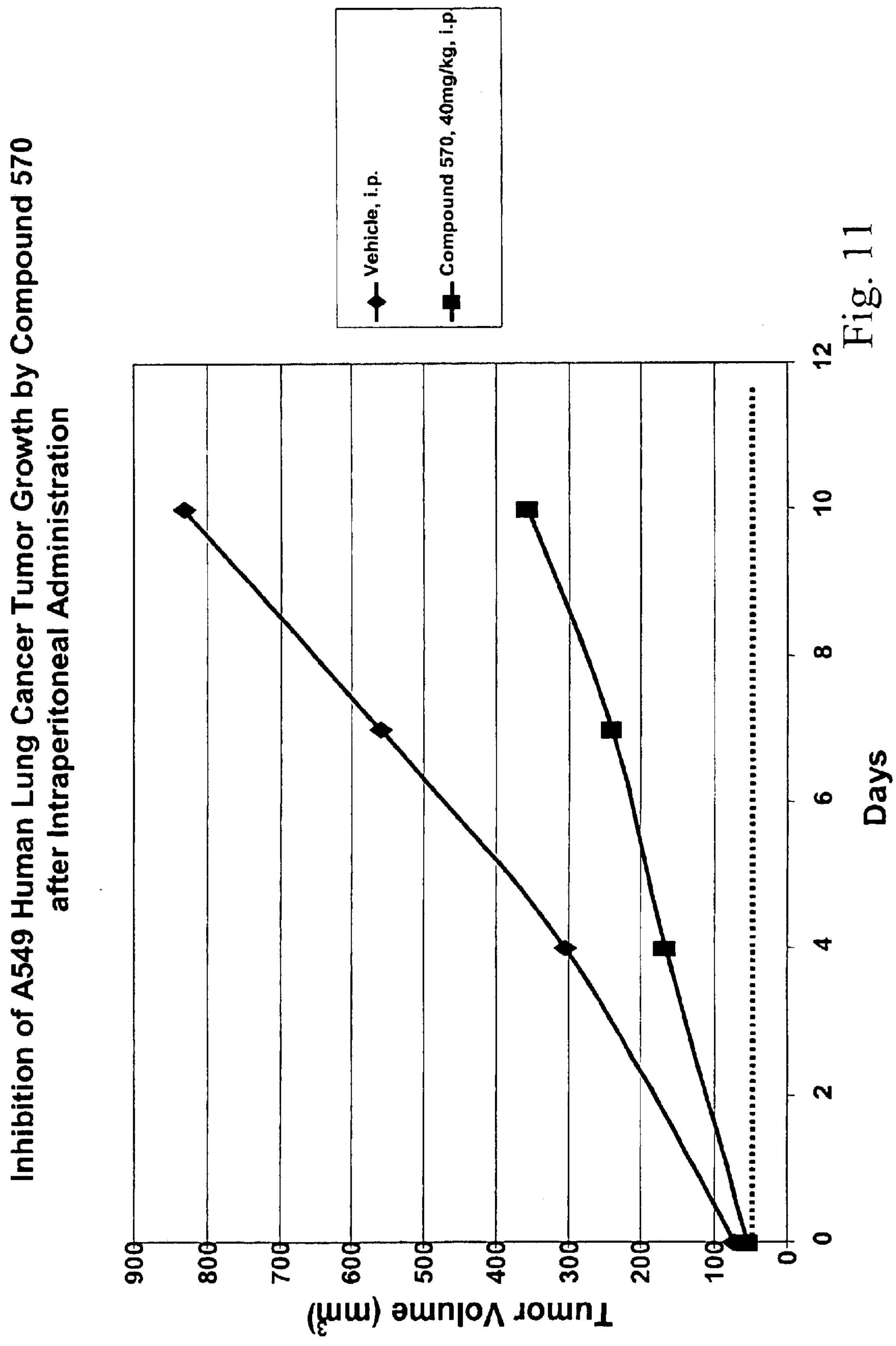

The invention provides compounds and methods for inhibiting histone deacetylase enzymatic activity. The invention also provides compositions and methods for treating cell proliferative diseases and conditions. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used (unless expressly stated otherwise):

As used herein, the terms "histone deacetylase" and "HDAC" are intended to refer to any one of a family of enzymes that remove acetyl groups from the α,ϵ-amino groups of lysine residues at the N-terminus of a histone. Unless otherwise indicated by context, the term "histone" is meant to refer to any histone protein, including H1, H2A, H2B, H3, H4, and H5, from any species. Preferred histone deacetylases include class I and class II enzymes. Preferably the histone deacetylase is a human HDAC, including, but not limited to, HDAC-1, HDAC-2, HDAC-3, HDAC4, HDAC-5, HDAC-6, HDAC-7, and HDAC-8. In some other preferred embodiments, the histone deacetylase is derived from a protozoal or fungal source.

The terms "histone deacetylase inhibitor" and "inhibitor of histone deacetylase" are used to identify a compound having a structure as defined herein, which is capable of interacting with a histone deacetylase and inhibiting its enzymatic activity. "Inhibiting histone deacetylase enzymatic activity" means reducing the ability of a histone deacetylase to remove an acetyl group from a histone. In some preferred embodiments, such reduction of histone deacetylase activity is at least about 50%, more preferably at least about 75%, and still more preferably at least about 90%. In other preferred embodiments, histone deacetylase activity is reduced by at least 95% and more preferably by at least 99%.

Preferably, such inhibition is specific, i.e., the histone deacetylase inhibitor reduces the ability of a histone deacetylase to remove an acetyl group from a histone at a concentration that is lower than the concentration of the inhibitor that is required to produce another, unrelated biological effect. Preferably, the concentration of the inhibitor required for histone deacetylase inhibitory activity is at least 2-fold lower, more preferably at least 5-fold lower, even more preferably at least 10-fold lower, and most preferably at least 20-fold lower than the concentration required to produce an unrelated biological effect.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3—CH_2—$), in certain circumstances a bivalent linking moiety can be "alkyl," in which case those skilled in the art will understand the alkyl to be a divalent radical (e.g., $—CH_2—CH_2—$), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B-, wherein a is 0 or 1. In such instances, when a is 0 the moiety is B- and when a is 1 the moiety is A-B-. Also, a number of moieties disclosed herein exist in multiple tautomeric forms, all of which are intended to be encompassed by any given tautomeric structure.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$–$C_3$-hydrocarbyl" includes a covalent bond, methyl, ethyl, propyl, and cyclopropyl.

The term "alkyl" as employed herein refers to straight and branched chain aliphatic groups having from 1 to 12 carbon atoms, preferably 1–8 carbon atoms, and more preferably 1–6 carbon atoms, which is optionally substituted with one, two or three substituents. Preferred alkyl groups include, without limitation, methyl, ethyl, propyl, isopropyl, butyl, isobutyl, secbutyl, tertbutyl, pentyl, and hexyl. A "$C_0$" alkyl (as in "$C_0$–$C_3$-alkyl") is a covalent bond (like "$C_0$" hydrocarbyl).

The term "alkenyl" as used herein means an unsaturated straight or branched chain aliphatic group with one or more carbon-carbon double bonds, having from 2 to 12 carbon atoms, preferably 2–8 carbon atoms, and more preferably 2–6 carbon atoms, which is optionally substituted with one, two or three substituents. Preferred alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms, preferably 2–8 carbon atoms, and more preferably 2–6 carbon atoms, which is optionally substituted with one, two or three substituents. Preferred alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Preferred alkylene groups include, without limitation, methylene, ethylene, propylene, and butylene. Preferred alkenylene groups include, without limitation, ethenylene, propenylene, and butenylene. Preferred alkynylene groups include, without limitation, ethynylene, propynylene, and butynylene.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally is optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are replaced by a heteratom selected from the group consisting of O, S, and N.

An "aryl" group is a $C_6$–$C_{14}$ aromatic moiety comprising one to three aromatic rings, which is optionally substituted. Preferably, the aryl group is a $C_6$–$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is $(C_1$–$C_6)$alk$(C_6$–$C_{10})$aryl, including, without limitation, benzyl, phenethyl, and naphthylmethyl.

A "heterocyclyl" or "heterocyclic" group is a ring structure having from about 3 to about 8 atoms, wherein one or more atoms are selected from the group consisting of N, O, and S. The heterocyclic group is optionally substituted on carbon at one or more positions. The heterocyclic group is also independently optionally substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocyles include, without limitation, tetrahydroquinoline and dihydrobenzofuran. Specifically excluded from the scope of this term are compounds having adjacent annular O and/or S atoms.

As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, from one to three heteroatoms per ring selected from the group consisting of N, O, and S. A "heteroaralkyl" or "heteroarylalkyl" group comprises a heteroaryl group covalently linked to an alkyl group, either of which is independently optionally substituted or unsubstituted. Preferred heteroalkyl groups comprise a $C_1$–$C_6$ alkyl group and a heteroaryl group having 5, 6, 9, or 10 ring atoms. Specifically excluded from the scope of this term are compounds having adjacent annular O and/or S atoms. Examples of preferred heteroaralkyl groups include pyridylmethyl, pyridylethyl, pyrrolylmethyl, pyrrolylethyl, imidazolylmethyl, imidazolylethyl, thiazolylmethyl, and thiazolylethyl. Specifically excluded from the scope of this term are compounds having adjacent annular O and/or S atoms.

An "arylene," "heteroarylene," or "heterocyclylene" group is an aryl, heteroaryl, or heterocyclyl group, as defined hereinabove, that is positioned between and serves to connect two other chemical groups.

Preferred heterocyclyls and heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

As employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—) nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, (b) $C_1$–$C_5$ alkyl or alkenyl or arylalkyl imino, carbamoyl, azido, carboxamido, mercapto, hydroxy, hydroxyalkyl, alkylaryl, arylalkyl, $C_1$–$C_8$ alkyl, $C_1$–$C_8$ alkenyl, $C_1$–$C_8$ alkoxy, $C_1$–$C_8$ alkoxycarbonyl, aryloxycarbonyl, $C_2$–$C_8$ acyl, $C_2$–$C_8$ acylamino, $C_1$–$C_8$ alkylthio, arylalkylthio, arylthio, $C_1$–$C_8$ alkylsulfinyl, arylalkylsulfinyl, arylsulfinyl, $C_1$–$C_8$ alkylsulfonyl, arylalkylsulfonyl, arylsulfonyl, $C_0$–$C_6$ N-alkyl carbamoyl, $C_2$–$C_{15}$ N,N-dialkylcarbamoyl, $C_3$–$C_7$ cycloalkyl, aroyl, aryloxy, arylalkyl ether, aryl, aryl fused to a cycloalkyl or heterocycle or another aryl ring, $C_3$–$C_7$ heterocycle, or any of these rings fused or spiro-fused to a cycloalkyl, heterocyclyl, or aryl, wherein each of the foregoing is further optionally substituted with one more moieties listed in (a), above; and (c) $—CH_2)_s—NR^{30}R^{31}$, wherein s is from 0 (in which case the nitrogen is directly bonded to the moiety that is substituted) to 6, and $R^{30}$ and $R^{31}$ are each independently hydrogen, cyano, oxo, carboxamido, amidino, $C_1$–$C_8$ hydroxyalkyl, $C_1$–$C_3$ alkylaryl, aryl-$C_1$–$C_3$ alkyl, $C_1$–$C_8$ alkyl, $C_1$–$C_8$ alkenyl, $C_1$–$C_8$ alkoxy, $C_1$–$C_8$ alkoxycarbonyl, aryloxycarbonyl, aryl-$C_1$–$C_3$ alkoxycarbonyl, $C_2$–$C_8$ acyl, $C_1$–$C_8$ alkylsulfonyl, arylalkylsulfonyl, arylsulfonyl, aroyl, aryl, cycloalkyl, heterocyclyl, or heteroaryl, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents from (a), above.

In addition, substituents on cyclic moieties (i.e., cycloalkyl, heterocyclyl, aryl, heteroaryl) include 5–6 membered mono- and 10–12 membered bi-cyclic moieties fused to the parent cyclic moiety to form a bi- or tri-cyclic fused ring system. For example, an optionally substituted phenyl includes the following:

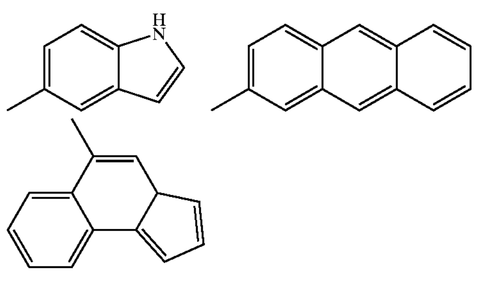

A "halohydrocarbyl" is a hydrocarbyl moiety in which from one to all hydrogens have been replaced with one or more halo.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally substituted. The term "sulfonamido" refers to a sulfonamide substituent attached by either the sulfur or the nitrogen atom. The term "amino" is meant to include $NH_2$, alkylamino, arylamino, and cyclic amino groups. The term "ureido" as employed herein refers to a substituted or unsubstituted urea moiety.

The term "radical" as used herein means a chemical moiety comprising one or more unpaired electrons.

A moiety that is substituted is one in which one or more hydrogens have been independently replaced with another chemical substituent. As a non-limiting example, substituted phenyls include 2-flurophenyl, 3,4-dichlorophenyl, 3-chloro-4-fluoro-phenyl, 2-fluor-3-propylphenyl. As another non-limiting example, substituted n-octyls include 2,4 dimethyl-5-ethy-octyl and 3-cyclopentyl-octyl. Included within this definition are methylenes (—$CH_2$—) substituted with oxygen to form carbonyl-CO—).

An "unsubstituted" moiety as defined above (e.g., unsubstituted cycloalkyl, unsubstituted heteroaryl, etc.) means that moiety as defined above that does not have any of the optional substituents for which the definition of the moiety (above) otherwise provides. Thus, for example, while an "aryl" includes phenyl and phenyl substituted with a halo, "unsubstituted aryl" does not include phenyl substituted with a halo.

Preferred embodiments of a particular genus of compounds of the invention include combinations of preferred embodiments. For example, embodiment 1A below identifies a preferred $Ay^1$ and embodiment 1B identifies preferred $Ar^1$ (both for compound (1) of embodiment 1). Thus, another preferred embodiment includes those compounds of formula (1) in embodiment 1 in which $Ay^1$ is as defined in embodiment 1A and $Ar^1$ is as defined in embodiment 1B.

Compounds

In a first aspect, the invention provides novel inhibitors of histone deacetylase. In embodiment 1 of the first aspect of the invention, the novel inhibitors of histone deacetylase are represented by formula (1):

(1)

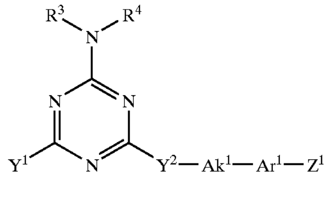

and pharmaceutically acceptable salts thereof, wherein $R^3$ and $R^4$ are independently selected from the group consisting of hydrogen, $L^1$, $Cy^1$, and -$L^1$-$Cy^1$, wherein $L^1$ is $C_1$–$C_6$ alkyl, $C_2$–$C_6$ heteroalkyl, or $C_3$–$C_6$ alkenyl; and $Cy^1$ is cycloalkyl, aryl, heteroaryl, or heterocyclyl, each of which optionally is substituted, and each of which optionally is fused to one or more aryl or heteroaryl rings, or to one or more saturated or partially unsaturated cycloalkyl or heterocyclic rings, each of which rings optionally is substituted; or $R^3$ and $R^4$ are taken together with the adjacent nitrogen atom to form a 5-, 6-, or 7-membered ring, wherein the ring atoms are independently selected from the group consisting of C, O, S, and N, and wherein the ring optionally is substituted, and optionally forms part of a bicyclic ring system, or optionally is fused to one or more aryl or heteroaryl rings, or to one or more saturated or partially unsaturated cycloalkyl or heterocyclic rings, each of which rings and ring systems optionally is substituted;

$Y^1$ is selected from the group consisting of —N($R^1$)($R^2$), —$CH_2$—C(O)—N($R^1$)($R^2$), halogen, and hydrogen, wherein $R^1$ and $R^2$ are independently selected from the group consisting of hydrogen, $L^1$, $Cy^1$, and -$L^1$-$Cy^1$, wherein $L^1$ is $C_1$–$C_6$ alkyl, $C_2$–$C_6$ heteroalkyl, or $C_3$–$C_6$ alkenyl; and $Cy^1$ is cycloalkyl, aryl, heteroaryl, or heterocyclyl, each of which optionally is substituted, and each of which optionally is fused to one or more aryl or heteroaryl rings, or to one or more saturated or partially unsaturated cycloalkyl or heterocyclic rings, each of which rings optionally is substituted; or $R^1$ and $R^2$ are taken together with the adjacent nitrogen atom to form a 5-, 6-, or 7-membered ring, wherein the ring atoms are independently selected from the group consisting of C, O, S, and N, and wherein the ring optionally is substituted, and optionally may form part of a bicyclic ring system, or optionally is fused to one or more aryl or heteroaryl rings, or to one or more saturated or partially unsaturated cycloalkyl or heterocyclic rings, each of which rings and ring systems optionally is substituted;

$Y^2$ is a chemical bond or N($R^0$), where $R^0$ is selected from the group consisting of hydrogen, alkyl, aryl, aralkyl, and acyl;

$Ak^1$ is $C_1$–$C_6$ alkylene, $C_1$–$C_6$-heteroalkylene (preferably, in which one —$CH_2$— is replaced with —NH—, and more preferably —NH—$CH_2$—), $C_2$–$C_6$ alkenylene or $C_2$–$C_6$ alkynylene;

$Ar^1$ is arylene or heteroarylene, either of which optionally is substituted; and $Z^1$ is selected from the group consisting of

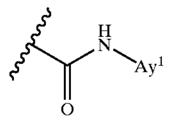
and
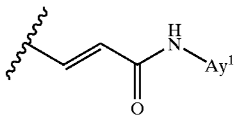

wherein $Ay^1$ is aryl or heteroaryl, which optionally is substituted.

Embodiment 1A. Preferably in the compounds according to embodiment 1 of the first aspect of the invention, $Ay^1$ is phenyl or thienyl, each substituted with —OH or —$NH_2$.

More preferably in the compounds according to embodiment 1, $Ay^1$ is optionally amino- or hydroxy-substituted phenyl or thienyl, wherein the amino or hydroxy substituent is preferably ortho to the nitrogen to which $Ay^2$ is attached.

More preferably in the compounds according to embodiment 1, $Ay^1$ is ortho aniline, ortho phenol, 3-amino-2-thienyl, or 3-hydroxy-2-thienyl, and tautomers thereof.

In some preferred embodiments of the compounds according to embodiment 1, $Z^1$ is

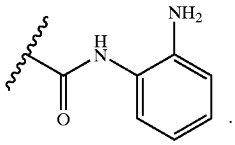

Embodiment 1B. In some preferred embodiments of the compounds according to embodiment 1, $Ar^1$ is phenylene. In some embodiments, $Ak^1$ is alkylene, preferably methylene. In some preferred embodiments, $Y^2$ is —NH—. In some preferred embodiments, $Y^1$ is $—N(R^1)(R^2)$ or $—CH_2—C(O)—N(R^1)(R^2)$.

In some embodiments of the compounds according to embodiment 1, $R^1$ and $R^2$ are each independently selected from the group consisting of hydrogen, $L^1$, $Cy^1$, and $-L^1-Cy^1$. In some embodiments, $R^1$ and/or $R^2$ is hydrogen. In other embodiments, $R^1$ and/or $R^2$ is alkyl or alkenyl, preferably allyl. In still other embodiments, $R^1$ and/or $R^2$ is aryl, heteroaryl, aralkyl, or heteroaralkyl, the rings of each of which optionally is substituted and optionally is fused to one or more aryl rings. Some preferred aryl, heteroaryl, aralkyl, and heteroaralkyl groups comprise a phenyl, pyridyl, or pyrrolyl ring. In still other embodiments, $R^1$ and/or $R^2$ is cycloalkyl, e.g., cyclopropyl, cyclopentyl, or cyclohexyl, which optionally is substituted and optionally is fused to one or more aryl rings.

In some embodiments of the compounds according to embodiment 1, $R^3$ and $R^4$ are each independently selected from the group consisting of hydrogen, $L^1$, $Cy^1$, and $-L^1-Cy^1$. In some embodiments, $R^3$ and/or $R^4$ is hydrogen. In other embodiments, $R^3$ and/or $R^4$ is alkyl or alkenyl, preferably allyl. In still other embodiments, $R^3$ and/or $R^4$ is aryl, heteroaryl, aralkyl, or heteroaralkyl, the rings of each of which optionally is substituted and optionally is fused to one or more aryl rings. Some preferred aryl, heteroaryl, aralkyl, and heteroaralkyl groups comprise a phenyl, pyridyl, or pyrrolyl ring. In still other embodiments, $R^3$ and/or $R^4$ is cycloalkyl, e.g., cyclopropyl, cyclopentyl, or cyclohexyl, which optionally is substituted and optionally is fused to one or more aryl rings.

As set forth above, $L^1$ is $C_1$–$C_6$ alkyl, $C_2$–$C_6$ heteroalkyl, or $C_3$–$C_6$ alkenyl. However, one skilled in the art will understand that when $L^1$ is not a terminal group, then $L^1$ is $C_1$–$C_6$ alkylene, $C_2$–$C_6$ heteroalkylene, or $C_3$–$C_6$ alkenylene. In some embodiments, $L^1$ is alkylene, preferably methylene or ethylene. In other embodiments, $L^1$ is alkenyl, preferably allyl. In some embodiments, $Cy^1$ is the radical of a heterocyclic group including, without limitation, piperidine, pyrrolidine, piperazine, and morpholine, each of which optionally is substituted and optionally is fused to one or more aryl rings. In other embodiments $Cy^1$ is cycloalkyl, e.g., cyclopropyl, cyclopentyl, or cyclohexyl. In still other embodiments, $Cy^1$ is aryl or heteroaryl, e.g., phenyl, pyridyl, or pyrrolyl, each of which optionally is substituted and optionally is fused to one or more aryl rings. In some embodiments, $Cy^1$ is fused to one or two benzene rings. In some embodiments, $Cy^1$ has between one and about five substituents selected from the group consisting of $C_1$–$C_4$ alkyl, $C_1$–$C_4$ alkoxy, and halo. Examples of preferred substituents include methyl, methoxy, and fluoro.

In some embodiments of the compounds according to embodiment 1, $R^1$ and $R^2$ and/or $R^3$ and $R^4$ are taken together with the adjacent nitrogen atom to form a 5- or 6-membered ring, wherein the ring atoms are independently selected from the group consisting of C, O, and N, and wherein the ring optionally is substituted, and optionally is fused to one or more aryl rings. In some preferred embodiments, $R^1$ and $R^2$ and/or $R^3$ and $R^4$ are taken together with the adjacent nitrogen atom to form a ring such as, for example, pyrrolidine, piperidine, piperazine, and morpholine, wherein the ring optionally is substituted, and optionally is fused to an aryl ring. In some embodiments, the ring comprising $R^1$ and $R^2$ or $R^3$ and $R^4$ is fused to a benzene ring. In some embodiments, the ring comprising $R^1$ and $R^2$ or $R^3$ and $R^4$ has a substituent comprising an aryl or cycloalkyl ring, either of which optionally is substituted and optionally is fused to a cycloalkyl, aryl, heteroaryl, or heterocyclic ring. Preferred substituents include, without limitation, phenyl, phenylmethyl, and phenylethyl, the phenyl ring of which optionally is fused to a cycloalkyl, aryl, or heterocyclic ring.

Embodiment 2. In a preferred embodiment, the HDAC inhibitors of the invention comprise compounds of formula 1(a):

(1a)

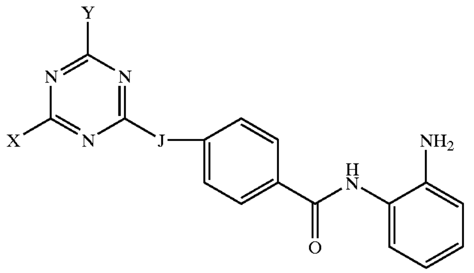

and pharmaceutically acceptable salts thereof, wherein

J is $C_1$–$C_3$-hydrocarbyl, $—N(R^{20})—$, $—N(R^{20})—CH_2—$, —O—, or $—O—CH_2—$;

$R^{20}$ is —H or -Me;

X and Y are independently selected from $—NH_2$, cycloalkyl, heterocyclyl, aryl, heteroaryl, and $A-(C_1–C_6\text{-alkyl})_n-B-$;

A is H, $C_1$–$C_6$-alkyloxy, cycloalkyl, heterocyclyl, aryl, or heteroaryl;

B is —NH—, —O—, or a direct bond; and n is 0 (in which case A is directly bonded to B) or 1.

Preferably in the compounds according to embodiment 2, A is phenyl optionally substituted with one or more moieties selected from halo (preferably chloro) and methoxy, and B is —NH—. In another preferred embodiment, A is selected from cyclopropyl, pyridinyl, and indanyl.

Preferably in the compounds according to embodiment 2, J is $—NH—CH_2—$, $—O—CH_2—$, $—N(CH_3)—CH_2—$, —CH=CH—, or $—CH_2—CH_2—$.

Preferably in the compounds according to embodiment 2, $R^{20}$ is —H.

In the compounds according to embodiment 2, X is preferably selected from

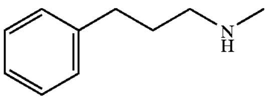
,

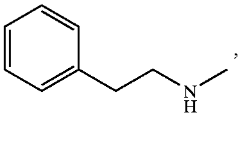
,
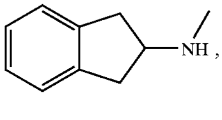
,

-continued
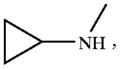 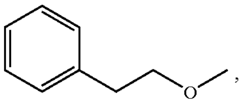
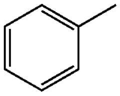 , —OMe, 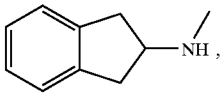
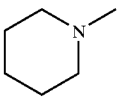 —$NH_2$ 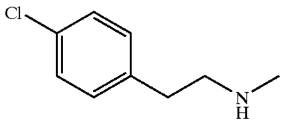
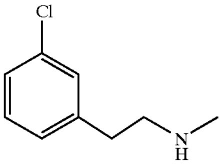 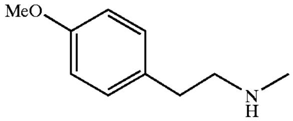
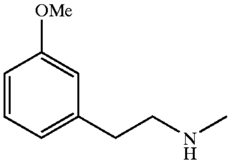 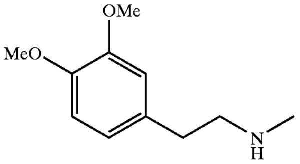
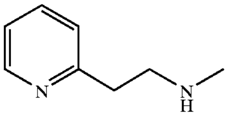 and 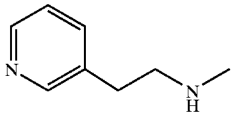 ;
and Y is preferably selected from
—$NH_2$, 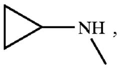 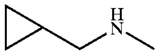 , n-BuNH,
-continued
$MeOCH_2CH_2NH$, 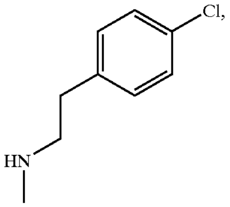
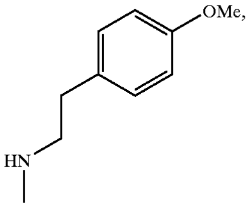 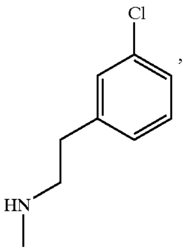
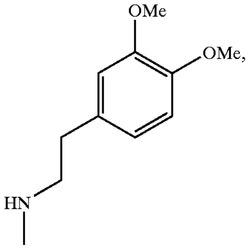 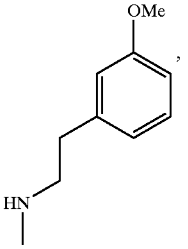
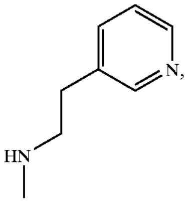 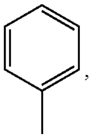 , —H Me
—OMe $CH_3(CH_2)_3NH$— and
—$CH_3O(CH_2)_2$—NH—.
In a more preferred embodiment of the compounds according to embodiment 2, the HDAC inhibitors of the invention comprise the following compounds of formula 1a:
| Cpd | J | X | Y |
|---|---|---|---|
| 204 | —NH— | 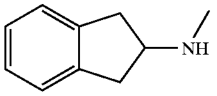 | —$NH_2$ |
| 207 | —$OCH_2$— | 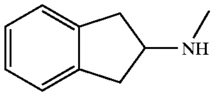 | —$NH_2$ |
| 210 | —$NHCH_2$— | 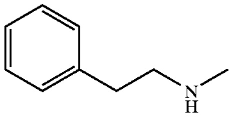 | —H |
| 212 | —$NHCH_2$— | —OMe | —OMe |

-continued
| Cpd | J | X | Y |
|---|---|---|---|
| 214 | $-NHCH_2-$ | 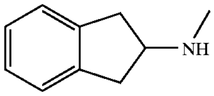 | —OMe |
| 216 | 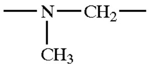 | 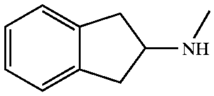 | —Me |
| 218 | $-NHCH_2-$ | 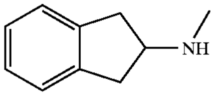 | —Me |
| 220 | —CH═CH— | $-NH_2$ | $-NH_2-$ |
| 223 | —CH═CH— | 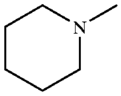 | $-NH_2$ |
| 224 | $-CH_2CH_2-$ | $-NH_2$ | $-NH_2$ |
| 470 | $-NHCH_2-$ | 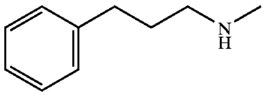 | $NH_2$ |
| 471 | $-NHCH_2-$ | 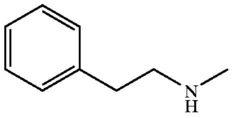 | 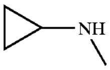 |
| 472 | $-NHCH_2-$ | 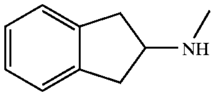 | 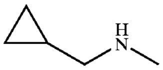 |
| 473 | $-NHCH_2-$ | 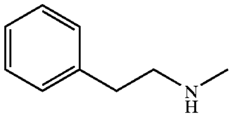 | n-BuNH |
| 474 | $-NHCH_2-$ | 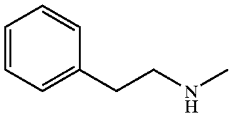 | $MeO(CH2)_2NH$ |
| 475 | $-NHCH_2-$ | 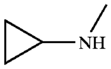 | 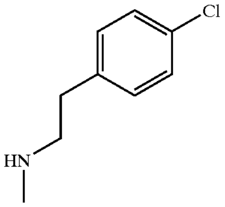 |
| 476 | $-NHCH_2-$ | 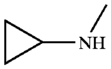 | 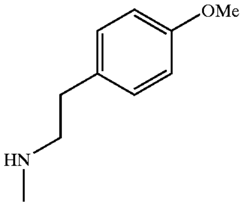 |

-continued
| Cpd | J | X | Y |
|---|---|---|---|
| 477 | $—NHCH_2—$ | 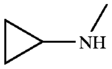 | 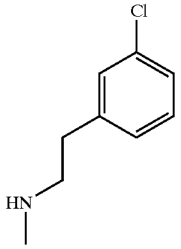 |
| 478 | $—NHCH_2—$ | 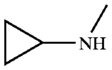 | 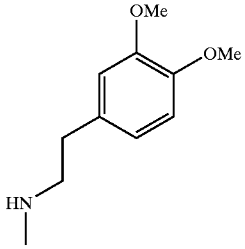 |
| 479 | $—NHCH_2—$ | 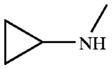 | 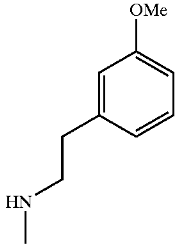 |
| 480 | $—NHCH_2—$ | 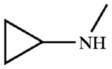 | 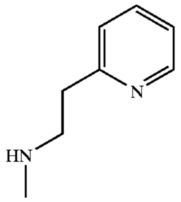 |
| 481 | $—NHCH_2—$ | 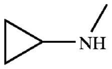 | 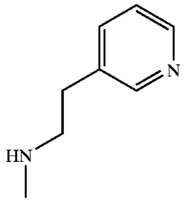 |
| 482 | $—NHCH_2—$ | 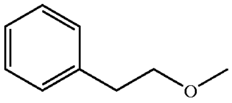 | 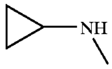 |
| 483 | $—NHCH_2—$ | 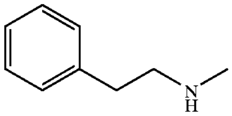 | Me |
| 484 | $—NHCH_2—$ | 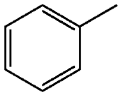 | $NH_2$ |

-continued

| Cpd | J | X | Y |
|---|---|---|---|
| | | and | |
| 485 | —$NHCH_2$— | 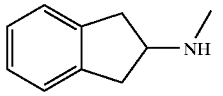 | 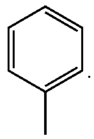. |

Embodiment 3. In a further embodiment, the novel histone deacetylase inhibitors of the invention are represented by formula (2):

(2)

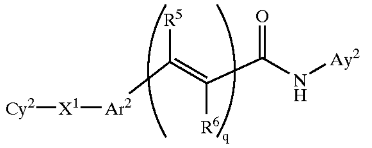

and pharmaceutically acceptable salts thereof, wherein $Cy^2$ is cycloalkyl, aryl, heteroaryl, or heterocyclyl, each of which is optionally substituted and each of which is optionally fused to one or more aryl or heteroaryl rings, or to one or more saturated or partially unsaturated cycloalkyl or heterocyclic rings, each of which rings is optionally substituted;

$X^1$ is selected from the group consisting of a covalent bond, $M^1$-$L^2$-$M^1$, and $L^2$-$M^2$-$L^2$ wherein $L^2$, at each occurrence, is independently selected from the group consisting of a chemical bond, $C_0$–$C_4$ hydrocarbyl, $C_0$–$C_4$-hydrocarbyl-(NH)—$C_0$–$C_4$-hydrocarbyl, $C_0$–$C_4$-hydrocarbyl-(S)—$C_0$–$C_4$-hydrocarbyl, and $C_0$–$C_4$-hydrocarbyl-(O)—$C_0$–$C_4$-hydrocarbyl, provided that $L^2$ is not a chemical bond when $X^1$ is $M^1$-$L^2$-$M^1$;

$M^1$, at each occurrence, is independently selected from the group consisting of —O—, —N($R^7$)—, —S—, —S(O)—, S$(O)_2$—, —S$(O)_2$N($R^7$)—, —N($R^7$)—S$(O)_2$—, —C(O)—, —C(O)—NH—, —NH—C(O)—, —NH—C(O)—O— and —O—C(O)—NH—, wherein $R^7$ is selected from the group consisting of hydrogen, alkyl, aryl, aralkyl, acyl, heterocyclyl, and heteroaryl; and $M^2$ is selected from the group consisting of $M^1$, heteroarylene, and heterocyclylene, either of which rings optionally is substituted;

$Ar^2$ is arylene or heteroarylene, each of which is optionally substituted;

$R^5$ and $R^6$ are independently selected from the group consisting of hydrogen, alkyl, aryl, and aralkyl;

q is 0 or 1; and $Ay^2$ is a 5–6 membered cycloalkyl, heterocyclyl, or heteroaryl substituted with an amino or hydroxy moiety (preferably these groups are ortho to the amide nitrogen to which $Ay^2$ is attached) and further optionally substituted;

provided that when $Cy^2$ is naphthyl, $X^1$ is —$CH_2$—, $Ar^2$ is phenyl, $R^5$ and $R^6$ are H, and q is 0 or 1, $Ay^2$ is not phenyl or o-hydroxyphenyl.

In a preferred embodiment of the compounds according to embodiment 3, when $Ay^2$ is o-phenol optionally substituted by halo, nitro, or methyl, $Ar^2$ is optionally substituted phenyl, $X^1$ is —O—, —$CH_2$—, —S—, —S—$CH_2$—, —S(O)—, —S$(O)_2$—, —C(O)—, or —$OCH_2$—, then $Cy^2$ is not optionally substituted phenyl or naphthyl.

In another preferred embodiment of the compounds according to embodiment 3, when $Ay^2$ is o-anilinyl optionally substituted by halo, $C_1$–$C_6$-alkyl, $C_1$–$C_6$-alkoxy or —$NO_2$, q is 0, $Ar^2$ is phenyl, and $X^1$ is —$CH_2$—, then $Cy^2$ is not substituted pyridone (which substituents of the pyridone are not limited to substituents described herein).

In another preferred embodiment of the compounds according to embodiment 3, when $X^1$ is —$CH_2$—, $Ar^2$ is optionally substituted phenyl, q is 1, and $R^6$ is H, then $Cy^2$ is not optionally substituted imidazole.

In another preferred embodiment of the compounds according to embodiment 3, when $Ar^2$ is amino or hydroxy substituted phenyl, $X^1$ is $C_0$–$C_8$-alkyl-$X^{1a}$—$C_0$–$C_8$-alkyl, wherein $X^{1a}$ is —$CH_2$—, —O—, —S—, —NH—, —C(O)—, then $Cy^2$ is not optionally substituted naphthyl or di- or -tetrahydronaphthalene.

In another preferred embodiment of the compounds according to embodiment 3, when $Ay^2$ is o-phenol, $Ar^2$ is substituted phenyl, $X^1$ is —O—, —S—, —$CH_2$—, —O—$CH_2$—, —S—$CH_2$—, or —C(O)—, and $R^5$ and $R^6$ are H, then $Cy^2$ is not optionally substituted naphthyl.

In another preferred embodiment of the compounds according to embodiment 3, when $Ay^2$ is o-anilinyl, q is 0, $Ar^2$ is unsubstituted phenyl, $X^1$ is —$CH_2$—, then $Cy^2$ is not substituted 6-hydroimidazolo[5,4-d]pyridazin-7-one-1-yl or substituted 6-hydroimidazolo[5,4-d]pyridazine-7-thione-1-yl.

Preferably in the compounds according to embodiment 3, $Ay^2$ is phenyl or thienyl, each substituted with —OH or —$NH_2$.

More preferably in the compounds according to embodiment 3, $Ay^2$ is optionally amino- or hydroxy-substituted phenyl or thienyl, wherein the amino or hydroxy substituent is preferably ortho to the nitrogen to which $Ay^2$ is attached.

More preferably in the compounds according to embodiment 3, $Ay^2$ is ortho aniline, ortho phenol, 3-amino-2-thienyl, or 3-hydroxy-2-thienyl, and tautomers thereof.

Embodiment 4. In another embodiment, the novel histone deacetylase inhibitors of the invention are those according to embodiment 3wherein q is 1;

$M^1$, at each occurrence, is selected from the group consisting of —N($R^7$)—, —S—, —C(O)—NH—, and —O—C(O)—NH—, where $R^7$ is selected from the group consisting of hydrogen, alkyl aryl, aralkyl, and acyl; and $Ay^2$ is anilinyl, which optionally is substituted.

In some preferred embodiments of the compounds according to embodiment 4, the —$NH_2$ group of $Ay^2$ is in an ortho position with respect to the nitrogen atom to which $Ay^2$ is attached. In some embodiments, $R^5$ and $R^6$ are independently selected from the group consisting of hydrogen and $C_1$–$C_4$ alkyl. In some preferred embodiments, $R^5$ and $R^6$ are hydrogen.

Embodiment 5. In some embodiments of the compounds according to embodiment 4, $Ar^2$ has the formula

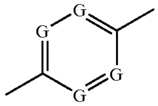,
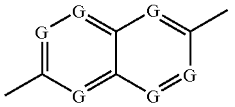,
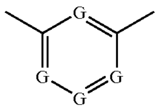, or
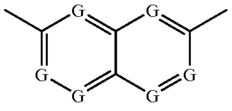

wherein G, at each occurrence, is independently N or C, and C optionally is substituted. In some preferred embodiments, $Ar^2$ has the formula

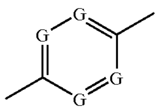 or
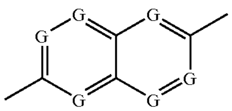.

In some preferred embodiments of the compounds according to embodiment 5, $Ar^2$ is selected from the group consisting of phenylene, pyridylene, pyrimidylene, and quinolylene.

In some embodiments of the compounds according to embodiment 4, $X^1$ is a chemical bond. In some embodiments, $X^1$ is $L^2$-$M^2$-$L^2$, and $M^2$ is selected from the group consisting of —NH—, —N($CH_3$)—, —S—, —C(O)—N(H)—, and —O—C(O)—N(H)—. In some embodiments, $X^1$ is $L^2$-$M^2$-$L^2$, where at least one occurrence of $L^2$ is a chemical bond. In other embodiments, $X^1$ is $L^2$-$M^2$-$L^2$, where at least one occurrence of $L^2$ is alkylene, preferably methylene. In still other embodiments, $X^1$ is $L^2$-$M^2$-$L^2$, where at least one occurrence of $L^2$ is alkenylene. In some embodiments, $X^1$ is $M^1$-$L^2$-$M^1$ and $M^1$ is selected from the group consisting of —NH—, —N($CH_3$)—, —S—, and —C(O)—N(H)—.

In some embodiments of the compounds according to embodiment 4, $Cy^2$ is aryl or heteroaryl, e.g., phenyl, pyridyl, imidazolyl, or quinolyl, each of which optionally is substituted. In some embodiments, $Cy^2$ is heterocyclyl, e.g.,

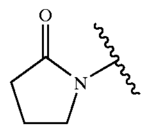,
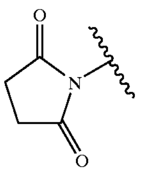,
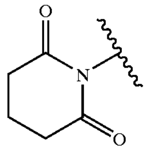,
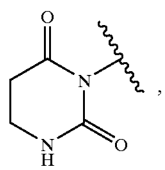,
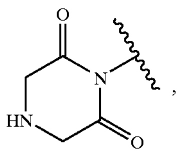,

-continued

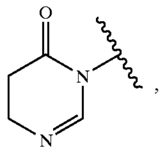,
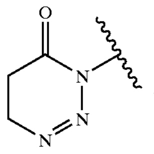, and
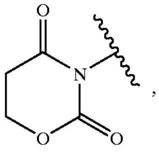, each of which optionally is substituted and optionally is fused to one or more aryl rings. In some embodiments, $Cy^2$ has from one and three substituents independently selected from the group consisting of alkyl, alkoxy, amino, nitro, halo, haloalkyl, and haloalkoxy. Examples of preferred substituents include methyl, methoxy, fluoro, trifluoromethyl, trifluoromethoxy, nitro, amino, aminomethyl, and hydroxymethyl.

Embodiment 6. In a preferred embodiment of the compounds of embodiment 3, the invention comprises compounds of structural formula (2a):

(2a)

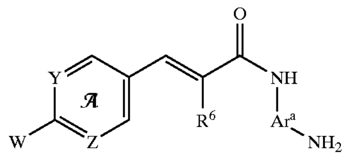

and pharmaceutically acceptable salts thereof, wherein $Ar^a$ is phenyl or thienyl;

$R^6$ is H, or $C_1$–$C_6$-alkyl (preferably —$CH_3$);

Y and Z are independently —CH= or —N=;

W is halo, (V'-$L^4$)$_t$-V-$L^3$-;

$L^3$ is a direct bond, —$C_1$–$C_6$-hydrocarbyl, —($C_1$–$C_3$-hydrocarbyl)$_{m1}$-X'—($C_1$–$C_3$-hydrocarbyl)$_{m2}$, —NH—($C_0$–$C_3$-hydrocarbyl), ($C_1$–$C_3$-hydrocarbyl)-NH—, or —NH—($C_1$–$C_3$-hydrocarbyl)-NH—;

m1 and m2 are independently 0 or 1;

X' is —N($R^{21}$)—, —C(O)N($R^{21}$)—, N($R^{21}$)C(O)—, —O—, or —S—;

$R^{21}$ is —H, V"—($C_1$–$C_6$-hydrocarbyl)$_c$;

$L^4$ is ($C_1$-$C_6$-hydrocarbyl)$_a$-M-($C_1$–$C_6$-hydrocarbyl)$_b$;

a and b are independently 0 or 1;

M is —NH—, —NHC(O)—, —C(O)NH—, —C(O)—, —$SO_2$—, —$NHSO_2$—, or —$SO_2$NH—

V, V', and V" are independently selected from cycloalkyl, heterocyclyl, aryl, and heteroaryl;

t is 0 or 1;

or W, the annular C to which it is bound, and Y together form a monocyclic cycloalkyl, heterocyclyl, aryl, or heteroaryl; and wherein the 𝔄 and $Ar^a$ rings are optionally further substituted with from 1 to 3 substituents independently selected from methyl, hydroxy, methoxy, halo, and amino.

In a preferred embodiment of the compound according to embodiment 6;

Y and Z are —CH= and $R^6$ is H;

W is V-$L^3$;

$L^3$ is —NH—CH— or —CH—NH—;

V is phenyl optionally substituted with from 1 to 3 moieties independently selected from halo, hydroxy, $C_1$–$C_6$-hydrocarbyl, $C_1$–$C_6$-hydrocarbyl-oxy or -thio (particularly methoxy or methylthio), wherein each of the hydrocarbyl moieties are optionally substituted with one or more moieties independently selected from halo, nitroso, amino, sulfonamido, and cyano; and $Ar^a$ is phenyl and the amino moieties to which it is bound are ortho to each other.
In some preferred embodiments of the compound according to embodiment 6, V is an optionally substituted ring moiety selected from:
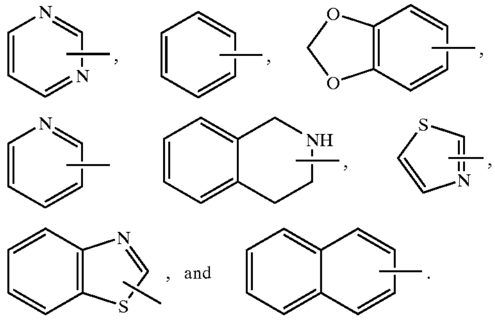
In another preferred embodiment of the compounds according to embodiment 6, W is selected from:
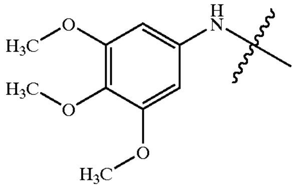
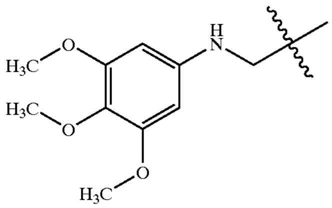
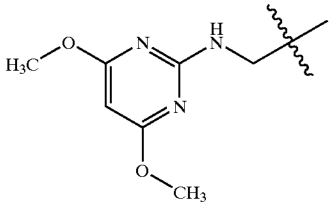
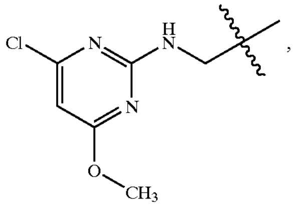
,
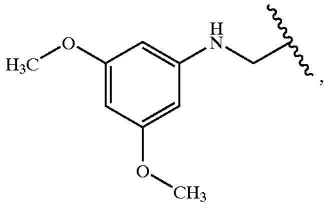
,
-continued
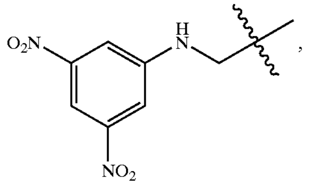
,
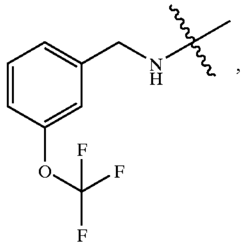
,
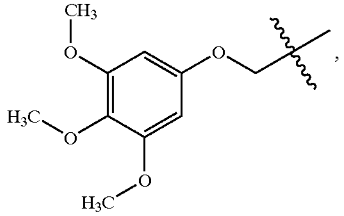
,
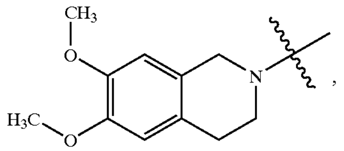
,
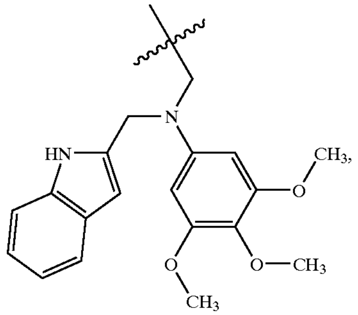
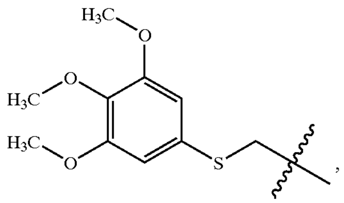
,
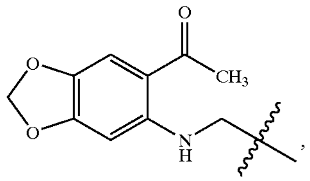
,
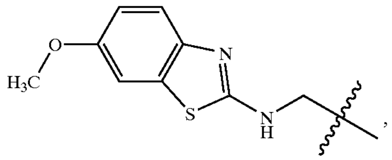
, -continued
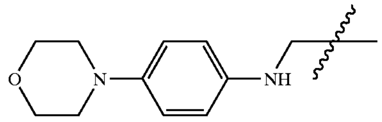,
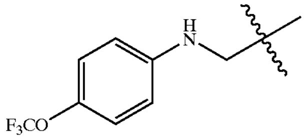,
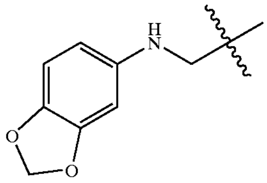, 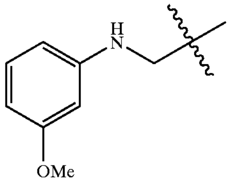,
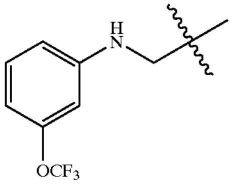, 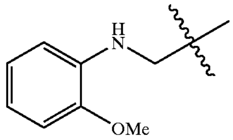,
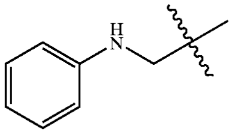,
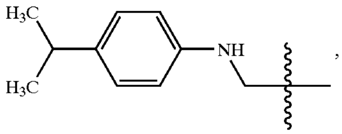,
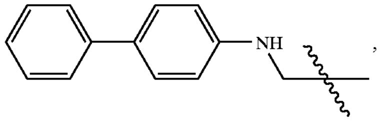,
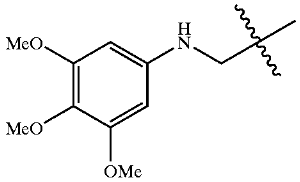, Br—,
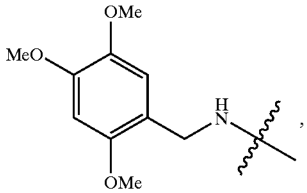,
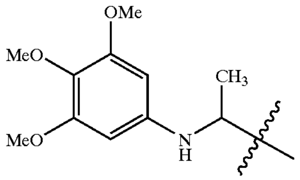, 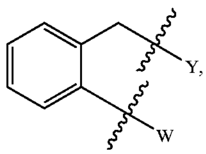
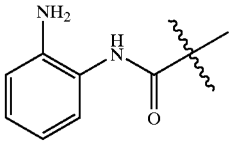,
-continued
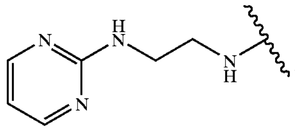,
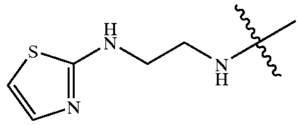,
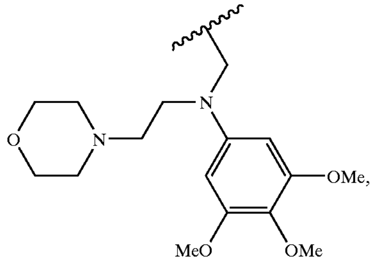
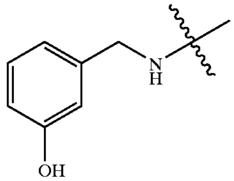, 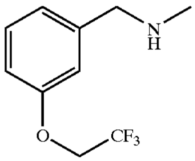,
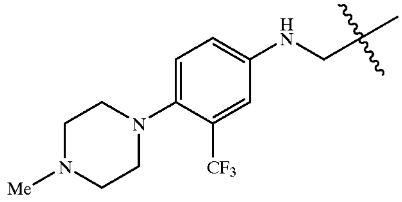,
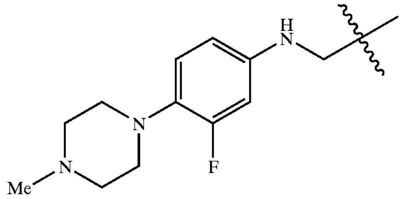,
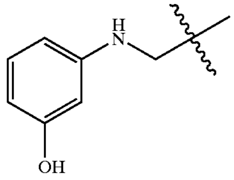, 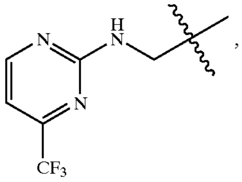,
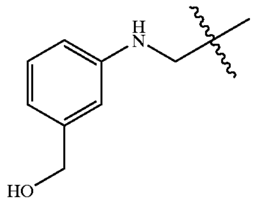,
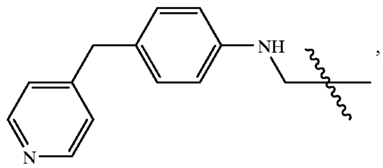, -continued
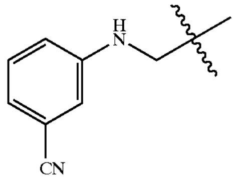
,
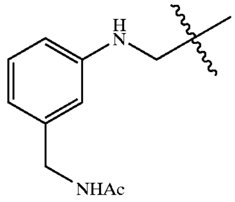
,
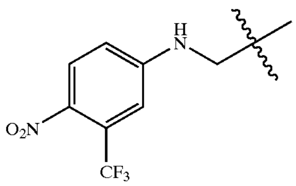
,
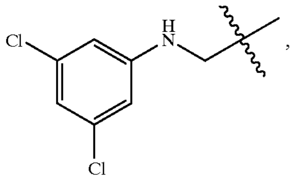
,
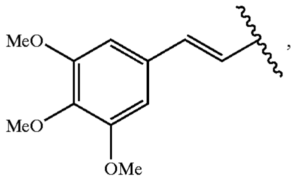
,
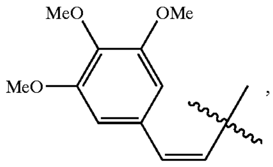
,
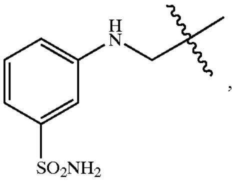
,
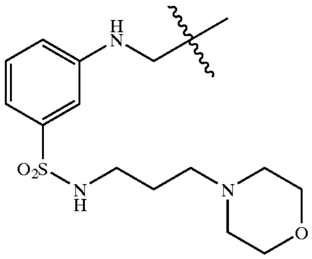
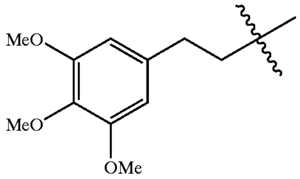
,
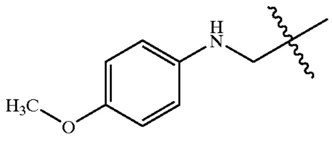
,
-continued
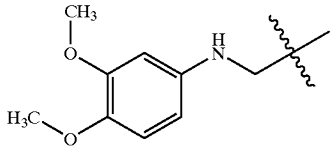
,
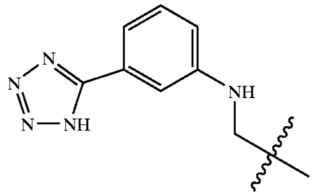
,
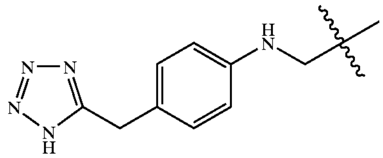
,
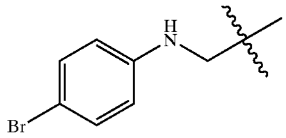
,
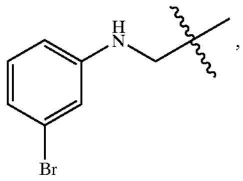
,
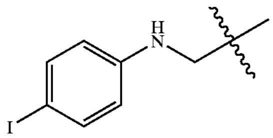
,
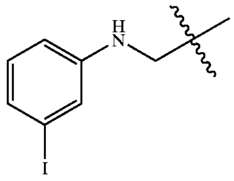
,
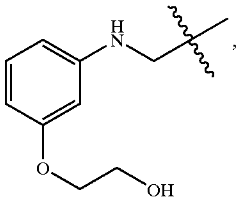
,
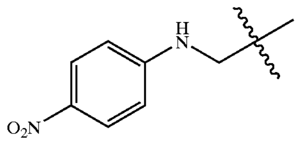
,
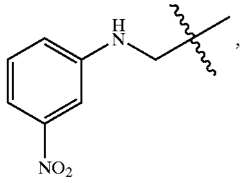
,
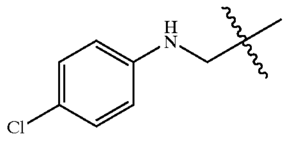
, -continued

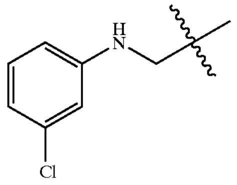,

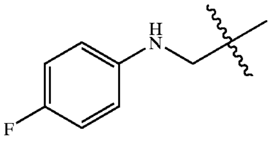,

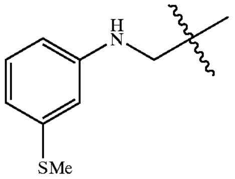,

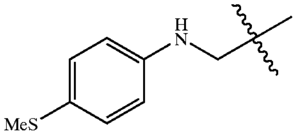,

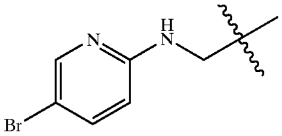,

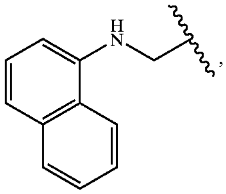, 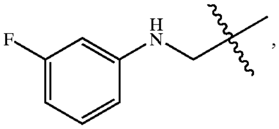,

-continued

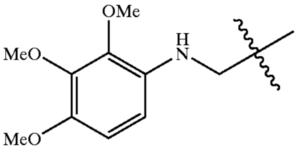,

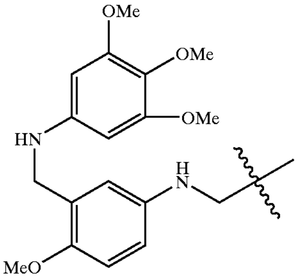,

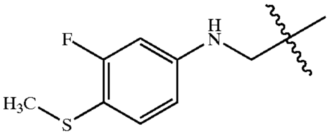, and

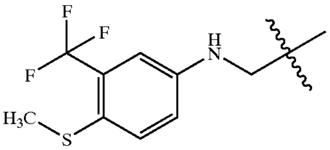.

In another preferred embodiment of the compounds according to embodiment 6, the 𝒜 and Ar[a] rings are not further substituted.

In a particularly preferred embodiment of the compounds according to embodiment 6, the compounds of the invention are selected from the following, in which, unless expressly displayed otherwise, Ar[a] is phenyl (and, preferably, the amide nitrogen and the amino nitrogen bound to Ar[a] are ortho to each other):

| Cpd | W | Y | Z | $R^6$ |
|---|---|---|---|---|
| 481 | 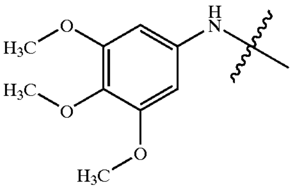 | CH | CH | H |

-continued
| Cpd | W | Y | Z | $R^6$ |
| --- | --- | --- | --- | --- |
| 484 | 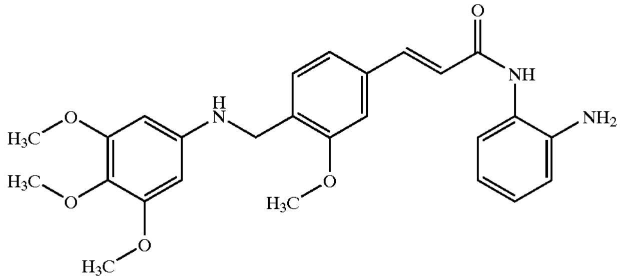 | | | |
| 492 | 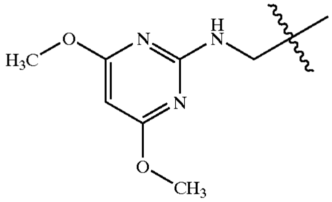 | CH | CH | H |
| 493 | 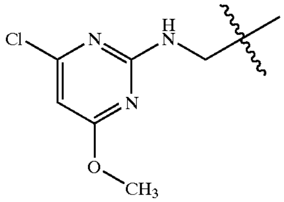 | CH | CH | H |
| 494 | 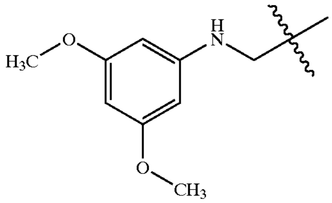 | CH | CH | H |
| 495 | 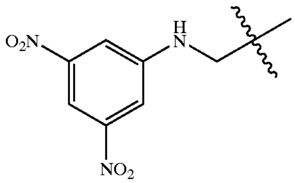 | CH | CH | H |
| 496 | 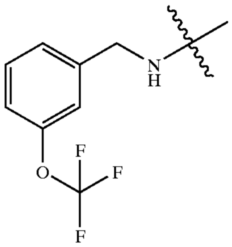 | CH | CH | H |

-continued
| Cpd | W | Y | Z | $R^6$ |
| --- | --- | --- | --- | --- |
| 497 | 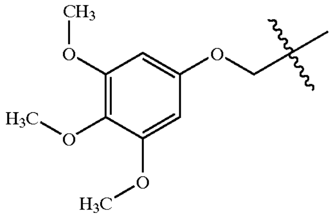 | CH | CH | H |
| 498 | 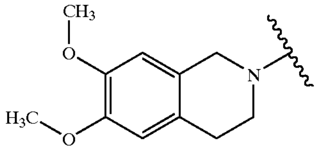 | CH | CH | H |
| 499 | 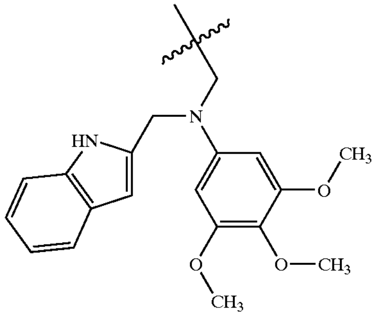 | CH | CH | H |
| 500 | 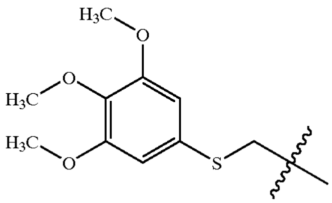 | CH | CH | H |
| 501 | 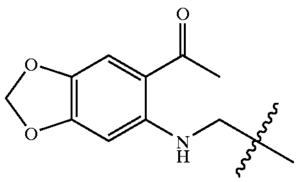 | CH | CH | H |
| 502 | 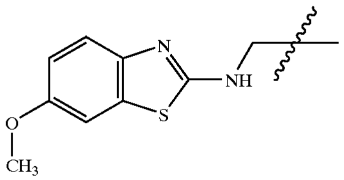 | CH | CH | H |
| 503 | 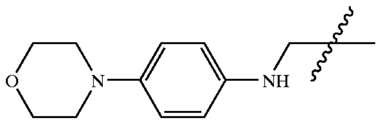 | CH | CH | H |

-continued
| Cpd | W | Y | Z | $R^6$ |
|---|---|---|---|---|
| 504 | 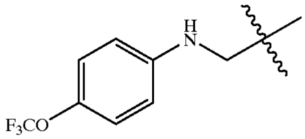 | CH | CH | H |
| 505 | 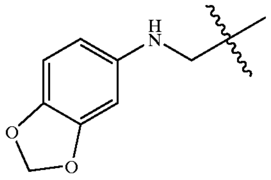 | CH | CH | H |
| 506 | 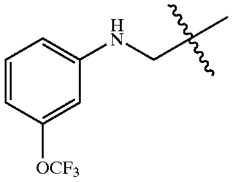 | CH | CH | H |
| 507 | 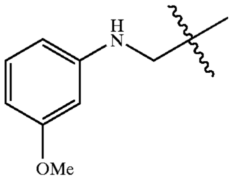 | CH | CH | H |
| 508 | 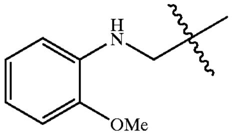 | CH | CH | H |
| 509 | 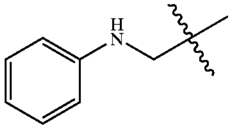 | CH | CH | H |
| 510 | 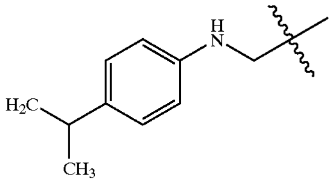 | CH | CH | H |
| 511 | 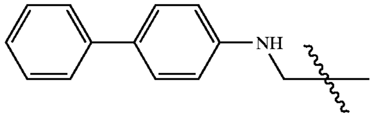 | CH | CH | H |
| 512 | 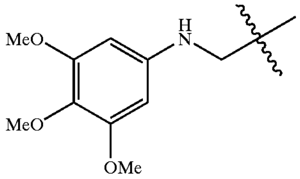 | CH | N | H |

-continued
| Cpd | W | Y | Z | $R^6$ |
|---|---|---|---|---|
| 516 | Br— | CH | CH | $CH_2$ |
| 517 | 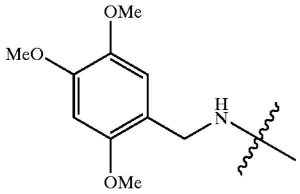 | CH | CH | $CH_3$ |
| 518 | 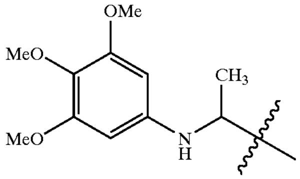 | CH | CH | $CH_3$ |
| 519 | 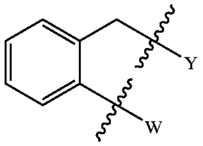 | CH | CH | H |
| 520 | 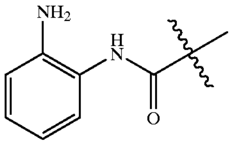 | CH | CH | H |
| 521 | 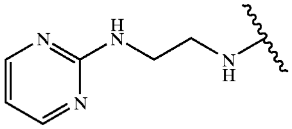 | N | CH | H |
| 522 | 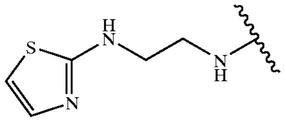 | N | CH | H |
| 523 | 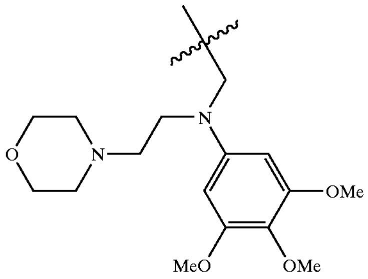 | CH | CH | H |
| 524 | 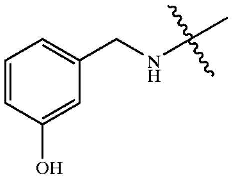 | N | CH | H |

-continued
| Cpd | W | Y | Z | $R^6$ |
|---|---|---|---|---|
| 525 | 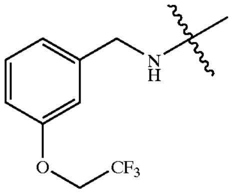 | N | CH | H |
| 526 | 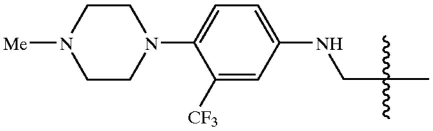 | CH | CH | H |
| 527 | 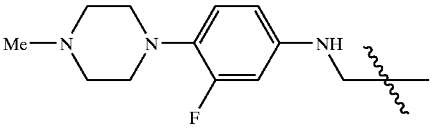 | CH | CH | H |
| 528 | 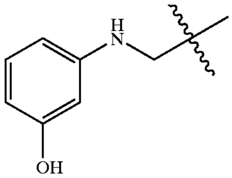 | CH | CH | H |
| 529 | 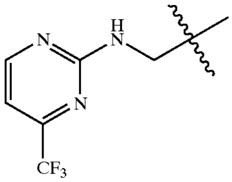 | CH | CH | H |
| 530 | 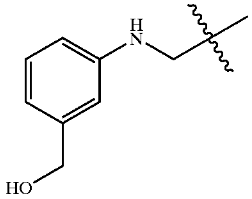 | CH | CH | H |
| 531 | 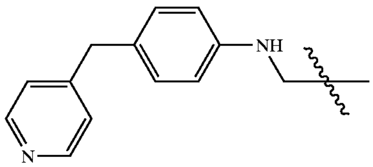 | CH | CH | H |
| 532 | 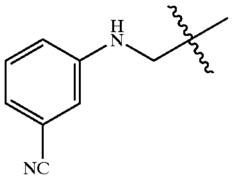 | CH | CH | H |

-continued
| Cpd | W | Y | Z | $R^6$ |
|---|---|---|---|---|
| 533 | 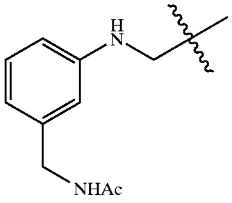 | CH | CH | H |
| 534 | 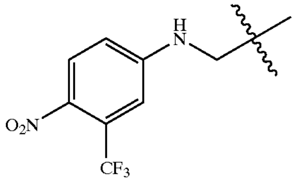 | CH | CH | H |
| 535 | 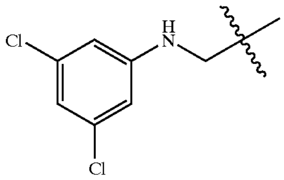 | CH | CH | H |
| 536 | 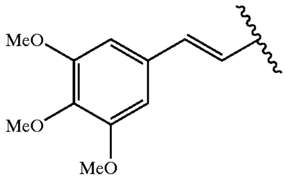 | CH | CH | H |
| 537 | 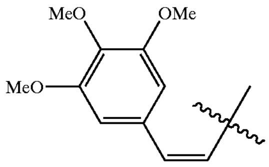 | CH | CH | H |
| 538 | 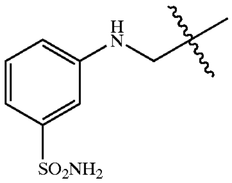 | CH | CH | H |
| 539 | 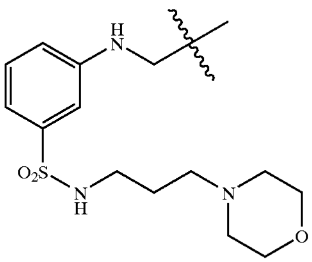 | CH | CH | H |

-continued
| Cpd | W | Y | Z | $R^6$ |
| --- | --- | --- | --- | --- |
| 540 | 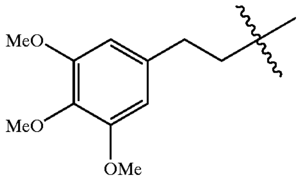 | CH | CH | H |
| 541 | 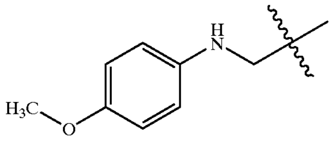 | CH | CH | H |
| 542 | 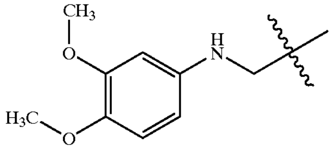 | CH | CH | H |
| 543 | 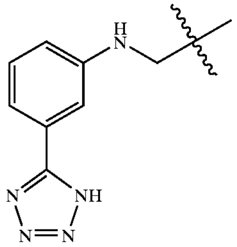 | CH | CH | H |
| 544 | 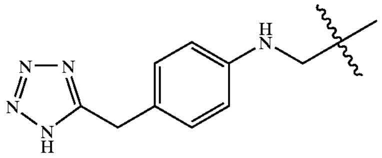 | CH | CH | H |
| 545 | 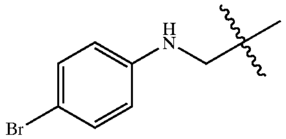 | CH | CH | H |
| 546 | 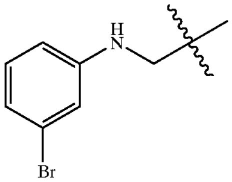 | CH | CH | H |
| 547 | 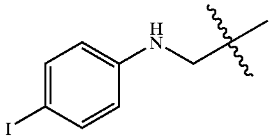 | CH | CH | H |

-continued
| Cpd | W | Y | Z | R6 |
|---|---|---|---|---|
| 548 | 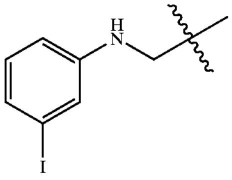 | CH | CH | H |
| 549 | 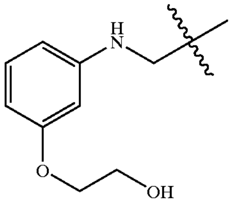 | CH | CH | H |
| 550 | 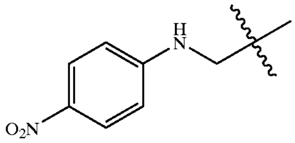 | CH | CH | H |
| 551 | 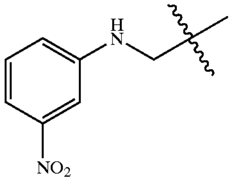 | CH | CH | H |
| 552 | 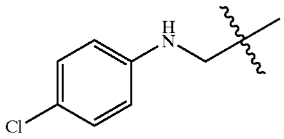 | CH | CH | H |
| 553 | 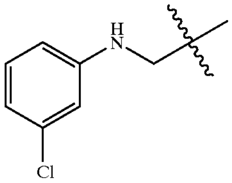 | CH | CH | H |
| 554 | 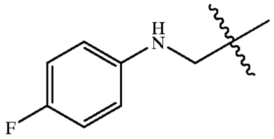 | CH | CH | H |
| 555 | 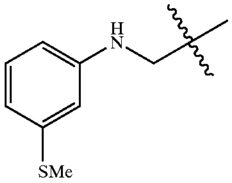 | CH | CH | H |

-continued
| Cpd | W | Y | Z | $R^6$ |
|---|---|---|---|---|
| 556 | 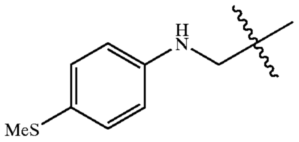 | CH | CH | H |
| 557 | 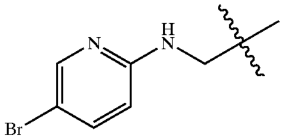 | CH | CH | H |
| 558 | 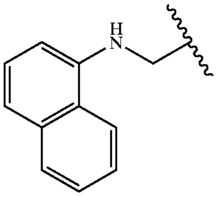 | CH | CH | H |
| 559 | 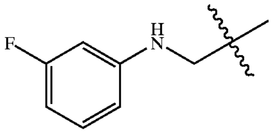 | CH | CH | H |
| 560 | 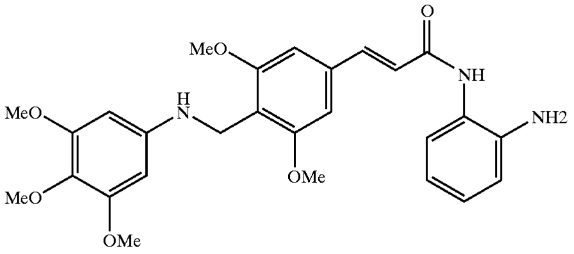 | | | |
| 561 | 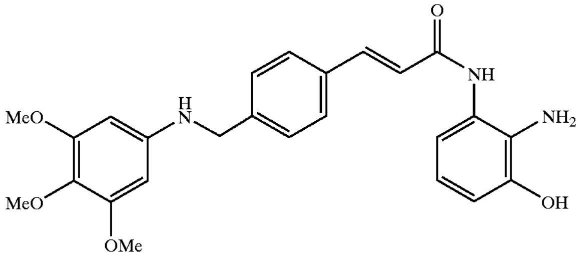 | | | |
| 562 | 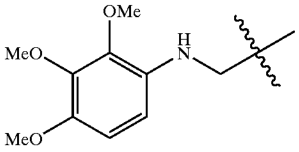 | CH | CH | H |

-continued
| Cpd | W | Y | Z | $R^6$ |
|---|---|---|---|---|
| 563 | 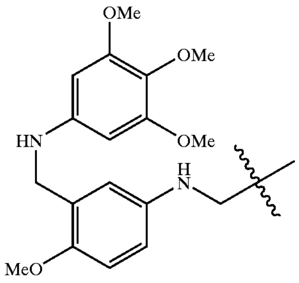 | CH | CH | H |
| 564 | 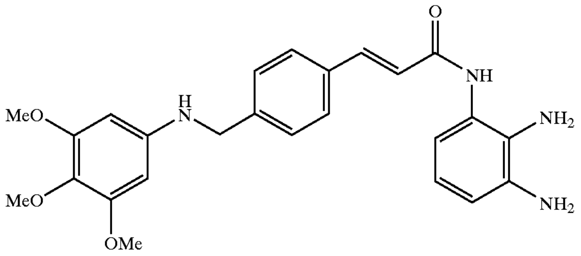 | | | |
| 565 | 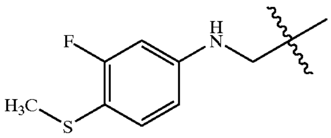 | CH | CH | H |
| 566 | 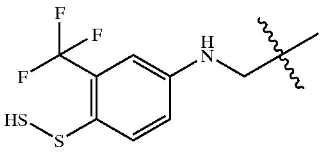 | CH | CH | H |
| 567 | 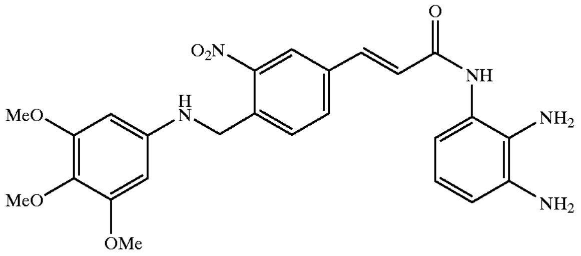 | | | |
| 568 | 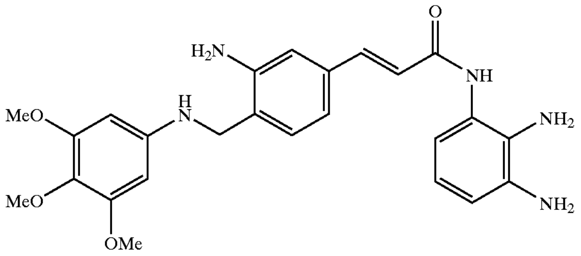 | | | |

-continued

| Cpd | W | Y | Z | $R^6$ |
|---|---|---|---|---|
| 569 | 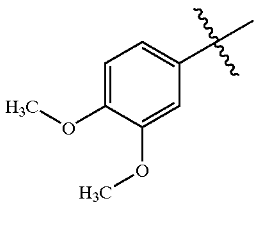 | CH | N | H |
| 570 | 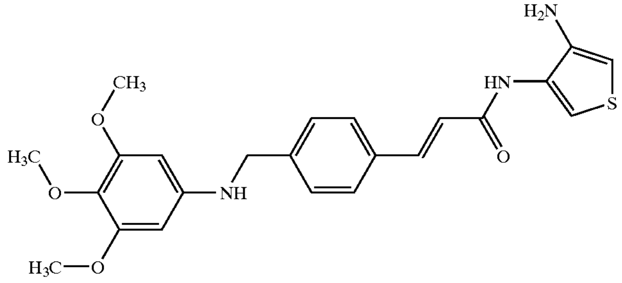 | | | |

Embodiment 7. In a preferred embodiment, the compounds of the invention comprise compounds of the formula (2b):

(2b)

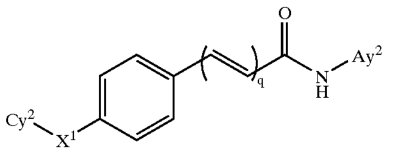

and pharmaceutically acceptable salts thereof, wherein $Ay^2$ is phenyl or thienyl, each substituted at the ortho position with —$NH_2$ or —OH and each further optionally substituted with one to three substituents independently selected from —$NH_2$, —OH, and halo;

q is 0 or 1;

$X^1$ is selected from —$CH_2$—, —NH—$CH_2$—, and —S—$CH_2$—;

$Cy^2$ is monocyclic or fused bicyclic aryl or heteroaryl optionally substituted with one to three substituents selected from $CH_3$—, $CH_3O$—, phenyl optionally substituted with one to three $CH_3O$—, morphylinyl, morphylinyl-$C_1$–$C_3$-alkoxy, cyano, and $CH_3C(O)NH$—;

provided that when $Cy^2$ is naphthyl, $X^1$ is —$CH_2$—, and q is 0 or 1, $Ay^2$ is not o-hydroxyphenyl.

Preferably in the compounds according to embodiment 7, $Ay^2$ is selected from:

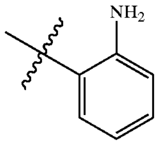,
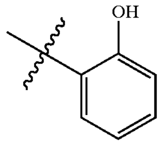,

-continued

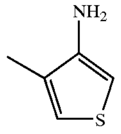
and
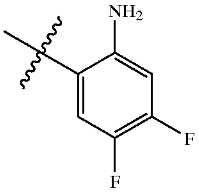
;

Preferably in the compounds according to embodiment 7, $Cy^2$ is phenyl, pyridinyl, pyrimidinyl, benzimidazolyl, benzothiazolyl, thienyl, tetrahydroquinozolinyl, or 1,3-dihydroquinazoline-2,4-dione, each optionally substituted with one to three $CH_3O$—. More preferably, $Cy^2$ is phenyl substituted with one to three $CH_3O$—.

Embodiment 8. In a further embodiment, the novel inhibitors of histone deacetylase are represented by formula (3):

(3)

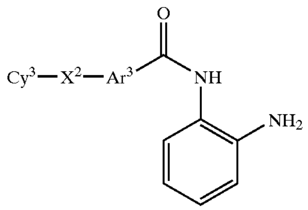

and pharmaceutical salts thereof, wherein $Ar^3$ is arylene or heteroarylene, either of which optionally is substituted;

$Cy^3$ is cycloalkyl, aryl, heteroaryl, or heterocyclyl, each of which optionally is substituted, and each of which optionally is fused to one or more aryl or heteroaryl rings, or to one or more saturated or partially unsaturated cycloalkyl or heterocyclic rings, each of which rings optionally is substituted;

provided that when $Cy^3$ is a cyclic moiety having —C(O)—, —C(S)—, —S(O)—, or —$S(O)_2$— in the ring, then $Cy^3$ is not additionally substituted with a group comprising an aryl or heteroaryl ring; and $X^2$ is selected from the group consisting of a chemical bond, $L^3$, $W^1$-$L^3$, $L^3$-$W^1$, $W^1$-$L^3$-$W^1$, and $L^3$-$W^1$-$L^3$, wherein $W^1$, at each occurrence, is S, O, or N($R^9$), where $R^9$ is selected from the group consisting of hydrogen, alkyl, aryl, and aralkyl; and $L^3$ is $C_1$–$C_4$ alkylene, $C_2$–$C_4$ alkenylene, or $C_2$–$C_4$ alkynylene;

provided that $X^2$ does not comprise a —C(O)—, —C(S)—, —S(O)—, or —$S(O)_2$— group; and further provided that when $Cy^3$ is pyridine, then $X^2$ is $L^3$, $W^1$-$L^3$, or $L^3$-$W^1$.

Preferably in the compounds according to embodiment 8, $X^2$ is selected from the group consisting of $L^3$, $W^1$-$L^3$, $L^3$-$W^1$, $W^1$-$L^3$-$W^1$, and $L^3$-$W^1$-$L^3$.

Preferably in the compounds according to embodiment 8, when $X^2$ is a chemical bond, then $Ar^3$ is not

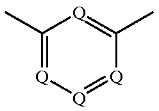

or

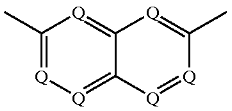

and $Cy^3$ is not the radical of a substituted or unsubstituted diazepine or benzofuran.

In some embodiments of the compounds according to embodiment 8, Q at each occurrence is C($R^8$), where $R^8$ is selected from the group consisting of hydrogen, alkyl, aryl, aralkyl, alkoxy, amino, nitro, halo, haloalkyl, and haloalkoxy. In some other embodiments, from one to about three variables Q are nitrogen. In some preferred embodiments, $Ar^3$ is selected from the group consisting of phenylene, pyridylene, thiazolylene, and quinolylene.

In some embodiments of the compounds according to embodiment 8, $X^2$ is a chemical bond. In other embodiments, $X^2$ is a non-cyclic hydrocarbyl. In some such embodiments, $X^2$ is alkylene, preferably methylene or ethylene. In other such embodiments, $X^2$ is alkenylene or alkynylene. In still other such embodiments, one carbon in the hydrocaryl chain is replaced with —NH— or —S—. In some preferred embodiments, $X^2$ is $W^1$-$L^3$-$W^1$ and $W^1$ is —NH— or —N($CH_3$)—.

Embodiment 9. In some embodiments of the compounds according to embodiment 8, $Cy^3$ is cycloalkyl, preferably cyclohexyl. In other embodiments, $Cy^3$ is aryl or heteroaryl, e.g., phenyl, pyridyl, pyrimidyl, imidazolyl, thiazolyl, oxadiazolyl, quinolyl, or fluorenyl, each of which optionally is substituted and optionally is fused to one or more aryl rings. In some embodiments, the cyclic moiety of $Cy^3$ is fused to a benzene ring. In some embodiments, $Cy^3$ has from one to three substituents independently selected from the group consisting of alky, alkoxy, aryl, aralkyl, amino, halo, haloalkyl, and hydroxyalkyl. Examples of preferred substituents include methyl, methoxy, fluoro, trifluoromethyl, amino, nitro, aminomethyl, hydroxymethyl, and phenyl. Some other preferred substituents have the formula —$K^1$—N(H)($R^{10}$), wherein $K^1$ is a chemical bond or $C_1$–$C_4$ alkylene;

$R^{10}$ is selected from the group consisting of Z' and -$Ak^2$-Z', wherein $Ak^2$ is $C_1$–$C_4$ alkylene; and Z' is cycloalkyl, aryl, heteroaryl, or heterocyclyl, each of which optionally is substituted, and each of which optionally is fused to one or more aryl or heteroaryl rings, or to one or more saturated or partially unsaturated cycloalkyl or heterocyclic rings.

Examples of such preferred substituents according to embodiment 9 include

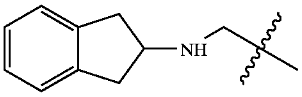

,

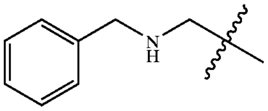

,

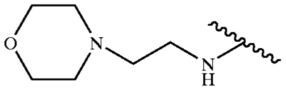

, and

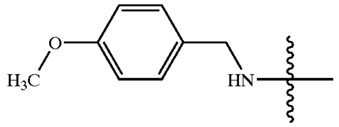

.

In some embodiments of the compounds according to embodiment 8, $Cy^3$ is heterocyclyl, e.g.,

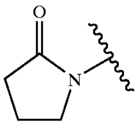

,

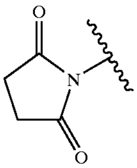

,

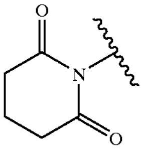

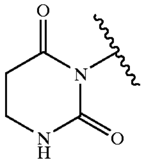

,

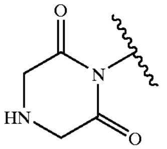

,

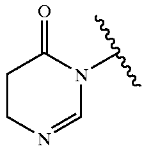

,

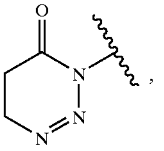

, and

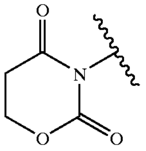

, each of which optionally is substituted and optionally is fused to one or more aryl rings. In some embodiments, the heterocycle of $Cy^3$ is fused to a benzene ring.

Preferably in the compounds of embodiment 8, when $Ar^4$ is quinoxalinylene, then $X^3$ is not —CH(OH)—.

In another preferred embodiment, $Ar^3$ is

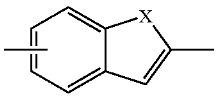

wherein X is —$CH_2$—, —NH—, O, or S. Preferably $Ar^3$ is

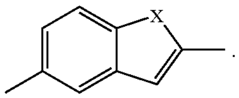

and X is S or O.

Embodiment 10. In a preferred embodiment, the novel histone deacetylase inhibitors of the invention are those according to embodiment 3wherein $Ay^2$ is ortho-anilinyl;

q is 0; and $X^1$ is $M^1$-$L^2$-$M^1$ or $L^2$-$M^2$-$L^2$.

In a preferred embodiment of the compounds according to embodiment 10, $Ar^2$ is aryl or heteroaryl; and $Cy^2$-$X^1$— is collectively selected from the group consisting of a) $A_1$-$L_1$-$B_1$-, wherein $A_1$ is an optionally substituted aryl, optionally substituted heteroaryl or optionally substituted heterocyclyl; wherein $L_1$ is —$(CH_2)_{0-1}NH(CH_2)_{0-1}$—, —NHC(O)—, or —$NHCH_2$—; and wherein $B_1$ is phenyl or a covalent bond;

b) $A_2$-$L_2$-$B_2$-, wherein $A_2$ is $CH_3(C{=}CH_2)$—, optionally substituted cycloalkyl, optionally substituted alkyl, or optionally substituted aryl; wherein $L_2$ is —C≡C—; and wherein $B_2$ is a covalent bond;

c) $A_3$-$L_3$-$B_3$-, wherein $A_3$ is an optionally substituted aryl, optionally substituted heteroaryl or optionally substituted heterocyclyl; wherein $L_3$ is a covalent bond; and wherein $B_3$ is —$CH_2NH$—;

d) $A_4$-$L_4$-$B_4$-, wherein $A_4$ is an optionally substituted aryl; wherein $L_4$ is —$NHCH_2$—; and wherein $B_4$ is a thienyl group;

e) $A_5$-$L_5$-$B_5$-, wherein $A_5$ is an optionally substituted heteroaryl or optionally substituted heterocyclyl; wherein $L_5$ is a covalent bond; and wherein $B_5$ is —$SCH_2$—;

f) morpholinyl-$CH_2$—, g) optionally substituted aryl;

h) $A_6$-$L_6$-$B_6$-, wherein $A_6$ is an optionally substituted aryl, optionally substituted heteroaryl or optionally substituted heterocyclyl; wherein $L_6$ is a covalent bond; and wherein $B_6$ is —$NHCH_2$—;

i) $A_7$-$L_7$-$B_7$-, wherein $A_7$ is an optionally substituted heteroaryl or optionally substituted heterocyclyl; wherein $L_7$ is a covalent bond; and wherein $B_7$ is —$CH_2$—;

j) aptionally substituted heteroaryl or optionally substituted heterocyclyl;

k) $A_8$-$L_8$-$B_8$-, wherein $A_8$ is optionally substituted phenyl; wherein $L_8$ is a covalent bond; and wherein $B_8$ is —O—;

l) $A_9$-$L_9$-$B_9$-, wherein $A_9$ is an optionally substituted aryl; wherein $L_9$ is a covalent bond; and wherein $B_9$ is a furan group;

m) $A_{10}$-$L_{10}$-$B_{10}$-, wherein $A_{10}$ is an optionally substituted heteroaryl or optionally substituted heterocyclyl; wherein $L_{10}$ is —$CH(CH_2CH_3)$—; and wherein $B_{10}$ is —$NHCH_2$—;

n) $A_{11}$-$L_{11}$-$B_{11}$-, wherein $A_{11}$ is an optionally substituted heteroaryl or optionally substituted heterocyclyl; wherein $L_{11}$ is a covalent bond; and wherein $B_{11}$ is —$OCH_2$—;

o) $A_{12}$-$L_{12\text{-}B12}$-, wherein $A_{12}$ is an optionally substituted aryl, optionally substituted heteroaryl or optionally substituted heterocyclyl; wherein $L_{12}$ is —NHC(O)—; and wherein $B_{12}$ is —N(optionally substituted aryl)$CH_2$—;

p) $A_{13}$-$L_{13}$-$B_{13}$-, wherein $A_{12}$ is an optionally substituted aryl, optionally substituted heteroaryl or optionally substituted heterocyclyl; wherein $L_{13}$ is a covalent bond; and wherein $B_{13}$ is —NHC(O)—;

q) $A_{14}$-$L_{14}$-$B_{14}$-, wherein $A_{14}$ is an optionally substituted aryl, optionally substituted heteroaryl or optionally substituted heterocyclyl; wherein $L_{14}$ is —NHC(O)(optionally substituted heteroaryl); and wherein $B_{14}$ is —S—S—;

r) $F_3CC(O)NH$—;

s) $A_{15}$-$L_{15}$-$B_{15}$-, wherein $A_{15}$ is an optionally substituted aryl, optionally substituted heteroaryl or optionally substituted heterocyclyl; wherein $L_{15}$ is —$(CH_2)_{0-1}NH$(optionally substituted heteroaryl)-; and wherein $B_{15}$ is —$NHCH_2$—;

t) $A_{16}$-$L_{16}$-$B_{16}$-, wherein $A_{16}$ is an optionally substituted aryl, optionally substituted heteroaryl or optionally substituted heterocyclyl; wherein $L_{16}$ is a covalent bond; and wherein $B_{16}$ is —N(optionally substituted alkyl)$CH_2$—; and u) $A_{16}$-$L_{16}$-$B_{16}$-, wherein $A_{16}$ is an optionally substituted aryl, optionally substituted heteroaryl or optionally substituted heterocyclyl; wherein $L_{16}$ is a covalent bond; and wherein $B_{16}$ is -(optionally substituted aryl-$CH_2)_2$—N—.

In another preferred embodiment of the compounds according to embodiment 10, $Cy^2$-$X^1$— is collectively selected from the group consisting of a) $D_1$-$E_1$-$F_1$-, wherein $D_1$ is an optionally substituted aryl, optionally substituted heteroaryl or optionally substituted heterocyclyl; wherein $E_1$ is —$CH_2$— or a covalent bond; and wherein. $B_1$ is a covalent bond;

b) $D_2$-$E_2$-$F_2$-, wherein $D_2$ is an optionally substituted aryl, optionally substituted heteroaryl or optionally substituted heterocyclyl; wherein $E_2$ is —$NH(CH_2)_{0-2}$—; and wherein $F_2$ is a covalent bond;

c) $D_3$-$E_3$-$F_3$-, wherein $D_3$ is an optionally substituted aryl, optionally substituted heteroaryl or optionally substituted heterocyclyl; wherein $E_3$ is —$(CH_2)_{0-2}NH$—; and wherein $F_3$ is a covalent bond;

d) $D_4$-$E_4$-$F_4$-, wherein $D_4$ is an optionally substituted aryl, optionally substituted heteroaryl or optionally substituted heterocyclyl; wherein $E_4$ is —$S(CH_2)_{0-2}$—; and wherein $F_4$ is a covalent bond;

e) $D_5$-$E_5$-$F_5$-, wherein $D_5$ is an optionally substituted aryl, optionally substituted heteroaryl or optionally substituted heterocyclyl; wherein $E_5$ is —$(CH_2)_{0-2}S$—; and wherein $F_5$ is a covalent bond; and f) $D_6$-$E_6$-$F_6$-, wherein $D_6$ is an optionally substituted aryl, optionally substituted heteroaryl or optionally substituted heterocyclyl; wherein $E_6$ is —$NH(CH_2)_{0-2}NH$—; and wherein $F_6$ is a covalent bond.

Embodiment 11. In a preferred embodiment, the HDAC inhibitors of the invention comprise compounds of embodiment 3 having formula (3b):

(3b)
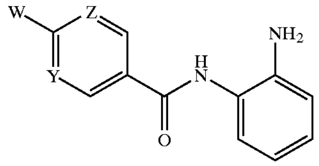
and pharmaceutically acceptable salts thereof, wherein Y and Z are independently N or CH and W is selected from the group consisting of:
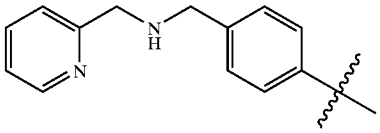
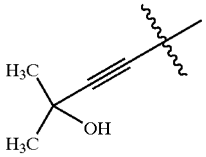
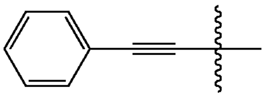
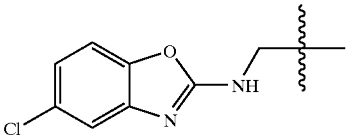
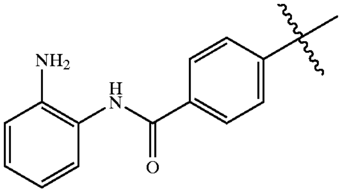
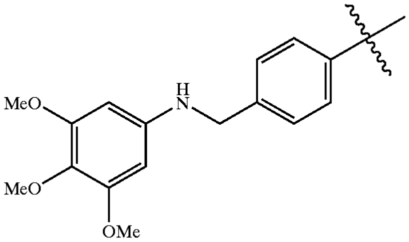
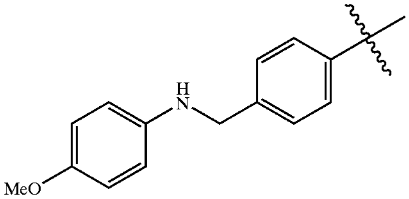
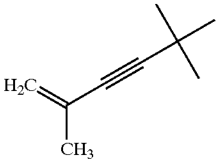
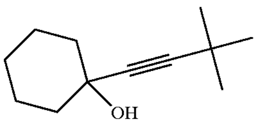
-continued
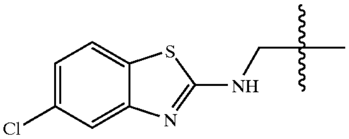
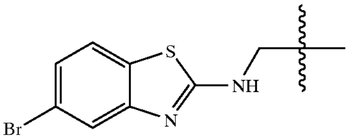
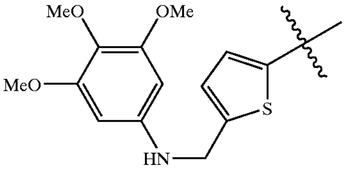
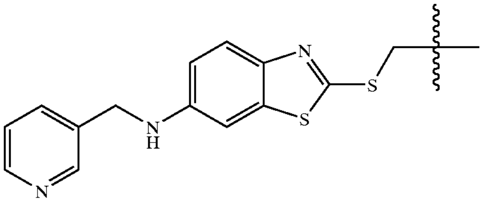
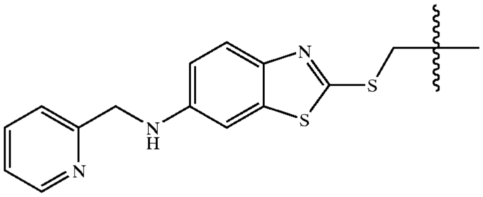
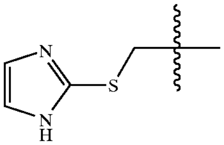
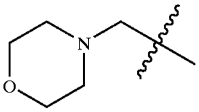
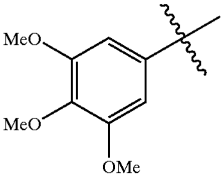
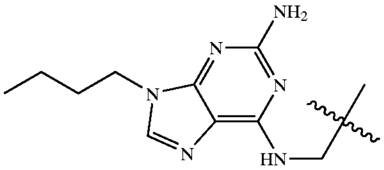
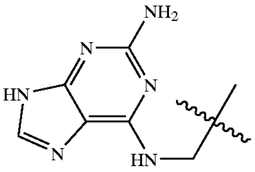
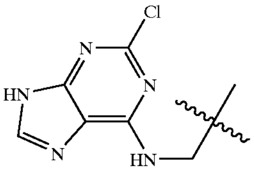
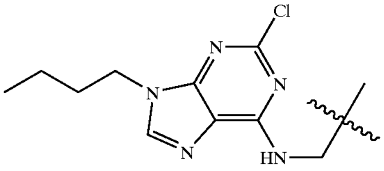

-continued
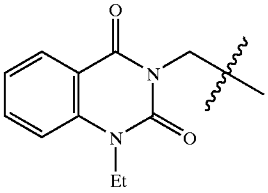
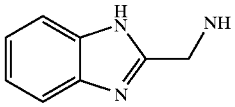
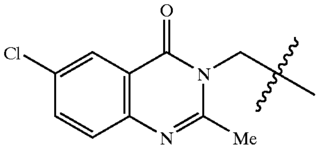
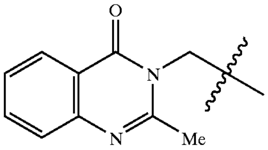
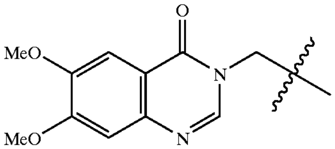
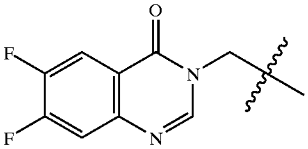
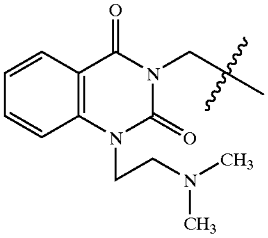
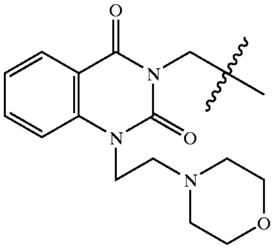
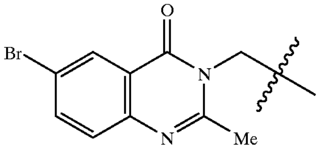
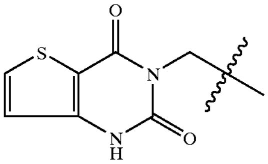
-continued
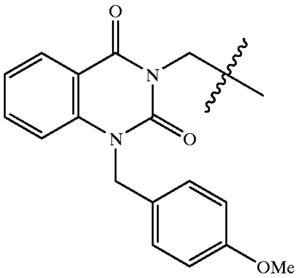
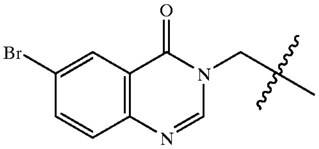
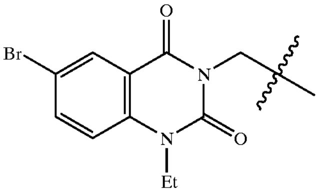
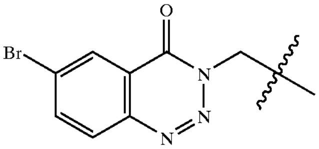
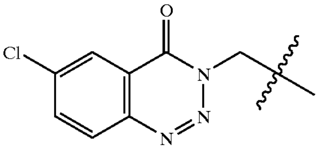
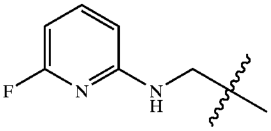
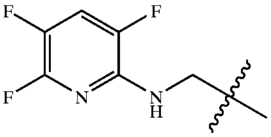
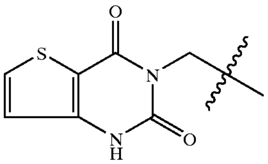
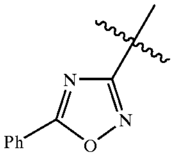
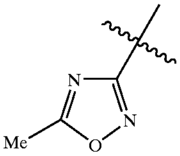
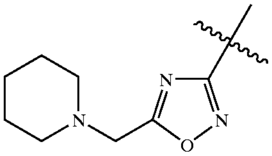
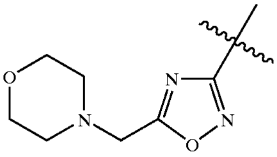

-continued
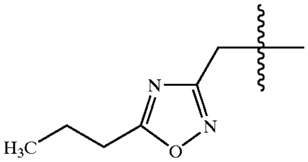
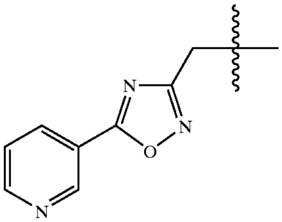
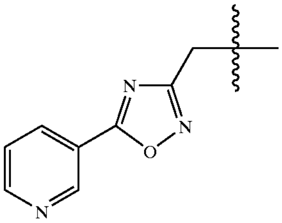
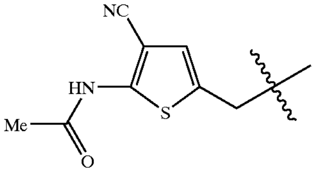
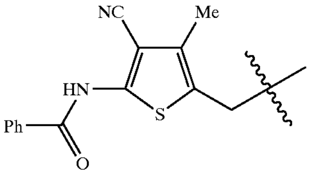
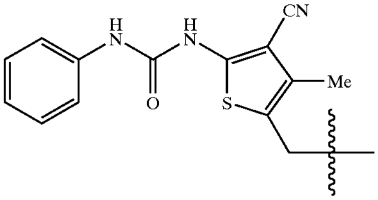
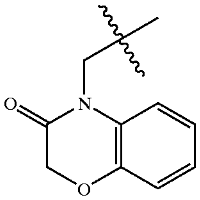
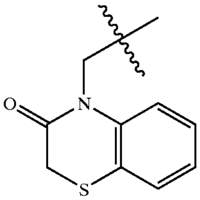
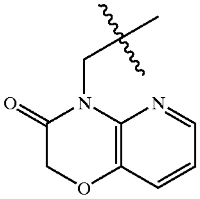
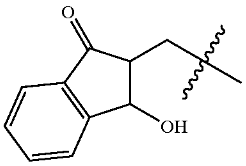
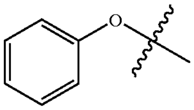
-continued
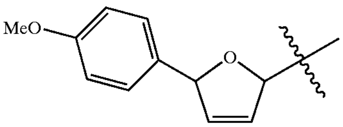
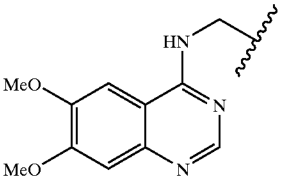
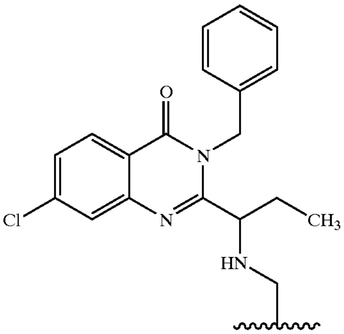
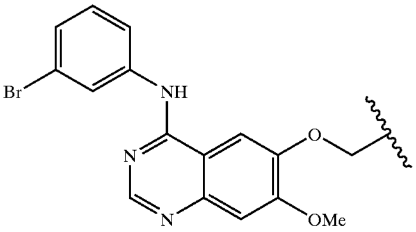
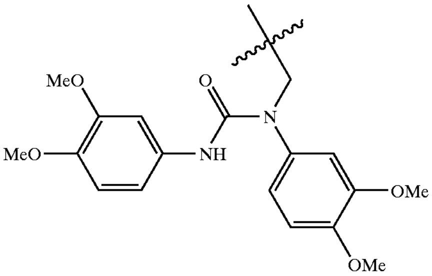
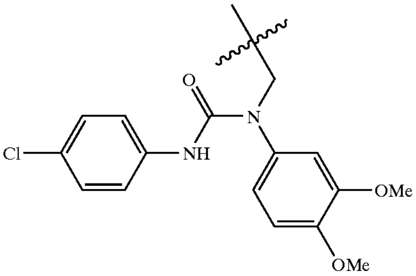
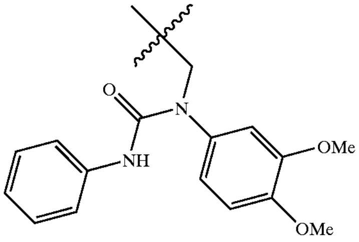

-continued
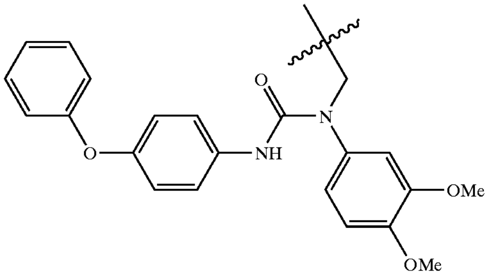
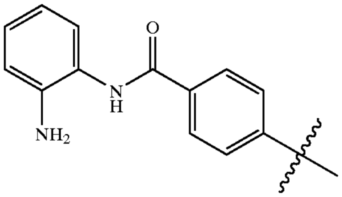
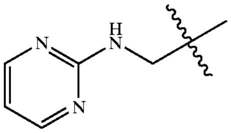
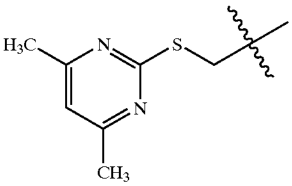
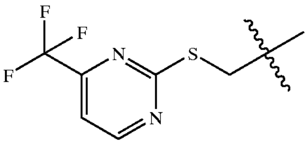
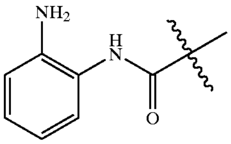
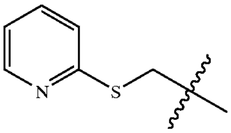
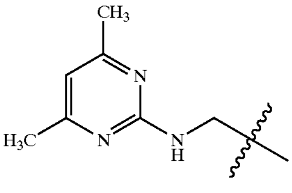
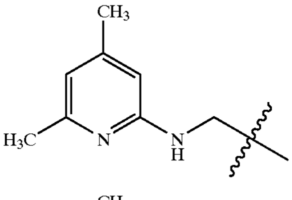
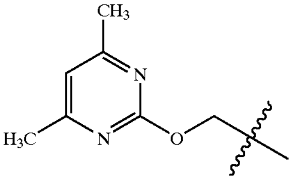
-continued
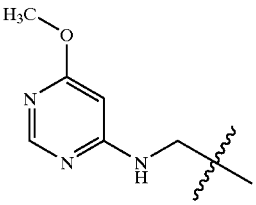
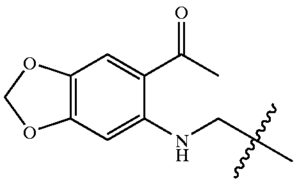
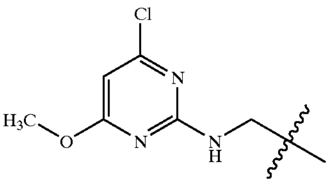
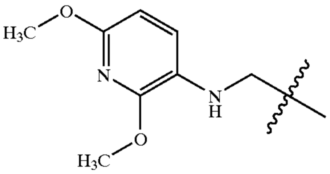
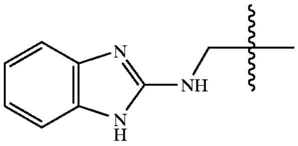
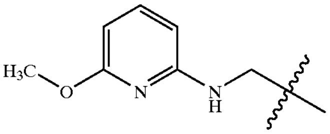
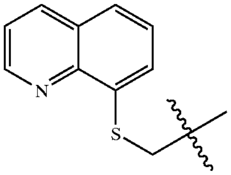
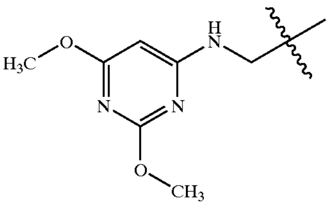
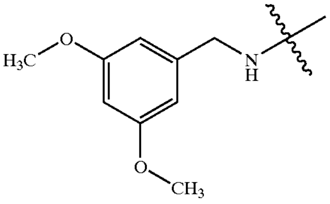

-continued
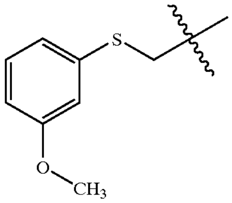
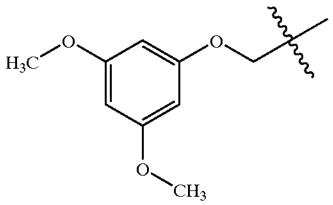
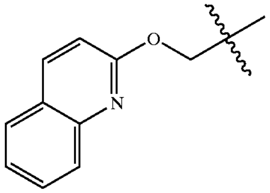
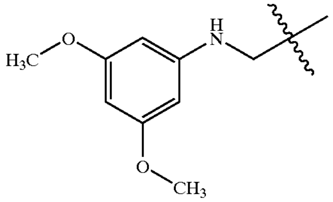
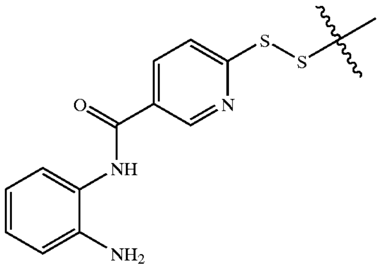
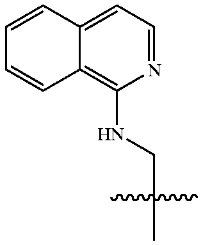
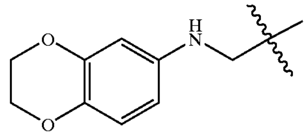
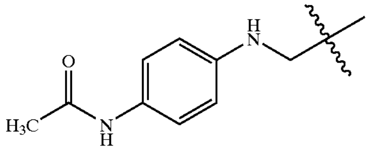
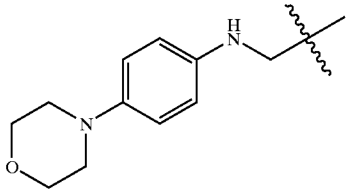
-continued
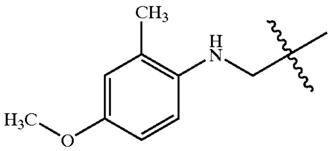
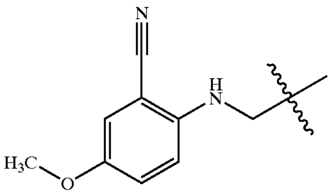
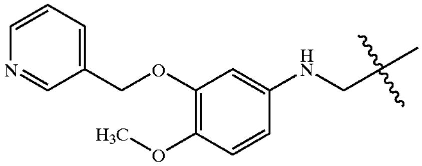
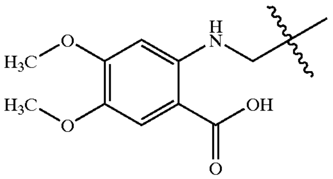
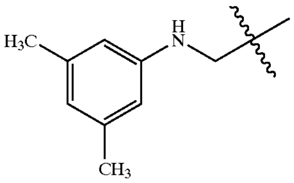
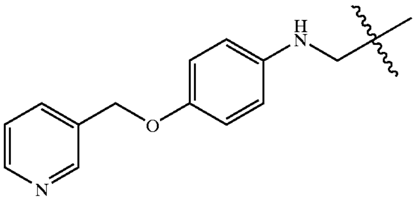
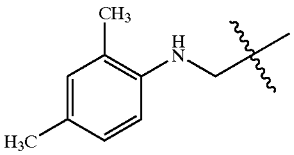
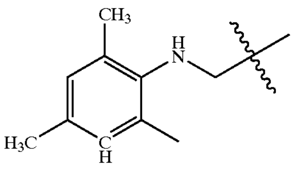
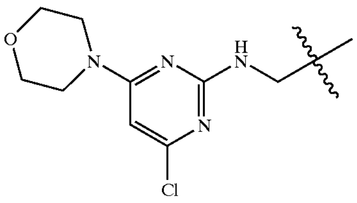

-continued
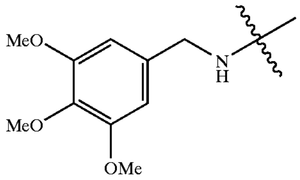
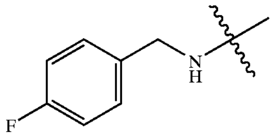
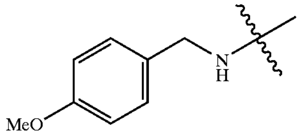
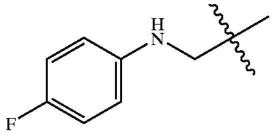
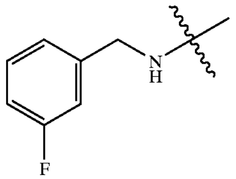
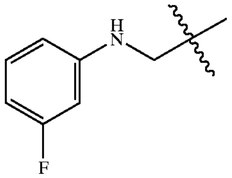
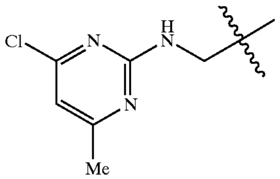
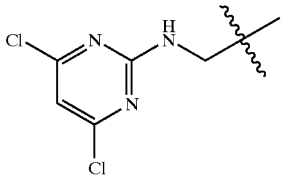
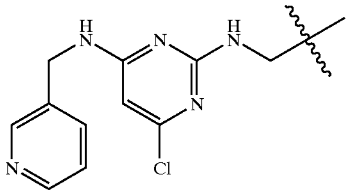
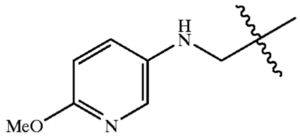
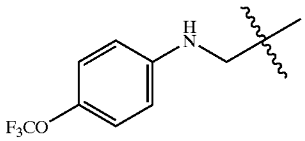
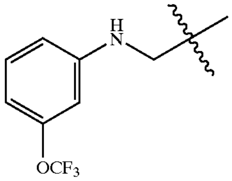
-continued
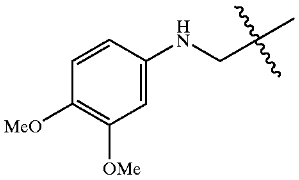
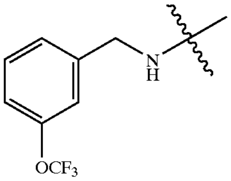
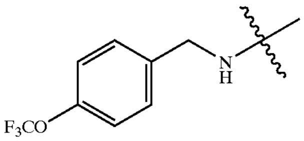
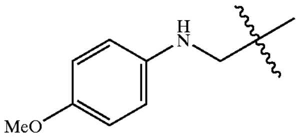
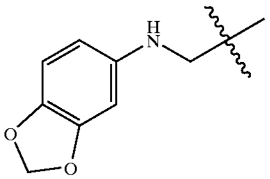
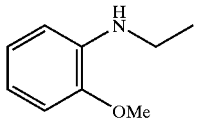
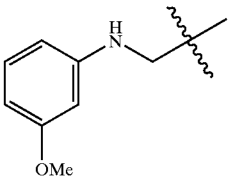
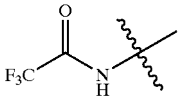
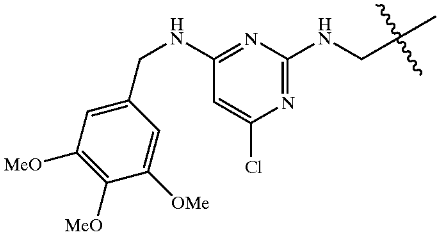
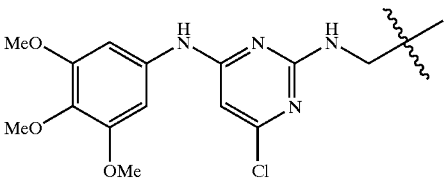
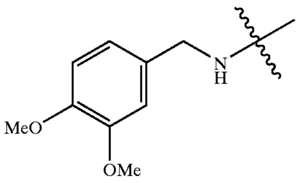

-continued
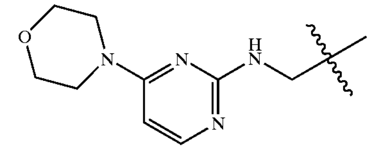
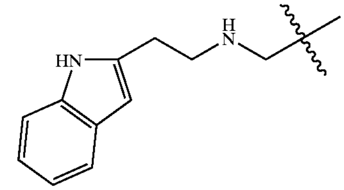
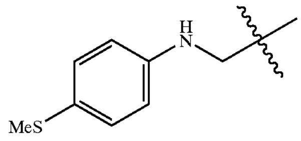
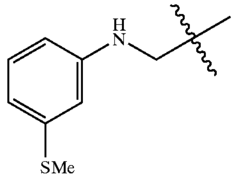
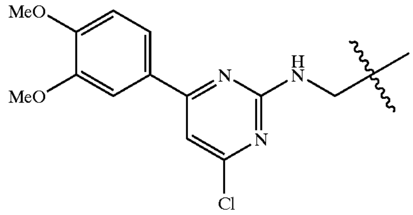
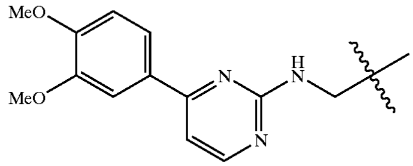
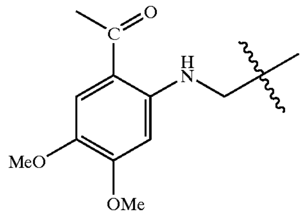
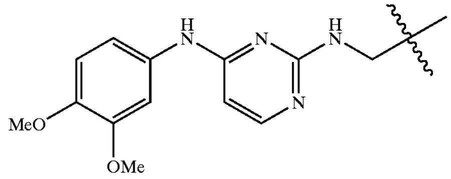
-continued
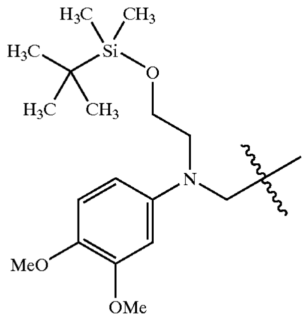
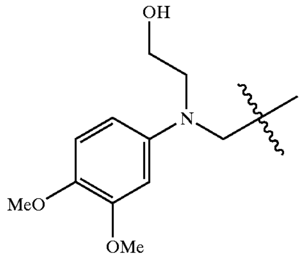
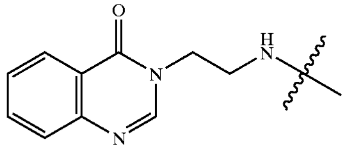
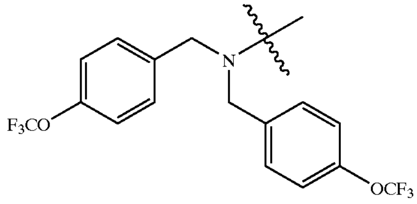
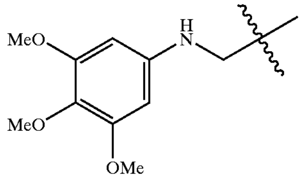
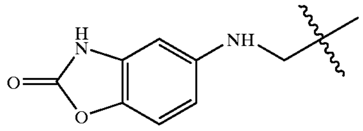
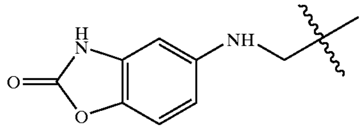
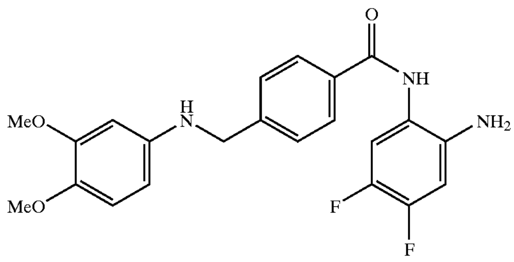

-continued
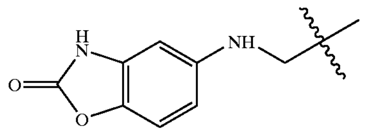
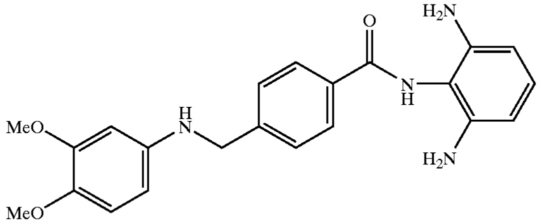
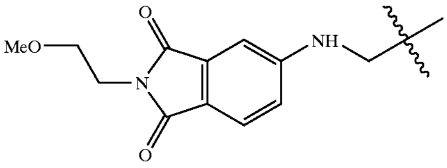
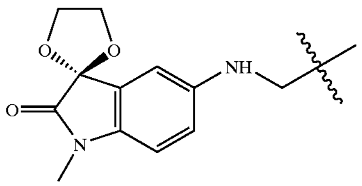
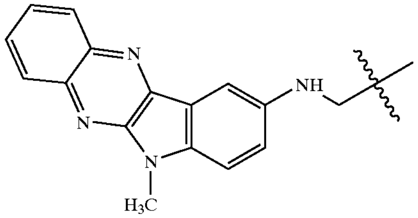
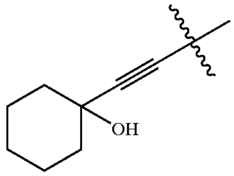
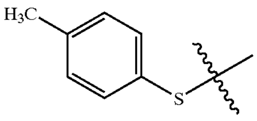
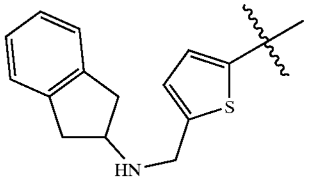
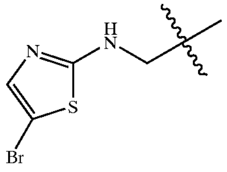
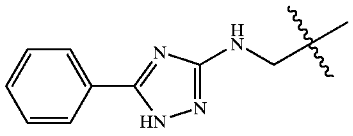
-continued
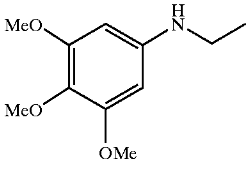
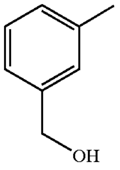
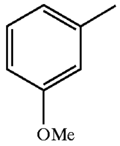
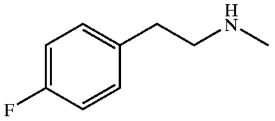
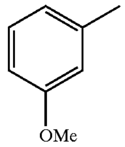
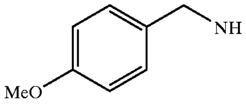
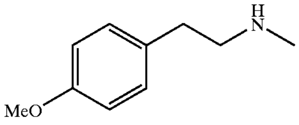
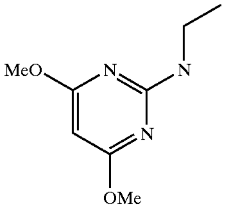
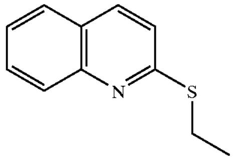
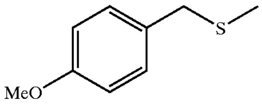
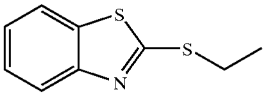
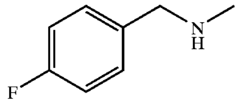
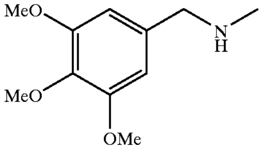
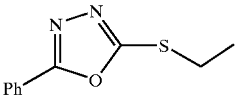
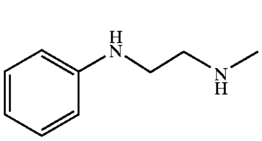
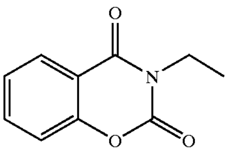
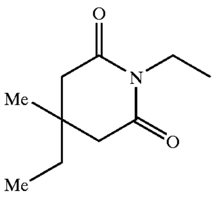
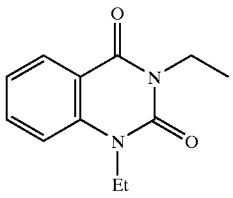
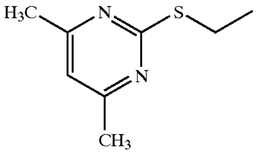

-continued
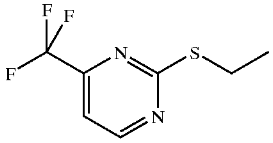
and
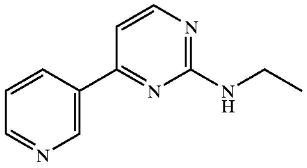
In a preferred embodiment of the compounds according to embodiment 11, the compounds comprise those wherein Y, Z and W are as defined below:
| Cpd | W | Y | Z |
|---|---|---|---|
| 164 | 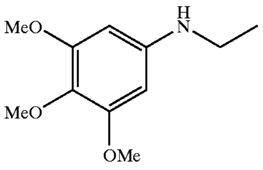 | CH | CH |
| 165 | 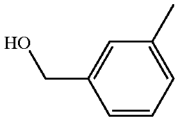 | N | CH |
| 166 | 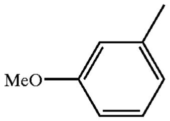 | CH | CH |
| 167 | 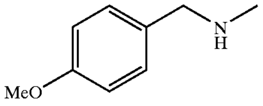 | CH | N |
| 168 | 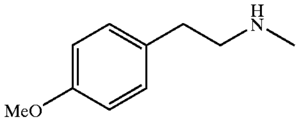 | CH | N |
| 169 | 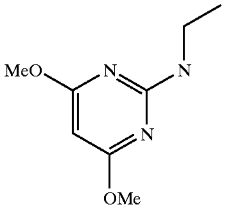 | CH | CH |
| 170 | 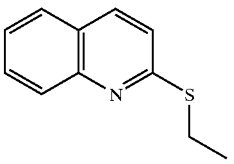 | CH | CH |
-continued
| Cpd | W | Y | Z |
|---|---|---|---|
| 171 | 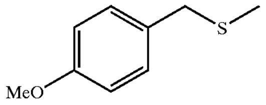 | N | CH |
| 172 | 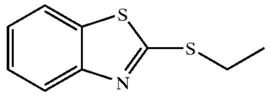 | CH | CH |
| 174 | 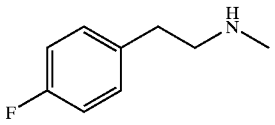 | CH | N |
| 175 | 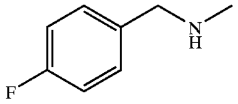 | CH | N |
| 176 | 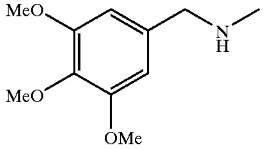 | CH | N |
| 177 | 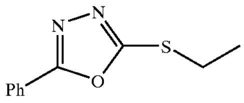 | CH | CH |
| 178 | 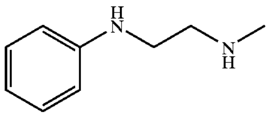 | N | CH |
| 179 | 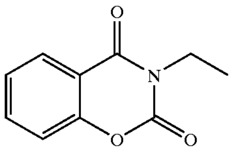 | CH | CH |
| 180 | 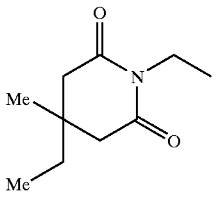 | CH | CH |
| 181 | 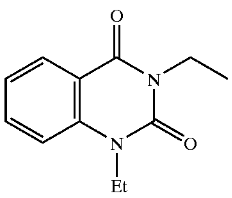 | CH | CH |

-continued
| Cpd | W | Y | Z |
| --- | --- | --- | --- |
| 182 | 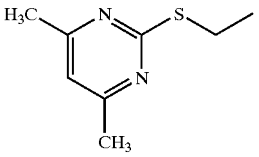 | CH | CH |
and
-continued
| Cpd | W | Y | Z |
| --- | --- | --- | --- |
| 183 | 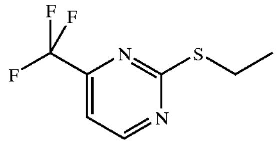 | CH | CH |
In another preferred embodiment of the compounds according to embodiment 11, the compounds comprise those wherein Y, Z and W are as defined below:
| Cpd | W | Y | Z |
| --- | --- | --- | --- |
| 187 | 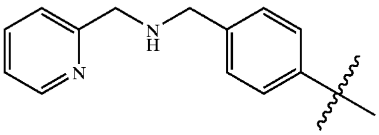 | CH | CH |
| 188 | 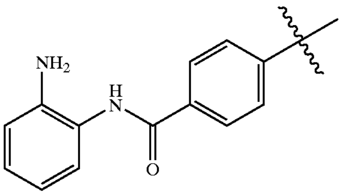 | CH | CH |
| 189 | 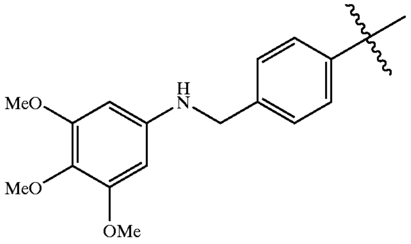 | CH | CH |
| 190 | 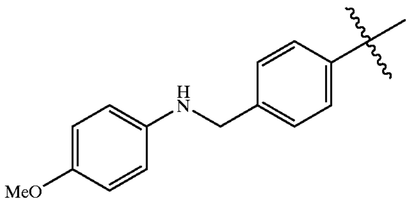 | CH | CH |
| 193 | 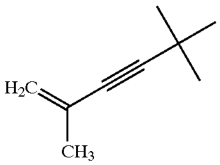 | CH | CH |
| 194 | 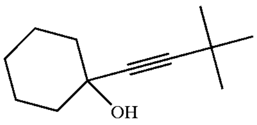 | CH | CH |

-continued
| Cpd | W | Y | Z |
|---|---|---|---|
| 195 | 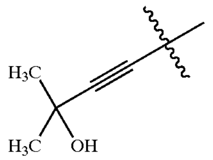 | CH | CH |
| 196 | 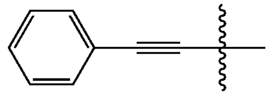 | CH | CH |
| 320 | 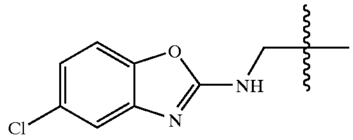 | CH | CH |
| 321 | 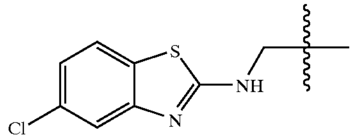 | CH | CH |
| 322 | 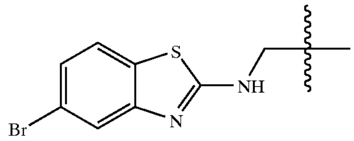 | CH | CH |
| 323 | 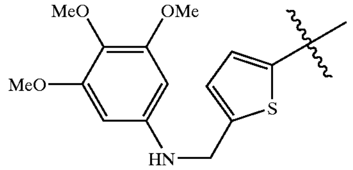 | CH | CH |
| 325 | 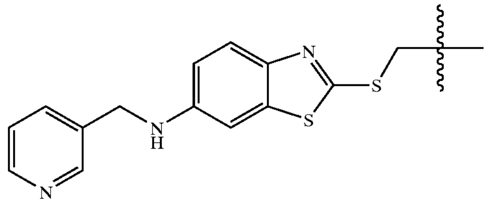 | CH | CH |
| 326 | 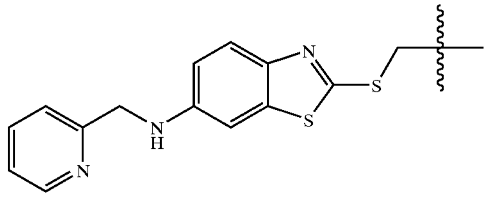 | CH | CH |
| 327 | 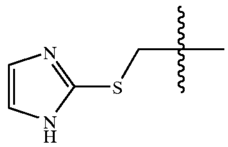 | CH | CH |

-continued
| Cpd | W | Y | Z |
|---|---|---|---|
| 328 | 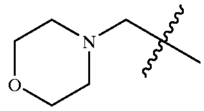 | CH | CH |
| 329 | 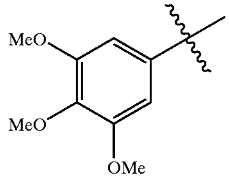 | CH | CH |
| 330 | 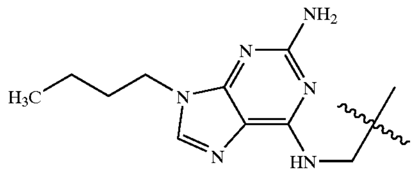 | CH | CH |
| 331 | 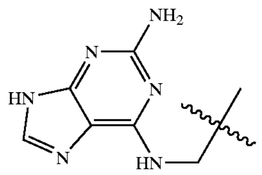 | CH | CH |
| 332 | 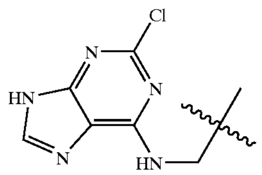 | CH | CH |
| 333 | 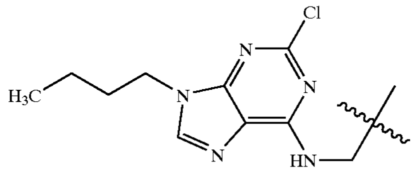 | CH | CH |
| 334 | 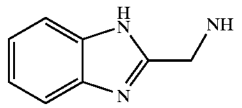 | CH | CH |
| 335 | 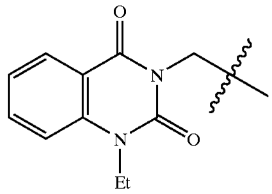 | CH | CH |
| 336 | 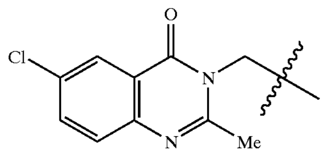 | CH | CH |

-continued
| Cpd | W | Y | Z |
|---|---|---|---|
| 337 | 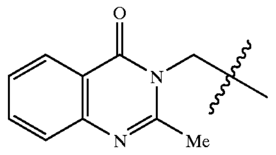 | CH | CH |
| 338 | 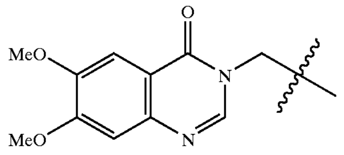 | CH | CH |
| 339 | 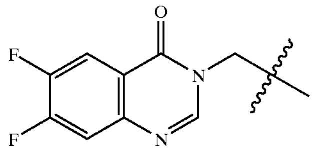 | CH | CH |
| 340 | 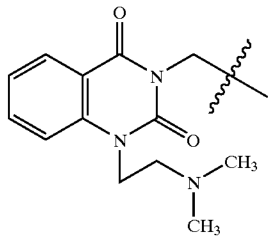 | CH | CH |
| 341 | 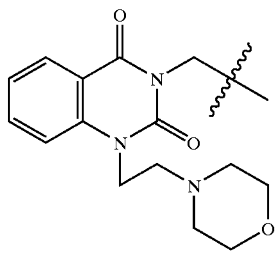 | CH | CH |
| 342 | 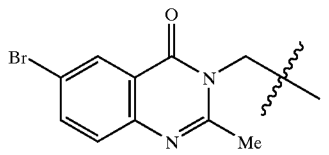 | CH | CH |
| 343 | 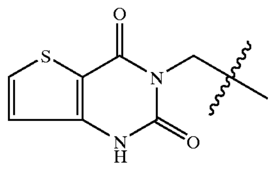 | CH | CH |
| 344 | 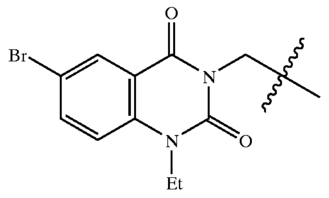 | CH | CH |

-continued
| Cpd | W | Y | Z |
| --- | --- | --- | --- |
| 345 | 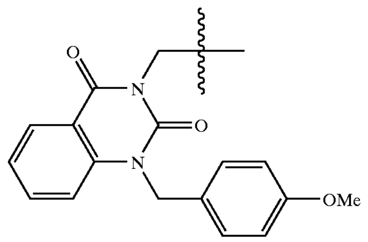 | CH | CH |
| 346 | 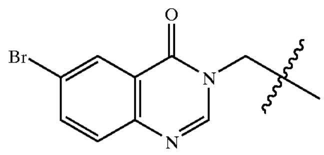 | CH | CH |
| 347 | 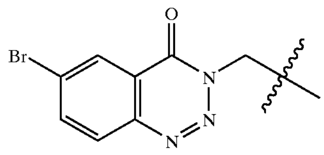 | CH | CH |
| 348 | 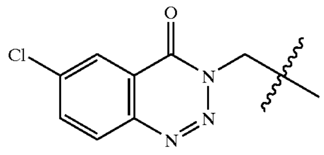 | CH | CH |
| 349 | 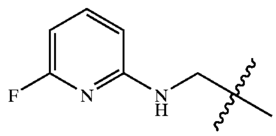 | CH | CH |
| 350 | 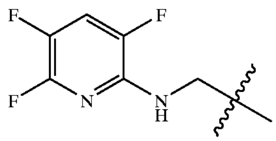 | CH | CH |
| 351 | 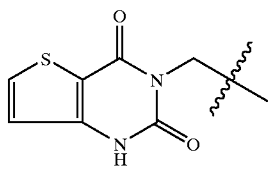 | CH | CH |
| 352 | 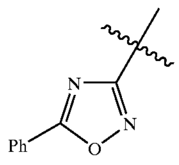 | CH | CH |
| 353 | 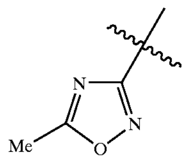 | CH | CH |

-continued
| Cpd | W | Y | Z |
|---|---|---|---|
| 354 | 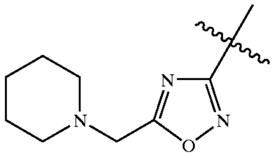 | CH | CH |
| 355 | 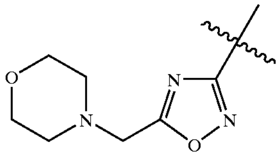 | CH | CH |
| 356 | 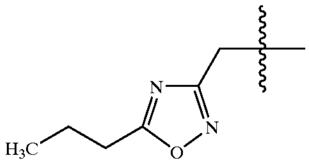 | CH | CH |
| 357 | 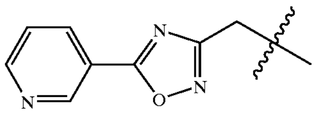 | CH | CH |
| 358 | 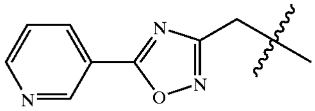 | CH | CH |
| 359 | 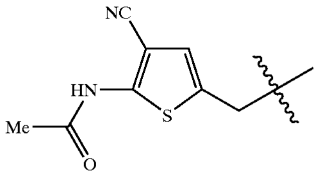 | CH | CH |
| 360 | 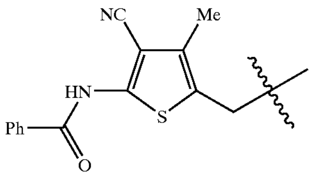 | CH | CH |
| 361 | 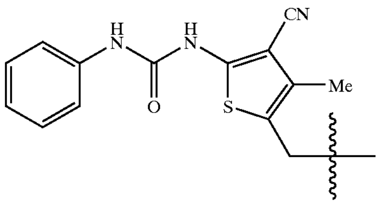 | CH | CH |
| 362 | 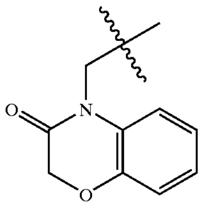 | CH | CH |

-continued
| Cpd | W | Y | Z |
| --- | --- | --- | --- |
| 363 | 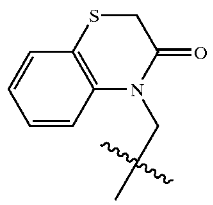 | CH | CH |
| 364 | 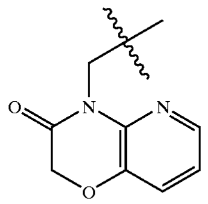 | CH | CH |
| 365 | 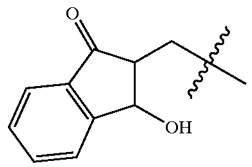 | CH | CH |
| 366 | 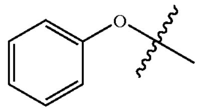 | CH | CH |
| 367 | 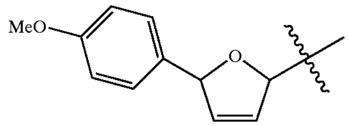 | CH | CH |
| 368 | 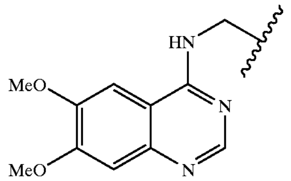 | CH | CH |
| 369 | 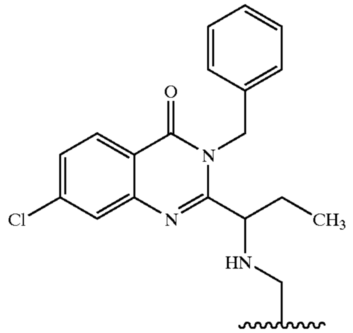 | CH | CH |

-continued
| Cpd | W | Y | Z |
|---|---|---|---|
| 370 | 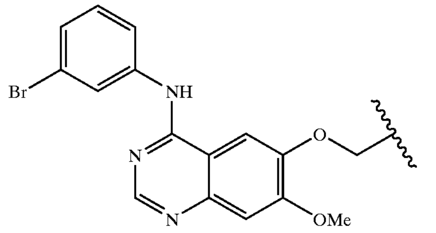 | CH | CH |
| 371 | 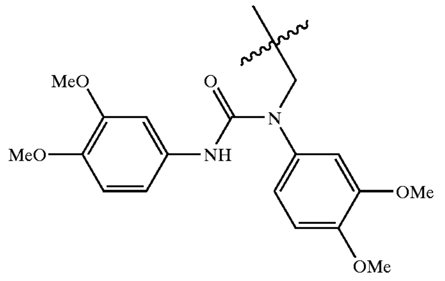 | CH | CH |
| 372 | 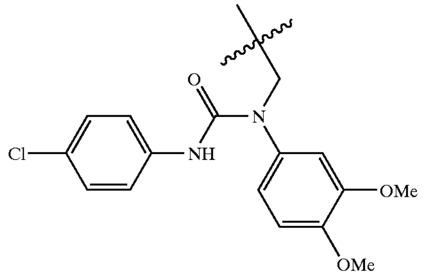 | CH | CH |
| 373 | 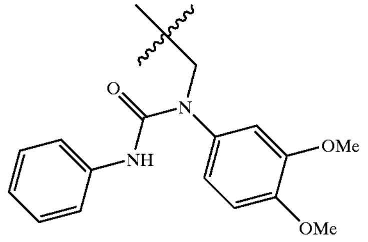 | CH | CH |
| 374 | 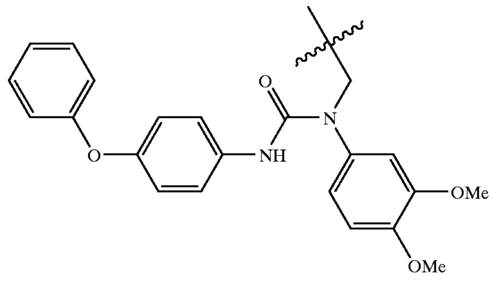 | CH | CH |
| 375 | 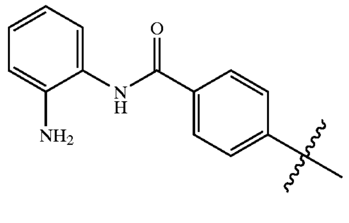 | CH | CH |

-continued
| Cpd | W | Y | Z |
|---|---|---|---|
| 377 | 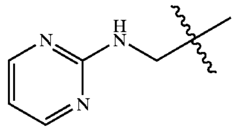 | CH | CH |
| 378 | 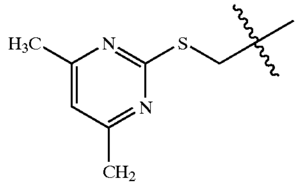 | CH | CH |
| 379 | 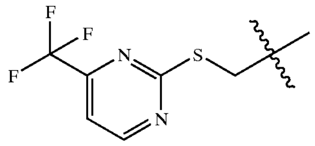 | CH | CH |
| 380 | 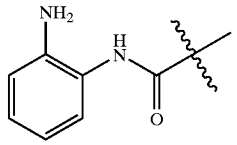 | N | CH |
| 381 | 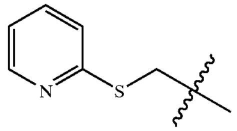 | CH | CH |
| 382 | 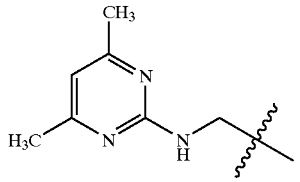 | CH | CH |
| 383 | 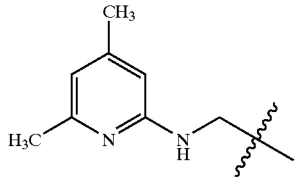 | CH | CH |
| 384 | 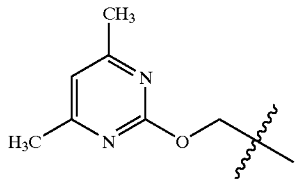 | CH | CH |

-continued
| Cpd | W | Y | Z |
|---|---|---|---|
| 385 | 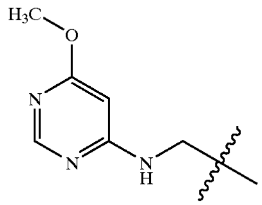 | CH | CH |
| 386 | 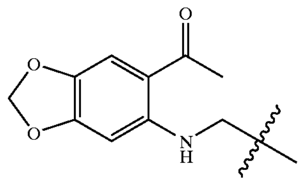 | CH | CH |
| 387 | 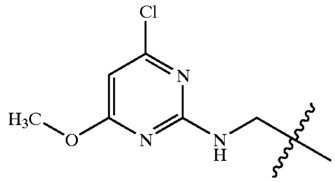 | CH | CH |
| 388 | 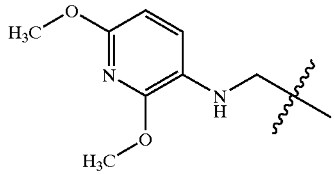 | CH | CH |
| 389 | 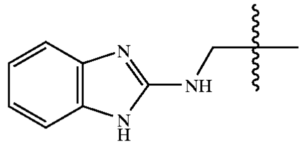 | CH | CH |
| 390 | 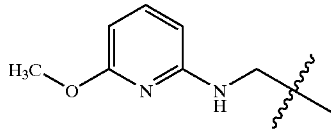 | CH | CH |
| 391 | 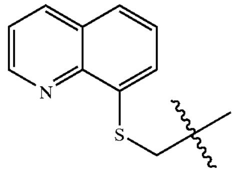 | CH | CH |
| 392 | 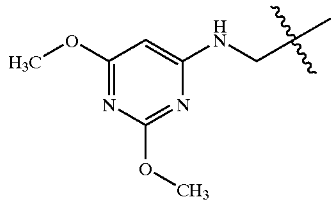 | CH | CH |

-continued
| Cpd | W | Y | Z |
| --- | --- | --- | --- |
| 393 | 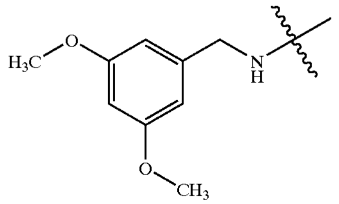 | CH | CH |
| 394 | 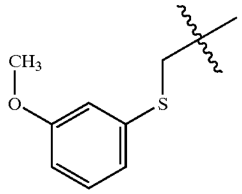 | CH | CH |
| 395 | 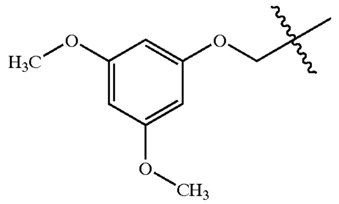 | CH | CH |
| 396 | 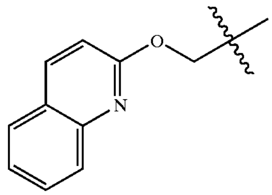 | CH | CH |
| 397 | 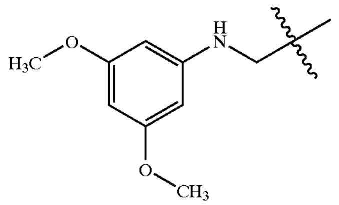 | CH | CH |
| 398 | 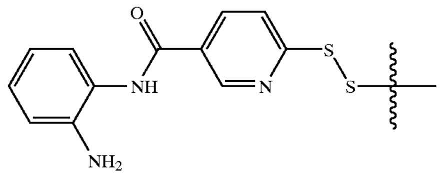 | CH | N |
| 399 | 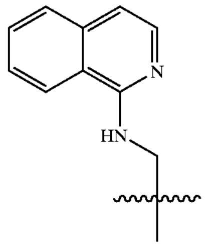 | CH | CH |

-continued
| Cpd | W | Y | Z |
|---|---|---|---|
| 400 | 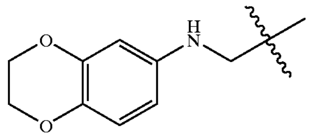 | CH | CH |
| 401 | 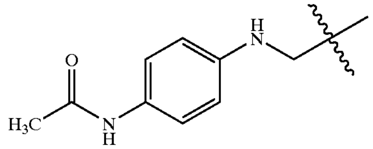 | CH | CH |
| 402 | 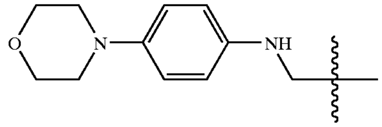 | CH | CH |
| 403 | 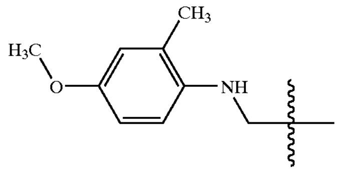 | CH | CH |
| 404 | 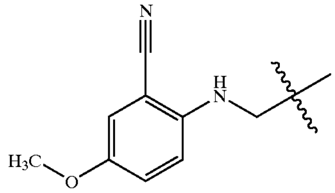 | CH | CH |
| 405 | 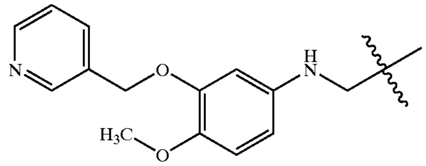 | CH | CH |
| 406 | 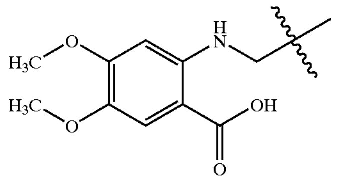 | CH | CH |
| 407 | 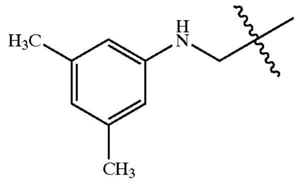 | CH | CH |
| 408 | 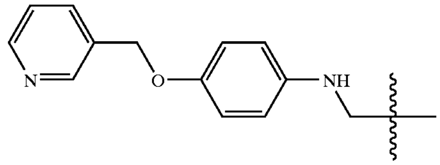 | CH | CH |

-continued
| Cpd | W | Y | Z |
| --- | --- | --- | --- |
| 409 | 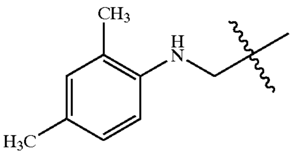 | CH | CH |
| 410 | 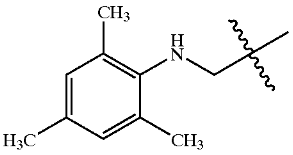 | CH | CH |
| 411 | 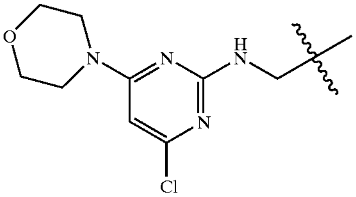 | CH | CH |
| 412 | 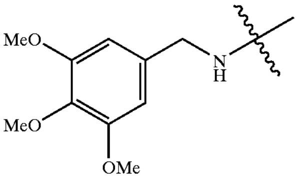 | CH | CH |
| 413 | 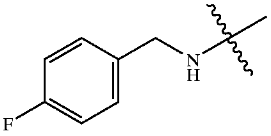 | CH | CH |
| 414 | 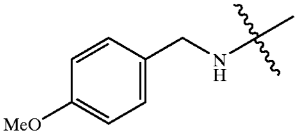 | CH | CH |
| 415 | 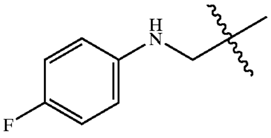 | CH | CH |
| 416 | 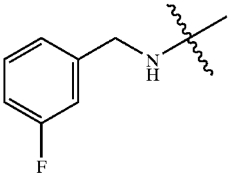 | CH | CH |

-continued
| Cpd | W | Y | Z |
| --- | --- | --- | --- |
| 417 | 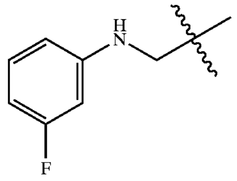 | CH | CH |
| 418 | 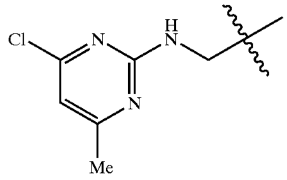 | CH | CH |
| 419 | 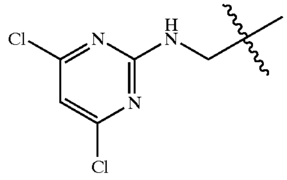 | CH | CH |
| 420 | 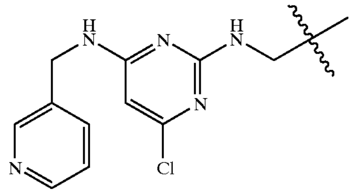 | CH | CH |
| 421 | 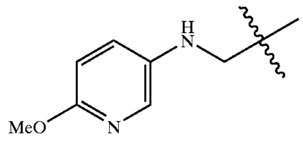 | CH | CH |
| 422 | 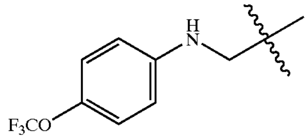 | CH | CH |
| 423 | 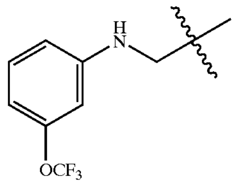 | CH | CH |
| 424b | 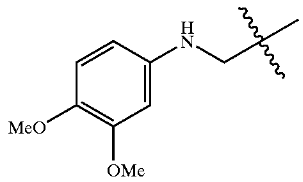 | CH | CH |

-continued
| Cpd | W | Y | Z |
|---|---|---|---|
| 425 | 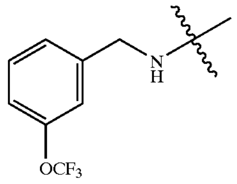 | CH | CH |
| 426 | 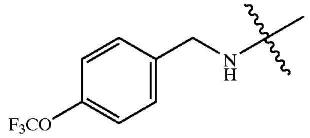 | CH | CH |
| 427 | 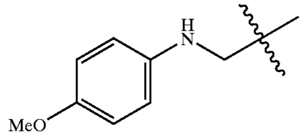 | CH | CH |
| 428 | 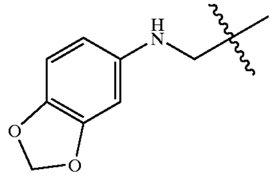 | CH | CH |
| 429 | 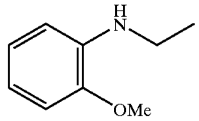 | CH | CH |
| 430 | 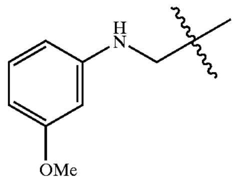 | CH | CH |
| 431 | 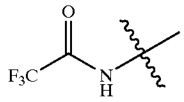 | CH | CH |
| 432 | 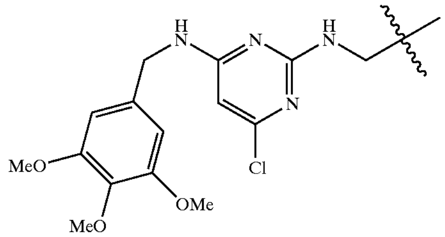 | CH | CH |
| 433 | 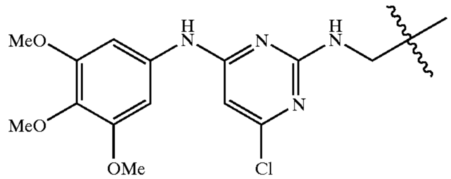 | CH | CH |

-continued
| Cpd | W | Y | Z |
|---|---|---|---|
| 434 | 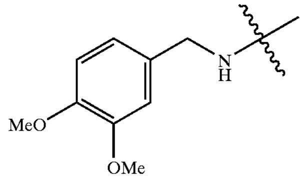 | CH | CH |
| 435 | 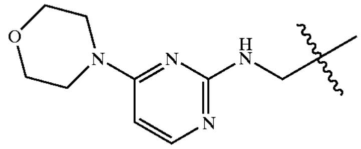 | CH | CH |
| 436 | 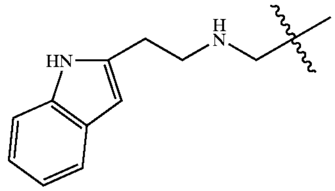 | CH | CH |
| 437 | 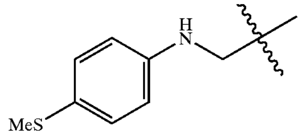 | CH | CH |
| 438 | 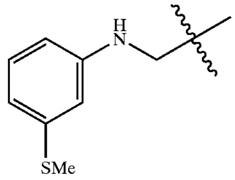 | CH | CH |
| 439 | 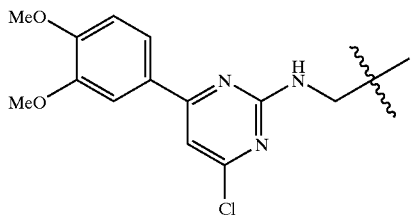 | CH | CH |
| 440 | 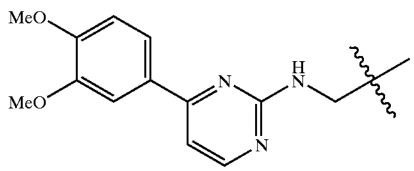 | CH | CH |
| 441 | 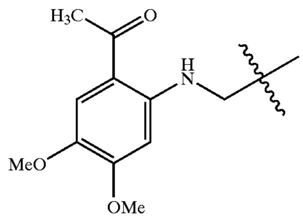 | CH | CH |

-continued
| Cpd | W | Y | Z |
|---|---|---|---|
| 442 | 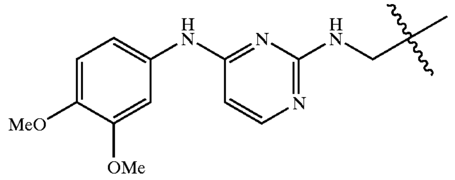 | CH | CH |
| 443 | 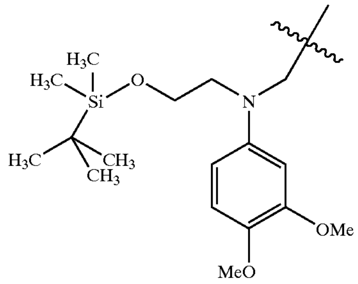 | CH | CH |
| 444 | 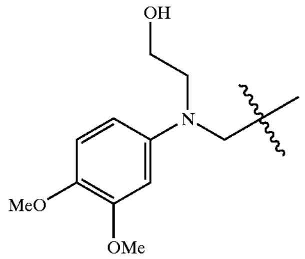 | CH | CH |
| 445 | 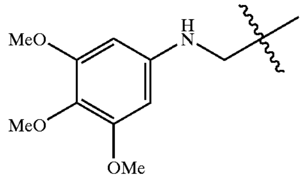 | CH | N |
| 446 | 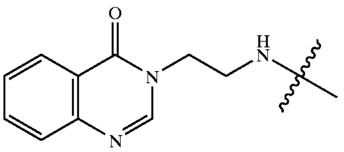 | CH | N |
| 447 | 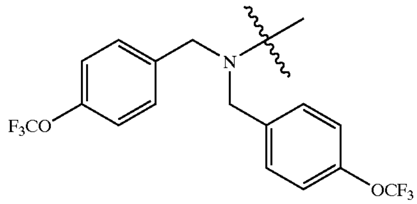 | CH | CH |
| 448 | 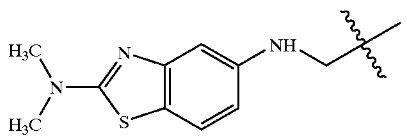 | CH | CH |

-continued
| Cpd | W | Y | Z |
|---|---|---|---|
| 449 | 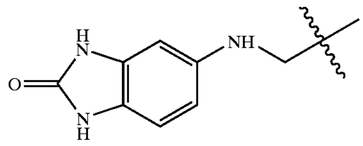 | CH | CH |
| 450 | 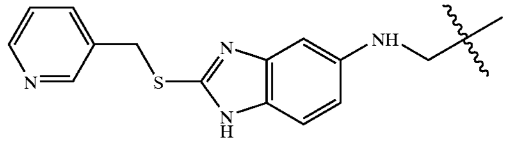 | CH | CH |
| 451 | 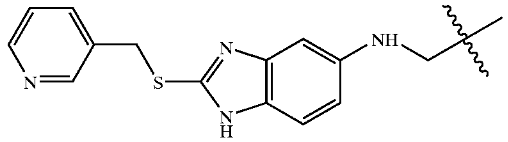 | CH | CH |
| 452 | 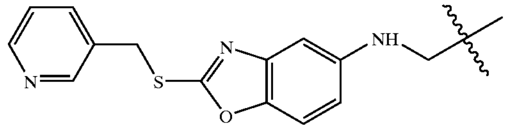 | CH | CH |
| 453 | 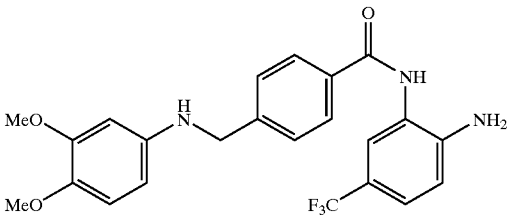 | | |
| 454 | 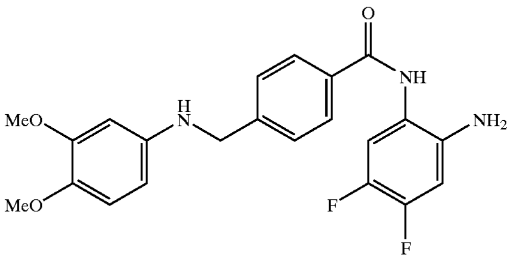 | | |
| 455 | 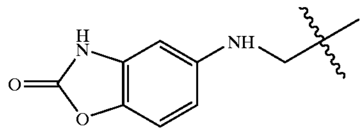 | CH | CH |
| 456 | 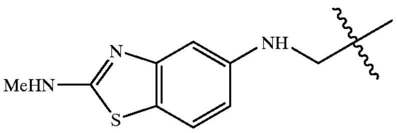 | CH | CH |

-continued
| Cpd | W | Y | Z |
|---|---|---|---|
| 457 | 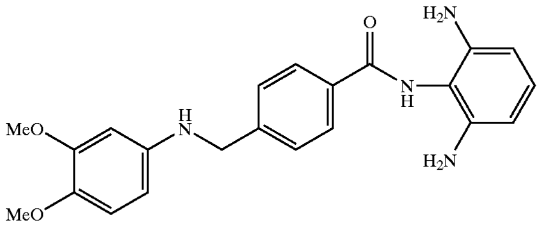 | | |
| 458 | 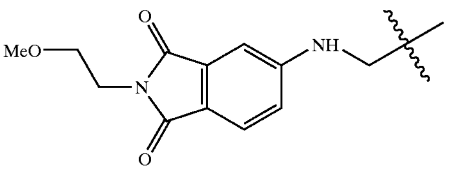 | CH | CH |
| 459 | 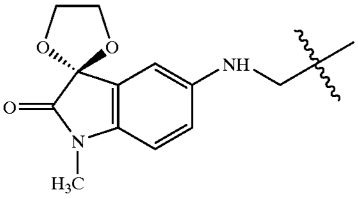 | CH | CH |
| 460 | 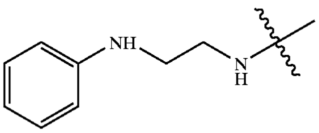 | CH | N |
| 461 | 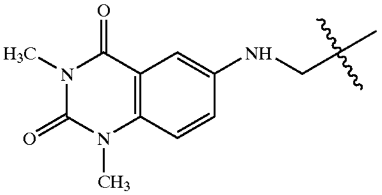 | CH | CH |
| 462 | 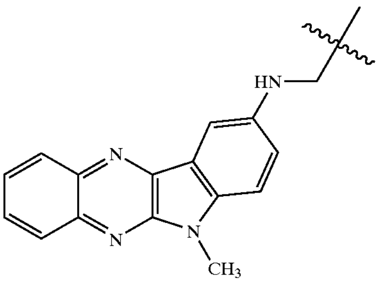 | CH | CH |
| 463 | 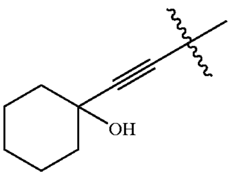 | N | CH |
| 464 | 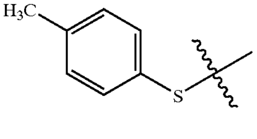 | N | CH |

-continued
| Cpd | W | Y | Z |
|---|---|---|---|
| 465 | 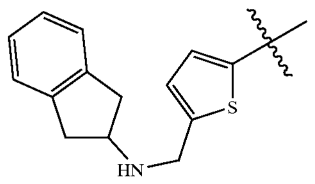 | CH | CH |
| 466 | 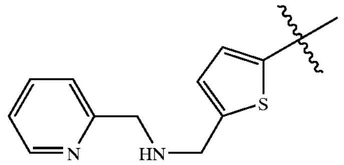 | CH | CH |
| 467 | 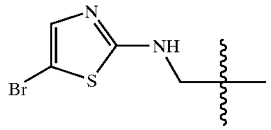 | CH | CH |
| 468 | 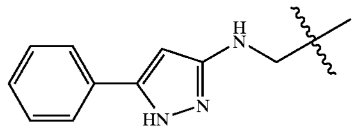 | CH | CH |
| 700 | 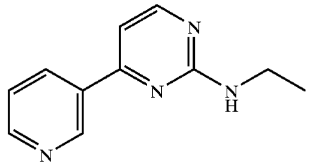 | CH | CH |
In yet another a preferred embodiment, the novel histone deacetylase inhibitors of the invention are selected from the group consisting of the following and their pharmaceutically acceptable salts:
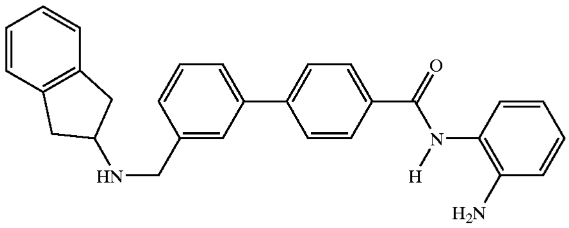
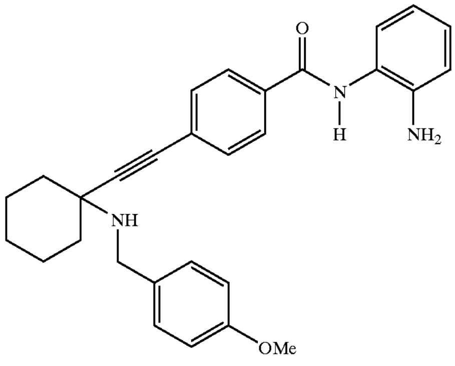
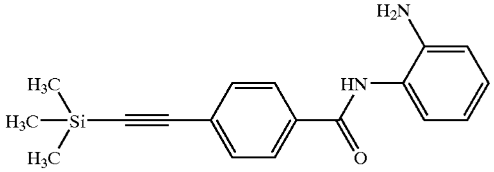
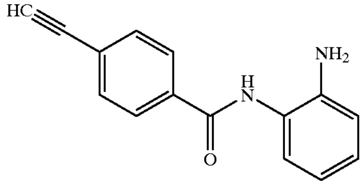

-continued
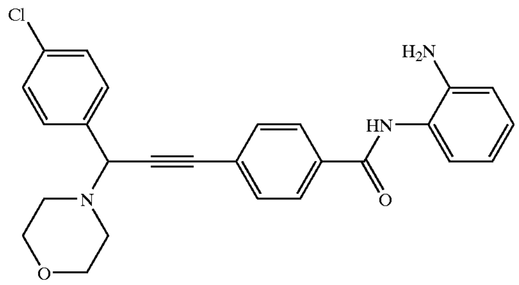
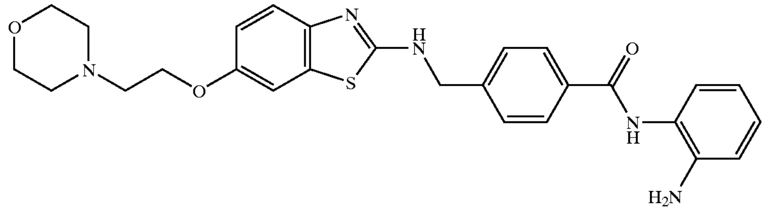
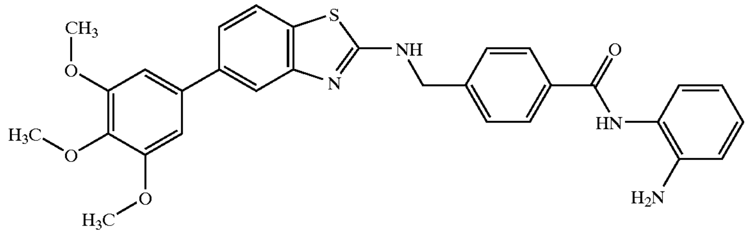
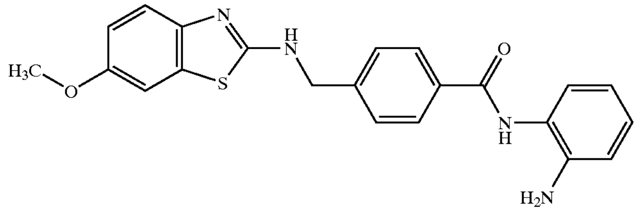
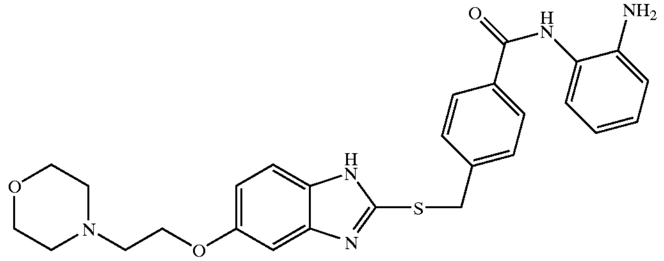
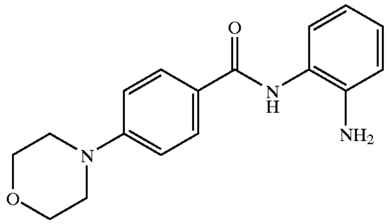
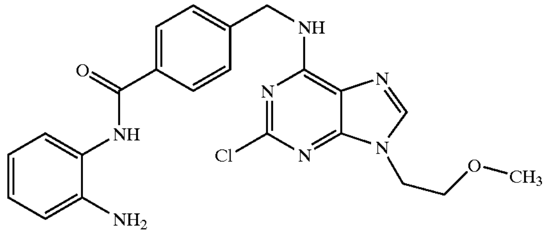
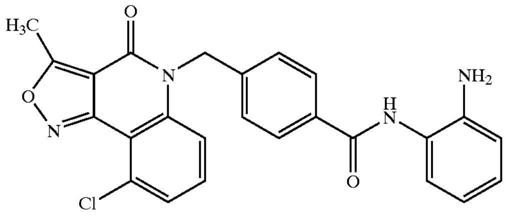
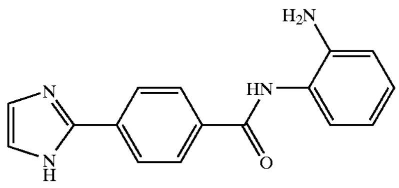
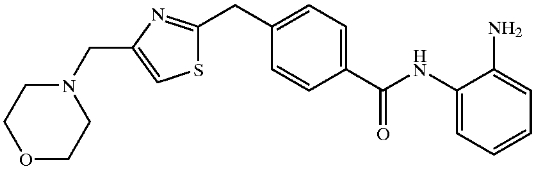

-continued
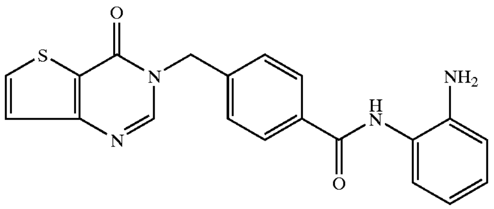
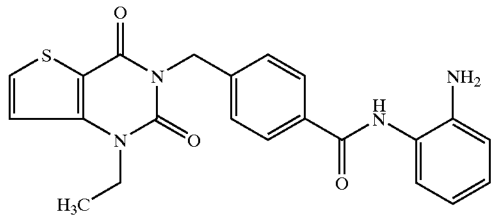
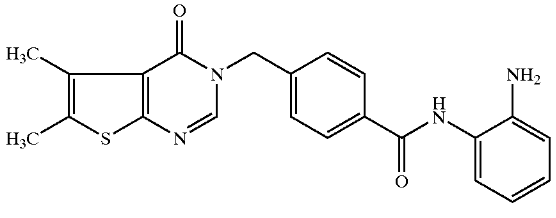
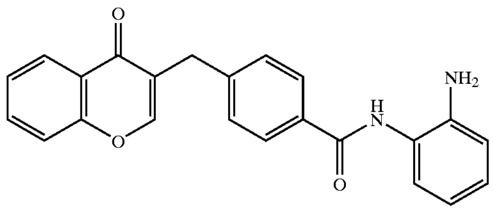
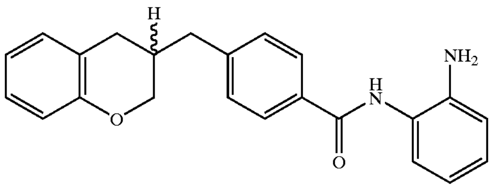
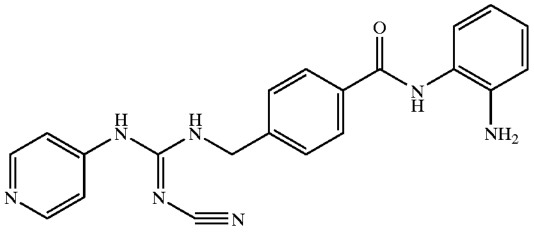
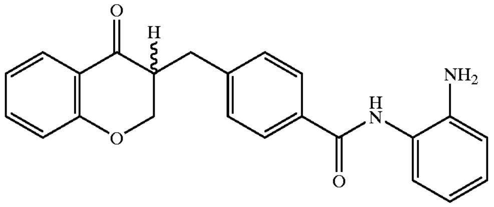
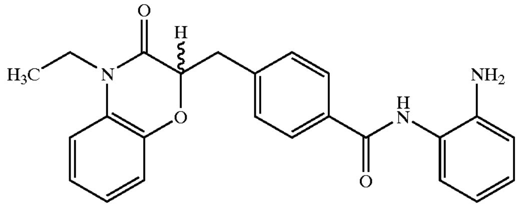
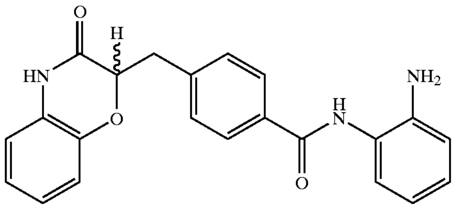
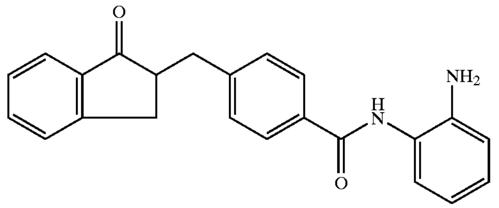
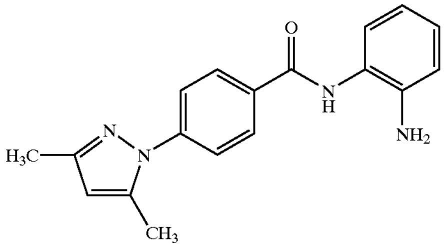
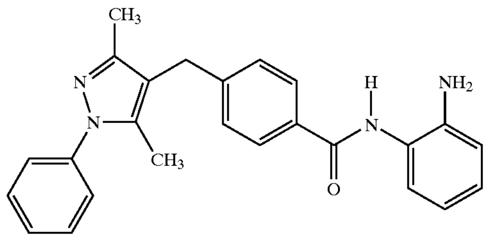
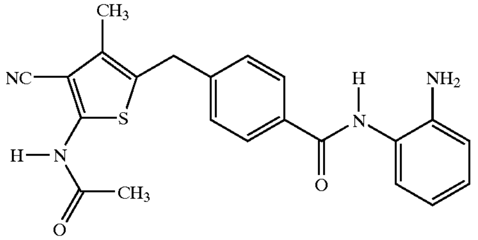
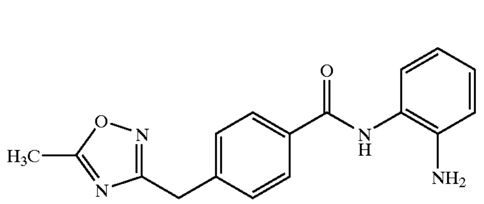

-continued
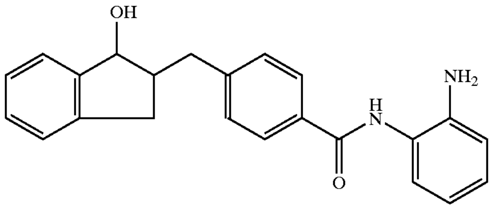
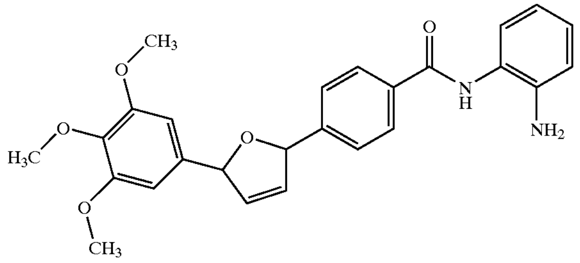
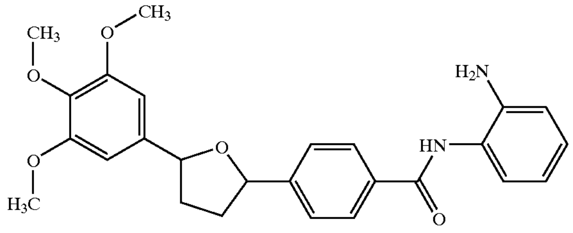
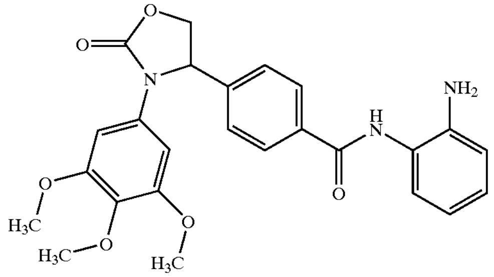
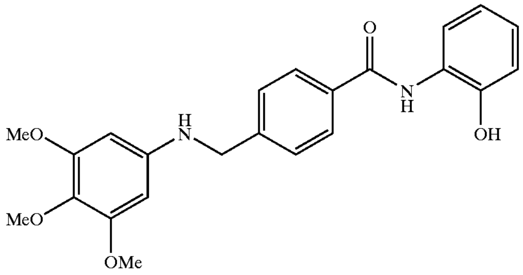
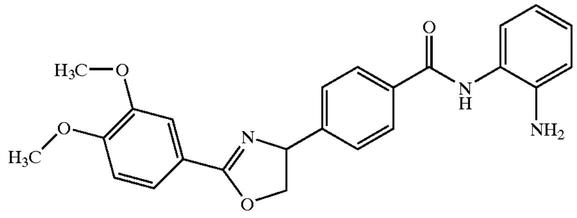
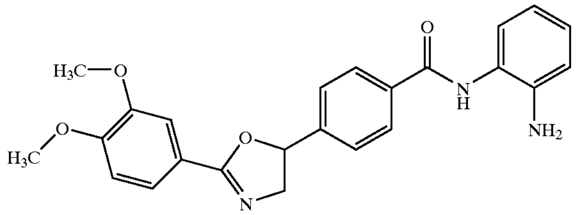
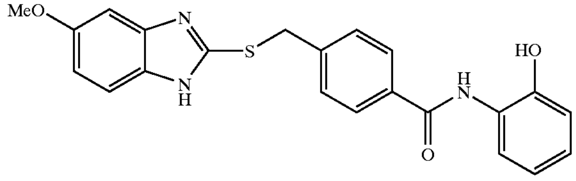
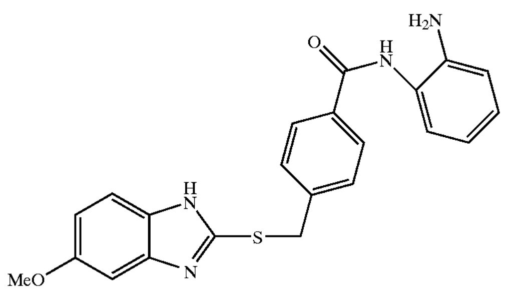
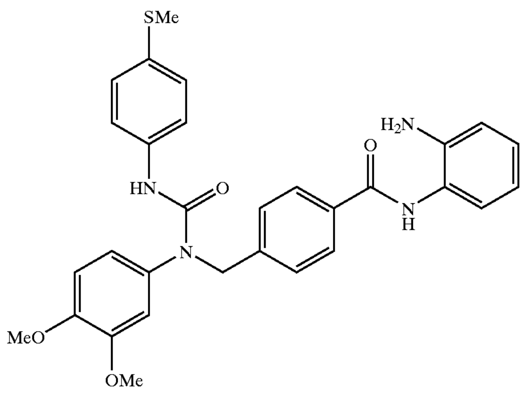

-continued
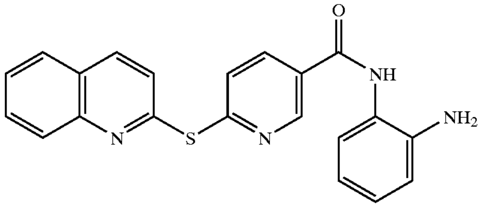
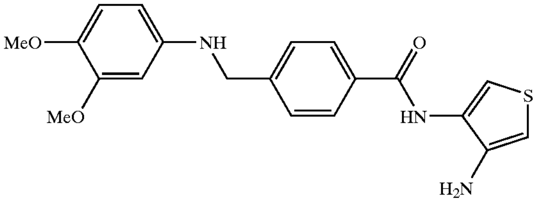
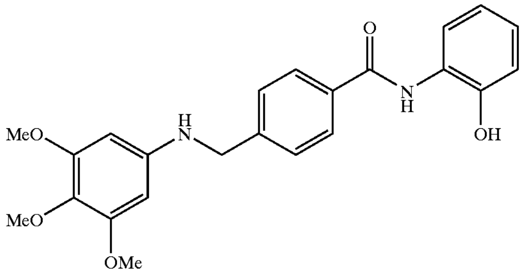
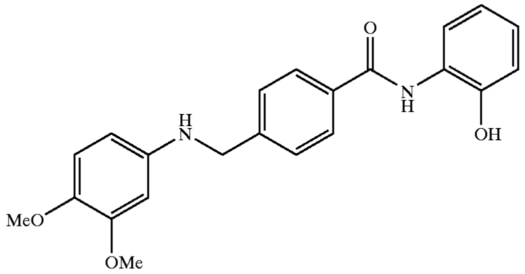
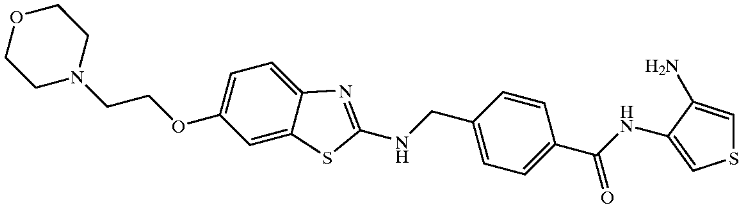
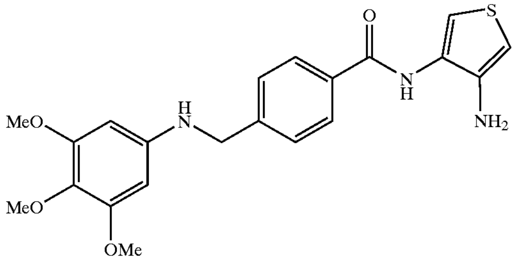
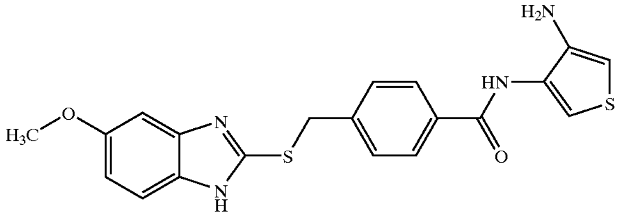
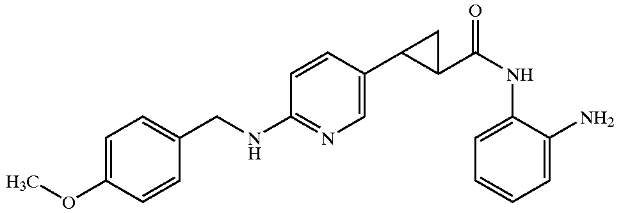
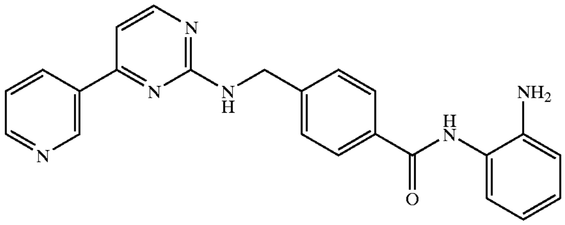
.

In another preferred embodiment, the compounds are selected from those listed in Tables 2a–b, 3a–d, 4a–c, and 5a–5f.

VII with 1,2-phenylenediamine in the presence of BOP reagent, triethylamine, and dimethylformamide (DMF) yields the anilinyl amide VIII.

Scheme 1

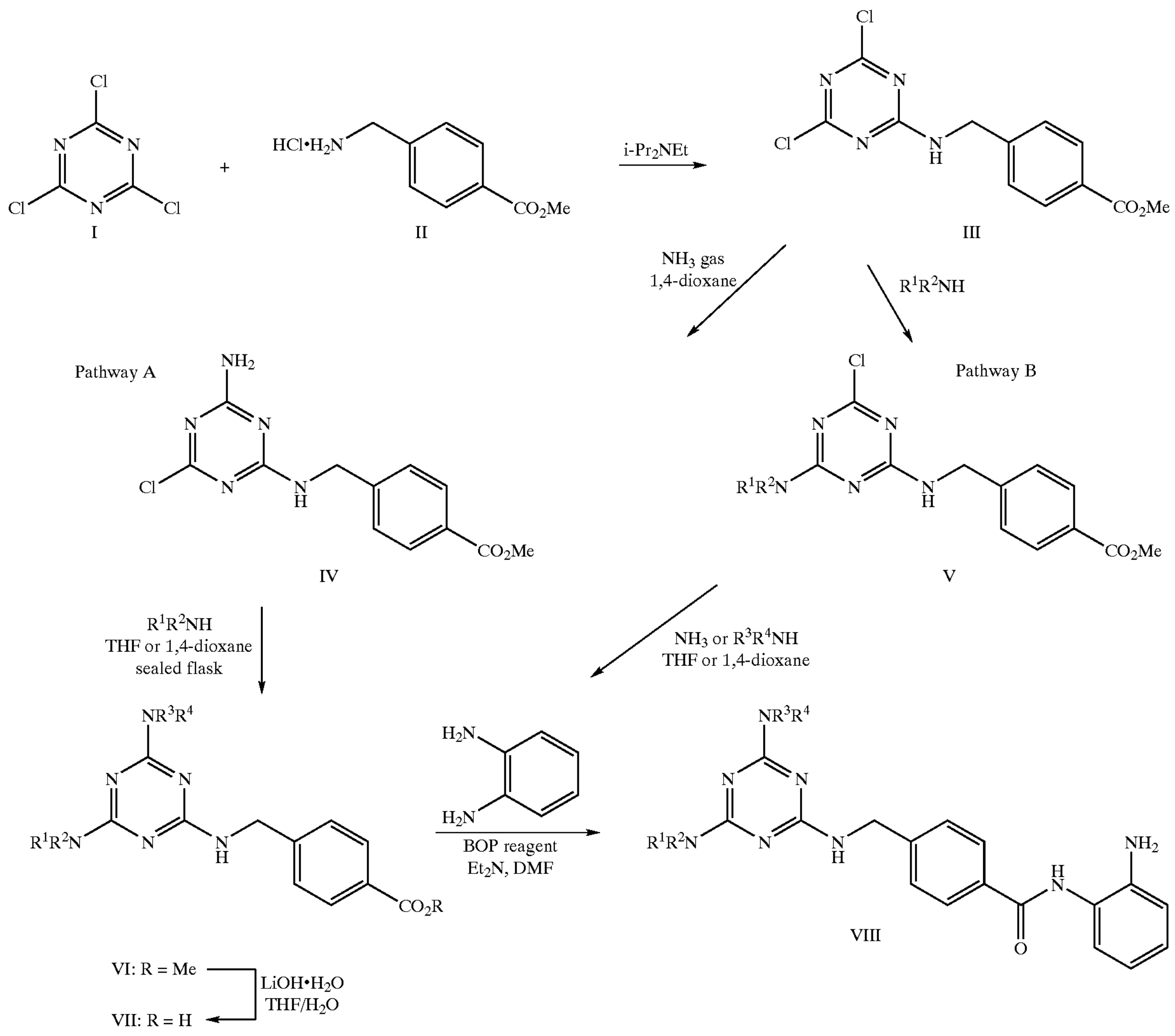

Synthesis

Compounds of formula (1), wherein Y' is —$N(R^1)(R^2)$, preferably may be prepared according to the synthetic route depicted in Scheme 1. Thus, trichlorotriazine I reacts with amine II in the presence of diisopropylethylamine to produce dichloroaminotriazine III. The amine $R^1R^2NH$ is added to dichloroaminotriazine III to produce diaminochlorotriazine V. Treatment of V with ammonia or $R^3R^4NH$ in tetrahydrofuran (THF) or 1,4 dioxane affords triaminotriazine VI.

Alternatively, dichloroaminotriazine III may be reacted with ammonia gas in 1,4 dioxane to produce diaminochlorotriazine IV. Treatment of IV with $R^1R^2NH$ in THF or 1,4 dioxane in a sealed flask then affords triaminotriazine VI.

Hydrolysis of the ester moiety in VI is effected by treatment with a hydroxide base, such as lithium hydroxide, to afford the corresponding acid VII. Treatment of the acid Compounds of formula (1), wherein $Y^1$ is —$CH_2$—C(O)—$N(R^1)(R^2)$, preferably may be prepared as outlined in Scheme 2. Thus, piperazine IX is treated with acetyl chloride and triethylamine to produce amide X. Reaction of X with dichloromorpholyltriazine and lithium hexamethyldisiloxane affords compound XI. The chloride of XI is converted to the anilinyl amide of XII as described above with respect to Scheme 1: treatment with the amine and diisopropylethylamine; followed by lithium hydroxide; followed by BOP reagent, phenylenediamine, triethylamine, and DMF.

Scheme 2

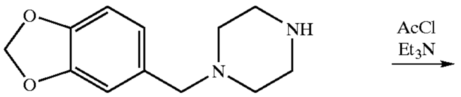

IX

-continued

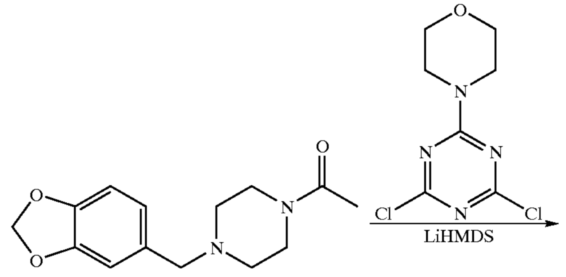

X

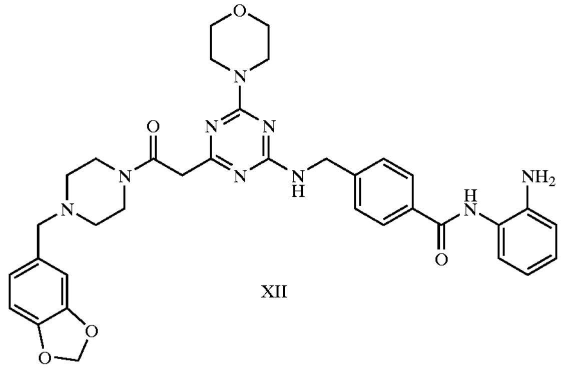

XII

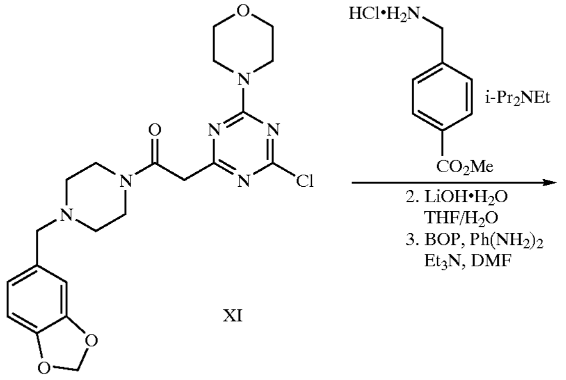

XI

Compounds of formula (2), wherein $Ar^2$ is pyridylene and $X^1$ comprises —$N(R^7)$—, compounds of formula (3), wherein $Ar^3$ is pyridylene and $X^2$ comprises —$N(R^9)$—, and compounds of formula (4), wherein $Ar^4$ is pyridylene and $X^3$ comprises —$N(R^{11})$—, preferably may be prepared according to the procedures illustrated in Scheme 3. Dibromopyridine XIII or XIV is treated with amine $RNH_2$ to produce aminobromopyridine XV or XVI, respectively. Treatment of XV or XVI with diacetoxypalladium, diphenylphosphinoferrocene, DMF, diisopropylethylamine, and phenylenediamine under carbon monoxide yields anilinyl amide XVII or XVIII, respectively.

Treatment of XV or XVI with tert-butylacrylate, diisopropylethylamine, dibenzylacetone palladium, and tri-o-tolylphosphine (POT) in DMF under nitrogen affords compounds XIX and XX, respectively. The ester moiety of XIX or XX is hydrolyzed to produce the corresponding acid moiety in XXI or XXII, respectively, by reaction with trifluoroacetic acid in dichloromethane. Treatment of the acid XXI or XXII with phenylenediamine, BOP, and triethylamine affords the anilinyl amide XXIII or XXIV, respectively.

Scheme 3

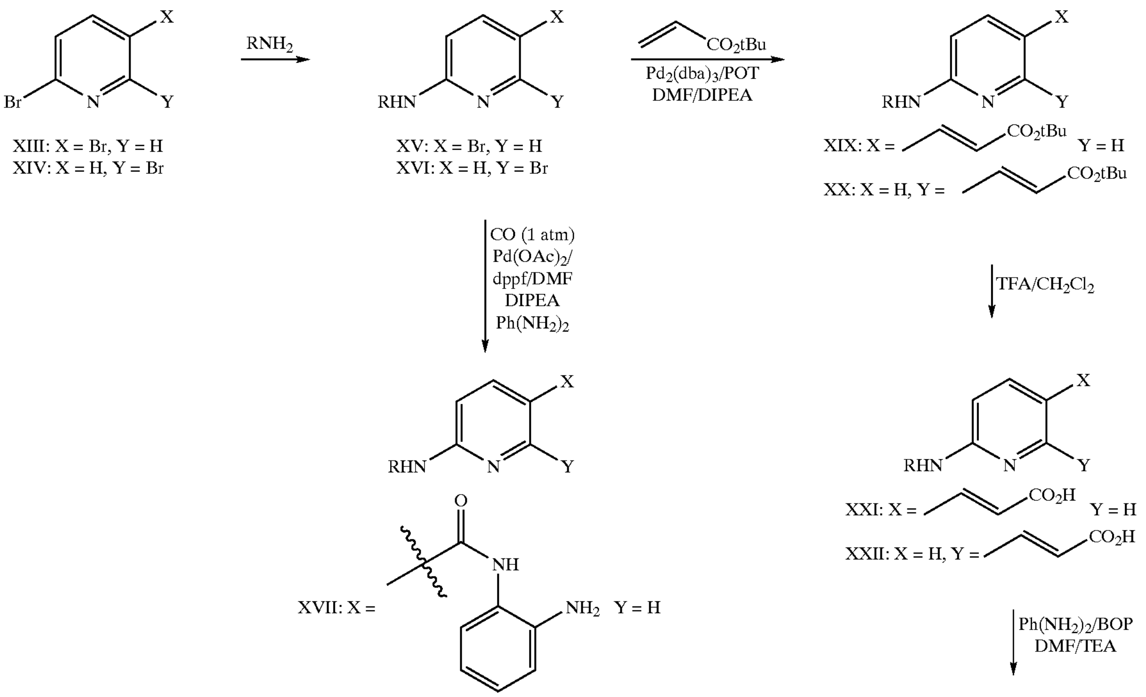

XIII: X = Br, Y = H
XIV: X = H, Y = Br

XV: X = Br, Y = H
XVI: X = H, Y = Br

XIX: X = Y = H
XX: X = H, Y =

XXI: X = Y = H
XXII: X = H, Y =

XVII: X = Y = H

-continued

XVIII: X = HY =

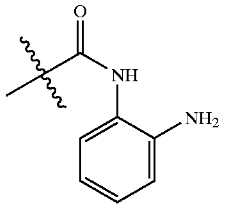

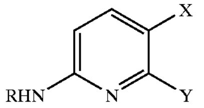

XXIII: X =

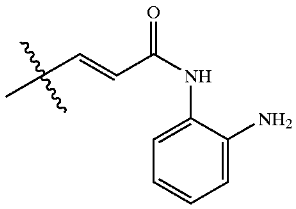

Y = H

XXIV: X = HY =

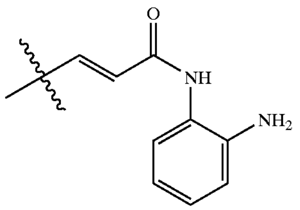

Compounds of formula (2), wherein $X^1$ comprises —O—C(O)—NH—, preferably may be prepared according to the synthetic route depicted in Scheme 4. Thus, carbinol XXV is added to bromobenzylamine XXVI with carbonyldiimidazole (CDI), triethylamine, and 1,8-diazabicyclo [5.4.0]undec-7-ene (DBU) in DMF to produce compound XXVII. The remaining synthetic steps in the production of anilinyl amide XXVIII are as described above for Scheme 3.

Scheme 4

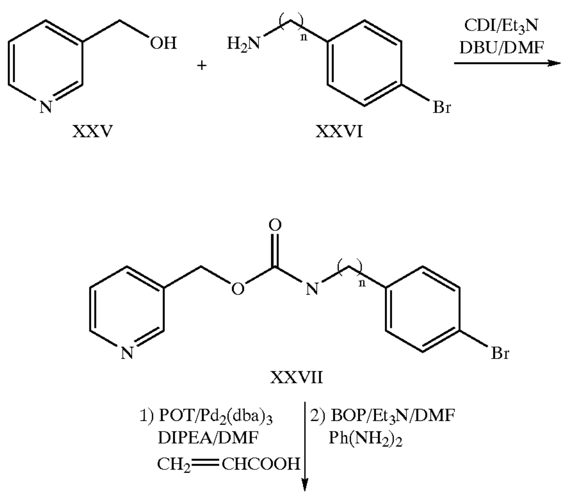

XXV XXVI

XXVII

-continued

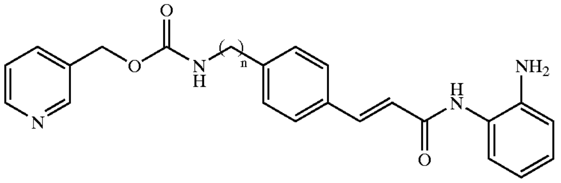

XXVIII

Compounds of formula (2), wherein $X^1$ comprises —N($R^7$)—, preferably may be prepared as outlined in Scheme 5. Amine XXIX is reacted with p-bromobenzylbromide in the presence of potassium carbonate in DMF to produce bromobenzylamine XXX. Treatment of XXX with nitroacrylanilide, dibenzylacetone palladium, POT, anddiisopropylethylamine in DMF affords nitroanilide XXXI. Nitroanilide XXXI is converted to the corresponding anilinyl amide XXXII by treatment with stannous chloride in methanol and water.

Treatment of amine XXXI in formic acid with paraformaldehyde provides methylamine XXXIII. The nitroanilide moiety in XXXIII is then converted to the corresponding anilinyl amide moiety in XXXIV by treatment with stannous chloride in methanol and water.

Scheme 5

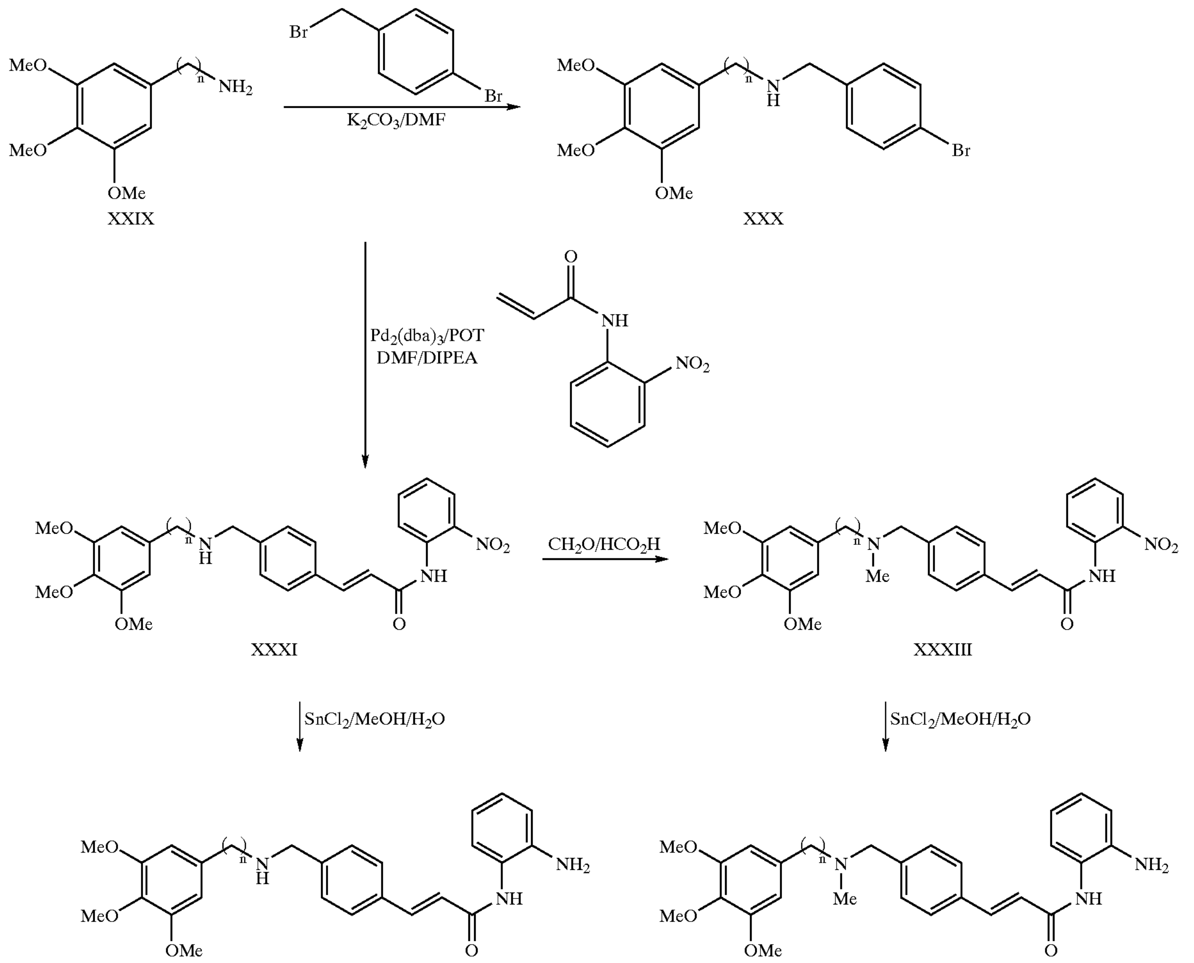

XXIX, XXX, XXXI, XXXIII, XXXII, XXXIV

Alternatively, compounds of formula (2), wherein $X^1$ comprises —$N(R^7)$—, may be prepared according to the synthetic route depicted in Scheme 6. Carboxylic acid XXXV in methanol is treated with hydrochloric acid to produce ester XXXVI. Conversion of the primary amine moiety in XXXVI to the secondary amine moiety in XXXVI is effected by treatment with a catalyst such as triethylamine, methoxybenzylchloride, sodium iodide, and potassium carbonate in DMF at 60° C. Ester XXXVI is converted to anilinyl amide XXXVII by treatment with sodium hydroxide, THF, and methanol, followed by BOP, triethylamine, and phenylenediamine in DMF, as described above for Scheme 3.

Scheme 6

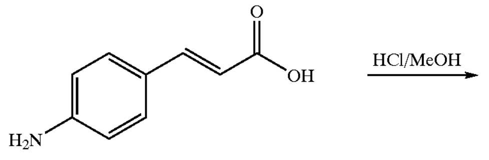

XXXV

-continued

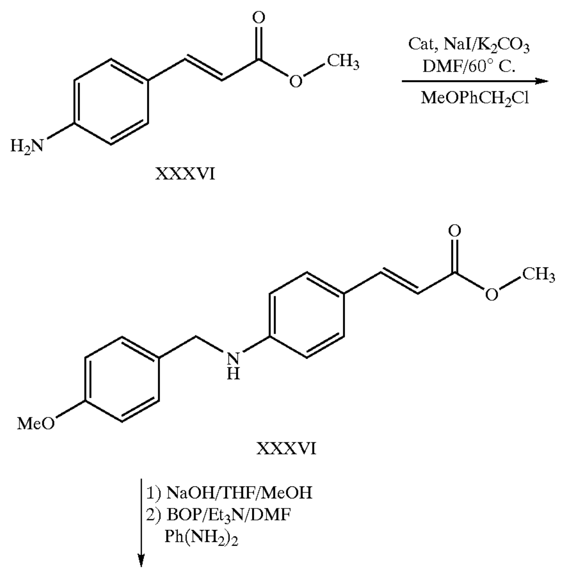

XXXVI, XXXVI

-continued

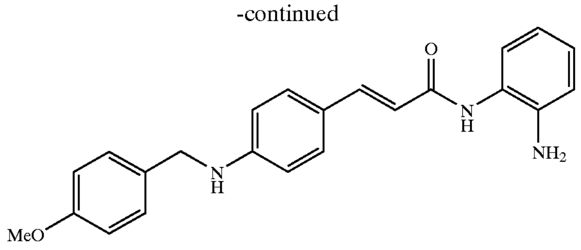

XXXVII

Compounds of formula (2), wherein $X^1$ comprises

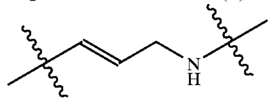

or —C(O)—NH—, preferably may be prepared according to the procedures illustrated in Scheme 7. Addition of amine 68 to haloaryl compound XXXVIII or XXXIX and potassium carbonate in DMF provides arylamine XL or XLI, respectively. Anilinyl amide XLII or XLIII is then prepared using procedures analogous to those set forth in Schemes 3–6 above.

Scheme 7

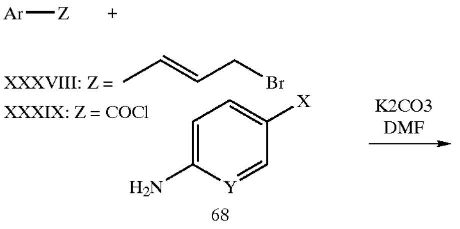

XXXVIII: Z =
XXXIX: Z = COCl
68
X = Br or I
Y = N or CH

-continued

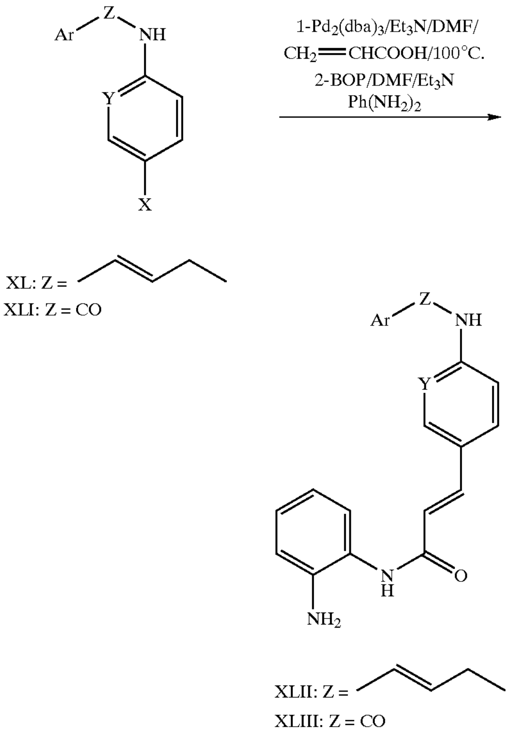

XL: Z =
XLI: Z = CO
XLII: Z =
XLIII: Z = CO

Compounds such as XLVII and XLIX preferably may be prepared as outlined in Scheme 8. Dibromopyridine is combined with diaminoethane to produce amine XLIV. Treatment of amine XLIV with isatoic anhydride LV in methanol and water, followed by refluxing in formic acid affords compound XLVI. Treatment of amine XLIV with the reaction products of benzylaminodiacetic acid and acetic anhydride provides compound XLVIII. Bromopyridylamines XLVI and XLVIII are then converted to the corresponding diene anilinylamides XLVII and XLIX, respectively, by procedures analogous to those set forth in Schemes 3–7 above.

Scheme 8

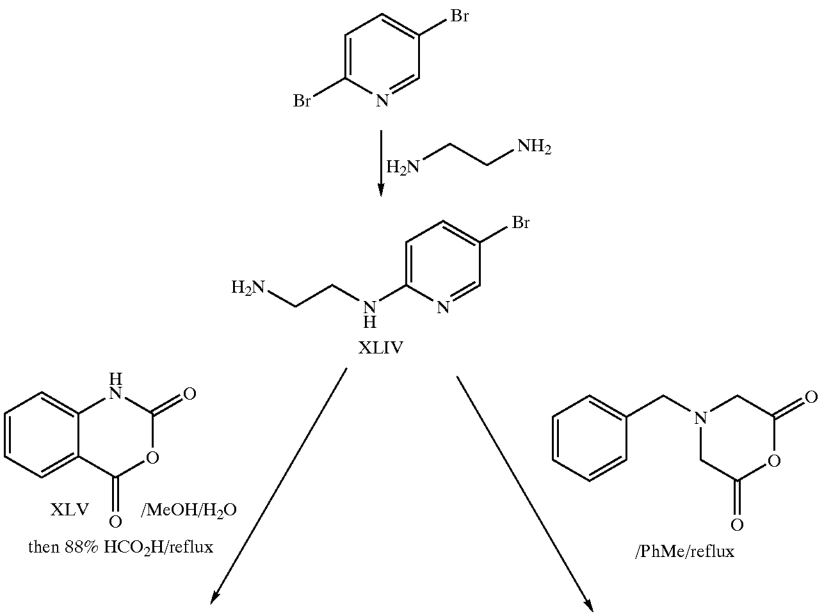

XLIV
XLV

-continued

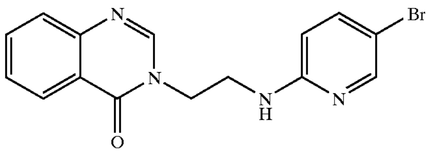

XLVI

1. $CO_2tBu$
$Pd_2(dba)_3$/POT
DMF/DIPEA/120° C.
2. $TFA/CH_2Cl_2$
r.T
3. $Ph(NH_2)_2$/BOP
DMF/TEA/rT

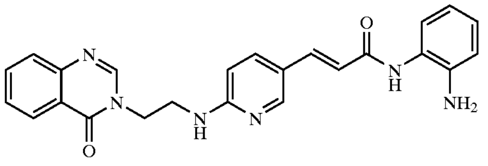

XLVII

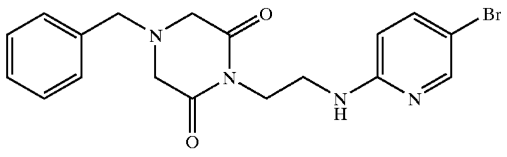

XLVIII

1. $CO_2tBu$
$Pd_2(dba)_3$/POT
DMF/DIPEA/120° C.
2. $TFA/CH_2Cl_2$
r.T
3. $Ph(NH_2)_2$/BOP
DMF/TEA/rT

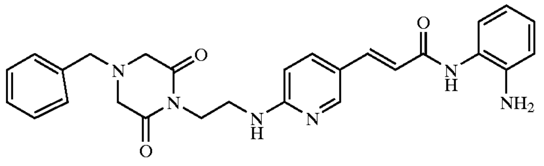

XLIX

Compounds such as LIV preferably may be prepared according to the synthetic route depicted in Scheme 9. Trichlorotriazine is treated with aminoindan and diisopropylethylamine to produce dichloroaminotriazine L. Treatment with bromobenzylamine and diisopropylethylamine affords diaminochlorotriazine LI. Addition of ammonia gas and dioxane provides triaminotriazine LII. Treatment with protected acrylanilide, triethylamine, POT, and dibenzylacetone palladium then yields diene anilinylamide LIII, which is deprotected with trifluoroacetic acid to provide the final product LIV.

Scheme 9

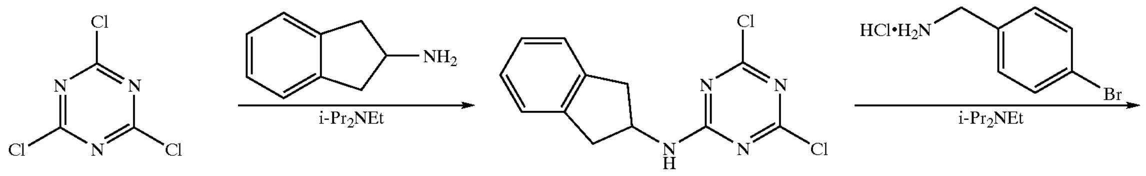

L

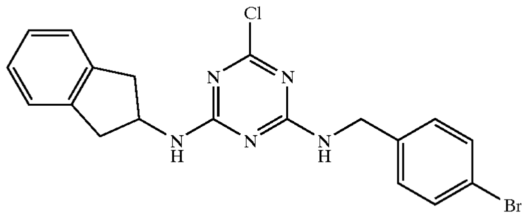

LI $NH_3$ gas
1,4-dioxane

-continued

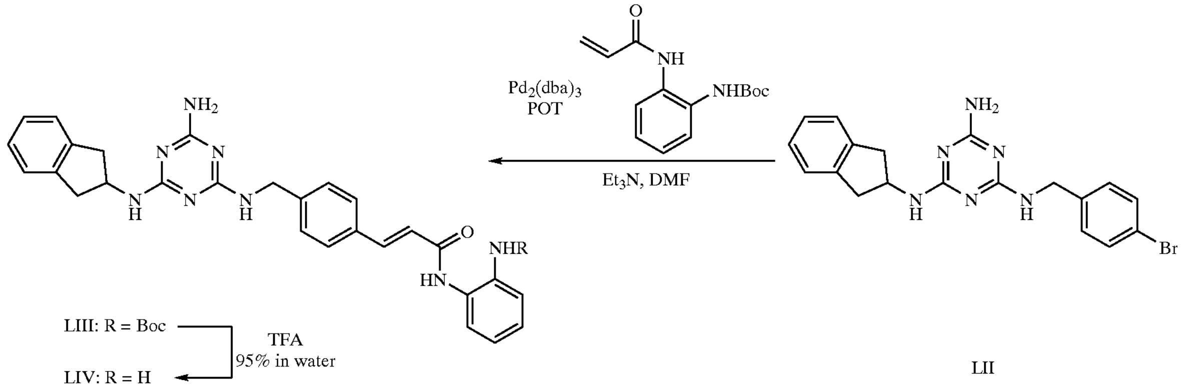

LIII: R = Boc

LIV: R = H

LII

Compounds of formula (2), wherein $Ar^2$ is quinolylene and $X^1$ comprises —$N(R^7)$—, compounds of formula (3), wherein $Ar^3$ is quinolylene and $X^2$ comprises —$N(R^9)$—, and compounds of formula (4), wherein $Ar^4$ is quinolylene and $X^3$ comprises —$N(R^{11})$—, preferably may be prepared according to the procedures illustrated in Scheme 10. Dihydroxyquinoline LV with dimethylaminopyridine (DMAP) in pyridine is treated with trifluoromethanesulfonic anhydride to provide bis(trifluoromethanesulfonyloxy)-quinoline LVI. Treatment of LVI with p-methoxybenzylamine affords aminoquinoline LVII. Anilinyl amides LVIII and LIX are then prepared using procedures analogous to those described for Schemes 1–9 above.

Compounds of formula (3), wherein $X^2$ comprises a sulfur atom, and compounds of formula (4), wherein $X^3$ comprises a sulfur atom, preferably may be prepared as outlined in Scheme 11. Bromide LX is converted to diaryl ester LXI using procedures analogous to those described for Scheme 6 above. Synthetic methods similar to those set forth in Scheme 1 above are then used to convert ester LXI to the corresponding acid LXIV. Alternatively, ester LXI may be treated with chloroethylmorphonline, sodium iodide, potassium carbonate, triethylamine, and tetrabutylammonium iodide (TBAI) in DMF to produce ester LXIII, which is then converted to acid LXIV as in Scheme 1. Conversion of the acid LXIV to the anilinyl amide LXV is effected by procedures analogous to those set forth in Scheme 1 above.

Scheme 10

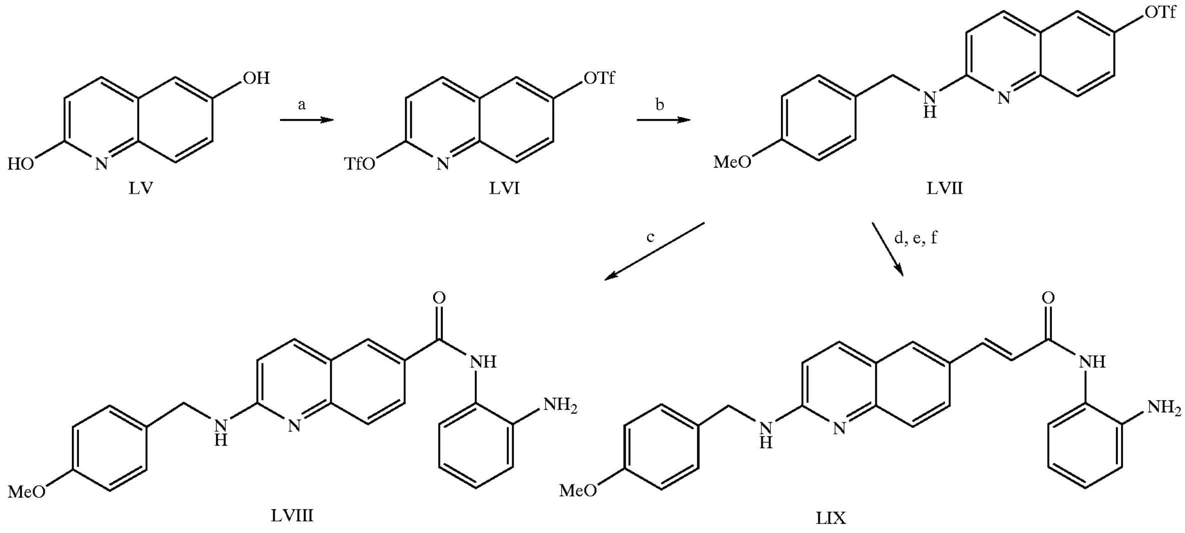

LV

LVI

LVII

LVIII

LIX a. $Tf_2O$/Py/DMAP/0 C.
b. p-methoxybenzylamine/120 C.
c. 1,2-phenylenediamine/CO(40 psi)/$Pd(OAc)_2$/dppf/DMF/DIPEA/70 C.
d. t Butylacrylate/$Pd_2(dba)_3$/POT/DMF/DIPEA/120 C.
e. TFA/DCM/rT
f. 1,2-phenylenediamine/BOP/DMF/TEA/rt Scheme 11

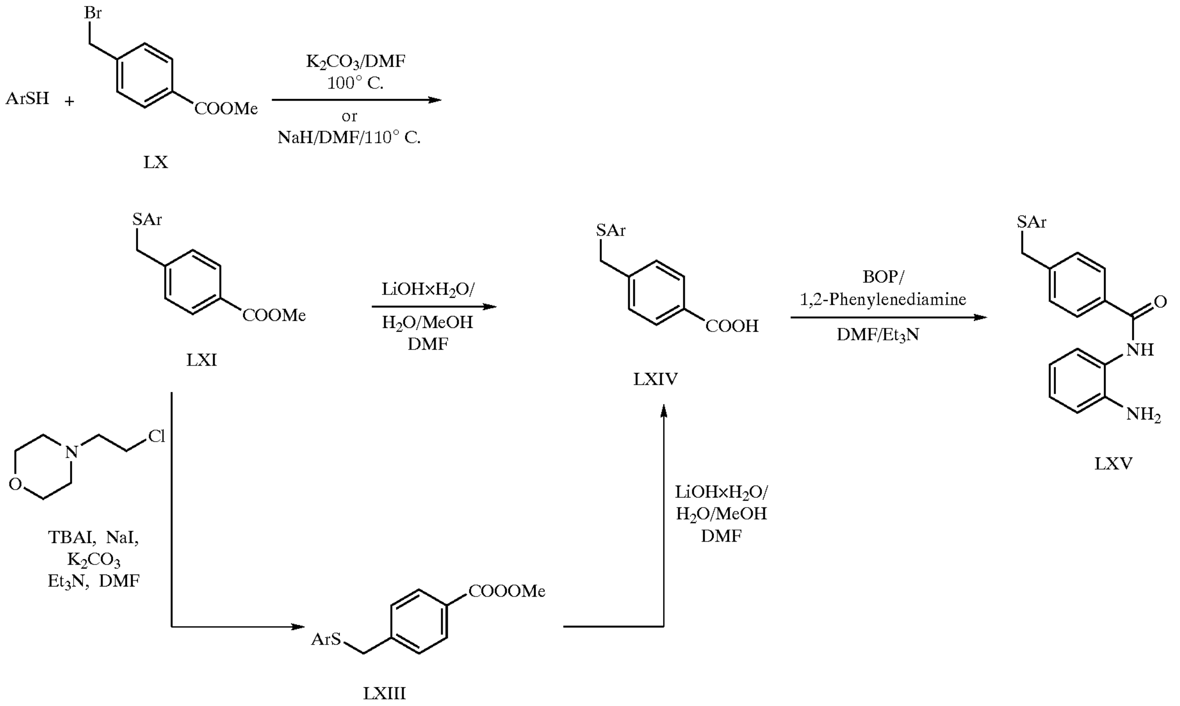

Alternatively, compounds of formula (3), wherein $X^2$ comprises a sulfur atom, and compounds of formula (4), wherein $X^3$ comprises a sulfur atom, may be prepared according to the procedures illustrated in Scheme 12. Sulfanyl anilinylamide LXVIII is prepared using procedures analogous to those set forth in. Schemes 3 and 5 above.

Scheme 12

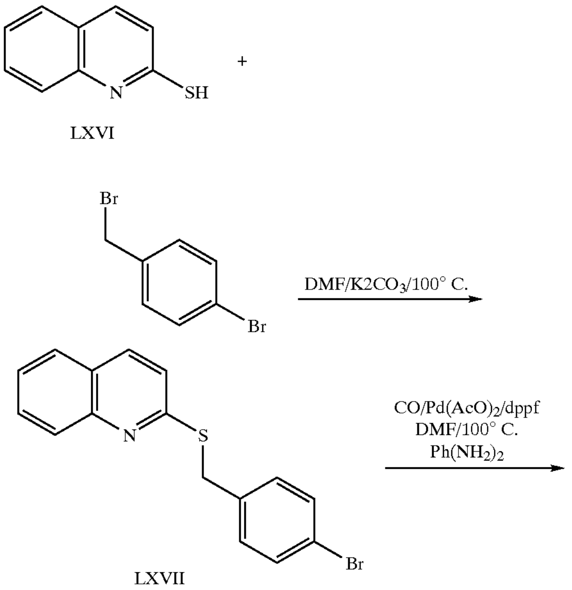

-continued

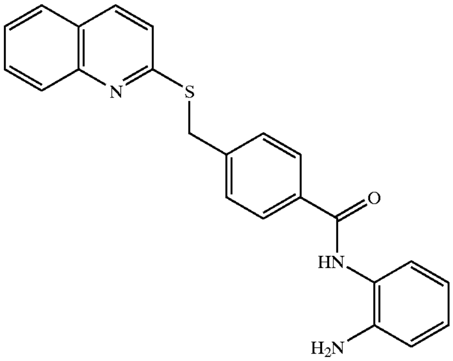

LXVIII

Compounds of formula (3), wherein $X^2$ comprises —N($R^9$)—, and compounds of formula (4), wherein $X^3$ comprises —N($R^{11}$)—, preferably may be prepared according to the synthetic route depicted in Scheme 13. Amino anilinyl amide LXXI is prepared according to synthetic steps similar to those described for Schemes 1 and 6 above.

Scheme 13

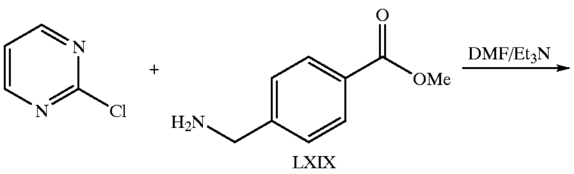

-continued

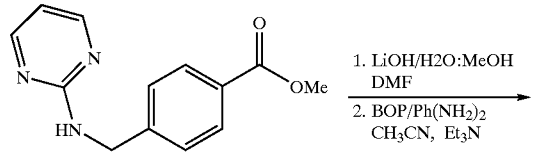

LXX

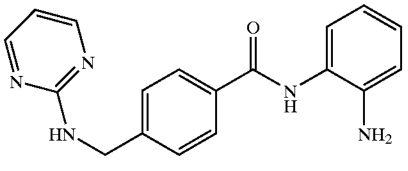

LXXI

Compounds of formula (3), wherein $X^2$ comprises a sulfur atom, and compounds of formula (4), wherein $X^3$ comprises a sulfur atom, preferably may be prepared as outlined in Scheme 14. Phenylenediamine is reacted with di-tert-butyldicarbonate, followed by iodobenzoic acid, dimethylaminopropylethylcarbodiimide, hydroxybenzotriazole, and triethylamine to provide protected anilinyl amide LXXII. The iodide moiety of LXXII is converted to the methyl ester moiety of LXXIII using procedures analogous to those set forth for Scheme 3 above. The methyl ester moiety of LXXIII is converted to the hydroxyl moiety of LXXIV by treatment with a reducing agent such as diisobutylaluminum hydride (DIBAL H). Addition of the heterocyclylsulfhydryl compound Het-SH with triphenylphosphine and diethylazodicarboxylate converts the hydroxyl moiety of LXXIV to the sulfanyl moiety of LXXV. LXXV is deprotected with trifluoroacetic acid to afford the sufanyl anilinyl amide LXXVI.

Scheme 14

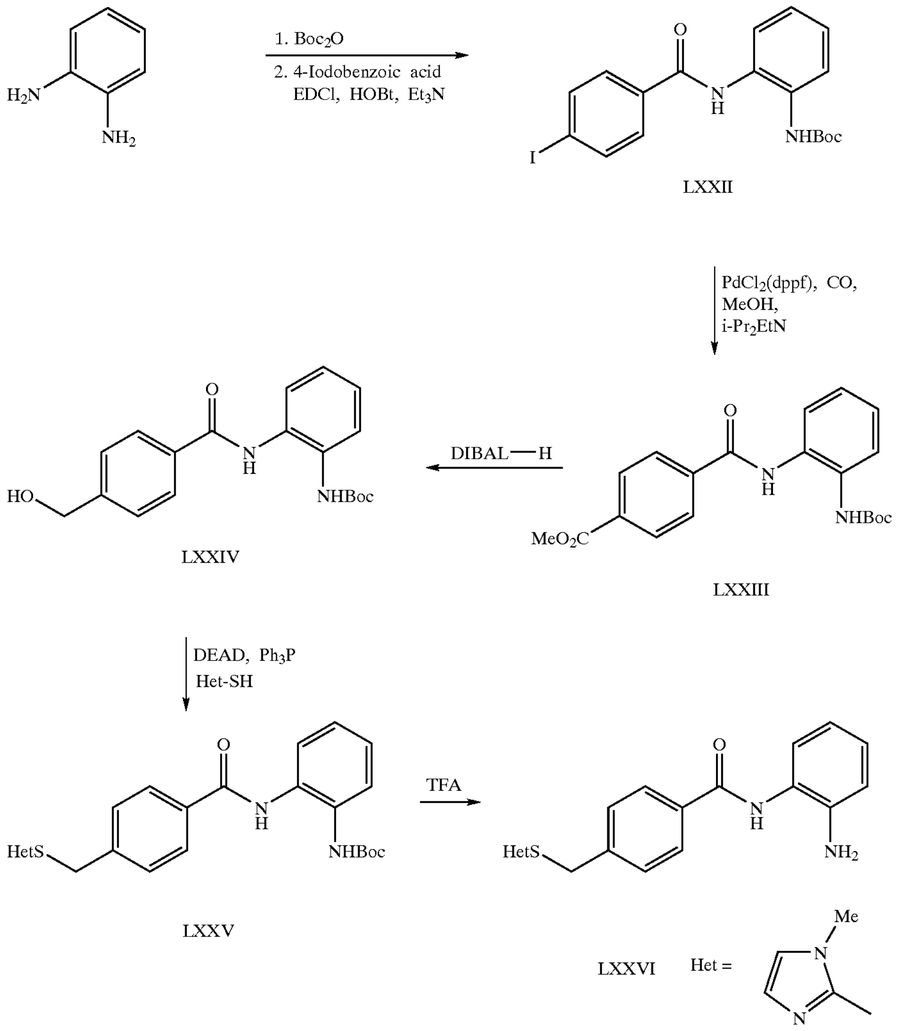

LXXII

LXXIII

LXXIV

LXXV

LXXVI

Compounds of formula (3), wherein $X^2$ is a chemical bond, preferably may be prepared according to the synthetic route depicted in Scheme 15. Thus, chloroarylanilinylamide LXXVII is treated with aryl boronic acid, benzene, ethanol, aqueous sodium carbonate, and triphenylphosphine palladium to afford the diarylanilinylamide LXXVIII.

Scheme 15

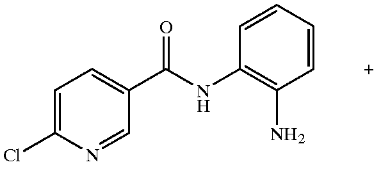

LXXVII

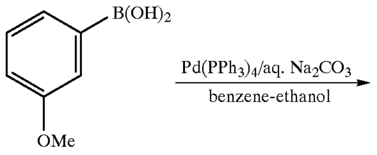

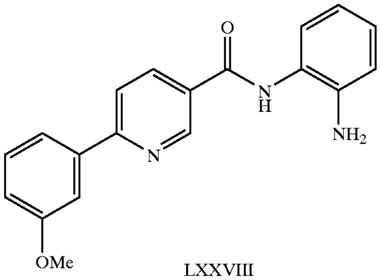

LXXVIII

Compounds such as LXXXI preferably may be prepared according to the procedues illustrated in Scheme 16. Thus, benzene-1,2-carbaldehyde LXXIX in acetic acid is treated with p-aminomethylbenzoic acid to produce the benzoic acid LXXX. The acid LXXX is converted to the corresponding anilinylamide LXXXI by treatment with hydroxybenzotriazole, ethylenedichloride, and phenylenediamine.

Scheme 16

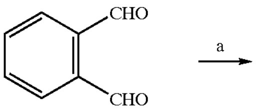

LXXIX

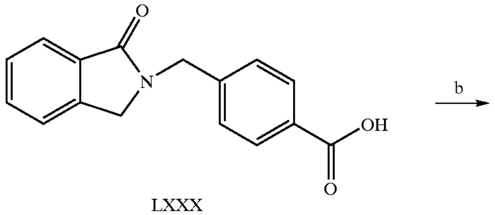

LXXX

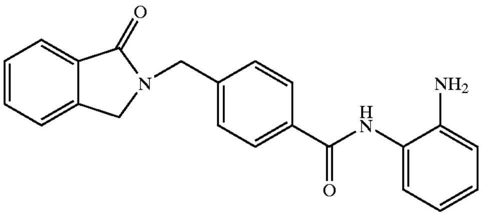

LXXXI a. p-aminomethylbenzoic/AcOH/5 min/reflux
b. HOBT/EDC/1,2,-diamino benzene Compounds such as LXXXVI and LXXXIX preferably may be prepared according to the procedures illustrated in Scheme 18. Phthalic anhydride LXXXV and p-aminomethylbenzoic acid are combined in acetic acid to produce an intermediate carboxylic acid, which is converted to the anilinylamide LXXXVI using procedures analogous to those set forth in Schemes 15 and 16 above.

The addition of 4-(2-aminoethyl)phenol to phthalic anhydride LXXXV in acetic acid affords the hydroxyl compound LXXXVII. The hydroxyl group of LXXXVII is converted to the triflate group of LXXXVIII by treatment with sodium hydride, THF, DMF, and phenylaminoditriflate. Treatment of LXXXVIII according to procedures analogous to those described for Scheme 3 above affords the anilinylamide LXXXIX.

Scheme 18

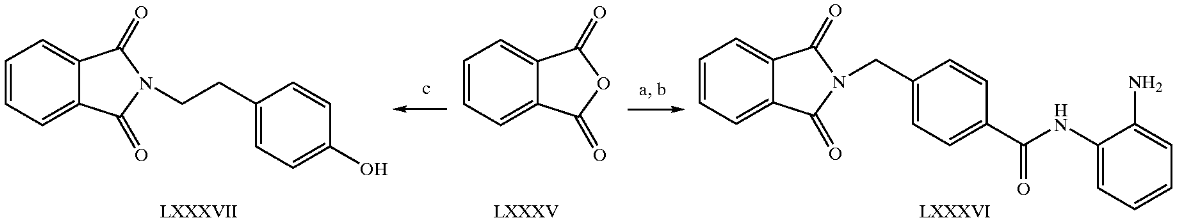

LXXXVII LXXXV LXXXVI

-continued

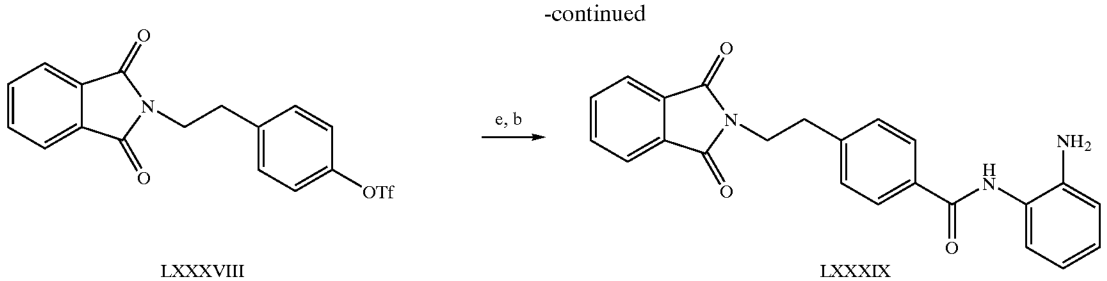

LXXXVIII LXXXIX a. p-aminomethylbenzoic acid/AcOH/reflux/3 hrs
b. HOBT/EDC/1,2-diamino benzene
c. 4-(2-aminoethyl)phenol/AcOH/5 hrs/reflux
d. $PhNTf_2$/NaH/ THF—DMF /30 min/0° C.
e. 1. CO/$Pd(OAc)_2$/dppf/$Et_3N$/ MeOH—DMF /4 days/75° C.
2. AcOH/HCl/3 hrs/reflux Compounds such as XCI–XCVI preferably may be prepared according to the synthetic route depicted in Scheme 19. Treatment of isatoic anhydride XC with p-aminomethylbenzoic acid in water and triethylamine, followed by formic acid affords an intermediate carboxylic acid, which is converted to anilinylamide XCI using procedures analogous to those described for Scheme 16 above.

Alternatively, treatment of isatoic acid XC with p-aminomethylbenzoic acid in water and triethylamine, follwed by hydrochloric acid and sodium nitrite affords an intermediate carboxylic acid, which is converted to anilinylamide XCII using procedures analogous to those described for Scheme 16 above.

Alternatively, treatment of isatoic acid XC with p-aminomethylbenzoic acid in water and triethylamine affords benzoic acid XCIII. Treatment of XCIII with sodium hydroxide, dioxane, methylchloroformate, and methanol affords an intermediate quinazolinedione carboxylic acid, the acid moiety of which is then converted to the anilinylamide moiety of XCIV using procedures analogous to those described for Scheme 16 above. Alternatively, the intermediate quanzolinedione carboxylic acid in DMF is treated with potassium carbonate and methyl iodide to produce an intermediate benzoic acid methyl ester, which is converted to an intermediate benzoic acid by treatment with sodium hydroxide, methanol, and water. The benzoic acid is then converted to the corresponding anilinylamide XCV using procedures analogous to those described for Scheme 16 above.

Alternatively, treatment of XCIII with acetic anhydride followed by acetic acid produces an intermediate carboxylic acid, which is converted to anilinylamide XCVI using procedures analogous to those described for Scheme 16 above.

Scheme 19

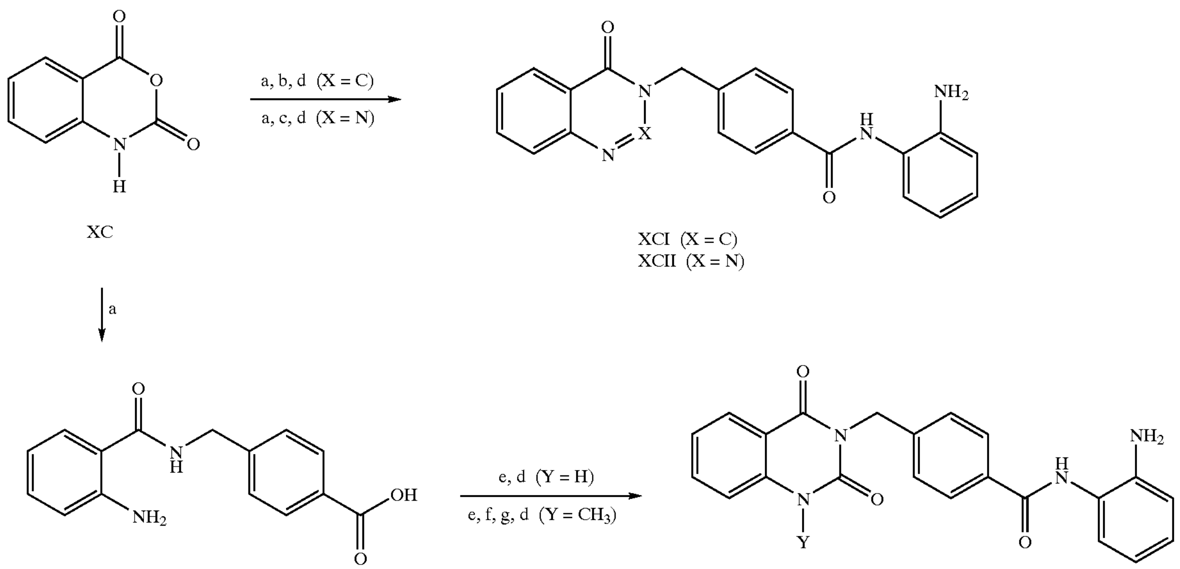

XC

XCI (X = C)
XCII (X = N)

XCIII

XCIV (Y = H)
XCV (Y = $CH_3$)

-continued

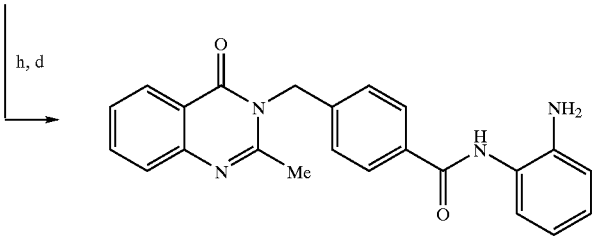

XCVI a. p-aminomethylbezoic acid/$H_2O$/$Et_3N$/3 hrs/40° C.
b. HCOOH/reflux/6 hrs
c. $NaNO_2$/HCl/0° C./2 hrs, then rt/12 hrs
d. HOBT/EDC/1,2-diamino benzene
e. ClCOOMe/KOH/2 hrs, 0° C.
f. RI/$K_2CO_3$/DMF/rt
g. NaOH/MeOH/$H_2O$
h. $Ac_2O$/1 hour/reflux then AcOH/48 hrs/reflux Compounds such as C preferably may be prepared as outlined in Scheme 20. Alkylamine XCVII is treated with thiocarbonyl diimidazole in dichloromethane, follwed by ammonium hydroxide to afford thiourea XCVIII. Treatment of thiourea XCVIII with methylmethoxyacrylate in dioxane and N-bromosuccinimide produces thiazole ester IC. The ester IC is converted to the corresponding anilinylamine C using procedures analogous to those set forth in Scheme 1 above.

Scheme 20

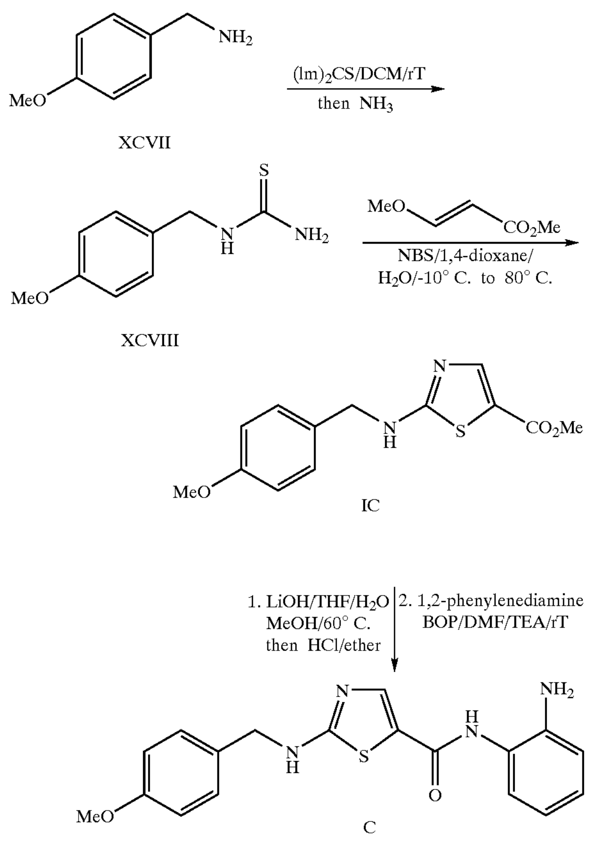

XCVII

XCVIII

IC

C

Compounds of formula (3), wherein $X^2$ is a chemical bond and $Cy^3$ has an amino substituent preferably may be prepared according to the synthetic route depicted in Scheme 21. Thus, protected iodoarylanilinylamide CI is treated according to procedures analogous to those described for Scheme 15 above afford the diarylanilinylamide CII. The aldehyde moiety in CII is converted to the corresponding secondary amine moiety by treatment with the primary amine and sodium triacetoxyborohydride followed by glacial acetic acid. The resultant compound is deprotected to yield CIII using procedures analogous to those set forth in Scheme 3 above.

Scheme 21

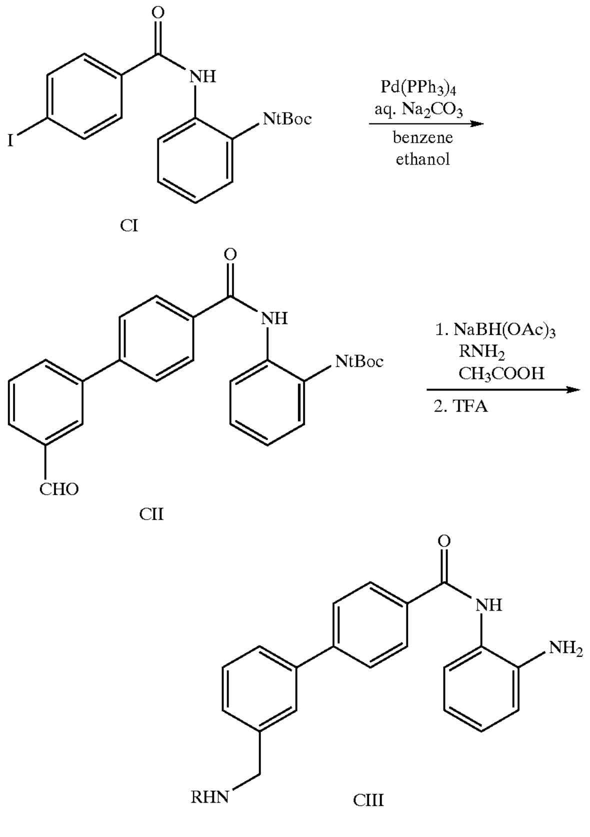

CI

CII

CIII

Compounds of formula (3), wherein $X^2$ comprises an alkynylene moiety, and compounds of formula (4), wherein $X^3$ comprises an alkynylene moiety, preferably may be prepared as outlined in Scheme 22. Treatment of protected iodoarylanilinylamide CI with triphenylphosphine palladium chloride, cuprous iodide, and 1-ethynylcyclohexylamine affords the alkynylarylanilinylamide CIV. The primary amine moiety in CIV is converted to the corresponding secondary amine and the aniline moiety is deprotected to afford CV using procedures analogous to those described for Scheme 21 above.

Scheme 22

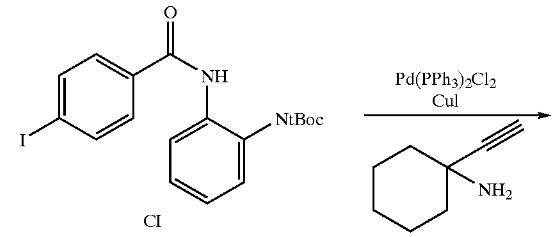

CI

-continued

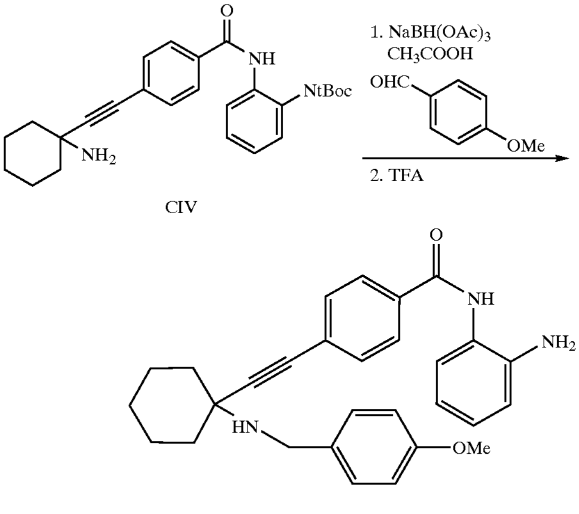

CIV

CV

Scheme 24

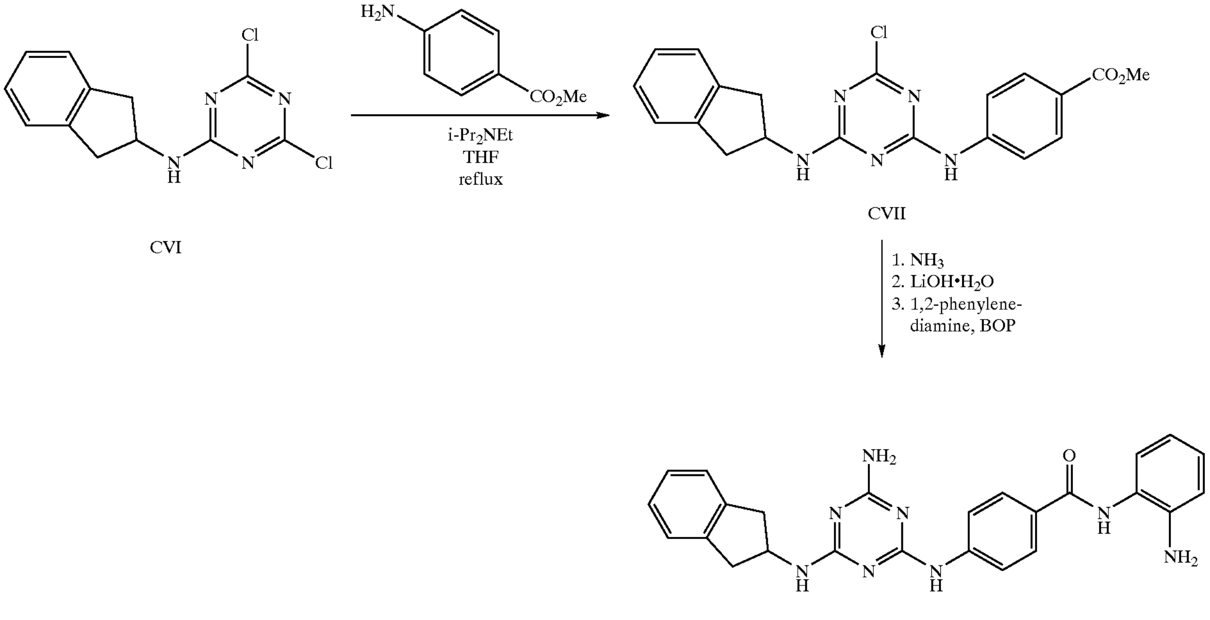

CVI

CVII

CVIII

Compounds such as CVIII preferably may be prepared according to the synthetic route depicted in Scheme 24. Dichloroaminotriazine CVI is treated with methyl-4-aminobenzoate in the presence of diisopropylethylamine to produce diaminotriazine CVII. Addition of ammonia gas and dioxane, followed by a saponification and a peptide coupling using the same procedures analogous to those described for Scheme 1 above.

Scheme 30

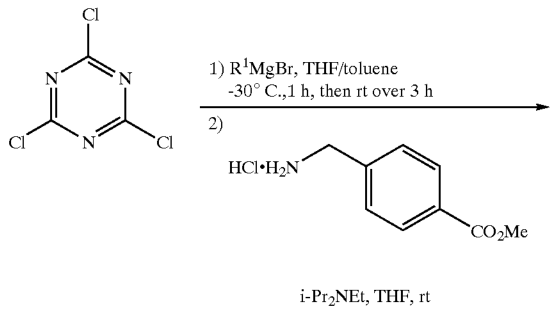

-continued

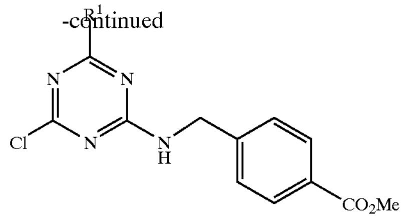

CIX

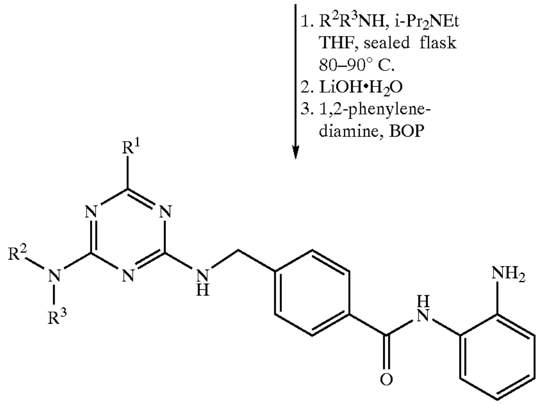

CX

Compounds such as CX preferably may be prepared according to the synthetic route depicted in Scheme 30. The Grignard reaction of trichloroaminotriazine with various alkyl magnesium bromide, followed by a treatment with methyl-4-aminobenzoate in the presence of diisopropylethylamine yields alkylaminotriazine CIX. Synthetic methods similar to those set forth in Scheme 1 above are then used to convert ester CIX to the corresponding anilinyl amide CX.

Scheme 32

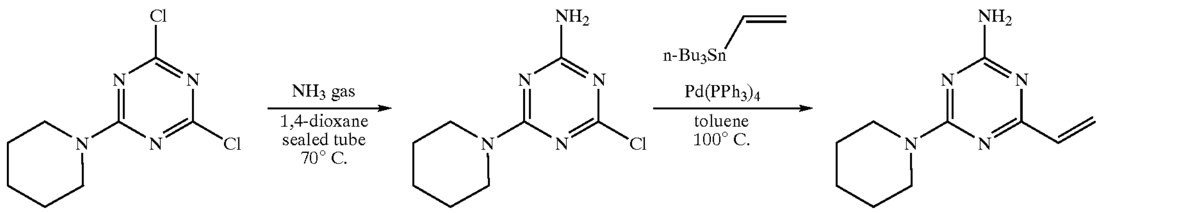

CXI

CXII

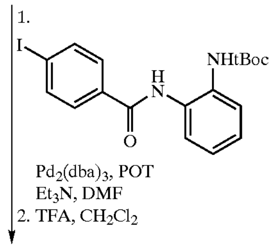

-continued

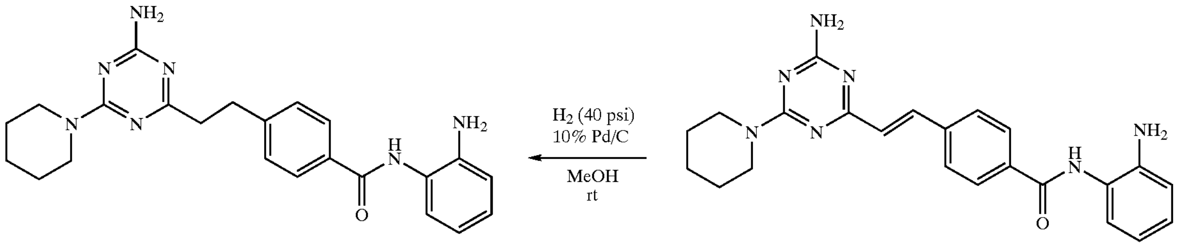

CXIV CXIII

Amination of dichlorotriazine proceeded using the usual condition described in Scheme 1 to afford CXI. Stille coupling using vinyl stannane provides CXII. Treatment with protected iodoanilide, triethylamine, POT and dibenzylacetone palladium then yields anilinylamide, which is deprotected with trifluoroacetic acid to provide the alkene CXIII. Hydrogenation of the alkene affords the final compound CXIV.

SchemE 33

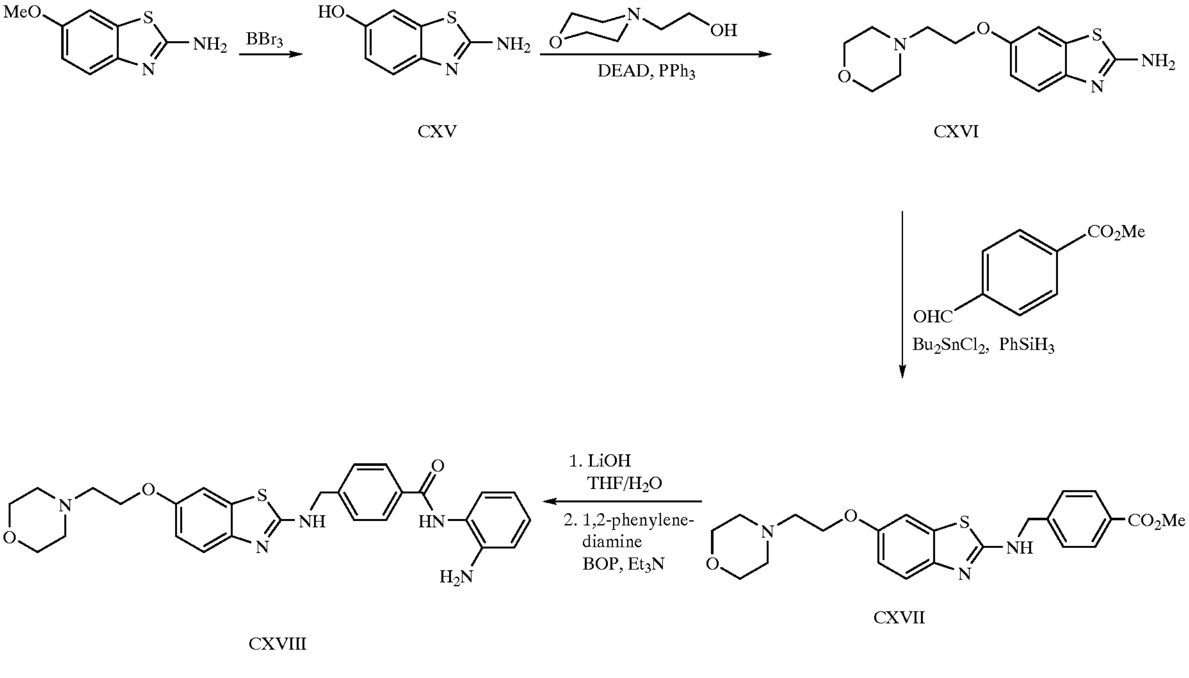

CXV CXVI CXVII CXVIII

Compounds such as CXVIII preferably may be prepared according to the synthetic route depicted in Scheme 33. Treatment of methoxyaminobenzothiazole with tribromide boron affords the corresponding acid CXV. Mitsunobu reaction using hydroxyethyl morpholine in the presence of diethylazodicarboxylate and triphenylphosphine yields the amine CXVI. Reductive amination with methyl-4-formylbenzoate using phenylsilane and tin catalyst yields to the ester CXVII. Saponification followed by the usual peptide coupling analogous to those describe for Scheme 1 above provides the desired anilide CXVIII.

Scheme 42
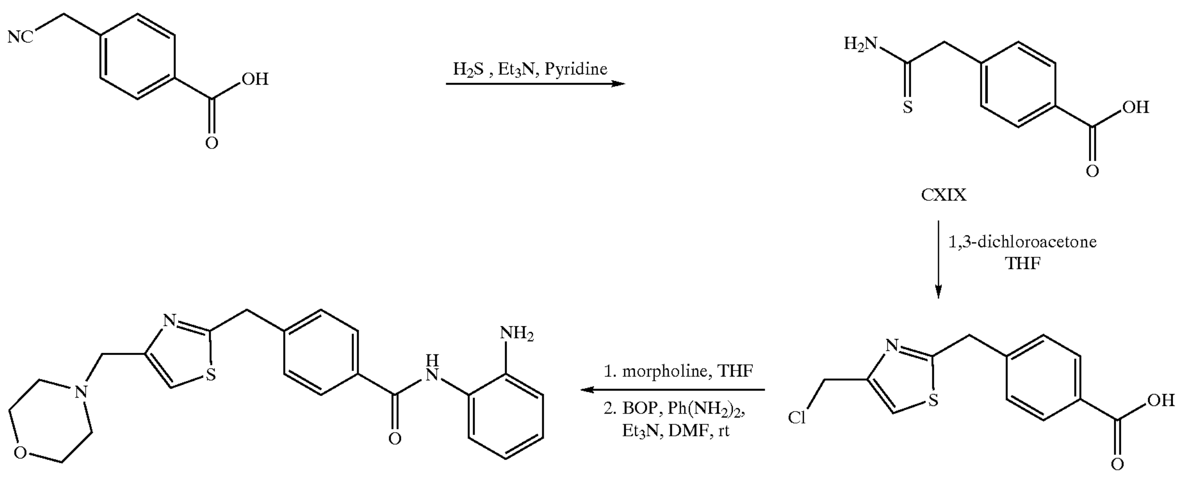
CXIX
CXXI CXX
Treatment 4-methylcyanobenzoic acid with hydrogen sulfide affords CXIX, which is subjected to cyclization in the presence of 1,3-dichloroacetone to yield CXX. Treatment with morpholine followed by a peptide coupling using the standard condition produces CXXI.
Scheme 49
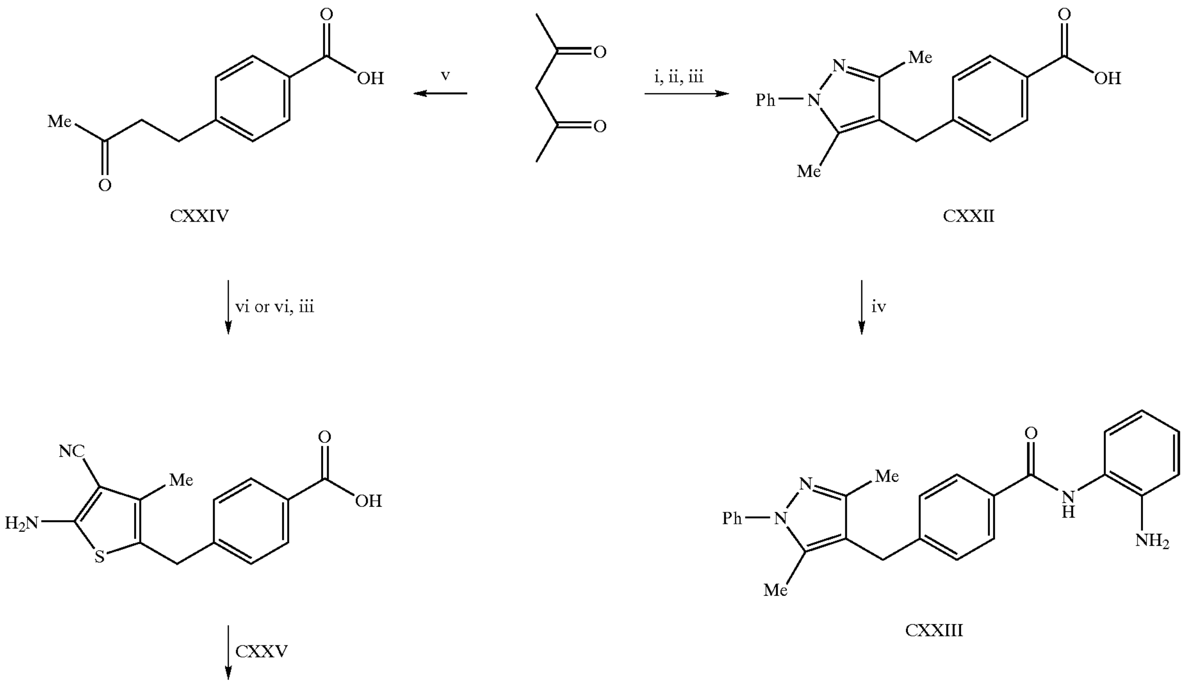
CXXIV CXXII
CXXIII
CXXV -continued

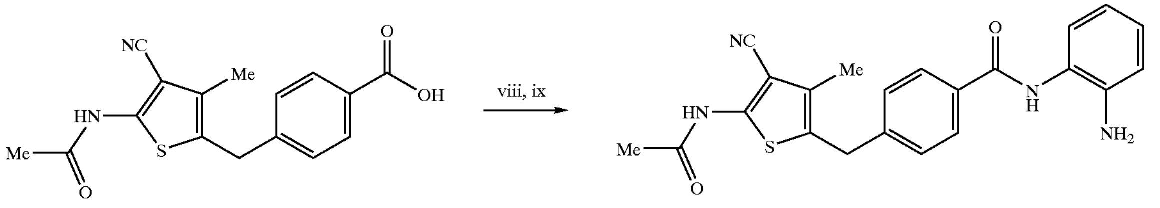

CXXVI CXXVII i: $BrCH_2C_6H_4COOMe/MeONa/THF$;
ii: $PhNHNH_2$;
iii: NaOH, then HCl
iv: HOBt/EDC × HCl then 1,2-diaminobenzene;
v: $BrCH_2C_6H_4COOMe/MeONa/MeOH$, then HCl/AcOH;
vi: $CH_2(CN)_2/S_8/Et_2NH$;
vii: AcCl;
viii: 2-N-Bocamino aniline;
ix: TFA;

Compounds such as CXXIII and CXXVII preferably may be prepared according to the synthetic scheme 49. Consecutive treatment of acetyl acetone with methyl bromomethylbenzoate in the presence of NaOMe and phenyl hydrazine followed by saponification, afforded the intermediate acid CXXII. This material was coupled with 1,2-diaminobenzene in a standard fashion to afford CXXIII.

Consecutive treatment of acetyl acetone with methyl bromomethylbenzoate in the presence of NaOMe and a 1:1 mixture AcOH—HCl (conc.) afforded the intermediate acid CXXIV. This keto-acid reacting with sulfur and malonodinitrile in the presence of a base, produced the thiophene CXXV, which was converted into the desired CX)VII using standard procedures.

Scheme 50

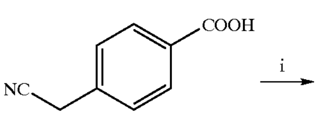

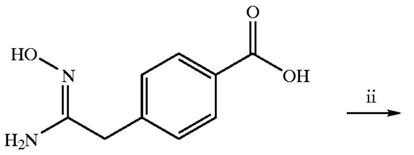

CXXVIII

-continued

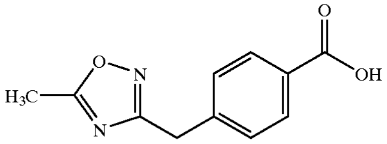

CXXIX iii

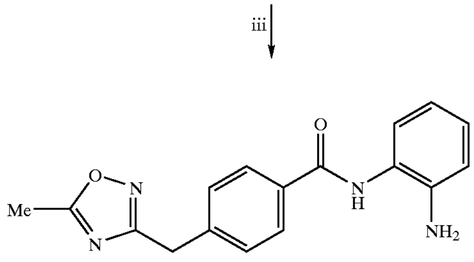

CXXX i: $NH_2OH/EtOH$;
ii: $Ac_2O$/pyridine;
iii: HOBt/EDC × HCl then 1,2-diaminobenzene;

Compounds such as CXXX preferably may be prepared according to the synthetic scheme 50. Treatment of 4-cyanomethylbenzoic acid with hydroxylamine produced the amidoxime CXXVIII, which upon treatment with acetic anhydride was converted into the oxadiazole CXXIX. The latter was coupled with 1,2-diaminobenzene in a standard fashion to afford CXXX.

Scheme 57

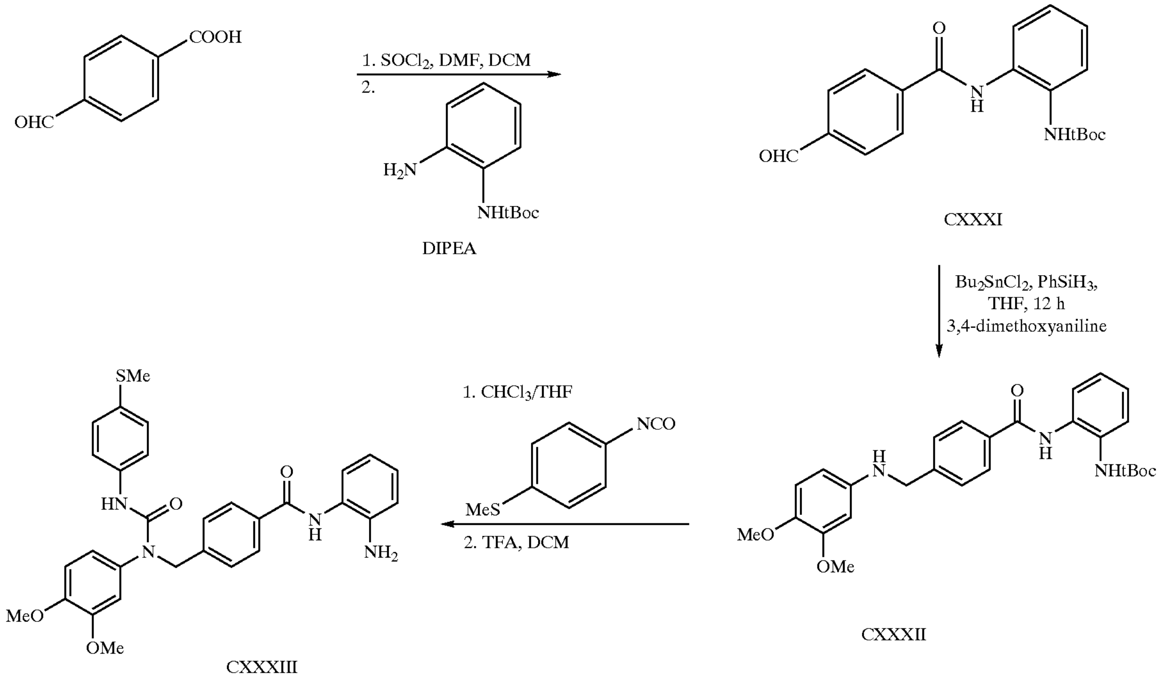

Compounds such as CXXXIII preferably may be prepared according to the synthetic route depicted in Scheme 57. Treatment of 4-formylbenzoic acid with thionyl chloride afford the acyl chloride which is coupled with protected anilide to produce CXXXI. Reductive amination with dimethoxyaniline using phenylsilane and tin catalyst yields to the protected anilide CXXXII. Treatment with isocyanate followed by deprotecton with trifluoroacetic acid provides the ureidoanilide CXXXIII.

Pharmaceutical Compositions

In a second aspect, the invention provides pharmaceutical compositions comprising an inhibitor of histone deacetylase according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain preferred embodiments, compounds of the invention are administered intravenously in a hospital setting. In certain other preferred embodiments, administration may preferably be by the oral route.

The characteristics of the carrier will depend on the route of administration. As used herein, the term “pharmaceutically acceptable” means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington’s Pharmaceutical Sciences, 18th Edition, ed. A. Gennaro, Mack Publishing Co., Easton, Pa., 1990.

As used herein, the term pharmaceutically acceptable salts refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z-, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01–3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

Inhibition of Histone Deacetylase

In a third aspect, the invention provides a method of inhibiting histone deacetylase in a cell, comprising contacting a cell in which inhibition of histone deacetylase is desired with an inhibitor of histone deacetylase according to the invention. Because compounds of the invention inhibit histone deacetylase, they are useful research tools for in vitro study of the role of histone deacetylase in biological processes. In addition, the compounds of the invention selectively inhibit certain isoforms of HDAC.

Measurement of the enzymatic activity of a histone deacetylase can be achieved using known methodologies. For example, Yoshida et al., J. Biol. Chem., 265: 17174–17179 (1990), describes the assessment of histone deacetylase enzymatic activity by the detection of acetylated histones in trichostabn A treated cells. Taunton et al., Science, 272: 408–411 (1996), similarly describes methods to measure histone deacetylase enzymatic activity using endogenous and recombinant HDAC-1.

In some preferred embodiments, the histone deacetylase inhibitor interacts with and reduces the activity of all histone deacetylases in the cell. In some other preferred embodiments according to this aspect of the invention, the histone deacetylase inhibitor interacts with and reduces the activity of fewer than all histone deacetylases in the cell. In certain preferred embodiments, the inhibitor interacts with and reduces the activity of one histone deacetylase (e.g., HDAC-1), but does not interact with or reduce the activities of other histone deacetylases (e.g., HDAC-2, HDAC-3, HDAC-4, HDAC-5, HDAC-6, HDAC-7, and HDAC-8). As discussed below, certain particularly preferred histone deacetylase inhibitors are those that interact with, and reduce the enzymatic activity of, a histone deacetylase that is involved in tumorigenesis. Certain other preferred histone deacetylase inhibitors interact with and reduce the enzymatic activity of a fungal histone deacetylase.

Preferably, the method according to the third aspect of the invention causes an inhibition of cell proliferation of the contacted cells. The phrase "inhibiting cell proliferation" is used to denote an ability of an inhibitor of histone deacetylase to retard the growth of cells contacted with the inhibitor as compared to cells not contacted. An assessment of cell proliferation can be made by counting contacted and non-contacted cells using a Coulter Cell Counter (Coulter, Miami, Fla.) or a hemacytometer. Where the cells are in a solid growth (e.g., a solid tumor or organ), such an assessment of cell proliferation can be made by measuring the growth with calipers and comparing the size of the growth of contacted cells with non-contacted cells.

Preferably, growth of cells contacted with the inhibitor is retarded by at least 50% as compared to growth of non-contacted cells. More preferably, cell proliferation is inhibited by 100% (i.e., the contacted cells do not increase in number). Most preferably, the phrase "inhibiting cell proliferation" includes a reduction in the number or size of contacted cells, as compared to non-contacted cells. Thus, an inhibitor of histone deacetylase according to the invention that inhibits cell proliferation in a contacted cell may induce the contacted cell to undergo growth retardation, to undergo growth arrest, to undergo programmed cell death (i.e., to apoptose), or to undergo necrotic cell death.

The cell proliferation inhibiting ability of the histone deacetylase inhibitors according to the invention allows the synchronization of a population of asynchronously growing cells. For example, the histone deacetylase inhibitors of the invention may be used to arrest a population of non-neoplastic cells grown in vitro in the G1 or G2 phase of the cell cycle. Such synchronization allows, for example, the identification of gene and/or gene products expressed during the G1 or G2 phase of the cell cycle. Such synchronization of cultured cells may also be useful for testing the efficacy of a new transfection protocol, where transfection efficiency varies and is dependent upon the particular cell cycle phase of the cell to be transfected. Use of the histone deacetylase inhibitors of the invention allows the synchronization of a population of cells, thereby aiding detection of enhanced transfection efficiency.

In some preferred embodiments, the contacted cell is a neoplastic cell. The term "neoplastic cell" is used to denote a cell that shows aberrant cell growth. Preferably, the aberrant cell growth of a neoplastic cell is increased cell growth. A neoplastic cell may be a hyperplastic cell, a cell that shows a lack of contact inhibition of growth in vitro, a benign tumor cell that is incapable of metastasis in vivo, or a cancer cell that is capable of metastasis in vivo and that may recur after attempted removal. The term "tumorigenesis" is used to denote the induction of cell proliferation that leads to the development of a neoplastic growth. In some embodiments, the histone deacetylase inhibitor induces cell differentiation in the contacted cell. Thus, a neoplastic cell, when contacted with an inhibitor of histone deacetylase may be induced to differentiate, resulting in the production of a non-neoplastic daughter cell that is phylogenetically more advanced than the contacted cell.

In some preferred embodiments, the contacted cell is in an animal. Thus, the invention provides a method for treating a cell proliferative disease or condition in an animal, comprising administering to an animal in need of such treatment a therapeutically effective amount of a histone deacetylase inhibitor of the invention. Preferably, the animal is a mammal, more preferably a domesticated mammal. Most preferably, the animal is a human.

The term "cell proliferative disease or condition" is meant to refer to any condition characterized by aberrant cell growth, preferably abnormally increased cellular proliferation. Examples of such cell proliferative diseases or conditions include, but are not limited to, cancer, restenosis, and psoriasis. In particularly preferred embodiments, the invention provides a method for inhibiting neoplastic cell proliferation in an animal comprising administering to an animal having at least one neoplastic cell present in its body a therapeutically effective amount of a histone deacetylase inhibitor of the invention.

It is contemplated that some compounds of the invention have inhibitory activity against a histone deacetylase from a protozoal source. Thus, the invention also provides a method for treating or preventing a protozoal disease or infection, comprising administering to an animal in need of such treatment a therapeutically effective amount of a histone deacetylase inhibitor of the invention. Preferably the animal is a mammal, more preferably a human. Preferably, the histone deacetylase inhibitor used according to this embodiment of the invention inhibits a protozoal histone deacetylase to a greater extent than it inhibits mammalian histone deacetylases, particularly human histone deacetylases.

The present invention further provides a method for treating a fungal disease or infection comprising administering to an animal in need of such treatment a therapeutically effective amount of a histone deacetylase inhibitor of the invention. Preferably the animal is a mammal, more preferably a human. Preferably, the histone deacetylase inhibitor used according to this embodiment of the invention inhibits a fungal histone deacetylase to a greater extent than it inhibits mammalian histone deacetylases, particularly human histone deacetylases.

The term therapeutically effective amount" is meant to denote a dosage sufficient to cause inhibition of histone deacetylase activity in the cells of the subject, or a dosage sufficient to inhibit cell proliferation or to induce cell differentiation in the subject. Administration may be by any route, including, without limitation, parenteral, oral, sublingual, transdermal, topical, intranasal, intratracheal, or intrarectal. In certain particularly preferred embodiments, compounds of the invention are administered intravenously in a hospital setting. In certain other preferred embodiments, administration may preferably be by the oral route.

When administered systemically, the histone deacetylase inhibitor is preferably administered at a sufficient dosage to attain a blood level of the inhibitor from about 0.01 μM to about 100 μM, more preferably from about 0.05 μM to about 50 μM, still more preferably from about 0.1 μM to about 25 μM, and still yet more preferably from about 0.5 μM to about 25 μM. For localized administration, much lower concentrations than this may be effective, and much higher concentrations may be tolerated. One of skill in the art will appreciate that the dosage of histone deacetylase inhibitor necessary to produce a therapeutic effect may vary considerably depending on the tissue, organ, or the particular animal or patient to be treated.

In certain preferred embodiments of the third aspect of the invention, the method further comprises contacting the cell with an antisense oligonucleotide that inhibits the expression of a histone deacetylase. The combined use of a nucleic acid level inhibitor (e.g., antisense oligonucleotide) and a protein level inhibitor (i.e., inhibitor of histone deacetylase enzyme activity) results in an improved inhibitory effect, thereby reducing the amounts of the inhibitors required to obtain a given inhibitory effect as compared to the amounts necessary when either is used individually. The antisense oligonucleotides according to this aspect of the invention are complementary to regions of RNA or double-stranded DNA that encode HDAC-1, HDAC-2, HDAC-3, HDAC-4, HDAC-5, HDAC-6, HDAC-7, and/or HDAC-8 (see e.g., GenBank Accession Number U50079 for HDAC-1, GenBank Accession Number U31814 for HDAC-2, and GenBank Accession Number U75697 for HDAC-3).

For purposes of the invention, the term "oligonucleotide" includes polymers of two or more deoxyribonucleosides, ribonucleosides, or 2'-substituted ribonucleoside residues, or any combination thereof. Preferably, such oligonucleotides have from about 6 to about 100 nucleoside residues, more preferably from about 8 to about 50 nucleoside residues, and most preferably from about 12 to about 30 nucleoside residues. The nucleoside residues may be coupled to each other by any of the numerous known internucleoside linkages. Such internucleoside linkages include without limitation phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane.

For purposes of the invention the term "2'-substituted ribonucleoside" includes ribonucleosides in which the hydroxyl group at the 2' position of the pentose moiety is substituted to produce a 2'-O-substituted ribonucleoside. Preferably, such substitution is with a lower alkyl group containing 1–6 saturated or unsaturated carbon atoms, or with an aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups. The term "2'-substituted ribonucleoside" also includes ribonucleosides in which the 2'-hydroxyl group is replaced with an amino group or with a halo group, preferably fluoro.

Particularly preferred antisense oligonucleotides utilized in this aspect of the invention include chimeric oligonucleotides and hybrid oligonucleotides.

For purposes of the invention, a "chimeric oligonucleotide" refers to an oligonucleotide having more than one type of internucleoside linkage. One preferred example of such a chimeric oligonucleotide is a chimeric oligonucleotide comprising a phosphorothioate, phosphodiester or phosphorodithioate region, preferably comprising from about 2 to about 12 nucleotides, and an alkylphosphonate or alkylphosphonothioate region (see e.g., Pederson et al. U.S. Pat. Nos. 5,635,377 and 5,366,878). Preferably, such chimeric oligonucleotides contain at least three consecutive internucleoside linkages selected from phosphodiester and phosphorothioate linkages, or combinations thereof.

For purposes of the invention, a "hybrid oligonucleotide" refers to an oligonucleotide having more than one type of nucleoside. One preferred example of such a hybrid oligonucleotide comprises a ribonucleotide or 2'-substituted ribonucleotide region, preferably comprising from about 2 to about 12 2'-substituted nucleotides, and a deoxyribonucleotide region. Preferably, such a hybrid oligonucleotide contains at least three consecutive deoxyribonucleosides and also contains ribonucleosides, 2'-substituted ribonucleosides, preferably 2'-O-substituted ribonucleosides, or combinations thereof (see e.g., Metelev and Agrawal, U.S. Pat. No. 5,652,355).

The exact nucleotide sequence and chemical structure of an antisense oligonucleotide utilized in the invention can be varied, so long as the oligonucleotide retains its ability to inhibit expression of the gene of interest. This is readily determined by testing whether the particular antisense oligonucleotide is active. Useful assays for this purpose include quantitating the mRNA encoding a product of the gene, a Western blotting analysis assay for the product of the gene, an activity assay for an enzymatically active gene product, or a soft agar growth assay, or a reporter gene construct assay, or an in vivo tumor growth assay, all of which are described in detail in this specification or in Ramchandani et al. (1997) Proc. Natl. Acad. Sci. USA 94: 684–689.

Antisense oligonucleotides utilized in the invention may conveniently be synthesized on a suitable solid support using well known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG) (see, e.g., Pon, R. T. (1993) Methods in Molec. Biol. 20: 465–496).

Particularly preferred oligonucleotides have nucleotide sequences of from about 13 to about 35 nucleotides which include the nucleotide sequences shown in Table 1. Yet additional particularly preferred oligonucleotides have nucleotide sequences of from about 15 to about 26 nucleotides of the nucleotide sequences shown in Table 1.

TABLE 1

| Oligo | Target | Accession Number | Nucleotide Position | Sequence | position within Gene |
|---|---|---|---|---|---|
| HDAC1 AS1 | Human HDAC1 | U50079 | 1585–1604 | 5'-GAAACGTGAGGGACTCAGCA-3' | 3'-UTR |
| HDAC1 AS2 | Human HDAC1 | U50079 | 1565–1584 | 5'-GGAAGCCAGAGCTGGAGAGG-3' | 3'-UTR |
| HDAC1 MM | Human HDAC1 | U50079 | 1585–1604 | 5'-GTTAGGTGAGGCACTGAGGA-3' | 3'-UTR |
| HDAC2 AS | Human HDAC2 | U31814 | 1643–1622 | 5'-GCTGAGCTGTTCTGATTTGG-3' | 3'-UTR |
| HDAC2 MM | Human HDAC2 | U31814 | 1643–1622 | 5'-CGTGAGCACTTCTCATTTCC-3' | 3'-UTR |
| HDAC3 AS | Human HDAC3 | AF039703 | 1276–1295 | 5'-CGCTTTCCTTGTCATTGACA-3' | 3'-UTR |
| HDAC3 MM | Human HDAC3 | AF039703 | 1276–1295 | 5'-GCCTTTCCTACTCATTGTGT-3' | 3'-UTR |
| HDAC4 AS1 | Human HDAC4 | AB006626 | 514–33 | 5-GCTGCCTGCCGTGCCCACCC-3' | 5'-UTR |
| HDAC4 MM1 | Human HDAC4 | AB006626 | 514–33 | 5'-CGTGCCTGCGCTGCCCACGG-3' | 5'-UTR |
| HDAC4 AS2 | Human HDAC4 | AB006626 | 7710–29 | 5'-TACAGTCCATGCAACCTCCA-3' | 3'-UTR |
| HDAC4 MM4 | Human HDAC4 | AB006626 | 7710–29 | 5'-ATCAGTCCAACCAACCTCGT-3' | 3'-UTR |
| HDAC5 AS | Human HDAC5 | AF039691 | 2663–2682 | 5'-CTTCGGTCTCACCTGCTTGG-3' | 3'-UTR |
| HDAC6 AS | Human HDAC6 | AJ011972 | 3791–3810 | 5'-CAGGCTGGAATGAGCTACAG-3' | 3'-UTR |
| HDAC6 MM | Human HDAC6 | AJ011972 | 3791–3810 | 5'-GACGCTGCAATCAGGTAGAC-3' | 3'-UTR |
| HDAC7 AS | Human HDAC7 | AF239243 | 2896–2915 | 5'-CTTCAGCCAGGATGCCCACA-3' | 3'-UTR |
| HDAC8 AS1 | Human HDAC8 | AF230097 | 51–70 | 5'-CTCCGGCTCCTCCATCTTCC-3' | 5'-UTR |
| HDAC8 AS2 | Human HDAC8 | AF230097 | 1328–1347 | 5'-AGCCAGCTGCCACTTGATGC-3' | 3'-UTR |

The following examples are intended to further illustrate certain preferred embodiments of the invention, and are not intended to limit the scope of the invention.

EXAMPLES

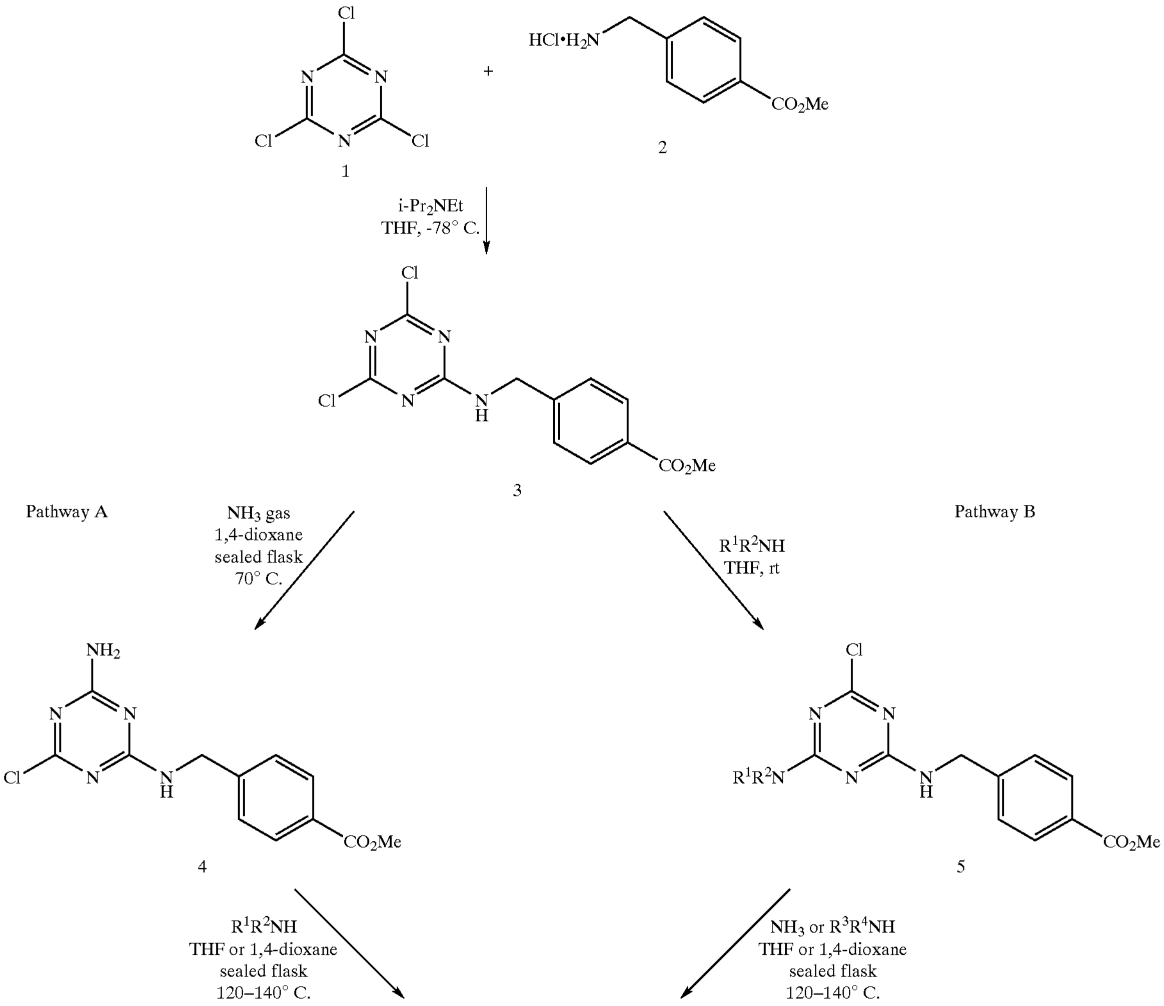

-continued

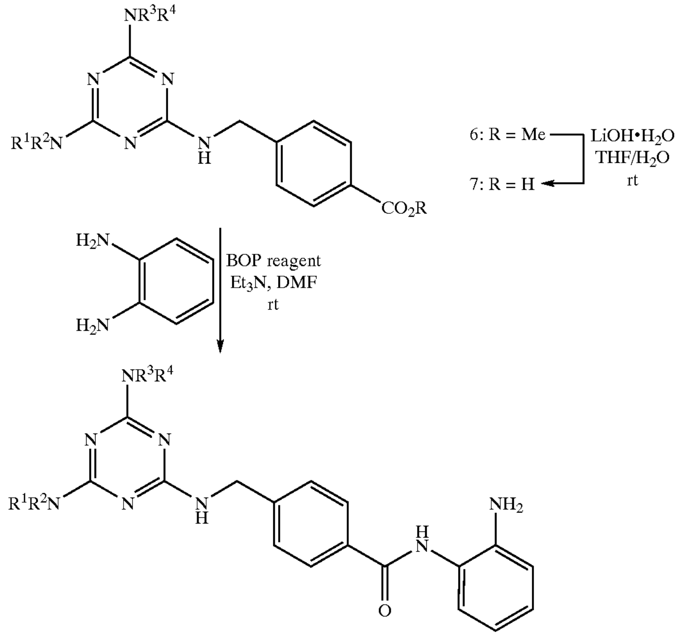

8
Example 1

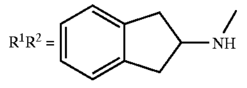

$R^3R^4$ = H

Example 1

4-{[4-Amino-6-(2-indanyl-amino)-[1,3,5]-triazin-2-yl-amino]-methyl}-N-(2-amino-phenyl)-benzamide (Compound 8)

Step 1: Methyl-4-[(4,6-dichloro-[1,3,5-triazin-2-yl-amino)-methyl]-benzoate (Compound 3)

To a stirred solution at −78° C. of cyanuric chloride 1 (8.23 g, 44.63 mmol) in anhydrous THF (100 mL) under nitrogen was added a suspension of methyl 4-(aminomethyl) benzoate.HCl 2 (10.00 g, 49.59 mmol), in anhydrous THF (50 mL), followed by i-$Pr_2$NEt (19.00 mL, 109.10 mmol). After 30 min, the reaction mixture was poured into a saturated aqueous solution of $NH_4Cl$, and diluted with AcOEt. After separation, the organic layer was successively washed with sat. $NH_4Cl$, $H_2O$ and brine, dried over anhydrous $MgSO_4$, filtered and concentrated. The crude residue was then purified by flash chromatography on silica gel (AcOEt/$CH_2Cl_2$: 5/95) to afford the title compound 3 (12.12 g, 38.70 mmol, 87% yield) as a pale yellow solid. $^1H$ NMR (300 MHz, $CDCl_3$) δ (ppm): AB system ($\delta_A$=8.04, $\delta_B$=7.38, J=8.5 Hz, 4H), 6.54 (bt, 1H), 4.76 (d, J=6.3 Hz, 2H), 3.93 (s, 3H).

Pathway A

Step 2: Methyl-4-[(4amino-6-chloro-[1,3,5]triazin-2-yl-amino)-methyl]-benzoate (Compound 4)

In a 150 mL sealed flask, a solution of 3 (6.00 g, 19.16 mmol) in anhydrous 1,4-dioxane (60 mL) was stirred at room temperature, saturated with $NH_3$ gas for 5 min, and warmed to 70° C. for 6 h. The reaction mixture was allowed to cool to room temperature, the saturation step with $NH_3$ gas was repeated at room temperature for 5 min, and the reaction mixture was warmed to 70° C. again for 18 h. Then, the reaction mixture was allowed to cool to room temperature, poured into a saturated aqueous solution of $NH_4Cl$, and diluted with AcOEt. After separation, the organic layer was successively washed with sat. $NH_4Cl$, $H_2O$ and brine, dried over anhydrous $MgSO_4$, filtered and concentrated. The crude residue was then purified by flash chromatography on silica gel (AcOEt/$CH_2Cl_2$: 30/70) to afford the title compound 4 (5.16 g, 17.57 mmol, 91% yield) as a white solid. $^1H$ NMR (300 MHz, $CDCl_3$) δ (ppm): AB system ($\delta_A$=8.01, $\delta_B$=7.35, J=8.1 Hz, 4H), 5.79 (bs, 1H), 5.40–5.20 (m, 2H), 4.72–4.63 (m, 2H), 3.91 (s, 3H).

Pathway B

Step 2: Methyl 4-[(4-chloro-6-(2-indanyl-amino)-(1,3,5] triazin-2-yl-amino)-methyl]-benzoate (Compound 5)

To a stirred solution at room temperature of 3 (3.00 g, 9.58 mmol) in anhydrous THF (50 mL) under nitrogen were added i-$Pr_2$NEt (8.34 mL, 47.90 mmol) and 2-aminoindan.HCl (1.95 g, 11.50 mmol) or $R^1R^2$NH (1.2 equiv), respectively. After 18 h, the reaction mixture was poured into a saturated aqueous solution of $NH_4Cl$, and diluted with AcOEt. After separation, the organic layer was successively washed with sat. $NH_4Cl$, $H_2O$ and brine, dried over anhydrous $MgSO_4$, filtered and concentrated to afford the title compound 5 (4.06 g, 9.91 mmol, quantitative yield) as a white powder. $^1H$ NMR (300 MHz, $CDCl_3$)δ (ppm): mixture of rotamers, 8.06–7.94 (m, 2H), 7.43–7.28 (m, 2H), 7.24–7.12 (m, 4H), 6.41 and 6.05 (2 bt, 1H), 5.68–5.44 (m, 1H), 4.92–4.54 (m, 3H), 3.92 (bs, 3H), 3.41–3.12 (m, 2H), 2.90–2.70 (m, 2H).

Step 3: Methyl-4-[(4-amino-6-(2-indanyl-amino)-[1,3,5] triazin-2-yl-amino)-methyl]-benzoate (Compound 6)

General Procedure for the Amination with $NH_3$ Gas:

In a 150 mL sealed flask, a solution of 5 (3.90 g, 9.51 mmol) in anhydrous 1,4-dioxane (80 mL) was stirred at room temperature, saturated with $NH_3$ gas for 5 min, and warmed to 140° C. for 6 h. The reaction mixture was allowed to cool to room temperature, the saturation step with $NH_3$ gas was repeated for 5 min, and the reaction mixture was warmed to 140° C. again for 18 h. Then, the reaction mixture was allowed to cool to room temperature, poured into a saturated aqueous solution of $NH_4Cl$, and diluted with AcOEt. After separation, the organic layer was successively washed with sit $NH_4Cl$, $H_2O$ and brine, dried over anhydrous $MgSO_4$, filtered and concentrated. The crude residue was then purified by flash chromatography on silica gel ($MeOH/CH_2Cl_2$: 3/97) to afford the title compound 6 (3.50 g, 8.96 mmol, 94% yield) as a pale yellow sticky solid. $^1H$ NMR (300 MHz, $CDCl_3$) δ (ppm): 7.99 (bd, J=8.2 Hz, 2H), 7.41–7.33 (m, 2H), 7.24–7.13 (m, 4H), 5.50–5.00 (m, 2H), 4.90–4.55 (m, 5H), 3.92 (s, 3H), 3.40–3.10 (m, 2H), 2.90–2.70 (m, 2H). $^{13}C$ NMR: (75 MHz, $CDCl_3$) δ (ppm): 166.88, 167.35, 166.07, 144.77, 141.07, 129.82, 128.93, 127.01, 126.61, 124.70, 52.06, 51.80, 44.25, 40.16. HRMS (calc.): 390.1804, (found): 390.1800.

Pathways A and B, Step 3. General Procedure with Primary and/or Secondary Amines:

In a 50–75 mL sealed flask, a stirred solution of 4 (500 mg, 1.70 mmol, 1 equiv), i-$Pr_2NEt$ (1.48 mL, 8.51 mmol, 5 equiv) and $R^1R^2NH$ or $R^3R^4NH$ (1.5–3 equiv) in anhydrous THF or 1,4-dioxane (20–30 mL) was warmed to 120–140° C. for 15–24 h. Then, the reaction mixture was allowed to cool to room temperature, poured into a saturated aqueous solution of $NH_4Cl$, and diluted with AcOEt. After separation, the organic layer was successively washed with sat. $NH_4Cl$, $H_2O$ and brine, dried over anhydrous $MgSO_4$, filtered and concentrated. The crude residue was then purified by flash chromatography on silica gel to afford the title compound.

Step 4: 4-[(4-Amino-6-(2-indanyl-amino)-[1,3,5]triazin-2-yl-amino)-methyl]-benzoic acid (Compound 7)

To a stirred solution at room temperature of 6 (2.07 g, 5.30 mmol) in THF (50 mL) was added a solution of $LiOH.H_2O$ (334 mg, 7.96 mmol) in water (25 mL). After 18 h, the reaction mixture was diluted in water and acidified with 1 N HCl until pH 5–6 in order to get a white precipitate. After 1 h, the suspension was filtered off and the cake was abundantly washed with water, and dried to afford the title compound 7 (1.73 g, 4.60 mmol, 87% yield) as a white solid. $^1H$ NMR (300 MHz, acetone-$d_6$) δ (ppm): 8.05 (bd, J=8.1 Hz, 2H), 7.56–7.42 (m, 2H), 7.30–7.10 (m, 4H), 5.90–5.65 (m, 2H), 4.85–4.60 (m, 4H), 3.40–2.80 (m, 4H). HRMS (calc.): 376.1648, (found): 376.1651.

Step 5: 4-{[4-Amino-6-(2-indanyl-amino)-[1,3,5]-triazin-2-yl-amino]-methyl}-N-(2-amino-phenyl-(benzamide (Compound 8)

To a stirred solution at room temperature of 7 (200 mg, 0.53 mmol) in anhydrous DMF (5 mL) under nitrogen were added $Et_3N$ (74 μl, 0.53 mmol) and BOP reagent (282 mg, 0.64 mmol), respectively. After 40 min, a solution of 1,2-phenylenediamine (64 mg, 0.58 mmol), $Et_3N$ (222 μl, 1.59 mmol) in anhydrous DMF (2 mL) was added dropwise. After 1.5 h, the reaction mixture was poured into a saturated aqueous solution of $NH_4Cl$, and diluted with AcOEt. After separation, the organic layer was successively washed with sat. $NH_4Cl$, $H_2O$ and brine, dried over anhydrous $MgSO_4$, filtered and concentrated. The crude residue was then purified by flash chromatography on silica gel ($MeOH/CH_2Cl_2$: 2/98→5/95) to afford the title compound 8 (155 mg, 0.33 mmol, 63% yield) as a pale yellow foam. $^1H$ NMR (300 MHz, acetone-$d_6$) δ (ppm): 9.04 (bs, 1H), 7.96 (bd, J=8.0 Hz, 2H), 7.50–7.40 (m, 2H), 7.30 (dd, J=8.0 Hz, 1.4 Hz, 1H), 7.22–7.08 (m, 4H), 6.99 (ddd, J=8.0 Hz, 7.5 Hz, 1.5 Hz, 1H), 6.86 (dd, J=8.0 Hz, 1.4 Hz, 1H), 6.67 (dt, J=7.5 Hz, 1.4 Hz, 1H), 6.60–5.49 (m, 4H), 4.80–4.50 (m, 4H), 3.30–3.08 (m, 2H), 2.96–2.74 (m, 2H).

Examples 2–28

Examples 2 to 28 describe the preparation of compounds 9 to 35 using the same procedure as described for compound 8 of Example 1. Characterization data are presented in Tables 2a and 2b.

TABLE 2a

Characterization of Compounds Prepared in Examples 2–28

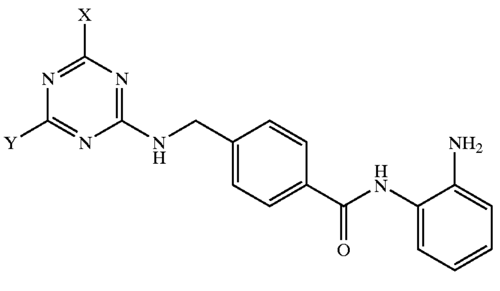

| Ex. | Cpd | Y | X | Name | Characterization | Schm |
|---|---|---|---|---|---|---|
| 2 | 9 | 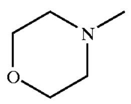 | $NH_2$ | 4-[(4-amino-6-morpholin-4-yl-[1,3,5]-triazin-2-ylamino)-methyl]-N-(2-amino-phenyl)-benzamide | $^1H$ NMR ($CDCl_3$) δ (ppm): 8.02 (s, 1H), 7.79 (d, J=8.0Hz, 2H), 7.34 (d, J=8.0Hz, 2H), 7.31 (m, 1H), 7.08 (dt, J=7.6Hz, 1.5Hz, 1H), 6.82 (t, J=6.7Hz, 2H), 5.62 (t, J=5.9Hz, 1H), 4.90 (bs, 2H), 4.61 (d, J=6.0Hz, 2H), 3.75–3.62 (m, 10H). | 1A |

TABLE 2a-continued

Characterization of Compounds Prepared in Examples 2–28

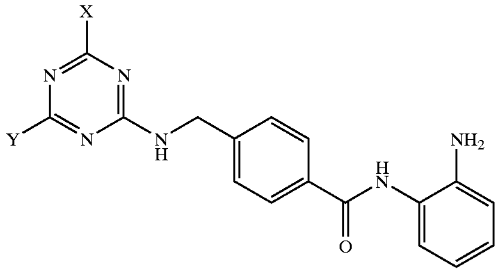

| Ex. | Cpd | Y | X | Name | Characterization | Schm |
|---|---|---|---|---|---|---|
| 3 | 10 | 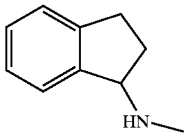 | $NH_2$ | 4-{[4-amino-6-(1-indanyl-amino)-[1,3,5]-triazin-2-ylamino]-methyl}-N-(2-amino-phenyl)-benzamide | $^1$H NMR (acetone-$d_6$) δ (ppm): 9.07 (bs, 1H), 8.05–7.95 (m, 2H), 7.55–7.45 (m, 2H), 7.37–7.10 (m, 5H), 7.04 (dt, J=7.6Hz, 1.6Hz, 1H), 6.90 (dd, J=8.0Hz, 1.4Hz, 1H), 6.71 (dt, J=7.6Hz, 1.4Hz, 1H), 6.65–5.55 (m, 5H), 4.75–4.60 (m, 3H), 3.05–2.75 (m, 2H), 2.60–2.45 (m, 1H)), 2.00–1.84 (m, 1H). HRMS (calc.): 466.2229, (found): 466.2225 | 1A |
| 4 | 11 | 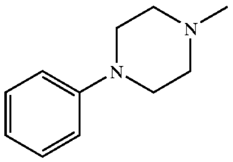 | $NH_2$ | N-(2-Amino-phenyl)-4-{[4-amino-6-(4-phenyl-piperazin-1-yl)-[1,3,5]triazin-2-ylamino]-methyl}-benzamide | $^1$H NMR (acetone-$d_6$) δ (ppm): mixture of rotamers, 9.05–9.00 (m, 1H), 7.98 (d, J=8.8Hz, 2H), 7.93 (s), 7.84 (d, J=8.0Hz), 7.72 (d, J=8.2Hz), 7.58–7.40 (m, 3H), 7.31–7.19 (m, 3H), 7.12–7.05 (m), 6.98 (d, J=8.1Hz, 2H), 6.86 (d, J=8.2Hz, 1H), 6.80 (t, J=7.1Hz, 1H), 6.67 (t, J=7.7Hz, 1H), 6.57–6.50 (m, 1H), 5.78–5.60 (m, 2H), 4.67–4.64 (m, 2H), 3.88–3.84 (m, 4H), 3.14 (s, 4H). HRMS (calc.): 477.2389 [$M^+$—$NH_4$], (found): 477.2383 | 1A |
| 5 | 12 | 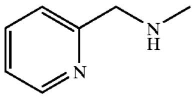 | $NH_2$ | 4-{[4-amino-6-(2-pyridinyl-methyl-amino)-[1,3,5]-triazin-2-ylamino]-methyl}-N-(2-amino-phenyl)-benzamide | $^1$H NMR (acetone-$d_6$) δ (ppm): 9.08 (bs, 1H), 8.51 (bs, 1H), 8.05–7.90 (m, 2H), 7.80–7.60 (m, 1H), 7.55–7.15 (m, 5H), 7.04 (dt, J=7.6Hz, 1.6Hz, 1H), 6.90Hz, (dd, J=8.0Hz, 1.4Hz, 1H), 6.71 (dt, J=7.6Hz, 1.4Hz, 1H), 6.85–6.55 (m, 1H), 5.84 (bs, 2H), 4.75–4.60 (m, 4H). HRMS (calc.): 441.2025, (found): 441.2029 | 1A |
| 6 | 13 | 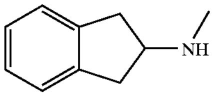 | 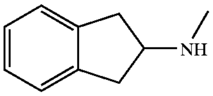 | 4-{[4,6-bis-(2-indanyl-amino)-[1,3,5]-triazin-2-ylamino]-methyl}-N-(2-amino-phenyl)-benzamide | $^1$H NMR (acetone-$d_6$) δ (ppm): 9.08 (bs, 1H), 8.05–7.95 (m, 2H), 7.56–7.44 (m, 2H), 7.34 (bd, J=7.7Hz, 7.27–7.10 (m, 8H), 7.04 (td, J=7.6Hz, 1.4Hz, 1H), 6.90 (dd, J=8.0Hz, 1.4Hz, 1H), 6.71 (dt, J=7.6Hz, 1.4Hz, 1H), 6.65–5.90 (m, 3H), 4.90–4.58 (m, 6H), 3.40–2.80 (m, 4H). HRMS (calc.): 582.2855, (found): 582.2838 | 1B |
| 7 | 14 | 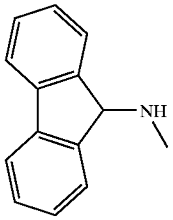 | $NH_2$ | 4-{[4-Amino-6-(9H-fluoren-9-ylamino)-[1,3,5]triazin-2-ylamino]-methyl}-N-(2-amino-phenyl)-benzamide | $^1$H NMR (acetone-$d_6$) δ (ppm): 9.05–9.00 (m, 1H), 8.03–7.87 (m, 2H), 7.80–7.70 (m, 2H), 7.63–7.20 (m, 9H), 7.00 (t, 1H), 6.86 (d, 1H), 6.66 (t, 1H), 6.50–5.50 (m, 6H), 4.75–4.55 (m, 3H). HRMS (calc.): 514.2229, (found): 514.2232 | 1B |

TABLE 2a-continued

Characterization of Compounds Prepared in Examples 2–28

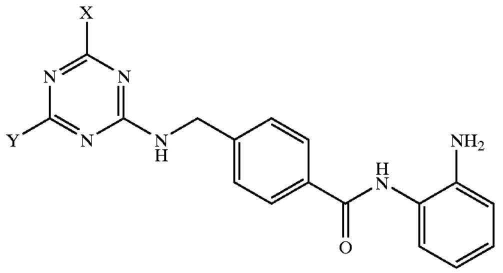

| Ex. | Cpd | Y | X | Name | Characterization | Schm |
|---|---|---|---|---|---|---|
| 8 | 15 | 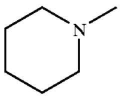 | $NH_2$ | N-(2-amino-phenyl)-4-[(4-amino-6-piperidin-1-yl-[1,3,5]-triazin-2-ylamino)-methyl]-benzamide | $^1H$ NMR ($CDCl_3$) δ (ppm): 7.96 (bs, 1H), 7.81 (d, J=8.0Hz, 2H), 7.38 (d, J=8.0Hz, 2H), 7.32 (d, J=8.0Hz, 1H), 7.08 (dt, J=7.7Hz, 1.4Hz, 1H), 6.83 (t, J=6.6Hz, 2H), 5.47 (bs, 1H), 4.80 (bs, 2H), 4.60 (d, J=6.0Hz, 2H), 3.88 (bs, 2H), 3.67 (t, J=5.2Hz, 4H), 1.66–1.58 (m, 2H,), 1.56–1.48 (m, 4H). | 1A |
| 9 | 16 | 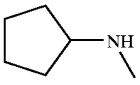 | $NH_2$ | 4-[(4-amino-6-cyclopentyl-amino-[1,3,5]-triazin-2-yl-amino)-methyl]-N-(2-amino-phenyl)-benzamide | $^1H$ NMR ($CDCl_3$) δ (ppm): 7.97 (bs, 1H), 7.82 (d, J=8.0Hz, 2H), 7.39–7.34 (m, 3H), 7.10 (dt, J=7.6Hz, 1.4Hz, 1H), 6.85 (t, J=7.0Hz, 2H), 5.56 (bs, 1H), 4.90 (bs, 3H), 4.62 (s, 2H), 4.25–4.19 (m, 1H) 3.88 (bs, 2H), 1.95 (m, 2H), 1.71–1.59 (m, 4H), 1.43–1.37 (m, 2H). | 1A |
| 10 | 17 | 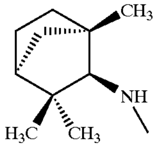 | $NH_2$ | (1R)-4-{[4-amino-6-(2-exo-fenchyl-amino)-[1,3,5]-triazin-2-ylamino]-methyl}-N-(2-amino-phenyl)-benzamide | $^1H$ NMR (acetone-$d_6$) δ (ppm): 9.08 (bs, 1H), AB system ($δ_A$ = 8.00, $δ_B$ = 7.51, J=8.0Hz, 4H), 7.33 (bd, J=7.7Hz, 1H), 7.03 (ddd, J=8.0Hz, 7.3Hz, 1.4Hz, 1H), 6.90 (dd, J=8.0Hz, 1.4Hz, 1H), 6.71 (dt, J=7.6Hz, 1.4Hz, 1H), 6.60–6.28 (m, 1H), 5.80–5.20 (m, 3H), 4.67 (bs, 4H), 3.87 (bd, J=9.1Hz, 1H), 1.80–1.60 (m, 4H), 1.56–1.42 (m, 1H), 1.34–1.00 (m including 2s, 8H), 0.84 (s, 3H). HRMS (calc.): 486.2855, (found): 486.2844 | 1A |
| 11 | 18 | 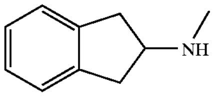 | 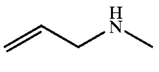 | 4-{[4-allyl-amino-6-(2-indanyl-amino)-[1,3,5]-triazin-2-ylamino]-methyl}-N-(2-amino-phenyl)-benzamide | $^1H$ NMR (acetone-$d_6$) δ (ppm): 9.07 (bs, 1H), 8.00 (bd, J=7.4Hz, 2H), 7.58–7.42 (m, 2H), 7.34 (bd, J=8.0Hz, 1H), 7.27–7.10 (m, 4H), 7.04 (td, J=7.6Hz, 1.5Hz, 1H), 6.90 (dd, J=8.0, 1.4Hz, 1H), 6.71 (dt, J=7.6Hz, 1.4Hz, 1H), 6.60–5.70 (m, 3H), 5.26–5.00 (m, 2H), 4.86–4.54 (m, 4H), 4.10–3.90 (m, 2H), 3.38–3.10 (m, 2H), 3.00–2.80 (m, 2H). HRMS (calc.): 506.2542, (found): 506.2533 | 1B |
| 12 | 19 | 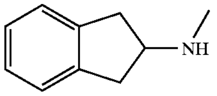 | 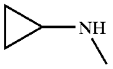 | 4-{[4-allyl-amino-6-(2-6-(2-indanyl-amino)-[1,3,5]-triazin-2-ylamino]-methyl}-N-(2-amino-phenyl)-benzamide | $^1H$ NMR (acetone-$d_6$) δ (ppm): 9.07 (bs, 1H), 8.00 (bd, J=7.7Hz, 2H), 7.60–7.40 (m, 2H), 7.33 (dd, J=7.8Hz, 1.3Hz, 1H), 7.28–7.10 (m, 4H), 7.04 (dt, J=7.6Hz, 1.5Hz, 1H), 6.90 (dd, J=7.8Hz, 1.4Hz, 1H), 6.71 (dt, J=7.6Hz, 1.3Hz, 1H), 6.67–5.80 (m, 2H), 4.90–4.50 (m, 4H), 3.40–3.10 (m, 2H), 3.05–2.70 (m, 3H), 0.75–0.43 (m, 4H). HRMS (calc.): 506.2542, (found): 506.2548 | 1B |

TABLE 2a-continued

Characterization of Compounds Prepared in Examples 2–28

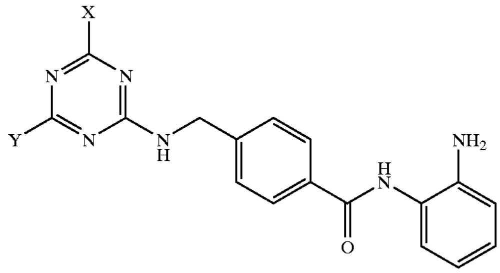

| Ex. | Cpd | Y | X | Name | Characterization | Schm |
|---|---|---|---|---|---|---|
| 13 | 20 | 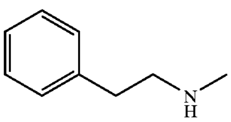 | $NH_2$ | 4-[(4-Amino-6-phenethylamino-[1,3,5]triazin-2-ylamino)-methyl]-N-(2-amino-phenyl)-benzamide | $^1H$ NMR (acetone-$d_6$) δ (ppm): 9.03 (s, 1H), 7.97 (d, J=7.7Hz, 2H), 7.55–7.40 (m, 2H), 7.35–7.10 (m, 6H), 6.99 (td J=8.0Hz, 1.3Hz, 1H), 6.86 (dd, J=8.0Hz, 1.3Hz, 1H), 6.67 (dt, J=8.0Hz, 1.4Hz, 1H), 6.62–5.40 (m, 5H), 4.75–4.45 (m, 3H), 3.59–3.45 (m, 2H), 2.95–2.70 (m, 2H). HRMS (calc.): 454.2229, (found): 454.2235 | 1A |
| 14 | 21 | 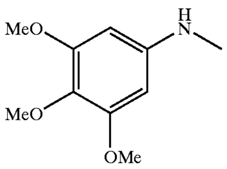 | $NH_2$ | N-(2-Amino-phenyl)-4-{[4-amino-6-(3,4,5-trimethoxy-phenylamino)-[1,3,5]triazin-2-ylamino]-methyl}-benzamide | $^1H$ NMR ($CDCl_3$/MeOD) δ (ppm): 7.72 (d, J=8.2Hz, 2H), 7.21 (d, J=8.2Hz, 2H), 7.04 (d, J=7.7Hz, 1H), 6.91 (td, J= 7.7Hz, 1.2Hz, 1H), 6.70–6.61 (m, 4H), 4.61 (bs, 2H), 3.58–3.52 (m, 9H). | 1B |
| 15 | 22 | 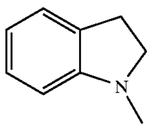 | $NH_2$ | 4-{[4-Amino-6-(2,3-dihydro-indol-1-yl)-[1,3,5]triazin-2-ylamino]-methyl}-N-(2-amino-phenyl)-benzamide | $^1H$ NMR ($CDCl_3$/MeOD) δ (ppm): 8.06 (bs, 1H), 7.82 (d, J=8.0Hz, 2H), 7.37 (d, J=8.2Hz, 2H), 7.13 (d, J=7.4Hz, 1H), 7.06 (d, J=7.4Hz, 1H), 7.02–6.96 (m, 2H), 6.84–6.71 (m, 3H), 4.61 (bs, 2H), 4.03 (t, J=8.5Hz, 2H), 3.02 (t, J=8.5Hz, 2H). | 1B |
| 16 | 23 | 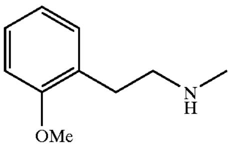 | $NH_2$ | 4-({4-Amino-6-[2-(2-methoxy-phenyl)-ethylamino]-[1,3,5]triazin-2-ylamino}-methyl)-N-(2-amino-phenyl)-benzamide | $^1H$ NMR (acetone-$d_6$) δ (ppm): mixture of rotamers, 9.06 (s, 1H), 7.96 (d, J=8.0Hz, 2H), 7.55–7.40 (m, 2H), 7.28 (d, J=7.4Hz, 1H), 7.21–6.70 (m, 6H), 6.67 (t, J=7.4Hz, 1H), 6.60–5.70 (m, 5H), 4.75–4.55 (m, 3H), 3.81 (s, 3H), 3.55–3.45 (m, 2H), 2.90–2.78 (m, 2H). HRMS (calc.): 484.2335, (found): 484.2331 | 1A |
| 17 | 24 | 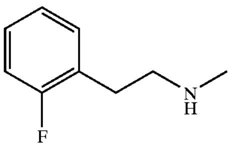 | $NH_2$ | 4-({4-Amino-6-[2-(2-fluoro-phenyl)-ethylamino]-[1,3,5]triazin-2-ylamino}-methyl)-N-(2-amino-phenyl)-benzamide | $^1H$ NMR (acetone-$d_6$) δ (ppm): mixture of rotainers, 9.03 (s, 1H), 7.97 (d, J=8.0Hz, 2H), 7.55–7.40 (m, 2H), 7.38–7.17 (m, 2H), 7.17–6.95 (m, 4H), 6.86 (dd, J=8.0Hz, 1.4Hz, 1H), 6.67 (t, J=7.0Hz, 1H), 6.50–5.60 (m, 5H), 4.75–4.55 (m, 3H), 3.60–3.52 (m, 2H), 2.95–2.85 (m, 2H). HRMS (calc.): 472.2135, (found): 472.2146 | 1A |
| 18 | 25 | 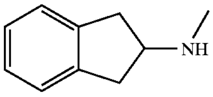 | 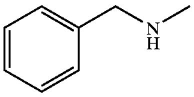 | 4-{[4-benzyl-amino-6-(2-indanyl-amino)-[1,3,5]-triazin-2-ylamino]-methyl}-N-(2-amino-phenyl)-benzamide | $^1H$ NMR (acetone-$d_6$) δ (ppm): 9.06 (bs, 1H), 8.04–7.93 (m, 2H), 7.57–7.12 (m, 12H), 7.04 (td, J=7.6Hz, 1.5Hz, 1H), 6.91 (dd, J=8.0Hz, 1.1Hz, 1H), 6.72 (bt, J=7.6Hz, 1H), 6.68–5.90 (m, 3H), 4.84–4.50 (m, 7H), 3.35–3.13 (m, 2H), 3.00–2.80 (m, 2H). HRMS (calc.): 556.2699, (found): 556.2706 | 1B |

TABLE 2a-continued

Characterization of Compounds Prepared in Examples 2–28

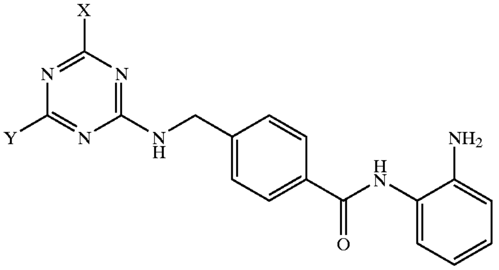

| Ex. | Cpd | Y | X | Name | Characterization | Schm |
|---|---|---|---|---|---|---|
| 19 | 26 | 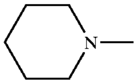 | 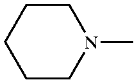 | N-(2-Amino-phenyl)-4-[(4,6-di-piperidin-1-yl-[1,3,5ltriazin-2-ylamino)-methyl]-benzamide | $^1H$ NMR: ($CDCl_3$) δ (ppm): 7.83 (d, J=8.2Hz, 3H), 7.44 (d, J=8.2Hz, 2H), 7.32 (d, J=7.4, 1H), 7.12–7.06 (m, 1H), 6.87–6.82 (m, 2H), 5.11 (t, J=6.2Hz, 1H), 4.64 (d, J=6.3Hz, 2H), 3.87 (bs, 2H), 3.69 (t, J=5.4Hz, 8H), 1.63–1.53 (m, 12H). | 1B |
| 20 | 27 | 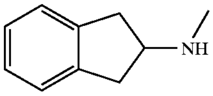 | 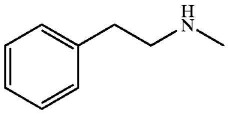 | 4-{[6-(2-indanyl-amino)-4-phenethyl-amino-[1,3,5]-triazin-2-ylamino]-methyl}-N-(2-amino-phenyl)-benzamide | $^1H$ NMR (acetone-$d_6$) δ (ppm): 9.07 (bs, 1H), 8.05–7.90 (m, 2H), 7.60–7.40 (m, 2H), 7.35–7.05 (m, 10H), 7.04 (td, J=7.6Hz, 1.5Hz, 1H), 6.90 (d, J=7.7Hz, 1H), 6.71 (t, J=7.3Hz, 1H), 6.60–5.70 (m, 3H), 4.95–4.50 (m, 5H), 3.70–2.80 (m, 8H). HRMS (calc.): 552.2750 [$M^+$—$NH_4$], (found): 552.2746 | 1B |
| 21 | 28 | 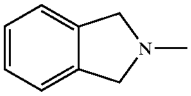 | $NH_2$ | 4-{[4-benzyl-amino-6-(2-indanyl-amino)-[1,3,5]-triazin-2-ylamino]-methyl}-N-(2-amino-phenyl)-benzamide | $^1H$ NMR ($CDCl_3$) δ (ppm): 7.83 (d, J=8.2Hz, 3H), 7.44 (d, J=8.2Hz, 2H), 7.32 (d, J=7.4, 1H), 7.12–7.06 (m, 1H), 6.87–6.82 (m, 2H), 5.11 (t, J=6.2Hz, 1H), 4.64 (d, J=6.3Hz, 2H), 3.87 (bs, 2H), 3.69 (t, J=5.4Hz), 1.63–1.53 (m, 12H). | 1A |
| 22 | 29 | 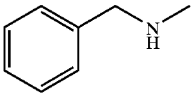 | $NH_2$ | 4-[(4-Amino-6-benzylamino-[1,3,5]triazin-2-ylamino)-methyl]-N-(2-amino-phenyl)-benzamide | $^1H$ NMR (acetone-$d_6$) δ (ppm): 9.04 (s, 1H), 7.95 (d, J=7.3Hz, 2H), 7.45 (d, J=7.1Hz, 2H), 7.38–7.15 (m, 6H), 7.00 (td, J=8.0Hz, 1.5Hz, 1H), 6.86 (dd, J=8.0Hz, 1.4Hz, 1H), 6.67 (dt, J=8.0Hz, 1.4Hz, 1H), 6.67–6.25 (m, 3H), 5.85–5.55 (m, 3H), 4.61 (d, J=6.3Hz, 2H), 4.54 (d, J=5.2Hz, 2H). HRMS (calc.): 440.2073, (found): 440.2078 | 1A |
| 23 | 30 | 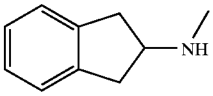 | 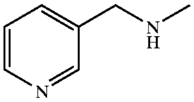 | 4-{[6-(2-indanyl-amino)-4-(3-pyridinyl-methyl-amino)-[1,3,5]-triazin-2-ylamino]methyl}-N-(2-amino-phenyl)-benzamide | $^1H$ NMR (acetone-$d_6$) δ (ppm): mixture of rotamers, 9.20–9.00 (m, 1H), 8.70–8.35 (m, 2H), 8.05–7.90 (m, 2H), 7.85–7.55 (m, 1H), 7.55–7.10 (m, 8H), 7.04 (dt, J=7.6Hz, 1.5Hz, 1H), 6.91 (bd, J=7.4Hz, 1H), 6.71 (bt, J=7.3Hz, 1H), 6.80–6.00 (m, 3H), 4.84–4.50 (m, 7H), 3.34–3.12 (m, 2H), 3.00–2.80 (m, 2H). HRMS (calc.): 539.2546 [$M^+$—$NH_4$], (found): 539.2533 | 1B |
| 24 | 31 | 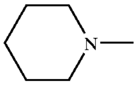 | 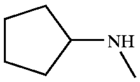 | N-(2-Amino-phenyl)-4-[(4-piperidin-1-yl-6-pyrrolidin-1-yl-[1,3,5]triazin-2-ylamino)-methyl]-benzamide | $^1H$ NMR ($CDCl_3$) δ (ppm): 7.89 (bs, 1H,), 7.82 (d, J=8.2Hz, 2H), 7.42 (d, J=8.0Hz, 2H), 7.32 (d, J=8.0Hz, 1H), 7.09 (dt, J=7.7Hz, 1.6Hz, 1H), 6.87–6.82 (m, 2H), 4.83 (bs, 1H), 4.62 (d, J=6.0Hz, 2H), 4.24 (m, 1H), 388 (bs, 1H), 2.04–1.96 (m, 2H), 1.70–1.52 (m, 10H), 1.46–1.38 (m, 2H). | 1B |

TABLE 2a-continued

Characterization of Compounds Prepared in Examples 2–28

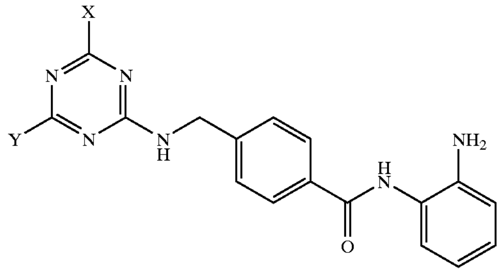

| Ex. | Cpd | Y | X | Name | Characterization | Schm |
|---|---|---|---|---|---|---|
| 25 | 32 | 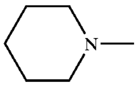 | 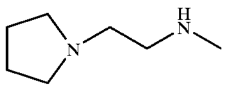 | N-(2-Amino-phenyl)-4-{[2-piperidin-1-yl-6-(2-pyrrolidin-1-yl-ethylamino)-pyrimidin-4-ylamino]-methyl}-benzamide | $^1$H NMR ($CDCl_3$) δ (ppm): 8.27 (bs, 1H), 7.74 (d, J=7.4Hz, 2H), 7.29 (m, 3H), 7.05 (dt, J=7.6Hz, 1.4Hz, 1H), 6.81–6.76 (m, 2H), 5.62 (bs, 2H), 4.57 (bs, 2H), 3.91 (bs, 2H), 3.69 (m, 4H), 3.45 (m, 2H), 2.57 (t, J=6.2Hz, 2H), 2.47 (m, 4H), 1.71 (m, 4H), 1.59–1.50 (m, 6H). | 1B |
| 26 | 33 | 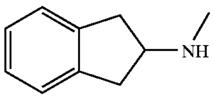 | 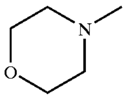 | 4-{[6-(2-indanyl-amino)-4-morpholin-4-yl-[1,3,5]-triazin-2-ylamino]-methyl}-N-(2-amino-phenyl)-benzamide | $^1$H NMR (acetone-$d_6$) δ (ppm): 9.07 (bs, 1H), 8.08–7.95 (m, 2H), 7.60–7.43 (m, 2H), 7.33 (d, J=8.0Hz, 1H), 7.28–7.12 (m, 4H), 7.04 (dt, J=7.6Hz, 1.4Hz, 1H), 6.91 (d, J=7.4Hz, 1H), 6.72 (t, J=7.4Hz, 1H), 6.55–6.05 (m, 2H), 4.86–4.60 (m, 5H), 3.80–3.56 (m, 8H), 3.38–3.12 (m, 2H), 3.04–2.82 (m, 2H). | 1B |
| 27 | 34 | 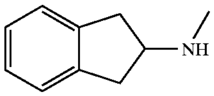 | 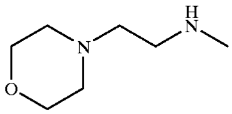 | N-(2-Amino-phenyl)-4-{[2-piperidin-1-yl-6-(2-pyrrolidin-1-yl-ethylamino)-pyrimidin-4-ylamino]-methyl}-benzamide | $^1$H NMR (acetone-$d_6$) δ (ppm): 9.08 (bs, 1H), 8.01 (bd, J=7.4Hz, 2H), 7.56–7.43 (m, 2H), 7.33 (bd, J=8.0Hz, 1H), 7.28–7.12 (m, 4H), 7.04 (dt, J=7.6Hz, 1.4Hz, 1H), 6.90 (dd, J=8.0Hz, 1.4Hz, 1H), 6.71 (dt, J=7.6Hz, 1.4Hz, 1H), 6.65–5.75 (m, 2H), 4.90–4.58 (m, 5H), 3.66–2.34 (m, 16H). | 1B |
| 28 | 35 | 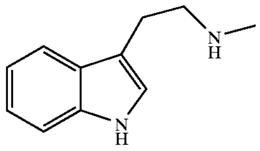 | $NH_2$ | 4-({4-Amino-6-[2-(1H-indol-3-yl)-ethylamino]-[1,3,5]triazin-2-ylamino}-methyl)-N-(2-amino-phenyl)-benzamide | $^1$H NMR (acetone-$d_6$) δ (ppm): 10.00 (s, 1H), 9.13 (s, 1H), 7.93 (d, J=8.0Hz, 2H), 7.70–7.50 (m, 1H), 7.50–7.22 (m, 4H), 7.18–6.91 (m, 4H), 6.85 (d, J=7.1Hz, 1H), 6.67 (t, J=7.4Hz, 1H), 6.40–5.90 (m, 3H), 4.75–4.50 (m, 2H), 4.37 (s, 2H), 3.62 (d, J=6.3Hz, 2H), 2.99 (s, 2H). | 1A |

TABLE 2b

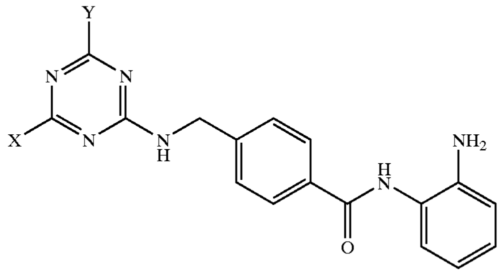

| Ex. | Cpd | X | Y | Name | Characterization | Schm |
|---|---|---|---|---|---|---|
| 329 | 470 | 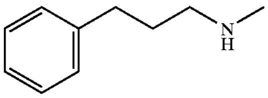 | $NH_2$ | 4-{[4-amino-6-(3-phenyl-propyl-1-amino)-[1,3,5]triazin-2-yl-amino]-methyl}-N-(2-amino-phenyl)-benzamide | $^1$H NMR (300MHz, acetone-$d_6$) δ (ppm): 9.03 (s, 1H), 7.96 (d, J=8.2Hz, 2H), 7.46 (d, J=7.7Hz, 2H), 7.35–7.10 (m, 6H), 7.00 (t, J=7.7Hz, 1H), 6.86(d, J=8.0Hz, 1H), 6.67 (t, J=7.7Hz, 1H), 6.60–5.40 (m, 6H), 4.62 (s, 2H), 3.35 (dd, J=12.1, 6.9Hz, 2H), 2.75–2.60 (m, 2H), 1.95–1.80 (m, 2H). | 1A |
| 330 | 471 | 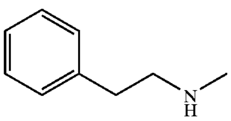 | 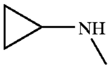 | N-(2-amino-phenyl)-4-[(4-cyclopropyl-amino-6-phenethyl-amino-[1,3,5]triazin-2-yl-amino)-methyl]-benzamide | $^1$H NMR (300MHz, acetone-$d_6$) δ (ppm): 9.04 (s, 1H), 7.96 (d, J=8.0Hz, 2H), 7.55–7.40 (m, 2H), 7.35-7.10 (m, 6H), 6.98 (t, J=7.4Hz, 1H), 6.85 (d, J=6.9Hz, 1H), 6.66 (t, J=7.3Hz, 1H), 6.20–5.50 (m, 3H), 4.80–4.50 (m, 4H), 3.65–3.45 (m, 2H), 3.00–2.60 (m, 2H), 0.80–0.40 (m, 4H). | 1B |
| 331 | 472 | 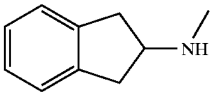 | 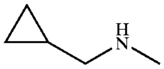 | N-(2-amino-phenyl)-4-{[4-cyclopropyl-methylamino-6-(2-indanyl-amino)-[1,3,5]-triazin-2-yl-amino]-methyl}-benzamide | $^1$H NMR (300MHz, acetone-$d_6$) δ (ppm): 9.06 (bs, 1H), 8.00 (bd, J=7.1, 2H), 7.50 (bs, 1H),), 7.33 (d, J=6.6Hz, 1H), 7.28–7.07 (m, 4H), 7.03 (td, J=7.6, 1.5Hz, 1H), 6.90 (dd, J=8.0, 1.4Hz, 1H), 6.71 (td, J=7.6, 1.4Hz, 1H), 6.55–5.70 (m, 3H), 4.90–4.50 (m, 5H), 3.40–2.80 (m, 6H), 1.07 (bs, 1H), 0.44 (bs, 2H), 0.23 (bs, 2H). | 1B |
| 332 | 473 | 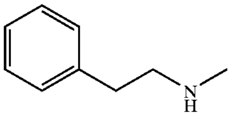 | n-BuNH | N-(2-amino-phenyl)-4-[(4-n-butyl-amino-6-phenethyl-amino-[1,3,5]triazin-2-yl-amino)-methyl]-benzamide | $^1$H NMR (300MHz, $CDCl_3$) δ (ppm): 8.08 (s, 1H), 7.83 (d, J=6.6Hz, 2H), 7.45–7.05 (m, 8H), 7.08 (td, J=7.8, 1.5Hz, 1H), 6.84 (t, J=8.1Hz, 2H), 6.70-5.00 (m, 3H), 4.70–4.50 (m, 2H), 3.65–3.50 (m, 2H), 3.45–3.25 (m, 2H), 2.40–2.25 (m, 2H), 1.60–1.45 (m, 2H), 1.45–1.00 (m, 2H), 1.00–0.8 (m, 3). | 1B |
| 333 | 474 | 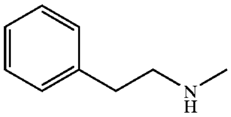 | $MeOCH_2CH_2NH$ | N-(2-amino-phenyl)-4-{[4-(2-methoxy-ethyl-1-amino)-6-phenethyl-amino-[1,3,5]triazin-2-yl-amino]-methyl}-benzamide | $^1$H NMR (300MHz, acetone-$d_6$) δ (ppm): 9.02 (s), 8.58 (s), 8.40 (dd, J=7.2, 2Hz, 1H), 7.97 (d, J=7.5Hz, 1H), 7.51–7.40 (m, 2H), 7.70-6.90 (m, 7H), 6.86 (dd, J=8.1, 1.2Hz), 6.76 (dd, J=7.5, 1.8Hz), 6.67 (td, J=7.8, 1.5Hz), 6.60–5.50 (m, 3H), 4.75–4.55 (m, 4H), 3.65–3.35 (m, 6H), 3.35–3.20 (s, 3H), 2.95–2.75 (m, 2H). | 1B |
| 334 | 475 | 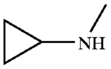 | 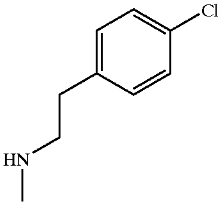 | N-(2-amino-phenyl)-4-{[4-(4-chloro-phenethyl-amino)-6-cyclopropyl-amino-[1,3,5]triazin-2-yl-amino]-methyl}-benzamide | $^1$H NMR (300MHz, acetone-$d_6$) δ (ppm): 9.02 (s, 1H), 8.02–7.91 (m, 2H), 7.58–7.40 (m, 2H), 7.28 (s, 4H), 7.20–7.05 (m, 1H), 6.99 (td, J=7.5, 1.8Hz, 1H), 6.86 (d, J=7.8Hz, 1H), 6.67 (t, J=6.9Hz, 1H), 6.60–5.60 (m, 3H), 4.75–4.50 (m, 4H), 3.65–3.40 (bs, 2H), 2.95–2.65 (m, 2H), 0.75–0.55 (m, 2H), 0.55–0.40 (m, 2H). | 1B |

TABLE 2b-continued

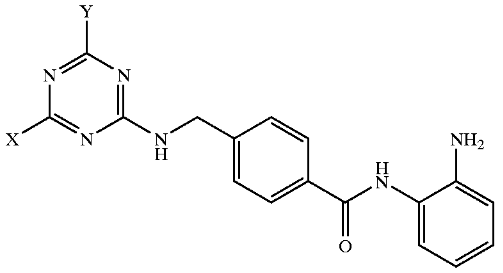

| Ex. | Cpd | X | Y | Name | Characterization | Schm |
|---|---|---|---|---|---|---|
| 335 | 476 | 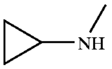 | 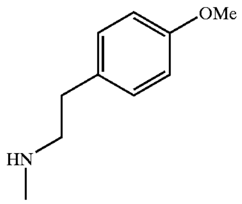 | N-(2-amino-phenyl)-4-{[6-cyclopropyl-amino-4-(4-methoxy-phenethyl-amino)-[1,3,5]triazin-2-yl-amino]-methyl}-benzamide | $^1$H NMR (300MHz, $CDCl_3$) δ (ppm): 8.55–7.72 (m, 4H), 7.55–6.75 (m, 9H), 6.75–5.30 (m, 3H), 4.69 (m, 2H), 3.85 (s, 3H), 3.63 (bs, 2H), 2.86 (m, 3H), 0.85 (bs, 2H), 0.61 (bs, 2H). | 1B |
| 336 | 477 | 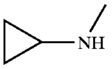 | 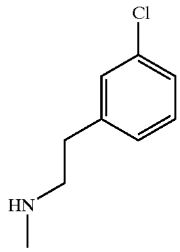 | N-(2-amino-phenyl)-4-{[4-(3-chloro-phenethyl-amino)-6-cyclopropyl-amino-[1,3,5]triazin-2-yl-amino]-methyl-benzamide | $^1$H NMR (300MHz, acetone-$d_6$) δ (ppm): 9.03 (s, 1H), 7.96 (d, J=7.5Hz, 2H), 7.60–7.37 (m, 2H), 7.37–7.12 (m, 5H), 6.99 (t, J=6.9Hz, 1H), 6.86 (d, J=6.9Hz, 1H), 6.67 (t, J=7.2Hz, 1H), 6.60–5.60 (m, 3H), 4.75–4.50 (m, 4H), 3.67–3.45 (m, 2H), 3.00–2.67 (m, 3H), 0.75–0.40 (m, 4H). | 1B |
| 337 | 478 | 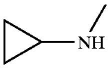 | 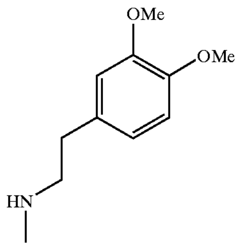 | N-(2-amino-phenyl)-4-{[6-cyclopropyl-amino-4-(3,4-dimethoxy-phenethyl-amino)-[1,3,5]triazin-2-yl-amino]-methyl}-benzamide | $^1$H NMR (300MHz, acetone-$d_6$) δ (ppm): 9.02 (s, 1H), 7.96 (d, J=8.1Hz, 2H), 7.60–7.40 (m, 2H), 7.29 (d, J=8.1Hz, 1H), 6.99 (td, J=8.1, 1.5Hz, 1H), 6.95–6.72 (m, 4H), 6.67 (td, J=7.8, 1.5Hz, 1H), 6.20–5.60 (m, 3H), 4.78–4.52 (m, 4H), 3.75 (s, 6H), 3.65–3.42 (m, 2H), 2.95–2.65 (m, 3H), 0.72–0.40 (m, 4H). | 1B |
| 338 | 479 | 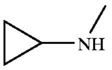 | 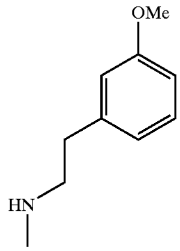 | N-(2-amino-phenyl)-4-{[6-cyclopropyl-amino-4-(3-methoxy-phenethyl-amino)-[1,3,5]triazin-2-yl-amino]-methyl}-benzamide | $^1$H NMR (300MHz, acetone-$d_6$) δ (ppm): 9.02 (s, 1H), 7.96 (d, J=7.8Hz, 2H), 7.60–7.35 (m, 2H), 7.29 (d, J=7.5Hz, 1H), 7.18 (t, J=7.8Hz, 1H), 6.99 (td, J=7.5, 1.5Hz, 1H), 6.90–6.70 (m, 4H), 6.67 (t, J=7.8Hz, 1H), 6.60–5.60 (m, 3H), 4.77–4.50 (m, 4H), 3.76 (s, 3H), 3.65–3.45 (m, 2H), 2.92–2.65 (m, 3H), 0.72–0.42 (m, 4H). | 1B |
| 339 | 480 | 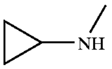 | 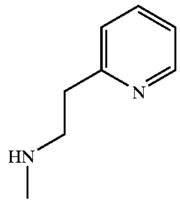 | N-(2-amino-phenyl)-4-{[6-cyclopropyl-amino-4-(2-pyridin-2-yl-ethyl-1-amino)-[1,3,5]triazin-2-yl-amino]-methyl}-benzamide | $^1$H NMR (300MHz, acetone-$d_6$) δ (ppm): 9.03 (s, 1H), 8.50 (d, J=1.2Hz, 1H), 7.96 (d, J=8.1Hz, 2H), 7.66 (t, J=7.5Hz, 1H), 7.60–7.40 (m, 2H), 7.35–7.08 (m, 3H), 6.99 (td, J=8.1, 1.5Hz, 1H), 6.86 (dd, J=8.1, 1.5Hz, 1H), 6.67 (td, J=7.8, 1.5Hz, 1H), 6.60–5.60 (m, 3H), 4.75–4.50 (m, 4H), 3.80–3.60 (m, 2H), 3.15–2.90 (m, 2H), 2.90–2.65 (m, 1H), 0.73–0.40 (m, 4H). | 1B |

TABLE 2b-continued

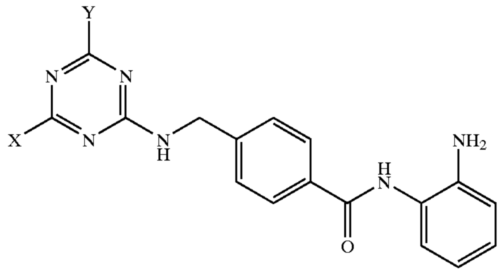

| Ex. | Cpd | X | Y | Name | Characterization | Schm |
|---|---|---|---|---|---|---|
| 340 | 481 | 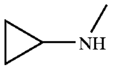 | 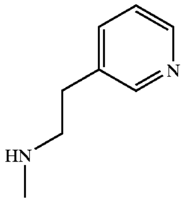 | N-(2-amino-phenyl)-4-{[6-cyclopropyl-amino-4-(3-pyridin-2-yl-ethyl-1-amino)-[1,3,5]triazin-2-yl-amino]-methyl}-benzamide | $^1$H NMR (300MHz, acetone-$d_6$) δ (ppm): 9.20–9.00 (m, 1H), 8.70–8.50 (m, 2H), 8.00 and 7.88 (2d, J=7.9Hz, 2H), 7.75–7.43 (m, 3H), 7.38–6.67 (m, 5H), 6.22–5.78 (m, 3H), 4.80–4.55 (m, 4H), 3.61 (bs, 2H), 3.20–2.65 (m, 3H), 0.80–0.45 (m, 4H). | 1B |
| 341 | 482 | 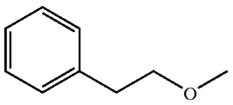 | 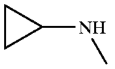 | N-(2-amino-phenyl)-4-[(4-cyclopropyl-amino-6-phenethyl-oxy-[1,3,5]triazin-2-yl-amino)-methyl-benzamide | $^1$H NMR (300MHz, acetone-$d_6$) δ (ppm): 9.04 (s, 1H), 7.98 (d, J=8.1Hz, 2H), 7.60–7.40 (m, 2H), 7.35–7.15 (m, 6H), 7.00 (td, J=7.5, 1.5Hz, 1H), 6.86 (d, J=8.1Hz, 1H), 6.67 (t, J=7.5Hz, 1H), 7.18–6.35 (m, 2H), 4.75–4.30 (m, 6H), 3.10–2.92 (m, 2H), 0.75–0.63 (m, 2H), 0.57–0.48 (m, 2H). | 1, 25 |
| 342 | 483 | 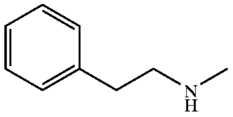 | Me | N-(2-amino-phenyl)-4-[(6-methyl-4-phenethylamino-[1,3,5]triazin-2-amino)-methyl]-benzamide | $^1$H NMR (300MHz, acetone-$d_6$) + □ DMSO-$d_6$) δ (ppm): mixture of rotamers, 9.62 (bs, 1H), 8.03 (d, J=8.0Hz, 2H), 7.80–7.44 (m, 3H), 7.40–7.10 (m, 8H), 7.01 (t, J=7.6Hz, 1H), 6.87 (d, J=7.9Hz, 1H), 6.67 (t, J=7.4Hz, 1H), 4.85 (bs, 2H), 4.72–4.54 (m, 2H), 3.63–3.42 (m, 2H), 2.96–2.74 (m, 2H), 2.21 and 2.13 (2s, 3H). | 30 |
| 343 | 484 | 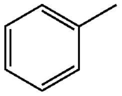 | $NH_2$ | N-(2-amino-phenyl)-4-[{4-amino-6-phenyl-[1,3,5]triazin-2-yl-amino]-methyl}-benzamide | $^1$H NMR (300MHz, acetone-$d_6$) δ (ppm): mixture of rotamers, 9.08 (bs, 1H), 8.48–8.36 (m, 2H), 8.02 (d, J=8.2Hz, 2H), 7.63–7.42 (m, 5H), 7.33 (d, J=7.7Hz, 1H), 7.19 (bs, 1H), 7.03 (t, J=7.4Hz, 1H), 6.88 (d, J=7.9Hz, 1H), 6.70 (t, J=7.6Hz, 1H), 6.35 and 6.25 (2bs, 2H), 4.87 and 4.75 (2d, J=5.9Hz, 2H), 4.65 (bs, 2H). | 30 |
| 344 | 485 | 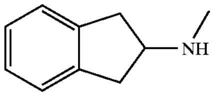 | 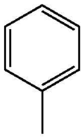 | N-(2-amino-phenyl)-4-{[6-(2-indanyl-amino)-4-phenyl-[1,3,5]-triazin-2-yl-amino]-methyl}-benzamide | $^1$H NMR (300MHz, acetone-$d_6$) δ (ppm): mixture of rotamers, 9.14–8.96 (m, 1H), 8.54–8.30 (m, 2H), 8.09–7.95 (m, 2H), 7.68–7.40 (m, 5H), 7.38–7.08 (m, 6H), 7.03 (t, J=7.3Hz, 1H), 6.94–6.76 (m, 2H), 6.71 (t, J=7.3Hz, 1H), 5.13–4.54 (m, 5H), 3.49–3.18 (m, 2H), 3.12–2.90 (m, 2H). | 30 |

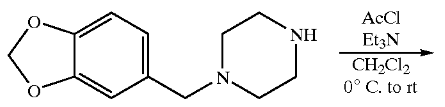

36

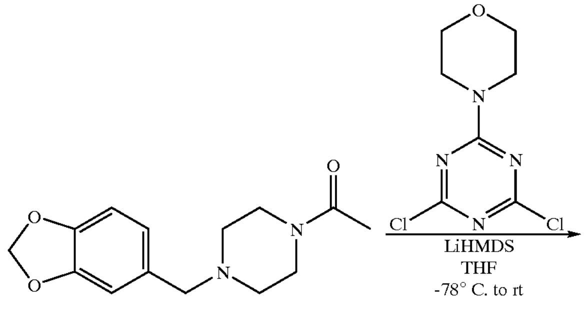

37

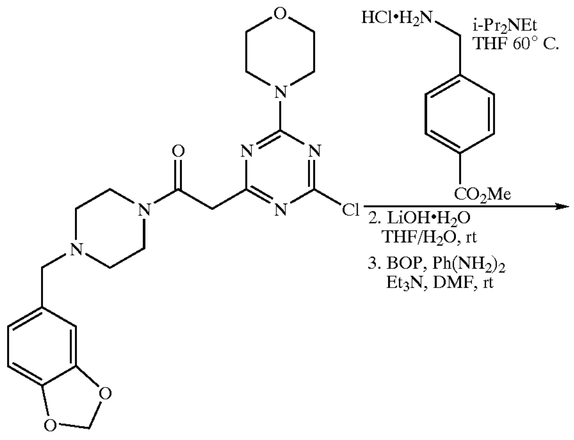

38

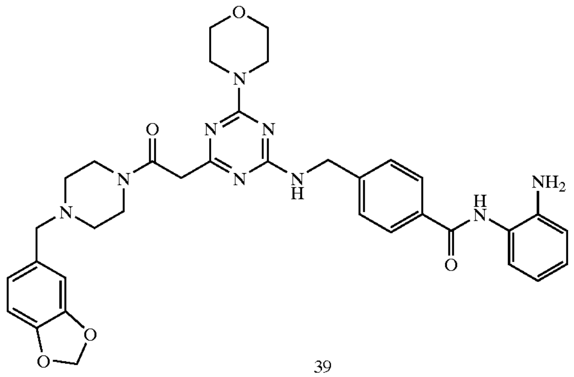

39

Example 29

N-(2-Amino-phenyl)-4-({4-[2-(4-benzo[1,3]dioxol-5-ylmethyl-piperazin-1-yl)-2-oxo-ethyl]-6-morpholin-4-yl-[1,3,5]triazin-2-ylamino}-methyl)-benzamide (Compound 39)

Step 1: N-Acetyl-1-piperonylpiperazine (Compound 37)

To a stirred solution at 0° C. of 1-piperonylpiperazine 36 (5.00 g, 22.7 mmol) in anhydrous $CH_2Cl_2$ (60 mL) was added $Et_3N$ (6.33 mL, 45;4 mmol) followed by acetyl chloride (1.94 mL, 27.2 mmol). The reaction mixture was stirred 30 min. at 0° C. and then 2 h at room temperature. The reaction mixture was poured into a saturated aqueous solution of $NH_4Cl$, and diluted with AcOEt. After separation, the organic layer was successively washed with sat. $NH_4Cl$, $H_2O$ and brine, dried over anhydrous $MgSO_4$, filtered and concentrated. The crude residue was then purified by flash chromatography on silica gel ($MeOH/CH_2Cl_2$: 4/96) to afford the title compound 37 (5.52 g, 21.11 mmol, 93% yield) as a yellow solid. $^1H$ NMR: (300 MHz, $CDCl_3$) δ (ppm): 6.83 (s, 1H), 6.72 (m, 2H), 5.92 (s, 2H), 3.59 (t, J=5.1 Hz, 2H), 3.44–3.40 (m, 4H), 2.42 (dt, J=5.1 Hz, 5.1 Hz, 4H), 2.06 (s, 3H).

Step 2: 2-Chloro-4-morpholin-4-yl-6-[2-(4-benzo[1,3]-dioxol-5-ylmethyl-piperazin-1-yl)-2-oxo-ethyl]-[1,3,5] triazine (Compound 38)

To a stirred solution of 37 (3.00 g, 11.4 mmol) in anhydrous THF (25 mL) at −78° C. was slowly added a solution of LiHMDS (11.4 mL, 11.4 mmol, 1 M in THF). The reaction mixture was stirred 1 h at −78° C. and a solution of 2,4-dichloro-6-morpholin-4-yl-[1,3,5]triazine (2.69 g, 11.4 mmol) in anhydrous THF (25 mL) was added. The reaction mixture was slowly warmed up at room temperature and the reaction was quenched after 16 h with a saturated aqueous solution of $NH_4Cl$. The THF was evaporated and the residue was diluted with AcOEt. The organic layer was successively washed with sat $NH_4Cl$ and brine, dried over anhydrous $MgSO_4$, filtered and concentrated. The crude residue was then purified by flash chromatography on silica gel ($MeOH/CH_2Cl_2$: 1/99→3/97) to afford the title compound 38 (4.84 g, 10.49 mmol, 92% yield) as a pale yellow solid. $^1H$ NMR (300 MHz, $CDCl_3$) δ (ppm): 6.84 (s, 1H), 6.77–6.69 (m, 2H), 5.95 (s, 2H), 3.75–3.43 (m, 16H), 2.42 (m, 4H).

Step 3: N-(2-Amino-phenyl)-4-({4-[2-(4-benzo[1,3]dioxol-5-ylmethyl-piperazin-1-yl)-2-oxo-ethyl)-6-morpholin-4-yl -[1,3,5]triazin-2-ylamino}-methyl)benzamide (Compound 39)

The title compound 39 was obtained following the same procedure as Example 1, step 5. $^1H$ NMR ($CDCl_3$) δ (ppm): 7.96 (bs, 1H), 7.87 (d, J=8.2 Hz, 2H), 7.39 (d, J=8.2 Hz, 2H), 7.33 (d, J=8.5 Hz, 1H), 7.10 (dt, J=7.6 Hz, 1.2 Hz, 1H), 6.87–6.81 (m, 3H), 6.75–6.68 (m, 2H), 5.93 (s, 2H), 5.67 (bs, 1H), 4.64 (s, 2H), 3.90 (bs, 2H), 3.75–3.35 (m, 16H), 2.45–2.30 (m, 4H).

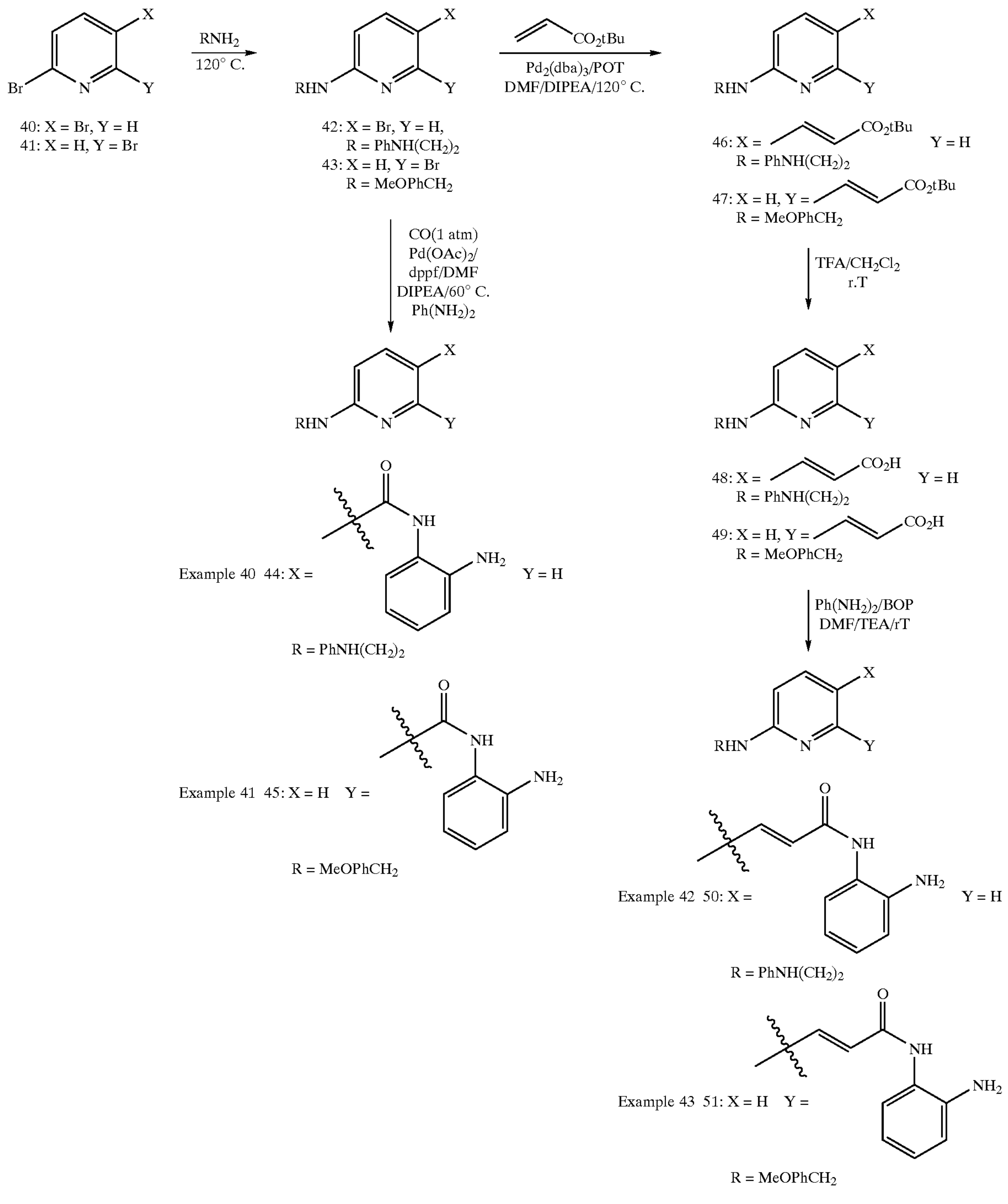

EXAMPLE 40

N-(2-aminophenyl)-6-(2-phenylamino-ethylamino)-nicotinamide (Compound 44)

Step 1: N-(5-Bromo-pyridin-2-yl)-N'-phenyl-ethane-1,2-diamine (Compound 42)

A mixture of 2,5-dibromopyridine 40 (2.08 g, 8.6 mmol) and phenyl-1,2-ethyldiamine (1.98 g, 14.6 mmol, 1.7 equiv.) was stirred under nitrogen at 120° C. for 6 h. After cooling down to room temperature, the solid mixture was ground in a mortar, dissolved in ethy) acetate (200 mL), washed with saturated $NaHCO_3$ (2×50 mL, dried ($MgSO_4$), filtered and concentrated. After a quick purification through a short chromatographic column (silica gel, elution 50% ether in hexanes), a pale yellow solid 42 (1.75 g, 6.01 mmol, 70% yield) was obtained. $^{13}C$ NMR (300 MHz, acetone-$d_6$) δ (ppm): 158.6, 149.6, 148.8, 139.9, 129.8, 117.1, 113.1, 110.8, 106.6, 43.9, 41.5. LMRS=294.0 (M+1).

Step 2: N-(2-aminophenyl)-6-(2-phenylamino-ethylamino)-nicotinamide (Compound 44)

A mixture of 5bromo-2-N-alkanyl-2-aminopyridine 42 (352 mg, 1.2 mmol), 1,2-phenylenediamine (3.95 mmol, 3.3 equiv.), $Pd(OAc)_2$ (0.31 mmol, 26% mol) and 1,1'-bis (diphenylphosphino) ferrocene (124 mg, 0.22 mmol) was suspended in degassed DMF (3 mL), treated with diisopropylethyl amine (0.9 mL, 5.2 mmol) and the system flushed with CO. The reaction mixture was warmed up to 60° C. and stirred under CO (balloon) for 18 h at this temperature. After evaporation of the DMF under vacuo, the residue was purified through a chromatographic column (silica gel, elution 3% to 6% methanol in dichloromethane) to give 258 mg (0.74 mmol, 62% yield) of the aminoanilide 44. $^1$H-NMR ($CD_3OD$-d4), δ (ppm): 8.67 (d, J=2.2 Hz, 1H), 7.97 (dd, J=8.9 Hz, 2.5 Hz, 1H), 7.58 (m, 1H), 7.51 (m, 1H), 7.15 (dd, J=7.7 Hz, 1.1 Hz, 1H), 7.08 (m, 2H), 6.89 (dd, J=8.0 Hz, 1.4 Hz, 1H), 6.76 (dt, J=7.7 Hz, 4.4 Hz, 1H), 6.67 (t, J=7.7 Hz, 2H), 6.60 (m, 2H), 4.87 (bs, 4H), 3.60 (t, J=6.3 Hz, 2H), 3.35 (t, J=6.3 Hz, 2H).

Example 41

N-(2-amino-phenyl)-6-(4-methoxy-benzylamino)-nicotinamide (Compound 45)

Step 1: N-(5-Bromo-pyridin-2-yl)-4-methoxybenzylamine (Compound 43)

A mixture of 2,6-dibromopyridine 41 (6.03 mmol, 2 equiv.) and para-methoxybenzyl amine (413 mg, 3.01 mmol) was stirred under nitrogen at 120° C. for 6 h. After identical work-up procedure described before and purification through a pad of silica gel (elution 50% ether in hexanes), a pale yellow solid 43 (773 mg, 2.60 mmol, 87% yield) was obtained. $^{13}$C NMR (300 MHz, $CDCl_3$) δ (ppm): 159.1, 139.7, 132.1, 130.5, 128.9, 127.2, 116.2, 114.3, 104.8, 55.4, 46.0. LMRS=295.0 (M+1).

Step 2: N-(2-amino-phenyl)-6-(4-methoxy-benzylamino)-nicotinamide (Compound 45)

Following the procedure described in Example 40, step 2, but substituting 43 for 42, the title compound 45 was obtained in 61% yield.

Example 42

N-(2-aminophenyl)-3-[6-(2-phenylamino-ethylamino)-pyridin-3-yl]-acrylamide (Compound 50)

Step 2: 3-[6-(2-Phenylamino-ethylamino)-pyridin-3-yl)-acrylic acid tert-butyl ester (Compound 46)

In a 50 mL flask, a mixture of 42 (308 mg, 1.05 mmol), tert-butylacrylate (0.8 mL, 5.5 mmol), diisopropylethylamine (0.8 mL, 4.6 mmol), tri-o-tolylphosphine (POT, 192 mg, 0.63 mmol), $Pd_2(dba)_3$ (73 mg, 0.08 mmol) in anhydrous DMF (4 mL) was stirred at 120° C. (preheated oil bath) for 2 h under nitrogen. After DMF removal, the crude residue was submitted to a chromatographic purification (column silica gel, 50% ether in hexanes) to afford 316 mg of 46 (88% yield). $^{13}$C NMR (300 MHz, $CDCl_3$) δ (ppm): 166.6, 159.3, 149.6, 147.8, 140.7, 134.9, 129.1, 119.8, 117.3, 115.9, 112.6, 107.8, 80.0, 43.5, 40.9, 28.1. LRMS=340.3 (M+1).

Step 3: 3-[6-(2-Phenylamino-ethylamino)-pyridin-3-yl)-acrylic acid (Compound 48)

Ester 46 (0.93 mmol) was dissolved 40% TFA in dichloromethane (10 mL) and the solution stirred at room temperature overnight. The solvent was removed under vacuo distilling with acetonitrile (3×10 mL) and stored under high vacuum for 6 h. The solid residue 48 was employed for the next reaction without further purification. LRMS=284.1 (M+1).

Step 4: N-(2-aminophenyl)-3-[6-(2-phenylamino-ethylamino)-pyridin-3-yl]-acrylamide (Compound 50)

A mixture of acid 48 (0.93 mmol), BOP (495 mg, 1.12 mmol) and 1,2-phenylenediamine (124 mg, 1.15 mmol) were dissolved in dry acetonitrile (4 mL) and treated with triethylamine (0.8 mL, 5.7 mmol). The solution was stirred under nitrogen at room temperature for 16 h. After concentration under vacuo, the crude was purified through chromatographic column (5% methanol in dichloromethane), then was crystallized from chloroform to give 50 (247 mg, 71% yield). $^1$H-NMR (DMSO-d6), δ (ppm): 9.25 (bs, 1H), 8.21 (d, J=1.6 Hz, 1H), 7.67 (d, J=8.5 Hz, 1H), 7.43 (d, J=15.7 Hz, 1H), 7.32 (d, J=7.4 Hz, 1H), 7.24 (t, J=1.0 Hz, 1H), 7.08 (t, J=7.4 Hz, 2H), 6.91 (t, J=8.0 Hz, 1H), 6.75 (dt, J=8.0 Hz, 0.4 Hz, 1H), 6.57 (m, 6H), 5.20 (bs, 1H), 3.48 (t, J=6.3 Hz, 2H), 3.33 (bs, 2H), 3.21 (t, J=6.3 Hz, 2H).

Example 43

N-(2-aminophenyl)-3-[6-(4-methoxy-benzylamino)-pyridin-2-yl-acrylamide (Compound 51)

Step 2: N-(2-aminophenyl)-3-[6-(4-methoxy-benzylamino)-pyridin-2-yl]-acrylamide (Compound 51)

Following the procedure described in Example 42, steps 2, 3, 4, but substituting 43 for 42, the title compound 51 was obtained in 50% yield (on 2 steps). $^1$H-MMR ($CDCl_3$), δ (ppm): 7.60 (bs, 1H), 7.55 (bs, 1H), 7.43 (t, J=7.7 Hz, 1H), 7.29 (d, J=8.3 Hz, 2H), 7.17 (d, J=15.1 Hz, 1H), 7.06 (t, J=7.7 Hz, 1H), 6.88 (d, J=8.3 Hz, 2H), 6.80 (m, 2H), 6.70 (m, 3H), 6.41 (d, J=8.5 Hz, 1H), 4.50 (d, J=5.5 Hz, 2H), 3.80 (s, 3H), 3.45 (bs, 2H).

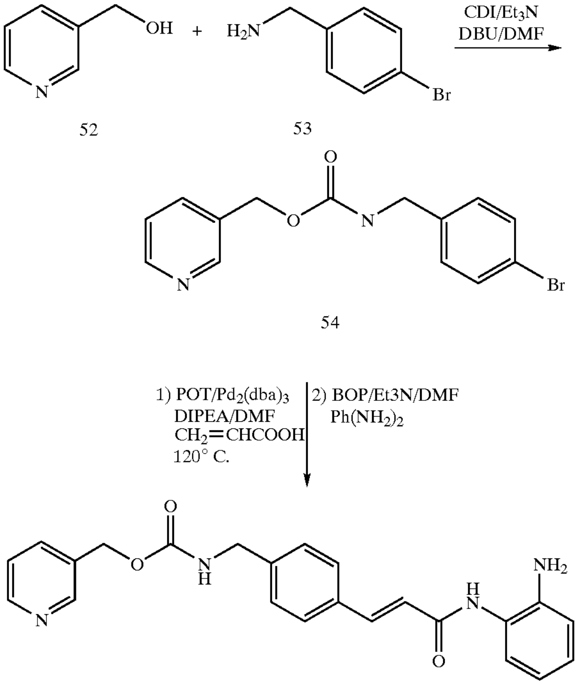

52 53 54 55

Example 44

Example 44

4-[2-(2-amino-phenylcarbamoyl)-vinyl]-benzyl] carbamic acid pyridin-3-yl methyl ester (Compound 55)

Step 1: (4-bromo-benzyl)-carbamic acid pyridin-3-yl-methyl ester (Compound 54)

4-bromobenzylamine HCl (3.0 g, 13.4 mmol) was dissolved in DMF (60 mL) at rt and then $Et_3N$ (4.13 mL, 29.7 mmol) was added dropwise over 10 min to give cloudy solution. To this, DBU (2.42 mL, 16.2 mmol) and 1,1'-carbonyl diimidazole (2.41 g, 14.8 mmol) were added. After being stirred for 1 h at rt, 3-pyridylcarbinol (1.44 mL, 14.8 mmol) was added dropwise over 10 min. The resulting reaction mixture was stirred overnight and then concentrated under reduced pressure. The residue obtained was diluted with ether/EtOAc (9:1) and then washed with $H_2O$. The organic layer was dried over $Na_2SO_4$, filtered and then concentrated to give the crude product which was recrystallized from EtOAc to give 2.55 g of product 54 (59% yield, LRMS=323 (M+1).

Step 2: 4-[2-(2-amino-phenylcarbamoyl)-vinyl]-benzyl)-carbamic acid pyridin-3-yl methyl ester (Compound 55)

Following the procedure described in Example 42, steps 2, 3, but substituting 54 for 42, and acrylic acid for tert-butyl acrylate the title compound 55 was obtained in an overall yield of 20%. $^1H$ NMR: (DMSO-d6) δ (ppm): 10.03 (s, 1H), 9.32 (s, 1H), 8.65 (s, 1H), 8.55 (d, J=3.3 Hz, 1H), 7.85 (d, J=7.69 Hz, 1H), 7.40–7.60 (m, 6H), 7.31 (d, J=7.69 Hz, 1H), 6.89 (dd, J=7.14 Hz, J=7 Hz, 1H), 6.71–6.79 (m, 2H), 6.55 (dd, J=7.1 Hz, J=7 Hz, 1H), 5.20 (s, 2H), 4.93 (bs, 2H).

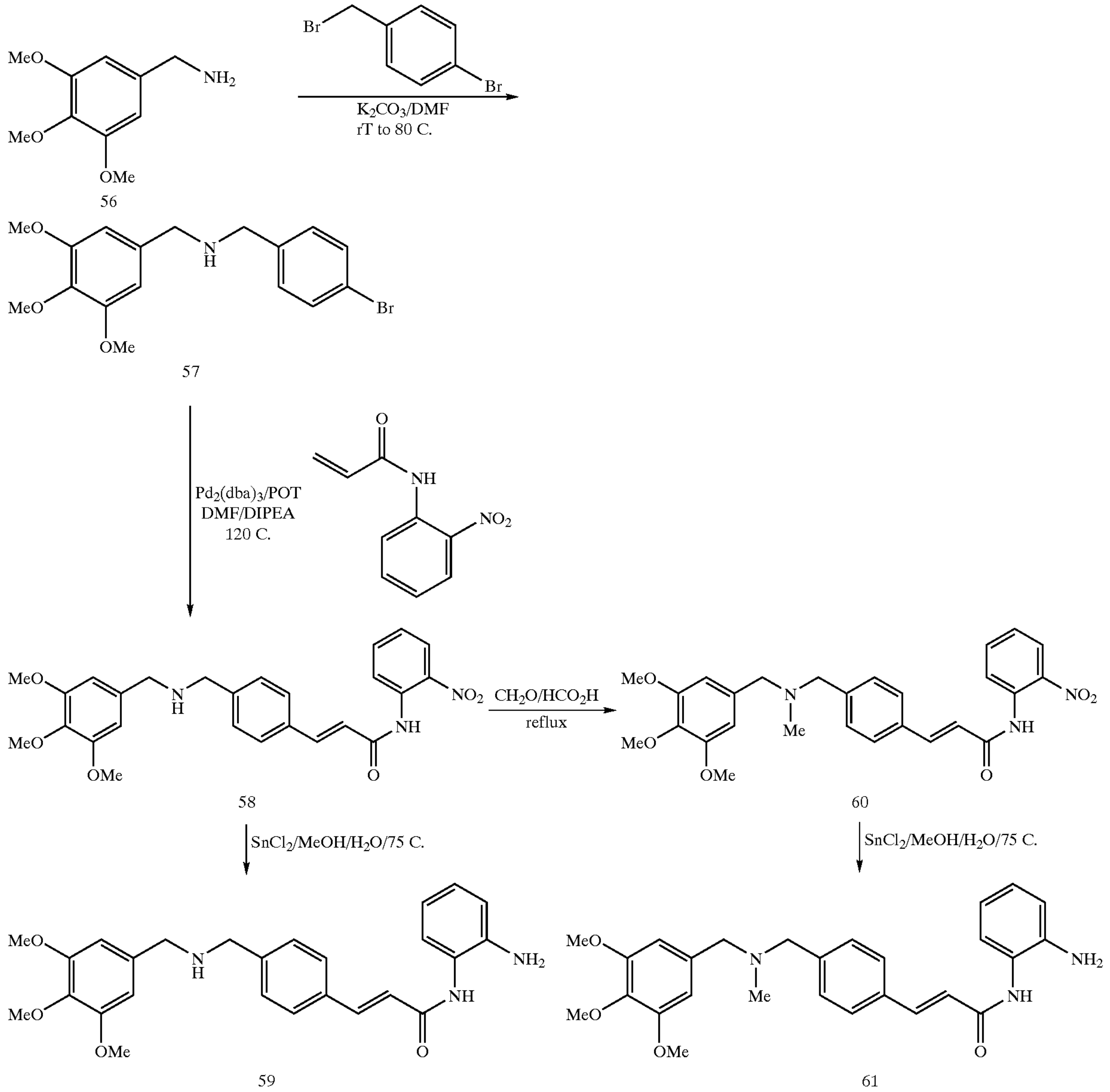

56, 57, 58, 60, 59 Example 45, 61 Example 46

Example 45

N-(2-aminophenyl)-3-{4-[(3,4,5-trimethoxy-benzylamino)-methyl]-phenyl}-acrylamide (Compound 59)

Step 1: (4-Bromo-benzyl)(3,4,5-trimethoxy-benzyl)-amine (Compound 57)

To a stirred suspension of $K_2CO_3$ (522 mg, 3.77 mmol) in dry DMF was added 3,4,5-trimethoxybenzylamine (1.10 mL, 6.44 mmol, 2.2 equiv.) followed by a solution of bromo benzylbromide (0.73 g, 2.91 mmol) in dry DMF (8 mL). The mixture was stirred at room temperature under nitrogen for two days in the dark, diluted with dichloromethane (200 mL), washed with brine, dried (MgSO4), filtered and concentrated. The crude residue was purified by chromatographic column on silica gel (elution 5% methanol in dichloromethane) to give 2.59 mmol (89% yield) of dibenzylamine 57. $^{13}C$ NMR (300 MHz, $CDCl_3$) δ (ppm): 152.5, 138.8, 136.1, 135.4, 130.6, 129.2, 119.8, 104.2, 59.9, 55.3, 52.6, 51.7. LRMS=368.4 (M+1).

Step 2: N-(2-Nitro-phenyl)-3-[4-[(3,4,5-trimethoxy-benzylamino)-methyl]-phenyl]-acrylamide (Compound 58)

Preparation of the Nitroacrylanilide

To a mixture of 2-nitroaniline (1.73 g, 12.5 mmol), DMAP (321 mg, 2.6 mmol) and 2,6-di-tert-butyl-4-methylphenol (308 mg) in dry dichloromethane (50 mL) at 0° C. was added triethylamine (10.6 mL, 76 mmol) followed by acryloychloride (3.2 mL, 38 mmol, 3.0 equiv.), and the mixture was stirred at room temperature for 16 h. The solution was diluted with dichloromethane (250 mL), cooled to 0° C. and the excess of reagent quenched with saturated $NaHCO_3$ (stirring for 1 h). The organic layer was then washed (5% $KHSO_4$, then brine), dried ($MgSO_4$), filtered and concentrated under reduced pressure. After purification through chromatographic column on silica gel (elution 50% ether in hexanes), 642 mg (3.34 mmol, 27% yield) of the amide was obtained. $^{13}C$ NMR (300 MHz, $CDCl_3$) δ (ppm): 163.6, 136.0, 135.6, 134.5, 131.3, 128.6, 125.4, 123.1, 121.8. LRMS=193.2 (M+1).

Step 3: N-(2-aminophenyl)-3-{4-[(3,4,5-trimethoxy-benzylamino)-methyl]-phenyl}-acrylamide (59)

A mixture of nitro-compound 58 (127 mg, 0.27 mmol), $SnCl_2$ (429 mg, 2.26 mmol, 8.4 equiv.) and $NH_4OAc$ (445 mg) was suspended in methanol (9.5 mL) and water (1.5 mL), and the mixture was heated at 70° C. for 45 min. The mixture was diluted with ethylacetate (100 mL) and washed with brine and then saturated $NaHCO_3$, dried ($MgSO_4$), filtered, and concentrated. Purification by chromatographic column on silica gel (elution 5 to 10% methanol in dichloromethane) gave 52 mg (43% yield) of 59. $^1H$-NMR ($CDCl_3$), δ (ppm): 8.25 (bs, 1H), 7.59 (d, J=15.6 Hz, 1H), 7.38 (d, J=7.5 Hz, 2H), 7.29 (d, J=7.5 Hz, 2H), 7.25 (m 1H), 7.02 (t, J=6.8 Hz, 1H), 6.75 (m, 2H), 6.62 (d, J=15.6 Hz, 1H), 6.58 (s, 2H), 3.97 (bs, 3H), 3.80 (s, 9H), 3.78 (s, 2H), 3.72 (s, 2H).

Example 46

N-(2-aminophenyl)-3-(4-{[(3,4,5-trimethoxy-benzyl)-amino]-methyl}-phenyl]-acrylamide (Compound 61)

Step 1: 3(-4-{[Methyl-(3,4,5-trimethoxy-benzyl)-amino]-methyl}-phenyl)-N-(2-nitro-phenyl)-acrylamide (Compound 60)

Amine 58 (180.2 mg, 0.38 mmol) was dissolved in 88% of $HCO_2H$ (6 mL), treated with excess of paraformaldehyde (7.67 mmol) and the mixture stirred at 70° C. for 2.5 h. A saturated $NaHCO_3$ solution, was added slowly, extracted with dichloromethane (2×75 mL), dried ($MgSO_4$), filtered and concentrated. After chromatographic column on silica gel (elution 3 to 5% methanol in dichloromethane), pure N-methyl amine 60 (118 mg, 63% yield) was obtained. $^{13}C$ NMR (300 MHz, $CDCl_3$) δ (ppm): 164.5, 153.1, 143.5, 142.3, 136.8, 136.1, 136.0, 135.3, 134.9, 132.9, 129.3, 128.2, 125.8, 123.1, 122.2, 120.3, 105.4, 62.2, 61.2, 60.8, 56.0, 42.5. LRMS=492.5 (M+1).

Step 2: N-(2-aminophenyl)-3-(4-{[(3,4,5-trimethoxy-benzyl)-amino]-methyl}-phenyl)-acrylamide (Compound 61)

Following the procedure described in Example 45, step 3, but substituting the nitro compound 60 for 58, the title compound 61 was obtained in 72% yield. $^1H$-NMR (DMSO-d6), δ (ppm): 9.15 (bs, 1H), 8.13 (bs, 1H), 7.58 (d, J=1.9 Hz, 1H), 7.30 (m 4H), 7.12 (d, J=7.7 Hz, 1H), 6.91 (m 3H), 6.75 (d, J=7.8 Hz, 1H), 6.57 (m 2H), 4.83 (bs, 2H), 4.43 (d, J=5.5 Hz, 2H), 3.72 (s, 3H), 3.33 (s, 3H).

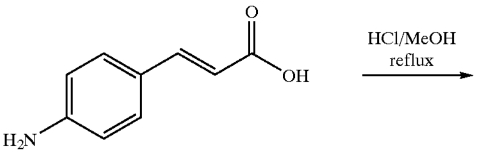

62

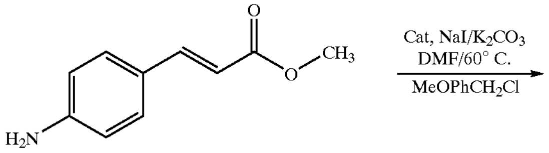

63

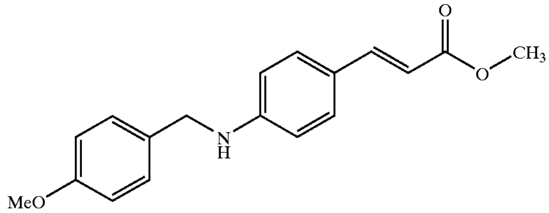

64

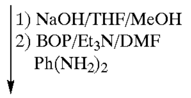

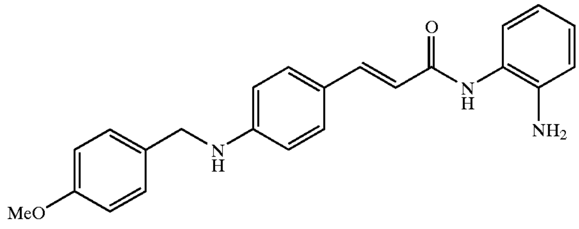

65
Example 47

Example 47

N-(2-aminophenyl)-3-{4-(4-methoxy-benzylamino)-phenyl}-acrylamide (Compound 65)

Step 1: Methyl-3-(4-amino-phenyl)-acrylate hydrochloride (Compound 63)

4-aminocinnamic acid (10.41 g, 0.052 mol) was dissolved in methanol (100 mL) at rt. A solution of HCl in dioxane (15.6 mL, 4 N) was then added. The reaction mixture was heated at reflux overnight. The clear solution was evaporated to a half volume and then settled down at rt. The white suspension obtained was collected by vacuum filtration. The mother liquid was evaporated again to a quart volume and cooled down to rt. The suspension was filtered again. The combined the solid collected from two filtration was dried in vacuo to give 7.16 g of 63 (64.3% yield). LRMS: 178 (M+1).

Step 2: Methyl-3-[4-(4-methoxy-benzylamino)-phenyl]-acrylate hydrochloride (Compound 64)

To a suspension of compound 63 (3.57 g, 16.7 mmol) in DMF (30 mL) was added $Et_3N$. after 10 min 4-methoxybenzyl chloride (2.0 g, 12.8 mmol), NaI (0.38 g, 2.6 mmol) and $K_2CO_3$ (3.53 g, 25.5 mmol) were added successively. The mixture was heated at 60° C. overnight and evaporated to dryness. The residue was partitioned between $NaHCO_3$ sat. solution (50 mL) and EtoAc (50 mL×3). The combined organic layers were washed with brine and then evaporated to dryness. The residue was purified by flash chromatography and then recrystallized from isopropylalcohol to give 1.16 g 64 (yield 30.6%, LRMS=298) and 1.46 g of 63 (49% recovered yield).

Step 3: N-(2-aminophenyl)-3-{4-(4-methoxybenzylamino)-phenyl}-acrylamide (Compound 65)

Following the procedure described in Example 42, step 4, but substituting 64 for 48, the title compound 65 was obtained in 32% yield. $^1$H NMR: (DMSO-d6) δ (ppm): 9.15 (s, 1H), 7.24 –7.38 (m, 6H), 6.84–6.90 (m, 3H), 6.72 (m, 2H), 6.49–6.60 (m, 4H), 4.84 (s, 2H ), 4.22 (d, J=5.77 Hz, 2H).

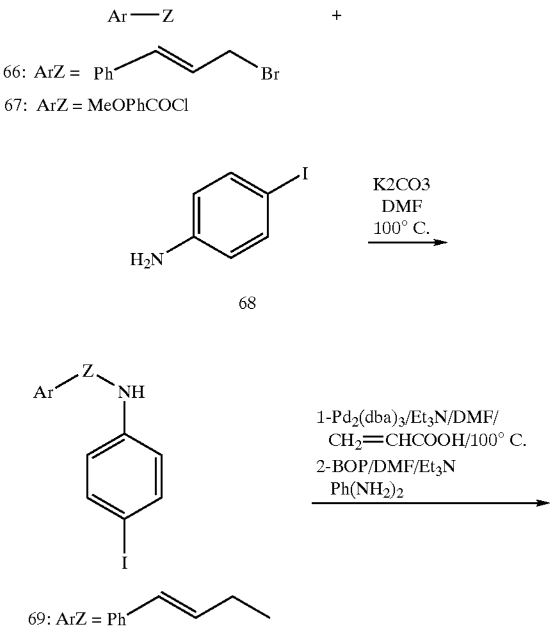

66: ArZ = Ph

67: ArZ = MeOPhCOCl

68

69: ArZ = Ph

70: ArZ = MeOPhCO

-continued

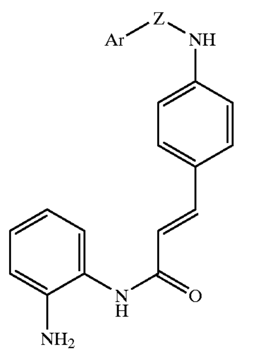

Example 48 71: ArZ = Ph 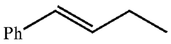

Example 49 72: ArZ = MeOPhCO

Example 48

N-(2-Amino-phenyl)-3-(4-styrylamino-phenyl)-acrylamide (Compound 71)

Step 1: N-(4-Iodo-phenyl)-(3-phenyl-allyl)-amine (Compound 69)

Following the procedure described in Example 47, step 2, but substituting 68 for 63, the title compound 69 was obtained in 70% yield. LRMS=288 (M+1)

Step 2: N-(2-Amino-phenyl)-3–4-styrylamino-phenyl)-acrylamide (71)

Following the procedure described in Example 42, steps 2, 4, but substituting 69 for 42, and acrylic acid for tertbutyl acrylate the title compound 71 was obtained in an overall yield of 60%. $^1$H NMR: (DMSO-$d_6$) δ (ppm): 9.22 (bs, 1H), 7.45 (d, J=6.9 Hz, 2H), 7.39 (d, J=9.0 Hz, 2H), 7.34 (d, J=7.4 Hz, 2H), 7.26 (dt, J=7.4 Hz, 6.8 Hz, 2H), 6:93 (dt, J=7.9 Hz, 7.1 Hz, 1H), 6.78 (d, J=7.9 Hz, 1H), 6.69 (d, J=8.5 Hz, 2H), 6.63–6.55 (m, 4H), 6.44–6.37 (m, 1H), 4.95 (bs, 2H), 3.95 (bs, 2H).

Example 49

N-(2-Amino-phenyl)-3-[4-(4-methoxy-benzamide)]-acrylamide (Compound 72)

Step 1: N-(4-Iodo-phenyl)-4-methoxy-benzamide (Compound 70)

Following the procedure described in Example 47, step 2, but substituting 68 for 63, the title compound 70 was obtained in 90% yield. LRMS=354.0 (M+1)

Step 2: N-(2-Amino-phenyl)-3-[4-(4-methoxy-benzamide)] acrylamide (Compound 72)

Following the procedure described in Example 42, steps 2, 4, but substituting 70 for 42, and acrylic acid for tertbutyl acrylate the title compound 72 was obtained in an overall yield of 90%. $^1$H NMR: (DMSO-$d_6$) δ (ppm): 9.4 (bs, 1H), 7.60(d, J=8.5 Hz, 1H), 7.54–7.45 (m, 3H), 7.87 (d, J=7.7 Hz, 1H), 7.10 (d, J=8.8 Hz, 1H), 6.95–6.77 (m, 3H), 6.62 (d, J=7.7 Hz, 2H), 6.08–6.04 (m, 2H), 4.98 (bs, 2H), 3.72 (s, 3H).

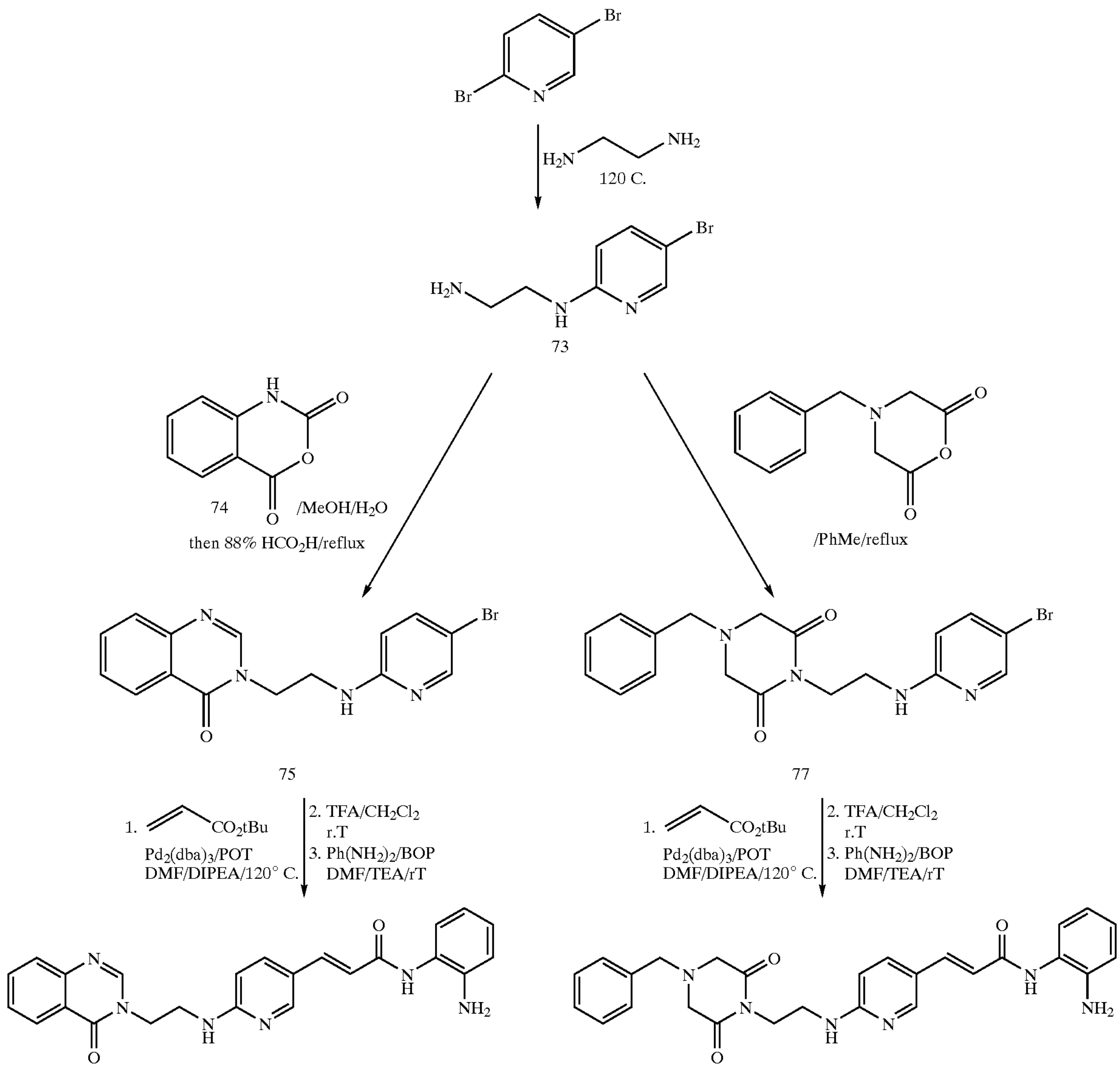

76
Example 50

78
Example 51

Example 50

N-(2-aminophenyl)-3-{6-[2-(4-oxo-4H-quinazolin-3-yl)-ethylamino]-pyridin-3-yl}-acrylamide (Compound 76)

Step 1: N-(5-Bromo-pyridin-2-yl)-ethane-1,2-diamine (Compound 73)

Following the procedure described in Example 40, step 1, but using 1,2-diaminoethane as alkyl amine, the title compound 73 was obtained in 84% yield. $^{13}C$ NMR (300 MHz, $CD_3OD$): 159.1, 148.7,140.7, 111.7, 107.2, 44.3, 41.7. LRMS=218.1 (M+1)

Step 2: 3-[2-(5-Bromo-pyridin-2-ylamino)-ethyl]-3H-quinazolin-4-one (Compound 75)

A suspension of primary amine 73 (1.17 g, 5.40 mmol) and isatoic anhydride 74 (880 mg, 5.40 mmol) in methanol (25 mL) was stirred for 3 h at 50° C. and then concentrated. The resulting oily residue was dissolved in 88% formic acid (20 mL) and refluxed overnight. After removal of formic acid, the solid residue was purified through column chromatography on silica gel (5% methanol in dichloromethane) to give 1.24 g (3.6 mmol, 67% yield) of 75. $^{13}C$ NMR (300 MHz, $CDCl_3$): 161.6, 156.8, 147.7, 147.6, 147.2, 139.8, 134.5, 127.4, 126.8, 126.3, 121.6, 110.1, 107.0, 46.3, 40.1. LRMS=347.1 (M+1).

Step 3: N-(2-aminophenyl)-3-[6-[2-(4-oxo-4H-quinazolin-3-yl)-ethylamino]-pyridin-3-yl]-acrylamide (Compound 76)

Following the procedure described in Example 42, steps 2 to 4, but substituting 75 for 42, the title compound 76 was obtained in an overall yield of 68%. $^{1}H$-NMR (DMSO-d6), δ (ppm): 9.24 (bs, 1H), 8.17 (dd, J=8.0 Hz, 1.6 Hz, 1H), 8.11 (bs, 1H), 8.08 (d, J=1.9 Hz, 1H), 7.82 (dt, J=8.5 Hz, 1.4 Hz, 1H), 7.64 (d, J=8.2 Hz, 2H), 7.25 (t, J=5.8 Hz, 1H), 6.90 (dt, J=15.7 Hz, 1H), 6.74 (dd, J=8.0 Hz, 1.4 Hz, 1H), 6.58 (m, 3H), 4.95 (bs, 2H), 4.17 (t, J=5.2 Hz, 2H), 3.68 (m, J=5.2 Hz, 2H).

Example 51

N-(2-aminophenyl)-3-{6-[2-(4-benzyl-2,6-dioxo-piperazin-1-yl)-ethylamino]-pyridin-3-yl}-acrylamide (Compound 78)

Step 2: 4-Benzyl-1-[2-(5-bromo-pyridin-2-ylamino)-ethyl]-piperazine-2,6-dione (Compound 77)

A suspension of benzyliminodiacetic acid (702 mg, 3.15 mmol) and acetic anhydride (15 mL) was stirred at 120° C. for 45 min. The reaction mixture was diluted with dry toluene and concentrated in vacuo to remove the volatiles. The residue was dissolved in dry toluene (15 mL) and transferred via cannula to a reaction flask containing the amine 73 (475 mg, 3.2 mmol). The mixture was heated at 90° C. for 16 h, concentrated and chromatographed by column on silica gel (elution 5% methanol in dichloromethane) to give 684 mg (1.70 mmol, 54% yield) of 77.

Step 3: N-(2-aminophenyl)-3-[6-[2-(4-benzyl-2,6-dioxo-piperazin-1-yl)-ethylamino]pyridin-3-yl]-acrylamide (Compound 78)

Following the procedure described in Example 42, steps 2 to 4, but substituting 77 for 42, the title compound 78 was obtained in an overall yield of 60%. $^{1}$H-NMR ($CD_3ODd4$), δ (ppm): 8.09 (d, J=1.8 Hz, 1H), 7.68 (dd, J=8.7 Hz, 2.1 Hz, 1H), 7.53 (d, J=15.6 Hz, 1H), 7.29 (m, 6H), 7.20 (dd, J=7.8 Hz, 1.2 Hz, 1H), 7.02 (dt, J=9.0 Hz, 1.2 Hz, 1H), 6.86 (dd, J=8.1 Hz, 1.2 Hz, 1H), 6.73 (dt, J=7.5 Hz, 1.5 Hz, 1H), 6.61 (d, J=15.6 Hz, 1H), 6.50 (d, J=8.7 Hz, 1H), 4.85 (bs, 3H), 3.97 (t, J=7.5 Hz, 2H), 3.60 (s, 2H), 3.57 (t, J=7.5 Hz, 2H), 3.38 (s, 4H).

Example 52

(E)-4-{[4-Amino-6-(2-indanyl-amino)-[1,3,5]triazin-2-yl-amino]-methyl}-N-(2-amino-phenyl)-cinnamide (Compound 83)

Step 1: 4,6-Dichloro-2-(2-indanyl-amino)-[1,3,5]triazine (Compound 79)

To a stirred solution at −78° C. of cyanuric chloride (13.15 g, 71.33 mmol) in anhydrous THF (100 mL) under nitrogen was slowly canulated a solution of 2-aminoindan (10.00 g, 75.08 mmol), i-$Pr_2$NEt (14.39 mL, 82.59 mmol) in anhydrous THF (60 mL. After 50 min, the reaction mixture was poured into a saturated aqueous solution of $NH_4Cl$, and diluted with AcOEt. After separation, the organic layer was successively washed with sat. $NH_4Cl$, $H_2O$ and brine, dried over anhydrous $MgSO_4$, filtered and concentrated. The crude residue was then purified by flash chromatography on silica gel (AcOEt/$CH_2Cl_2$:2/98→5/95) and by co-precipitation (AcOEt/hexanes) to afford the title compound 79 (18.51 g, 65.78 mmol, 92% yield) as a beige powder. $^{1}$H NMR (300 MHz, $CDCl_3$) δ (ppm): 7.29–7.18 (m, 4H), 6.02 (bd, J=6.3 Hz, 1H), 4.94–4.84 (m, 1H), 3.41 (dd, J=16.2, 6.9 Hz, 2H), 2.89 (dd, J=16.1, 4.5 Hz, 2H).

Step 2: 2-(4-Bromo-benzyl-amino)-4-chloro-6-(2-indanyl-amino)-[1,3,5]triazine (Compound 80)

To a stirred solution at room temperature of 79 (2.68 g, 9.52 mmol) in anhydrous THF (50 mL) under nitrogen were added i-$Pr_2$NEt (4.79 mL, 27.53 mmol) and 4-bromobenzylamine. HCl (2.45 g, 11.01 mmol), respectively. After 17 h, the reaction mixture was poured into a saturated aqueous solution of $NH_4Cl$, and diluted with AcOEt. After separation, the organic layer was successively

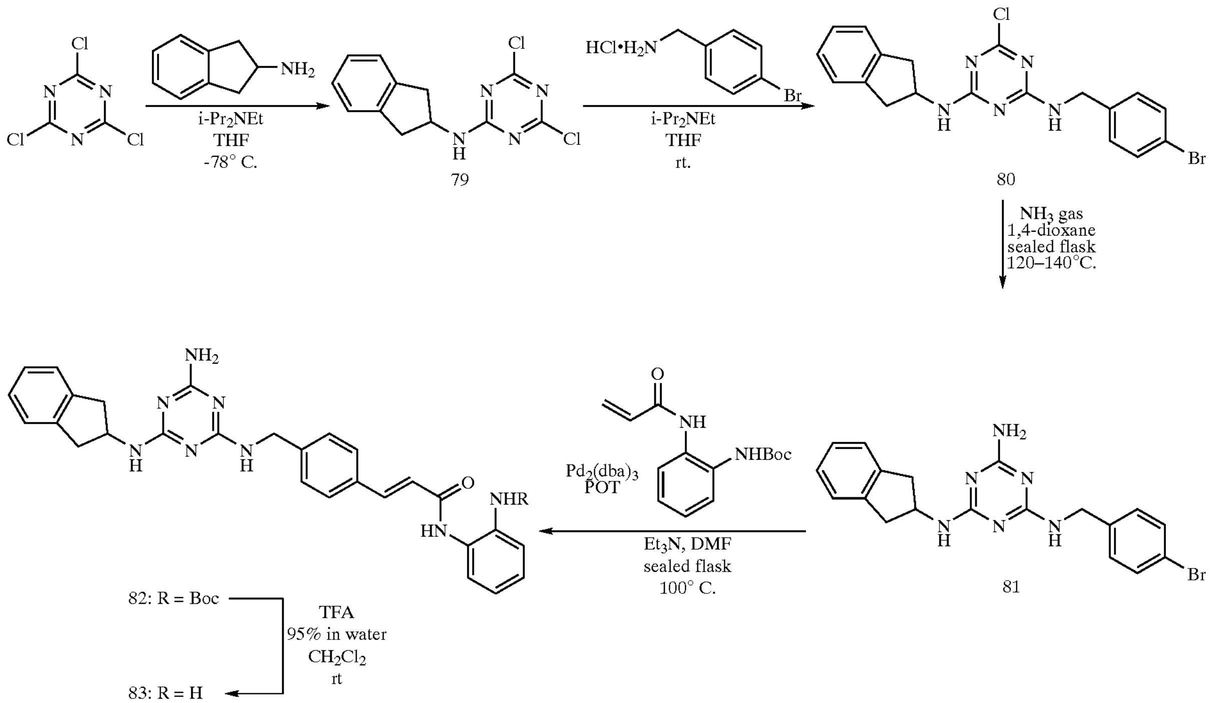

Example 52 washed with sat. $NH_4Cl$, $H_2O$ and brine, dried over anhydrous $MgSO_4$, filtered and concentrated. The crude residue was then purified by flash chromatography on silica gel ($AcOEt/CH_2Cl_2$:3/97→5/95) to afford the title compound 80 (4.00 g, 9.29 mmol, 97% yield) as a white powder. $^1H$ NMR (300 MHz, $CDCl_3$) δ (ppm): mixture of rotamers, 7.52–7.42 (m, 2H), 7.26–7.11 (m, 6H), 6.51 and 6.12 (2 m, 1H), 5.72–5.46 (m, 1H), 4.94–4.64 (m, 1H), 4.62–4.46 (m, 2H), 3.43–3.16 (m, 2H), 2.92–2.74 (m, 2H).

Step 3: 4-Amino-2-(4-bromo-benzyl-amino)-6-(2-indanyl-amino)-[1,3,5]triazine (Compound 81)

In a 75 mL sealed flask, a solution of 80 (2.05 g, 4.76 mmol) in anhydrous 1,4-dioxane (60 mL) was stirred at room temperature, saturated with $NH_3$ gas for 5 min, and warmed to 140° C. for 18 h. The reaction mixture was allowed to cool to room temperature, the saturation step with $NH_3$ gas was repeated for 5 min, and the reaction mixture was warmed to 140° C. again for 24 h. Then, the reaction mixture was allowed to cool to room temperature, poured into 1N HCl, and diluted with AcOEt. After separation, the organic layer was successively washed with sat. $NH_4Cl$, $H_2O$ and brine, dried over anhydrous $MgSO_4$, filtered and concentrated. The crude residue was then purified by flash chromatography on silica gel ($MeOH/CH_2Cl_2$:5/95) to afford the title compound 81 (1.96 g, 4.76 mmol, quantitative yield) as a colorless foam. $^1H$ NMR (300 MHz, $CDCl_3$) δ (ppm): 7.43 (d, J=8.2 Hz, 2H), 7.25–7.12 (m, 6H), 5.70–5.10 (m, 2H), 5.00–4.65 (m, 3H), 4.52 (bs, 2H), 3.40–3.10 (m, 2H), 2.90–2.65 (m, 2H).

Step 4: (E)-4-{[4-Amino-6-(2-indanyl-amino)-[1,3,5]triazin-2-ylamino]methyl}-N-[2-(N-t-butoxycarbonyl)-amino-phenyl]-cinamide (Compound 82)

Preparation of N-[2-(N-t-Butoxycarbonyl)-amino-phenyl]-acrylamide

Following the procedure described in Example 45, step 2, but substituting the nitro-compound 2-(N-t-butoxycarbonyl)-amino-aniline for 2-nitroaniline, the title compound was obtained in 77% yield. $^1H$ NMR (300 MHz, $CDCl_3$) δ (ppm): 8.51 (bs, 1H), 7.60–7.45 (m, 1H), 7.38–7.28 (m, 1H), 7.20–7.05 (m, 2H), 6.98 (bs, 1H), 6.41 (dd, J=17.0 Hz, 1.1 Hz, 1H), 6.25 (dd, J=16.9 Hz, 10.0 Hz, 1H), 5.76 (dd, J=10.2 Hz, 1.4 Hz, 1H), 1.52 (s, 9H).

In a 50 mL sealed flask, a solution of 81 (300 mg, 0.73 mmol), the acrylamide (230 mg, 0.88 mmol), $Et_3N$ (407 μl, 2.92 mmol), tri-o-tolylphosphine (POT, 13 mg, 0.04 mmol), $Pd_2(dba)_3$ (20 mg, 0.02 mmol) in anhydrous DMF (10 mL) was stirred at room temperature, saturated with $N_2$ gas for 15 min, and warmed to 100° C. for 15 h. Then, the reaction mixture was allowed to cool to room temperature, poured into a saturated aqueous solution of $NH_4Cl$, and diluted with AcOEt. After separation, the organic layer was successively washed with sat. $NH_4Cl$, $H_2O$ and brine, dried over anhydrous $MgSO_4$, filtered and concentrated. The crude residue was then purified by flash chromatography on silica gel ($MeOH/CH_2Cl_2$:2/98→5/95) to afford the title compound 82 (240 mg, 0.41 mmol, 56% yield) as a beige solid. $^1H$ NMR (300 MHz, $COCl_3$) δ (ppm): 8.46 (bs, 1H), 7.71 (bd, J=15.7 Hz, 1H), 7.62–7.05 (m, 13H), 6.54 (bd, J=15.9 Hz, 1H), 5.95–4.90 (m, 4H), 4.85–4.48 (m, 3H), 3.40–3.14 (m, 2H), 2.90–2.70 (m, 2H), 1.52 (s, 9H).

Step 5: (E)-4-{[4-Amino-6-(2-indanyl-amino)-[1,3,5]triazin-2-yl-amino]-methyl}-N-(2-amino-phenyl)-cinnamide (Compound 83)

To a stirred solution at room temperature of 82 (230 mg, 0.39 mmol) in $CH_2Cl_2$ (5 mL) was added TFA (1 mL, 95% in water). After 18 h, the reaction mixture was poured into a saturated aqueous solution of $NaHCO_3$, and diluted with AcOEt. After separation, the organic layer was successively washed with sat. $NaHCO_3$, $H_2O$ and brine, dried over anhydrous $MgSO_4$, filtered and concentrated. The crude residue was then purified by flash chromatography on silica gel ($MeOH/CH_2Cl_2$:5/95) to afford the title compound 83 (170 mg, 0.35 mmol, 89% yield) as a yellow solid. $^1H$ NMR (300 MHz, acetone-$d_6$) δ (ppm): 8.87 (bs, 1H), 7.69 (d, J=15.7 Hz, 1H), 7.59 (bd, J=7.7 Hz, 2H), 7.49–7.34 (m, 3H), 7.28–7.11 (m, 4H), 7.05–6.91 (m, 2H), 6.88 (dd, J=8.0, 1.4 Hz, 1H), 6.69 (td, J=7.6, 1.4 Hz, 1H), 6.65–5.50 (m, 4H), 4.83–4.53 (m, 5H), 3.34–3.11 (m, 2H), 2.98–2.80 (m, 2H).

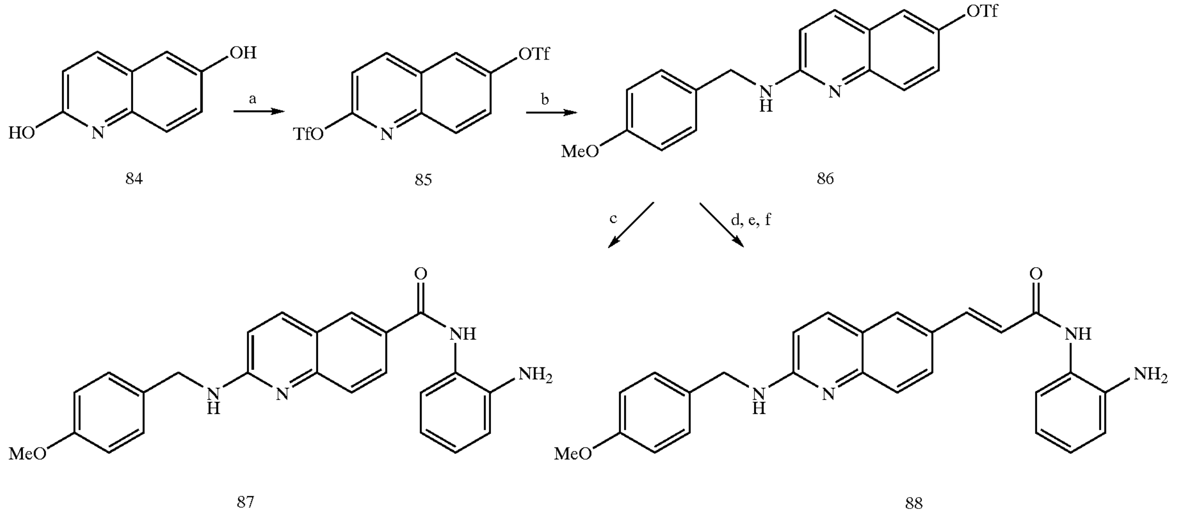

a. $Tf_2O$/Py/DMAP/0° C.
b. p-methoxybenzylamine/ 120° C.
c. 1,2-phenylenediamine/CO(40psi)/$Pd(OAc)_2$/dppf/DMF/DIPEA/70° C.
d. t Butylacrylate/$Pd_2(dba)_3$/POT/DMF/DIPEA/120° C.
e. TFA/DCM/rT
f. 1,2-phenylenediamine/BOP/DMF/TEA/rT

Example 53

N-(2-aminophenyl)-2-(4-methoxy-benzylamino)-quinolin-6-yl-amide (Compound 87)

Step 1: 2,6-ditrifluoromethanesulfonyloxy-quinoline (Compound 85):

A solution of 2,6-dihydroxyquinoline 84 (1.254 g, 7.78 mmol) and DMAP (a few crystals) in dry pyridine (15 mL) was treated with neat trifluoromethanesulfonic anhydride (5.2 g, 18.4 mmol, 1.2 equiv.) and stirred at 0° C. for 5 h. This solution was then poured on a mixture brine/sat $NaHCO_3$ and extracted with dichloromethane (2×150 mL), dried ($MgSO_4$), filtered and concentrated. Purification by column chromatography on silica gel (30% to 50% ether in hexanes) gave 2.58 g (6.1 mmol, 78% yield) of 85. $^{13}C$ NMR (300 MHz, $CDCl_3$): 154.5, 147.8, 144.6, 142.0, 131.6, 127.8, 124.9, 119.3, 118.7, 114.9. LRMS=426.0 (M+1).

Step 2: N-(2-aminophenyl)-2-(4-methoxy-benzylamino)-quinolin-6-yl-amide (Compound 87)

Following the procedure described in Example 40, steps 1, 2, but substituting 85 for 40, the title compound 87 was obtained in 92% yield. $^1$HNMR (DMSO-d6), δ (ppm): 9.66 (bs, 1H), 8.32 (s, 1H), 8.05 (d, J=8.8 Hz, 1H), 7.96 (dd, J=9.1 Hz, 2.2 Hz, 1H), 7.72 (d, J=2.2 Hz, 1H), 7.55 (dd, J=8.5 Hz, 2.2 Hz, 1H), 7.34 (dd, J=8.5 Hz, 2.2 Hz, 1H), 7.20 (d, J=7.7 Hz, 1H), 6.97 (t, J=7.7 Hz, 1H), 6.90 (m 2H), 6.80 (d, J=7.9 Hz, 1H), 6.61 (t, J=6.3 Hz, 1H), 4.90 (bs 2H), 4.58 (d, J=3.3 Hz, 2H), 3.73 (s, 3H), 3.33 (bs, 1H).

Example 54

N-(2-aminophenyl)-3-[2-(4-methoxy-benzylamino)-quinolin-6-yl]-acrylamide (Compound 88)

Step 3: N-(2-aminophenyl)-3-[2-(4-methoxy-benzylamino)-quinolin-6-yl]-acrylamide (Compound 88)

Following the procedure described in Example 42, steps 1 to 4, but substituting 85 for 40, the title compound 88 was obtained in an overall yield of 71%. $^1$H-NMR (DMSO-d6), δ (ppm): 9.70 (bs, 1H), 9.40 (bs, 1H), 8.20 (d, J=8.9 Hz, 1H), 8.03 (bs, 2H), 7.94 (d, J=7.2 Hz, 1H), 7.64 (dd, J=15.7 Hz, 2.5 Hz, 1H), 7.41 (d, J=8.5 Hz, 2H), 7.39 (m, 1H), 7.14 (d, J=8.9 Hz, 1H), 7.05 (d, J=15.7 Hz, 1H), 6.97 (m, 1H), 6.95 (d, J=8.5 Hz, 2H), 6.81 (d, J=8.0 Hz, 1H), 6.65 (t, J=7.2 Hz, 1H), 4.76 (s, 2H), 3.75 (s, 3H).

Examples 55–84

Examples 55 to 84 describe the preparation of compounds 89 to 118 using the same procedures as described for compounds 44 to 88 in Examples 40 to 54. Characterization data are presented in Tables 3a–d.

TABLE 3a

Characterization of Compounds Prepared in Examples 42–84

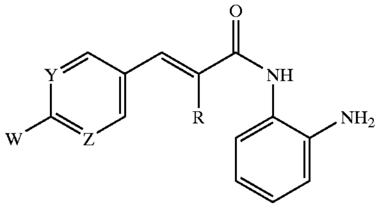

| Ex. | Cpd. | W | Y | Z | R | Name | Characterization | Schm |
|---|---|---|---|---|---|---|---|---|
| 42 | 50 | 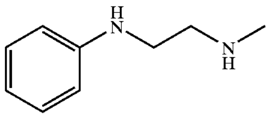 | N | CH | H | N-(2-aminophenyl)-3-[6-(2-phenylamino-ethylamino)-pyrindin-3-yl]-acrylamide | $^1$H-NMR (DMSO-d6), δ (ppm): 9.25 (bs, 1H), 8.21 (d, J=1.6Hz, 1H), 7.67 (d, J=8.5Hz, 1H), 7.43 (d, J=15.7Hz, 1H), 7.32 (d, J=7.4Hz, 1H), 7.24 (t, J=1.0Hz, 1H), 7.08 (t, J=7.4Hz, 2H), 6.91 (t, J=8.0Hz, 1H), 6.75 (dt, J=8.0Hz, 0.4Hz, 1H), 6.57 (m, 6H), 5.20 (bs, 1H), 3.48 (t, J=6.3Hz, 2H), 3.33 (bs, 2H), 3.21 (t, J=6.3Hz, 2H) | 3 |
| 44 | 55b | 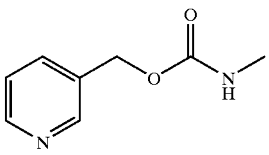 | CH | CH | H | {4-[2-(2-amino-phenylcarbamoyl)-vinyl]-phenyl}-carbamic acid pyridin-3-yl methyl ester | $^1$H NMR: (DMSO-d6) δ (ppm): 10.03 (s, 1H), 9.32 (s, 1H), 8.65 (s, 1H), 8.55 (d, J=3.3Hz, 1H), 7.85 (d, J=7.69Hz, 1H), 7.40–7.60 (m, 6H), 7.31 (d, J=7.69Hz, 1H), 6.89 (dd, J=7.14Hz, J=7Hz, 1H), 6.71–6.79 (m, 2H), 6.55 (dd, J=7.1Hz, J=7Hz, 1H), 5.20 (s, 2H), 4.93 (bs, 2H). | 4 |
| 45 | 59 | 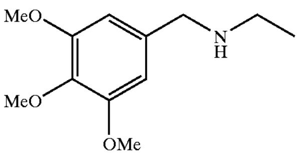 | CH | CH | H | N-(2-aminophenyl)-3-{4-[(3,4,5-trimethoxy-benzylamino)-methyl]-phenyl}-acrylamide | $^1$H-NMR ($CDCl_3$), δ (ppm): 8.25 (bs, 1H), 7.59 (d, J=15.6Hz, 1H), 7.38 (d, J=7.5Hz, 2H), 7.29 (d, J=7.5Hz, 2H), 7.25 (m 1H), 7.02 (t, J=6.8Hz, 1H), 6.75 (m, 2H), 6.62 (d, J=15.6Hz, 1H), 6.58 (s, 2H), 3.97 (bs, 3H), 3.80 (s, 9H), 3.78 (s, 2H), 3.72 (s, 2H). | 5 |

TABLE 3a-continued

Characterization of Compounds Prepared in Examples 42–84

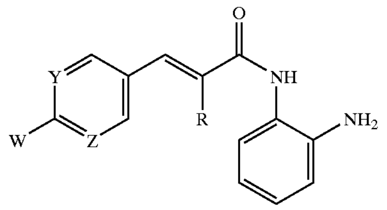

| Ex. | Cpd. | W | Y | Z | R | Name | Characterization | Schm |
|---|---|---|---|---|---|---|---|---|
| 46 | 61b | 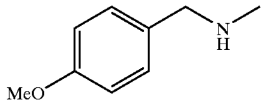 | N | CH | Me | N-(2-aminophenyl)-3-[6-(4-methoxy-benzylamino)-pyridin-3-yl]-2-methyl-acrylamide | $^1$H-NMR (DMSO-d6), δ (ppm): 9.15 (bs, 1H), 8.13 (bs, 1H), 7.58 (d, J=1.9Hz, 1H), 7.30 (m 4H), 7.12 (d, J=7.7Hz, 1H), 6.91 (m 3H), 6.75 (d, J=7.8Hz, 1H), 6.57 (m, 2H), 4.83 (bs, 2H), 4.43 (d, J=5.5Hz, 2H), 3.72 (s, 3H), 3.33 (s, 3H). | 3 |
| 47 | 65 | 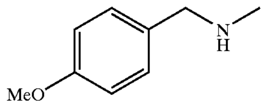 | CH | CH | H | N-(2-amino-phenyl)-3-[4-(4-methoxy-benzylamino)-phenyl]-acrylamide | $^1$H NMR: (DMSO-d6) δ (ppm): 9.15 (s, 1H), 7.24–7.38 (m, 6H), 6.84–6.90 (m, 3H), 6.72 (m, 2H), 6.49–6.60 (m, 4H), 4.84 (s, 2H), 4.22 (d, J=5.77Hz, 2H). | 6 |
| 48 | 71 | 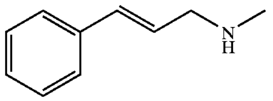 | CH | CH | H | N-(2-Amino-phenyl)-3-(4-styrylamino-phenyl)-acrylamide | $^1$H NMR: (DMSO-$d_6$) δ (ppm): 9.22 (bs, 1H), 7.45 (d, J=6.9Hz, 2H), 7.39 (d, J=9.0Hz, 2H), 7.34 (d, J=7.4Hz, 2H), 7.26 (dt, J=7.4Hz, 6.8Hz), 6.93 (dt, J=7.9Hz, 7.1Hz, 1H), 6.78 (d, J=7.9Hz, 1H), 6.69 (d, J=8.5Hz, 2H), 6.63–6.55 (m, 4H), 6.44–6.37 (m, 1H), 4.95 (bs, 2H), 3.95 (bs, 2H). | 7 |
| 49 | 72 | 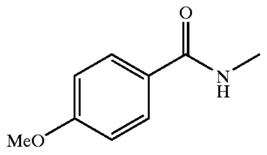 | CH | CH | H | N-{4-[2-(2-Amino-phenylcarbamoyl)-vinyl]-phenyl}-4-methoxy-benzamide | $^1$H NMR: (DMSO-$d_6$) δ (ppm): 9.4 (bs, 1H), 7.60 (d, J=8.5Hz, 1H), 7.54–7.45 (m, 3H), 7.87 (d, J=7.7Hz, 1H), 7.10 (d, J=8.8Hz, 1H), 6.95–6.77 (m, 3H), 6.62 (d, J=7.7Hz, 2H), 6.08–6.04 (m, 2H), 4.98 (bs, 2H), 3.72 (s, 3H). | 7 |
| 50 | 76 | 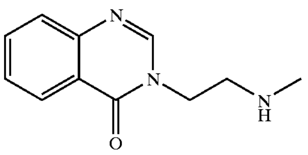 | N | CH | H | N-(2-aminophenyl)-3-{6-[2-(4-oxo-4H-quinazolin-3-yl)-ethylamino]-pyridin-3-yl}-acrylamide | $^1$H-NMR (DMSO-d6), δ (ppm): 9.24 (bs, 1H), 8.17 (dd, J=8.0Hz, 1.6Hz, 1H), 8.11 (bs, 1H), 8.08 (d, J=1.9Hz, 1H), 7.82 (dt, J=8.5Hz, 1.4Hz, 1H), 7.64 (d, J=8.2Hz, 2H), 7.25 (t, J=5.8Hz, 1H), 6.90 (dt, J=15.7Hz, 1H), 6.74 (dd, J=8.0Hz, 1.4Hz, 1H), 6.58 (m, 3H), 4.95 (bs, 2H), 4.17 (t, J=5.2Hz, 2H), 3.68 (m, J=5.2Hz, 2H). | 8 |
| 51 | 78 | 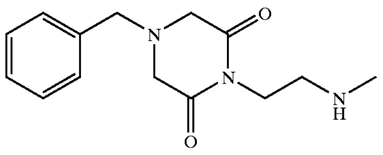 | N | CH | H | N-(aminophenyl)-3-{6-[2-(4-benzyl-2,6-dioxo-piperazin-1-yl)-ethylamino]-pyridin-3-yl}-acrylamide | $^1$H-NMR ($CD_3OD$-d4), δ (ppm): 8.09 (d, J=1.8Hz, 1H), 7.68 (dd, J=8.7Hz, 2.1Hz, 1H), 7.53 (d, J=15.6Hz, 1H), 7.29 (m, 6H), 7.20 (dd, J=7.8Hz, 1.2Hz, 1H), 7.02 (dt, J=9.0Hz, 1.2Hz, 1H), 6.86 (dd, J=8.1Hz, 1.2Hz, 1H), 6.73 (dt, J=7.5Hz, 1.5Hz, 1H), 6.61 (d, J=15.6Hz, 6.50 (d, J=8.7Hz, 1H), 4.85 (bs, 3H), 3.97 (t, J=7.5Hz, 2H), 3.60 (s, 2H), 3.57 (t, J=7.5Hz, 2H), 3.38 (s, 4H). | 8 |

TABLE 3a-continued

Characterization of Compounds Prepared in Examples 42–84

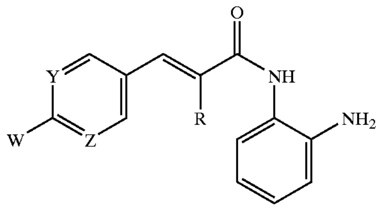

| Ex. | Cpd. | W | Y | Z | R | Name | Characterization | Schm |
|---|---|---|---|---|---|---|---|---|
| 52 | 83 | 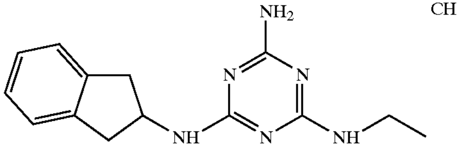 | CH | CH | H | (E)-4-{[4-Amino-6-(2-indanyl-amino)-[1,3,5]triazin-2-ylamino]-methyl}-N-(2-amino-phenyl)-cinamide | $^1$H NMR (300MHz, acetone-$d_6$) δ (ppm): 8.87 (bs, 1H), 7.69 (d, J=15.7Hz, 1H), 7.59 (bd, J=7.7Hz, 2H), 7.49–7.34 (m, 3H), 7.28–7.11 (m, 4H), 7.05–6.91 (m, 2H), 6.88 (dd, J=8.0, 1.4Hz, 1H), 6.69 (td, J=7.6, 1.4Hz, 1H), 6.65–5.50 (m, 4H), 4.83–4.53 (m, 5H), 3.34–3.11 (m, 2H), 2.98–2.80 (m, 2H). | 9 |
| 55 | 89 | 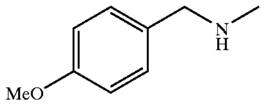 | N | CH | H | N-(2-aminophenyl)-3-[6-(4-methoxy-benzylamino)-pyridin-3-yl]-acrylamide | $^1$H-NMR (DMSO-d6), δ (ppm): 9.24 (bs, 1H), 8.19 (d, J=1.6Hz, 1H), 7.64 (d, J=8.5Hz, 1H), 7.52 (t, J=5.5Hz, 1H), 7.42 (d, J=15.7Hz, 1H), 7.32 (d, J=7.4Hz, 1H), 7.26 (d, J=8.5Hz, 2H), 6.90 (m, 1H), 6.88 (dd, J=8.5Hz, 2H), 6.74 (d, J=6.9 Hz, 1H), 6.58 (m, 3H), 4.92 (bs, 2H), 4.45 (d, J=5.5Hz, 2H), 3.72 (s, 3H). | 3 |
| 56 | 90 | 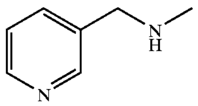 | N | CH | H | N-(2-aminophenyl)-3-{6-[pyridin-3-ylmethyl)-amino]-pyridin-3-yl}-acrylamide | $^1$H-NMR ($CD_3OD$-d4), δ (ppm): 8.47 (bs, 1H), 8.33 (bs, 1H), 8.02 (m, 1H), 7.73 (m, 1H), 7.61 (d, J=8.5Hz, 1H), 7.46 (d, J=15.4Hz, 1H), 7.29 (m, 1H), 7.14 (d, J=7.7Hz, 1H), 6.94 (d, J=7.4Hz, 1H), 6.80 (d, J=7.9Hz, 1H), 6.66 (t, J=7.9Hz, 1H), 6.53 (m, 2H), 4.54 (m, 2H), 3.59 (bs, 2H). | 3 |
| 57 | 91 | 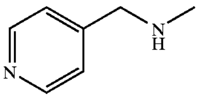 | N | CH | H | N-(2-aminophenyl)-3-{6-[(pyridin-4-ylmethyl)-amino]-pyridin-3-yl}-acrylamide | $^1$H-NMR (DMSO-d6), δ (ppm): 9.27 (bs, 1H), 8.48 (dd, J=1.6Hz, 4.4, 1H), 8.16 (d, J=1.6Hz, 1H), 7.70 (m 2H), 7.42 (d, J=15.6Hz, 1H), 7.31 (m 3H), 6.90 (t, J=6.9Hz, 1H), 6.73 (d, J=6.9Hz, 1H), 6.58 (m 4H), 4.98 (bs, 2H), 4.57 (d, J=6.0Hz, 2H). | 3 |
| 58 | 92 | 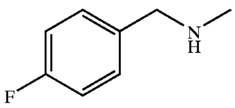 | N | CH | H | N-(2-aminophenyl)-3-[6-(4-fluoro-benzylamino)-pyridin-3-yl]-acrylamide | $^1$H-NMR (DMSO-d6), δ (ppm): 9.24 (bs, 1H), 8.18 (d, J=1.6Hz, 1H), 7.65 (dd, J=8.8Hz, 0.8Hz, 1H), 7.60 (t, J=5.8Hz, 1H), 7.42 (d, J=15.7Hz, 1H), 7.36 (m, 3H), 7.13 (t, J=8.8Hz, 2H), 6.90 (t, J=7.4Hz, 1H), 6.73 (dd, J=6.9Hz, 1.0Hz, 1H), 6.58 (m, 3H), 4.91 (bs, 2H), 4.50 (d, J=6.0Hz, 2H). | 3 |
| 59 | 93 | 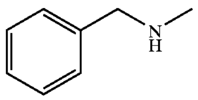 | N | CH | H | N-(2-aminophenyl)-3-(6-benzylamino-pyridin-3-yl)-acrylamide | $^1$H-NMR (DMSO-d6), δ (ppm): 9.24 (bs, 1H), 8.17 (d, J=1.9Hz, 1H), 7.65 (dd, J=8.8Hz, 1.6Hz, 1H), 7.60 (t, J=6.0Hz, 1H), 7.41 (d, J=15.7Hz, 1H), 7.31 (m, 5H), 7.23 (m, 1H), 6.89 (dt, J=8.0Hz, 1.6Hz, 1H), 6.73 (dd, J=8.0Hz, 1.5Hz, 1H), 6.58 (m 3H), 4.92 (bs, 2H), 4.53 (d, J=6.0Hz, 2H) | 3 |

TABLE 3a-continued

Characterization of Compounds Prepared in Examples 42–84

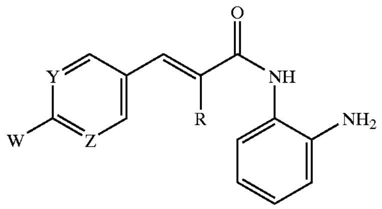

| Ex. | Cpd. | W | Y | Z | R | Name | Characterization | Schm |
|---|---|---|---|---|---|---|---|---|
| 60 | 94 | 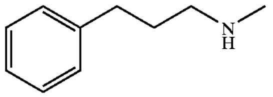 | N | CH | H | N-(2-aminophenyl)-3-[6-(3-phenyl-propylamino)-pyridin-3-yl]-acrylamide | $^1$H-NMR (DMSO-d6), δ (ppm): 9.22 (bs, 1H), 8.18 (ds, 1H), 7.63 (d, J=8.8Hz, 1H), 7.42 (d, J=15.4Hz, 1H), 7.22 (m 7H), 6.90 (t, J=7.7Hz, 1H), 6.75 (d, J=8.0Hz, 1H), 6.57 (m 3H), 4.92 (bs, 2H), 3.29 (dt, J=7.7Hz, 6.0Hz, 2H), 2.66 (t, J=7.7Hz, 2H), 1.84 (m, J=7.7Hz, 2H). | 3 |
| 61 | 95 | 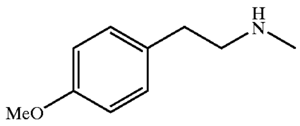 | N | CH | H | N-(2-aminophenyl)-3-{6-[2-(4-methoxy-phenyl)-ethylamino]-pyridin-3-yl}-acrylamide | $^1$H-NMR (DMSO-d6), δ (ppm): 9.22 (bs, 1H), 8.19 (bs, 1H), 7.62 (d, J=8.5Hz, 1H), 7.42 (d, J=15.7Hz, 1H), 7.32 (d, J=7.8Hz, 1H), 7.16 (d, J=7.8Hz, 2H), 7.13 (m, 1H), 6.91 (m, 1H), 6.85 (d, J=7.9Hz, 1H), 6.74 (d, J=7.8Hz, 1H), 6.57 (m 3H), 4.92 (bs, 2H), 3.71 (s, 3H), 3.47 (dd, J=7.3Hz, 6.0Hz, 2H), 2.78 (t, J=7.3Hz, 2H). | 3 |
| 62 | 96 | 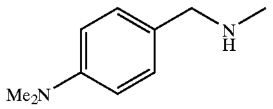 | N | CH | H | N-(2-aminophenyl)-3-[6-(4-dimethylamino-benzylamino)-pyridin-3-yl]-acrylamide | $^1$H-NMR (DMSO-d6), δ (ppm): 9.23 (bs, 1H), 8.18 (bs, 1H), 7.63 (d, J=8.2Hz, 1H), 7.41 (m 2H), 7.31 (d, J=7.4Hz, 1H), 7.15 (d, J=8.5Hz, 2H), 6.90 (t, J=7.4Hz, 1H), 6.74 (d, J=7.0Hz, 1H), 6.68 (d, J=8.5Hz, 2H), 6.58 (m, 3H), 4.91 (bs, 2H), 4.39 (d, J=5.5Hz, 2H), (bs, 2H). | 3 |
| 63 | 97 | 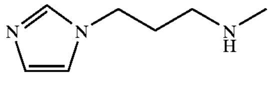 | N | CH | H | N-(2-aminophenyl)-3-[6-(3-imidazol-1-yl-propylamino)-pyridin-3-yl]-acrylamide | $^1$H-NMR ($CD_3OD$-d4), δ (ppm): 8.09 (bs, 1H), 8.05 (d, J=1.9Hz, 1H), 7.67 (m, 2H), 7.49 (d, J=15.7Hz, 1H), 7.28 (m, 2H), 7.17 (m, 2H), 6.98 (dt, J=13.7Hz, 7.7Hz, 1H), 6.83 (dd, J=8.0Hz, 1.1Hz, 1H), 6.69 (dt, J=9.1Hz, 1.4Hz, 1H), 6.58 (d, J=15.7Hz, 1H), 6.51 (d, J=8.8Hz, 1H), 4.15 (t, J=7.1Hz, 2H), 3.29 (m, 2H), 2.08 (m, J=6.9Hz, 2H). | 3 |
| 64 | 98 | 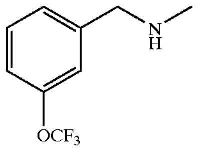 | N | CH | H | N-(2-aminophenyl)-3-[6-(3-trifluoromethoxy-benzylamino)-pyridin-3-yl]-acrylamide | $^1$H-NMR (acetone-d6), δ (ppm): 8.75 (bs, 1H), 8.23 (d, J=1.9Hz, 1H), 7.69 (d, J=8.2Hz, 1H), 7.55 (d, J=15.4Hz, 1H), 7.43 (m, 2H), 7.34 (bs, 2H), 7.19 (d, J=6.6Hz, 1H), 6.93 (m, 2H), 6.83 (dd, J=8.0Hz, 1.4Hz, 1H), 6.67 (m, 3H), 4.71 (d, J=6.3Hz, 2H), 4.65 (bs, 2H). | 3 |
| 65 | 99 | 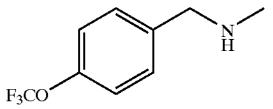 | N | CH | H | N-(2-aminophenyl)-3-[6-(4-trifluoromethoxy-benzylamino)-pyridin-3-yl]-acrylamide | $^1$H-NMR (acetone-d6), δ (ppm): 8.81 (bs, 1H), 8.21 (d, J=1.9Hz, 1H), 7.66 (d, J=7.4Hz, 1H), 7.56 (d, J=15.7Hz, 2H), 7.49 (d, 2H), J=8.2Hz, 1H), 7.34 (d, J=8.1Hz, 1H), 7.25 (t, J=8.0Hz, 1H), 6.93 (m, 2H), 6.73 (m, 3H), 4.67 (d, J=6.0Hz, 2H), 4.66 (bs, 2H). | 3 |

TABLE 3a-continued

Characterization of Compounds Prepared in Examples 42–84

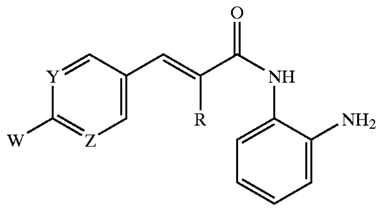

| Ex. | Cpd. | W | Y | Z | R | Name | Characterization | Schm |
|---|---|---|---|---|---|---|---|---|
| 66 | 100 | 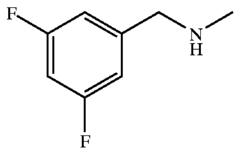 | N | CH | H | N-(2-aminophenyl)-3-[6-(3,5-difluoro-benzylamino)-pyridin-3-yl]-acrylamide | $^1$H-NMR (DMSO-d6), δ (ppm): 9.25 (bs, 1H), 8.18 (d, J=2.2Hz, 1H), 7.67 (m, 2H), 7.42 (d, J=15.7Hz, 1H), 7.31 (d, J=7.7Hz, 1H), 7.08 (dt, J=9.3Hz, 2.2Hz, 1H), 7.03 (dd, J=8.8Hz, 1.9Hz, 2H), 6.90 (dt, J=7.3Hz, 1.4Hz, 1H), 6.73 (dd, J=8.0Hz, 1.4Hz, 1H), 6.60 (m 3H), 4.92 (bs, 2H), 4.56 (d, J=6.0Hz, 2H). | 3 |
| 67 | 101 | 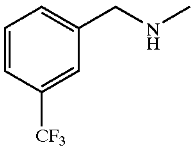 | N | CH | H | N-(2-aminophenyl)-3-[6-(3-trifluoromethyl-benzylamino)-pyridin-3-yl]-acrylamide | $^1$H-NMR (DMSO-d6), δ (ppm): 9.25 (bs, 1H), 8.14 (bs, 1H), 7.86 (m, 6H), 7.42 (d, J=15.6Hz, 1H), 7.31 (d, J=7.4Hz, 1H), 6.90 (dt, J=8.8, 1.1Hz, 1H), 6.74 (dd, J=8.0Hz, 1.4Hz, 1H), 6.60 (m 3H), 4.96 (bs, 2H), 4.63 (d, J=5.8Hz, 2H). | 3 |
| 68 | 102 | 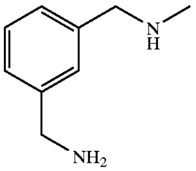 | N | CH | H | 3-[6-(3-aminomethyl-benzylamino)-pyridin-3-yl]-N-(2-aminophenyl)-acrylamide | $^1$H-NMR (DMSO-d6), δ (ppm): 9.28 (bs, 1H), 8.17 (bs, 1H), 7.66 (d, J=5.8Hz, 2H), 7.37 (m, 6H), 6.88 (dd, J=8.0Hz, 0.9Hz, 1H), 6.73 (dd, J=8.0Hz, 0.9Hz, 1H), 6.59 (m 3H), 4.55 (d, J=5.8Hz, 2H), 3.96 (s, 2H), 3.37 (bs, 4H). | 3 |
| 70 | 104 | 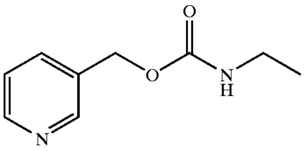 | CH | CH | H | {4-[2-(2-amino-phenylcarbmoyl)-vinyl]-benzyl}-carbamic acid pyridin-3-yl methyl ester | $^1$H NMR: (DMSO-d6) δ (ppm): 9.36 (s, 1H), 8.57 (s, 1H), 8.51 (d, J=4.6Hz, 1H), 7.91 (m, 1H), 7.77 (d, J=7.68Hz, 1H), 7.28–7.57 (m, 7H), 6.88 (dd, J=15.66Hz, 4.40Hz, 2H), 6.73 (m, 1H), 6.56 (m, 1H), 5.01 (s, 2H), 4.93 (bs, 2H), 4.10 (d, J=6.04Hz, 2H). | 4 |
| 71 | 105 | 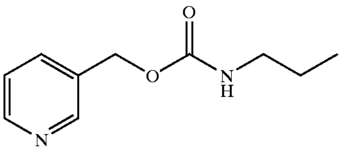 | CH | CH | H | (2-{4-[2-(2-amino-phenylcarbamoyl)-vinyl]-phenyl}-ethyl}-carbamic acid pyridin-3-yl methyl ester | $^1$H NMR: (DMSO-d6) δ (ppm): 9.34 (s, 1H), 8.52 (m, 2H), 7.71 (d, J=7.69Hz, 1H), 7.20–7.60 (m, 8H), 6.87 (m, 2H), 6.73 (m, 1H), 6.56 (m, 1H), 5.03 (s, 2H), 4.92 (s, 2H), 3.30 (m, 2H), 2.75 (m, 2H). | 4 |
| 72 | 106 | 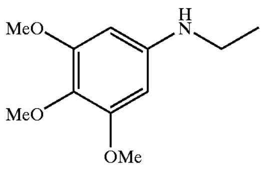 | CH | CH | H | N-(2-aminophenyl)-3-{4-[(3,4,5-trimethoxy-phenylamino)-methyl]-phenyl}-arylamide | $^1$H-NMR (acetone-d6), δ (ppm): 8.49 (bs, 1H), 8.41 (d, J=7Hz, 1H), 7.63 (d, J=15.6Hz, 1H), 7.56 (d, J=8Hz, 2H), 7.45 (d, J=8Hz, 2H), 7.07 (m, 2H), 6.90 (d, J=15.6Hz, 1H), 6.76 (m, 1H), 6.74 (m, 1H), 5.99 (s, 2H), 4.36 (s, 2H), 3.69 (s, 6H), 3.68 (bs, 2H), 3.67 (s, 3H). | 5 |
| 73 | 107 | 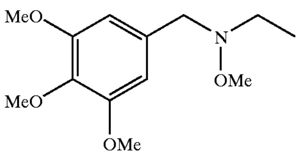 | CH | CH | H | N-(2-aminophenyl)-3-(4-{[(3,4,5-trimethoxy-benzyl)-amino]-methyl}-pheyl)-arylamide | $^1$H-NMR ($CDCl_3$), δ (ppm): 7.70 (bs, 1H), 7.43 (d, J=7.4Hz, 1H), 7.33 (d, J=4.9Hz, 2H), 7.26 (d, J=4.9Hz, 2H), 7.25 (m, 1H), 7.03 (t, J=7.4Hz, 1H), 6.78 (d, J=7.4Hz, 1H), 6.75 (m, 1H), 6.61 (s, 2H), 6.57 (m, 1H), 4.08 (bs, 2H), 3.86 (s, 6H), 3.83 (s, 3H), 3.50 (s, 2H), 3.47 (s, 2H), 2.21 (s, 3H). | 5 |

TABLE 3a-continued

Characterization of Compounds Prepared in Examples 42–84

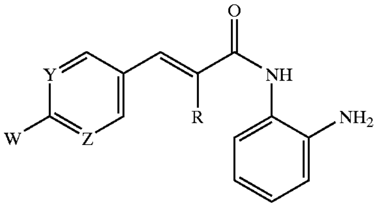

| Ex. | Cpd. | W | Y | Z | R | Name | Characterization | Schm |
|---|---|---|---|---|---|---|---|---|
| 74 | 108 | 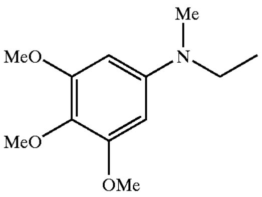 | CH | CH | H | N-(2-aminophenyl)-3-{4-[(3,4,5-trimethoxy-phenyl)-amino]-methyl}-phenyl}-arylamide | $^1$H-NMR ($CDCl_3$), δ (ppm): 7.74 (d, J=15.4Hz, 1H), 7.50 (d, J=7.4Hz, 2H), 7.25 (m 3H), 7.06 (t, J=1.9Hz, 1H), 6.82 (d, J=7.4Hz, 2H), 6.58 (d, J=15.4Hz, 1H), 5.96 (s, 2H), 4.50 (s, 2H), 3.79 (s, 6H), 3.78 (bs, 2H), 3.77 (s, 3H), 3.00 (s, 3H). | 5 |
| 75 | 109 | 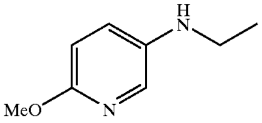 | CH | CH | H | N-(2-Amino-phenyl)-3-{4-[(6-methoxy-pyridin-3-ylamino)-methyl]-phenyl}-acrylamide | $^1$H NMR: (DMSO-$d_6$) δ (ppm): 9.4 (bs, 1H), 7.60(d, J=8.5Hz, 1H), 7.54–7.45 (m, 3H), 7.87 (d, J=7.7Hz, 1H), 7.10 (d, J=8.8Hz, 1H), 6.95–6.77 (m, 3H), 6.62 (d, J=7.7Hz, 2H), 6.08–6.04 (m, 2H), 4.98 (bs, 2H), 3.72 (s, 3H). | 5 |
| 76 | 110 | 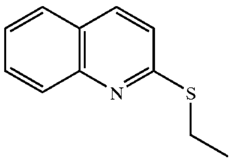 | CH | CH | H | N-(2-Amino-phenyl)-3-[4-(quinolin-2-ylsulfanylmethyl)-phenyl]-acrylamide | $^1$H NMR: (DMSO-$d_6$) δ (ppm): 9.41 (bs, 1H), 8.21 (d, J=8.5, 1H), 7.97 (dt, J=7.7, 8.8Hz, 2H), 7.78 (dt, J=7.1Hz, 8.2Hz, 1H), 7.61–7.53 (m, 5H), 7.40 (dd, J=8.5Hz, 7.6Hz, 2H), 6.97–6.77 (m, 4H), 6.6 (dt, J=7.7Hz, 7.5Hz, 1H), 4.98 (bs, 2H), 4.65 (bs, 2H). | 5 |
| 77 | 111 | 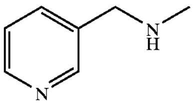 | CH | CH | H | N-(2-amino-phenyl)-3-{4-[(pyridin-3-ylmethyl)-amino]-phenyl}-acrylamide | $^1$H NMR: (DMSO-d6) δ (ppm): 9.15 (s, 1H), 7.24–7.38 (m, 6H), 6.84–6.90 (m, 3H), 6.72 (m, 2H), 6.49–6.60 (m, 4H), 4.84 (s, 2H), 4.22 (d, J=5.77Hz, 2H). | 6 |
| 78 | 112 | 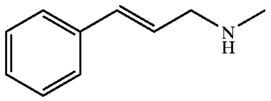 | N | CH | H | N-(2-Amino-phenyl)-3-(6-styrylamino-pyridin-3-yl)-acrylamide | $^1$H NMR: (DMSO-$d_6$) δ (ppm): 7.96 (d, J=9.1Hz, 2H), 7.55 (d, J=14.2Hz, 1H), 7.48 (d, J=7.4Hz, 2H), 7.39–7.29 (m, 4H), 7.07–6.91 (m, 3H), 6.81–6.64 (m, 3H), 6.47–6.38 (m, 1H), 4.21 (bs, 2H). | 7 |
| 79 | 113 | 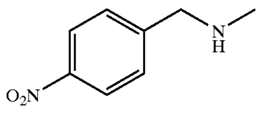 | N | N | H | N-(2-amino-phenyl)-3-[2-(4-nitro-benzylamino)-pyrimidin-5-yl]-acrylamide | $^1$H NMR: (DMSO-d6) δ (ppm): 9.30 (s, 1H), 8.58 (bs, 2H), 8.36 (m, 1H), 8.20 (m, 2H), 7.58 (m, 2H), 7.28–7.42 (m, 2H), 6.52–6.92 (m, 4H), 4.90 (s, 2H), 4.64 (d, J=6Hz, 2H). | 7 |
| 80 | 114 | 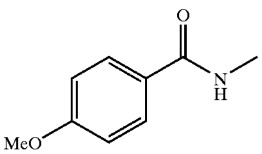 | N | CH | H | N-(5-[2-(2-Amino-phenylcarbamoyl-vinyl)-pyridin-2-yl)-4-methoxy-benzamide | $^1$H NMR: (DMSO-$d_6$) δ (ppm): 10.87 (bs, 1H), 9.45 (bs, 1H), 8.66 (bs, 1H), 8.33 (d, J=7.4Hz, 1H), 8.14–8.08 (m, 3H), 7.63 (d, J=15.6Hz, 1H), 7.40 (d, J=7.7Hz, 1H), 7.08 (d, J=6.8Hz, 2H), 6.97 (d, J=12.3Hz, 2H), 6.80 (d, J=7.9Hz, 1H), 6.63 (dt, J=7.7Hz, 7.4Hz, 1H), 5.06 (bs, 2H), 3.88 (s, 3H) | 7 |

TABLE 3a-continued

Characterization of Compounds Prepared in Examples 42–84

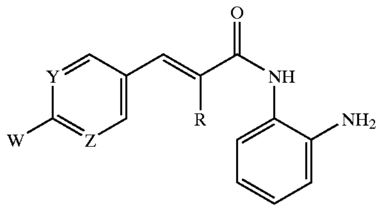

| Ex. | Cpd. | W | Y | Z | R | Name | Characterization | Schm |
|---|---|---|---|---|---|---|---|---|
| 81 | 115 | 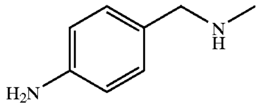 | N | N | H | 3-[2-(4-amino-benzylamino)-pyrimidin-5-yl]-N-(2-amino-phenyl)-acrylamide | $^1$H NMR: (DMSO-d6) δ (ppm): 9.27 (s, 1H), 8.83 (s, 2H), 7.97 (t, J=6Hz, 1H), 7.37 (d, J=15.9Hz, 1H), 7.29 (d, J=7.11Hz, 1H), 6.96 (d, J=8.24Hz, 2H), 6.88 (m, 1H), 6.70 (m, 2H), 6.55 (m, 1H), 6.47 (d, J=8.2Hz, 2H), 4.90 (s, 4H), 4.34 (d, J=6.0Hz, 2H). | 7 |
| 82 | 116 | 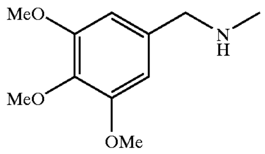 | N | CH | H | N-(2-aminophenyl)-3-[6-(3,4,5-trimethoxy-benzylamino)-pyridin-3-yl]-acrylamide | $^1$H-NMR ($CDCl_3$), δ (ppm): 8.38 (bs, 1H), 7.49 (m, 1H), 7.42 (dd, J=8.5Hz, 2.2Hz, 1H), 7.41 (m, 1H), 7.30 (d, J=7.9Hz, 1H), 7.10 (bs, 1H), 7.02 (t, J=7.4Hz, 1H), 6.75 (d, J=15.0Hz, 1H), 6.73 (m 1H), 6.65 (m, 2H), 6.36 (d, J=8.8Hz, 1H), 6.23 (d, J=15.0Hz, 1H), 4.34 (s, 2H and bs, 2H), 3.84 (s, 3H), 3.81 (s, 6H). | 7, 3 |
| 83 | 117 | 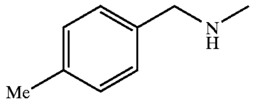 | N | CH | H | N-(2-Amino-phenyl)-3-[6-(4-methyl-benzylamino)-pyridin-3-yl]-acrylamide | $^1$H NMR: (DMSO-$d_6$) δ (ppm): 8.28 (bs, 1H), 7.98 (d, J=9.6Hz, 1H), 7.57 (d, J=15.6Hz, 1H), 7.38 (d, J=7.7Hz, 1H), 7.29 (d, J=7.9Hz, 2H), 7.22 (d, J=7.6Hz, 2H), 7.08 (dt, J=8.2Hz, 7.7Hz, H), 6.98 (d, J=9.1Hz, 2H), 6.87 (t, J=8.2Hz, 1H), 6.75 (d, J=15.1Hz, 1H), 4.57 (s, 2H), 2.53 (s, 3H). | 7 |
| 84 | 118 | 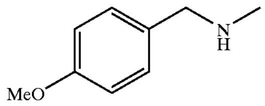 | N | N | H | N-(2-amino-phenyl)-3-[2(4-methoxy-benzylamino)-pyrimidin-5-yl]-acrylamide | $^1$H NMR: (DMSO-d6) δ (ppm): 9.27 (s, 1H), 8.54 (s, 2H), 8.12 (m, 1H), 7.30 (m, 4H), 6.53–6.91 (m, 6H), 4.90 (s, 2H), 4.46 (d, J=4.9Hz, 2H), 3.7 (s, 3H). | 7 |
| 84b | 118b | 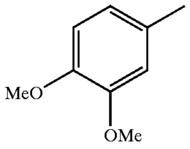 | N | CH | H | N-(2-Amino-phenyl)-3-[6-(3,4-dimethoxy-phenyl)-pyridin-3-yl]-acrylamide | $^1$H NMR (20% $CD_3OD$ in $CDCl_3$): □□8.75 (s, 1H), 7.95 (m, 1H), 7.74–7.59 (m, 3H), 7.50 (m, 1H), 7.24 (d, J=7.8Hz, 1H), 7.07 (m, 1H), 6.95 (d, J=8.4Hz, 1H), 6.89–6.83 (m, 3H), 3.96 (s, 3H), 3.91 (s, 3H). | 9, 15 |

TABLE 3b

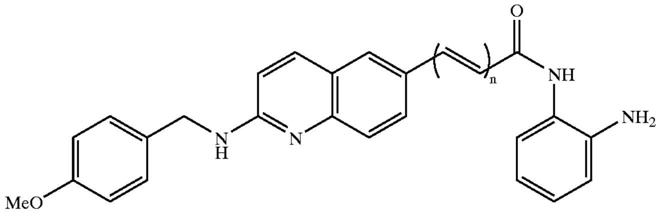

| Ex. | Cpd. | n | Name | Characterization | Scheme |
|---|---|---|---|---|---|
| 53 | 87 | 0 | 2-(4-methoxy-benzylamino)-quinoline-6-carboxylic acid (2-aminophenyl)-amide | $^1$H-NMR (DMSO-d6), δ (ppm): 9.66 (bs, 1H), 8.32 (s, 1H), 8.05 (d, J=8.8Hz, 1H), 7.96 (dd, J=9.1Hz, 2.2Hz, 1H), 7.72 (d, J=2.2 Hz, 1H), 7.55 (dd, J=8.5Hz, 2.2Hz, 1H), 7.34 (dd, J=8.5Hz, 2.2Hz, 1H), 7.20 (d, J=7.7Hz, 1H), 6.97 (t, J=7.7Hz, 1H), 6.90 (m 2H), 6.80 (d, J=7.9Hz, 1H), 6.61 (t, J=6.3Hz, 1H), 4.90 (bs 2H), 4.58 (d, J=3.3Hz, 2H), 3.73 (s, 3H), 3.33 (bs, 1H). | 10 |
| 54 | 88 | 1 | N-(2-aminophenyl)-3-[2-(4-methoxy-benzylamino)-quinolin-6-yl]-acrylamide | $^1$H-NMR (DMSO-d6), δ (ppm): 9.70 (bs, 1H), 9.40 (bs, 1H), 8.20 (d, J=8.9Hz, 1H), 8.03 (bs, 2H), 7.94 (d, J=7.2Hz, 1H), 7.64 (dd, J=15.7Hz, 2.5Hz, 1H), 7.41 (d, J=8.5Hz, 2H), 7.39 (m, 1H), 7.14 (d, J=8.9Hz, 1H), 7.05 (d, J=15.7 Hz, 1H), 6.97 (m, 1H), 6.95 (d, J=8.5Hz, 2H), 6.81 (d, J=8.0Hz, 1H), 6.65 (t, J=7.2Hz, 1H), 4.76 (s, 2H), 3.75 (s, 3H). | 10 |

TABLE 3c

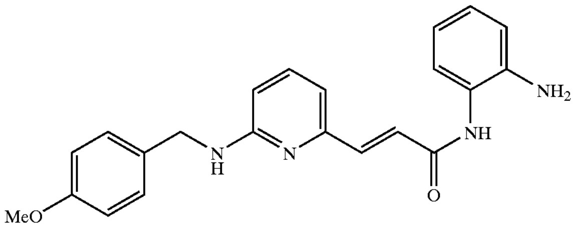

| Ex. | Cpd. | Name | Characterization | Scheme |
|---|---|---|---|---|
| 43 | 51 | N-(2-aminophenyl)-3-[6-(4-methoxy-benzylamino)-pyridin-2-yl]-acrylamide | $^1$H-NMR ($CDCl_3$), δ (ppm): 7.60 (bs, 1H), 7.55 (bs, 1H), 7.43 (t, J=7.7Hz, 1H), 7.29 (d, J=8.3Hz, 2H), 7.17 (d, J=15.1Hz, 1H), 7.06 (t, J= | 3 |

TABLE 3c-continued

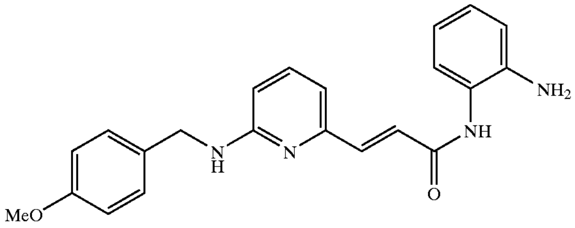

| Ex. | Cpd. | Name | Characterization | Scheme |
|---|---|---|---|---|
| | | | 7.7Hz, 1H), 6.88 (d, J=8.3Hz, 2H), 6.80 (m, 2H), 6.70 (m, 3H), 6.41 (d, J=8.5Hz, 1H), 4.50 (d, J=5.5Hz, 2H), 3.80 (s, 3H), 3.45 (bs, 2H). | |

TABLE 3d

| Ex. | Cpd | W | Y | Z | R | Name | Characterization | Schm |
|---|---|---|---|---|---|---|---|---|
| 347 | 492 | 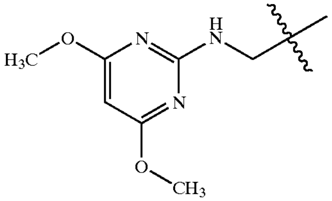 | CH | CH | H | N-(2-Amino-phenyl)-3-{4-[(4,6-dimethoxy-pyrimidin-2-ylamino)-methyl]phenyl}-acrylamide | $^1$H-NMR (DMSO-d6), δ (ppm): 9.36 (bs, 1H), 7.55 (d, J=7.4Hz, 2H), 7.48 (s, 1H), 7.38 (d, J=7.9Hz, 2H), 7.33 (d J=7.9Hz, 1H), 6.91 (m, 2H), 6.73 (d, J=8.2Hz, 1H), 6.56 (dd, J=7.4, 7.7Hz, 1H), 5.35 (s, 1H), 4.93 (bs, 2H), 4.46 (dd, J=6.04 2H), 3.32 (s, 6H) | 3, 7 |
| 348 | 493 | 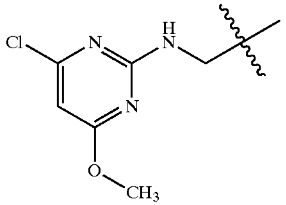 | CH | CH | H | N-(2-Amino-phenyl)-3-{4-[(4-chloro-6-methoxy-pyrimidin-2-ylamino)-methyl]-phenyl}-acrylamide | $^1$H-NMR (DMSO-d6), δ (ppm): 9.37 (bs, 1H), 7.58–7.50 (m, 3H), 7.37–7.32 (m, 3H), 6.94–6.83 (m, 2H), 6.75 (d J=8.0Hz, 1H), 6.57 (t, J=7.5, 1H), 6.13 (bs, 1H), 4.94 (bs, 2H), 4.48 (d, J=6.0, 2H), 3.84 (s, 3H) | 3, 7 |
| 349 | 494 | 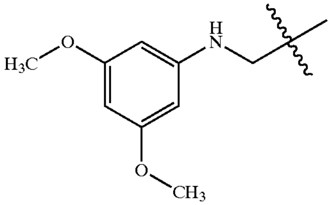 | CH | CH | H | N-(2-Amino-phenyl)-3-[4-(3,5-dimethoxy-benzylamino)-phenyl]-acrylamide | $^1$H-NMR (DMSO-d6), δ (ppm): 9.38 (bs, 1H), 7.55–7.40 (m 6H), 6.88–6.57 (m, 3H), 6.35–6.32 (m, 1H), 5.73 (m, 3H), 4.94 (s, 2H), 4.26 (s , 2H), 3.63 (s, 6H). | 3, 7 |
| 350 | 495 | 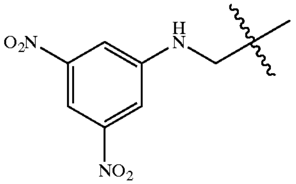 | CH | CH | H | N-(2-Amino-phenyl)-3-[4-(3,5-dinitro-benzylamino)-phenyl]-acrylamide | $^1$H-NMR (DMSO-d6), δ (ppm): 9.38 (bs, 1H), 7.74 (bs, 3H), 7.61 (d, J=8.2Hz, 2H), 7.56–7.44 (m, 3H), 7.32 (d J=8.0Hz, 1H), 6.91–6.85 (m, 2H), 6.73 (d, J=7.9Hz, 1H), 6.66–6.56 (m, 1H), 4.93 (bs, 2H), 4.52 (bs, 2H). | 3, 7 |

TABLE 3d-continued

| Ex. | Cpd | W | Y | Z | R | Name | Characterization | Schm |
|---|---|---|---|---|---|---|---|---|
| 351 | 496 | 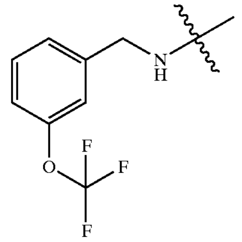 | CH | CH | H | N-(2-Amino-phenyl)-3-[4-(3-trifluoromethoxy-benzylamino)-phenyl]-acrylamide | $^{1}$H-NMR (DMSO-d6), δ (ppm): 9.22 (bs, 1H), 7.52 (d, J=7.9Hz, 2H), 7.44 (bs, 1H), 7.38 (bs, 3H), 7.28 (d J=6.9Hz, 2H), 6.95–6.92 (m, 2H), 6.79 (d, J=8.2Hz, 1H), 6.69–6.59 (m, 3H), 4.95 (bs, 2H), 4.45 (bs, 2H). | 58 |
| 352 | 497 | 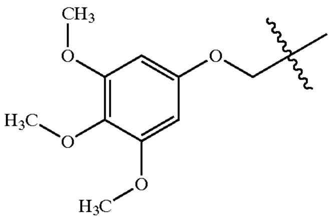 | CH | CH | H | N-(2-Amino-phenyl)-3-[(4-(3,4,5-trimethoxy-phenoxymethyl)-phenyl]-acrylamide | $^{1}$H-NMR (DMSO-d6), δ (ppm): 9.45 (bs, 1H), 8.01 (bs, 2H), 7.78–7.5 (m, 4H), 7.49–7.40 (m, 1H), 6.98 (dd, J=7.0, 8.2Hz, 1H), 6.82 (d, J=7.0Hz, 1H), 6.64 (dd, J=7.0, 7.6Hz, 1H), 6.41 (bs, 2H), 5.17 (s, 2H), 3.81 (s, 6H), 3.64 (s, 3H). | 3, 7 |
| 353 | 498 | 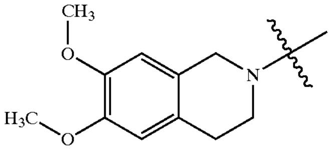 | CH | CH | H | N-(2-Amino-phenyl)-3-[4-(6,7-dimethoxy-3,4-dihydro-1H-isoquinolin-2-yl)-phenyl]-acrylamide | $^{1}$H-NMR (DMSO-d6), δ (ppm): 9.22 (bs, 1H), 7.17 (d, J=8.2Hz, 2H), 6.97 (d, J=8.2Hz, 2H), 6.93 (d, J=7.6Hz, 1H), 6.85 (bs, 1H), 6.77 (bs, 1H), 6.60–6.53 (m, 3H), 6.43–6.40 (m, 2H), 4.97 (bs, 2H), 4.43 (bs, 2H), 3.78 (s, 3H) 3.77 (s, 3H), 2.87–2.85 (m, 2H), 2.65–2.62 (m, 2H). | 37 |
| 354 | 499 | 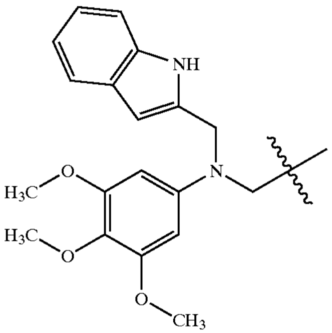 | CH | CH | H | N-(2-Amino-phenyl)-3-(4-{[(1H-indol-2-ylmethyl)-(3,4,5-trimethyl-phenyl)-amino]-methyl}-phenyl)-acrylamide | $^{1}$H-NMR (DMSO-d6), δ (ppm): 10.77 (bs, 1H), 9.39 (bs, 1H), 7.62 (d, J=7.9Hz, 1H), 7.49 (d, J=5.7Hz, 2H), 7.37 (d, J=7.9Hz, 2H), 7.26 (d, J=7.9, 2H), 7.10 (t, J=7.5Hz, 2H), 7.00–6.83 (m, 4H), 6.78 (d, J=7.9Hz, 1H), 6.61 (t, J=7.5Hz, 1H), 5.98 (s, 1H), 5.32 (bs, 1H), 4.98 (bs, 2H), 4.32 (d, J=5.2Hz, 2H), 3.98 (bs, 2H), 3.73 (s, 3H), 3.67 (s, 3H), 3.64 (s, 3H). | 58 |

TABLE 3d-continued

| Ex. | Cpd | W | Y | Z | R | Name | Characterization | Schm |
|---|---|---|---|---|---|---|---|---|
| 355 | 500 | 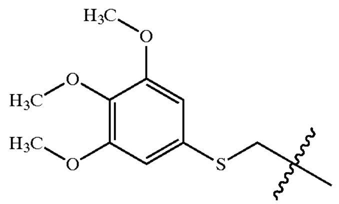 | CH | CH | H | N-(2-Amino-phenyl)-3-[4-(3,4,5-trimethoxy-phenylsulfanylmethyl)-phenyl]-acrylamide | $^1$H-NMR (DMSO-d6), δ (ppm): 9.69 (bs, 1H), 8.04 (d, J=8.3Hz, 2H), 7.78 (d, J=8.3Hz, 2H), 7.58–7.55 (m, 2H), 7.06 (d, J=6.2Hz, 1H), 6.96 (d, J=7.3Hz, 1H), 6.90 (d, J=7.0Hz, 1H), 6.60 (bs, 1H), 5.81 (s, 2H), 4.34 (bs, 2H), 3.78 (s, 6H), 3.67 (s, 3H). | 3, 7 |
| 356 | 501 | 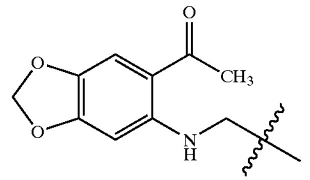 | CH | CH | H | 3-{4-[(6-Acetyl-benzo[1,3]dioxol-5-ylamino)-methyl]-phenyl}-N-(2-amino-phenyl)-acrylamide | $^1$H-NMR (DMSO-d6), δ (ppm): 9.81 (bs, 1H), 7.95 (d, J=7.9Hz, 2H), 7.58 (d, J=7.9Hz, 2H), 7.39 (bs, 1H), 7.21 (d, J=7.4Hz, 1H), 7.02–7.00 (m, 2H), 6.85 (d, J=7.5Hz, 1H), 6.64 (t, J=7.4Hz, 1H), 6.60 (bs, 1H), 6.36 (bs, 1H), 6.00 (d, J=2.2Hz, 2H), 4.60 (bs, 2H), 2.50 (bs, 3H). | 58 |
| 357 | 502 | 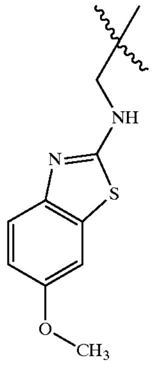 | CH | CH | H | N-(2-Amino-phenyl)-3-{4-[(methoxy-benzothiazol-2-ylamino)-methyl]-phenyl}-acrylamide | $^1$H-NMR (DMSO-d6), δ (ppm): 9.43 (bs, 1H), 8.37 (bs, 1H), 7.66–7.57 (m, 3H), 7.49 (d, J=7.5Hz, 2H), 7.37–7.33 (m, 3H), 6.96–6.90 (m, 1H), 6.87 (d, J=8.8Hz, 1H), 6.80 (d, J=7.9Hz, 1H), 6.63 (t, J=7.5Hz, 1H), 4.99 (bs, 2H), 4.64 (bs, 2H), 3.37 (s, 3H). | 58 |

TABLE 3d-continued

| Ex. | Cpd | W | Y | Z | R | Name | Characterization | Schm |
|---|---|---|---|---|---|---|---|---|
| 358 | 503 | 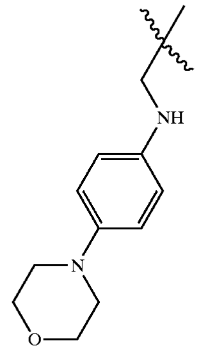 | CH | CH | H | N-(2-Amino-phenyl)-3-{4-[(4-morpholin-4-yl-phenylamino)-methyl]-phenyl}-acrylamide | $^1$H-NMR (DMSO-d6), δ (ppm): 9.42 (bs, 1H), 7.63–7.56 (m, 3H), 7.47 (d, J=7.9Hz, 2H), 7.39 (d, J=7.5Hz, 1H), 6.95 (d, J=8.3Hz, 1H), 6.82 (bs, 1H), 6.77 (d, J=8.4Hz, 2H), 6.66–6.56 (m, 3H), 5.91 (bs, 1H), 5.01 (bs, 2H), 4.30 (bs, 2H), 3.74 (bs, 4H), 2.93 (bs, 4H). | 58 |
| 359 | 504 | 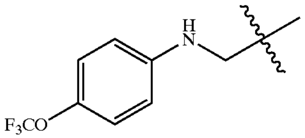 | CH | CH | H | N-(2-Amino-phenyl)-3-{4-[(4-trifluoromethyl-phenylamino)-methyl]-phenyl}-acrylamide | $^1$H-NMR (DMSO-$d_6$), δ (ppm): 9.42 (s, 1H), 7.64 (d, J=7.9Hz, 2H), 7.59 (d, J=15.9Hz, 1H), 7.48 (d, J=8.0 Hz, 2H), 7.39 (d J=7.4Hz, 1H), 7.10 (d, J=8.2Hz, 2H), 6.99 (d, J=7.1Hz, 1H), 6.92 (d, J=15.4Hz, 1H), 6.81 (dd, J=1.3, 8.0Hz, 1H), 6.61–6.68 (m, 4H), 4.99 (s, 2H), 4.36 (d, J=6.0Hz, 2H). | 3, 33 |
| 360 | 505 | 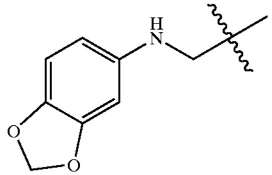 | CH | CH | H | N-(2-Amino-phenyl)-3-[4-(benzo[1,3]dioxol-5-ylaminomethyl)-phenyl-acrylamide | $^1$H-NMR (DMSO-$d_6$), δ (ppm): 9.42 (s, 1H), 7.63 (d, J=7.7Hz, 2H), 7.59 (d, J=15.4Hz, 1H), 7.47 (d, J=8.0Hz, 2H), 7.40 (d, J=7.7Hz, 1H), 6.99 (d, J=7.1Hz, 1H), 6.92 (d, J=16.2Hz, 1H), 6.81 (dd, J=1.4, 8.0Hz, 1H), 6.68 (d, J=8.2Hz, 1H), 6.62 (dd, J=1.4, 7.7Hz, 1H), 6.34 (d, J=2.2Hz, 1H), 6.05 (m, 2H), 5.87 (s, 2H), 4.99 (s, 2H), 4.29 (d, J=6.0Hz, 2H). | 3, 33 |
| 361 | 506 | 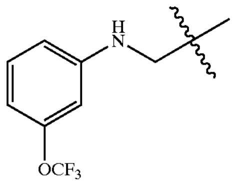 | CH | CH | H | N-(2-Amino-phenyl)-3-{4-[3-trifluoromethoxy-phenylamino)-methyl]-phenyl}-acrylamide | $^1$H-NMR (DMSO-$d_6$), δ (ppm): 9.43 (s, 1H), 7.57–7.66 (m, 3H), 7.48 (d, J=7.6Hz, 2H), 7.40 (d, J=7.6Hz, 1H), 7.20 (dd, J=8.2, 8.2Hz, 1H), 6.99 (d, J=7.6Hz, 1H), 6.93 (d, J=15.2Hz, 1H), 6.81 (m, 2H), 6.64 (m, 2H), 6.49–6.55 (m, 2H), 5.00 (s, 2H), 4.38 (d, J=5.3Hz, 2H). | 3, 33 |

TABLE 3d-continued

| Ex. | Cpd | W | Y | Z | R | Name | Characterization | Schm |
|---|---|---|---|---|---|---|---|---|
| 362 | 507 | 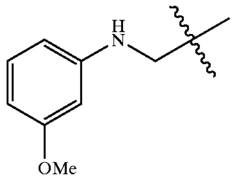 | CH | CH | H | N-(2-Amino-phenyl)-3-{4-[(2-methoxy-phenylamino)-methyl]-phenyl}-acrylamide | $^1$H-NMR (DMSO-$d_6$), δ (ppm): 9.42 (s, 1H), 7.63 (d, J=7.7Hz, 2H), 7.59 (d, J=15.8Hz, 1H), 7.47 (d, J=7.6Hz, 2H), 7.40 (d, J=7.6Hz, 1H), 6.90–7.02 (m, 3H), 6.81 (d, J=7.6Hz, 1H), 6.64 (dd, J=7.0, 7.0Hz, 1H), 6.36 (m, 1H), 6.24 (d, J=8.2Hz, 1H), 6.18 (m, 2H), 5.00 (s, 2H), 4.34 (d, J=5.3Hz, 2H), 3.69 (s, 3H). | 3, 33 |
| 363 | 508 | 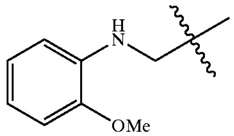 | CH | CH | H | N-(2-Amino-phenyl)-3-{4-[(2-methoxy-phenylamino)-methyl]-phenyl}-acrylamide | $^1$H-NMR (DMSO-$d_6$), δ (ppm): 9.42 (s, 1H), 7.62 (d, J=7.0Hz, 2H), 7.58 (d, J=15.2Hz, 1H), 7.46 (d, J=7.6Hz, 2H), 7.40 (d, J=7.0Hz, 1H), 6.94–7.00 (m, 1H), 6.87 (d, J=7.6Hz, 2H), 6.81 (d, J=7.6Hz, 1H), 6.73 (dd, J=7.6, 7.6Hz, 1H), 6.56–6.66 (m, 2H), 6.45 (d, J=7.6Hz, 1H), 5.68 (t, J=5.9Hz, 1H), 4.99 (s, 2H), 4.41 (d, J=6.4Hz, 2H), 3.87 (s, 3H). | 3, 33 |
| 364 | 509 | 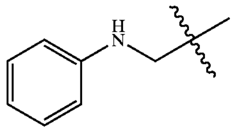 | CH | CH | H | N-(2-Amino-phenyl)-3-(4-phenylaminomethyl-phenyl)-acrylamide | $^1$H-NMR (DMSO-$d_6$), δ (ppm): 9.42 (s, 1H), 7.63 (d, J=7.9Hz, 2H), 7.59 (d, J=15.8Hz, 1H), 7.48 (d, J=7.9Hz, 2H), 7.39 (d, J=7.5Hz, 1H), 7.10 (2d, J=7.5, 7.5Hz, 2H), 6.99 (d, J=7.5Hz, 1H), 6.92 (d, J=16.2Hz, 1H), 6.81 (d, J=7.5Hz, 1H), 6.55–6.64 (m, 4H), 6.32 (t, J=6.0, 1H), 4.99 (s, 2H), 4.35 (d, J=5.7Hz, 2H). | 3, 33 |
| 365 | 510 | 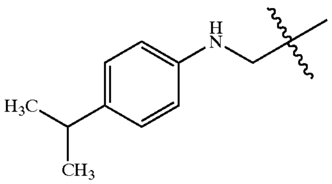 | CH | CH | H | N-(2-Amino-phenyl)-3-{4-[(4-isopropyl-phenylamino)-methyl]-phenyl}-acrylamide | $^1$H-NMR (DMSO-$d_6$), δ (ppm): 9.42 (s, 1H), 7.62 (d, J=7.0Hz, 2H), 7.59 (d, J=15.8Hz, 1H), 7.47 (d, J=8.2Hz, 2H), 7.40 (d, J=7.6Hz, 1H), 6.89–6.99 (m, 4H), 6.81 (d, J=7.6Hz, 1H), 6.64 (dd, J=7.0, 7.6Hz, 1H), 6.56 (d, J=8.2Hz, 2H), 6.14 (t, J=5.9Hz, 1H), 4.99 (s, 2H), 4.32 (d, J=5.9Hz, 2H), 2.76 (m, 1H), 1.17 (d, J=7.0Hz, 6H). | 3, 33, |
| 366 | 511 | 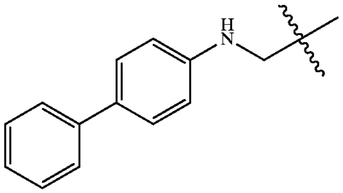 | CH | CH | H | N-(2-Amino-phenyl)-3-[4-(biphenyl-4-ylaminomethyl)-phenyl]-acrylamide | $^1$H-NMR (DMSO-$d_6$), δ (ppm): 9.43 (s, 1H), 7.57–7.66 (m, 5H), 7.40–7.52 (m, 7H), 7.27 (dd, J=7.0, 7.6Hz, 1H), 6.98 (d, J=7.6Hz, 1H), 6.93 (d, J=15.2Hz, 1H), 6.81 (d, J=8.2Hz, 1H), 6.73 (d, J=8.2Hz, 2H), 6.64 (dd, J=7.6 Hz, 1H), 6.56 (t, J=5.9Hz, 1H), 4.99 (s, 2H), 4.12 (d, J=5.9Hz, 2H). | 3, 33 |

TABLE 3d-continued

| Ex. | Cpd | W | Y | Z | R | Name | Characterization | Schm |
|---|---|---|---|---|---|---|---|---|
| 367 | 512 | 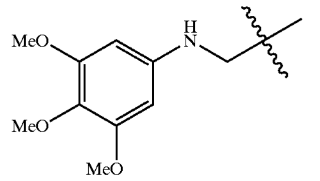 | CH | N | H | N-(2-Amino-phenyl)-3-{6-[(3,4,5-trimethoxy-phenylamino)-methyl]-pyridin-3-yl}-acrylamide | $^1$H-NMR (DMSO-$d_6$), δ (ppm): 9.50 (s, 1H), 8.81 (s, 1H), 8.05 (d, J=8.2Hz, 1H), 7.64 (d, J=15.7Hz, 1H), 7.52 (d, J=8.2Hz, 1H), 7.39 (d, J=7.4Hz, 1H), 6.96–7.05 (m, 2H), 6.81 (d, J=8.0Hz, 1H), 6.64 (dd, J=7.4, 7.4Hz, 1H), 6.26 (m, 1H), 5.96 (s, 2H), 5.01 (s, 2H), 4.43 (d, J= 5.5Hz, 2H), 3.72 (s, 6H), 3.56 (s, 3H). | 3, 33 |
| 369 | 514 | 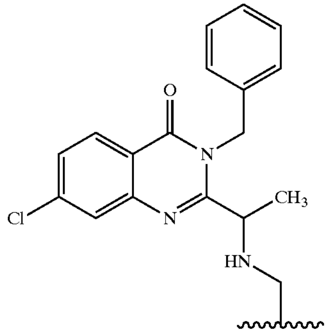 | CH | CH | H | N-(2-Amino-phenyl)-3-(4-{[1-(3-benzyl-7-chloro-4-oxo-3,4-dihydro-quinazolin-2-yl)-ethylamino]-methyl}-phenyl)-acrylamide | [1]1H-NMR (DMSO-d6), δ (ppm): 9.50 (s, 1H), 8.28 (d, J= 8.4Hz, 1H), 7.81–7.72 (s, 3H), 7.66 (d, J=8.1Hz, 2H), 7.88 (d, J=15.6Hz, 1H), 7.50 (d, J=8.1Hz, 2H), 7.45–7.26 (m, 4H), 7.24–7.15 (m, 2H), 7.00–6.86 (m, 2H), 6.84 (d, J=8.1Hz, 1H), 6.68 (t, J=7.5Hz, 1H), 5.45 (d, J= 16.8Hz, 1H), 533 (d, J=16.8Hz, 1H), 4.62 (bs, 1H), 4.25 (d, J=12.9Hz, 1H), 4.92 (d, J=12.9Hz, 1H), 1.91 (m, 2H), 1.28 (m, 1H), 0.90 (m, 1H), 0.72 (t, J=7.5Hz, 3H). | 55 |
| 371 | 516 | Br— | CH | CH | CH | N-(2-Amino-phenyl)-3-(4-bromo-phenyl)-acrylamide | $^1$H NMR: (Acetone-$d_6$) δ (ppm): 9.47 (bs, 1H), 7.72–7.56 (m, 5H), 7.39 (d, J=7.4Hz, 1H), 7.00–6.95 (m, 2H), 6.81 (d, J=6.9Hz, 1H), 6.64 (t, J=7.1Hz, 1H), 5.00 (bs, 2H). | 14 |
| 372 | 517 | 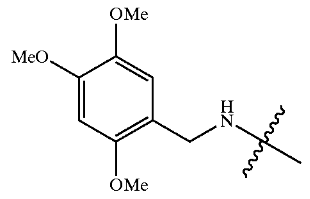 | CH | CH | CH | N-(2-Amino-phenyl)-4-(2,4,5-trimethoxy-benzylamino)-benzamide | $^1$H NMR: ($CD_3OD$) δ (ppm): 7.61 (d, J=15.4Hz, 1H), 7.44 (d, J=8.4Hz, 2H), 7.25 (d, J=7.5Hz, 1H), 7.10 (t, J=7.5Hz, 1H), 7.00 (s, 1H), 6.94 (d, J=8.4Hz, 1H), 6.81 (t, J=7.0Hz, 1H), 6.76 (s, 1H) 6.70 (d, J=8.4Hz, 2H), 6.92 (d, J=15.4Hz, 1H), 4.35 (s, 2H), 3.94 (s, 3H), 3.92 (s, 3H), 3.77 (s, 3H). | 1, 7, 10 |
| 373 | 518 | 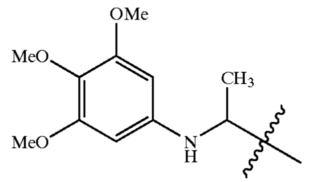 | CH | CH | CH | N-(2-Amino-phenyl)-3-{4-[1-(3,4,5-trimethoxy-phenylamino)-ethyl]-phenyl}-acrylamide | 1H NMR (DMSO-d6) δ (ppm): 9.24 (s, 1H), 8.00 1(d, J=12Hz, 1H); 7.80 (d, J=12Hz, 1H), 7.40–7.70 (m, 7H), 6.80–7.00 (m, 2H), 6.70 (d, J=12Hz,1H), 6.20 (s, 2H), 4.50 (m, 1H), 3.70 (s, 6H), 3.50 (s, 3H), 1.50 (d, 3H). | 58 |

TABLE 3d-continued

| Ex. | Cpd | W | Y | Z | R | Name | Characterization | Schm |
|---|---|---|---|---|---|---|---|---|
| 374 | 519 | 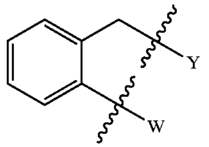 | C | CH | H | N-(2-Amino-phenyl)-3-(9H-fluoren-2-yl)-acrylamide | $^1$H NMR (300MHz, DMSO-$d_6$) 6 (ppm): 9.41 (s, 1H), 8.00 (t, J=7.9Hz, 2H), 7.88 (s, 1H), 7.77–7.56 (m, 3H), 7.52–7.32 (m, 3H), 7.00 (d, J=15.8Hz, 1H), 6.96 (t, J=7.5Hz, 1H), 6.80 (d,J=7.9Hz, 1H), 6.63 (t, J=7.5Hz, 1H), 5.00 (s, 2H), 4.03 (s, 2H). | 59 |
| 375 | 520 | 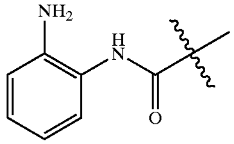 | CH | CH | H | N-(2-Amino-phenyl)-4-[2-(2-amino-phenylcarbamoyl)-vinyl]-benzamide | $^1$H NMR (300MHz, DMSO-$d_6$) δ (ppm): 9.71 (s, 1H), 9.43 (s, 1H), AB system ($δ_A$ = 8.05, $δ_B$ =7.75, J=7.9Hz, 4H), 7.62 (d, J=15.8Hz, 1H), 7.36 (d, J=7.9Hz, 1H), 7.18 (d, J=7.5Hz, 1H), 7.05–6.88 (m, 3H), 6.78 (t, J=7.9 Hz, 2H), 6.65–6.55 (m, 2H), 4.96 and 4.92 (2s, 4H). | 59 |
| 376 | 521 | 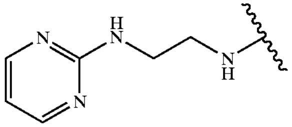 | N | CH | H | N-(2-Amino-phenyl)-3-{6-[2-(pyrimidin-2-ylamino)-ethylamino]-pyridin-3-yl}-acrylamide | $^1$H NMR (300MHz, DMSO-$d_6$) δ (ppm): 9.29 (s, 1H), 8.32 (d, J=4.9Hz, 2H), 8.24 (d, J=1.9Hz, 1H), 7.71 (d, J=6.9Hz, 1H), 7.48 (d, J=15.7Hz, 1H), 7.38 (d, J=7.7 Hz, 1H), 7.26 (bs, 2H), 6.96 (t, J=6.9Hz, 1H), 6.80 (dd, J=1.1, 7.7Hz, 1H), 6.69–6.61 (m, 4H), 5.00 (s, 2H), 3.52 (bs, 4H), | 3 |
| 377 | 522 | 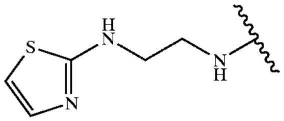 | N | CH | H | N-(2-Amino-phenyl)-3-{6-[2-(thiazol-2-ylamino)-ethylamino]-pyridin-3-yl}-acrylamide | $^1$H NMR (300MHz, $CD_3OD$) δ (ppm): 8.12 (s, 1H), 8.08 (s, 1H), 7.78 (d, J=8.8Hz, 1H), 7.54 (d, J=15.4Hz, 1H), 7.19 (d, J=8.0Hz, 1H), 7.04 (t, J=7.4Hz, 1H), 6.87 (d, J=8.0Hz, 1H), 6.75 (t, J=7.4Hz, 1H), 6.64 (d, J=15.4Hz, 1H), 6.65 (s, 1H), 4.90 (s, 5H), 3.50–3.45 (m, 4H), 3.30 (d, J=1.3Hz, 1H). | 3 |
| 378 | 523 | 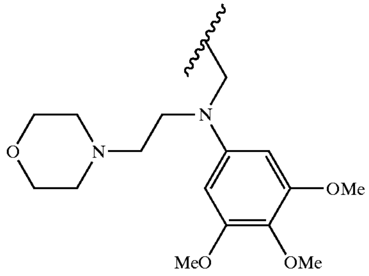 | CH | CH | H | N-(2-Amino-phenyl)-3-(4-{[(2-morpholin-4-yl-ethyl)-(3,4,5-trimethoxy-phenyl)-amino]-methyl}-phenyl)-acrylamide | $^1$H-NMR ($CD_3OD$), δ (ppm): 7.83 (d, J=15.6Hz, 1H), 7.67 (d, J=7.8Hz, 2H), 7.62–7.58 (m, 2H), 7.53–7.51 (m, 2H), 7.49 (d, J=7.8Hz, 2H), 7.01 (d, J=15.6Hz, 1H), ), 4.99 (bs, 9H), 4.84 (bs, 2H), 4.22 (t, J=6.5Hz, 2H), 4.05 (s, 4H), 3.85 (s, 6H), 3.76 (s, 3H), 3.57–3.50 (m, 4H). | 3, 33, 57 |

TABLE 3d-continued

| Ex. | Cpd | W | Y | Z | R | Name | Characterization | Schm |
|---|---|---|---|---|---|---|---|---|
| 379 | 524 | 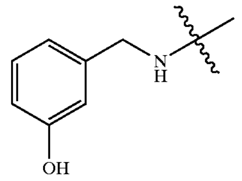 | N | CH | H | N-(2-Amino-phenyl)-3-[6-(3-hydroxy-benzylamino)-pyridin-3-yl]-acrylamide | $^1$H-NMR (DMSO-$d_6$), δ (ppm): 9.32 (s, 1H), 9.26 (s, 1H), 8.19 (s, 1H), 7.66 (d, J=8.5Hz, 1H), 7.57 (t, J=6.0Hz, 1H), 7.41 (d, J=15.7Hz, 1H), 7.32 (d J=7.7Hz), 7.10 (t, J=7.6Hz, 1H), 6.91 (t, J=7.6Hz, 1H), 6.75 (m, 3H), 6.59 (m, 4H), 4.98 (bs, 2H), 4.46 (d, J=5.8Hz, 2H). | 3 |
| 380 | 525 | 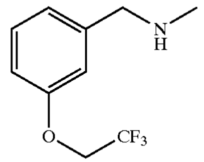 | N | CH | H | N-(2-Amino-phenyl)-3-(6-[3-(2,2,2-trifluoro-ethoxy)-benzylamino]-pyridin-3-yl}-acrylamide | $^1$H-NMR (DMSO-$d_6$), δ (ppm): 9.25 (s, 1H), 8.18 (s, 1H), 7.67 (d, J=8.8Hz, 1H), 7.59 (t, J=6.0Hz, 1H), 7.42 (d, J=15.7Hz, 1H), 7.30 (m, 2H), 7.00 (m, 2H), 6.92 (m, 2H), 6.74 (d, J=8.0Hz, 1H), 6.60 (m, 3H), 4.92 (s, 2H), 4.73 (q, J=8.8Hz, 2H), 4.52 (d, J=5.8Hz, 2H). | 3 |
| 381 | 526 | 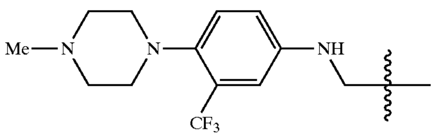 | CH | CH | H | N-(2-Amino-phenyl)-3-(4-{[3-hydroxy-4-(4-methyl-piperazin-1-yl)-phenylamino]-methyl}-phenyl)-acrylamide | $^1$H-NMR ($CD_3OD$), δ (ppm): 7.64 (d, J=15.6Hz, 1H), 7.56 (d, J=8.0Hz, 2H), 7.49 (m, 1H), 7.40 (d, J=8.0Hz, 2H), 7.21 (m, 2H), 7.03 (t, J=7.6Hz, 1H), 6.88–6.71 (m, 4H), 4.88 (bs, 4H), 4.34 (s, 2H), 2.86 (t, J=4.1Hz, 4H), 2.67 (bs, 4H), 2.41 (s, 3H). | 3, 33, 58 |
| 382 | 527 | 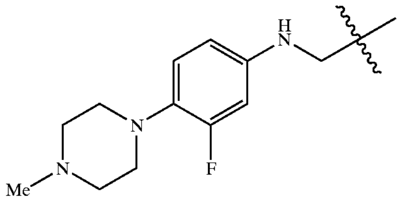 | CH | CH | H | N-(2-Amino-phenyl)-3-(4-{[3-fluoro-4-(4-methyl-piperazin-1-yl)-phenylamino]-methyl}-phenyl)-acrylamide | $^1$H-NMR (DMSO-$d_6$, δ (ppm): 9.43 (s, 1H), 7.61 (d, J=8.0Hz, 2H), 7.45 (d, J=8.0Hz, 2H), 7.38 (d, J=7.6Hz, 1H), 7.00–6.88 (m, 2H), 6.85–6.79 (m, 2H), 6.63 (t, J=7.6Hz, 1H), 6.44–6.30 (m, 3H), 4.99 (bs, 2H), 4.30 (d, J=5.5Hz, 2H), 2.87 (bs, 4H), 2.55 (m, 4H), 2.27 (s, 3H). | 3, 33, 58 |
| 383 | 528 | 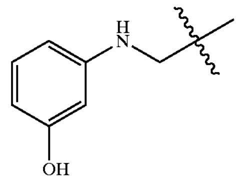 | CH | CH | H | N-(2-Amino-phenyl)-3-{4-[(3-hydroxy-phenylamino)-methyl]-phenyl}-acrylamide | $^1$H-NMR ($CDCl_3$), δ (ppm): 7.49 (d, J=14.0Hz, 1H); 7.32 (d, J=7.2Hz, 2H), 7.15 (d, J=7.2Hz, 2H), 7.05 (m, 1H), 6.96 (m, 1H), 6.90 (m, 3H), 6.76 (m, 1H), 6.55 (d, J=14.0Hz, 1H), 6.03 (m, 1H), 5.99 (m, 1H), 4.30 (bs, 5H), 4.10 (s, 2H). | 3, 33 |

TABLE 3d-continued

| Ex. | Cpd | W | Y | Z | R | Name | Characterization | Schm |
|---|---|---|---|---|---|---|---|---|
| 384 | 529 | 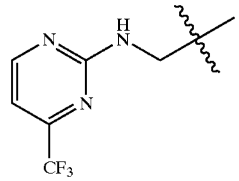 | CH | CH | H | N-(2-Amino-phenyl)-3-{4-[(4-trifluoromethyl-pyrimidin-2-ylamino)-methyl]-phenyl}-acrylamide | $^1$H-NMR ($CD_3OD$), δ (ppm): 7.73 (d, J=16.0Hz, 1H); 7.63 (d, J=8.5Hz, 1H), 7.58 (d, J=8.0Hz, 2H), 7.46 (d, J=8.0Hz, 2H), 7.38 (d, J=8.5Hz, 1H), 7.20 (d, J=8.0Hz, 1H), 7.03 (dt, J=7.7, 1.4Hz, 1H), 6.89 (d, J=1.1Hz, 1H), 6.85 (m, 1H), 6.73 (dt, J=7.7, 1.1Hz, 1H), 6.56 (d, J=16.0Hz, 1H), 5.27 (s, 2H), 4.87 (bs, 2H), 4.62 (s, 2H). | 3, 33 |
| 385 | 530 | 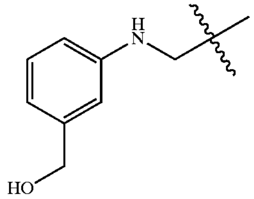 | CH | CH | H | N-(2-Amino-phenyl)-3-{4-[(3-hydroxymethyl-phenylamino)-methyl]-phenyl}-acrylamide | $^1$H-NMR (DMSO-$d_6$), δ (ppm): 9.90 (s, 1H), 7.58 (m, 3H), 7.43 (d, J=8.0Hz, 2H); 7.37 (d, J=8.0Hz, 1H), 7.11 (m, 1H), 7.00 (m, 3H), 6.85 (d, J=15.4Hz, 1H), 6.63 (s, 1H), 6.51 (d, J=7.4,Hz, 1H), 6.46 (d, J=7.7Hz, 1H), 4.35 (s, 2H), 4.32 (s, 2H). | 3, 33 |
| 386 | 531 | 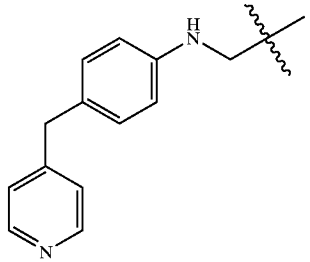 | CH | CH | H | N-(2-Amino-phenyl)-3-{4-[(4-pyridin-4-ylmethyl-phenylamino)-methyl]-phenyl}-acrylamide | $^1$H-NMR (DMSO-$d_6$), δ (ppm): 9.66 (s, 1H), 8.46 (d, J=4.7Hz, 2H); 7.55 (d, J=8.0Hz, 2H), 7.50 (d, J=15.7Hz, 1H), 7.39 (d, J=8.0Hz, 2H), 7.28 (d, J=4.7Hz, 2H), 7.00 (d, J=15.7Hz, 1H), 6.92 (d, J=6.9Hz, 2H), 6.90 (m, 1H), 6.75 (d, J=8Hz, 1H), 6.58 (m, 2H), 6.52 (d, J=6.9, Hz, 2H), 6.10 (bs, 1H), 4.26 (bs, 2H), 3.80 (s, 2H), (d, J=1.9Hz, 2H). | 3, 33 |
| 387 | 532 | 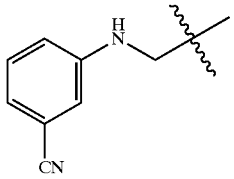 | CH | CH | H | N-(2-Amino-phenyl)-3-{4-[(3-cyano-phenylamino)-methyl]-phenyl}-acrylamide | $^1$H-NMR (DMSO-$d_6$), δ (ppm): 9.38 (s, 1H), 7.58 (d, J=7.7Hz, 2H); 7.54 (d, J=15.9Hz, 1H), 7.41 (d, J=7.7Hz, 2H), 7.33 (d, J=8.0Hz, 1H), 7.24 (t, J=7.7Hz, 1H), 6.92–6.83 (m, 5H), 6.75 (d, J=8.0Hz, 1H), 6.58 (t, J=7.4Hz, 1H), 4.95 (bs, 2H), 4.34 (d, J=5.8Hz, 2H). | 3, 33 |

TABLE 3d-continued

| Ex. | Cpd | W | Y | Z | R | Name | Characterization | Schm |
|---|---|---|---|---|---|---|---|---|
| 388 | 533 | 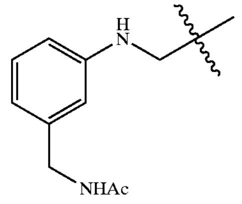 | CH | CH | H | 3-(4-{[3-(Acetylamino-methyl)-phenylamino]-methyl}-phenyl)-N-(2-amino-phenyl)-acrylamide | $^1$H-NMR (DMSO-$d_6$), δ (ppm): 9.37 (bs, 1H), 8.21 (t, J=5.8Hz, 1H), 7.56 (d, J=7.7Hz, 2H), 7.53 (d, J=15.7Hz, 1H), 7.41 (d, J=8.0Hz, 2H), 7.33 (d, J=7.1Hz, 1H), 6.97 (m, 1H), 6.85 (d, J=15.7Hz, 1H), 6.74 (dd, J=1.4, 8.0Hz, 1H), 6.58 (dt, J=1.4, 8.0Hz, 1H), 6.50 (bs, 1H), 6.41 (d, J=8.0Hz, 2H), 6.30 (t, J=6.0Hz, 1H), 4.94 9bs, 2H), 4.28 (d, J=6.0Hz, 2H), 4.09 (d, J=6.0Hz, 2H), 1.83(s, 3H). | 3, 33 |
| 389 | 534 | 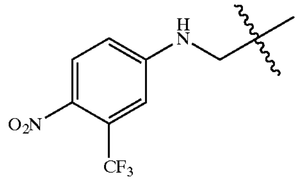 | CH | CH | H | N-(2-Amino-phenyl)-3-{4-[(4-nitro-3-trifluoromethyl-phenylamino)-methyl]-phenyl}-acrylamide | $^1$H-NMR (DMSO-$d_6$), δ (ppm): 9.37 (bs, 1H), 7.56 (d, J=8.0Hz, 2H), 7.53 (d, J=15.7Hz, 1H), 7.41 (d, J=8.0Hz, 2H), 7.33 (d, J=7.7Hz, 1H), 6.92 (d, J=7.7Hz, 2H), 6.85 (d, J=15.7Hz, 1H), 6.74 (d, J=8.0Hz, 1H), 6.67–6.55 (m, 4H), 5.84 (t, J=5.8Hz, 1H), 4.94 (bs, 2H), 4.22 (d, J=5.8Hz, 2H). | 3, 33 |
| 390 | 535 | 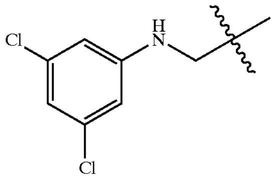 | CH | CH | H | N-(2-Amino-phenyl)-3-{4-[(3,5-dichloro-phenylamino)-methyl]-phenyl}-acrylamide | $^1$H-NMR (DMSO-$d_6$), δ (ppm): 9.39 (bs, 1H), 7.60 (d, J=8.0Hz, 2H), 7.54 (d, J=15.7Hz, 1H), 7.40 (d, J=8.0Hz, 2H), 7.33 (d, J=7.1Hz, 1H), 6.97–6.89 (m, 2H), 6.87 (d, J=15.7Hz, 1H), 6.75 (dd, J=1.4, 8.0Hz, 1H), 6.60–6.55 (m, 4H), 4.95 (bs, 2H), 4.33 (d, J=6.0Hz, 2H). | 3, 33 |
| 391 | 536 | 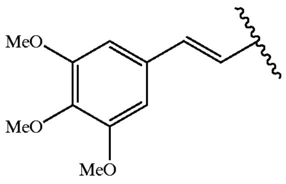 | CH | CH | H | N-(2-Amino-phenyl)-3-{4-[2-(3,4,5-trimethoxy-phenyl)-vinyl]-phenyl}-arcylamide | $^1$H-NMR ($CDCl_3$), δ (ppm): 8.12 (bs, 1H), 7.64 (d, J=14.2Hz, 1H), 7.42 (bs, 4H), 7.23 (bs, 2H), 6.97 (d, J=14.2Hz, 1H), 6.94–6.82 (m, 4H), 6.70 (s, 2H), 4.11 (bs, 2H), 3.87 (s, 6H), 3.84 (s, 3H). | 3 |
| 392 | 537 | 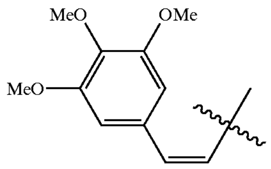 | CH | CH | H | N-(2-Amino-phenyl)-3-{4-[2-(3,4,5-trimethoxy-phenyl)-vinyl]-phenyl}-arcylamide | $^1$H-NMR (DMSO-$d_6$), δ (ppm): 8.49 (s, 1H), 7.58 (d, J=15.7Hz, 1H), 7.33 (d, J=8.5Hz, 1H), 7.23 (m, 4H), 7.00 (d, J=8.5Hz, 1H), 6.73 (d, J=5.0Hz, 2H), 6.69 (d, J=5.0Hz, 2H), 6.58 (d, J=15.4Hz, 1H), 6.53 (bs, 2H), 6.47 (s, 2H), 3.85 (s, 3H), 3.63 (s, 6H). | 3 |

TABLE 3d-continued

| Ex. | Cpd | W | Y | Z | R | Name | Characterization | Schm |
|---|---|---|---|---|---|---|---|---|
| 393 | 538 | 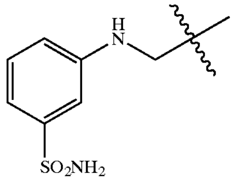 | CH | CH | H | N-(2-Amino-phenyl)-3-{4-[(3-sulfmoyl-phenylamino)-methyl]-phenyl}-acrylamide | $^1$H-NMR ($CD_3OD/CDCl_3$), δ (ppm): 7.61 (d, J=15.7Hz, 1H), 7.45 (d, J=8.1Hz, 2H), 7.29 (d, J=8.1Hz, 2H), 7.18 (dd, J=8.0Hz, 2H), 7.12 (d, J=15.7Hz, 1H), 7.10 (m, 1H), 7.03 (t, J=7.4Hz, 1H), 6.83–6.66 (m, 4H), 3.93 (bs, all NH signals). | 1, 3, 33 |
| 394 | 539 | 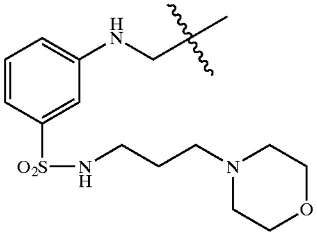 | CH | CH | H | N-(2-Amino-phenyl)-3-(4-{[3-(3-morpholin)-phenylamino]-methyl}-phenyl)-acrylamide | $^1$H-NMR ($CDCl_3$), δ (ppm): 8.34 (bs, 1H), 7.64 (d, J=15.4Hz, 1H), 7.37 (d, J=8.0Hz, 2H), 7.34 (m, 1H), 7.26 (d J=8.0Hz, 2H), 7.23 (d, J=15.4Hz, 1H), 7.14 (d, J=7.8Hz, 1H), 7.04 (m, 2H), 6.74 (m, 4H), 4.85 (bs, 1H), 4.30 (d, J=4.4Hz, 2H), 3.69 (t, J=4.4Hz, 4H), 2.99 (t, J=5.8Hz, 2H), 2.40 (bs, 6H), 1.59 (t, J=4.4Hz, 2H). | 3, 33, 42 |
| 395 | 540 | 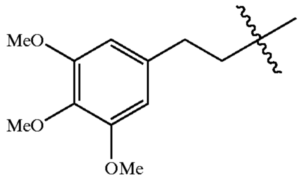 | CH | CH | H | N-(2-Amino-phenyl)-3-{4-[2-(3,4,5-trimethoxy-phenyl)-ethyl]-phenyl}-acrylamide | $^1$H-NMR ($CDCl_3$), δ (ppm): 8.53 (s, 1H), 7.72 (d, J=15.6Hz, 1H), 7.38 (d, J=7.7Hz, 2H), 7.33 (m, 1H), 7.16 (d, J=7.7Hz, 2H), 7.07 (m, 1H), 6.79 (m, 2H), 6.69 (d, J=15.6Hz, 1H), 6.41 (s, 2H), 4.04 (bs, 2H), 3.91 (s, 3H), 3.85 (s, 6H), 2.94 (m, 4H). | 3, 33 |
| 396 | 541 | 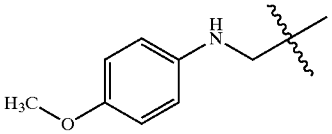 | CH | CH | H | N-(2-Amino-phenyl)-3-{4-[(4-methoxy-phenylamino)-methyl]-phenyl}-acrylamide | $^1$H-NMR (DMSO-$d_6$), δ (ppm): 9.35 (s, 1H), 7.56 (d, J=7.5Hz, 2H), 7.52 (d, J=15.4Hz, 1H), 7.40 (d, J=7.5Hz, 2H), 7.33 (d, J=7.7Hz, 1H), 6.92 (d, J=7.7Hz, 1H), 6.85 (d, J=15.4Hz, 1H), 6.75 (d, J=8.0Hz, 1H), 6.67 (d J=8.6Hz, 2H), 6.58 (m, 1H), 6.52 (d, J=8.6Hz, 2H), 5.84 (t, J=5.5Hz, 1H), 4.23 (d, J=5.5Hz, 2H), 3.61 (s, 3H). | 3, 33 |
| 397 | 542 | 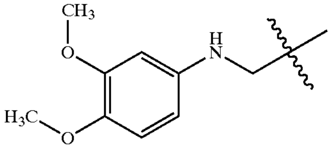 | CH | CH | H | N-(2-Amino-phenyl)-3-{4-[(3,4-dimethoxy-phenylamino)-methyl]-phenyl}-acrylamide | $^1$H-NMR ($CDCl_3$), δ (ppm): 8.48 (s, 1H), 7.60 (d, J=15.4Hz, 1H), 7.27 (m, 5H), 6.97 (t, J=7.5Hz, 1H), 6.70 (m, 3H), 6.59 (d, J=15.4Hz, 1H), 6.25 (s, 1H), 6.12 (d, J=7.1Hz, 1H), 4.23 (s, 2H), 3.93 (bs, 3H), 3.75 (s, 3H), 3.73 (s, 3H). | 3, 33 |

TABLE 3d-continued

| Ex. | Cpd | W | Y | Z | R | Name | Characterization | Schm |
| --- | --- | --- | --- | --- | --- | --- | --- | --- |
| 398 | 543 | 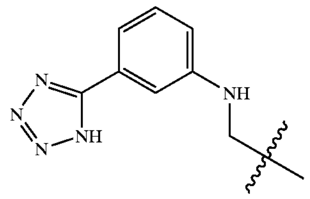 | CH | CH | H | N-(2-Amino-phenyl)-3-(4-{[3-(1H-tetrazol-5-yl)-phenylamino]-methyl}-phenyl)-acrylamide | $^1$H-NMR ($CD_3OD$), δ (ppm): 7.75 (d, J=15.2Hz, 1H), 7.60 (d, J=7.6Hz, 2H), 7.48 (d, J=7.6Hz, 2H), 7.33 (m, 3H), 7.27 (m, 3H), 7.20 (m, 1H), 6.84 (m, 2H), 5.48 (bs, 5H), 4.46 (s, 2H). | 3, 33 |
| 399 | 544 | 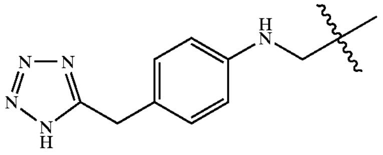 | CH | CH | H | N-(2-Amino-phenyl)-3-(4-{[4-(1H-tetrazol-5-ylmethyl)-phenylamino]-methyl}-phenyl)-acrylamide | $^1$H-NMR ($CD_3OD$), δ (ppm): 7.75 (d, J=15.2Hz, 1H), 7.58 (d, J=8.2Hz, 2H), 7.42 (d, J=8.2Hz, 2H), 7.29 (m, 2H), 7.20 (m, 2H), 7.04 (d, J=8.2Hz, 2H), 6.83 (d, J=15.2Hz, 1H), 6.67 (d, J=8.2Hz, 2H), 5.48 (bs, 5H), 4.39 (s, 2H), 4.16 (s, 2H). | 3, 33 |
| 400 | 545 | 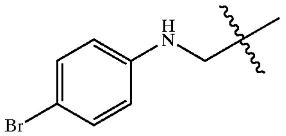 | CH | CH | H | N-(2-Amino-phenyl)-3-{4-[(4-bromo-phenylamino)-methyl]-phenyl}-acrylamide | $^1$H NMR (300MHz, DMSO-$d_6$) δ (ppm): 9.42 (s, 1H), 7.62 (d, J=8.5Hz, 2H), 7.59 (d, J=15.6Hz, 1H), 7.45 (d, J=8.0Hz, 2H), 7.40 (d, J=7.5Hz, 1H), 7.23 (d, J=8.5Hz, 2H), 6.98 (d, J=7.5Hz, 1H), 6.92 (d, J=15.6Hz, 1H), 6.80 (d, J=8.0Hz, 1H), 6.66–6.57 (m, 4H), 4.99 (bs, 2H), 4.34 (d, J=5.8Hz, 2H). | 3, 33 |
| 401 | 546 | 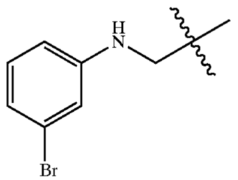 | CH | CH | H | N-(2-Amino-phenyl)-3-{4-[(3-bromo-phenylamino)-methyl]-phenyl}acrylamide | $^1$H NMR (300MHz, DMSO-$d_6$) δ (ppm): 9.36 (s, 1H), 7.57 (d, J=7.6Hz, 2H), 7.54 (d, J=15.8Hz, 1H), 7.40 (d J=8.2Hz, 2H), 7.33 (d, J=7.6Hz, 1H), 7.00–6.91 (m, 2H), 6.86 (d, J=15.8Hz, 1H), 6.74 (d, J=8.2Hz, 2H), 6.66–6.54 (m, 4H), 4.93 (bs, 2H), 4.30 (d, J=5.3Hz, 2H). | 3, 33 |
| 402 | 547 | 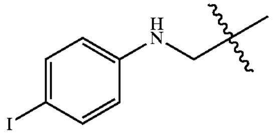 | CH | CH | H | N-(2-Amino-phenyl)-3-{4-[(4-iodo-phenylamino)-methyl]-phenyl}-acrylamide | $^1$H NMR (300MHz, DMSO-$d_6$) δ (ppm): 9.36 (s, 1H), 7.56 (d, J=8.0Hz, 2H), 7.53 (d, J=15.8Hz, 1H), 7.39 (d, J=8.0Hz, 2H), 7.35 (m, 1H), 7.31 (d, J=8.2Hz, 2H), 6.92 (d, J=7.1Hz, 1H), 6.85 (d, J=15.8Hz, 1H), 6.75 (d J=7.7Hz, 1H), 6.57 (t, J=8.0Hz, 1H), 6.52 (t, J=6.0Hz, 1H), 6.42 (d, J=8.5Hz, 2H), 4.94 (bs, 2H), 4.28 (d, J=6.0Hz, 2H). | 3, 33 |

TABLE 3d-continued

| Ex. | Cpd | W | Y | Z | R | Name | Characterization | Schm |
|---|---|---|---|---|---|---|---|---|
| 403 | 548 | 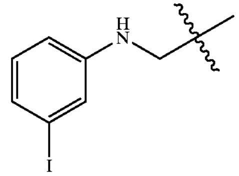 | CH | CH | H | N-(2-Amino-phenyl)-3-{4-[(3-iodo-phenylamino)-methyl]-phenyl}-acrylamide | $^1$H NMR (300MHz, DMSO-$d_6$) δ (ppm): 9.40 (s, 1H), 7.57 (d, 7.6Hz, 2H), 7.53 (d, 15.6Hz, 1H), 7.40 (d J=8.2Hz, 2H), 7.33 (d, J=7.6Hz, 1H), 6.92 (m, 3H), 6.84 (m, 2H), 6.74 (d, J=7.6Hz, 1H), 6.60–6.50 (m, 3H), 4.93 (bs, 2H), 4.28 (d, J=5.9Hz, 2H). | 3, 33 |
| 404 | 549 | 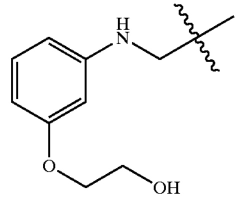 | CH | CH | H | N-(2-Amino-phenyl)-3-(4-{[3-(2-hydroxy-ethoxy)-phenylamino]-methyl}-phenyl)-acrylamide | $^1$H NMR (300MHz, DMSO-$d_6$) δ (ppm): 9.42 (s, 1H), 7.63 (d, J=8.2Hz, 2H), 7.60 (d, J=15.3Hz, 1H), 7.46 (d, J=8.2Hz, 2H), 7.40 (d, J=7.6Hz, 1H), 7.03–6.98 (m, 2H), 6.91 (d, J=15.3Hz, 1H), 6.81 (d, J=7.6Hz, 1H), 6.64 (t, J=7.6Hz, 1H), 6.36 (t, J=5.9Hz, 1H), 6.28–6.22 (m, 3H), 4.99 (bs, 3H), 4.61 (s, 2H), 4.34 (d, J=5.0Hz, 2H) 4.28 (d, J=5.0Hz, 2H). | 3, 33 |
| 405 | 550 | 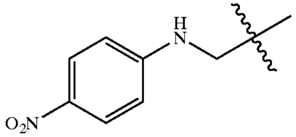 | CH | CH | H | N-(2-Amino-phenyl)-3-{4-[(4-nitro-phenylamino)-methyl]-phenyl}-acrylamide | $^1$H NMR (300MHz, DMSO-$d_6$) δ (ppm): 9.38(s, 1H), 7.99 (d J=9.1Hz, 2H), 7.85 (t, J=5.9Hz, 1H), 7.60 (d, J=7.6Hz, 2H), 7.54 (d, J=15.8Hz, 1H), 7.40 (d, J=7.6Hz, 2H), 7.34 (d, J=7.6Hz, 1H), 6.94–6.92 (m, 1H), 6.88 (d, J=15.8Hz, 1H), 6.75 (d, J=7.6Hz, 1H), 6.68 (d, J=9.1Hz, 2H), 6.58 (t, J=7.6Hz, 1H), 4.94 (bs, 2H), 4.46 (d, J=5.9Hz, 2H) | 3, 33 |
| 406 | 551 | 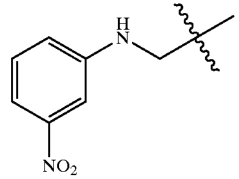 | CH | CH | H | N-(2-Amino-phenyl)-3-{4-[(3-nitro-phenylamino)-methyl]-phenyl}-acrylamide | $^1$H NMR (300MHz, DMSO-$d_6$) δ (ppm): 9.37 (s, 1H), 7.59 (d, J=7.6Hz, 2H), 7.54 (d, J=15.2Hz, 1H), 7.43 (d, J=7.6Hz, 2H), 7.36–7.28 (m, 4H), 7.05–6.98 (m, 2H), 6.92 (d, J=7.6Hz, 1H), 6.88 (d, J=15.2Hz, 1H), 6.75 (d, J=7.6Hz, 1H), 6.58 (t, J=7.6Hz, 1H), 4.96 (bs, 2H), 4.39 (d, J=5.3Hz, 2H). | 3, 33 |
| 407 | 552 | 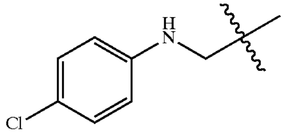 | CH | CH | H | N-(2-Amino-phenyl)-3-{4-[(4-chloro-phenylamino)-methyl]-phenyl}-acrylamide | $^1$H NMR (300MHz, DMSO-$d_6$) δ (ppm): 9.43 (s, 1H), 7.62 (d, J=7.6Hz, 2H), 7.59 (d, J=15.8Hz, 1H), 7.46 (d, J=7.6Hz, 2H), 7.40 (d, J=7.6Hz, 1H), 7.12 (d, J=8.8Hz, 2H), 6.98 (d, J=7.6Hz, 1H), 6.93 (d, J=15.8Hz, 1H), 6.81 (d, J=7.6Hz, 1H), 6.62 (d, J=8.8Hz, 2H), 6.55 (bs, 2H), 4.99 (bs, 2H), 4.46 (d, J=5.9Hz, 2H), 4.35 (d, J=5.9Hz, 2H) | 3, 33 |

TABLE 3d-continued

| Ex. | Cpd | W | Y | Z | R | Name | Characterization | Schm |
|---|---|---|---|---|---|---|---|---|
| 408 | 553 | 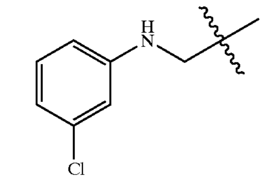 | CH | CH | H | N-(2-Amino-phenyl)-3-{4-[(4-chloro-phenylamino)-methyl]-phenyl}-acrylamide | $^1$H NMR (300MHz, DMSO-$d_6$) δ (ppm): 9.50 (s, 1H), 7.65 (d, J=8.2Hz, 2H), 7.61 (d, J=15.4Hz, 1H), 7.47 (d, J=7.6Hz, 2H), 7.43 (m, 1H), 6.93 (d, J=7.0Hz, 1H), 6.79 (d, J=15.4Hz, 1H), 6.68 (m, 3H), 6.59 (m, 3H), 5.24 (bs, 2H), 4.31 (s, 2H). | 3, 33 |
| 409 | 554 | 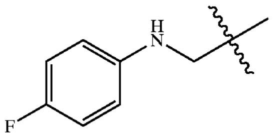 | CH | CH | H | N-(2-Amino-phenyl)-3-{4-[(4-fluoro-phenylamino)-methyl]-phenyl}-acrylamide | $^1$H NMR (300MHz, DMSO-$d_6$) δ (ppm): 9.37 (s, 1H), 7.63 (d, J=8.2Hz, 2H), 7.60 (d, J=15.4Hz, 1H), 7.47 (d, J=7.6Hz, 2H), 7.41 (m, 1H), 7.01–6.90 (m, 4H), 6.75 (d, J=7.6Hz, 1H), 6.67–6.59 (m, 3H), 6.27 (bs, 1H), 4.95 (bs, 2H), 4.27 (s, 2H). | 3, 33 |
| 410 | 555 | 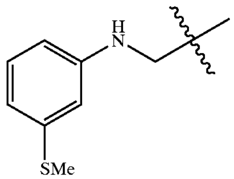 | CH | CH | H | N-(2-Amino-phenyl)-3-{4-[(3-methylsulfanyl-phenylamino)-methyl]-phenyl]-acrylamide | $^1$H NMR (300MHz, $CD_3OD$) δ (ppm): 7.64 (d, J=15.9Hz, 1H), 7.47 (d, J=7.5Hz, 2H), 7.32 (d, J=7.5Hz, 2H), 7.19 (d, J=7.5Hz, 1H), 7.03 (t, J=7.8Hz, 1H), 6.82 (d, J=7.5Hz, 1H), 6.77 (d, J=7.8Hz, 1H), 6.70 (d, J=15.9Hz, 1H), 6.56 (d, J=7.8Hz, 1H), 6.49 (s, 1H), 6.37 (d, J=7.8Hz, 1H), 4.29 (s, 2H), 4.05 (bs, 4H), 2.37 (s, 3H). | 3, 33 |
| 411 | 556 | 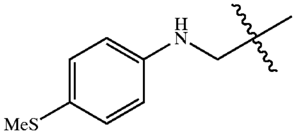 | CH | CH | H | N-(2-Amino-phenyl)-3-{4-[(4-methylsulfanyl-phenylamino)-methyl]-phenyl]-acrylamide | $^1$H NMR (300MHz, DMSO-$d_6$) δ (ppm): 9.36 (S, 1H), 7.57 (d, J=7.5Hz, 2H), 7.53 (d, J=15.8Hz, 1H), 7.40 (d J=7.9Hz, 2H), 7.34 (d, J=7.9Hz, 1H), 7.07 (d, J=8.3Hz, 2H), 6.92 (d, J=7.5Hz, 1H), 6.87 (d, J=15.8Hz, 1H), 6.75 (d, J=7.9Hz, 1H), 6.60–6.54 (m, 3H), 6.39 (t, J=5.7Hz, 1H), 4.93 (bs, 2H), 4.29 (d, J=6.1Hz, 2H), 2.32 (s, 3H),. | 3, 33 |
| 412 | 557 | 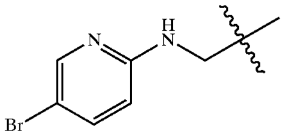 | CH | CH | H | N-(2-Amino-phenyl)-3-{4-[(5-bromo-pyridin-2-ylamino)-methyl]-phenyl}-acrylamide | $^1$H NMR (300MHz, DMSO-$d_6$) δ (ppm): 9.36 (s, 1H), 8.02 (d, J=1.7Hz, 1H), 7.57–7.50 (m, 4H), 7.38–7.32 (m, 4H), 6.92 (d, J=7.5Hz, 1H), 6.86 (d, J=16.3Hz, 1H), 6.75 (d, J=7.9Hz, 1H), 6.59 (d, J=7.5Hz, 1H), 6.53 (d, J=9.2Hz, 1H), 4.94 (bs, 2H), 4.48 (d, J=5.7Hz, 2H). | 3, 33 |
| 413 | 558 | 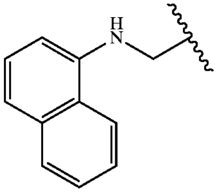 | CH | CH | H | N-(2-Amino-phenyl)-3-[4-(naphthalen-1-ylaminomethyl)-phenyl]-acrylamide | $^1$H NMR (300MHz, DMSO-$d_6$) δ (ppm): 9.37 (s, 1H), 8.25 (m, 1), 7.76 (m, 1H), 7.57 (m, 2H), 7.47 (m, 4H), 7.33 (d, J=7.0Hz, 1H), 7.17 (m, 1H), 7.07 (d, J=8.2Hz, 1H), 6.99 (t, J=5.3Hz, 1H), 6.92 (d, J=7.0Hz, 1H), 6.85 (d, J=16.4Hz, 1H), 6.74 (d, J=7.6Hz, 1H), 6.57 (t, J=7.6Hz, 1H), 6.36 (t, J=7.6Hz, 1H), 4.90 (s, 2H), 4.54 (d, J=5.3Hz, 2H). | 3, 33 |

TABLE 3d-continued

| Ex. | Cpd | W | Y | Z | R | Name | Characterization | Schm |
|---|---|---|---|---|---|---|---|---|
| 414 | 559 | 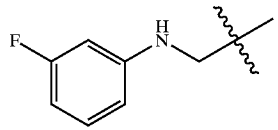 | CH | CH | H | N-(2-Amino-phenyl)-3-{4-[(3-fluoro-phenylamino)-methyl]-phenyl}-acrylamide | $^1H$ NMR (300MHz, DMSO-$d_6$) δ (ppm): 9.39 (s, 1H), 7.57 (d, J=7.0Hz, 2H), 7.53 (d, J=15.4Hz, 1H), 7.40 (d, J=7.6Hz, 2H), 7.36 (d, J=7.6Hz, 1H), 7.02 (q, J=7.6Hz, 1H), 6.90 (m, 2H), 6.76 (d, J=8.2Hz, 1H), 6.58 (m, 1H), 6.40 (d, J=8.2Hz, 1H), 6.29 (m, 2H), 4.90 (s, 1H), 4.29 (bs, 2H), 4.02 (s, 2H). | 3, 33 |
| 415 | 560 | 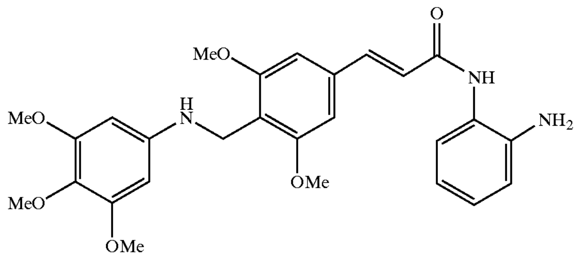 | | | | N-(2-Amino-phenyl)-3-{3,5-dimethoxy-4-[(3,4,5-trimethoxy-phenylamino)-methyl]-phenyl}-acrylamide | $^1H$-NMR ($CDCl_3$), δ (ppm): 7.73 (bs, 1H), 7.63 (d, J=14.9Hz, 1H), 6.81 (m, 3H), 6.70 (m 2H), 6.68–6.56 (m, 2H), 6.07 (s, 2H), 4.35 (s, 2H), 3.86 (s, 6H), 3.81 (s, 6H), 3.75 (s, 3H). | 60 |
| 416 | 561 | 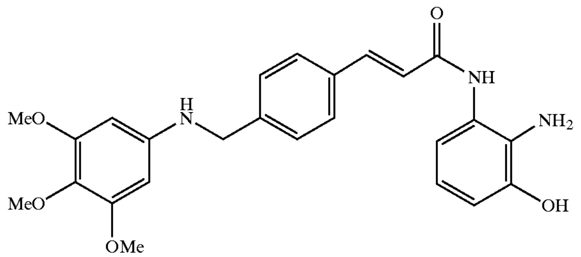 | | | | N-(2-Amino-3-hydroxy-phenyl)-3-{4-[(3,4,5-trimethoxy-phenylamino)-methyl]-phenyl}-acrylamide | $^1H$ NMR (300MHz, $CDCl_3$) δ (ppm): 9.22 (s, 1H), 9.11 (s, 1H), 7.57 (d, J=7.9Hz, 2H), 7.64 (d, J=15.8Hz, 1H), 7.44 (d, J=7.9Hz, 2H) 6.96 (d, J=15.8Hz, 1H) 6.78 (t J=7.9Hz, 1H), 6.23 (t, J=7.9Hz, 1H), 6.16 (d, J=7.9Hz, 1H), 6.09 (t, J=6.2Hz, 1H), 5.89 (s, 2H), 4.77 (bs, 2H), 4.27 (d, J=5.7Hz, 2H), 5.89 (s, 6H), 5.76 (s, 3H). | 3, 33 |
| 417 | 562 | 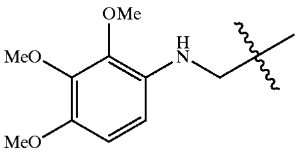 | CH | CH | H | N-(2-Amino-phenyl)-3-{4-[(2,3,4-trimethoxy-phenylamino)-methyl]-phenyl}-acrylamide | $^1H$ NMR (300MHz, $CDCl_3$) δ (ppm): 8.25 (s, 1H), 7.74 (d, J=15.5Hz, 1H), 7.44 (d, J=7.9Hz, 2H), 7.37 (d, J=7.9Hz, 2H), 7.34–7.29 (m, 2H), 7.08 (t, J=7.5Hz, 1H), 6.82 (t, J=7.5Hz, 1H), 6.79 (m, 1H), 6.66 (d, J=15.5Hz, 1H), 6.60 (d, J=8.8Hz, 1H), 6.31 (d, J=8.8Hz, 1H), 4.36 (s, 2H), 4.18 (bs, 2H), 3.98 (s, 3H), 3.96 (s, 3H), 3.84 (s, 3H). | 3, 33 |

TABLE 3d-continued

| Ex. | Cpd | W | Y | Z | R | Name | Characterization | Schm |
|---|---|---|---|---|---|---|---|---|
| 418 | 563 | 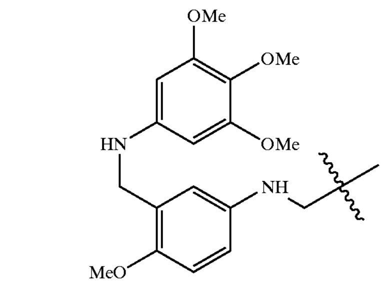 | CH | CH | H | N-(2-Amino-phenyl)-3-[4-({4-methoxy-3-[(3,4,5-trimethoxy-phenylamino)-methyl]-phenylamino}-methyl)-phenyl]-acrylamide | $^1$H NMR (300MHz, $CDCl_3$) δ (ppm): 8.58 (s, 1H), 7.66 (d, J=15.4Hz, 1H), 7.33–7.28 (m, 3H), 7.23 (d, J=7.0Hz, 2H), 7.04 (t, J=7.0Hz, 1H), 6.77–6.70 (m, 4H), 6.64 (d, J=15.4Hz, 1H), 6.53 (d, J=7.5Hz, 1H), 5.90 (s, 2H), 4.27 (s, 2H), 4.25 (s, 2H), 4.08 (bs, 4H), 3.82 (s, 6H), 3.77 (s, 6H). | 3, 33 |
| 419 | 564 | 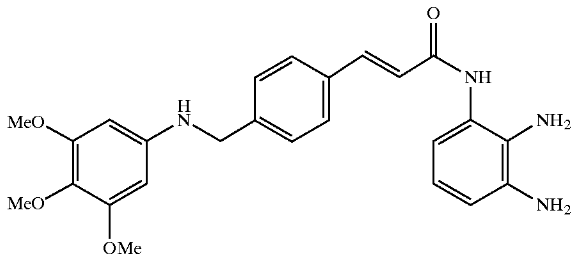 | | | | N-(2,3-Diamino-phenyl)-3-{4-[(3,4,5-trimethoxy-phenylamino)-methyl]-phenyl}-acrylamino | $^1$H NMR (300MHz, $CDCl_3$) δ (ppm): 7.64 (d, J = 15.4Hz, 1H), 7.48 (d, J = 7.5Hz, 2H), 7.35 (d, J = 7.5Hz, 2H), 7.31–7.24 (m, 2H), 6.86 (s, 1H), 6.73 (d, J=15.4Hz, 1H), 5.84 (s, 2H), 4.27 (s, 2H), 4.00 (bs, 6H), 3.71 (s, 6H), 3.68 (s, 3H). | 3, 33 |
| 420 | 565 | 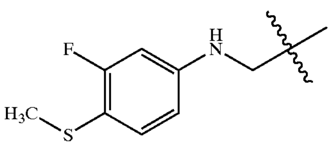 | CH | CH | H | N-(2-Amino-phenyl)-3-{4-[(3-fluoro-4-methylsulfanyl-phenylamino)-methyl]-phenyl}-acrylamide | $^1$H-NMR (DMSO-$d_6$), δ (ppm): 9.38 (bs, 1H), 7.58 (d, J=7.5Hz, 2H), 7.54 (d, J=15.4Hz), 1H), 7.40 (d, J=7.9Hz, 2H), 7.33 (d, J=7.9Hz, 1H), 7.14 (t, J=8.3Hz, 1H), 6.94–6.89 (m, 2H), 6.81 (d, J=15.7Hz, 1H), 6.74 (d, J=8.3Hz, 1H), 6.58 (t, J=7.5Hz, 1H), 6.43–6.38 (m, 2H), 4.94 (bs, 2H), 4.30 (d, J=5.7Hz, 2H). 2.28 (s, 3H). | 3, 33 |
| 421 | 566 | 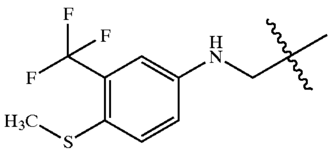 | CH | CH | H | N-(2-Amino-phenyl)-3-{4-[(4-methylsulfanyl-3-trifluoromethyl-phenylamino)-methyl]-phenyl}-acrylamide | $^1$H-NMR (DMSO-$d_6$), δ (ppm): 9.39 (bs, 1H), 7.59 (d, J=7.9Hz, 2H), 7.54 (d, J=15.8Hz, 1H), 7.41 (d, J=7.9Hz, 2H), 7.36 (d, J=7.9Hz, 1H), 7.33 (d, J=6.2Hz, 1H), 6.96–6.90 (m, 4H), 6.82 (d, J=15.8Hz, 1H), 6.79–6.74 (m, 1H), 6.58 (t, J=7.5Hz, 1H), 4.95 (bs, 2H), 4.35 (d, J=6.2Hz, 2H), 2.35 (s, 3H). | 3, 33 |

TABLE 3d-continued
| Ex. | Cpd | W | Y | Z | R | Name | Characterization | Schm |
|---|---|---|---|---|---|---|---|---|
| 422 | 567 | 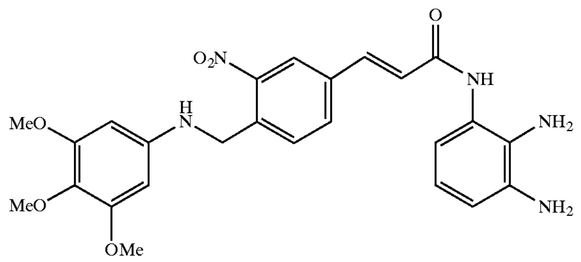 | | | | N-(2-Amino-phenyl)-3-{3-nitro-4-[(3,4,5-trimethoxy-phenylamino)-methyl]-phenyl}-acrylamide | $^1$H-NMR (DMSO-$d_6$), δ (ppm): 9.50 (s, 1H), 8.09 (s, 1H), 7.80 (d, J=15.4Hz, 1H), 7.81 (s, 2H), 7.34 (d, J=7.9Hz, 1H), 6.94 (d, J=7.5Hz, 1H), 6.88 (d, J=15.4Hz, 1H), 6.76 (d, J=7.9Hz, 1H), 6.58 (t, J=7.5Hz, 1H), 6.26 (t, J=6.2Hz, 1H), 5.90 (s, 2H), 4.96 (bs, 2H), 4.39 (d, J=5.7Hz, 2H), 3.66 (s, 6H), 3.51 (s, 3H). | 3, 33 |
| 423 | 568 | 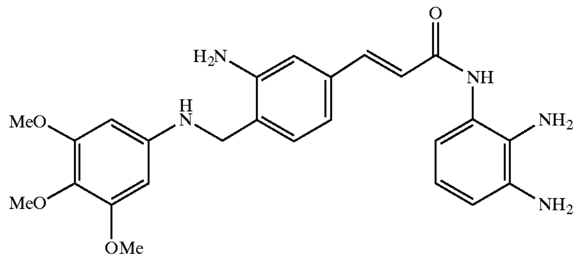 | | | | N-(2-Amino-phenyl)-3-{3-amino-4-[(3,4,5-trimethoxy-phenylamino)-methyl]-phenyl}-acrylamide | $^1$H-NMR (DMSO-$d_6$), δ (ppm): 9.29 (s, 1H), 7.72 (d, J=15.4Hz, 1H), 7.33 (m, 2H), 6.90 (1H); 6.71 (2H), 6.62 (3H), 5.97 (1H), 5.87 (2H), 5.49 (2H), 4.96 C2H) , 4.10 (2H), 3.65 (6H), 3.51 (3H). | 3, 33 |

TABLE 3d-continued
| Ex. | Cpd | W | Y | Z | R | Name | Characterization | Schm |
|---|---|---|---|---|---|---|---|---|
| 424 | 569 | 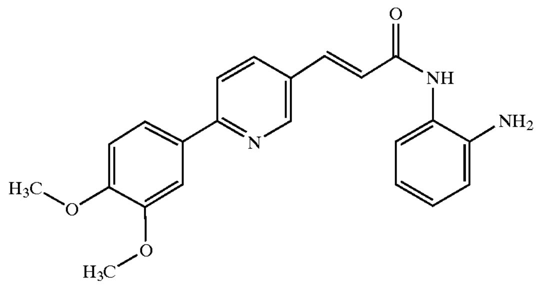 | | | | N-(2-Amino-phenyl)-3-[6-(3,4-dimethyloxy-phenyl)-pyridin-3-yl]-acrylamide | LRMS: calc: 375.4, found: 376.4 | 3, 15, 33 |
| 425 | 570 | 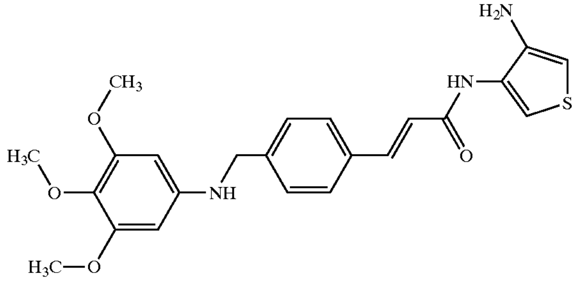 | | | | N-(4-Amino-thiophen-3-yl)-3-{4-[(4-morpholin-4-yl-phenylamino)-methyl]-phenyl}-acrylamide | $^{1}$H-NMR (DMSO-d6), δ (ppm): 9.64 (bs, 1H), 7.65 (d, J=7.9Hz, 2H), 7.60 (d, J=14.0Hz, 1H), 7.50 (d, J=7.9Hz, 2H), 6.90 (d, J=15.8Hz, 1H), 6.15 (d, J=4.0Hz, 1H), 5.95 (s, 2H), 5.82 (s, 1H), 4.89 (bs, 2H), 4.33 (d, J=5.7Hz, 2H), 3.71 (s, 6H), 3.57 (s, 3H). | 3, 33, 60 |

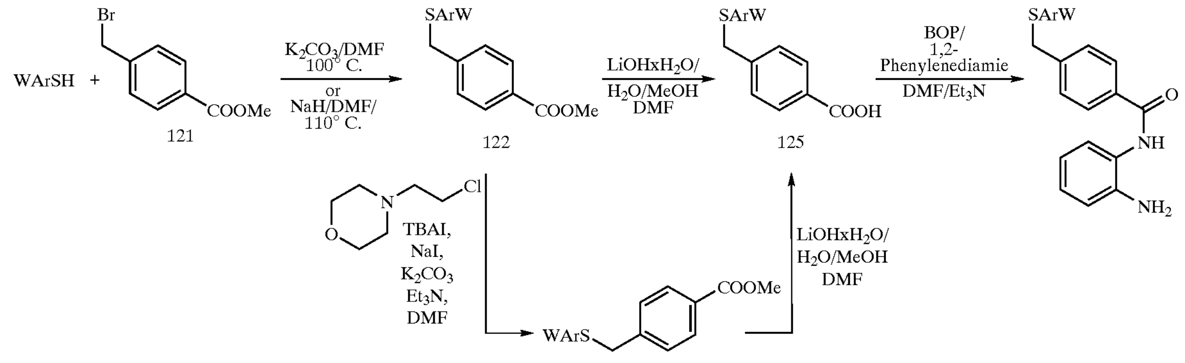

124

119: WArS = 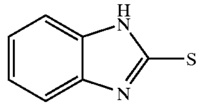

Example 85 126: WArS = 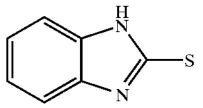

120: WArS = 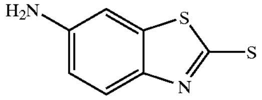

Example 87 128: WArS = 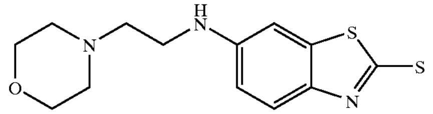

Example 85

N-(2-Amino-phenyl)-4-(1H-benzimidazol-2-ylsulfanylmethyl)-benzamide (Compound 126)

Step 1: 4-(1H-Benzimidazol-2-ylsulfanylmethyl)-benzoic acid methyl ester (Compound 122)

Following the procedure described in Example 47, step 2, but using 119 and substituting 121 for 63, the title compound 122 was obtained in 95% yield. LRMS=299.1 (M+1).

Step 2: N-(2-Amino-phenyl)-4-(1H-benzimidazol-2-ylsulfanylmethyl)-benzamide (126)

Following the procedure described in Example 1, steps 4 and 5, but substituting 122 for 6, the title compound 126 was obtained in 62% yield. $^1H$ NMR: (DMSO-$d_6$) δ (ppm): 9.57 (s, 1H), 7.89 (d, J=8.2 Hz, 2H), 7.55 (d, J=8.2 Hz, 2H), 7.53 (bs, 2H), 7.36 (bs, 2H), 7.14–7.08 (m, 3H), 6.94 (t, J=8.2 Hz, 1H), 6.74 (d, J=6.9 Hz, 1H), 6.56 (t, J=8.0 Hz, 1H), 4.87 (bs, 2H), 4.62 (s, 2H).

Example 87

N-(2-Amino-phenyl)-4-[6-(2-morpholin-4-ethylamino)-benzothiazol-2-ylsulfanylmethyl]-benzamide (Compound 128)

Step 1: 4-(6-Amino-benzothiazol-2-ylsulfanylmethyl)-benzoic acid methyl ester (122)

Following the procedure described in Example 47, step 2, but using 120 and substituting 121 for 63, the title compound 122 was obtained in 45% yield. LRMS=331.0 (M+1).

Step 2: 4-[6-(2-Morpholin-4-yl-ethylamino)-benzothiazol-2-ylsulfanylmethyl]-benzoic acid methyl ester (Compound 124)

To a solution of 4-(6-Amino-benzothiazol-2-ylsulfanylmethyl)-benzoic acid methyl ester 122 (800 mg, 2.42 mmol), in DMF (24 mL), were added successively solid 4-(2-chloroethyl)morpholine hydrochloride (296 mg, 2.66 mmol), $K_2CO_3$(611 mg, 5.08 mmol), NaI (363 mg, 2.42 mmol), $Et_3N$ (370 μL, 2.66 mmol) and tetrabutylammonium iodide (894 mg, 2.42 mmol), The mixture was stirred at 120° C. for 24 h and more 4-(2-chloroethyl)morpholine hydrochloride (296 mg, 2.66 mmol) was added. The mixture was stirred for 8 h at 120° C. and the solvent was removed in vacuo. The resulting black syrup was partitioned between $H_2O$ and EtOAc. The organic layer was successively washed with HCl 1N and saturated aqueous $NaHCO_3$. The precipitate was extracted twice with EtOAc, dried over $MgSO_4$ and concentrated. Purification by flash chromatography (MeOH/$CHCl_3$:5:95 to 10:90) afforded 48 mg (4% yield) of 124 as a light yellow oil. LRMS=444.1 (M+1).

Step 3: N-(2-Amino-phenyl)-4-[6-(2-morpholin-4-yl-ethylamino)-benzothiazol-2-ylsulfanylmethyl]-benzamide (Compound 128)

Following the procedure described in Example 1, steps 4 and 5, but substituting 124 for 6, the title compound 128 was obtained in 76% yield. $^1H$ NMR: (Acetone-$d_6$) δ (ppm): 9.06 (bs, 1H), 7.98 (d, J=8.2 Hz, 2H), 7.63 (d, J=8.5 Hz, 2H), 7.62 (d, J=8.8 Hz, 2H), 7.29 (d, J=8.0 Hz, 1H), 7.06 (d, J=2.2 Hz, 1H), 7.02–6.97 (m, 1H), 6.87–6.82 (m, 2H), 6.66 (dt, J=7.4 Hz, 1.4 Hz, 1H), 4.63 (s, 2H), 3.64–3.60 (m, 4H), 3.25 (t, J=6.3 Hz, 2H), 2.63 (t, J=6.3 Hz, 2H), 2.54–2.42 (m, 4H).

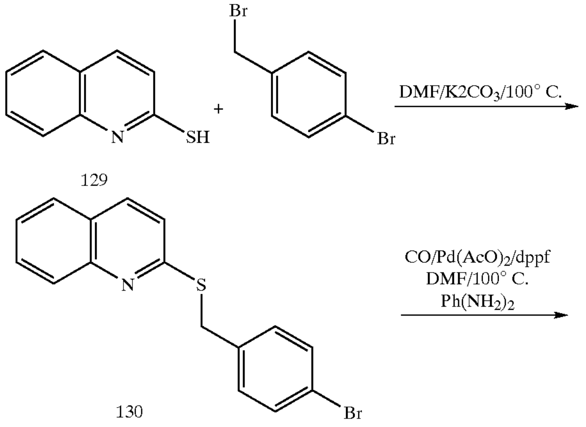

-continued

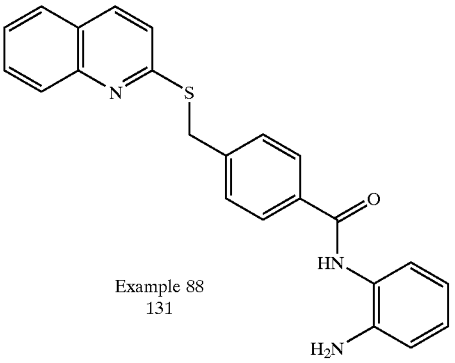

Example 88
131

Example 88

N-(2-Amino-phenyl)-4-(quinolin-2-ylsulfanylmethyl)-benzamide (Compound 131)

Step 1: 2-(4-Bromo-benzylsulfanyl)-quinoline (Compound 130)

Following the procedure described in Example 47, step 2, but substituting 129 for 63, the title compound 130 was obtained in 89% yield. LRMS=332.0 (M+1).

Step 2: N-(2-Amino-phenyl)-4-(quinolin-2-ylsulfanylmethyl)-benzamide (131)

Following the procedure described in Example 40, step 2, but substituting 129 for 42, the title compound 131 was obtained in 70% yield. $^{1}$H NMR: (DMSO-$d_6$) δ (ppm): 9.62 (bs, 1H), 8.21 (d, J=8.8 Hz, 1H), 8.00–7.89 (m, 4H), 7.79 (dd, J=6.8 Hz, 1.3 Hz, 1H), 7.68 (d, J=6.3 Hz, 2H), 7.56 (t, J=6.8 Hz, 1H), 7.44 (d, J=8.7 Hz, 1H), 7.17 (d, J=8.2 Hz, 1H), 6.99 (dt, J=7.9 Hz, 7.4 Hz, 1H), 6.79 (d, J=6.9 Hz, 1H), 6.61 (dt, J=7.7 Hz, 7.4 Hz, 1H), 4.69 (s, 2H).

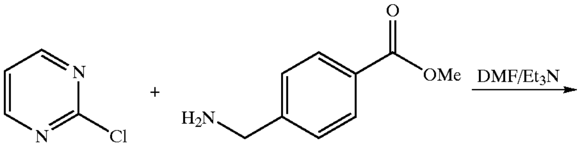

132

-continued

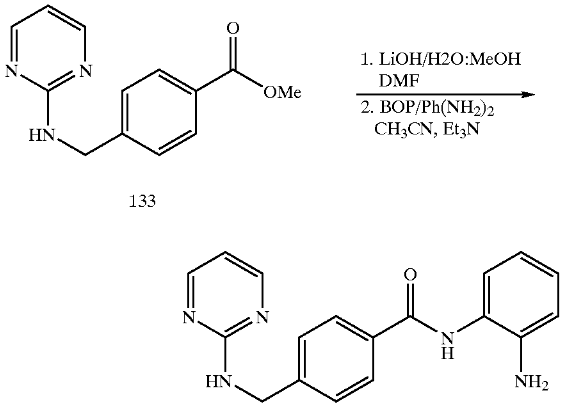

133

134
Example 89

Example 89

N-(2-Amino-phenyl)-4-(pyrimidin-2-ylaminomethyl)-benzamide (Compound 134)

Step 1: 4-(Pyrimidin-2-ylaminomethyl-benzoic acid methyl ester (Compound 133)

Following the procedure described in Example 47, step 2, but substituting 132 for 63, the title compound 133 was obtained in 76% yield. LRMS=244.2 (M+1).

Step 2: N-(2-Amino-phenyl)-4-(pyrimidin-2-yl-aminomethyl)-benzamide (134)

Following the procedure described in Example 1, steps 4 and 5, but substituting 129 for 6, the title compound 134 was obtained in 91% yield. $^{1}$H NMR: (DMSO-$d_6$) δ (ppm): 9.6 (bs, 1H), 8.32 (d, J=4.9 Hz, 2H), 7.97 (dt, J=9.9 Hz, 7.9 Hz, 2H), 7.85–7.83 (m, 1H), 7.47, (d, J=8.2 Hz, 2H), 7.20 (d, J=7.9 Hz, 1H), 7.01 (dt, J=7.7 Hz, 7.4 Hz, 1H), 6.82 (d, J=7.9 Hz, 1H), 6.66–6.62 (m, 1H), 4.98 (bs, 2H), 4.61 (d, 2H).

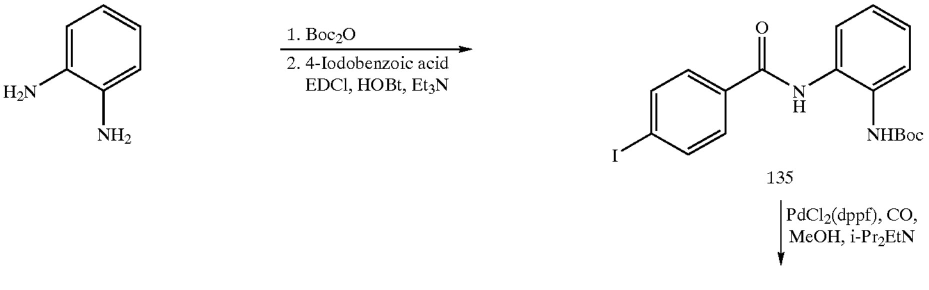

135

-continued

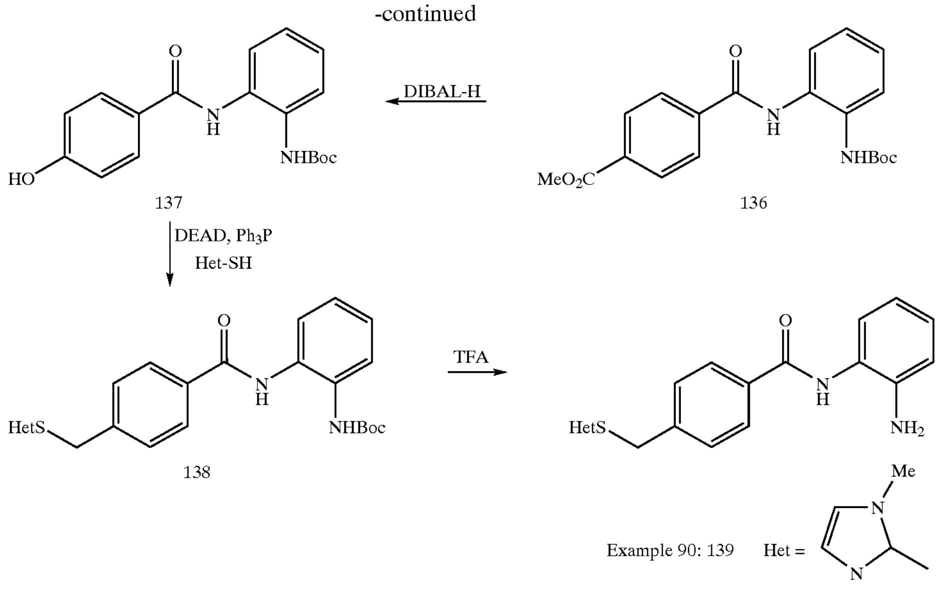

137
136
138
Example 90: 139 Het =

Example 90

N-(2-Amino-phenyl)-4-(1-methyl-1H-imidazol-2-ylsulfanylmethyl]-benzamide (Compound 139)

Step 1: [2-(4-Iodo-benzoylamino)-phenyl]-carbamic acid tert-butyl ester (Compound 135)

To a solution of di-tertbutyldicarbonate (39 g, 181 mmol) in THF (139 mL) placed in a water bath, was added 1,2-phenylenediamine (15 g, 139 mmol) and DMAP (1.7 g. 14 mmol). The mixture was stirred at r.t. for 16 h and the solvent was removed in vacuo. The crude material was partitioned between EtOAc and water. The organic layer was washed with HCl 1 N and then with aqueous saturated $NaHCO_3$. The combined organic layers were washed with brine, dried over $MgSO_4$ and concentrated affording the compound (18.9 g, 65% yield) as a light beige powder. LRMS=209.1 (M+1).

To a solution of 4-iodobenzoic acid (8.0 g, 32.3 mmol) in DMF (65 mL) at r.t., were successively added 1-[3-(dimethylamino)propyl]-3-ethylcabodiimide hydrochloride (8.0 g, 41.9 mmol) and 1-hydroxybenzotriazole (5.2 g, 38.7 mmol). The mixture was stirred for 1 h and a solution of (2-amino-phenyl)-carbamic acid tert-butyl ester (6.3 g, 30.2 mmol) in DMF (20 mL) was added to the mixture via cannula, followed by triethylamine (5.9 mL, 4.9 mmol). The mixture was stirred for 16 h and the solvent was removed in vacuo. The crude material was partitioned between chloroform and water. The organic layer was washed with aqueous saturated $NaHCO_3$, dried over $MgSO_4$ and concentrated to a light brown syrup which was crystallized in hot EtOAc or $Et_2O$, yielding 135 (9.3 g, 70% yield) as a white solid. LRMS=461.0 ($M+Na^+$).

Step 2: N-[2-tert-butoxycarbonylamino-phenyl)-terephtalamic acid methyl ester (Compound 136)

Following the procedure described in Example 40, step 2, but substituting 135 for 42, the title compound 136 was obtained in 95% yield. LRMS=393.1 ($M+Na^+$).

Step 3: [2(4-Hydroxymethylbenzoylamino)-phenyl]-carbamic acid tert-butyl ester (137)

To a solution of 136 (7.5 g, 20.6 mmol) in THF (40 mL), cooled down to −20° C. under $N_2$, was added a 1M solution of DIBAL-H (122 mL, 122 mmol) in toluene. After stirring for 18 h. at r.t., the mixture was cooled down to 0° C. and carefully quenched by a dropwise addition of $H_2O$ (10 mL) and of 2N NaOH (5 mL). The aluminum salts were allowed to decant and the supernatant was removed. The organic layer was washed with $H_2O$, 1 N HCl (6 times), satd. aqueous $NaHCO_3$, brine, dried over $MgSO_4$ and concentrated (2.04 g, 43%). Purification of the crude material by flash chromatography (EtOAc/hexanes 50:50 to 70:30) afforded 137 (1.14 g, 16% yield) as a solid foam. LRMS=365.2 ($M+Na^+$).

Step 4: {2-[4-(1-Methyl-imidazol-2-ylsulfanylmethyl)-benzoylamino]-phenyl}-carbamic acid tert-butyl ester (Compound 138)

To a solution of N-methyl-2-mercaptoimidazole (28 mg, 0.25 mmol) in THF (1 mL), at r.t. under $N_2$ atmosphere were successively added 137 (70 mg, 0.20 mmol), triphenylphosphine (70 mg, 0.27 mmol) followed by dropwise addition of diethyl azodicarboxylate (48 μL, 0.31 mmol). The mixture was stirred for 2 h and the solvent was removed in vacuo. Purification by flash chromatography using $MeOH/CHCl_3$ (5:95) as the eluent afforded the title compound 138 (81 mg), in 91% yield, which was found to contain some diethyl hydrazodicarboxylate residus. The compound was used as is without further purification.

Step 5: N-(2-Amino-phenyl)-4-(1-methyl-1H-imidazol-2-ylsulfanylmethyl]-benzamide (Compound 139)

Following the procedure described in Example 42, step 3, but substituting 138 for 46, the title compound 139 was obtained in 62% yield. $^1H$ NMR: (Acetone-$d_6$) δ (ppm): 9.07 (bs, 1H), 7.93 (d, J=8.2 Hz, 2H), 7.37 (d, J=8.2 Hz, 2H), 7.29 (d, J=8.0 Hz, 1H), 7.10 (d, J=1.1 Hz, 1H), 7.03–6.96 (m, 2H), 6.86 (dd, J=8.0 Hz, 1.4 Hz, 1H), 6.67 (dt, J=7.4 Hz, 1.1 Hz, 1H), 4.63 (bs, 2H), 4.29 (s, 2H), 3.42 (s, 3H).

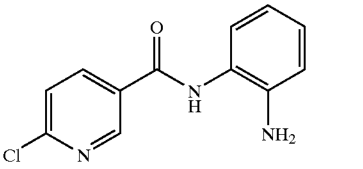

+

140

-continued

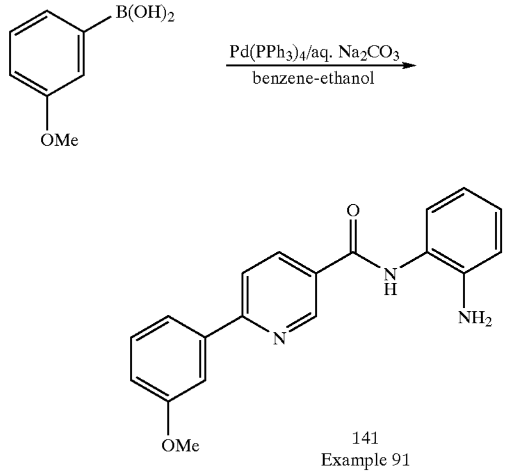

141
Example 91

Example 91

N-(2-Amino-phenyl)-6-(3-methoxyphenyl)-nicotinamide (Compound 141)

To a mixture of 3-methoxyphenyl boronic acid (152 mg, 1.0 mmol) and 140 (248 g, 1.0 mmol) were added benzene (8 mL) and ethanol (4 mL) followed by 2 M $Na_2CO_3$ aqueous solution (3.2 mL, 6.4 mmol). The reaction mixture was stirred under nitrogen for 30 min and then $Pd(PPh_3)_4$(58 mg, 0.05 mmol) was quickly added. After 24 h of reflux, the mixture was cooled to room temperature, filtered through a pad of celite and rinsed with ethyl acetate (30 mL). The organic solution was washed with brine (5 mL), dried ($MgSO_4$), and concentrated. Purification by flash silica gel chromatography (Hexane/Ethyl acetate:1/1) afforded 141 (302 mg, 95% yield). $^1H$ NMR ($CDCl_3$) δ (ppm): 9.11 (d, J=1.8 Hz, 1H), 8.30 (dd, J=8.4 Hz, 1.8 Hz, 1H), 7.57 (d, J=8.4 Hz, 1H), 7.52–7.47 (m, 1H), 7.36 (m, 1H), 7.22 (m, 1H), 7.09–6.78 (m, 4H), 3.84 (s, 3H), 3.39 (br s, 2H).

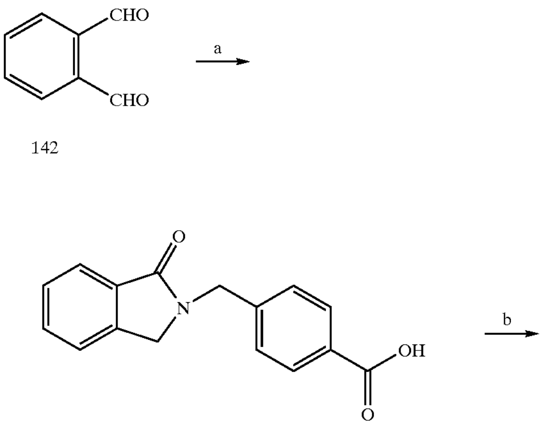

142

143

-continued

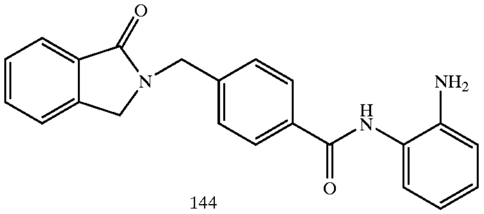

144
Example 92 a. p-aminomethylbenzoic acid/AcOH/5 min/reflux
b. HOBT/EDC/1,2-diamino benzene

Example 92

N-(2-Amino-phenyl)-4-(1-oxo-1,3-dihydro-isoindol-2-ylmethyl)-benzamide (Compound 144)

Step 1: 4-(1-Oxo-1,3-dihydro-isoindol-2-ylmethyl)-benzoic acid (Compound 143)

To a solution of benzene-1,2-carbaldehyde 142 (1.0 g, 7.46 mmol) in 10 mL of acetic acid was added 4-aminomethylbenzoic acid (1.13 g, 7.46 mmol). The reaction mixture was refluxed 5 min and cooled to the room temperature. A crystalline precipitate was formed and triturated with $CH_2Cl_2$ to produce the title compound 143 (1.29 g, 49%).

Step 2: N-(2-Amino-phenyl)-4-(1-oxo-1,3-dihydroisoindol-2-ylmethyl)-benzamide (Compound 144)

To a solution of the carboxylic acid (0.32 g, 0.89 mmol) in DMF (8 mL) at rt, was added HOBt (0.16 g, 1.15 mmol) and EDC (0.25 g, 1.33 mmol) and the solution was stirred for 1.5 h. Lastly, phenylenediamine (0.12 g, 1.07 mmol) was added and the mixture was allowed to stir for 18–20 h. DMF was removed in vacuo and the crude was partitioned between ethyl acetate and $H_2O$. The organic layer was dried over $Na_2SO_4$ and concentrated. Purification by column, chromatography ($CH_2Cl_2$-MeOH (19:1)) afforded 144 in 46% yield. $^1H$ NMR: (DMSO-$d_6$) □9.71 (s, 1H), 7.46 (d, J=8.0 Hz, 2H), 7.80 (d, J=8.0 Hz, 2H), 7.55–7.70 (m, 3H), 7.46 (d, J=8.2 Hz, 2H), 7.20 (d, J=7.7 Hz, 1H), 7.02 (t, J=7.7 Hz, 1H), 6.83 (d, J=8.0 Hz, 1H), 6.65 (t, J=7.4 Hz, 1H), 4.93 (bs, 2 H), 4.87 (s, 2 H), 4.47 (s, 2H).

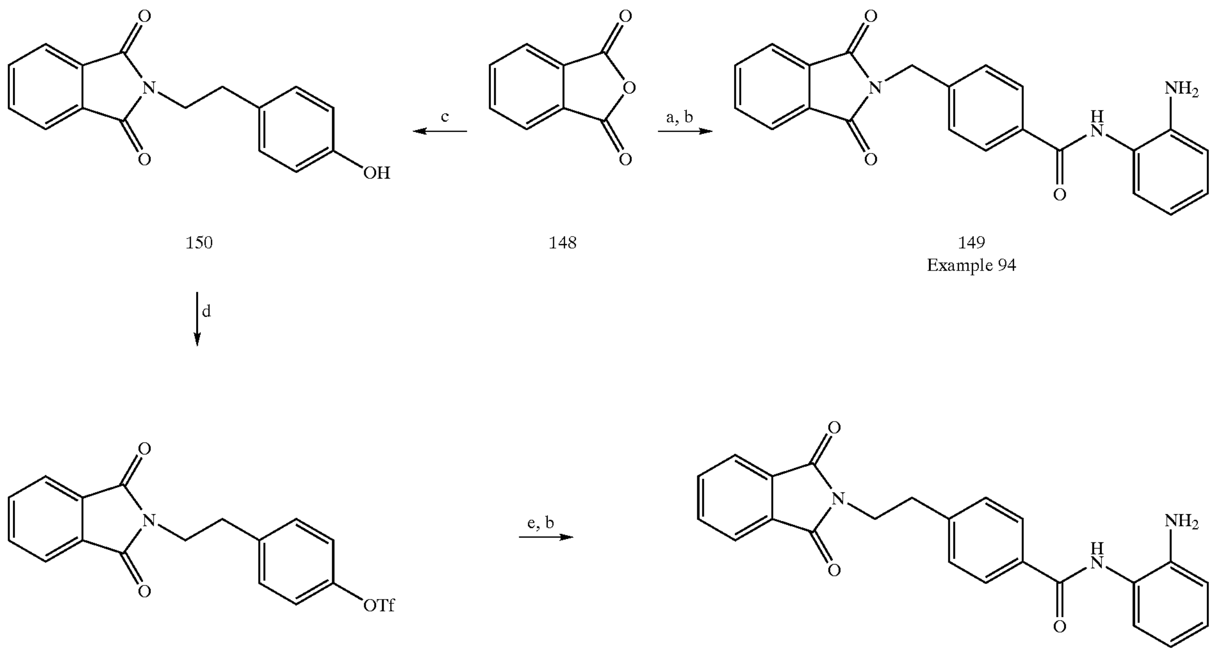

150 148 149 Example 94

151 152 Example 95 a. p-aminomethylbenzoic acid/AcOH/reflux/3 hrs
b. HOBT/EDC/1,2-diamino benzene
c. 4-(2-aminoethyl)phenol/AcOH/5 hrs/reflux
d. $PhNTf_2$/NaH/THF-DMF/30 min/0° C.
e. 1. CO/$Pd(OAc)_2$/dppf/$Et_3N$/MeOH-DMF/4 days/75° C.
2. AcOH/HCl/3 hrs/reflux Example 94

N-(2-Amino-phenyl)-4-(1,3-dioxo-1,3-dihydro-isoindol-2-ylmethyl)-benzamide (Compound 149)

Phthalic anhydride 148 (1.3 g, 8.9 mmol) and 4-aminomethylbenzoic acid in 20 mL acetic acid were refluxing for 3 h, cooled to the room temperature and evaporated to yield a solid residue which was triturated with water, filtered off and dried to produce the intermediate carboxylic acid (1.7 g, 68%). LMRS=282.0 (M+1).

Following a procedure analogous to that described in Example 92, step 2, but substituting the acid for 143, the title compound 149 was obtained in 17% yield. $^1H$ NMR: (DMSO $d_6$) □9.59 (s, 1H), 7.82–7.91 (m, 6H), 7.40 (d, J=8.0 Hz, 2H), 7.11 (d, J=7.7 Hz, 1H), 6.93 (t, J=7.7 Hz, 1H), 6.73 (d, J=8.0 Hz, 1H), 6.55 (t, J=7.4 Hz, 1H), 4.83 (bs, 4H).

Example 95

N-(2-Amino-phenyl)-4-[2-(1,3-dioxo-1,3-dihydro-isoindol-2-yl)ethyl]-benzamide (Compound 152)

Step 1: 2-[2-(4-Hydroxy-phenyl)-ethyl]isoindole-1,3-dione (Compound 150)

Following a procedure analogous to that described in Example 94, step 1, but substituting 4-aminomethylbenzoic acid for tyramine the title compound 150 was obtained in 48% yield. LMRS=268.0 (M+1).

Step 2: 4-[2-(1,3-dioxo-1,3-dihydro-isoindol-2-yl)ethyl)-phenyl trifluoromethane-sulfonate (151)

To a solution of sodium hydride (90 mg, 25 mmol) in dry THF (20 mL) at 0° C., 150 (500 mg, 8.9 mmol) was added followed by the addition of dry DMF (2 mL). The reaction mixture was stirred for 20 min at 0° C., treated portionwise with $PhN(Tf)_2$, stirred for additional 2 h and evaporated to produce a solid material which was purified by chromatography on a silica gel column, ($CH_2Cl_2$-MeOH (19:1)) to provide 151 (639 mg, 86% yield). LMRS=400.0 (M+1).

Step 3: N-(2-Amino-phenyl)-4-[2-(1,3-diox-1,3-dihydro-isoindol-2-yl)-ethyl]-benzamide (Compound 152)

Following a procedure analogous to that described in Example 40, step 2, but substituting 151 for 42, the title compound 152 was obtained in 15% yield. $^1H$ NMR: (DMSO $d_6$) □9.57 (s, 1H), 7.78–7.87 (m, 6H), 7.31 (d, J=8.0 Hz, 2H), 7.12 (d, J=7.7 Hz, 1H), 6.93 (t, J=6.9 Hz, 1H), 6.74 (d, J=8.0 Hz, 1H), 6.56 (t, J=7.4 Hz, 1H), 4.83 (bs, 2 H), 3.85 (t, J=7.1 Hz, 2 H), 3.00 (t, J=7.1 Hz, 2 H).

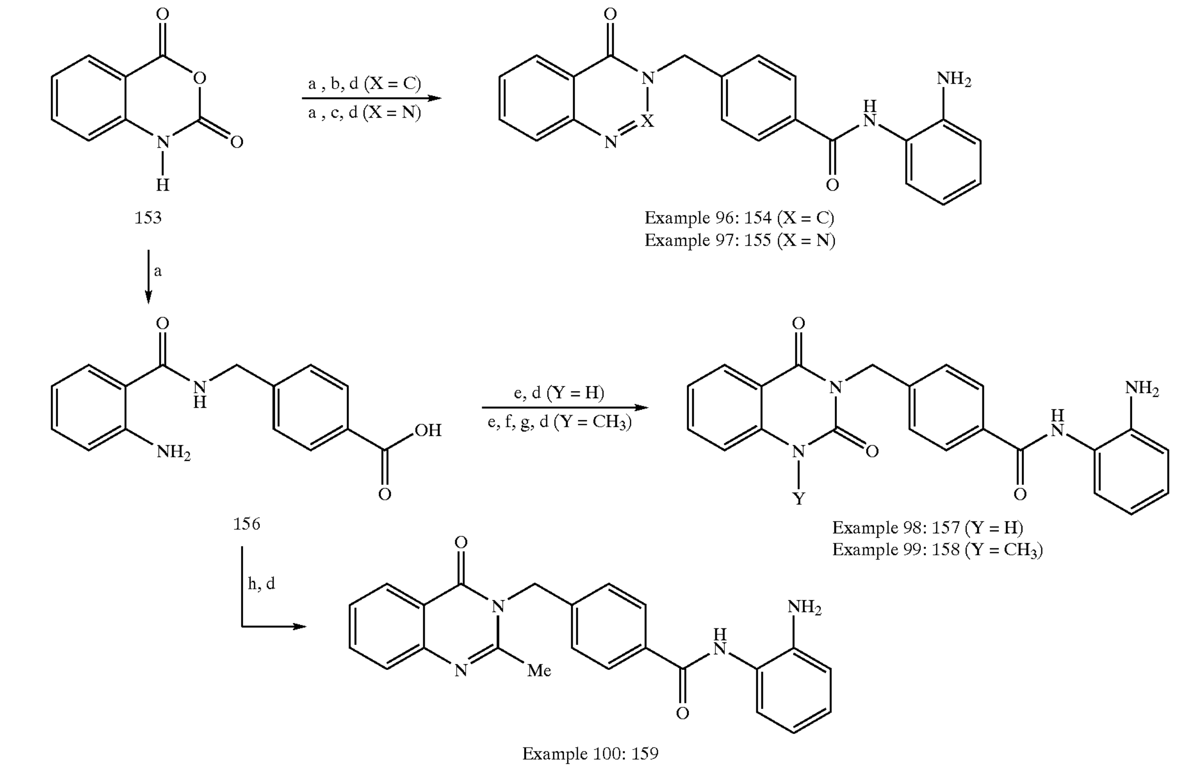

a. p-aminomethylbenzoic acid/H₂O/Et₂N/3 hrs/40° C.
b. HCOOH/reflux/6 hrs
c. NaNO₂/HCl/0° C. 2 hrs, then rt/12 hrs
d. HOBT/EDC/1,2-diamino benzene
e. ClCOOMe/KOH/2 hrs, 0° C.
f. RI/K₂CO₃/DMF/rt
g. NaOH/MeOH/H₂O
h. Ac₂O/1 hour/reflux then AcOH/48 hrs/reflux

Example 96

N-(2-Amino-phenyl)-4-(4-oxo-4H-quinazolin-3-ylmethyl)-benzamide (Compound 154)

A suspension of 4-aminomethyl benzoic acid (1.00 g, 6.60 mmol) in water (20 mL) was treated with Et₃N (0.86 mL, 6.60 mmol) followed by the addition of isatoic anhydride 153 (980 mg, 6.00 mmol). The reaction mixture was heated 3 h at 40° C. and evaporated to form an oily residue, which was refluxing in formic acid (20 mL) for 7 h. Formic acid was removed in vacuum to produce a solid, which was triturated with water and filtered off to provide the carboxylic acid (1.61 g, 96%). LMRS=281.0 (M+1).

Following a procedure analogous to that described in Example 92, step 2, but substituting the carboxylic acid for 143, the title compound 154 was obtained was obtained in 43% yield. $^1$H NMR: (DMSO d$_6$) □9.71 (s, 1H), 8.68 (s, 1H), 8.23 (d, J=8.0 Hz, 1H), 8.01 (d, J=8.0 Hz, 1H), 7.92 (t, J=8.0, 2H), 7.78 (d, J=8.0 Hz, 1H), 7.63 (t, J=7.4, 1H), 7.55 (d, J=7.7 Hz, 2H), 7.22 (d, J=7.4 Hz, 1H), 7.04 (t, J=7.1 Hz, 1H), 6.85 (d, J=8.0 Hz, 1H), 6.67 (t, J=7.4 Hz, 1H), 5.35 (s, 2 H).

Example 97

N-(2-Amino-phenyl)-4-(4-oxo-4H-benzo[d][1,2,3]triazin-3-ylmethyl)-benzamide (Compound 155)

A suspension of 4-aminomethyl benzoic acid (1.00 g, 6.60 mmol) in water (20 mL) was treated with Et₃N (0.86 mL, 6.60 mmol) followed by the addition of isatoic anhydride (980 mg, 6.00 mmol). The reaction mixture was heated 3 h at 40° C. and cooled to 0° C. The cold reaction mixture was acidified with conc. HCl (5 mL) and treated drop wise with NaNO₂ solution (520 mg, 7.5 mmol in 5 mL water) over 5 min period of time, then left overnight at room temperature. A precipitate formed which was collected, washed with water and dried to provide the carboxylic acid (1.62 g, 96%). LMRS=282.0 (M+1).

Following a procedure analogous to that described in Example 92, step 2, but substituting the carboxylic acid for 143, the title compound 155 was obtained in 27% yield. $^1$H NMR: (DMSO d$_6$) □9.62 (s, 1H), 8.25 (t, J=6.7 Hz, 2H), 8.11 (ddd, J=7.1 Hz, 1.4 Hz, 1H), 7.93–7.98 (m, 3H), 7.49 (d, J=8.2 Hz, 2H), 7.13 (d, J=7.7 Hz, 1H), 6.94 (t, J=8.0 Hz, 1H), 6.75 (d, J=8.0 Hz, 1H), 6.57 (t, J=7.7 Hz, 1H), 5.66 (s, 2 H), 4.87 (bs, 2 H).

Example 98

N-(2-Amino-phenyl)-4-(2,4-dioxo-1,4-dihydro-2H-quinazolin-3-ylmethyl)-benzamide (Compound 157)

Step 1: 4-[(2-Amino-benzoylamino)-methyl]-benzoic acid (Compound 155)

To a suspension of 4-aminomethylbenzoic acid (5.09 g, 33.7 mmol) in H₂O (50 mL), was added Et₃N (4.7 mL, 33.7 mmol) followed by isatoic anhydride 153 (5.0 g, 30.6 mmol). The brown mixture was heated at 40° C. for 2 h until the mixture became homogeneous and then $Et_3N$ was removed in vacuo. The resulting aqueous solution was acidified (10% $HCl/H_2O$) and the mixture was partitioned between $H_2O$ and ethyl acetate. The combined organic extracts were dried over $Na_2SO_4$, filtered and evaporated to give 156 as a white solid (6.0 g, 72%). LMRS=271.0 (M+1).

Step 2: N-(2-Amino-phenyl)-4-(2,4-dioxo-1,4-dihydro-2H-quinazolin-3-ylmethyl)-benzamide (Compound 157)

the carboxylic acid 156 (1.72 g, 6.36 mmol) was suspended in a solution of NaOH (2.55 g, 63.6 mmol) in $H_2O$ (12 mL). To this solution was added dioxane (10 mL) until mixture became homogeneous. The solution was cooled to 0° C. in an ice-bath and methyl chloroformate (1.25 mL, 16.1 mmol) was added portionwise over 2 h. After completion of the reaction, the excess methyl chloroformate and dioxane were removed in vacuo and the mixture was diluted with methanol (80 mL) and $H_2O$ (20 mL). The solution was heated to 50° C. for 1 h. until the cyclization was complete. Methanol was removed in vacuo and then the aqueous layer was extracted with ethyl acetate. Subsequently, the aqueous phase was acidified (10% $HCl/H_2O$) and extracted with ethyl acetate (2×300 mL). These organic extracts were combined, dried over $Na_2SO_4$, filtered and evaporated to dryness. The resulting crude was triturated with warm methanol to afford the carboxylic acid as a white solid (1.7 g, 90%). LMRS=319.0 (M+Na).

Following a procedure analogous to that described in Example 92, step 2, but substituting the quinazolinedione carboxylic acid for 143, the title compound 157 was obtained. $^1H$ NMR: (DMSO-$d_6$) δ11.56 (brs, 1H), 9.59 (brs, 1H), 7.96–7.88 (m, 3H), 7.67 (dt, J=8.4, 1.4 Hz, 1H), 7.30 (d, J=7.8 Hz, 2H), 7.21 (t, J=7.5 Hz, 2H), 7.13 (d, J=6.9 Hz, 1H), 6.92 (dt, J=6.9, 1.2 Hz, 1H), 6.75 (d, J=6.9 Hz, 1H), 6.57 (t, J=6.9 Hz, 1H), 5.15 (brs, 2H), 4.86 (brs, 2H).

Example 99

N-(2-Amino-phenyl)-4-(1-methyl-2,4-dioxo-1,4-dihydro-2H-quinazolin-3-ylmethyl)-benzamide (Compound 158)

Step 2: 4-(1-Methyl-2,4-dioxo-1,4-dihydro-2H-quinazolin-3-ylmethyl)-benzoic acid methyl ester To a soluton of the quinazolinedione carboxylic acid (1.0 g, 3.38 mmol) in DMF (7 mL), was added $K_2CO_3$ (1.4 g, 10.1 mmol) and the mixture was then cooled to 0° C. Subsequently, MeI (1.05 mL, 16.9 mmol) was added and the mixture was allowed to warm to rt in the ice bath overnight. Excess methyl iodide and DMF were removed in vacuo and the crude was partitioned between ethyl acetate and $H_2O$. The aqueous phase was washed again with ethyl acetate, the combined organic extracts were dried over $Na_2SO_4$ and then concentrated in vacuo to yield the desired product as an off-white solid (0.93 g, 85%). LMRS=325.0 (M+1).

Step 3: 4-(1-Methyl-2,4-dioxo-1,4-dihydro-2H-quinazolin-3-ylmethyl)-benzoic acid To a suspension of the methyl ester (1.25 g, 3.85 mmol) in methanol (35 mL), was added 1N NaOH (30 mL, 38.5 mmol) and the mixture was heated to 45–50° C. for 3 h. until it became homogeneous. Methanol was removed in vacuo and the crude was partitioned between ethyl acetate and $H_2O$. The aqueous phase was acidified (10% $HCl/H_2O$) and extracted with ethyl acetate (2×300 mL). These organic extracts were dried over $Na_2SO_4$ and concentrated in vacuo to afford product 5 as a white solid (1.15 g, 96%). LMRS=311.0 (M+1).

Step 4: N-(2-Amino-phenyl)-4-(1-methyl-2,4-dioxo-1,4-dihydro-2H-quinazolin-3-ylmethyl-benzamide (Compound 158)

Following a procedure analogous to that described in Example 92, step 2, but substituting the carboxylic acid for 143, the title compound 158 was obtained in 10% yield. $^1H$ NMR: (DMSO-$d_6$) δ 9.59 (brs, 1H), 8.03 (d, J=7.8 Hz, 1H), 7.89 (d, J=7.8 Hz, 2H) 7.80 (dt, J=6.9, 1.5 Hz, 1H), 7.49 (d, J=8.7 Hz, 1H), 7.42 (d, J=8.1 Hz, 2H), 7.32 (t, J=7.7 Hz, 1H), 7.13 (d, J=7.8 Hz, 1H), 6.95 (t, J=7.6 Hz, 1H), 6.75 (d, J=7.8 Hz, 1H), 6.57 (t, J=7.5 Hz, 1H), 5.21 (brs, 2H), 4.86 (brs, 2H), 3.54 (s, 3H).

Example 100

N-(2-Amino-phenyl)-4-(2-methyl-4-oxo-4H-quinazolin-3-ylmethyl)-benzamide (Compound 159)

A suspension of 156 (903 mg, 3.34 mmol) in acetic anhydride (15 mL) was heated at 50° C. for 1 h. Acetic anhydride was evaporated under vacuum and the solid material formed was dissolved in acetic acid (30 mL). This solution was refluxed 48 h and evaporated to form another solid material, which was recrystallized from a mixture AcOEt/$CHCl_3$ to produce the intermediate carboxylic acid (420 mg, 43% yield). LMRS=385.0 (M+1).

Following a procedure analogous to that described in Example 92, step 2, but substituting the carboxylic acid for 143, the title compound 159 was obtained in 49% yield. $^1H$ NMR: (DMSO) δ (ppm): 9.64 (bs, 1H), 8.17 (dd, J=8.0, 1.6 Hz, 1H), 7.95 (d, J=8.2 Hz, 2H), 7.95 (dd, J=8.8, 2.5 Hz, 1H), 7,84 (ddd, J=7.6, 7.0, 1.5 Hz, 1H), 7.64 (d, J=7.7 Hz, 1H), 7.53 (ddd, J=7.6, 7.6, 1.1 Hz, 1H), 7.33 (d, J=8.2 Hz, 2H), 7.14 (dd, J=7.7, 1.1 Hz, 1H), 6.96 (ddd, J=7.6, 7.6, 1.5 Hz, 1H), 6.77 (dd, J=8.0, 1.4 Hz, 1H), 6.58 (ddd, J=7.6, 7.6, 1.3 Hz, 1H), 5.46 (s, 2H), 4.89 (bs, 2H) 2.5 (s, 3H, overlaps with the DMSO signals).

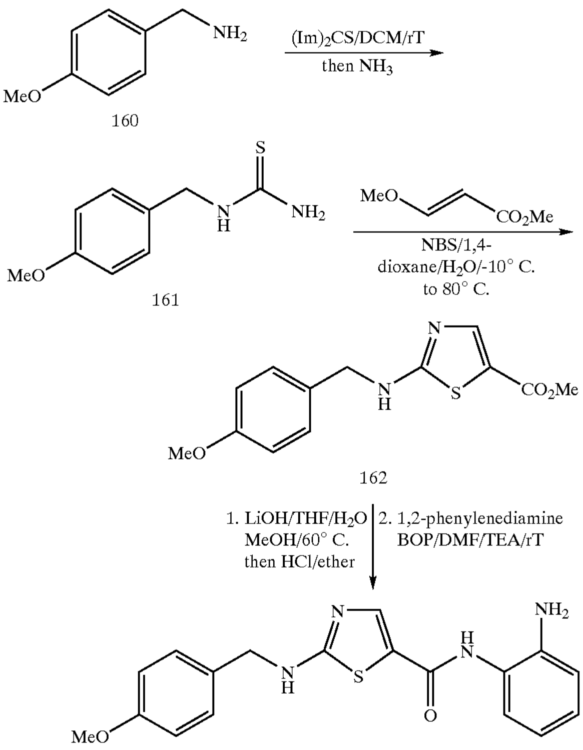

160

161

162

163

Example 101

Example 101

N-(2-aminophenyl)-2-(4-Methoxy-benzylamino)-thiazol-5-yl-amide (Compound 163)

Step 1: 4-Methoxybenzyl-thiourea (Compound 161)

To a solution of thiocarbonyl diimidazole (1.23 g, 6.22 mmol, 1.5 equiv.) in dry dichloromethane (10 mL), neat alkylamine 160 (4.15 mmol, 1.0 equiv.) was added dropwise at 0° C., and the solution stirred from 0° C. to 15° C. during 16 h. A solution of concentrated ammonium hydroxide (3 mL, 45 mmol, 3.6 equiv.) in 1,4-dioxane (6 mL) was added at 0° C. and stirred at room temperature for 7 h. The solution was diluted with ethyl acetate (250 mL), washed with brine (2×50 mL), dried ($MgSO_4$), filtered and concentrated. After purification by column chromatography (silica gel, elution 5% methanol in dichloromethane), 161 was obtained as yellow solid (700.2 mg, 3.6 mmol, 86% yield). $^1H$ NMR: (Acetone-$d_6$) δ (ppm): 7.53 (bs, 1H), 7.28 (d, J=8.8 Hz, 2H), 6.87 (d, J=8.8 Hz, 2H), 6.67 (bs, 2H), 4.67 (s, 2H), 3.77 (s, 3H). LMRS=197.1 (M+1).

Step 2: 2-(4-Methoxybenzylamino)thiazole-5-carboxylic acid methyl ester (Compound 162)

A solution of trans methyl-2-methoxyacrylate (461 mg, 3.97 mmol, 1 equiv.) in 50% 1,4-dioxane in water (4 mL) stirred at −10° C., was treated with N-bromosuccinimide (792 mg, 4.46 mmol, 1.12 equiv.), stirred at the same temperature for 1 h, transferred to a flask containing the thiourea 161 (700.2 mg, 3.6 mmol) and the mixture was stirred at 80° C. for 2 h. After cooling down to room temperature, concentrated $NH_4OH$ (0.8 mL) was added, stirred for 10 min and the resulting precipitated filtered and washed with water, giving 363 mg (1.3 mmol, 36% yield) of 162, plus 454 mg additional (91% pure by HPLC) as residue from evaporation of the filtrated (ca. 77% overall yield). $^1H$ NMR: (Acetone-$d_6$) δ (ppm): 7.97 (bs, 1H), 7.72 (bs, 1H), 7.33 (d, J=8.1 Hz, 2H), 6.90 (d, J=8.1 Hz, 2H), 4.52 (s, 2H), 3.78 (s, 3H), 3.75 (s, 3H). LMRS=279.1 (M+1).

Step 3: N-2-aminophenyl)-2-(4-Methoxy-benzylamino)-thiazol-5-yl-amide (Compound 163)

Following the procedure described in Example 1, steps 4 and 5, but substituting 162 for 6, the title compound 163 was obtained in 50% yield. $^1H$-NMR (methanol-d4), δ (ppm): 7.86 (s, 1H), 7.29 (d, J=8.8 Hz, 2H), 7.11 (dd, J=8.0 Hz, 1.4 Hz, 1H), 7.04 (dt, J=8.0 Hz, 1.4 Hz, 1H), 6.90 (d, J=8.8 Hz, 2H), 6.86 (m, 1H), 6.74 (dt, J=7.4 Hz, 1.4 Hz, 1H), 4.85 (bs, 4H), 4.45 (s, 2H), 3.78 (s, 3H).

Examples 102–121

Examples 102 to 121 describe the preparation of compounds 164 to 183 using the same procedures as described for compounds 62 to 163 in Examples 47 to 101. Characterization data are presented in Tables 4a and 4b.

TABLE 4a

Characterization of Compounds Prepared in Examples 102–121

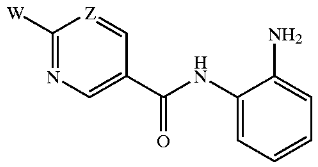

| Ex. | Cpd | W | Y | Z | Name | Characterization | Schm |
|---|---|---|---|---|---|---|---|
| 102 | 164 | 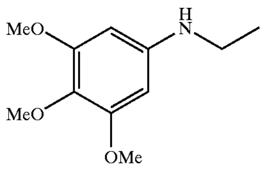 | CH | CH | N-(2-Amino-phenyl)-4-[(3,4,5-trimethoxy-phenylamino)-methyl]-benzamide | $^1H$ NMR: (Acetone-$d_6$) δ (ppm): 9.09 (bs, 1H), 7.99 (d, J=8.2Hz, 2H), 7.54 (d, J=8.0Hz, 2H), 7.29 (d, J=7.7Hz, 1H), 7.00 (t, J=6.6Hz, 1H), 6.86 (dd, J=8.0Hz, 1.1Hz, 1H), 6.67 (t, J=8.0Hz, 1H), 5.99 (s, 2H), 5.46 (bs, 1H), 4.64 (bs, 2H), 4.43 (s, 2H), 3.69 (s, 6H), 3.60 (s, 3H). | 11 |
| 103 | 165 | 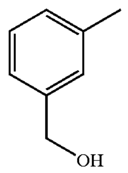 | N | CH | N-(2-Amino-phenyl)-6-(3-hydoxymethyl-phenyl)-nicotinamide | $^1H$ NMR (20% $CD_3OD$ in $CDCl_3$) δ (ppm): 9.14 (d, J=1.8Hz, 1H), 8.33 (dd, J=8.4Hz, 1.8Hz, 1H), 7.93 (s, 1H), 7.82 (m, 2H), 7.50–7.40 (m, 2H), 7.22–6.45 (m, 4H), 4.69 (s, 2H). | 15 |
| 104 | 166 | 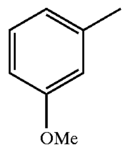 | CH | CH | N-(2-Amino-phenyl)-4-(3-methoxy-pheny)-benzamide | $^1H$ NMR ($CD_3OD$) δ (ppm): 7.98 (d, J=8.4Hz, 2H), 7.65 (d, J=8.4Hz, 2H), 7.31–7.04 (m, 5H), 6.92–6.80 (m, 3H), 3.84 (s, 3H) | 15 |
| 105 | 167 | 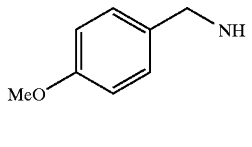 | CH | N | N-(2-amino-phenyl)-6-(4-methoxy-benzylamino)-nicotinamide | $^1H$ NMR (DMSO-$d_6$) δ (ppm): 9.33 (s, 1H), 8.61 (d, J=2.5Hz, 1H), 7.89 (dd, J=8.8Hz, 2.2Hz, 1H), 7.57 (t, J=5.8Hz, 1H), 7.24 (d, J=8.52Hz, 2H), 7.11 (d, J=7.69Hz, 1H), 6.90 (m, 3H), 6.73 (d, J=8.0Hz, 1H), 6.50–6.58 (m, 2H), 4.83 (s, 2H), 4.45 (d, J=5.8Hz, 2H), 3.70 (s, 3H). | 6 |

TABLE 4a-continued

Characterization of Compounds Prepared in Examples 102–121

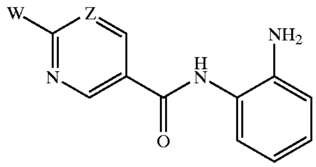

| Ex. | Cpd | W | Y | Z | Name | Characterization | Schm |
|---|---|---|---|---|---|---|---|
| 106 | 168 | 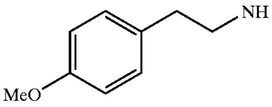 | CH | N | N-(2-amino-phenyl)-6-[2-(4-methoxy-phenyl)-ethylamino]-nicotinamide | $^1$H NMR (DMSO-$d_6$) δ (ppm): 9.42 (s, 1H), 8.72 (d, J=2.5Hz, 1H), 7.97 (dd, J=8.8Hz, 2.5Hz, 1H), 7.23 (m, 4H), 6.81–7.03 (m, 4H), 6.64 (m, 1H), 6.56 (d, J=9.1Hz, 1H), 4.92 (s, 2H), 3.78 (s, 3H), 3.55 (m, 2H), 2.85 (t, J=7.3Hz, 2H). | 6 |
| 107 | 169 | 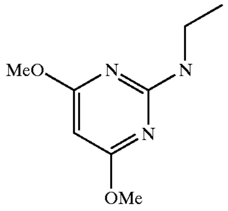 | CH | CH | N-(2-Amino-phenyl)-4-[(4,6-dimethoxy-pyrimidin-2-ylamino)-methyl]-benzamide | $^1$H NMR: (DMSO-$d_6$) δ (ppm): 9.63 (bs, 1H), 7.95 (d, J=7.9Hz, 2H), 7.85–7.82 (m, 1H), 7.48 (d, J=7.9Hz, 2H), 7.20 (d, J=7.1Hz, 1H), 7.03 (dt, J=7.6Hz, 7.4Hz, 1H), 6.81 (d, J=7.9Hz, 1H), 6.63 (dt, J=7.9Hz, 7.7Hz, 1H), 4.94 (bs, 2H), 4.54 (d, J=6.0Hz, 2H), 3.79 (bs, 6H). | 11 |
| 108 | 170 | 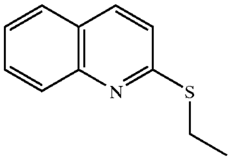 | CH | CH | N-(2-Amino-phenyl)-4-(quinolin-2-ylsulfanylmethyl)-benzamide | $^1$H NMR: (DMSO-$d_6$) δ (ppm): 9.62 (bs, 1H), 8.21 (d, J=8.8Hz, 1H), 8.00–7.89 (m, 4H), 7.79 (dd, J=6.8Hz, 1.3Hz, 1H), 7.68 (d, J=6.3Hz, 2H), 7.56 (t, J=6.8Hz, 1H), 7.44 (d, J=8.7Hz, 1H), 7.17 (d, J=8.2Hz, 1H), 6.99 (dt, J=7.9Hz, 7.4Hz, 1H), 6.79 (d, J=6.9Hz, 1H), 6.61 (dt, J=7.7Hz, 7.4Hz, 1H), 4.69 (s, 2H). | 11 |
| 109 | 171 | 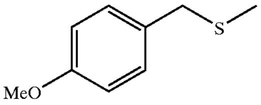 | N | CH | N-(2-Amino-phenyl)-6-(4-methoxy-benzylsulfanyl)-nicotinamide | $^1$H NMR: (DMSO-$d_6$) δ (ppm): 9.06 (bs, 1H), 8.17 (dt, J=10.9Hz, 9.0Hz, 1H), 7.46 (d, J=8.5Hz, 1H), 7.39 (d, J=8.2Hz, 2H), 7.21–7.13 (m, 2H), 7.01 (dt, J=7.6Hz, 7.4Hz, 1H), 6.91 (d, J=8.5Hz, 2H), 6.80 (d, J=7.9Hz, 1H), 6.62 (t, J=7.4Hz, 1H), 5.01 (bs, 2H), 4.47 (s, 2H), 3.76 (s, 3H). | 12 |
| 110 | 172 | 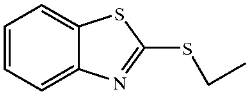 | CH | CH | N-(2-Amino-phenyl)-4-(benzothiazol-2-ylsulfanylmethyl]-benzamide | $^1$H NMR: (DMSO-$d_6$) δ (ppm): 8.01 (d, J=8.0Hz, 1H), 7.93 (d, J=8.2Hz, 2H), 7.90 (dd, J=4.4Hz, 0.6Hz, 1H), 7.63 (d, J=8.2Hz, 2H), 7.48 (dt, J=8.0Hz, 0.8Hz, 1H), 7.37 (td, J=7.1Hz, 1.1Hz, 1H), 7.14 (d, J=7.1Hz, 1H), 6.96 (t, J=6.3Hz, 1H), 6.76 (d, J=7.7Hz, 1H), 6.58 (t, J=6.6Hz, 1H), 4.88 (s, 2H), 4.73 (s, 2H). | 11 |
| 112 | 174 | 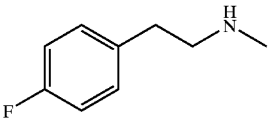 | CH | N | N-(2-amino-phenyl)-6-[2-(4-fluoro-phenyl)-ethylamino]-nicotinamide | $^1$H NMR (DMSO-$d_6$) δ (ppm): 9.34 (s, 1H), 8.64 (d, J=2.5Hz, 1H), 7.89 (dd, J=9Hz, 2Hz, 1H), 7.16–7.22 (m, 3H), 7.06–7.20 (m, 3H), 6.90–6.96 (m, 1H), 6.72–6.78 (m, 1H), 6.46–6.60 (m, 2H), 4.92 (s, 2H), 3.50 (m, 2H), 2.92 (m, 2H). | 6 |
| 113 | 175 | 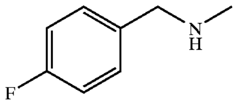 | CH | N | N-(2-amino-phenyl)-6-(4-fluoro-benzylamino)-nicotinamide | $^1$H NMR (DMSO-$d_6$) δ (ppm): 9.34 (s, 1H), 8.61 (d, J=2.2Hz, 1H), 7.91 (dd, J=8.8Hz, 2.2Hz, 1H), 7.66 (t, J=6Hz, 1H), 7.32–7.37 (m, 2H), 7.08–7.38 (m, 3H), 6.93 (m, 1H), 6.74 (m, 1H), 6.52–6.58 (m, 2H), 4.84 (s, 2H), 4.51 (d, J=6.0 | 6 |
| 114 | 176 | 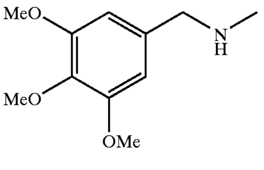 | CH | N | N-(2-amino-phenyl)-6-(3,4,5-trimethoxy-benzylamino)-nicotinamide | $^1$H NMR (DMSO-$d_6$) δ (ppm): 9.34 (s, 1H), 8.63 (d, J=2.2Hz, 1H), 7.92 (dd, J=8.8Hz, 2.2Hz, 1H), 7.57 (t, J=6Hz, 1H), 7.10 (m, 1H), 6.93 (m, 1H), 6.74 (m, 1H), 6.66 (s, 2H), 6.56 (m, 2H), 4.84 (s, 2H), 4.45 (d, J=6Hz, 2H), 3.73 (s, 6H), 3.31 (s, 3H). | 6 |

TABLE 4a-continued

Characterization of Compounds Prepared in Examples 102–121

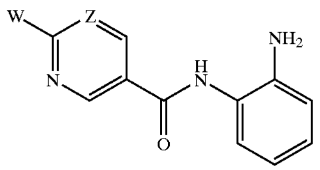

| Ex. | Cpd | W | Y | Z | Name | Characterization | Schm |
|---|---|---|---|---|---|---|---|
| 115 | 177 | 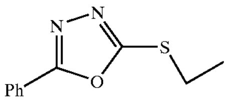 | CH | CH | N-(2-Amino-phenyl)-4-(5-phenyl-[1,3,4]oxadiazol-2-ylsulfanylmethyl]-benzamide | $^1$H NMR: (Acetone-$d_6$) δ (ppm): 9.08 (bs, 1H), 8.02 (dd, J=7.1Hz, 1.9Hz, 4H), 7.69 (d, J=8.5Hz, 2H), 7.62–7.57 (m, 3H), 7.28 (d, J=7.7Hz, 1H), 7.03–6.97 (m, 1H), 6.86 (d, J=6.6Hz, 1H), 6.67 (t, J=7.7Hz, 1H), 4.70 (s, 2H), 4.63 (bs, 2H). | 14 |
| 116 | 178 | 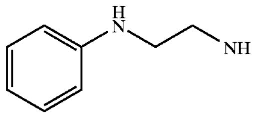 | N | CH | N-(2-aminophenyl)-6-(2-phenylamino-ethylamino)-nicotinamide | $^1$H-NMR ($CD_3OD$-d4), δ (ppm): 8.67 (d, J=2.2Hz, 1H), 7.97 (dd, J=8.9Hz, 2.5Hz, 1H), 7.58 (m, 1H), 7.51 (m, 1H), 7.15 (dd, J=7.7Hz, 1.1Hz, 1H), 7.08 (m, 2H), 6.89 (dd, J=8.0Hz, 1.4Hz, 1H), 6.76 (dt, J=7.7Hz, 4.4Hz, 1H), 6.67 (t, J=7.7Hz, 2H), 6.60 (m, 2H), 4.87 (bs, 4H), 3.60 (t, J=6.3Hz, 2H), 3.35 (t, J=6.3Hz, 2H). | 11 |
| 117 | 179 | 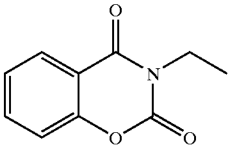 | CH | CH | N-(2-Amino-phenyl)-4-(2,4-dioxo-4H-benzo[e][1,3]oxazin-3-ylmethyl)-benzamide | $^1$H NMR: (DMSO-$d_6$) δ (ppm): 9.62 (s, 1H), 8.00 (dd, J=8.2Hz, 1.9Hz, 1H), 7.80–7.92 (m, 3H), 7.42–7.50 (m, 4H), 7.13 (d, J=7.1Hz, 1H), 6.95 (ddd, J=8.0Hz, 1.6Hz, 1H), 6.75 (dd, J=8.0Hz, 1.4Hz, 1H), 6.57 (t, J=7.7Hz, 1H), 5.13 (s, 2H), 4.87 (bs, 2H). | 11 |
| 118 | 180 | 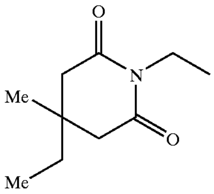 | CH | CH | N-(2-Amino-phenyl)-4-(4-ethyl-4-methyl-2,6-dioxo-piperidin-1-ylmethyl)-benzamide | $^1$H NMR: (DMSO-$d_6$) δ (ppm): 9.59 (s, 1H), 7.88 (d, J=8.2Hz, 2H), 7.31 (d, J=8.2Hz, 2H), 7.13 (d, J=7.4Hz, 1H), 6.95 (t, J=8.0Hz, 1H), 6.75 (d, J=8.0Hz, 1H), 6.57 (t, J=7.4Hz, 1H), 4.87 (s, 2H), 4.86 (bs, 2H), 2.61 (s, 2H), 2.55 (s, 2H), 1.31 (q, J=7.7Hz, 2H), 0.91 (s, 3H), 0.80 (t, J=7.4Hz, 3H). | 11 |
| 119 | 181 | 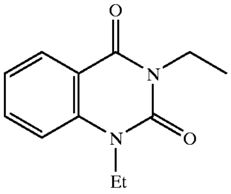 | CH | CH | N-(2-Amino-phenyl)-4-(1-ethyl-2,4-dioxo-1,4-dihydro-2H-quinazolin-3-ylmethyl)-benzamide | $^1$H NMR: ($CDCl_3$) δ (ppm): 8.23 (dd, J=7.8Hz, 1.5Hz, 1H), 8.01 (bs, 1H), 7.80 (d, J=8.0Hz, 2H), 7.71–7.65 (m, 1H), 7.55 (d, J=8.2Hz, 2H), 7.27–7.20 (m, 3H), 7.05 (dt, J=7.7, 1.5Hz, 1H), 6.81–6.77 (m, 2H), 5.29 (bs, 2H), 4.18 (q, J=7.3 Hz, 2H), 3.86 (bs, 2H), 1.33 (t, J=7.1Hz, 3H). | 19 |
| 120 | 182 | 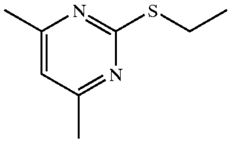 | CH | CH | N-(2-Amino-phenyl)-4-(4,6-dimethyl-pyrimidin-2-ylsulfanylmethyl)-benzamide | $^1$H NMR: (DMSO-$d_6$) δ (ppm): 9.66 (bs, 1H), 7.96 (d, J=7.9Hz, 2H), 7.61 (d, J=7.9Hz, 2H), 7.21 (d, J=7.9Hz, 1H), 7.04–6.99 (m, 2H), 6.82 (d, J=7.9Hz, 1H), 6.64 (t, J=7.4Hz, 1H), 4.49 (s, 2H), 2.42 (s, 6H). | 11 |
| 121 | 183 | 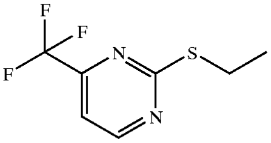 | CH | CH | N-(2-Amino-phenyl)-4-(4-trifluoromethyl-pyrimidin-2-ylsulfanylmethy)benzamide | $^1$H NMR: (DMSO-$d_6$) δ (ppm): 9.66 (bs, 1H), 9.07 (d, J=5.2Hz, 1H), 7.97 (d, J=7.4Hz, 2H), 7.78 (d, J=4.7Hz, 1H), 7.63 (d, J=7.4Hz, 2H), 7.19 (d, J=7.7Hz, 1H), 7.01 (dt, J=7.7Hz, 7.4Hz, 1H), 6.81 (d, J=8.2Hz, 1H), 6.64 (dt, J=7.4Hz, 7.1Hz, 1H), 4.94 (bs, 2H), 4.57 (s, 2H). | 11 |

TABLE 4b

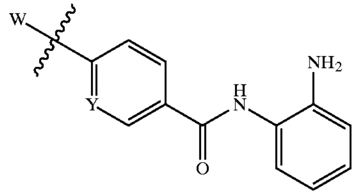

| Ex. | Cpd | W | Y | Z | Name | Characterization | Schm |
|---|---|---|---|---|---|---|---|
| 123 | 187 | 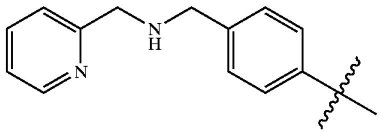 | CH | CH | N-(2-Aminophenyl)-4-[3-(pyridin-2ylmethyl-aminomethyl)phenyl)]-benzamide | $^1$H NMR (20% $CD_3OD$ in $CDCl_3$) δ (ppm): 8.46 (m, 1H), 7.95 (d, J=8.4Hz, 2H), 7.64–6.70 (m, 14 H), 3.80 (br s, 4H). | 21 |
| 124 | 188 | 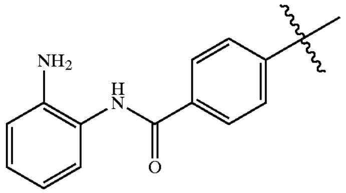 | CH | CH | Biphenyl-4,4'-dicarboxylic acid bis-[(2-amino-phenyl)-amide] | $^1$H NMR ($CD_3OD$) δ (ppm): 9.80 (bs, 2H), 8.16 (d, J=7.9Hz, 4H), 7.96 (d, J=7.9Hz, 4H), 7.23 (d, J=7.4Hz, 2H), 7.03 (dd, J=6.9, 7.4Hz, 2H), 6.84 (d, J=8.2Hz, 2H), 6.66 (dd, J=6.9, 7.7Hz, 2H), 5.06 (bs, 4H). | 1 |
| 125 | 189 | 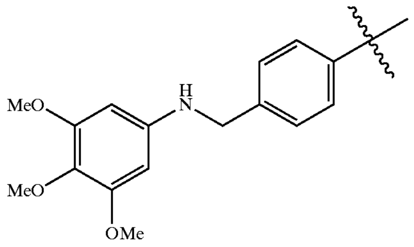 | CH | CH | N-(2-Amino-phenyl)-4-[4-{(3,4,5-trimethoxy-phenylamino)-methyl}phenyl]-benzamide | $^1$H NMR (DMSO-$d_6$) δ (ppm): 10.15 (1H, brs), 8.17 (2H, d, J=8.0), 7.90 (2H, d, J=8.2), 7.87 (1H, brs), 7.72 (1H, d, J=6.6), 7.54 (2H, m), 7.40 (1H, d, J=8.5), 7.25 (1H, m), 7.16 (1H, d, J=7.4), 7.07 (1H, m), 6.08 (2H, s), 4.42 (2H, s), 3.73 (6H, s), 3.58 (3H, d, J=0.8) | 21 |

TABLE 4b-continued

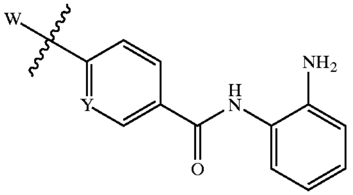

| Ex. | Cpd | W | Y | Z | Name | Characterization | Schm |
|---|---|---|---|---|---|---|---|
| 126 | 190 | 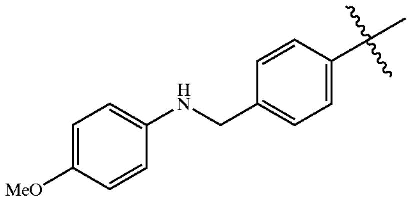 | CH | CH | N-(2-Amino-phenyl)-4-[4-{(4-methoxy-phenylamino)-methyl}-phenyl]-benzamide | $^1$H NMR (DMSO-$d_6$) δ (ppm): 10.03 (1H, brs), 8.17 (2H, d, J=7.7), 7.83(3H, m), 7.76(1H, d, J=7.1), 7.52 (2H, m), 7.35 (1H, d, J=8.0), 7.17 (1H, m), 7.08–6.93 (6H, m), 4.50 (3H, s), 3.75 (2H, s) | 21 |
| 128 | 193 | 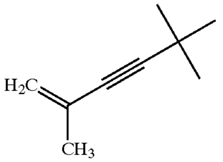 | CH | CH | N-(2-Amino-phenyl)-4-(3-methyl-but-3-en-1-ynyl)-benzamide | LRMS calc: 276.03, found: 277.2 $(MH)^+$ | 22 |
| 129 | 194 | 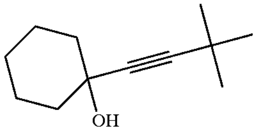 | CH | CH | N-(2-Amino-phenyl)-4-(1-hydroxy-cyclohexylethynyl)-benzamide | LRMS calc: 334.4, found: 335 $(MH)^+$ | 22 |
| 130 | 195 | 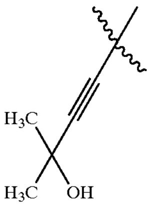 | CH | CH | N-(2-Amino-phenyl)-4-(3-hydroxy-3-methyl-but-1-ynyl)-benzamide | LRMS calc: 294.35, found: 295.1 $(MH)^+$ | 22 |

TABLE 4b-continued

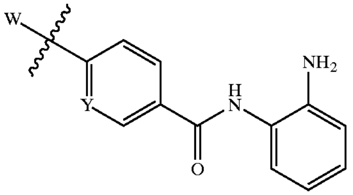

| Ex. | Cpd | W | Y | Z | Name | Characterization | Schm |
|---|---|---|---|---|---|---|---|
| 131 | 196 | 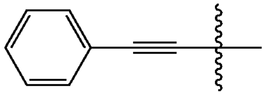 | CH | CH | N-(2-Amino-phenyl)-4-phenylethynyl-benzamide | LRMS calc: 312.37, found: 313.2 $(MH)^+$ | 22 |
| 180 | 320 | 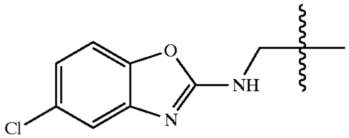 | CH | CH | N-(2-Amino-phenyl)-4-[(5-chloro-benzooxazol-2-ylamino)-methyl]-benzamide | $^1$H NMR: (Acetone-$d_6$) δ (ppm): 9.67 (s, 1H), 8.85 (s, 1H), 8.01 (d, J=8.2Hz, 2H), 7.55 (d, J=8.2Hz, 2H), 7.45 (d, J=8.8Hz, 1H), 7.36 (d, J=2.3Hz, 1H), 7.22 (d, J=7.6Hz, 1H), 7.07 (dd, J=8.8, 2.3Hz, 1H), 7.02 (d, J=7.0Hz, 1H), 6.84 (d, J=7.6Hz, 1H), 6.65 (t, 7.0Hz, 1H), 4.94 (s, 2H), 4.67 (d, J=5.3Hz, 2H). | 35 |
| 181 | 321 | 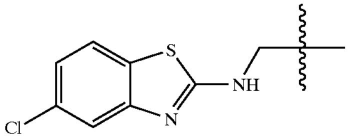 | CH | CH | N-(2-Amino-phenyl)-4-{[4-(4-chloro-phenyl)-thiazol-2-ylamino]-methyl}-benzamide | $^1$H NMR: (DMSO-$d_6$) δ (ppm): 9.67 (bs, 1H), 8.36 (t, J=5.8Hz, 1H), 8.00 (d, J=8.2Hz, 2H), 7.89 (d, J=8.2Hz, 2H), 7.57 (d, J=8.2Hz, 2H), 7.48 (d, J=8.2Hz, 2H), 7.20 (s, 1H), 7.02 (t, J=8.5Hz, 1H), 6.83 (d, J=7.7Hz, 1H), 6.65 (t, J=7.1Hz, 1H), 4.92 (bs, 2H), 4.65 (d, J=5.8Hz, 2H). | 35 |
| 182 | 322 | 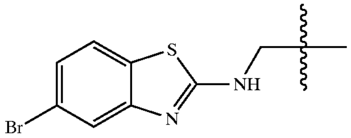 | CH | CH | N-(2-Amino-phenyl)-4-[(5-bromo-benzothiazol-2-ylamino)-methyl]-benzamide | $^1$H NMR: (DMSO-$d_6$) δ (ppm): 6.97 (s, 1H), 8.78 (bs, 1H), 8.01 (d, J=8.8Hz, 2H), 8.00 (s, 1H), 7.55 (d, J=8.2Hz, 2H), 7.43–7.35 (m, 2H), 7.22 (d, J=7.6Hz, 1H), 7.03 (t, J=7.0Hz, 1H), 6.83 (d, J=7.6Hz, 1H), 6.65 (t, J=7.6Hz, 1H). 4.94 (s, 2H), 7.74 (d, J=5.9Hz, 2H). | 33, 34 |
| 183 | 323 | 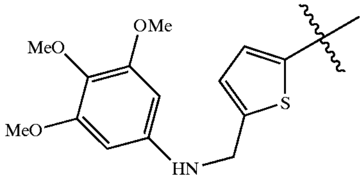 | CH | CH | N-(2-Amino-phenyl)-4-{5-[(3,4,5-trimethoxy-phenylamino)-methyl]-thiophen-2-ylmethyl}-benzamide | LRMS calc: 489.58, found: 490 $(MH)^+$ | 21 |

TABLE 4b-continued

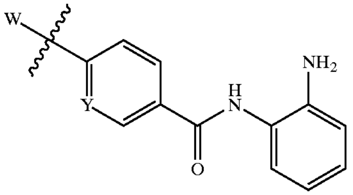

| Ex. | Cpd | W | Y | Z | Name | Characterization | Schm |
|---|---|---|---|---|---|---|---|
| 184 | 325 | 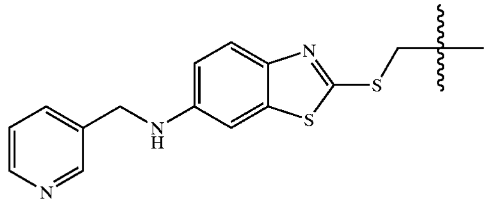 | CH | CH | N-(2-Amino-phenyl)-4-{6-[(pyridin-3-ylmethyl)-amino]-benzothiazol-2-ylsulfanylmethyl}-benzamide | $^{1}$H NMR: (Acetone-$d_6$) δ (ppm): 8.65 (d, J=1.4Hz, 1H), 8.44 (dd, J=4.7, 3.0Hz, 1H), 7.97 (d, J=8.2 Hz, 2H), 7.81–7.77 (m, 1H), 7.63 (m, 3H), 7.33–7.26 (m, 2H), 7.09 (d, J=2.5Hz, 1H), 7.02–6.97 (m, 1H), 6.91 (dd, J=8.8, 2.5Hz, 1H), 6.86 (dd, J=8.0, 1.4Hz, 1H), 6.69–6.64 (m, 1H), 4.64 (s, 2H), 4.47 (s, 2H). | 11 |
| 185 | 326 | 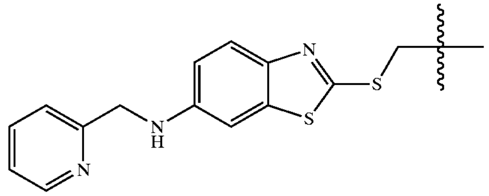 | CH | CH | N-(2-Amino-phenyl)-4-{6-[(pyridin-2-ylmethyl)-amino]-benzothiazol-2-ylsulfanylmethyl}-benzamide | $^{1}$H NMR: (DMSO-$d_6$) δ (ppm): 9.59 (s, 1H), 8.52–8.51 (m, 1H), 7.89 (d, J=8.24Hz, 2H), 7.71 (td, J=7.7, 1.9Hz, 1H), 7.59–7.53 (m, 3H), 7.34 (d, J=8.0Hz, 1H), 7.25–7.21 (m, 1H), 7.12 (d, J=6.9, Hz, 1H), 6.98–6.96 (m, 1H), 6.93 (d, J=7.4Hz, 1H), 6.81 (dd, J=9.1, 2.5 Hz, 1H), 6.76–6.73 (m, 1H), 6.67 (t, J=5.8Hz, 1H), 6.56 (t, J=7.4Hz, 1H), 4.87 (s, 1H), 4.58 (s, 2H), 4.38 (d, J=6.3Hz, 2H). | 11, 34 |
| 186 | 327 | 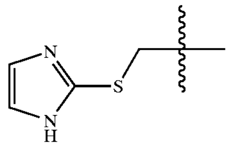 | CH | CH | N-(2-Amino-phenyl)-4-(1H-imidazol-2-ylsulfanylmethyl)-benzamide | $^{1}$H NMR: (DMSO-$d_6$) δ (ppm): 12.23 (bs, 1H), 9.59 (s, 1H), 7.86 (d, J=8.2Hz, 2H), 7.34 (d, J=8.5Hz, 2H), 7.14–7.12 (m, 2H), 6.94–6.92 (m, 2H), 6.76 (d, J=6.6Hz, 1H), 6.57 (t, J=7.4Hz, 1H), 4.87 (s, 2H), 4.29 (s, 2H). | 14 |
| 187 | 328 | 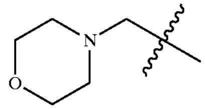 | CH | CH | N-(2-Amino-phenyl)-4-morpholin-4-ylmethyl-benzamide | $^{1}$H NMR: ($CD_3OD$) δ (ppm): 8.03 (d, J=8.4Hz, 2H), 7.58 (d, J=7.9Hz, 2H), 7.26 (d, J=7.0Hz, 1H), 7.16 (t, J=6.6Hz, 1H), 6.98 (d, J=7.0Hz, 1H), 6.85 (t, J=7.5Hz, 1H), 3.78 (t, J=4.4Hz, 4H), 3.68 (s, 2H), 2.57–2.54 (m, 4H). | 37 |

TABLE 4b-continued

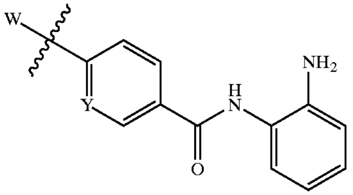

| Ex. | Cpd | W | Y | Z | Name | Characterization | Schm |
|---|---|---|---|---|---|---|---|
| 188 | 329 | 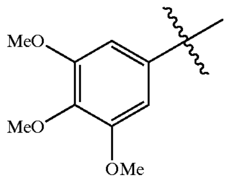 | CH | CH | 3',4',5'-Trimethoxy-biphenyl4-carboxylic acid (2-amino-phenyl)-amide | $^1$H NMR: ($CD_3OD$) δ (ppm): 8.14 (d, J=7.9Hz, 2H), 7.85 (d, J=8.4Hz, 2H), 7.29 (d, J=7.9Hz, 2H), 7.17 (t J=7.0Hz, 1H), 7.04 (s, 2H), 7.00 (d, J=8.4Hz, 1H), 6.87 (t, J=7.5Hz, 1H), 4.95 (s, 6H), 4.01 (s, 3H). | 37 |
| 189 | 330 | 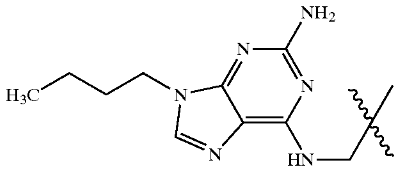 | CH | CH | 4-[(2-Amino-9-butyl-9H-purin-6-ylamino)-methyl]-N-(2-amino-phenyl)-benzamide | $^1$H NMR: (DMSO-$d_6$) δ (ppm): 9.65 (s, 1H), 7.96 (d, J=7.7Hz, 2H), 7.95 (bs, 2H) 7.78 (s, 1H), 7.52 (d, J=7.9Hz, 2H), 7.22 (d, J=7.7Hz, 1H), 7.02 (dd, J=7.3, 8.0Hz, 1H), 6.8 (d, J=8.0Hz, 1H), 6.65 (dd, J=7.3, 7.7Hz, 1H), 5.91 (s, 2H), 4.94 (bs, 2H), 4.77 (bs, 2H), 4.01 (t, J=7.1Hz, 1H), 1.78 (m, 2H), 1.3 (m, 2H), 0.95 (t, J=7.4,Hz, 1H) | 39 |
| 190 | 331 | 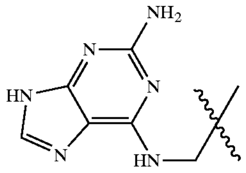 | CH | CH | N-(2-Amino-phenyl)-4-[(2-amino-9H-purin-6-ylamino)-methyl]-benzamide | $^1$H NMR (DMSO-$d_6$) δ (ppm): 10.16 (s, 1H), 9.60 (br, 1H), 8.24 (s, 1H), 8.08 (d, J=8.0Hz, 2H), 7.62 (m, 1H), 7.60 (d, J=8.0Hz, 2H), 7.40 (m, 1H), 7.20 (m, 2H), 7.08 (m, 1H), 4.90 (m, 2H), 4.6 (br, 4H) | 39 |
| 191 | 332 | 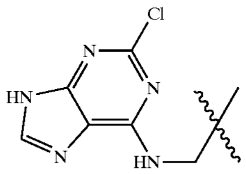 | CH | CH | N-(2-Amino-phenyl)-4-[(2-chloro-9H-purin-6-ylamino)-methyl]-benzamide | $^1$H NMR (DMSO-$d_6$) δ (ppm): 9.67 (m, 1H), 8.80 (m, 1H), 8.24 (s, 1H), 7.99 (d, J=7.8Hz, 2H), 7.52 (d, J=7.8Hz, 2H), 7.21 (d, J=7.8Hz, 1H), 7,02 (dd, J=6.3, 7.8Hz, 1H), 6.82 (d, J=8.1Hz, 1H), 6.70 (d6, J=6.3, 8.1Hz, 1H), 4.94 (br, 2H), 4.77 (br, 2H) | 39 |

TABLE 4b-continued

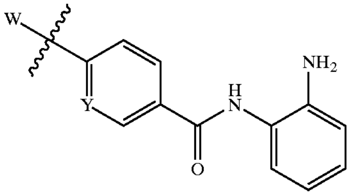

| Ex. | Cpd | W | Y | Z | Name | Characterization | Schm |
|---|---|---|---|---|---|---|---|
| 192 | 333 | 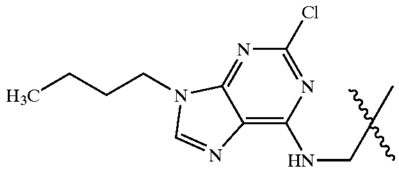 | CH | CH | N-(2-Amino-phenyl)-4-[(9-butyl-2-chloro-9H-purin-6-ylamino)-methyl]-benzamide | $^1H$ NMR (DMSO-$d_6$) δ (ppm): 9.60 (s, 1H), 8.72 (br, 1H), 8.21 (s, 1H), 7.92 (d, J = 8.0Hz, 2H), 7.45 (d, J=8.0Hz, 2H), 7.15 (d, J=8.0Hz, 1H), 6.96 (dd, J=6.7, 8.0Hz, 1H), 6.77 (d, J=8.0Hz, 1H), 6.85 (dd, J=6.7, 8.0Hz, 2H), 4.88 (s, 1H), 4.71 (m, 2H), 4.11 (m, 2H), 1.76 (m, 2H), 1.25 (m, 2H), 0.89 (t, J=7.1Hz, 3H) | 39 |
| 193 | 334 | 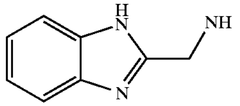 | CH | CH | N-(2-Amino-phenyl)-4-[(1H-benzoimidazol-2-ylmethyl)-amino]-benzamide | $^1H$ NMR: (DMSO-$d_6$) δ (ppm): 12.39 (bs, 1H), 9.32 (s, 1H), 7.81 (d, J=8.2Hz, 2H), 7.56 (bs, 1H), 7.21–7.17 (m, 3H), 6.99–6.97 (m, 2H), 6.81 (d, J=8.2Hz, 1H), 6.77 (d, J=8.8Hz, 2H), 6.63 (t, J=7.0Hz, 1H), 4.85 (s, 2H), 4.62 (d, J=5.3Hz, 2H). | 11 |
| 194 | 335 | 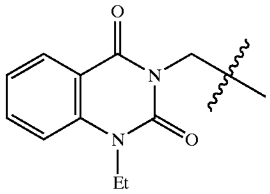 | CH | CH | N-(2-Amino-phenyl)-4-(1-ethyl-2,4-dioxo-1,4-dihydro-2H-quinazolin-3-ylmethyl)-benzamide | $^1H$ NMR: ($CDCl_3$) δ (ppm): 8.23 (dd, J=7.8, 1.5Hz, 1H), 8.01 (bs, 1H), 7.80 (d, J=8.0Hz, 2H), 7.71–7.65 (m, 1H), 7.55 (d, J=8.2Hz, 2H), 7.27–7.20 (m, 3H), 7.05 (td, J=7.7, 1.5Hz, 1H), 6.81–6.77 (m, 2H), 5.29 (bs, 2H), 4.18 (q, J=7.3Hz, 2H), 3.86 (bs, 2H), 1.33 (t, J=7.1Hz, 3H). MS: (calc.) 414.2; (obt.) 415.3 $(MH)^+$ | 19 |
| 195 | 336 | 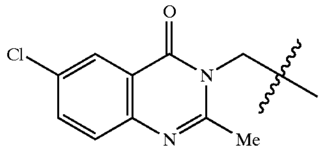 | CH | CH | N-(2-Amino-phenyl)-4-(6-chloro-2-methyl-4-oxo-4H-quinazolin-3-ylmethyl)-benzamide | $^1H$ NMR: (DMSO) δ (ppm): 9.69 (bs, 1H, NH), 8.71 (s, 1H), 8.16 (d, J=2.5Hz, 1H), 8.01 (d, J=8.2Hz, 2H), 7.95 (dd, J=8.8, 2.5Hz, 1H), 7.81 (d, J=8.8Hz, 1H), 7.74 (d, J=8.2Hz, 2H), 7.20 (d, J=7.1Hz, 1H), 7.02 (td, J=7.6, 1.5Hz, 1H), 6.82 (dd, J=8.0, 1.4Hz, 1H), 6.64 (td, J=7.6, 1.4Hz, 1H), 5.34 (s, 2H), 4.94 (bs, 2H). MS: (calc.) 404.1; (obt.) 405.0 $(MH)^+$ | 19 |

TABLE 4b-continued

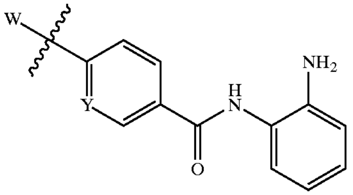

| Ex. | Cpd | W | Y | Z | Name | Characterization | Schm |
|---|---|---|---|---|---|---|---|
| 196 | 337 | 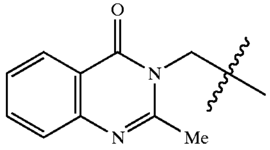 | CH | CH | N-(2-Amino-phenyl)-4-(2-methyl4-oxo-4H-quinazolin-3-ylmethyl)-benzamide | $^1$H NMR: (DMSO) δ (ppm): 9.64 (bs, 1H), 8.17 (dd, J=8.0, 1.6Hz, 1H), 7.95 (d, J=8.2Hz, 2H), 7.95 (dd, J=8.8, 2.5Hz, 1H), 7.84 (ddd, J=7.6, 7.0, 1.5Hz, 1H), 7.64 (d, J=7.7Hz, 1H), 7.53 (ddd, J=7.6, 7.6, 1.1Hz, 1H), 7.33 (d, J=8.2Hz, 2H), 7.14 (dd, J=7.7, 1.1Hz, 1H), 6.96 (ddd, J=7.6, 7.6, 1.5Hz, 1H), 6.77 (dd, J=8.0, 1.4Hz, 1H), 6.58 (ddd, J=7.6, 7.6, 1.3Hz, 1H), 5.46 (s, 2H), 4.89 (bs, 2H) 2.5 (s, 3H). MS: (calc.) 384.2; (obt.) 385.0 (MH)$^+$ | 19 |
| 197 | 338 | 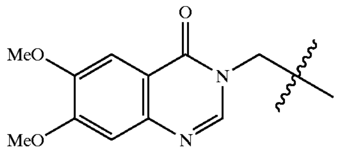 | CH | CH | N-(2-Amino-phenyl)-4-(6,7-dimethoxy-4-oxo-4H-quinazolin-3-ylmethyl)-benzamide | $^1$H NMR: (DMSO) δ (ppm): 9.62 (bs, 1H), 8.50 (s, 1H), 8.41 (d, J=8.2Hz, 2H), 7.47 (s, 1H), 7.46 (d, J=7.7Hz, 2H), 7.17 (s, 1H), 7.15 (d, J=8.5Hz, 1H), 6.96 (ddd, J=7.7, 7.7, 1.1Hz, 1H), 6.76 (d, J=6.9Hz, 1H), 6.58 (dd, J=6.9, 6.9Hz, 1H), 5.26 (s, 2H), 4.88 (bs, 2H), 3.91 (s, 3H), 3.87 (s, 3H). MS: (calc.) 430.2; (obt.) 431.1 (MH)$^+$ | 19 |
| 198 | 339 | 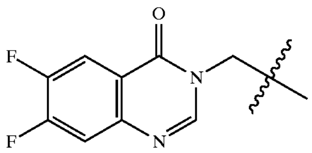 | CH | CH | N-(2-Amino-phenyl)-4-(6,7-difluoro-4-oxo-4H-quinazolin-3-ylmethyl)-benzamide | $^1$H NMR: (DMSO) δ (ppm): 9.66 (bs, 1H), 8.69 (s, 1H), 8.07 (dd, J=8.8, 10.4Hz, 1H), 7.96 (d, J=8.2Hz, 2H), 7.82 (dd, J=14.3, 11.3Hz, 1H), 7.48 (d, J=8.2Hz, 2H), 7.15 (d, J=6.9Hz, 1H), 6.96 (ddd, J=7.6, 7.6, 1.5Hz, 1H), 6.76 (dd, J=8.1, 1.2Hz, 1), 6.58 (ddd, J=7.5, 7.5, 1.2Hz, 1H), 5.28 (s, 2H), 4.89 (bs, 2H), MS: (calc.) 406.1; (obt.) 407.0 (MH)$^+$ | 19 |
| 199 | 340 | 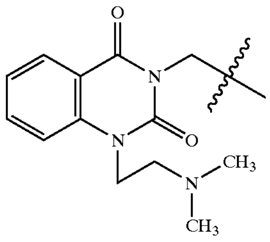 | CH | CH | N-(2-Amino-phenyl)-4-[1-(2-dimethylamino-ethyl)-2,4-dioxo-1,4-dihydro-2H-quinazolin-3-ylmethyl]-benzamide | $^1$H NMR: (DMSO) δ (ppm): 9.61 (bs, 1H), 8.09 (dd, J=7.8, 1.5Hz, 1H), 7.91 (d, J=8.2Hz, 2H), 7.81 (ddd, J=7.8, 7.8, 1.6Hz, 1H), 7.52 (d, J=8.2Hz, 1H), 7.42 (d, J=8.2Hz, 2H), 7.32 (dd, J=7.6, 7.6Hz, 1H), 7.14 (d, J=6.9Hz, 1H), 6.96 (ddd, J=7.6, 7.6, 1.5Hz, 1H), 6.77 (dd, J=7.8, 1.2Hz, 1H), 6.59 (ddd, J=7.5, 7.5, 1.2Hz, 1H), 5.22 (s, 2H), 4.88 (bs, 2H), 4.24 (t, J=7.1Hz, 2H), 2.5 (m, 2H) 2.22 (s, 6H). MS: (calc.) 457.2; (obt.) 458.1 (MH)$^+$ | 19 |

TABLE 4b-continued

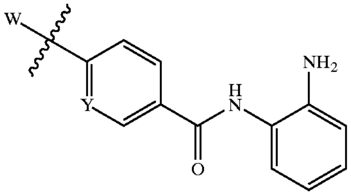

| Ex. | Cpd | W | Y | Z | Name | Characterization | Schm |
|---|---|---|---|---|---|---|---|
| 200 | 341 | 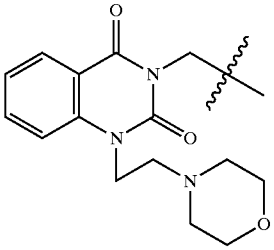 | CH | CH | N-(2-Amino-phenyl)-4-[1-(2-morpholin-4-yl-ethyl)-2,4-dioxo-1,4-dihydro-2H-quinazolin-3-ylmethyl]-benzamide | $^1$H NMR: (DMSO) δ (ppm): 9.61 (bs, 1H), 8.09 (dd, J=8.0, 1.6Hz, 1H), 7.92 (d, J=8.2Hz, 2H), 7.81 (ddd, J=7.8, 7.8, 1.6Hz, 1H), 7.54 (d, J=8.5Hz, 1H), 7.43 (d, J=8.2Hz, 2H), 7.32 (dd, J=7.4, 7.4Hz, 1H), 7.14 (d, J=7.4Hz, 1H), 6.96 (ddd, J=7.6, 7.6, 1.5Hz, 1H), 6.77 (dd, J=8.0, 1.4Hz, 1H), 6.59 (ddd, J=7.6, 7.6, 1.4Hz, 1H), 5.22 (s, 2H), 4.87 (bs, 2H), 4.28 (t, J=6.7Hz, 2H), 3.50 (t, J=4.5Hz, 4H), 2.58 (t, J=6.7Hz, 2H), 2.47–2.44 (m, 4H). MS: (calc.) 499.2; (obt.) 500.3 $(MH)^{+\cdot}$ | 19 |
| 201 | 342 | 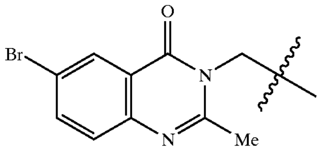 | CH | CH | N-(2-Amino-phenyl)-4-(6-bromo-2-methyl-4-oxo-4H-quinazolin-3-ylmethyl)-benzamide | $^1$H NMR: (DMSO) δ (ppm): 9.65 (bs, 1H), 8.25 (d, J=2.5Hz, 1H), 7.99 (ddd, J=8.5, 2.5, 0.8Hz, 1H), 7.95 (d, J=8.8Hz, 2H), 7.60 (d, J=8.8Hz, 1H), 7.34 (d, J=8.2Hz, 2H), 7.14 (d, J=7.4Hz, 1H), 6.96 (dd, J=7.4, 7.4Hz, 1H), 6.76 (d, J=8.0Hz, 1H), 6.59 (dd, J=7.4, 7.4Hz, 1H), 5.45 (s, 2H), 4.88 (bs, 2H). MS: (calc.) 462.1; (obt.) 463.1 $(MH)^{+\cdot}$ | 19 |
| 202 | 343 | 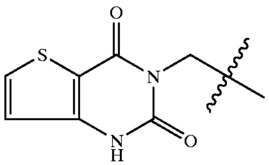 | CH | CH | N-(2-Amino-phenyl)-4-(2,4-dioxo-1,4-dihydro-2H-thieno[3,2-d]pyrimidin-3-ylmethyl)-benzamide | $^1$H NMR: (DMSO) δ (ppm): 9.61 (bs, 1H), 8.10 (dd, J=5.2, 0.5Hz, 1H), 7.91 (d, J=8.2Hz, 2H), 7.40 (d, J=8.2Hz, 2H), 7.15 (d, J=7.1Hz, 1H), 6.98–6.94 (m, 2H), 6.77 (dd, J=8.0, 1.1Hz, 1H), 6.58 (dd, J=7.1, 7.1Hz, 1H), 5.12 (s, 2H), 4.88 (bs, 2H). MS: (calc.) 392.1; (obt.) 393.0 $(MH)^{+\cdot}$ | 43 |
| 203 | 344 | 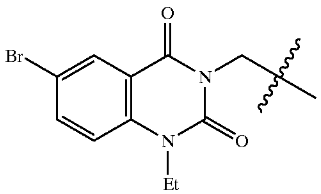 | CH | CH | N-(2-Amino-phenyl)-4-(6-bromo-1-ethyl-2,4-dioxo-1,4-dihydro-2H-quinazolin-3-ylmethyl)-benzamide | $^1$H NMR: (DMSO) δ (ppm): 9.61 (bs, 1H), 8.15 (d, J=2.5Hz, 1H), 7.95 (dd, J=9.1, 4.9Hz, 1H), 7.91 (d, J=8.2Hz, 2H), 7.53 (d, J=9.3Hz, 1H), 7.42 (d, J=8.2Hz, 2H), 7.15 (d, J=6.9Hz, 1H), 6.96 (ddd, J=7.6, 7.6, 1.5Hz, 1H), 6.77 (dd, J=8.1, 1.5Hz, 1H), 6.59 (ddd, J=7.6, 7.6, 1.4Hz, 1H), 5.20 (s, 2H), 4.88 (bs, 2H) 4.14 (q, J=7.0, 2H), 1.21 (t, J=7.0, 3H). MS: (calc.) 492.1; (obt.) 493.0 $(MH)^{+\cdot}$ | 19 |

TABLE 4b-continued

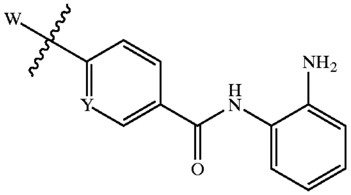

| Ex. | Cpd | W | Y | Z | Name | Characterization | Schm |
|---|---|---|---|---|---|---|---|
| 204 | 345 | 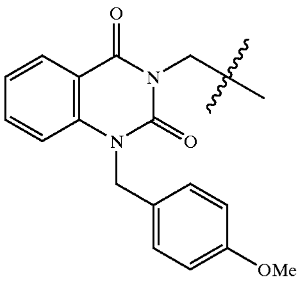 | CH | CH | N-(2-Amino-phenyl)-4-[1-(4-methoxy-benzyl)-2,4-dioxo-1,4-dihydro-2H-quinazolin-3-ylmethyl]-benzamide | $^1$H NMR: (DMSO) δ (ppm): 9.62 (bs, 1H), 8.10 (dd, J=7.7, 1.6Hz, 1H), 7.93 (d, J=8.2Hz, 2H), 7.71 (ddd, J=7.9, 7.9, 1.5Hz, 1H), 7.46 (d, J=8.2Hz, 2H), 7.38 (d, J=8.2Hz, 2H), 7.31 (d, J=7.4Hz, 1H), 7.26 (d, J=8.8Hz, 2H), 7.15 (d, J=6.6Hz, 1H), 6.96 (ddd, J=7.6, 7.6, 1.2Hz, 1H), 6.89 (d, J=8.8Hz, 2H), 6.77 (dd, J=8.0, 1.4Hz, 1H), 6.59 (ddd, J=7.5, 7.5, 1.2Hz, 1H), 5.33 (s, 2H), 5.28 (s, 2H), 4.89 (bs, 2H), 3.71 (s, 3H). MS: (calc.) 506.2; (obt.) 507.1 $(MH)^{+\cdot}$ | 19 |
| 205 | 346 | 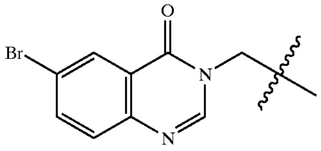 | CH | CH | N-(2-Amino-phenyl)-4-(6-bromo-4-oxo-4H-quinazolin-3-ylmethyl)-benzamide | $^1$H NMR: (DMSO) δ (ppm): 9.61 (bs, 1H), 8.66 (s, 1H), 8.24 (d, J=2.5Hz, 1H), 8.00 (dd, J=8.7, 2.3Hz, 1H), 7.95 (d, J=8.2Hz, 2H), 7.68 (d, J=8.8Hz, 1H), 7.48 (d, J=8.2Hz, 2H), 7.15 (d, J=8.0Hz, 1H), 7.96 (ddd, J=7.6, 7.6, 1.5Hz, 1H), 6.77 (dd, J=8.0, 1.1Hz, 1H), 6.59 (dd, J=7.4, 7.4Hz, 1H), 5.28 (s, 2H), 4.87 (bs, 2H). MS: (calc.) 448.0; (obt.) 449.0 $(MH)^{+\cdot}$ | 19 |
| 206 | 347 | 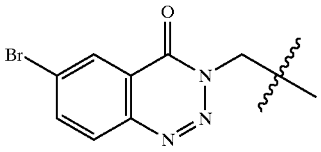 | CH | CH | N-(2-Amino-phenyl)-4-(6-bromo-4-oxo-4H-benzo[d][1,2,3]triazin-3-ylmethyl-benzamide | $^1$H NMR: (DMSO) δ (ppm): 9.63 (bs, 1H), 8.38 (d, J=1.9Hz, 1H), 8.28 (dd, J=8.8, 2.2Hz, 1H), 8.19 (d, J=8.8Hz, 1H), 7.95 (d, J=8.0Hz, 2H), 7.50 (d, J=8.2Hz, 2H), 7.15 (d, J=6.9Hz, 1H), 7.96 (ddd, J=7.6, 7.6, 1.5Hz, 1H), 6.77 (dd, J=8.0, 1.4Hz, 1H), 6.59 (ddd, J=7.6, 7.6, 1.4Hz, 1H), 5.67 (s, 2H), 4.87 (bs, 2H). MS: (calc.) 449.0; (obt.) 450.0 $(MH)^{+\cdot}$ | 19 |
| 207 | 348 | 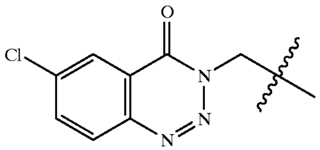 | CH | CH | N-(2-Amino-phenyl)-4-(6-chloro-4-oxo-benzo[d][1,2,3]triazin-3-ylmethyl)-benzamide | $^1$H NMR: (DMSO) δ (ppm): 9.63 (bs, 1H), 8.30–8.24 (m, 2H), 8.15 (ddd, J=8.6, 2.5, 0.8Hz, 1H), 7.95 (d, J=8.0Hz, 2H), 7.50 (d, J=8.2Hz, 2HH), 7.15 (d, J=8.0Hz, 1H), 7.96 (dd, J=7.4, 7.4Hz, 1H), 6.77 (d, J=8.0Hz, 1H), 6.59 (dd, J=7.4, 7.4Hz, 1H), 5.67 (s, 2H), 4.88 (bs, 2H). MS: (calc.) 405.1; (obt.) 406.0 $(MH)^+$ | 19 |

TABLE 4b-continued

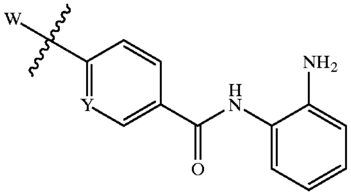

| Ex. | Cpd | W | Y | Z | Name | Characterization | Schm |
|---|---|---|---|---|---|---|---|
| 208 | 349 | 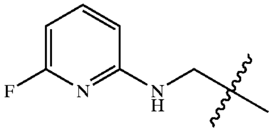 | CH | CH | N-(2-Amino-phenyl)-4-[(3-fluoro-2-pyridinyl-amino)-methyl]-benzamide | $^1$H NMR (acetone-$d_6$) δ (ppm): 9.07 (bs, 1H), 8.02 (d, J=8.2Hz, 2H), 7.64–7.44 (m, 3H), 7.33 (dd, J=7.8, 1.5Hz, 1H), 7.03 (td, J=7.6, 1.5Hz, 1H), 6.90 (dd, J=8.0, 1.4Hz, 1H), 6.78 (bs, 1H), 6.71 (td, J=7.6 1.4Hz, 1H), 6.48 (dd, J=8.1, 2.6Hz, 1H), 6.16 (dd, J=7.7, 2.5Hz, 1H), 4.76–4.55 (m, 4H). HRMS (calc.): 336.1386, (found): 336.1389. | 11 |
| 209 | 350 | 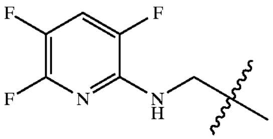 | CH | CH | N-(2-Amino-phenyl)-4-4(3,4,5-trifluoro-2-pyridinyl-amino)-methyl]-benzamide | $^1$H NMR (acetone-$d_6$) δ (ppm): 9.06 (bs, 1H), AB system ($\delta_A$ = 8.02, $\delta_B$ = 7.56, J=8.3Hz, 4H), 7.74–7.65 (m, 1H), 7.33 (d, J=8.0, 1H), 7.03 (td, J=7.6, 15Hz, 1H), 6.96–6.83 (m, 2H), 6.71 (td, J=7.6, 1.4Hz, 1H), 4.74 (d, J=6.3Hz, 2H), 4.65 (bs, 2H). | 11 |
| 210 | 351 | 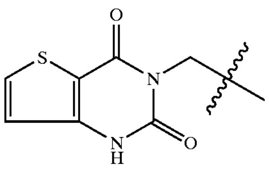 | CH | CH | N-(2-Amino-phenyl)-4-(2,4-dioxo-1,4-dihydro-2H-thieno[3,2-d]pyrimidin-3-ylmethyl)-benzamide | $^1$H NMR: (DMSO) δ (ppm): 9.61 (bs, 1H), 8.10 (dd, J=5.2, 0.5Hz, 1H), 7.91 (d, J=8.2Hz, 2H), 7.40 (d, J=8.2Hz, 2H), 7.15 (d, J=7.1Hz, 1H), 6.98–6.94 (m, 2H), 6.77 (dd, J=8.0, 1.1Hz, 1H), 6.58 (dd, J=7.1, 7.1Hz, 1H), 5.12 (s, 2H), 4.88 (bs, 2H). MS: (calc.) 392.1; (obt.) 393.0 $(MH)^{+\cdot}$ | 43 |
| 211 | 352 | 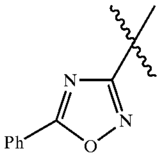 | CH | CH | N-(2-Amino-phenyl)-4-(5-phenyl-[1,2,4]oxadiazol-3-yl)-benzamide | $^1$H NMR: (DMSO) δ (ppm): 9.85 (bs, 1H), 8.24–8.19 (m, 6H), 7.79–7.66 (m, 3H), 7.20 (d, J=7.5Hz, 1H), 7.00 (dd, J=7.3, 7.3Hz, 1H), 6.80 (d, J=7.9Hz, 1H), 6.61 (dd, J=7.3, 7.3Hz, 1H), 4.96 (bs, 2H). MS: (calc.) 356.1; (obt.) 357.0 $(MH)^{+\cdot}$ | 50 |
| 212 | 353 | 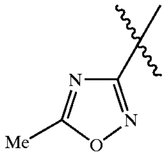 | CH | CH | N-(2-Amino-phenyl)-4-(5-methyl-[1,2,4]oxadiazol-3-yl)-benzamide | $^1$H NMR: (DMSO) δ (ppm): 9.81 (bs, 1H), 8.17–8.11 (m, 4H), 7.18 (d, J=7.9Hz, 1H), 6.99 (dd, J=7.7, 7.7Hz, 1H), 6.79 (d, J=7.9Hz, 1H), 6.61 (dd, J=7.5, 7.5Hz, 1H), 4.94 (bs, 2H), 2.70 (s, 3H). MS: (calc.) 294.1; (obt.) 295.0 $(MH)^{+\cdot}$ | 50 |

TABLE 4b-continued

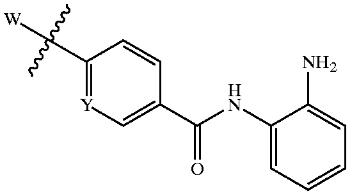

| Ex. | Cpd | W | Y | Z | Name | Characterization | Schm |
|---|---|---|---|---|---|---|---|
| 213 | 354 | 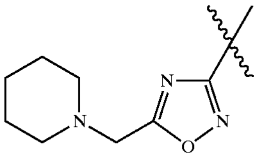 | CH | CH | N-(2-Amino-phenyl)-4-(5-piperidin-1-ylmethyl-[1,2,4]oxadiazol-3-yl)-benzamide | $^1$H NMR: (acetone) δ (ppm): 9.29 (bs, 1H), 8.21 (m, 4H), 7.31(d, J=8.0Hz, 1H), 7.03(dd, J=7.0, 7.0Hz, 1H), 6.88 (d, J=7.3Hz, 1H), 6.69 (dd, J=7.3, 7.3Hz, 1H), 4.68 (bs, 2H), 3.94 (s, 2H), 2.58 (t, J=5.1Hz), 1.63–1.55 (m, 4H), 1.47–1.43 (m, 2H). MS (Calc) 377.2; (Obt.) 378.3 (MH) + | 50 |
| 214 | 355 | 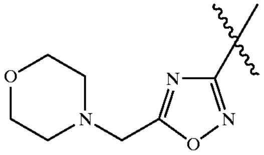 | CH | CH | N-(2-Amino-phenyl)-4-(5-morpholin-4-ylmethyl-[1,2,4]oxadiazol-3-yl)-benzamide | $^1$H NMR: (acetone) δ (ppm): 9.28 (bs, 1H), 8.21 (m, 4H), 7.31 (d, J=8.1Hz, 1H), 7.03 (dd, J=7.0, 7.0Hz, 1H), 6.88 (d, J=7.3Hz, 1H), 6.69 (dd, J=7.3, 7.3Hz, 1H), 4.67 (bs, 2H), 4.01 (s, 2H), 3.66 (t, J=4.8Hz), 2.65 (t, J=4.4Hz). MS: (Calc.) 379.2; (Obt.): 380.2 (MH)+ | 50 |
| 215 | 356 | 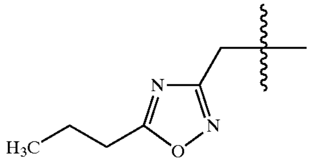 | CH | CH | N-(2-Amino-phenyl)-4-(5-propyl-[1,2,4]oxadiazol-3-ymethyl)-benzamide | $^1$H NMR. (DMSO) δ (ppm): 9.62 (s, 1H), 7.93 (d, J=7.9Hz, 2H), 7.42 (d, J=7.9Hz, 1H), 7.16 (d, J=7.5Hz, 1H), 6.97 (t, J=7.0Hz, 1H), 6.77 (d, J=7.9Hz, 1H), 6.59 (t, J=7.5Hz, 1H), 4.88 (s, 2H), 4.16(s, 2H), 2.87 (t, 7.0, 2H), 1.72 (q, J=7.5Hz, 2H), 0.92 (t, J=7.0Hz, 3H). $(MH)^+$: 337.2. | 50 |
| 216 | 357 | 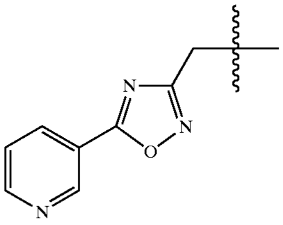 | CH | CH | N-(2-Amino-phenyl)-4-(5-pyridin-3-yl-[1,2,4]oxadiazol-3-ymethyl)-benzamide | $^1$H NMR: (DMSO) δ (ppm): 9.64 (s, 1H), 9.24 d, J=1.8Hz, 1H), 8.86 (dd, J=1.3Hz, J=4.8Hz, 1H), 8.45 (dd, J=1.8Hz, J=6.2Hz, 1H), 7.96.(d, J=7.9Hz, 2H), 7.66 (dd, J=4.8Hz, J=7.9Hz, 1H), 7.50 (d, J=8.4Hz, 2H), 7.16 (d, J=7.5Hz, 1H), 6.96 (t, J=7.0Hz, 1H), 6.77 (d, J=7.5Hz, 1H), 6.59 (t, J=7.5Hz, 1H), 4.89 (s, 2H), 4.31 (s, 2H). $(MH)^+$. 372.3. | 50 |

TABLE 4b-continued

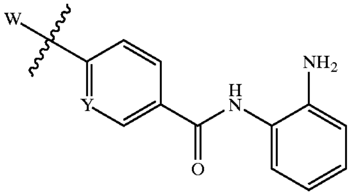

| Ex. | Cpd | W | Y | Z | Name | Characterization | Schm |
|---|---|---|---|---|---|---|---|
| 217 | 358 | 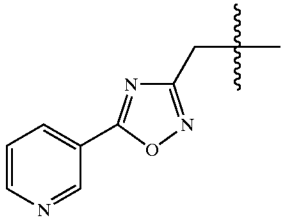 | CH | CH | N-(2-Amino-phenyl)-4-(5-pyridin-4-yl-[1,2,4]oxadiazol-3-ymethyl)-benzamide | $^{1}$H NMR: (DMSO) δ (ppm): 9.63 (s, 1H), 8.87 (d, J=6.2Hz, 2H); 7.95–8.02 (m, 3H), 7.50 (d, J=7.9Hz, 2H), 7.16 (d, J=7.5Hz, 2H), 6.97 (t, J=7.0Hz, 1H), 6.77 (d, J=7.0Hz, 1H), 6.59 (t, J=7.9Hz, 1H), 4.89 (s, 2H), 4.33 (s, 2H), $(MH)^+$: 372.3. | 50 |
| 218 | 359 | 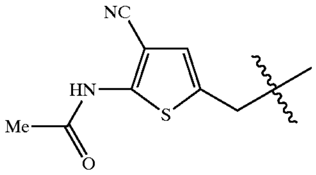 | CH | CH | 4-(5-Acetylamino-4-cyano-thiophen-2-ylmethyl)-N-(2-amino-phenyl)-benzamide | 1H NMR (DMSO) δ (ppm): 11.62 (s, 1H), 9.60 (bs, 1H), 7.93 (d, J=8.1Hz, 2H), 7.39 (d, J=8.1Hz, 2H), 6.97 (d, J=7.3Hz, 1H), 7.15 (d, J=7.3Hz, 1H), 6.98–6.94 (m, 2H), 6.77 (d, J=7.3Hz, 1H), 6.591 (dd, J=7.7, 7.7Hz, 1H), 4.89 (bs, 2H), 4.13 (s, 2H), 2.17 (s, 3H). LRMS: 390.1 (calc) 391.2 (found). | 49 |
| 219 | 360 | 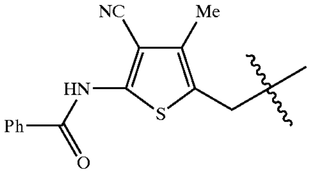 | CH | CH | 4-(5-Benzoylamino-4-cyano-3-methyl-thiophen-2-ylmethyl)-N-(2-amino-phenyl)-benzamide | 1H NMR (DMSO) δ (ppm): 11.77 (s, 1H) 9.61 (s, 1H); 7.93 (d, J=7.0Hz, 4H), 7.52–7.63 (m, 3H), 7.38 (d, J=7.6Hz, 2H), 7.16 (d, J=7.6Hz, 1H), 6.96 (t, J=7.6Hz, 1H), 6.77 (d, J=7.6Hz, 1H), 6.59 (t, J=7.6Hz, 1H), 4.89 (s, 2H), 4.15 (s, 2H), 2.24 (s, 3H). $(MH)^+$: 467.0 | 49 |

TABLE 4b-continued

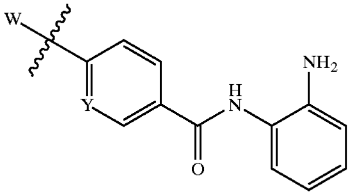

| Ex. | Cpd | W | Y | Z | Name | Characterization | Schm |
|---|---|---|---|---|---|---|---|
| 220 | 361 | 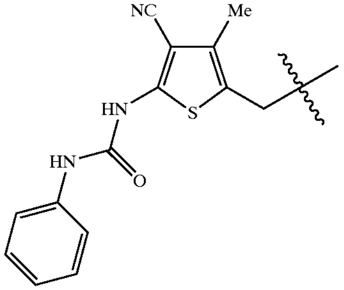 | CH | CH | N-(2-Amino-phenyl)-4-[4-cyano-3-methyl-5-(3-phenyl)-ureido)-thiophen-2-ylmethyl]-benzamide | 1H NMR (DMSO) δ (ppm): 10.12 (s, 1H), 9.61 (s, 1H), 9.21 (s, 1H); 7.93 (d, J=7.6Hz, 2H), 7.27–7.43 (m, 6H), 7.16 (d, J=7.6Hz, 1H), 6.93–7.05 (m, 2H) 6.77 (d, J=8.2Hz, 1H), 6.59 (t, J=7.6Hz, 1H), 4.88 (s, 2H), 4.08 (s, 2H), 2.19 (s, 3H). $(MH)^+$: 482.4 | 49 |
| 221 | 362 | 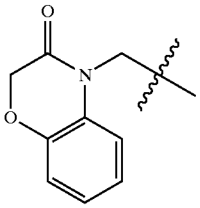 | CH | CH | N-(2-Amino-phenyl)-4-(3-oxo-2,3-dihydro-benzo[1,4]oxazin-4-ylmethyl)-benzamide | $^1$H NMR: (DMSO) δ (ppm): 9.60 (s, 1H), 7.92 (d, J=8.2Hz, 2H), 7.40 (d, J=8.0Hz, 2H), 7.13 (d, J=6.9Hz, 1H), 6.92–7.04 (m, 5H), 6.75 (dd, J=8.1Hz, 1.1Hz, 1H), 6.57 (td, J=7.4Hz, 1.4Hz, 1H), 5.24 (s, 2H), 4.88 (bs, 2H); 4.82 (s, 2H). $(MH)^+$: 374.1 | 11 |
| 222 | 363 | 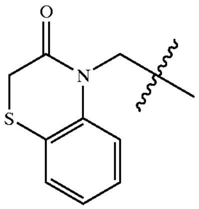 | CH | CH | N-(2-Amino-phenyl)-4-(3-oxo-2,3-dihydro-benzo[1,4]thiazin-4-ylmethyl)-benzamide | $^1$H NMR: (DMSO) δ (ppm): 9.58 (s, 1H), 7.90 (d, J=8.2Hz, 2H), 7.42 (dd, J=8.0Hz, J=1.4Hz, 1H), 7.32 (d, J=8.2Hz, 2H), 7.19–7.11 (m, 3H), 7.04–6.92 (m, 2H), 6.75 (dd, J=8.0Hz, 1.4Hz, 1H), 6.57 (td, J=8.0Hz, 1.6Hz, 1H), 5.31 (s, 2H); 4.88 (bs, 2H); 3.70 (s, 2H). $(MH)^+$: 390.1 | 11 |

TABLE 4b-continued

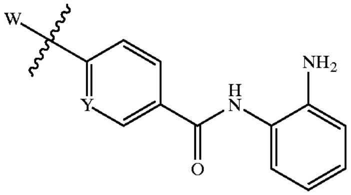

| Ex. | Cpd | W | Y | Z | Name | Characterization | Schm |
|---|---|---|---|---|---|---|---|
| 223 | 364 | 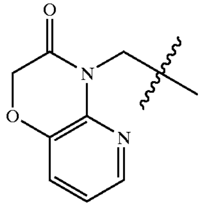 | CH | CH | N-(2-Amino-phenyl)-4-(3-oxo-2,3-dihydro-pyrido[3,2-b][1,4]oxazin-4-ylmethyl)-benzamide | $^1$H NMR: (DMSO) δ (ppm): 9.57 (bs, 1H), 7.98 (d, J=4.7Hz, 1H), 7.89 (d, J=8.2Hz, 2H), 7.45–7.40 (m, 3H), 7.15 (d, J=8.2Hz, 1H), 7.09–7.05 (m, 1H), 6.96 (dd, J=7.6, 7.6Hz, 1H), 6.76 (d, J=8.2Hz, 1H), 6.58 (dd, J=7.6, 7.6Hz, 1H), 5.31 (s, 2H), 4.90 (bs, 2H), 4.87 (s, 2H). $(MH)^+$: 375.1 | 11 |
| 224 | 365 | 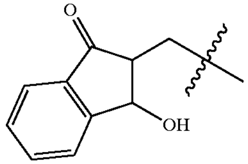 | CH | CH | N-(2-Amino-phenyl)-4-(1-hydroxy-3-oxo-indan-2-ylmethyl)-benzamide | $^1$H NMR: (DMSO) δ (ppm): 9.67 (s, 1H); 7.98 (d, J=8.2Hz, 2H), 7.73–7.84 (m, 3H), 7.53–7.62 (m, 3H), 7.24 (d, J=7.6Hz, 1H), 7.04 (t, J=7.6Hz, 1H), 6.85 (d, J=8.2Hz, 1H), 6.67 (t, J=7.6Hz, 1H), 5.68 (d, J=7.0Hz, 1H), 5.27 (t, J=6.4Hz, 1H), 4.95 (s, 2H), 3.21–3.30 (m, 1H), 3.11–3.13 (m, 2H). $(MH)^+$: 373.1 | 46 |
| 225 | 336 | 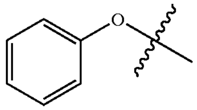 | CH | CH | N-(2-Amino-phenyl)-4-phenoxy-benzamide | $^1$H NMR: (DMSO) δ (ppm): 9.61 (s, 1H); 8.01 (d, J=8.8Hz, 2H), 7.45 (t, J=7.6Hz, 2H), 7.06–7.24 (m, 6H), 6.97 (t, J=7.6Hz, 1H), 6.78 (d, J=7.4Hz, 1H), 6.59 (t, J=7.6Hz, 1H), 4.88 (s, 2H). $(MH)^+$: 305.0 | 1 |
| 226 | 367 | 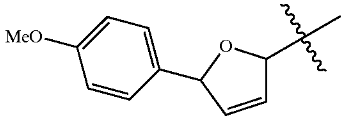 | CH | CH | N-(2-Amino-phenyl)-4-[5-(4-methoxy-phenyl)-2,5-dihydro-furan-2-yl]-benzamide | $^1$H NMR ($CDCl_3$) δ (ppm): 8.77 (s,1H), 7.93 (d, J=8.1Hz, 2H), 7.42 (d, J=8.4Hz, 2H), 7.38–6.98 (m, 6H), 6.91 (d, J=8.4Hz, 2H), 6.09–5.98 (m, 4H), 3.81 (s, 3H). | 52 |

TABLE 4b-continued

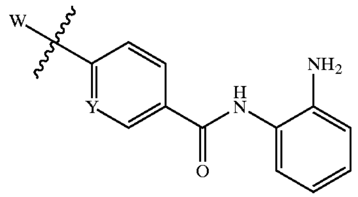

| Ex. | Cpd | W | Y | Z | Name | Characterization | Schm |
|---|---|---|---|---|---|---|---|
| 230 | 371 | 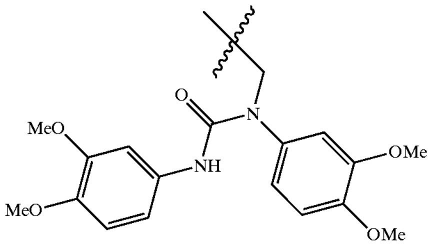 | CH | CH | N-(2-Amino-phenyl)-4-[1,3-bis-(3,4-dimethoxy-phenyl)-ureidom-ethyl]-benzamide | $^1$H NMR (DMSO-d$_6$): δ 10.08 (brs, 1H), 7.99 (d, J=7.9Hz, 2H), 7.70 (s, 1H), 7.49 (d, J=8.35Hz, 4H), 7.39–7.33 (m, 1H), 7.30–6.90 (m, 7H), 6.87 (dd, J=2.2, 8.35Hz, 1H), 6.78 (dd, J=2.2, 8.35Hz, 1H), 5.01 (s, 2H), 3.80 (s, 3H), 3.77 (s, 3H), 3.75 (s, 6H). | 57 |
| 231 | 372 | 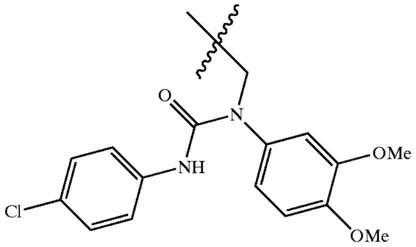 | CH | CH | N-(2-Amino-phenyl)-4-[3-(4-chloro-phenyl)-1-(3,4-dimethoxy-phenyl)-ureidomethyl]-benzamide | $^1$H NMR (CDCl$_3$): δ 8.02 (brs, 1H), 7.90 (d, J=7.9Hz, 2H), 7.46 (d, J=7.5Hz, 2H), 7.42–7.24 (m, 6H), 7.16 (t, J=7.5Hz, 1H), 6.91 (brd, J=5.71Hz, 3H), 6.75 (brd, J=8.3Hz, 1H), 6.70 (d, J=1.8Hz, 1H), 4.99 (s, 1H), 3.97 (s, 3H), 3.86 (s, 3H). | 57 |
| 232 | 373 | 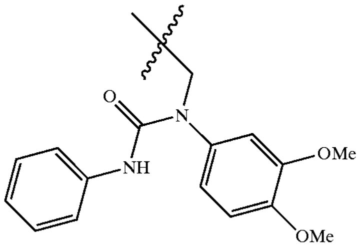 | CH | CH | N-(2-Amino-phenyl)-4-[1-(3,4-dimethoxy-phenyl)-3-phenyl-ureidomethyl]-benzamide | $^1$H NMR (DMSO-d$_6$): δ 10.10 (brs, 1H), 7.99 (d, J=7.9Hz, 2H), 7.88 (s, 1H), 7.80–7.72 (m, 1H), 7.50 (dd, J=7.0, 5.7Hz, 4H), 7.37 (d, J=7.9Hz, 1H), 7.30–6.94 (m, 7H), 6.78 (d, J=6.6Hz, 1H), 5.03 (s, 2H), 3.80 (s, 3H), 3.78 (s, 3H). | 57 |

TABLE 4b-continued

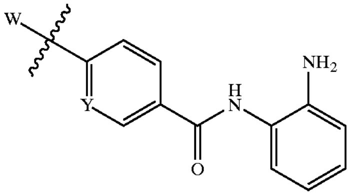

| Ex. | Cpd | W | Y | Z | Name | Characterization | Schm |
|---|---|---|---|---|---|---|---|
| 233 | 374 | 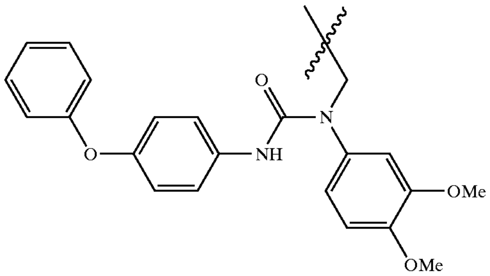 | CH | CH | N-(2-Amino-phenyl)-4-[1-(3,4-dimethoxy-phenyl)-3-(4-phenoxy-phenyl)-ureidomethyl]-benzamide | $^1$H NMR ($CDCl_3$): δ 8.02 (brs, 1H), 7.92 (d, J=7.9Hz, 2H), 7.49 (d, J=8.35Hz, 2H), 7.43–7.32 (m, 5H), 7.10–7.30 (2m, 5H), 7.19–7.10 (m, 2H), 7.01 (dd, J=8.35, 2.2Hz, 3H), 6.94 (d, J=7.5Hz, 1H), 6.92 (d, J=8.8Hz, 1H), 6.77 (dd, J=8.8, 2.2Hz, 1H), 6.72 (d, J=2.2Hz, 1H), 6.34 (s, 2H), 5.02 (s, 2H), 3.98 (s, 3H), 3.87 (s, 3H). | 57 |
| 234 | 375 | 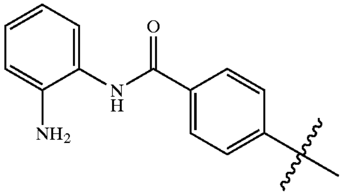 | CH | CH | Biphenyl-4,4'-dicarboxylic acid bis-[(2-amino-phenyl)-amide] | $^1$H NMR ($CD_3OD$) δ (ppm): 9.80 (bs, 2H), 8.16 (d, J=7.9Hz, 4H), 7.96 (d, J=7.9Hz, 4H), 7.23 (d, J=7.4Hz, 2H), 7.03 (dd, J=6.9, 7.4Hz, 2H), 6.84 (d, J=8.2Hz, 2H), 6.66 (dd, J=6.9, 7.7Hz, 2H), 5.06 (bs, 4H). | 15 |
| 236 | 377 | 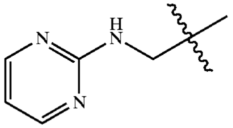 | CH | CH | N-(2-Amino-phenyl)-4-(pyrimidin-2-ylaminomethyl)-benzamide | $^1$H-NMR (DMSO-d6), δ (ppm): 9.6 (bs, 1H), 8.32 (d, J=4.9Hz, 2H) 7.97 (dt, J=7.9, 9.9Hz, 2H), 7.85–7.83 (m, 1H), 7.47, (d, J=8.2Hz, 2H), 7.20 (d, J=7.9Hz, 1H), 7.01 (dt, J=7.4, 7.7Hz, 1H), 6.82 (d, J=7.9Hz, 1H), 6.66–6.62 (m, 1H), 4.98 (bs, 2H), 4.61 (d, 2H). | 13 |
| 237 | 378 | 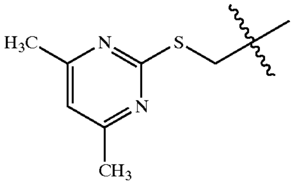 | CH | CH | N-(2-Amino-phenyl)-4-(4,6-dimethyl-pyrimidin-2-ylsulfanylmethyl)-benzamide | $^1$H-NMR (DMSO-d6), δ (ppm): 9.66 (bs, 1H), 7.96 (d, J=7.9Hz, 2H), 7.61 (d, J=7.9Hz, 2H), 7.21 (d, J=7.9Hz, 1H), 7.04–6.99 (m, 2H), 6.82 (d, J=7.9Hz, 1H), 6.64 (t, J=7.4Hz, 1H), 4.49 (s, 2H), 2.42 (s, 6H). | 11 |

TABLE 4b-continued

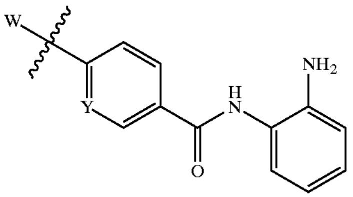

| Ex. | Cpd | W | Y | Z | Name | Characterization | Schm |
|---|---|---|---|---|---|---|---|
| 238 | 379 | 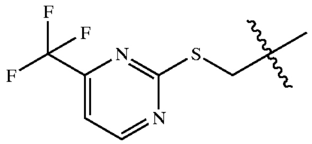 | CH | CH | N-(2-Amino-phenyl)-4-(4-trifluoromethyl-pyrimidin-2-ylsulfanylmethyl)-benzamide | $^1$H-NMR (DMSO-d6), δ (ppm): 9.66 (bs, 1H), 9.07 (d, J=5.2Hz, 1H), 7.97 (d, J=7.4Hz, 2H), 7.78 (d, J=4.7Hz, 1H), 7.63 (d, J=7.4Hz, 2H), 7.19 (d, J=7.7Hz, 1H), 7.01 (dt, J=7.4, 7.7Hz, 1H), 6.81 (d, J=8.2Hz, 1H), 6.64 (dt, J=7.1, 7.4Hz, 1H), 4.94 (bs, 2H), 4.57 (s, 2H). | 11 |
| 239 | 380 | 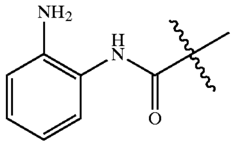 | N | CH | Pyridine-2,5-dicarboxylic acid bis-[(2-amino-phenyl)-amide] | $^1$H-NMR (DMSO-d6), δ (ppm): 10.23 (bs, 1H), 10.04 (bs, 1H), 9.30 (s, 1H), 8.62 (dd, J=1.8, 8.0Hz, 1H), 8.30 (d, J=8.1Hz, 1H), 7.55 (d, J=7.4Hz, 1H), 7.24 (d J=7.4Hz, 1H), 7.04 (dd, J=7.0, 14.0Hz, 2H), 6.90–6.83 (m, 2H), 6.74–6.63 (m, 2H), 5.11 (bs, 4H). | 1 |
| 240 | 381 | 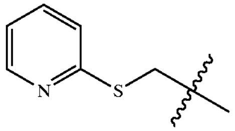 | CH | CH | N-(2-Amino-phenyl)-4-(pyridin-2-ylsulfanylmethyl)-benzamide | $^1$H-NMR (DMSO-d6), δ (ppm): 9.66 (bs, 1H), 8.52 (bs, 1H), 7.96 (d, J=7.4Hz, 2H), 7.69 (d, J=5.8Hz, 1H), 7.59 (d, J=7.4Hz, 2H), 7.38 (d, J=7.7Hz, 1H), 7.19 (bs, 2H), 7.00 (d, J=6.9Hz, 1H), 6.83 (d, J=6.9Hz, 1H), 6.64 (dd, J=6.7, 7.2Hz, 1H), 4.94 (bs, 2H), 4.55 (b + s, 2H). | 11 |
| 241 | 382 | 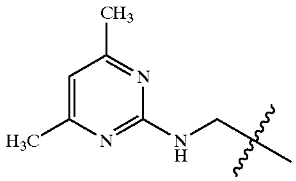 | CH | CH | N-(2-Amino-phenyl)-4-[(4,6-dimethyl-pyrimidin-2-ylamino)-methyl]-benzamide | $^1$H-NMR (DMSO-d6), δ (ppm): 9.65 (bs, 1H), 7.96 (d, J=7.9Hz, 2H), 7.57 (d, J=6.3Hz, 1H), 7.47 (d, J=7.7Hz, 2H), 7.21 (d, J=7.4Hz, 1H), 7.00 (d, J=5.8Hz, 1H), 6.59 (d, J=6.6Hz, 1H), 6.64 (dd, J=6.0, 7.4Hz, 1H), 5.01 (s, 2H), 4.61 (d, J=6.0Hz, 2H), 2.24 (s, 6H). | 33 |

TABLE 4b-continued

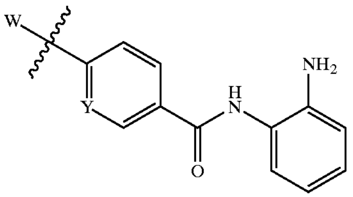

| Ex. | Cpd | W | Y | Z | Name | Characterization | Schm |
|---|---|---|---|---|---|---|---|
| 242 | 383 | 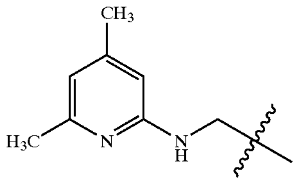 | CH | CH | N-(2-Amino-phenyl)-4-[(4,6-dimethyl-pyridin-2-ylamino)-methyl]-benzamide | $^1$H-NMR (DMSO-d6), δ (ppm): 9.66 (bs, 1H), 7.98 (d, J=7.9Hz, 2H),7.50 (d, J=8.2Hz, 2H), 7.96 (d, J=7.9Hz, 1H), 7.01 (dd, J=7.7, 7.4Hz, 1H), 6.82 (d, J=7.9Hz, 1H), 6.64 (t, J=7.4Hz, 1H), 6.33 (s, 1H), 6.25 (s, 1H), 4.58 (d, J=4.4Hz, 2H), 2.28 (s, 3H), 2.17 (s, 3H). | 33 |
| 243 | 384 | 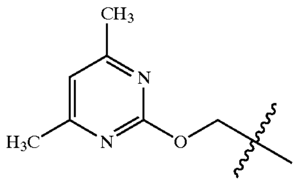 | CH | CH | N-(2-Amino-phenyl)-4-(4,6-dimethyl-pyrimidin-2-yloxymethyl)-benzamide | $^1$H-NMR (DMSO-d6), δ (ppm): 9.58 (bs, 1H), 7.88 (d, J=5.8Hz, 2H), 7.46 (d, J=8.2Hz, 2H), 6.90–6.81 (m, 1H), 6.68 (d, J=7.9Hz, 1H), 6.50 (t, J=7.4Hz, 1H), 6.40–6.38 (m, 1H), 6.29–6.26 (m, 1H), 5.33 (s, 2H), 2.25 (s, 6H). | 11 |
| 244 | 385 | 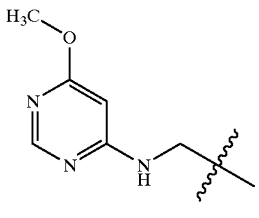 | CH | CH | N-(2-Amino-phenyl)-4-[(6-methoxy-pyrimidin-4-ylamino)-methyl]-benzamide | $^1$H-NMR (DMSO-d6), δ (ppm): 9.64 (bs, 1H), 8.21 (bs, 1H), 7.95 (d, J=7.96Hz, 2H), 7.83 (d, J=5.8Hz, 1H), 7.44 (d, J=7.9Hz, 2H), 7.19 (d, J=7.7Hz, 1H), 7.00 (dd, J=7.4, 7.7Hz, 1H), 6.80 (d, J=7.9Hz, 1H), 6.64 (d, J=7.1Hz, 1H), 4.96 (bs, 2H), 4.58 (bs, 2H), 3.81 (s, 3H). | 33 |
| 245 | 386 | 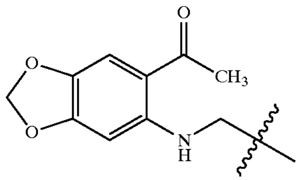 | CH | CH | 4-[(6-Acetyl-benzo[1,3]dioxol-5-ylamino)-methyl]-N-(2-amino-phenyl)-benzamide | $^1$H-NMR (DMSO-d6), δ (ppm): 9.79 (bs, 1H), 7.99 (d, J=8.5Hz, 2H), 7.48 (d, J=7.96Hz, 2H), 7.39 (bs, 1H), 7.21 (d, J=7.4Hz, 1H), 7.02 (dd, J=7.1, 7.7Hz, 1H), 6.83 (d, J=7.7Hz, 1H), 6.64 (t, J=7.4Hz, 1H), 6.36 (bs, 1H), 6.00 (d, J=2.2Hz, 2H), 4.59 (bs, 2H), 2.52 (bs, 3H). | 33 |

TABLE 4b-continued

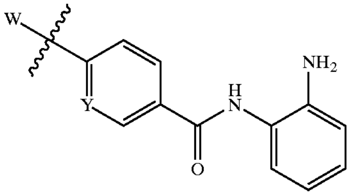

| Ex. | Cpd | W | Y | Z | Name | Characterization | Schm |
|---|---|---|---|---|---|---|---|
| 246 | 387 | 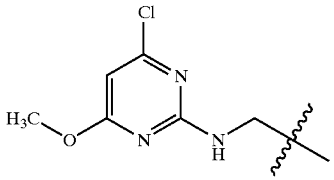 | CH | CH | N-(2-Amino-phenyl)-4-[(4-chloro-6-methoxy-pyrimidin-2-ylamino)-methyl]-benzamide | $^1$H-NMR (DMSO-d6), δ (ppm): 9.66 (bs, 1H), 7.96 (d, J=7.9Hz, 2H), 7.47 (bs, 2H), 7.39 (bs, 1H), 7.19 (d, J=7.4Hz, 1H), 7.00 (dd, J=6.9, 7.4Hz, 1H), 6.81 (d, J=7.1Hz, 1H), 6.63 (dd, J=7.7, 6.8Hz, 1H), 6.10 (bs, 1H), 4.56 (d, J=6.0Hz,, 2H), 3.83 (s, 3H). | 33 |
| 247 | 388 | 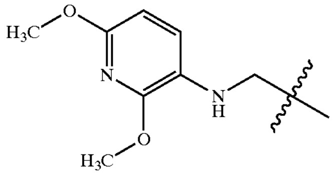 | CH | CH | N-(2-Amino-phenyl)-4-[(2,6-dimethoxy-pyridin-3-ylamino)-methyl]-benzamide | $^1$H-NMR (DMSO-d6), δ (ppm): 9.63 (bs, 1H), 7.94 (d, J=6.9Hz, 2H), 7.47 (d, J=6.59Hz, 2H), 7.15 (d, J=7.9Hz, 1H), 6.99 (dd, J=5.7, 7.4Hz, 1H), 6.80 (d, J=7.8Hz, 1H), 6.71 (d, J=6.6Hz, 1H), 6.62 (dd, J=7.7, 7.1Hz, 1H), 6.15 (d, J=8.2Hz, 1H), 4.96 (bs, 2H), 4.38 (bs, 2H), 3.94 (s, 3H), 3.75 (s, 3H). | 33 |
| 248 | 389 | 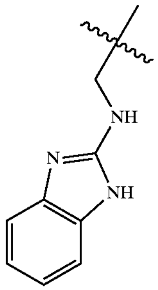 | CH | CH | N-(2-Amino-phenyl)-4-[(1H-benzoimidazol-2-ylamino)-methyl]-benzamide | $^1$H-NMR (DMSO-d6), δ (ppm): 10.9 (bs, 1H), 9.64 (bs, 1H), 7.99 (bs, 2H), 7.55 (bs, 2H), 7.21–7.17 (m, 3H), 7.14–6.81 (m, 4H), 6.64 (d, J=6.0Hz, 1H), 4.92 (bs, 2H), 4.65 (bs, 2H). | 33 |
| 249 | 390 | 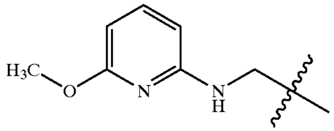 | CH | CH | N-(2-Amino-phenyl)-4-[(6-methoxy-pyridin-2-ylamino)-methyl]-benzamide | $^1$H-NMR (DMSO-d6), δ (ppm): 9.60 (bs, 1H), 7.96 (d, J=7.9Hz, 1H), 7.52–7.50 (m, 2H), 7.37–7.30 (m, 1H), 7.25–7.21 (m, 2H), 7.19–6.99 (m, 1H), 6.84–6.81 (m, 1H), 6.67–6.64 (m, 1H), 6.11–6.07 (m, 1H), 5.93–5.89 (m, 1H), 4.93 (bs, 2H), 4.56 (d, J=5.8Hz, 2H), 3.80 (s, 3H). | 37 |

TABLE 4b-continued

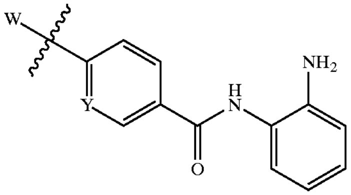

| Ex. | Cpd | W | Y | Z | Name | Characterization | Schm |
|---|---|---|---|---|---|---|---|
| 250 | 391 | 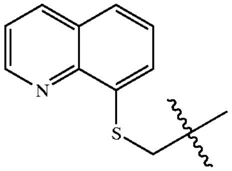 | CH | CH | N-(2-Amino-phenyl)-4-(quinolin-8-ylsulfanylmethyl)-benzamide | $^1$H-NMR (DMSO-d6), δ (ppm): 9.68 (bs, 1H), 8.95 (bs, 2H), 8.43–8.38 (m, 1H), 7.90 (bs, 2H), 7.80–7.55 (m, 6H), 7.22 (d, J=7.7Hz, 1H), 7.03 (d, J=7.7Hz, 1H), 6.63 (d, J=7.4Hz, 1H), 5.05 (bs, 2H), 4.48 (d, J=7.7, 2H). | 11 |
| 251 | 392 | 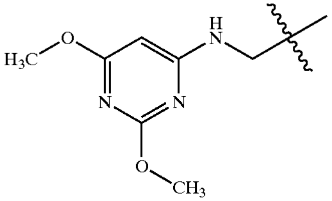 | CH | CH | N-(2-Amino-phenyl)-4-[(2,6-dimethoxy-pyrimidin-4-ylamino)-methyl]-benzamide | $^1$H-NMR (DMSO-d6), δ (ppm): 9.66 (bs, 1H), 7.97 (d, J=7.9Hz, 2H), 7.84 (t, J=5.9Hz, 1H), 7.46 (d, J=7.46Hz, 2H), 7.20 (d, J=7.9Hz, 1H), 7.04 (d, J=6.6Hz, 1H), 6.83 (d, J=7.9Hz, 1H), 6.64 (dd, J=7.7, 7.4Hz, 1H), 5.51 (bs, 1H), 4.57 (bs,, 2H), 3.82 (s, 3H), 3.84 (S, 3H). | 37 |
| 252 | 393 | 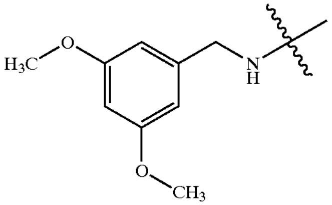 | CH | CH | N-(2-Amino-phenyl)-4-(3,5-dimethoxy-benzylamino)-benzamide | $^1$H-NMR (DMSO-d6), δ (ppm): 9.63 (bs, 1H), 7.79 (d, J=8.5Hz, 2H), 7.19 (d, J=6.6Hz, 1H), 7.00 (dd, J=7.9, 7.1Hz, 1H), 6.62 (t, J=6.0Hz, 1H), 6.82 (dd, J=1.4, 7.9Hz, 1H), 6.67 (d, J=8.8Hz, 2H), 6.58 (bs, 2H), 6.42 (bs, 1H), 4.87 (bs, 2H), 4.34 (d, J=6.0Hz, 2H), 3.77 (s, 6H). | 37 |

TABLE 4b-continued

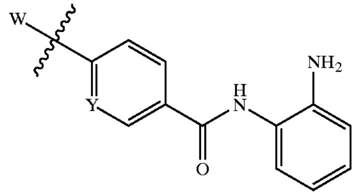

| Ex. | Cpd | W | Y | Z | Name | Characterization | Schm |
|---|---|---|---|---|---|---|---|
| 253 | 394 | 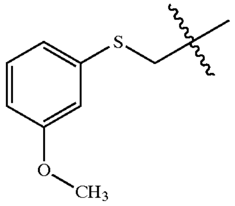 | CH | CH | N-(2-Amino-phenyl)-4-(3-methoxy-phenylsulfanylmethyl)-benzamide | $^1$H-NMR (DMSO-d6), δ (ppm): 9.66 (bs, 1H), 7.96 (d, J=7.9Hz, 2H), 7.55 (d, J=8.2Hz, 2H), 7.29–7.20 (m, 2H), 7.02–6.95 (m, 2H), 6.84–6.79 (m, 1H), 6.67–6.62 (m, 1H), 6.57–6.54 (m, 1H), 6.44–6.41 (m, 1H), 4.93 (bs, 2H), 4.41 (bs, 2H), 3.79 (s, 3H). | 11 |
| 254 | 395 | 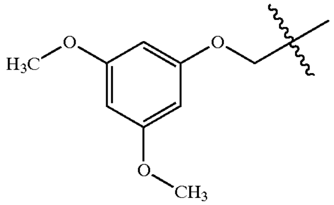 | CH | CH | N-(2-Amino-phenyl)-4-(3,5-dimethoxy-phenoxymethyl)-benzamide | $^1$H-NMR (DMSO-d6), δ (ppm): 9.72 (bs, 1H), 8.05 (d, J=8.2Hz, 2H), 7.61 (d, J=7.9Hz, 2H), 7.24 (d, J=7.4Hz, 1H), 7.04 (dd, J=6.9, 7.1Hz, 1H), 6.85 (d, J=6.9Hz, 1H), 6.66 (dd, J=7.4, 7.7Hz, 1H), 6.27 (s, 2H), 6.26 (s, 1H), 5.23 (s, 2H), 5.21 (bs, 2H), 3.77 (s, 6H). | 11 |
| 255 | 396 | 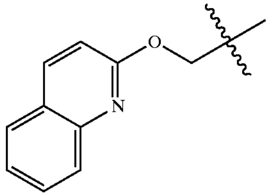 | CH | CH | N-(2-Amino-phenyl)-4-(quinolin-2-yloxymethyl)-benzamide | $^1$H-NMR (DMSO-d6), δ (ppm): 9.70 (bs, 1H), 8.35 (d, J=9.1Hz, 2H), 8.05 (d, J=7.9Hz, 2H), 7.96 (d, J=7.9Hz, 1H), 7.85 (d, J=8.2Hz, 1H), 7.76–7.69 (m, 2H), 7.51 (dd, J=6.9, 7.1Hz, 1H), 7.24–7.16 (m, 2H), 7.02 (dd, J=6.9, 7.4Hz, 1H), 6.83 (d, J=8.2Hz, 1H), 6.66 (d, J=7.4Hz, 1H), 5.66 (s, 2H), 4.94 (bs, 2H). | 11 |

TABLE 4b-continued

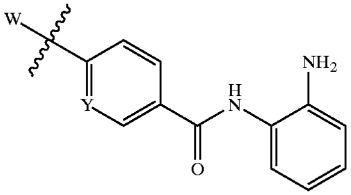

| Ex. | Cpd | W | Y | Z | Name | Characterization | Schm |
|---|---|---|---|---|---|---|---|
| 256 | 397 | 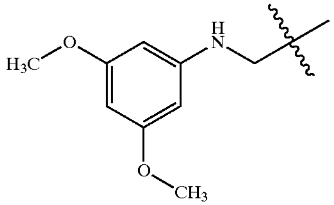 | CH | CH | N-(2-Amino-phenyl)-4-[(3,5-dimethoxy-phenylamino)-methyl]-benzamide | $^1$H-NMR (DMSO-d6), δ (ppm): 9.62 (bs, 1H), 7.96 (d, J=7.9Hz, 2H), 7.49 (d, J =7.9Hz, 2H), 7.19 (d, J=7.9Hz, 1H), 7.00 (dd, J=7.5, 7.9Hz, 1H), 6.81 (d, J=7.9Hz, 1H), 6.63 (dd, J=7.0, 8.0Hz, 1H), 5.78 (s, 2H), 5.76 (s, 1H), 4.92 (bs,, 2H), 4.35 (d, J=5.7, 2H), 3.65 (s, 6H). | 33 |
| 257 | 398 | 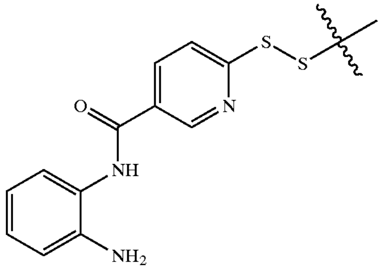 | CH | N | bis(N-(2-Amino-phenyl)-nicotinamide)-6-disulfide | $^1$H-NMR (DMSO-d6), δ (ppm): 9.82 (bs, 2H), 9.08 (bs, 2H), 8.34 (d, J=8.3Hz, 2H), 7.83 (d, J=8.3Hz, 2H), 7.18 (d, J=7.5Hz, 2H), 7.01 (dd, J=6.3, 7.0Hz, 2H), 6.80 (d, J=7.9Hz, 2H), 6.61 (t, J=7.03Hz, 2H), 5.05 (bs, 4H). | 1 |
| 258 | 339 | 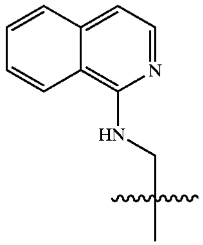 | CH | CH | N-(2-Amino-phenyl)-4-(isoquinolin-1-ylaminomethyl)-benzamide | $^1$H-NMR (DMSO-d6), δ (ppm): 9.90 (bs, 1H), 8.16 (bs, 2H), 7.65 (d, J=4.8Hz, 2H), 7.54 (bs, 2H), 7.25 (d, J=7.0Hz, 2H), 7.11 (bs, 2H), 7.07–7.02 (m, 2H), 6.84 (d, J=7.9Hz, 1H), 6.67 (bs, 1H), 5.01 (bs, 2H), 4.88 (bs, 2H). | 33 |

TABLE 4b-continued

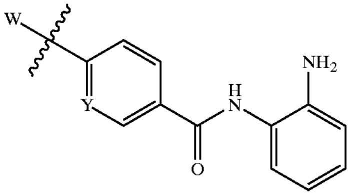

| Ex. | Cpd | W | Y | Z | Name | Characterization | Schm |
|---|---|---|---|---|---|---|---|
| 259 | 400 | 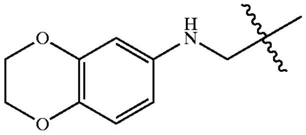 | CH | CH | N-(2-Amino-phenyl)-4-[(2,3-dihydro-benzo[1,4]dioxin-6-ylamino)-methyl]-benzamide | $^1$H-NMR (DMSO-d6), δ (ppm): 9.66 (bs, 1H), 7.97 (d, J=7.0Hz, 2H), 7.51 (d, J=7.0Hz, 2H), 7.22 (d, J=7.5Hz, 1H), 7.02–6.97 (m, 1H), 6.84 (bs, 1H), 6.82–6.71 (m, 2H), 6.16 (d, J=6.6Hz, 1H), 6.08 (s, 1H), 4.32 (bs, 2H), 4.16–4.13 (m, 2H). | 33 |
| 260 | 401 | 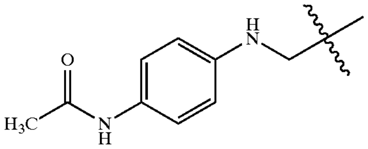 | CH | CH | 4-[(4-Acetylamino-phenylamino)-methyl]-N-(2-amino-phenyl)-benzamide | $^1$H-NMR (DMSO-d6), δ (ppm): 9.66 (bs, 1H), 9.56 (bs, 1H), 7.97 (d, J=7.9Hz, 2H), 7.53 (d, J=7.9Hz, 2H), 7.28 (d, J=8.8Hz, 2H), 7.22 (d, J=7.9Hz, 1H), 7.02 (t, J=7.5Hz, 1H), 6.83 (d, J=7.9Hz, 1H), 6.65 (t, J=7.5Hz, 1H), 6.55 (d, J=8.3Hz, 2H), 4.98 (bs, 2H), 4.38 (bs, 2H), 2.00 (s, 3H). | 33 |
| 261 | 402 | 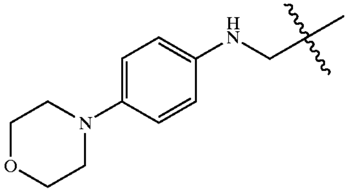 | CH | CH | N-(2-Amino-phenyl)-4-[(4-morpholin-4-yl-phenylamino)-methyl]-benzamide | $^1$H-NMR (DMSO-d6), δ (ppm): 9.65 (bs, 1H), 7.98 (d, J=7.9Hz, 2H), 7.52 (d, J=7.9Hz, 2H), 7.21 (d, J=7.5Hz, 1H), 7.02 (dd, J=7.0, 7.9Hz, 1H), 6.83 (d, J=7.9Hz, 1H), 6.78 (d, J=8.8Hz, 2H), 6.64 (t, J=7.5Hz, 1H), 6.55 (d, J=8.8Hz, 2H), 4.94 (bs, 2H), 4.35 (d, J=5.7Hz, 2H), 3.74 (t, J=4.4Hz, 4H), 2.92 (t, J=4.4Hz, 4H). | 33 |
| 262 | 403 | 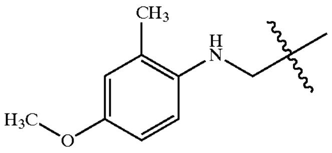 | CH | CH | N-(2-Amino-phenyl)-4-[(4-methoxy-2-methyl-phenylamino)-methyl]-benzamide | $^1$H-NMR (DMSO-d6), δ (ppm): 9.64 (bs, 1H), 7.96 (d, J=7.6Hz, 2H), 7.52 (d, J=7.6Hz, 2H), 7.21 (d, J=8.2Hz, 1H), 7.02 (t, J=8.2, 7.0Hz, 1H), 6.83 (d, J=8.2Hz, 1H), 6.71–6.53 (m, 3H), 6.32–6.30 (m, 1H), 4.94 (bs, 2H), 4.45 (d, J=5.9Hz, 2H), 3.65 (s, 3H), 2.23 (s, 3H). | 33 |

TABLE 4b-continued

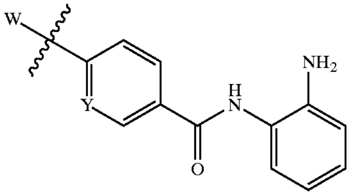

| Ex. | Cpd | W | Y | Z | Name | Characterization | Schm |
|---|---|---|---|---|---|---|---|
| 263 | 404 | 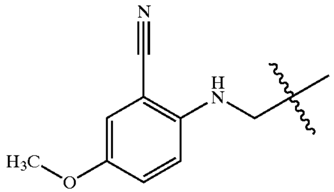 | CH | CH | N-(2-Amino-phenyl)-4-[(2-cyano-4-methoxy-phenylamino)-methyl]-benzamide | $^1$H-NMR (DMSO-d6), δ (ppm): 9.65 (bs, 1H), 7.98 (d, J=7.4Hz, 2H), 7.56 (d, J=7.5Hz, 2H), 7.19 (d, J=7.9Hz, 1H), 6.99 (d, J=7.5Hz, 1H), 6.82 (d, J=7.9Hz, 1H), 6.63 (t, J=6.6Hz, 2H), 6.27 (s, 1H), 4.93 (bs, 2H), 4.55 (d, J=5.3Hz, 2H), 3.69 (s, 6H). | 33 |
| 264 | 405 | 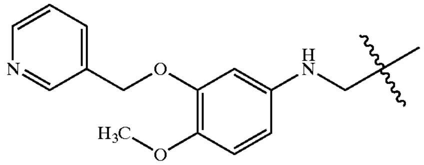 | CH | CH | N-(2-Amino-phenyl)-4-{[4-methoxy-3-(pyridin-3-ylmethoxy)-phenylamino]-methyl}-benzamide | $^1$H-NMR (DMSO-d6), δ (ppm): 9.62 (s, 1H), 8.72 (s, 1H), 8.49 (d, J=10.1Hz, 1H), 7.93 (d, J=7.9Hz, 2H), 7.68 (d, J=6.6Hz, 1H), 7.37 (d, J=7.5Hz, 2H), 7.16 (d J=7.5Hz, 1H), 6.97 (t, J=7.5Hz, 1H), 6.78 (d, J=7.9Hz, 1H), 6.69 (d, J=8.8Hz, 1H), 6.62 (d, J=7.5Hz, 1H), 6.23 (d, J=2.6Hz, 1H), 6.09 (J=8.8Hz, 1H), 5.76 (s, 1H), 4.64 (bs, 4H), 3.62 (s, 3H). | 33 |
| 265 | 406 | 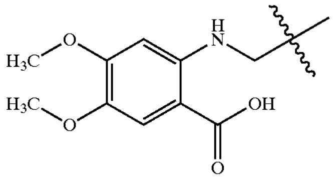 | CH | CH | 2-[4-(2-Amino-phenylcarbamoyl)-benzylamino]-4,5-dimethoxy-benzoic acid | $^1$H-NMR (DMSO-d6), δ (ppm): 9.67 (bs, 1H), 8.00 (d, J=7.9Hz, 2H), 7.54 (d, J=7.9Hz, 2H), 7.34 (s, 1H), 7.20 (d, J=7.9Hz, 2H), 7.0 (t, J=7.9Hz, 1H), 6.82 (d, J=7.9Hz, 1H), 6.62 (t, J=7.9Hz, 1H), 6.31 (s, 1H), 4.95 (bs, 2H), 4.62 (bs, 2H), 3.75 (s, 3H), 3.70 (s, 3H). | 33 |
| 266 | 407 | 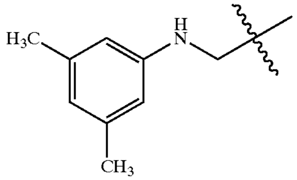 | CH | CH | N-(2-Amino-phenyl)-4-[(3,5-dimethyl-phenylamino)-methyl]-benzamide | $^1$H-NMR (DMSO-d6), δ (ppm): 9.60 (s, 1H), 7.93 (d, J=7.9Hz, 2H), 7.45 (d, J=7.9Hz, 2H), 7.16 (d, J=7.5Hz, 1H), 6.97 (t, J=7.5Hz, 1H), 6.78 (d, J=7.9Hz, 1H), 6.58 (t, J=7.0Hz, 1H), 6.19–6.17 (m, 3H), 4.88 (s, 2H), 4.32 (d, J=5.7Hz, 2H), 2.10 (s, 6H). | 33 |

TABLE 4b-continued

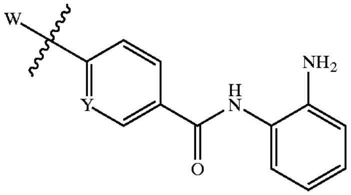

| Ex. | Cpd | W | Y | Z | Name | Characterization | Schm |
|---|---|---|---|---|---|---|---|
| 267 | 408 | 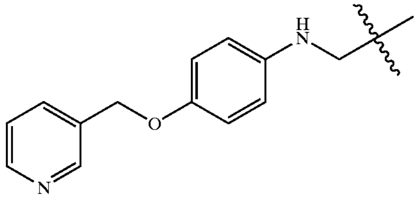 | CH | CH | N-(2-Amino-phenyl)-4-{[4-(pyridin-3-ylmethoxy)-phenylamino]-methyl}-benzamide | $^1$H-NMR (DMSO-d6), δ (ppm): 9.65 (s, 1H), 8.72 (s, 1H), 8.54 (s, 1H), 8.49 (d, J=10.9Hz, 1H), 7.97 (d, J=7.9Hz, 2H), 7.71 (d, J=7.9Hz, 1H), 7.44 (d, J=8.3Hz, 2H), 7.41–7.36 (m, 1H), 7.20 (d, J=7.9Hz, 1H), 7.00 (t, J=7.4Hz, 1H), 6.83 (d, J=7.0Hz, 1H), 6.70–6.60 (m, 4H), 4.62 (s, 4H). | 33 |
| 268 | 409 | 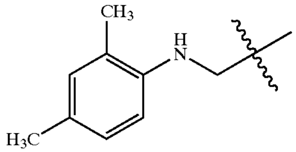 | CH | CH | N-(2-Amino-phenyl)-4-[(2,4-dimethyl-phenylamino)-methyl]-benzamide | $^1$H-NMR (DMSO-d6), δ (ppm): 9.58 (s, 1H), 7.90 (d, J=7.9Hz, 2H), 7.45 (d, J=7.5Hz, 2H), 7.15 (d, J=7.5Hz, 1H), 6.96 (t, J=7.5Hz, 1H), 6.79 (s, 1H), 6.76 (d, J=9.6Hz, 1H), 6.68 (d, J=7.9Hz, 1H), 6.59 (t, J=7.0Hz, 1H), 6.22 (d, J=7.9Hz, 1H), 4.89 (bs, 2H), 4.39 (d, J=5.7Hz, 2H), 2.15 (s, 3H), 2.10 (s, 3H). | 33 |
| 269 | 410 | 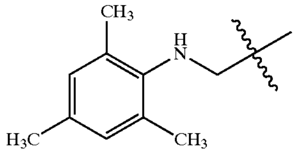 | CH | CH | N-(2-Amino-phenyl)-4-[(2,4,6-trimethyl-phenylamino)-methyl]-benzamide | $^1$H-NMR ($CD_3OD$), δ (ppm): 7.91 (d, J=7.9Hz, 2H), 7.43 (d, J=8.5Hz, 2H), 7.18 (d, J=7.5Hz, 1H), 7.08 (t, J=7.5Hz, 1H), 6.92 (d, J=7.9Hz, 1H), 6.77 (s, 3H), 4.15 (bs, 2H), 2.19 (s, 9H). | 33 |
| 270 | 411 | 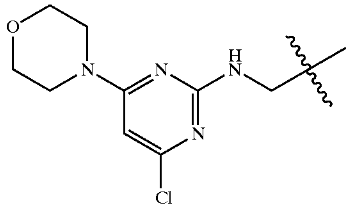 | CH | CH | N-(2-Amino-phenyl)-4-[(4-chloro-6-morpholin-4-yl-pyrimidin-2-ylamino)-methyl]-benzamide | $^1$H NMR (300MHz, DMSO-$D_6$) δ *** (ππμ): 9.66 (s, 1H), 7.97 (d, J=8.0Hz, 2H), 7.82 (m, 1H), 7.47 (d, J=7.7Hz, 2H), 7.21 (d, J=8.2Hz, 1H), 7.03 (dd, J=7.1, 7.1Hz, 1H), 6.84 (d, J=7.7Hz, 1H), 6.65 (dd, J=7.4, 7.4Hz, 1H), 6.17 (bs, 1H), 4.94 (s, 2H, $NH_2$), 4.53 (d, J=5.8Hz, 2H), 3.58 (m, 4H), 3.62 (m, 4H). | 24, 33 |

TABLE 4b-continued

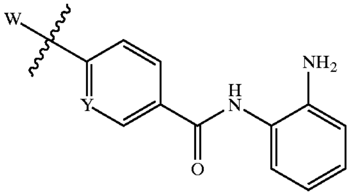

| Ex. | Cpd | W | Y | Z | Name | Characterization | Schm |
|---|---|---|---|---|---|---|---|
| 271 | 412 | 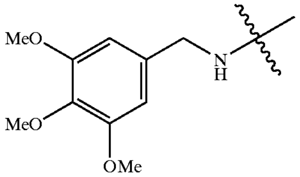 | CH | CH | N-(2-Amino-phenyl)-4-(3,4,5-trimethoxy-benzylamino)-benzamide | $^1$H NMR (300 MHz, DMSO-$d_6$) δ (ppm): 9.33 (s, 1H), 7.81 (d, J=8.8Hz, 2H), 7.19 (d, J=7.7Hz, 1H), 6.99 (m, 1H), 6.87 (dd, J=6.0, 5.8Hz, 1H), 6.82 (m, 1H), 6.77 (s, 2H), 6.71 (d, J=8.8Hz, 2H), 6.64 (m, 1H), 4.87 (s, 2H, $NH_2$). 4.32 (d, J=5.5Hz, 2H), 3.81 (s, 6H), 3.79 (s, 3H). | 33 |
| 272 | 413 | 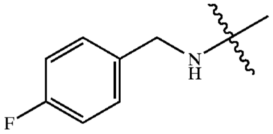 | CH | CH | N-(2-Amino-phenyl)-4-(4-fluoro-benzylamino)-benzamide | $^1$H NMR (300MHz, DMSO-$d_6$) δ δ (ppm): 9.31 (s, 1H), 7.79 (d, J=8.7Hz, 2H), 7.45 (dd, J=5.8, 8.5Hz, 2H), 7.21 (m, 3H), 6.91 (m, 2H), 6.81 (dd, J=1.1, 8.0Hz, 1H), 6.67 (d, J=8.8Hz, 2H), 6.62 (dd, J=1.0, 7.2Hz, 1H), 4.86 (s, 2H, $NH_2$), 4.39 (d, J=6.0Hz, 2H). | 33 |
| 273 | 414 | 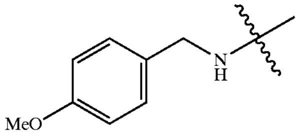 | CH | CH | N-(2-Amino-phenyl)-4-(4-methoxy-benzylamino)-benzamide | $^1$H NMR (300MHz, DMSO-$d_6$) δ (ppm): 9.31 (s, 1H), 7.79 (dd, J=1.1, 8.5Hz, 2H), 7.33 (d, J=7.1Hz, 2H), 7.19 (d, J=7.7Hz, 1H), 6.97 (m, 3H), 6.84 (m, 2H), 6.65 (m, 3H), 4.86 (s, 2H, $NH_2$), 4.33 (d, J=5.5Hz, 2H), 3.58 (d, J=1.6Hz, 3H). | 33 |
| 274 | 415 | 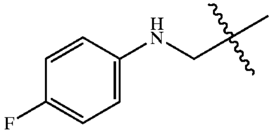 | CH | CH | N-(2-Amino-phenyl)-4-[(4-fluoro-phenylamino)-methyl]-benzamide | $^1$H NMR (300MHz, DMSO-$d_6$) δ (ppm): 9.66 (s, 1H), 7.99 (d, J=7.9Hz, 2H), 7.53 (d, J=8.0Hz, 2H), 7.21 (d, J=8.0Hz, 1H), 7.02 (ddd J=1.6, 7.1, 8.2Hz, 1H), 6.93 (dd, J=8.8, 9Hz, 2H), 6.83 (dd, J=1.1, 8.0Hz, 1H), 6.63 (m, 3H), 6.35 (t, J=6.2Hz, 1H), 4.94 (s, 2H, $NH_2$), 4.38 (d, J=6.3Hz, 2H). | 33 |

TABLE 4b-continued

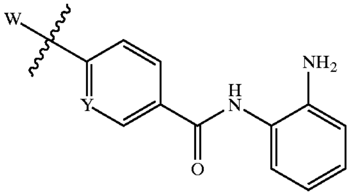

| Ex. | Cpd | W | Y | Z | Name | Characterization | Schm |
|---|---|---|---|---|---|---|---|
| 275 | 416 | 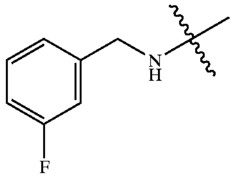 | CH | CH | N-(2-Amino-phenyl)-4-(3-fluoro-benzylamino)-benzamide | $^1H$ NMR (300MHz, DMSO-$d_6$) δ (ppm): 9.32 (s, 1H), 7.79 (d, J=8.8Hz, 2H), 7.44 (m, 1H), 7.26 (m, 1H), 7.18 (dd, J=1.4, 8.0Hz, 2H), 7.12 (ddd, J=1.7, 8.0, 8.2Hz, 1H), 6.99 (m. 2H), 6.81 (dd, J=1.4, 8.0Hz, 1H), 6.67 (dd, J=1.6, 8.8Hz, 2H), 6.62 (dd, J=1.4, 7.4Hz, 1H), 4.87 (s, 2H, $NH_2$), 4.45 (d, J=6.0Hz, 2H). | 33 |
| 276 | 417 | 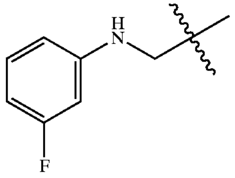 | CH | CH | N-(2-Amino-phenyl)-4[(3-fluoro-phenylamino)-methyl]-benzamide | $^1H$ NMR (300MHz, DMSO-$d_6$) δ (ppm): 9.66 (s, 1H), 7.99 (d, J=8.2Hz, 2H), 7.52 (d, J=8.0Hz, 2H), 7.21 (d, J=7.7Hz, 1H), 6.99–7.14 (m, 2H), 6.83 (d, J=8.0Hz, 1H), 6.76 (m, 1H), 6.64 (dd, J=7.4, 7.4Hz, 1H), 6.46 (d, J=8.2Hz, 1H), 6.34 (m, 2H), 4.94 (s, 2H, $NH_2$), 4.41 (d, J=6.0Hz, 2H). | 33 |
| 277 | 418 | 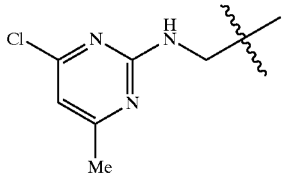 | CH | CH | N-(2-Amino-phenyl)-4-[(4-chloro-6-methyl-pyrimidin-2-ylamino)-methyl]-benzamide | $^1H$ NMR (300MHz, DMSO-$D_6$) δ (ppm): 9.66 (s, 1H), 8.23 (m, 1H), 7.98 (d, J=8.2Hz, 2H), 7.47 (d, J=8.5Hz, 2H), 7.21 (d, J=7.7Hz, 1H), 7.03 (ddd, J=1.5, 7.1, 8.0Hz, 1H), 6.83 (dd, J=1.5, 8.1Hz, 1H), 6.65 (m, 2H), 4.94 (s, 2H, $NH_2$), 4.61 (m, 2H), 2.32 (s, 3H). | 33 |
| 278 | 419 | 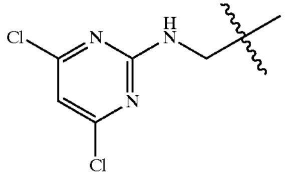 | CH | CH | N-(2-Amino-phenyl)-4-[(4,6-dichloro-pyrimidin-2-yiamino)-methyl]-benzamide | $^1H$ NMR (300MHz, DMSO-$D_6$) δ (ppm): 9.69 (s, 1H), 8.82 (m, 1H), 7.99 (d, J=8.2Hz, 2H), 7.48 (d, J=8.0Hz, 2H), 7.27 (d, J=7.7Hz, 1H), 7.04 (d, J=7.7Hz, 1H), 7.0 (d, J=1.6Hz, 1H), 6.84 (d, J=8.2Hz, 1H), 6.67 (m, 1H), 5.0 (bs, 2H, NH2), 4.60 (d, J=6.3Hz, 2H). | 33 |

TABLE 4b-continued

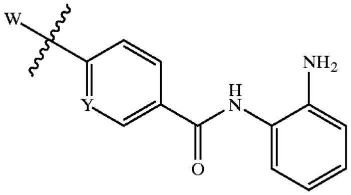

| Ex. | Cpd | W | Y | Z | Name | Characterization | Schm |
|---|---|---|---|---|---|---|---|
| 279 | 420 | 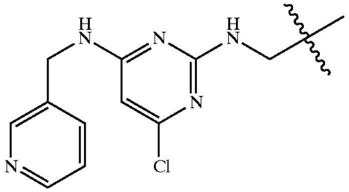 | CH | CH | N-(2-Amino-phenyl)-4-({4-chloro-6-[(pyridin-3-ylmethyl)-amino]-pyrimidin-2-ylamino}-methyl)-benzamide | $^1$H NMR (300MHz, DMSO-$D_6$) δ (ppm): 9.87 (s, 1H), 8.49 (bs, 2H), 7.26–8.02 (bm, 8H), 7.22 (d, J=8.0Hz, 1H), 7.03 (dd, J=7.4, 7.4Hz, 1H), 6.84 (d, J=8.2Hz, 1H), 6.66 (dd, J=7.1, 8.0Hz, 1H), 5.86 (bs, 1H), 4.95 (s, 2H, $NH_2$), 4.51 (m, 2H). | 24, 33 |
| 280 | 421 | 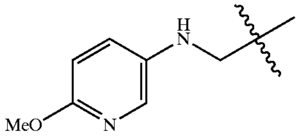 | CH | CH | N-(2-Amino-phenyl)-4-[(6-methoxy-pyridin-3-ylamino)-methyl]-benzamide | $^1$H NMR (300MHz, DMSO-$D_6$) δ (ppm): 9.66 (s, 1H), 7.99 (d, J=8.4Hz, 2H), 7.54 (d, J=7.9Hz, 2H), 7.50 (d, J=2.6Hz, 1H), 7.21 (d, J=7.5Hz, 7.9Hz, 1H), 7.12 (dd, J=3.08Hz, 8.79Hz, 1H), 7.02 (dd, J=7.0Hz, 7.5Hz, 1H), 6.83 (d, J=7.0Hz, 1H), 6.65 (m, 2H), 6.15 (t, J=6.16Hz, 1H), 4.94 (s, 2H, $NH_2$), 4.39 (d, J=6.15Hz, 2H), 3.75 (s, 3H). | |
| 281 | 422 | 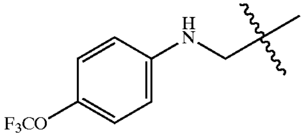 | CH | CH | N-(2-Amino-phenyl)-4-[(4-trifluoromethoxy-phenylamino)-methyl]-benzamide | $^1$H NMR (300MHz, DMSO-$d_6$) δ (ppm): 9.66 (s, 1H), 7.99 (d, J=8.0Hz, 2H), 7.53 (d, J=8.2Hz, 2H), 7.21 J=7.7Hz, 1H), 7.09 (d, J=9.1Hz, 2H), 7.03 (dd, J=7.1, 8.2Hz, 1H), 6.83 (d, J=8.0Hz, 1H), 6.71 (t, J=6.0Hz, 1H), 6.63–6.67 (m, 3H), 4.94 (s, 2H, $NH_2$), 4.42 (d, J=6.0Hz, 2H). | 33 |
| 282 | 423 | 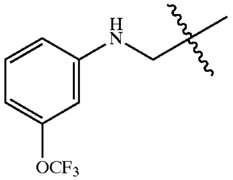 | CH | CH | N-(2-Amino-phenyl)-4-[(3-trifluoromethoxy-phenylamino)-methyl]-benzamide | $^1$H NMR (300MHz, DMSO-$d_6$) δ (ppm): 9.67 (s, 1H), 8.00 (d, J=8.2Hz, 2H), 7.53 (d, J=8.2Hz, 2H), 7.19 (m, 2H), 7.03 (ddd, J=1.5, 8.0, 8.8Hz, 1H), 6.85 (m, 2H), 6.63 (m, 2H), 6.55 (s, 1H), 6.50 (m, 1H), 4.94 (s, 2H, $NH_2$), 4.44 (d, J=6.0Hz, 2H). | 33 |

TABLE 4b-continued

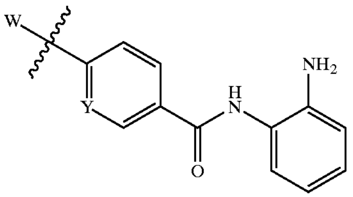

| Ex. | Cpd | W | Y | Z | Name | Characterization | Schm |
|---|---|---|---|---|---|---|---|
| 283a | 424b | 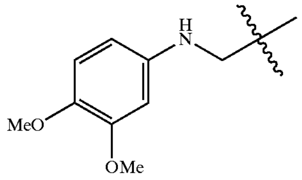 | CH | CH | N-(2-Amino-pheny)-4-[(3,4-dimethoxy-phenylamino)-methyl]-benzamide | $^{1}$H NMR (300MHz, DMSO-$d_6$) δ (ppm): 9.65 (s, 1H), 7.98 (d, J=7.9Hz, 2H), 7.54 (d, J=7.9Hz, 2H), 7.22 (d, J=7.9Hz, 1H), 7.02 (dd, J=7.9Hz, 7.9Hz, 1H), 6.83 (d, J=7.9Hz, 1H), 6.72 (d, J=8.79Hz, 1H), 6.45 (dd, J=7.49Hz, 7.49Hz, 1H), 6.39 (d, J=2.2Hz, 1H), 6.01–6.08 (m, 2H), 4.94 (s, 2H, $NH_2$), 4.36 (d, J=6.16Hz, 2H), 3.72 (s, 3H), 3.65 (s, 3H). | 33 |
| 284 | 425 | 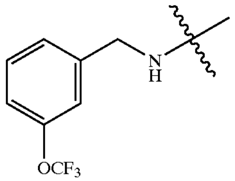 | CH | CH | N-(2-Amino-phenyl)-4-(3-trifluoromethoxy-benzylamino)-benzamide | $^{1}$H NMR (300MHz, DMSO-$d_6$) δ (ppm): 9.31 (s, 1H), 7.80 (d, J=8.8Hz, 2H), 7.45–7.56 (m, 2H), 7.39 (s, 7.29 (d, J=7.7Hz, 1H), 7.18 (d, J=6.6Hz, 1H), 6.96–7.03 (m, 2H), 6.81 (d, J=6.9Hz, 1H), 6.68 (d, J=8.8Hz, 2H), 6.64 (d, J=7.7Hz, 1H), 4.86 (s, 2H, $NH_2$), 4.48 (d, J=5.8Hz, 2H). | 33 |
| 285 | 426 | 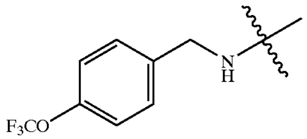 | CH | CH | N-(2-Amino-phenyl)-4-(4-trifluoromethoxy-benzylamino)-benzamide | $^{1}$H NMR (300MHz, DMSO-$d_6$) δ (ppm): 9.31 (s, 1H), 7.79 (d, J=8.8Hz, 2H), 7.54 (d, J=8.8Hz, 2H), 7.39 (d, J=8.0Hz, 2H), 7.18 (dd, J=1.4, 7.7Hz, 1H), 6.99 (ddd, J=1.4, 8.0, 8.5Hz, 2H), 6.81 (dd, J=1.4, 8.0, 1H), 6.68 (d, J=8.8Hz, 2H), 4.85 (s, 2H, $NH_2$), 4.45 (d, J=6.0Hz, 2H). | 33 |
| 286 | 427 | 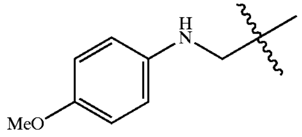 | CH | CH | N-(2-Amino-phenyl)-4-[(4-methoxy phenylamino)-methyl]-benzamide | $^{1}$H NMR (300MHz, DMSO-$d_6$) δ (ppm): 9.64 (s, 1H), 7.97 (d, J=8.2Hz, 2H), 7.53 (d, J=8.5Hz, 2H), 7.21 (d, J=1.4, 8.0Hz, 1H), 7.02 (ddd, J=1.4, 7.4, 8.0Hz, 1H), 6.83 (dd, J=1.4, 8.0Hz, 1H), 6.74 (m, 2H), 6.65 (ddd, J=1.4, 7.7, 8.8Hz, 1H), 6.58 (m, 2H), 5.99 (t, J=6.3Hz, 1H), 4.93 (s, 2H, $NH_2$), 4.36 (d, J=6.0Hz, 2H), 3.68 (s, 3H). | 33 |

TABLE 4b-continued

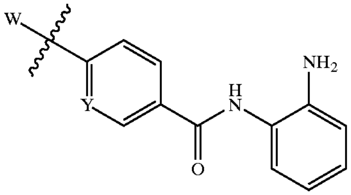

| Ex. | Cpd | W | Y | Z | Name | Characterization | Schm |
|---|---|---|---|---|---|---|---|
| 287 | 428 | 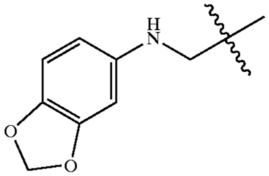 | CH | CH | N-(2-Amino-phenyl)-4-benzo[1,3]dioxol-5-ylaminomethyl)-benzamide | $^1$H NMR (300MHz, DMSO-$d_6$) δ (ppm): 9.65 (s, 1H), 7.98 (d, J=7.9Hz, 2H), 7.52 (d, J=7.9Hz, 2H), 7.21 (d, J=7.5Hz, 1H), 7.02 (dd, J=7.0, 7.0Hz, 1H), 6.83 (d, J=7.5Hz, 1H), 6.63–6.69 (m, 2H), 6.33 (d, J=2.2Hz, 1H), 6.15 (t, J=6.16Hz, 1H), 6.04 (dd, J=2.2, 8.4Hz, 1H), 5.86 (s, 2H), 4.94 (s, 2H, $NH_2$), 4.35 (d, J=6.16Hz, 2H). | 33 |
| 288 | 429 | 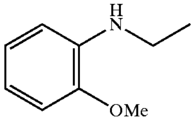 | CH | CH | N-(2-Amino-phenyl)-4-[(2-methoxy-phenylamino)-methyl]-benzamide | $^1$H NMR (300MHz, DMSO-$d_6$) δ (ppm): 9.63 (s, 1H), 7.90 (d, J=8.2Hz, 2H), 7.52 (d, J=8.2Hz, 2H), 7.22 (d, J=7.7Hz, 1H), 7.02 (ddd, J=1.4, 7.1, 8.0Hz, 1H), 6.86 (m, 2H), 6.56–6.75 (m, 3H), 6.43 (dd, J=1.6, 7.7Hz, 1H), 5.75 (t, J=6.3Hz, 1H), 4.93 (s, 2H, $NH_2$), 4.47 (d, J=6.3Hz, 2H), 3.88 (s, 3H). | 33 |
| 289 | 430 | 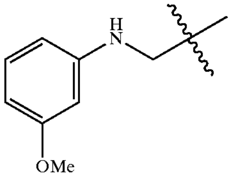 | CH | CH | N-(2-Amino-phenyl)-4-[(3-methoxy-phenylamino)-methyl]-benzamide | $^1$H NMR (300MHz, DMSO-$d_6$) δ (ppm): 9.61 (s, 1H), 7.98 (d, J=8.0Hz, 2H), 7.53 (d, J=8.2Hz, 2H), 7.21 (dd, J=1.1, 7.7Hz, 1H), 6.97–7.05 (m, 2H), 6.82 (dd, J=1.2, 8.1Hz, 1H), 6.46 (ddd, J=1.4, 7.7, 8.0Hz, 1H), 6.41 (t, J=6.3Hz, 1H), 6.16–6.25 (m, 3H), 4.93 (s, 2H, $NH_2$), 4.39 (d, J=6.0Hz, 2H), 3.69 (s, 3H). | 33 |
| 290 | 431 | 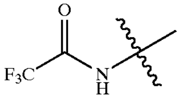 | CH | CH | N-(2-Amino-phenyl)-4-(2,2,2-trifluoro-acetylamino)-benzamide | $^1$H NMR (300MHz, DMSO-$d_6$) δ (ppm): 11.53 (s, 1H), 9.71 (s, 1H), 8.08 (d, J=8.2Hz, 2H), 7.86 (d, J=8.8Hz, 2H), 7.23 (d, J=7.6Hz, 1H), 7.03 (dd, J=7.0, 7.6Hz, 1H), 6.84 (d, J=8.2Hz, 1H), 6.66 (dd, J=7.0, 7.6Hz, 1H), 4.96 (s, 2H, $NH_2$). | 14 |

TABLE 4b-continued

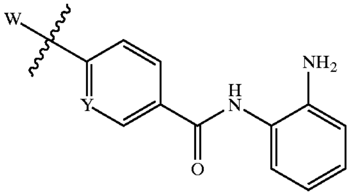

| Ex. | Cpd | W | Y | Z | Name | Characterization | Schm |
|---|---|---|---|---|---|---|---|
| 291 | 432 | 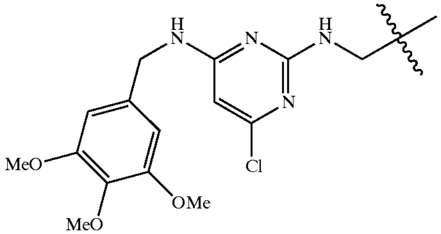 | CH | CH | N-(2-Amino-phenyl)-4-{[4-chloro-6-(3,4,5-trimethoxy-benzylamino)-pyrimidin-2-ylamino]-methyl}-benzamide | $^1$H NMR (300MHz, DMSO-$d_6$) δ (ppm): 9.64 (s, 1H), 7.95 (d, J=7.5Hz, 2H), 7.70 (bs, 2H), 7.45 (d, J=8.14Hz, 2H), 7.22 (d, J=7.9Hz, 1H), 7.03 (dd, J=7.0, 7.5Hz, 1H), 6.84 (d, J=7.9,Hz, 1H), 6.60–6.72 (m, 3H), 5.87 (s, 1H), 4.93 (s, 2H, $NH_2$), 4.54 (d, J=6.2Hz, 2H), 4.43 (bs, 2H), 3.78 (s, 6H), 3.68 (s, 3H). | 24, 33 |
| 292 | 433 | 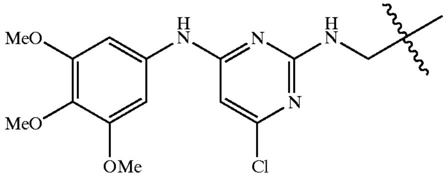 | CH | CH | N-(2-Amino-phenyl)-4-{[4-chloro-6-(3,4,5-trimethoxy-phenylamino)-pyrimidin-2-ylamino]-methyl}-benzamide | $^1$H NMR (300MHz, DMSO-$d_6$) δ (ppm): 9.65 (s, 1H), 9.43 (s, 1H), 7.97 (m, 3H), 7.46 (bs, 2H), 7.21 (d, J=7.5Hz, 1H), 7.02 (m, 3H), 6.83 (d, J=7.0Hz, 1H), 6.65 (dd, J=7.5, 7.5Hz, 1H), 6.08 (s, 1H), 4.93 (s, 2H, $NH_2$), 4.69 (bs, 2H), 3.65 (s, 9H). | 24, 33 |
| 293 | 434 | 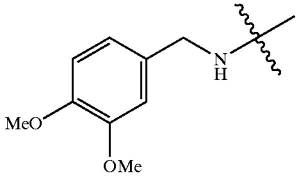 | CH | CH | N-(2-Amino-phenyl)-4-(3,4-dimethoxy-benzylamino)-benzamide | $^1$H NMR (300MHz, DMSO-$d_6$) δ (ppm): 9.31 (s, 1H), 7.79 (d, J=8.8Hz, 2H), 7.19 (d, J=7.9Hz, 2H), 7.04 (s, 1H), 6.92–7.01 (m, 3H), 6.80–6.87 (m, 2H), 6.69 (d, J=8.8Hz, 2H), 6.62 (m, 1H), 4.87 (s, 2H, NH2), 4.32 (d, J=5.7Hz, 2H), 3.80 (s, 3H), 3.78 (s, 3H). | 33 |
| 294 | 435 | 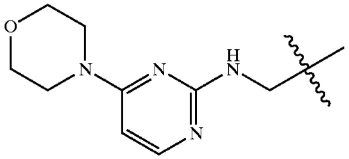 | CH | CH | N-(2-Amino-phenyl)-4-[(4-morpholin-4-yl-pyrimidin-2-ylamino)-methyl]-benzamide | $^1$H NMR (300MHz, DMSO-$d_6$) δ (ppm): 9.64 (s, 1H), 7.95 (d, J=8.4Hz, 2H), 7.87 (d, J=7.9Hz, 1H), 7.47 (d, J=7.9Hz, 2H), 7.31 (bs, 1H), 7.21 (d, J=7.5, 1H), 7.02 (dd, J=7.9Hz, 1H), 6.83 (d, J=7.9Hz, 1H), 6.65 (dd, J=7.0, 7.0Hz, 1H), 6.09 (d, J=6.2Hz, 1H), 4.94 (s, 2H, $NH_2$), 4.54 (d, J=5.7Hz, 2H), 3.67 (s, 4H), 3.53 (s, 4H). | 24, 1, 33 |

TABLE 4b-continued

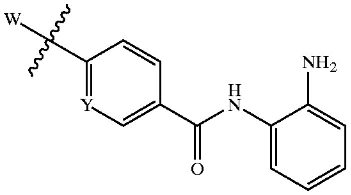

| Ex. | Cpd | W | Y | Z | Name | Characterization | Schm |
|---|---|---|---|---|---|---|---|
| 295 | 436 | 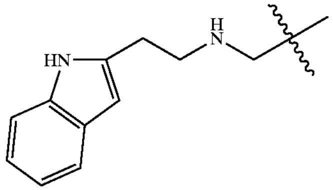 | CH | CH | N-(2-Amino-phenyl)-4-{[2-(1H-indol-3-yl)-ethylamino]-methyl}-benzamide | $^1$H NMR (300MHz, DMSO-$d_6$) δ (ppm): 10.82 (s, 1H), 9.65 (s, 1H), 7.98 (d, J=8.4Hz, 2H), 7.56 (d, J=7.9Hz, 1H), 7.51 (d, J=8.4Hz, 2H), 7.38 (d, J=7.9Hz, 2H), 7.18–723 (m, 2H), 7.11 (dd, J=7.0, 8.0Hz, 1H), 7.01 (m, 2H), 6.83 (d, J=7.9Hz, 1H), 6.51 (dd, J=7.5, 6.6Hz, 1H), 4.93 (s, 2H, $NH_2$), 3.89 (s, 2H), 2.89 (m, 4H). | 57 |
| 296 | 437 | 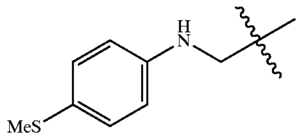 | CH | CH | N-(2-Amino-phenyl)-4-[(4-methylsulfanyl-phenylamino)-methyl]-benzamide | $^1$H NMR (300MHz, DMSO-$d_6$) δ (ppm): 9.67 (s, 1H), 7.99 (d, J=7.5Hz, 2H), 7.52 (d, J=7.5Hz, 2H), 7.21(d, J=7.5Hz, 1H), 7.13 (d, J=7.5Hz, 2H), 7.03 (dd, J=7.5, 7.5Hz, 1H), 6.83 (d, J=7.9Hz, 1H), 6.53 (m, 4H), 4.95 (s, 2H, $NH_2$), 4.41 (d, J=5.7Hz, 2.37 (s, 3H). | 33 |
| 297 | 438 | 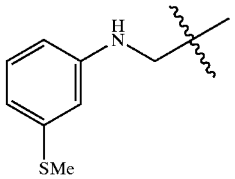 | CH | CH | N-(2-Amino-phenyl)-methylsulfanyl-phenylamino)-methyl]-benzamide | $^1$H NMR (300MHz, DMSO-$d_6$) δ (ppm): 9.66 (s, 1H), 7.99 (d, J=7.5Hz, 2H), 7.53 (d, J=7.5Hz, 2H), 7.21 (d, J=7.5Hz, 1H), 7.03 (m, 2H), 6.83 (d, J=7.9Hz, 1H), 6.65 (dd, J=7.5, 7.5Hz, 1H), 6.39–6.51 (m, 4H), 4.94 (s, 2H, $NH_2$), 4.41 (d, J=5.7Hz, 2H), 2.42 (s, 3H). | 33 |
| 298 | 349 | 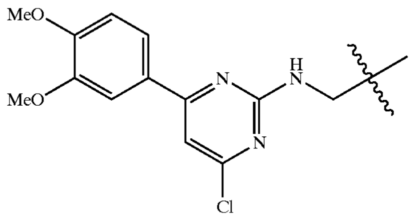 | CH | CH | N-(2-Amno-phenyl)-4-{[4-chloro-6-(3,4-dimethoxy-phenyl)-pyrimidin-2-ylamino]-methyl}-benzamide | $^1$H NMR (300MHz, DMSO-$d_6$) δ (ppm): 9.66 (s, 1H), 8.37 (s, 1H), 7.99 (d, J=7.5Hz, 2H), 7.68–7.79 (m, 2H), 7.55 (bs, 2H), 7.37 (s, 1H), 7.20 (d, J=7.1Hz, 1H), 7.11 (bs, 1H), 7.02 (dd, J=7.5, 7.5Hz, 1H), 6.82 (d, J=7.9Hz, 1H), 6.64 (dd, J=7.5, 7.5Hz, 1H), 4.93 (s, 2H, $NH_2$), 4.86 (s, 2H), 3.88 (s, 6H). | 15, 33 |

TABLE 4b-continued

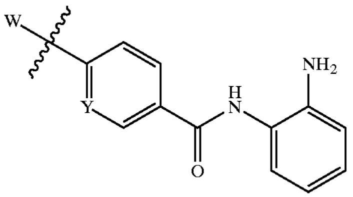

| Ex. | Cpd | W | Y | Z | Name | Characterization | Schm |
|---|---|---|---|---|---|---|---|
| 299 | 440 | 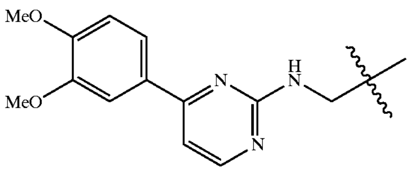 | CH | CH | N-(2-Amino-phenyl)-4-{[4-(3,4-dimethoxy-phenyl)-pyrimidin-2-ylamino]-methyl}-benzamide | $^1$H NMR (300MHz, DMSO-$d_6$) δ (ppm): 9.64 (s, 1H), 8.35 (d, J=4.8Hz, 1H), 7.97 (d, J=7.9Hz, 2H), 7.89 (m, 1H), 7.72 (m, 2H), 7.55 (d, J=7.5Hz, 2H), 7.2 (d, J=5.3Hz, 2H), 7.10 (d, J=8.4Hz, 1H), 7.01 (m, 1H), 6.82 (d, J=7.0Hz, 1H), 6.41 (t, J=7.5Hz, 1 H), 4.92 (s, 2H, $NH_2$), 4.68 (d, J=6.2Hz, 2H), 3.82 (s, 6H). | 15, 1, 33 |
| 300 | 441 | 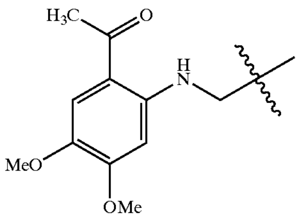 | CH | CH | 4-[(2-Acetyl-4,5-dimethoxy-phenylamino)-methyl]-N-(2-amino-phenyl)-benzamide | $^1$H NMR (300MHz, DMSO-$d_6$) δ (ppm): 9.68 (s, 1H), 9.45 (t, J=5.7Hz, 1H), 8.01 (d, J=7.9Hz, 2H), 7.54 (d, J=8.4Hz, 2H), 7.32 (s, 1H), 7.21 (d, J=7.5Hz, 1H), 7.02 (dd, J=6.6, 7.5Hz, 1H), 6.83 (d, J=7.5Hz, 1H), 6.65 (dd, J=7.0, 7.5Hz, 1H), 6.31 (s, 1H), 4.95 (s, 2H, $NH_2$), 4.63 (d, J=5.7Hz, 2H), 3.78 (s, 3H), 3.76 (s, 3H). | 33 |
| 301 | 442 | 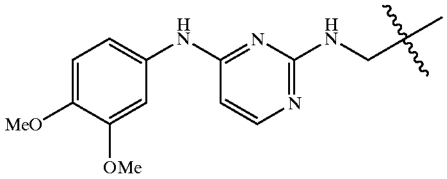 | CH | CH | N-(2-Amino-phenyl)-4-{[4-(3,4-dimethoxy-phenylamino)-pyrimidin-2-ylamino]-methyl}-benzamide | $^1$H NMR (300MHz, $CD_3OD$ + $CDCl_3$) δ (ppm): 7.99 (d, J=7.9Hz, 2H), 7.80 (d, J=6.2Hz, 1H), 7.76 (s, 1H), 7.52 (d, J=8.4Hz, 2H), 7.27 (m, 1H), 7.14 (m, 1H), 7.05 (dd, J=2.2, 8.8Hz, 1H), 6.95 (d, J=7.9Hz, 1H), 6.88 (d, J=8.8Hz, 1H), 6.83 (d, J=7.9Hz, 1H), 6.08 (d, J=6.2Hz, 1H), 4.75 (s, 2H), 3.79 (s, 3H), 3.42 (s, 3H). | 1, 33 |

TABLE 4b-continued

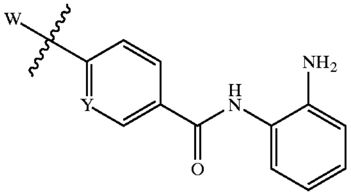

| Ex. | Cpd | W | Y | Z | Name | Characterization | Schm |
|---|---|---|---|---|---|---|---|
| 302 | 443 | 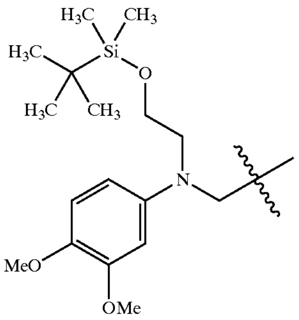 | CH | CH | N-(2-Amino-phenyl)-4-{[[2-(tert-butyl-dimethyl-silanyloxy)-ethyl]-(3,4-dimethoxy-phenyl)-amino]-methyl}-benzamide | $^1$H NMR (300MHz, DMSO-$d_6$) δ (ppm): 9.66 (s, 1H), 7.96 (d, J=8.4Hz, 2H), 7.42 (d, J=7.9Hz, 2H), 7.20 (d, J=7.5Hz, 1H), 7.02 ((dd, J=6.6, 8.4Hz, 1H), 6.83 (d, J=7.0Hz, 1H), 6.77 (d, J=8.8Hz, 1H), 6.65 (dd, J=7.0, 7.0Hz, 1H), 6.44 (d, J=2.6Hz, 1H), 6.19 (dd, J=2.6, 8.8Hz, 1H), 4.93 (s, 2H), 4.67 (s, 2H), 3.88 (t, J=5.7Hz, 2H), 3.71 (s, 3H), 3.67 (s, 3H), 3.60 (t, J=5.5Hz), 0.96 (s, 9H), 0.06 (s, 6H). | 33 |
| 303 | 444 | 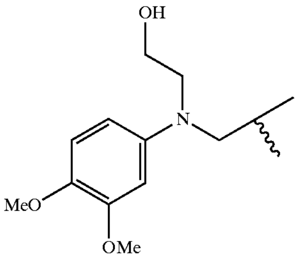 | CH | CH | N-(2-Amino-phenyl)-4-{[(3,4-dimethoxy-phenyl)-(2-hydroxy-ethyl)-amino]-methyl}-benzamide | $^1$H NMR (300MHz, DMSO-$d_6$) δ (ppm) δ (ppm): 9.65 (s, 1H), 7.96 (d, J=7.5Hz, 2H), 7.42 (d, J=7.5Hz, 2H), 7.21 (d, J=7.5Hz, 1H), 7.02 ((dd, J=7.0, 7.5Hz, 1H), 6.83 (d, J=7.9Hz, 1H), 6.78 (d, J=8.8Hz, 1H), 6.65 (dd, J=7.0, 7.5Hz, 1H), 6.44 (s, 1H), 6.19 (d, J=8.8Hz, 1H), 4.94 (s, 2H), 4.79 (m, 1H), 4.66 (s, 2H), 3.67 and 3.71 (2s and broading underneath, 8H), 3.55 (m, 2H). | 33, 23 |
| 304 | 445 | 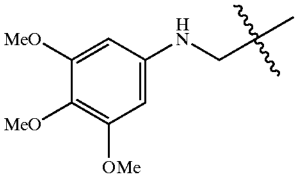 | CH | N | N-(2-Amino-phenyl)-6-[(3,4,5-trimethoxy-phenylamino)-methyl]-nicotinamide | $^1$H NMR (300MHz, DMSO-$d_6$) δ (ppm): 9.82 (s, 1H), 9.13 (s, 1H), 8.33 (d, J=8.0Hz, 1H), 7.56 (d, J=8.5Hz, 1H), 7.21 (d, J=7.7Hz, 1H), 7.03 ((dd, J=7.4, 7.7Hz, 1H), 6.82 (d, J=8.0Hz, 1H), 6.40 (dd, J=7.4, 7.7Hz, 1H), 6.31 (t, J=5.8Hz, 1H), 5.96 (s, 2H), 5.01 (s, 2H), 4.48 (d, J=5.8Hz, 2H), 3.70 (s, 6H), 3.56 (s, 3H). | 33 |

TABLE 4b-continued

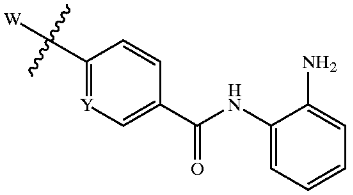

| Ex. | Cpd | W | Y | Z | Name | Characterization | Schm |
|---|---|---|---|---|---|---|---|
| 305 | 446 | 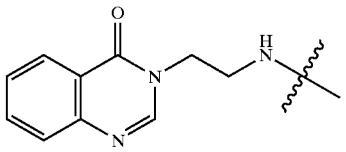 | CH | N | N-(2-Amino-phenyl)-6-[2-(4-oxo-4H-quinazolin-3-yl)-ethylamino]-nicotinamide | $^1$H NMR (300MHz, DMSO-$d_6$) δ (ppm): 8.69 (d, J=2.2Hz, 1H), 8.46 (s, 1H), 8.40 (d, J=8.8Hz, 1H), 8.32–8.36 (m, 1H), 7.91–7.96 (m, 1H), 7.77 (m, 1H), 7.67 (m, 1H) 7.5 (m, 4H), 7.2 (s, 1H), 4.46 (t, J=5.9Hz, 1H), 4.09 (t, J=5.9Hz, 2H). | 3 |
| 306 | 447 | 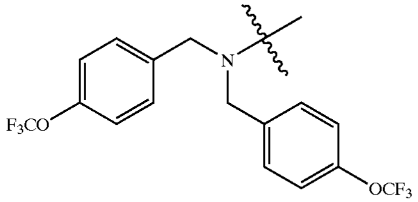 | CH | CH | N-(2-Amino-phenyl)-4-[bis-(3-trifluoromethoxy-benzyl)-amino]-benzamide | $^1$H NMR (300MHz, DMSO-$d_6$) δ (ppm): 9.37 (s, 1H), 7.84 (d J=8.8Hz, 2H), 7.54 (dd, J=7.9, 7.9Hz, 2H), 7.18–7.37 (m, 6H), 7.17 (d, J=7.0Hz, 1H), 6.99 (dd, J=7.0, 7.9Hz, 1H), 6.82 (m, 3H), 6.63 (dd, J=7.5, 7.5Hz, 1H), 4.94 (s, 4H), 4.86 (s, 2H). | 33 |
| 307 | 448 | 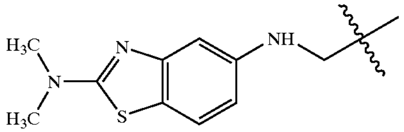 | CH | CH | N-(2-Amino-phenyl)-4-[(2-dimethylamino-benzothiazol-5-ylamino)-methyl]-benzamide | $^1$H NMR (300MHz, DMSO-$d_6$) δ (ppm): 9.58 (s, 1H), 7.92 (d, J=7.9Hz, 2H), 7.49 (d, J=7.9Hz, 2H), 7.34 (d, J=8.8Hz, 1H), 7.15 (d, J=7.5Hz, 1H), 6.96 (t, J=7.9Hz, 1H), 6.76 (d, J=7.9Hz, 1H), 6.59 (d, J=7.5Hz, 1H), 6.55 (s, 1H), 6.44 (d, J=8.4Hz, 1H), 6.34 (t, J=5.7Hz, 1H), 4.88 (bs, 2H), 4.37 (d, J=5.7Hz, 2H), 3.06 (s, 6H). | 33 |
| 308 | 449 | 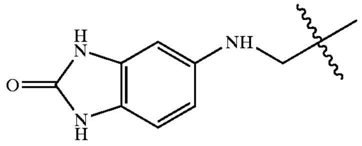 | CH | CH | N-(2-Amino-phenyl)-4-[(2-oxo-2,3-dihydro-1H-benzoimidazol-5-ylamino)-methyl]-benzamide | $^1$H NMR (300MHz, DMSO-$d_6$) δ (ppm): 10.2 (s, 1H), 10.1 (s, 1H), 9.62 (s, 1H), 7.94 (d, J=7.9Hz, 2H), 7.41 (d, J=7.9Hz, 2H), 7.15 (d, J=7.5Hz, 1H), 6.96 (t, J=7.5Hz, 1H), 6.77 (d, J=7.9Hz, 1H), 6.69 (d, J=8.4Hz, 1H), 6.59 (t, J=7.5Hz, 1H), 6.34 (d, J=8.4Hz, 1H), 6.34 (t, J=8.4Hz, 1H), 6.30 (s, 1H), 4.89 (bs, 2H), 4.72 (s, 2H). | 33 |

TABLE 4b-continued

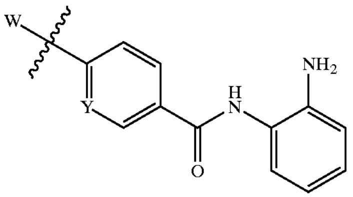

| Ex. | Cpd | W | Y | Z | Name | Characterization | Schm |
|---|---|---|---|---|---|---|---|
| 309 | 450 | 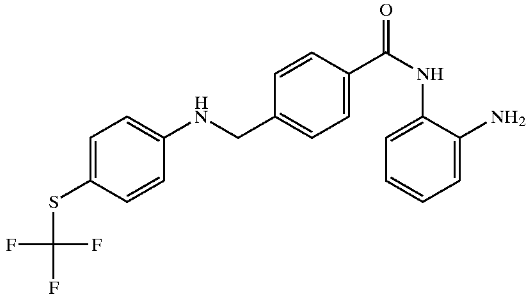 | CH | CH | N-(2-Amino-phenyl)-4-[(4-trifluoromethylsulfanyl-phenylamino)-methyl]-benzamide | $^1$H NMR (300 MHz, DMSO-$d_6$) δ (ppm): 9.60 (s, 1H), 7.94 (d, J=7.9Hz, 2H), 7.46 (d, J=7.9Hz, 2H), 7.35 (d, J=8.4Hz, 2H), 7.15 (d, J=7.9Hz, 1H), 7.11 (d, J=6.2Hz, 1H), 6.97 (t, J=7.0Hz, 1H), 6.77 (d, J=7.5Hz, 1H), 6.66 (d, J=8.4Hz, 2H), 6.60 (t, J=7.9Hz, 1H), 4.88 (bs, 2H), 4.72 (d, J=6.2Hz, 2H). | 33 |
| 310 | 451 | 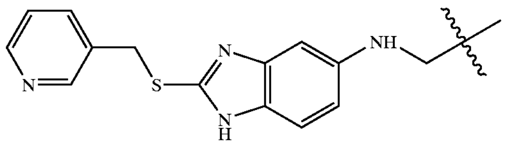 | CH | CH | N-(2-Amino-phenyl)-4-{[2-(pyridin-3-ylmethylsulfanyl)-1H-benzoimidazol-5-ylamino]-methyl}-benzamide | $^1$H NMR (300MHz, $CD_3OD$) δ (ppm): 8.67 (d, J=1.8Hz, 1H), 8.47 (dd, J=1.3, 4.4Hz, 1H), 8.08 (s, 1H), 8.03 (d, J=7.9Hz, 2H), 7.92 (d, J=8.4Hz, 1H), 7.87 (d, J=7.9Hz, 2H), 7.58 (d, J=8.4Hz, 1H), 7.36–7.30 (m, 3H); 7.20–7.15 (m, 1H), 7.08 (dt, J=1.3, 8.4Hz, 1H), 6.94 (dd, J=1.3, 7.9Hz, 1H), 6.77 (d, J=2.2Hz, 1H), 6.74 (d, J=2.2Hz, 1H), 6.65 (d, J=1.8Hz, 1H), 4.55 (s, 2H); 4.20 (bs, 2H); 3.36 (s, 2H). | 33 |
| 311 | 452 | 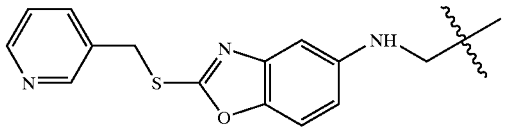 | CH | CH | N-(2-Amino-phenyl)-4-{[2-(pyridin-3-ylmethylsulfanyl)-benzooxazol-5-ylamino]-methyl}-benzamide | $^1$H NMR (300MHz, $CD_3OD$) δ (ppm): 8.60 (s, 1H), 8.36 (d, J=4.4Hz, 1H), 7.89 (d, J=7.9Hz, 2H), 7.87 (m, 1H); 7.47 (d, J=7.9Hz, 2H), 7.30 (t, J=6.6Hz, 1H), 7.20–7.15 (m, 2H); 7.04 (t, J=7.5Hz, 1H), 6.87 (d, J=7.9Hz, 1H), 6.73 (t, J=7.5Hz, 1H), 6.66 (s, 1H); 6.61 (d, J=8.8Hz, 1H), 4.87 (s, 2H); 4.45 (s, 2H); 4.37 (s, 2H); 3.35 (s, 2H). | 33 |

TABLE 4b-continued

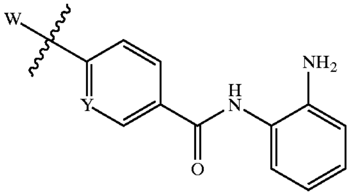

| Ex. | Cpd | W | Y | Z | Name | Characterization | Schm |
|---|---|---|---|---|---|---|---|
| 312 | 453 | 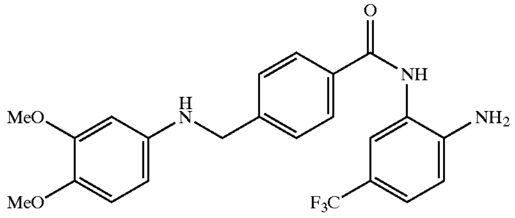 | | | N-(2-Amino-5-trifluoromethyl-phenyl)-4-[(3,4-dimethoxy-phenylamino)-methyl]-benzamide | $^1$H NMR (300MHz, $CDCl_3$) δ (ppm): 8.21 (s, 1H); 7.90 (d, J=8.4Hz, 2H); 7.54 (m, 1H); 7.50 (d, J=8.4Hz, 2H); 7.41–7.34 (m, 2H); 6.87 (d, J=8.4Hz, 1H); 7.77 (d, J=8.4Hz, 1H); 6.35 (d, J=2.2Hz, 1H); 6.20 (dd, J=2.2, 8.8Hz, 1H); 4.43 (s, 2H); 4.29 (s, 2H); 3.84 (s, 6H). | 33 |
| 313 | 454 | 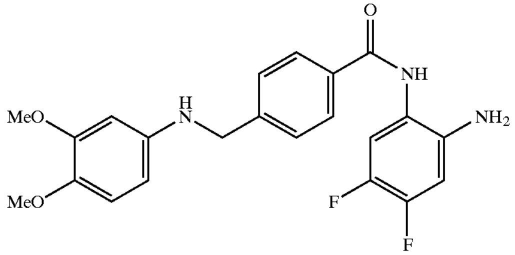 | | | N-(2-Amino-4,5-difluoro-phenyl)-4-[(3,4-dimethoxy-phenylamino)-methyl]-benzamide | $^1$H NMR (300MHz, $CDCl_3$) δ (ppm): 8.21 (s, 1H); 7.84 (d, J=7.9Hz, 2H); 7.45 (d, J=7.9Hz, 2H); 7.20 (dd, J=2.6, 8.4Hz, 1H); 6.76 (d, J=8.8Hz, 1H); 6.57 (dd, J=3.9, 7.9Hz, 1H); 6.32 (d, J=2.6Hz, 1H); 6.16 (dd, J=2.6, 8.4Hz, 1H); 4.40 (s, 2H); 3.82 (s, 9H). | 33 |
| 314 | 455 | 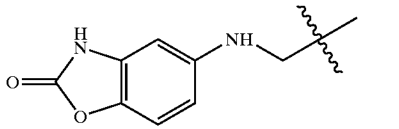 | CH | CH | N-(2-Amino-phenyl)-4-[(2-oxo-2,3-dihydro-benzooxazol-5-ylamino)-methyl]-benzamide | $^1$H NMR (300MHz, DMSO-$d_6$) δ (ppm): 9.60 (s, 1H); 7.93 (d, J=7.9Hz, 2H); 7.47 (d, J=7.9Hz, 2H); 7.16 (d, J=7.5Hz, 1H); 6.97 (m, 2H); 6.78 (d, J=7.5Hz, 1H); 6.59 (t, J=7.5Hz, 1H); 6.35 (t, J=5.7Hz, 1H); 6.27 (m, 2H); 4.88 (bs, 2H); 4.34 (d, J=6.2Hz, 2H). | 33 |
| 315 | 456 | 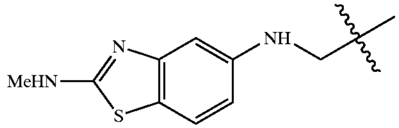 | CH | CH | N-(2-Amino-phenyl)-4-[(2-methylamino-benzothiazol-5-ylamino)-methyl]-benzamide | $^1$H NMR (300MHz, DMSO-$d_6$) δ (ppm): 7.92 (d, J=7.9Hz, 2H), 7.66 (d, J=4.4Hz, 1H), 7.49 (d, J=7.9Hz, 2H), 7.26 (d, J=8.4Hz, 1H), 7.15 (d, J=7.9Hz, 1H), 6.96 (d, J=8.4Hz, 1H), 6.59 (t, J=7.9Hz, 1H), 6.53 (s, 1H), ); 6.40 (dd, J=1.3, 8.4Hz, 1H); 6.28 (t, J=5.7Hz, 1H), 4.88 (bs, 2H), 4.36 (d, J=5.7Hz, 2H), 2.85 (d, J=4.4Hz, 3H). | 33 |

TABLE 4b-continued

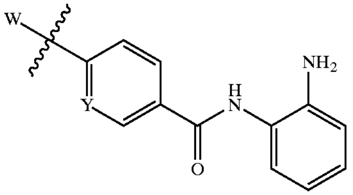

| Ex. | Cpd | W | Y | Z | Name | Characterization | Schm |
|---|---|---|---|---|---|---|---|
| 316 | 457 | 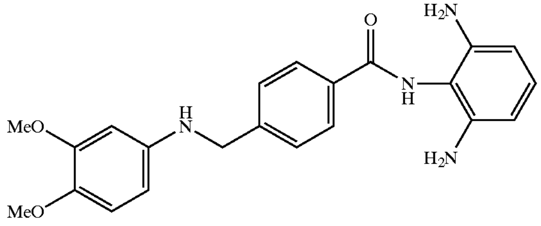 | | | N-(2,6-Diamino-phenyl)-4-[(3,4-dimethoxy-phenylamino)-methyl]-benzamide | $^1$H NMR (300MHz, $CDCl_3$) δ (ppm): 8.09 (s, 1H); 7.88 (d, J=7.5Hz, 2H); 7.48 (d, J=7.5Hz, 2H); 6.97 (d, J=7.9Hz, 1H); 6.73 (d, J=8.4Hz, 2H); 6.64 (d, J=7.9Hz, 1H); 6.29 (s, 1H); 6.14 (d, J=8.4Hz, 1H); 4.39 (s, 2H); 3.81 (s, 3H); 3.80 (s, 3H); 3.70 (bs, 5H). | 33 |
| 317 | 458 | 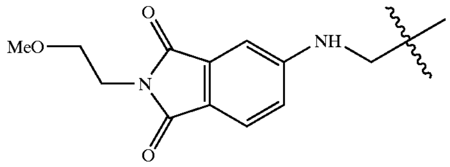 | CH | CH | N-(2-Amino-phenyl)-4-{[2-(2-methoxy-ethyl)-1,3-dioxo-2,3-dihydro-1H-isoindol-5-ylamino]-methyl}-benzamide | $^1$H NMR (300MHz, DMSO-$d_6$) δ (ppm): 9.61 (s, 1H); 7.95 (d, J=7.9Hz, 2H); 7.73 (t, J=5.7Hz, 1H); 7.52 (d, J=8.4Hz, 1H); 7.47 (d, J=7.9Hz, 2H); 7.15 (d, J=7.9Hz, 1H); 6.97 (d, J=7.5Hz, 1H); 6.92 (bs, 1H); 6.86 (d, J=8.4Hz, 1H); 6.77 (d, J=7.9Hz, 1H); 6.59 (t, J=7.5Hz, 1H); 4.89 (bs, 2H); 4.54 (d, J=5.7Hz, 2H); 3.65 (t, J=5.3Hz, 2H); 3.47 (t, J=5.3Hz, 2H); 3.20 (s, 3H); | 33 |
| 318 | 459 | 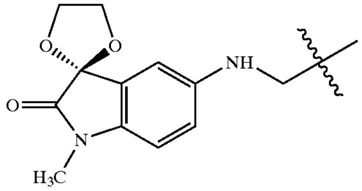 | CH | CH | N-(2-Amino-phenyl)-4-{[3-spiro[1',2']dioxolane-1-methyl-2-oxo-2,3-dihydro-1H-indol-5-ylamino)-methyl}-benzamide | $^1$H NMR (300MHz, DMSO-$d_6$) δ (ppm): 9.59 (s, 1H); 7.92 (d, J=8.3Hz, 2H); 7.46 (d, J=8.3Hz, 2H); 7.15 (d, J=7.5Hz, 1H); 6.96 (t, J=7.0Hz, 1H); 6.78–6.71 (m, 3H); 6.62–6.54 (m, 2H); 6.26 (t, J=7.5Hz, 1H) 4.87 (s, 2H); 4.36–4.32 (m, 4H); 4.23–4.19 (m, 2H), 2.98 (s 3H). | 33 |
| 319 | 460 | 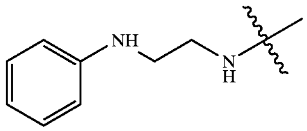 | CH | N | N-(2-Amino-phenyl)-6-(2-phenylamino-ethylamino)-nicotinamide | $^1$H NMR (300MHz, $CD_3OD$) δ (ppm): 8.67 (d, J=2.2Hz, 1H), 7.97 (dd, J=2.5, 8.9Hz, 1H), 7.58 (m, 1H); 7.51 (m, 1H); 7.15 (dd, J=1.1, 7.7Hz, 1H), 7.08 (m, 2H); 6.89 (dd, J=1.4, 8.0Hz, 1H), 6.76 (dt, J=4.4, 7.7Hz, 1H), 6.67 (d, J=7.7Hz, 2H), 6.60 (m, 2H); 4.87 (bs, 2H); 3.60 (t, J=6.3Hz, 2H), 3.35 (t, J=6.3Hz, 2H). | 33 |

TABLE 4b-continued

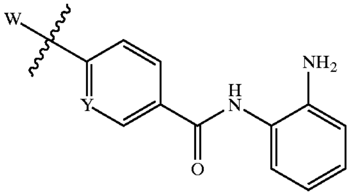

| Ex. | Cpd | W | Y | Z | Name | Characterization | Schm |
|---|---|---|---|---|---|---|---|
| 320 | 461 | 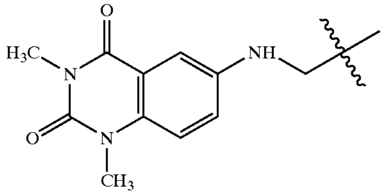 | CH | CH | N-(2-Amino-phenyl)-4-[(1,3-dimethyl-2,4-dioxo-1,2,3,4-tetrahydro-quinazolin-6-ylamino)-methyl]-benzamide | $^{1}$H NMR (300MHz, DMSO-$d_6$) δ (ppm): 9.59 (s, 1H); 7.92 (d, J=7.9Hz, 2H); 7.47 (d, J=7.9Hz, 2H); 7.22 (d, J=8.8Hz, 1H); 7.16–7.09 (m, 3H); 6.96 (t, J=7.5Hz, 1H); 6.76 (d, J=7.9Hz, 1H); 6.65–6.56 )m, 2H); 4.87 (s, 2H); 4.42 (d, J=5.3Hz, 2H); 3.44 (s, 3H); 3.26 (s, 3H). | 33 |
| 321 | 462 | 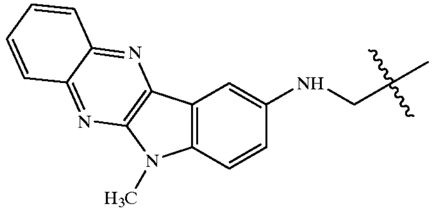 | CH | CH | N-(2-Amino-phenyl)-4-[(6-methyl-6H-indolo[2,3-b]quinoxalin-9-ylamino)-methyl]-benzamide | $^{1}$H NMR (300MHz, DMSO-$d_6$) δ (ppm): 9.60 (s, 1H); 8.19 (d, J=8.4Hz, 1H); 8.05 (d, J=8.4Hz, 1H); 7.95 (d, J=7.9Hz, 2H); 7.76 (t, J=7.0Hz, 1H); 7.65 (t, J=7.9Hz, 1H); 7.57 (d, J=7.9Hz, 2H); 7.54 (d, J=8.8Hz, 1H); 7.41 (d, J=1.3Hz, 1H); 7.22 (dd, J=1.8, 8.8Hz, 1H); 7.14 (d, J=7.9Hz, 1H); 6.95 (t, J=7.5Hz, 1H); 6.76 (t, J=7.9Hz, 1H); 6.57 (t, J=7.5Hz, 1H); 6.51 (bs, 1H); 4.86 (bs, 2H); 4.54 (d, J=4.8Hz, 2H); 3.85 (s, 3H). | 33 |
| 322 | 463 | 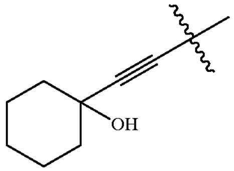 | N | CH | N-(2-Amino-phenyl)-6-(1-hydroxy-cyclohexylethynyl)-nicotinamide | LRMS calc: 335.40, found: 336.1 $(MH)^+$ | 14, 3 |
| 323 | 464 | 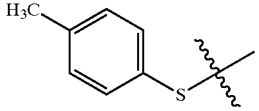 | N | CH | N-2-Amino-phenyl)-6-p-tolylsulfanyl-nicotinamide | LRMS calc: 335.42, found: 336.1 $(MH)^+$ | 14, 3 |

TABLE 4b-continued

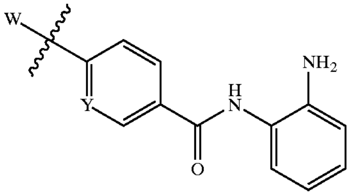

| Ex. | Cpd | W | Y | Z | Name | Characterization | Schm |
|---|---|---|---|---|---|---|---|
| 324 | 465 | 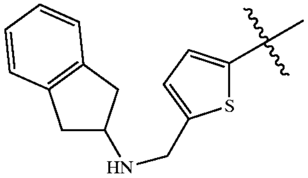 | CH | CH | N-(2-Amino-phenyl)-4-[5-(indan-2-ylaminomethyl)-thiophen-2-ylmethyl]-benzamide | LRMS calc: 453.6, found: 454.2 $(MH)^+$ | 21 |
| 325 | 466 | 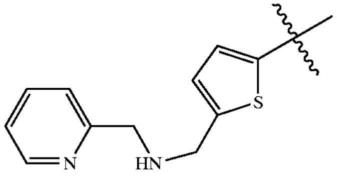 | CH | CH | N-(2-Amino-phenyl)-4-[5-(pyridin-2-ylaminomethyl)-thiophen-2-ylmethyl]-benzamide | LRMS calc: 414.52, found: 415 $(MH)^+$ | 21 |
| 326 | 467 | 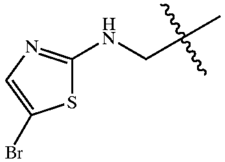 | CH | CH | N-(2-Amino-phenyl)-4-[(5-bromo-thiazol-2-ylamino)methyl]-benzamide | LRMS calc: 403.3, found: 404 $(MH)^+$ | 21 |
| 327 | 468 | 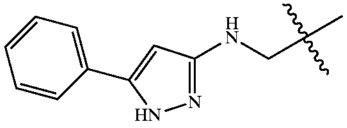 | CH | CH | N-(2-Amino-phenyl)-4-[(5-phenyl-1H-pyrazol-3-ylamino)-methyl]-benzamide | LRMS calc: 483.45, found: 484.1 $(MH)^+$ | 21 |

TABLE 4c

Characterization of Additional Compounds

| Ex. | Cpd | Compound | Name | Characterization | Schm |
|---|---|---|---|---|---|
| 426 | 571 | 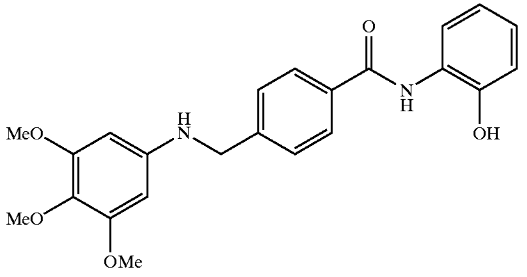 | N-(2-Hydroxy-phenyl)-4-[(3,4,5-trimethoxy-phenylamino)-methyl]-benzamide | $^1$H NMR (DMSO-$d_6$): δ 9.57(brs, 1H), 7.98(d, J=8.3Hz, 2H), 7.75(d, J=7.5Hz, 1H), 7.57(d, J=8.3Hz, 2H), 7.07(t, J=8.3Hz, 1H), 6.95(d, J=7.0Hz, 1H), 6.85(t, J=7.9Hz, 1H), 6.21(t, J=6.1Hz, 1H), 5.95(s, 2H), 4.38(d, J=5.7Hz, 2H), 3.70(s, 6H), 3.56(s, 3H). | 33, 55 |
| 427 | 572 | 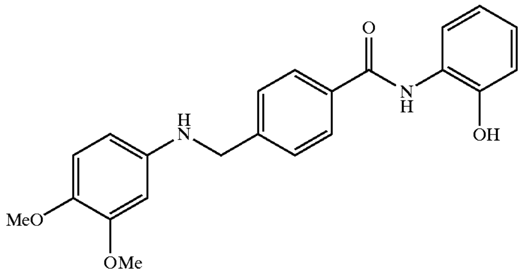 | N-(2-hydroxy-phenyl)-4-[(3,4-Dimethoxy-phenylamino)-methyl]-benzamide | $^1$H NMR (300MHz, DMSO-$D_6$) δ (ppm): 9.9(bs, 1H), 9.53(s, 1H), 7.97(d, J=7.9Hz, 2H), 7.73(d, J=7.5Hz, 1H), 7.55(d, J=7.9Hz, 2H), 7.08(dd, J=7.5, 7.5Hz, 1H), 6.96(d, J=7.9, Hz, 1H), 6.88(dd, J=7.5, 7.5Hz, 1H), 6.72(d, J=8.8Hz, 1H), 6.38(s, 1H), 6.05(m, 2H), 4.36(d, J=5.7Hz, 2H), 3.72(s, 3H), 3.65(s, 3H). | 33, 55 |
| 428 | 573 | 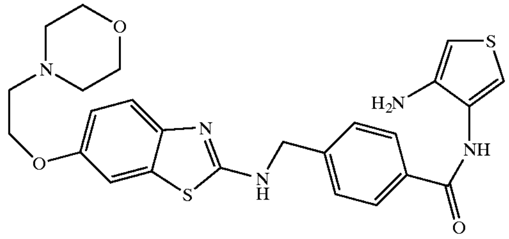 | N-(4-Amino-thiophen-3-yl)-4-{[6-(2-morpholin-4-yl-ethoxy)-benzothiazol-2-ylamino]-methyl}-benzamide | $^1$H NMR: (Acetone-$d_6$) δ (ppm): 9.09(bs, 1H), 8.03(d, J=7.9Hz, 2H), 7.96(d, J=7.5Hz, 1H), 7.65(d, J=7.9Hz, 2H), 7.61(d, J=3.5Hz, 1H), 7.51(bs, 2H), 7.41(d, J=8.8Hz, 1H), 7.36(s, 1H), 6.95(d, J=6.2Hz, 1H), 6.35(d, J=3.5Hz, 1H), 4.85(s, 2H), 4.20(t, J=5.7Hz, 2H), 3.69)t, J=4.4Hz, 4H), 2.87–2.81(m, 2H), 2.62–2.57(m, 4H). | 33, 60 |

TABLE 4c-continued

Characterization of Additional Compounds

| Ex. | Cpd | Compound | Name | Characterization | Schm |
| --- | --- | --- | --- | --- | --- |
| 429 | 574 | 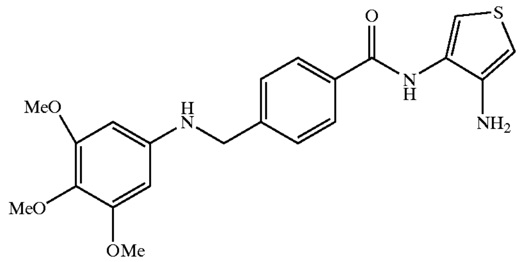 | N-(4-Amino-thiophen-3-yl)-4-[(3,4,5-trimethoxy-phenylamino)-methyl]-benzamide | $^1$H NMR (DMSO-$d_6$): δ 9.66(brs, 1H), 7.94(d, J=7.5Hz, 2H), 7.56(d, J=7.9Hz, 2H), 6.22–6.16(m, 1H), 5.94(s, 2H), 4.91(s, 2H), 4.38(d, J=5.7Hz, 4H), 3.70(s, 6H), 3.55(s, 3H). | 33, 60 |
| 430 | 575 | 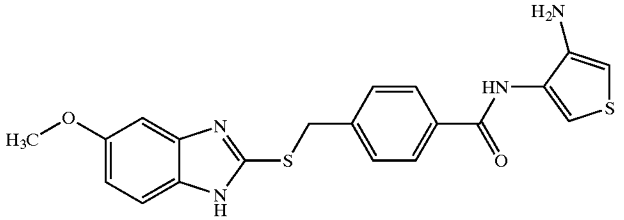 | N-(4-Amino-thiophen-3-yl)-4-(5-methoxy-1H-benzoimidazol-2-ylsulfanylmethyl)-benzamide | (DMSO) δ (ppm): 12.43(bs, 1H), 9.59(bs, 1H), 7.84(d, J=8.1Hz, 2H), 7.56(d, J=8.1Hz, 2H), 7.48(d, J=3.7Hz, 1H), 7.32(bs, 1H, SCH), 6.96(bs, 1H, SCH), 6.74(dd, J=8.8, 2.2Hz, 1H), 6.11(d, J=3.7Hz, 1H), 4.84(s, 2H), 4.59(s, 2H), 3.76(s, 3H). LRMS: 410.1(calc) (M); 411.2(found)(M + H) + | 36, 60 |
| 431 | 576 | 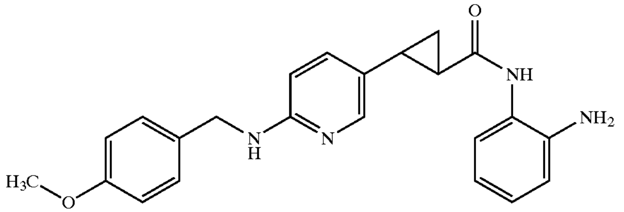 | 2-[4-(4-Methoxy-benzylamino)-phenyl]-cyclopropanecarboxylic acid (2-amino-phenyl)-amide | $^1$H-NMR (DMSO-d6), δ (ppm): 9.22(bs, 1H), 8.19(bs, 1H), 7.63(d, J=7.1Hz, 1H), 7.53(t, J=4.2Hz, 1H), 7.41(dd, J=9.2, 1.5Hz, 1H), 7.25(d, J=8.3Hz, 2H), 7.06(d, J=7.1Hz, 1H), 6.85(d, J=8.3Hz, 2H), 6.62–6.59(m, 3H), 4.51(d, J=4.2Hz, 2H), 3.78(s, 3H), 2.77(d, J=3.1Hz, 1H), 2.45(d, J=1.1Hz, 1H), 1.22(m, 1H), 1.05(m, 1H). | |

TABLE 4c-continued

Characterization of Additional Compounds

| Ex. | Cpd | Compound | Name | Characterization | Schm |
|---|---|---|---|---|---|
| 432 | 577 | 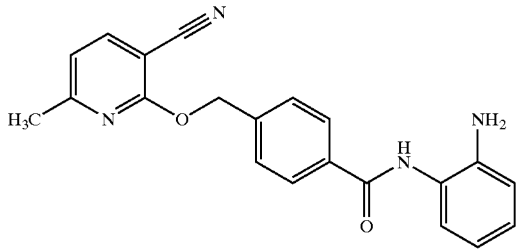 | N-(2-Amino-phenyl)-4-(3-cyano-6-methyl-pyridin-2-yloxymethyl)-benzamide | $^1$H NMR (DMSO-$d_6$) δ (ppm): 9.72(brs, 1H), 8.23(d, J=7.5Hz, 1H), 8.06(d, J=7.9Hz, 2H), 7.67(d, J=7.9Hz, 2H), 7.23(d, J=7.9Hz, 1H), 7.15(d, J=7.9Hz, 1H), 7.03(t, J=7.5Hz, 1H), 6.84(d, J=7.9Hz, 1H), 6.65(t, J=7.5hz, 1H), 5.62(brs, 2H), 4.97(brs, 2H) | 11 |
| 433 | 578 | 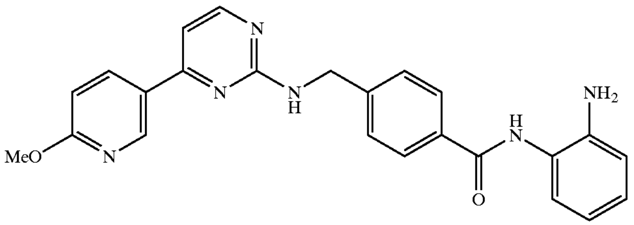 | N-(2-Amino-phenyl)-4-{[4-(6-methoxy-pyridin-3-yl)-pyrimidin-2-ylamino]-methyl}-benzamide | $^1$H NMR (300MHz, DMSO-$D_6$) δ (ppm): 9.63(s, 1H), 8.95(d, J=2.2Hz, 1H), 8.40(d, J=5.3Hz, 2H), 7.96(m, 3H), 7.54(d, J=7.5Hz, 2H), 7.22(dd, J=5.3, 7.8Hz, 2H), 7.01(m, 2H), 6.83(d, J=7.5Hz, 1H), 6.64(dd, J=7.0, 7.9Hz, 1H), 4.92(s, 2H), 4.70(d, J=6.2Hz, 2H), 3.98(s, 3H). | 15, 33 |
| 434 | 579 | 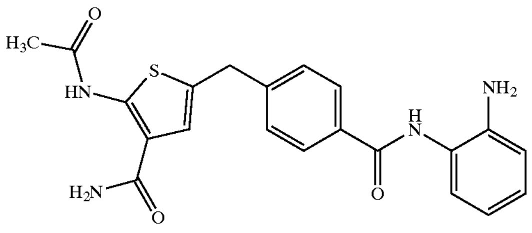 | 2-Acetylamino-5-[4-(2-amino-phenylcarbamoyl)-benzyl]-thiophene-3-carboxamide | $^1$H NMR: (DMSO) δ (ppm): 11.98(bs, 1H), 9.61(bs, 1H), 7.93(d, J=8.1Hz, 2H), 7.81(s, 1H), 7.45(s, 1H), 7.38(d, J=8.1Hz, 1H), 7.19(s, 1H), 7.16(d, J=7.3Hz, 1H), 6.97(dd, J=7.0, 7.0Hz, 1H), 6.77(d, J=7.3Hz, 1H), 6.59(dd. J=7.3, 7.3Hz, 1H), 4.88(bs, 2H), 4.10(s, 2H), 2.15(s, 3H). | 49 |

TABLE 4c-continued

Characterization of Additional Compounds

| Ex. | Cpd | Compound | Name | Characterization | Schm |
|---|---|---|---|---|---|
| 435 | 580 | 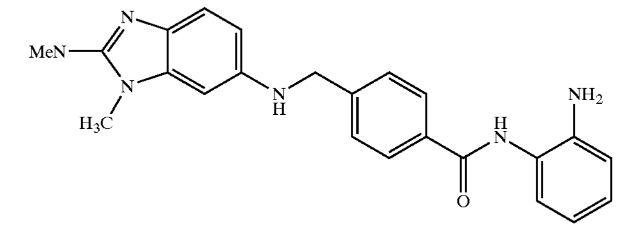 | N-(2-Amino-phenyl)-4-[(3-methyl-2-methylamino-3H-benzoimidazol-5-ylamino)-methyl]-benzamide | $^1$H NMR (DMSO) δ (ppm): 9.56(s, 1H), 7.90(d, J=7.9Hz, 2H), 7.49(d, J=7.9Hz, 2H), 7.15(d, J=7.5Hz, 1H), 6.95(t, J=7.5Hz, 1H), 6.78(dd, J=13.2, 8.35Hz, 2H), 6.58(t, J=7.5Hz, 1H), 6.39(s, 1H), 6.31(m, 2H), 5.75(t, J=6.15Hz, 1H), 4.87(s, 2H), 4.32(d, J=5.7Hz, 2H), 3.34(s, 3H), 2.82(d, J=8.5Hz, 3H). | 61 |
| 438 | 591 | 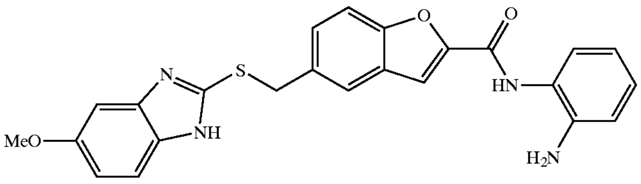 | 5-(5-Methoxy-1H-benzoimidazol-2-ylsulfanylmethyl)-benzofuran-2-carboxylic acid (2-amino-phenyl)amide | $^1$H NMR (DMSO) δ (ppm): 9.84(s, 1H), 7.84(s, 1H), 7.67(s, 1H), 7.63(d, J=8.5Hz, 1H), 7.55(d, J=9.0Hz, 1H), 7.17(d, J=8.0Hz, 1H), 6.97(t, J=7.5Hz, 1H), 6.78(d, J=8.0Hz, 1H), 6.78–6.74(m, 3H), 6.59(t, J=7.5Hz, 1H), 5.71(s, 2H), 4.94(s, 1H), 4.65(s, 2H), 3.76(s, 3H). | 64 |
| 439 | 592 | 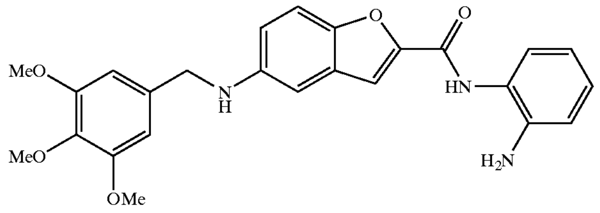 | 5-(3,4,5-Trimethoxy-benzylamino)-benzofuran-2-carboxylic acid (2-amino-phenyl)-amide | $^1$H NMR (DMSO) δ(ppm): 9.69(s, 1H), 7.47(s, 1H), 7.41(d, J=8.8Hz, 1H), 7.19(d, J=6.6Hz, 1H), 6.97(dd, J=7.5, 7.5Hz, 1H), 6.89(dd, J=8.8, 2.2Hz, 1H), 6.79–6.78(m, 2H), 6.74(s, 2H), 6.60(dd, J=7.5, 7.5Hz, 1H), 6.14(t, J=5.7Hz, 1H), 4.92(s, 2H), 4.21(d, J=5.7Hz, 1H), 3.75(s, 6H), 3.31(s, 3H). | 64 |

Scheme 21

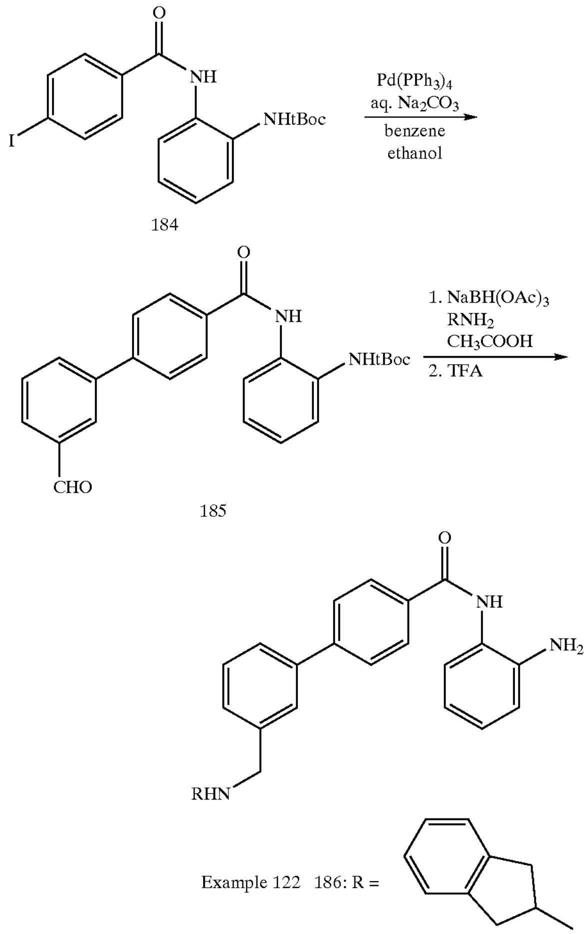

Example 122

Step 1: {2-[(3'-Formyl-biphenyl-4-carbonyl)-amino]-phenyl}-carbamic acid tertbutyl ester (185)

Following the procedure described in Example 15, step 1, but substituting 184 for 140, the title compound 185 was obtained in 74% yield. $^1$H NMR ($CDCl_3$): δ 10.10 (s, 1H), 9.41(s, 1H), 8.13 (m, 1H), 8.07 (d, J=8.4 Hz, 2H), 7.89 (m, 2H), 7.77 (m, 1H), 7.70 (d, J=8.4 Hz, 2H), 7.64 (m, 1H), 7.27–7.09 (m, 3H), 7.03 (s, 1H), 1.52 (s, 9H).

Step 2: N-(2-Aminophenyl)-4-[3-(indan-2-ylaminomethyl) phenyl)]-benzamide (186)

To a stirred solution of biphenyl aldehyde (104 mg, 0.25 mmol) and 2-aminoindane (33.3 mg, 0.25 mmol) in dichloroethane (1 mL) was added sodium triacetoxyborohydride (80 mg, 0.375 mmol) followed by a glacial acetic acid (15 ul, 0.25 mmol), and then the mixture was stirred at room temperature for 3 h. After a removal of the volatiles, the residue was partitioned between ethyl acetate and 10% aqueous sodium bicarbonate solution. The combined organic layers were washed with water, dried and concentrated. Purification by flash chromatography (10% methanol in chloroform) gave the desired Boc-monoprotected product (112 mg, 84% yield) as a white solid. $^1$H NMR ($CDCl_3$): δ9.21 (s, 1H), 8.03 (d, J=8.7 Hz, 2H), 7.83 (m, 1H), 7.69 (d, J=8.7 Hz, 2H), 7.65 (s, 1H), 7.54–7.38 (m, 3H), 7.28 (m, 7H), 6.82 (s, 1H), 3.95 (s, 2H), 3.74 (m, 1H), 3.22 (dd, J=15.6, 6.9 Hz, 2H), 2.89 (dd, J=15.6, 6.6 Hz, 2H), 1.53 (s, 9H).

Following the procedure described in Example 42, step 3, but substituting the previous compound for 46, the title compound 186 was obtained in 98% yield. $^1$H NMR (20% $CD_3OD$ in $CDCl_3$): δ 7.95 (d, J=8.4 Hz, 2H), 7.65 (d, J=8.4 Hz, 2H), 7.57 (m, 1H), 7.54–6.79 (m, 11H), 3.95 (s, 2H), 3.66 (m, 1H), 3.16 (dd, J=15.6, 6.9 Hz, 2H), 2.81 (dd, J=15.6, 6.6 Hz, 2H).

Examples 123–126

Examples 123 to 126 (Compounds 187–190) were prepared using the same procedure as described for compound 186 in Example 122 (scheme 21).

Scheme 22

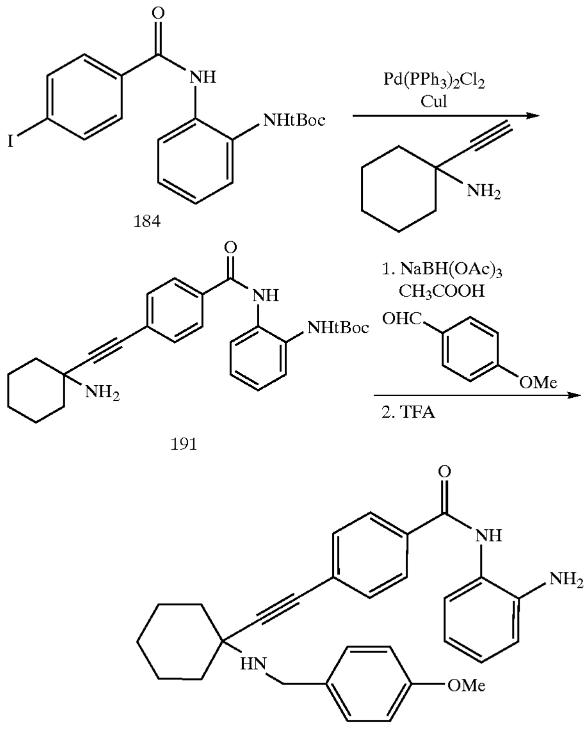

Example 127

Example 127

Step 1: {2-[4-(1-Amino-cyclohexylethynyl)-benzoylamino] phenyl}-carbamic acid tertbutyl ester (191)

A mixture of iodide 184 (438 mg, 1.0 mmol), $Pd(PPh_3)_2Cl_2$ (35 mg, 0.05 mmol), triphenylphosphine (7.6 mg, 0.025 mmol), and 1-ethynylcyclohexylamine (185 mg, 1.5 mmol) was stirred at room temperature in THF (4 mL) containing triethylamine (0.56 mL, 4.0 mmol) for 20 min. To this CuI (3.8 mg, 0.02 mmol) was added and stirring continued for 2 h. The reaction mixture was then diluted with ethyl acetate (30 mL), washed with water, and the organic layer was dried and concentrated. Purification by flash chromatography (10% methanol in chloroform) gave the desired product 191 (420 mg, 97% yield). $^1$H NMR ($CDCl_3$): δ 9.36 (s, 1H), 7.94 (d, J=8.4 Hz, 2H), 7.77 (d, J=7.5 Hz, 1H), 7.47 (d, J=8.4 Hz, 2H), 7.25–6.85 (m, 3H), 2.10–1.30 (m, 10H), 1.51 (s, 9H).

Step 2: N-(2-Aminophenyl)-4-[1-(4-methoxy-benzylamino)-cyclohexylethynyl]-benzamide (192)

Following the procedure described in Example 122, step 2, but substituting p-anisaldehyde for 2-aminoindane, the title compound 192 was obtained in 74% yield. $^1H$ NMR ($CDCl_3$): δ 8.44 (s, 1H), 7.82 (d, J=8.1 Hz, 2H), 7.47 (d, J=8.1 Hz, 2H), 7.31 (d, J=8.4 Hz, 2H), 7.23 (m, 1H), 7.05 (m,1H), 6.84 (d, J=8.7 Hz, 2H), 6.78 (m, 2H), 3.97 (s, 2H), 3.76 (s, 3H), 2.10–1.30 (m, 10H).

dried over anhydrous $MgSO_4$, filtered and concentrated. The crude residue was then purified by flash chromatography on silica gel (AcOEt/hexane: 20/80→50/50) to afford the title compound 197 (4.42 g, 10.83 mmol, 94% yield) as a yellow powder. $^1H$ NMR (300 MHz, $CDCl_3$) δ (ppm): 9.26 (bs, Scheme 23

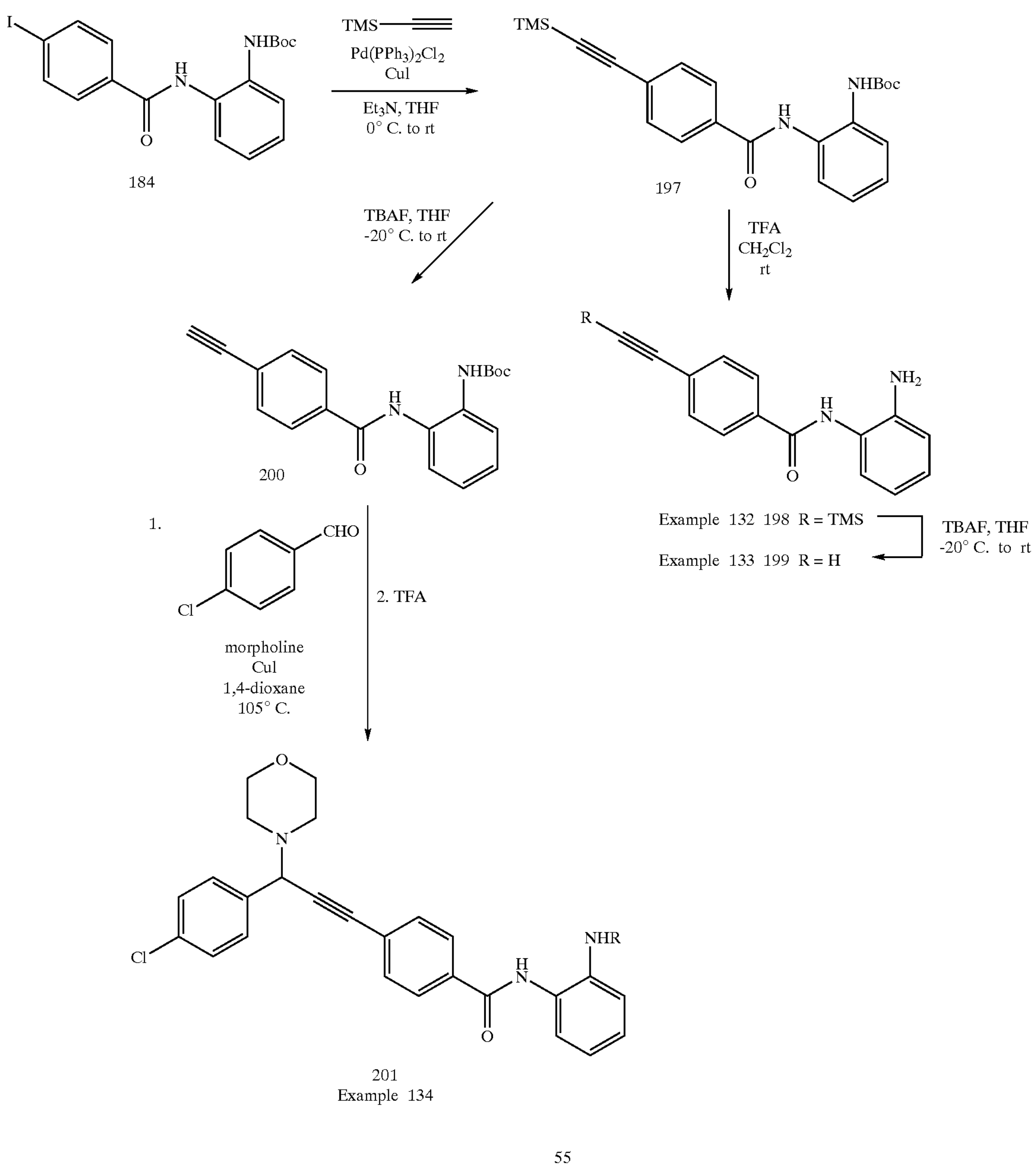

184, 197, 200

Example 132 198 R = TMS

Example 133 199 R = H

201
Example 134

Example 133

Step 1: N-[2-(t-butyloxycarbonyl)-amino-phenyl]-4-(trimethysilylethynyl)-benzamide (197)

To a stirred solution of 184 (5.00 g, 11.41 mmol) in anhydrous THF (100 ml) under nitrogen at 0° C. were added $Pd(PPh_3)_2Cl_2$ (240 mg, 0.34 mmol), CuI (130 mg, 0.69 mmol), and trimethylsilylacetylene (2.10 ml, 14.84 mmol), respectively. Then, anhydrous $Et_3N$ (6.36 ml, 45.66 mmol) was added dropwise. The temperature was slowly warmed up to room temperature over 4 h. The reaction mixture was poured into a saturated aqueous solution of $NH_4Cl$, and diluted with ethyl acetate. After separation, the organic layer was successively washed with sat. $NH_4Cl$, $H_2O$ and brine, 1H), AB system ($\delta_A$=7.91, $\delta_B$=7.55, J=8.3 Hz, 4H), 7.85 (d, J=7.9 Hz, 1H), 7.32–7.13 (m, 3H), 6.70 (bs, 1H), 1.53 (s, 9H), 0.28 (s, 9H).

Step 2: N-(2-Amino-phenyl)-4-(trimethylsilylethynyl) benzamide (198)

Following the procedure described in Example 42, step 3, but substituting the previous compound for 46, the title compound 198 (70 mg, 0.23 mmol) was obtained as a white solid with a major fraction composed of a mixture of 198 and 199. $^1H$ NMR (300 MHz, acetone-$d_6$) δ (ppm): 9.20 (bs, 1H), AB system ($\delta_A$=8.07, $\delta_B$=7.62, J=8.2 Hz, 4H), 7.32 (d, J=7.6 Hz, 1H), 7.05 (td, J=7.6, 1.2 Hz, 1H), 6.90 (d, J=7.6 Hz, 1H), 6.72 (t, J=7.3 Hz, 1H), 4.66 (bs, 2H), 0.30 (s, 9H).

Step 3: N-(2-Amino-phenyl)-4-ethynylbenzamide (199)

To a stirred solution at −20° C. of a mixture of 198 and 199 in anhydrous THF (15 ml) under nitrogen was added a solution of TBAF (1 ml, 1.0 M in THF). The reaction mixture was allowed to warm up to room temperature over 2 h and stirred at room temperature for 18 h. Then, the reaction mixture was poured into a saturated aqueous solution of $NH_4Cl$ and diluted with ethyl acetate. After separation, the organic layer was successively washed with sat. $NH_4Cl$, $H_2O$ and brine, dried over anhydrous $MgSO_4$, filtered and concentrated. The crude residue was then purified by flash chromatography on silica gel (AcOEt/hexane: 30/70) to afford the title compound 199 (215 mg, 0.91 mmol, 46% yield over 2 steps) as a pale yellow powder. $^1H$ NMR (300 MHz, acetone-$d_6$) δ (ppm): 9.19 (bs, 1H), AB system ($δ_A$=8.08, $δ_B$=7.66, J=8.5 Hz, 4H), 7.33 (d, J=7.6 Hz, 1H), 7.05 (t, J=7.3 Hz, 1H), 6.91 (d, J=7.6 Hz, 1H), 6.72 (t, J=7.6 Hz, 1H), 4.67 (bs, 2H), 3.88 (s, 1H).

Example 134

Step 1: N-[2-(t-Butyloxycarbonyl)-amino-phenyl]-4-ethynylbenzamide (200)

To a stirred solution at −20° C. of a mixture of 199 (3.48 g, 8.53 mmol) in anhydrous THF (50 ml) under nitrogen was slowly added a solution of TBAF (9.4 ml, 9.38 mmol, 1.0 M in THF). The reaction mixture was allowed to warm up to room temperature over 2 h and stirred at room temperature for 4 h. Then, the reaction mixture was concentrated, diluted with ethyl acetate, and successively washed with a saturated aqueous solution of $NH_4Cl$, $H_2O$ and brine, dried over anhydrous $MgSO_4$, filtered and concentrated. The crude residue was then purified by flash chromatography on silica gel (AcOEt/hexane: 25/75→30/70) to afford the title compound 200 (2.53 g, 7.53 mmol, 88% yield) as a pale yellow foam. $^1H$ NMR (300 MHz, $CDCl_3$) δ (ppm): 9.31 (bs, 1H), AB system ($δ_A$=7.94, $δ_B$=7.59, J=8.5 Hz, 4H), 7.83 (d, J=7.6 Hz, 1H), 7.30–7.10 (m, 3H), 6.75 (bs, 1H), 3.23 (s, 1H), 1.53 (s, 9H).

Step 2: N-(2-amino-phenyl)-4-[3-(4-chlorophenyl)-3-morpholin-4-yl-1-propyn-1-yl]-benzamide (201)

To a stirred solution at room temperature of 200 (200 mg, 0.60 mmol) in anhydrous 1,4-dioxane (5 ml) under nitrogen were added 4-chlorobenzaldehyde (100 mg, 0.71 mmol), morpholine (60 μl, 0.68 mmol), and CuI (6 mg, 0.03 mmol), respectively. The reaction mixture was bubbled with nitrogen for 5 min and warmed up to 105° C. After 18 h, the reaction mixture was allowed to cool to room temperature, diluted with ethyl acetate, and successively washed with a saturated aqueous solution of $NH_4Cl$, $H_2O$ and brine, dried over anhydrous $MgSO_4$, filtered and concentrated. The crude residue was then purified by flash chromatography on silica gel (AcOEt/hexane:40/60) to afford the desired compound (193 mg, 0.35 mmol, 59% yield) as a pale yellow foam. $^1H$ NMR (300 MHz, $CDCl_3$) δ (ppm): 9.40 (bs, 1H), AB system ($δ_A$=7.96, $δ_B$=7.36, J=8.5 Hz, 4H), 7.79 (d, J=7.9 Hz, 1H), 7.59 (d, J=8.4 Hz, 4H), 7.25–7.10 (m, 3H), 6.91 (s, 1H), 4.80 (s, 1H), 3.82–3.68 (m, 4H), 2.69–2.58 (m, 4H), 1.53 (s, 9H).

Following the procedure described in Example 42, step 3, but substituting the previous compound for 46, the tide compound 201 was obtained in 67% yield. $^1H$ NMR (300 MHz, DMSO-$d_6$) δ (ppm): 9.80 (bs, 1H), AB system ($δ_A$=8.06, $δ_B$=7.71, J=8.1 Hz, 4H), AB system ($δ_A$=7.65, $δ_B$=7.52, J=8.3 Hz, 4H), 7.20 (d, J=7.9 Hz, 1H), 7.02 (t, J=7.3 Hz, 1H), 6.82 (d, J=7.0 Hz, 1H), 6.64 (t, J=7.5 Hz, 1H), 5.10 (s, 1H), 4.97 (bs, 2H), 3.72–3.58 (m, 4H), 2.67–2.46 (m, 4H).

Scheme 24

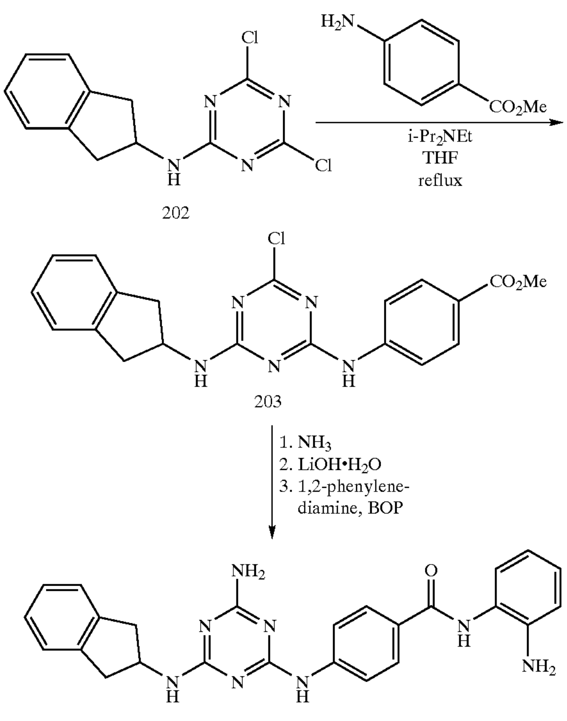

202

203

Example 135 204

Example 135

Step 1: Methyl 4-(4-chloro-6-(2-indanyl-amino)-[1,3,5]triazin-2-yl-amino)-benzoic ester (203)

To a stirred solution at room temperature of 202 (2.00 g, 7.11 mmol) in anhydrous THF (50 ml) under nitrogen were added i-$Pr_2$NEt (1.86 ml, 10.66 mmol) and methyl 4-aminobenzoate (1.29 g, 8.53 mmol) or $ArNH_2$ (1.2 equiv), respectively. The reaction mixture was then refluxed for 24 h. After cooling, the reaction mixture was poured into a saturated aqueous solution of $NH_4Cl$, and diluted with AcOEt. After separation, the organic layer was successively washed with sat. $NH_4Cl$, $H_2O$ and brine, dried over anhydrous $MgSO_4$, filtered and concentrated. The crude residue was then purified by flash chromatography on silica gel (AcOEt/$CH_2Cl_2$:2/98→5/95) to afford the title compound 203 (1.70 g, 4.30 mmol, 60% yield) as a beige powder. $^1H$ NMR (300 MHz, $CDCl_3$) δ (ppm): mixture of rotamers, 2 AB system ($δ_A$=8.03, $δ_{A'}$=8.00, $δ_B$=7.70, $δ_{B'}$=7.61, $J_{AB}$=$J_{A'B'}$=8.8 Hz, 4H), 7.43 and 7.31 (2 bs, 1H), 7.29–7.19 (m, 4H), 5.84 and 5.78 (2 d, J=7.2 and 7.7 Hz, 1H), 4.98–4.77 (2 m, 1H), 3.91 and 3.90 (2 s, 3H), 3.41 (dd, J=16.1, 7.0 Hz, 2H), 2.94 and 2.89 (2 dd, J=15.9, 4.9 Hz, 2H).

Step 2: 4-[4-amino-6-(2-indanyl-amino)-[1,3,5]-triazin-2-ylamino]-N-(2-amino-phenyl)-benzamide (204)

The title compound 204 was obtained from 203 in 3 steps following the same procedure as Example 1, Pathway B steps 3–5. $^1H$ NMR (300 MHz, acetone-$d_6$) δ (ppm): mixture of rotamers, 8.98 (m, 1H), 8.49 and 8.28 (2m, 1H), 8.10–7.92 (m, 4H), 7.35–7.14 (m, 5H), 7.03 (td, J=7.6, 1.5 Hz, 1H), 6.90 (dd, J=6.6, 1.3 Hz, 1H), 6.71 (td, J=7.6, 1.3 Hz, 1H), 6.57 and 6.42 (2m, 1H), 6.04 and 5.86 (2m, 2H), 4.92–4.76 (m, 1H), 4.70–4.58 (m, 1H), 3.44–3.26 (m, 2H), 3.08–2.92 (m, 2H). HRMS (calc.): 452.2073. (found): 452.2062.

Scheme 25

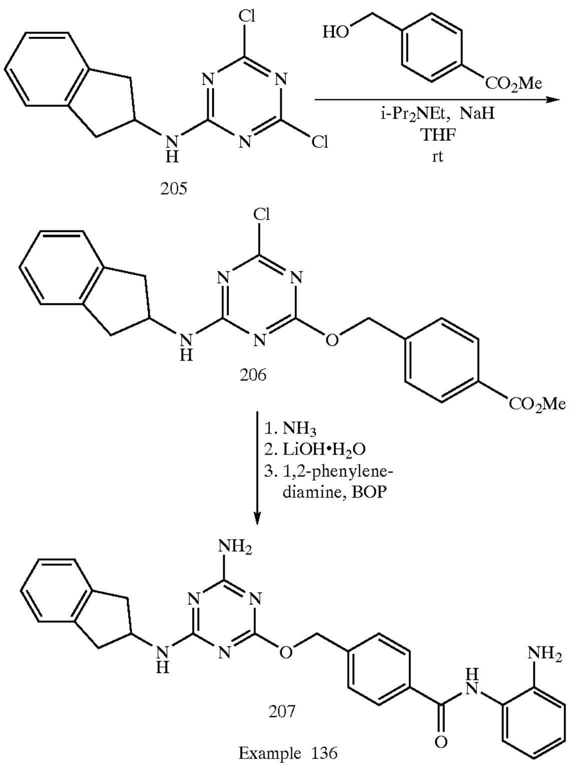

205

206

207

Example 136

Scheme 26

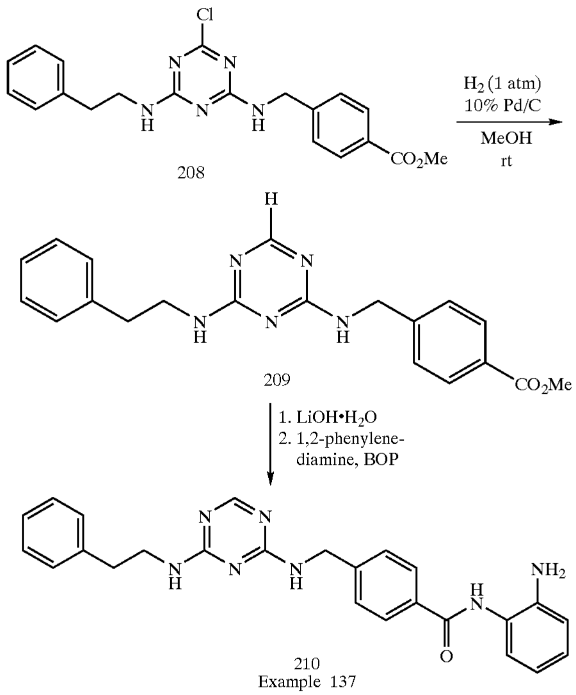

208

209

210

Example 137

Example 136

Step 1: Methyl 4-[(4-chloro-6-(2-indanyl-amino)-[1,3,5]triazin-2-yloxyl)-methyl]-benzoic ester (206)

To a stirred solution at 0° C. of 205 (2.00 g, 7.11 mmol) in anhydrous THF (50 ml) under nitrogen were added i-$Pr_2$NEt (1.86 ml, 10.66 mmol) and methyl 4-(hydroxymethyl)benzoate (1.30 g, 7.82 mmol). After few minutes, NaH (95%, 186 mg, 7.11 mmol) was added portionwise. Then, the reaction mixture was allowed to warm to room temperature. After 24 h, the reaction mixture was poured into a saturated aqueous solution of $NH_4Cl$, and diluted with AcOEt. After separation, the organic layer was successively washed with sat $NH_4Cl$, $H_2O$ and brine, dried over anhydrous $MgSO_4$, filtered and concentrated. The crude residue was then purified by flash chromatography on silica gel (AcOEt/$CH_2Cl_2$:2/98) to afford the title compound 206 (2.00 g, 4.88 mmol, 69% yield) as a colorless sticky foam. $^1H$ NMR (300 MHz, $CDCl_3$) δ (ppm): mixture of rotamers, 2 AB system ($\delta_A$=8.06, $\delta_{A'}$=8.03, $\delta_B$=7.52, $\delta_{B'}$=7.46, $J_{AB}$=$J_{AB'}$=8.5 Hz, 4H), 7.26–7.17 (m, 4H), 5.94 and 5.85 (2 bd, J=7.8 Hz, 1H), 5.48 and 5.39 (2 s, 2H), 4.92–4.76 (2 m, 1H), 3.94 and 3.92 (2 s, 3H), 3.39 and 3.33 (2 dd, J=16.0, 7.0 Hz, 2H), 2.89 and 2.84 (2 dd, J=16.0, 4.9 Hz, 2H).

Step 2: 4-[[4-amino-6-(2-indanyl-amino)-[1,3,5]-triazin-2-yloxy]methyl]-N-(2-amino-phenyl)-benzamide (207)

The title compound 207 was obtained from 206 in 3 steps following the same procedure as Example 1, Pathway B steps 3–5. $^1H$ NMR (300 MHz, acetone-$d_6$+DMSO-$d_6$) δ (ppm): 9.49 (m, 1H), 8.12–8.03 (m, 2H), 7.60 (t, J=7.7 Hz, 2H), 7.35 (d, J=7.1 Hz, 1H), 7.28–7.13 (m, 4H), 7.07–6.94 (m, 2H), 6.90 (dd, J=7.3, 1.4 Hz, 1H), 6.70 (td, J=7.3, 1.1 Hz, 1H), 6.44 (bs, 1H), 6.25 (bs, 1H), 5.47 and 5.41 (2s, 2H), 4.87–4.68 (m, 3H), 3.35–3.20 (m, 2H), 3.02–2.88 (m, 2H). HRMS (calc.): 467.2070. (found): 467.2063.

Example 210

Methyl 4-[(4-chloro-6phenethyl-amino-[1,3,5]triazin-2-yl-amino)-methyl]benzoic ester (208)

The title compound 208 was obtained from 2 following the same procedure as in Example 1, pathway B steps 2 ($R^1R^2$NH=phenethylamine).

Step 1: Methyl 4-[(4-phenethylamino-[1,3,5]triazin-2-yl-amino)-methyl]-benzoic ester (209)

To a degazed solution of 208 (300 mg, 0.75 mmol) in MeOH (35 mL) was added 10% Pd/C (24 mg, 0.023 mmol). The reaction mixture was stirred under a 1 atm pressure of $H_2$ at room temperature for 20 h then it was purged with $N_2$. The palladium was removed by filtration through celite and the reaction mixture was concentrated. The crude residue was purified by flash chromatography on silica gel (MeOH/$CH_2Cl_2$:4/96) to afford the title compound 209 (135 mg, 0.37 mmol, 50% yield). $^1H$ NMR (300 MHz, $CDCl_3$) δ (ppm): 8.08 (d, J=8.1 Hz, 2H), 7.46 (d, J=8.1 Hz, 2H), 7.50–7.15 (m, 6H), 4.85–4.65 (m, 2H), 3.98 (s, 3H), 3.82–3.62 (m, 2H), 3.05–2.85 (m, 2H).

Step 2: N-(2-Amino-phenyl)-4-[(4-phenethyl-amino-[1,3,5]triazin-2-yl-amino)-methyl]-benzamide (210)

The title compound 210 was obtained from 209 in 2 steps following the same procedure as in Example 1, steps 4 and 5. $^1H$ NMR: (300 MHz, acetone-$d_6$) δ (ppm): 9.03 (s, 1H), 8.17–7.87 (m, 3H), 7.49 (dd, J=19.2, 8.2 Hz, 2H), 7.32–7.03 (m, 6H), 6.99 (t, J=7.6 Hz, 1H), 6.86 (d, J=8.0 Hz, 1H), 6.67 (t, J=7.4 Hz, 1H), 6.60–6.30 (m, 2H), 4.72 (t, J=6.3 Hz, 1H), 4.65–4.56 (m, 1H), 3.67–3.51 (m, 2H), 2.95–2.80 (m, 2H).

Scheme 27

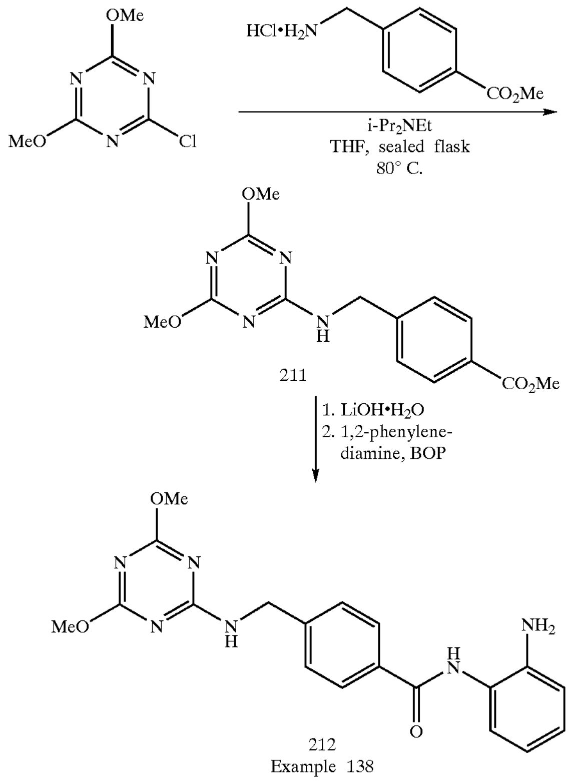

Example 138

Step 1: Methyl 4-[(4,6-dimethoxy-[1,3,5]triazin-2-yl-amino)-methyl]-benzoic ester (211)

In a 75 ml sealed flask, a stirred suspension of 2-chloro-4,6-dimethoxy-1,3,5-triazine (540 mg, 3.08 mmol), methyl 4-(aminomethyl)benzoate.HCl 2 (689 mg, 3.42 mmol), i-$Pr_2NEt$ (1.49 ml, 8.54 mmol) in anhydrous THF (30 ml) was warmed at 80° C. for 5 h. Then, the reaction mixture was allowed to cool to room temperature, poured into a saturated aqueous solution of $NH_4Cl$, and diluted with AcOEt. After separation, the organic layer was successively washed with sat. $NH_4Cl$, $H_2O$ and brine, dried over anhydrous $MgSO_4$, filtered and concentrated. The crude residue was then purified by flash chromatography on silica gel (AcOEt/$CH_2Cl$:10/90→30/70) to afford the title compound 211 (870 mg, 2.86 mmol, 93% yield) as a white solid. $^1H$ NMR (300 MHz, $CDCl_3$) δ (ppm): AB system ($\delta_A$=8.01, $\delta_B$=7.39, $J_{AB}$=8.5 Hz, 4H), 6.08–6.00 (m, 1H), 4.73 (d, J=6.3 Hz, 2H), 3.95 (s, 6H), 3.92 (s, 3H).

The title compound 212 was obtained from 211 in 2 steps following the same procedure as Example 1, steps 4 and 5. $^1H$ NMR (300 MHz, acetone-$d_6$+ΣDMSO-$d_6$) δ (ppm): 9.58 (bs, 1H), 8.27 (t, J=6.3 Hz, 1H), AB system ($\delta_A$=8.04, $\delta_B$=7.53, $J_{AB}$=8.4 Hz, 4H), 7.31 (d, J=6.9 Hz, 1H),), 7.02 (td, J=7.6, 1.6 Hz, 1H), 6.88 (dd, J=7.9, 1.4 Hz, 1H), 6.68 (td, J=7.6, 1.4 Hz, 1H), 4.86–4.78 (m, 2H), 4.69 (d, J=6.3 Hz, 2H), ), 3.90 and 3.89 (2s, 6H). HRMS (calc.): 380.1597. (found): 380.1601.

Step 2: N-(2-Amino-phenyl)-4-[(4,6-dimethoxy-[1,3,5]-triazin-2-yl-amino)-methyl]-benzamide (212)

Scheme 28

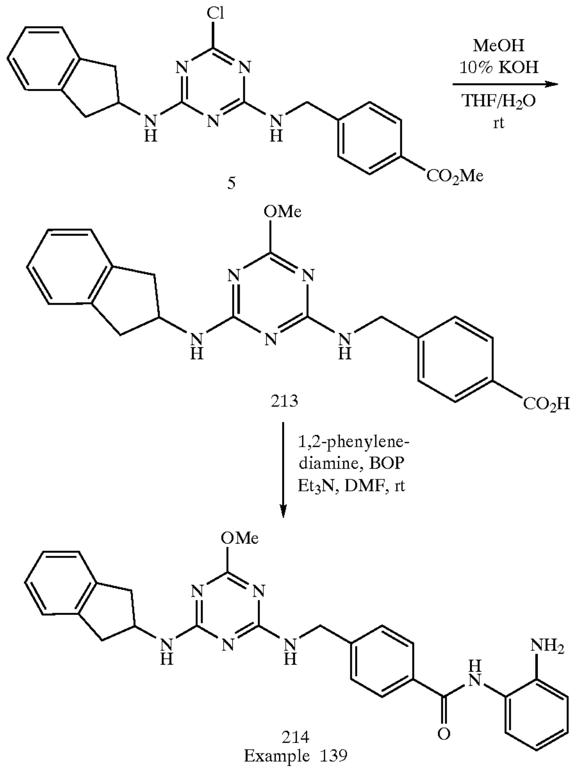

Example 139

Step 1: 4-[(6-2-indanyl-amino)-4-methoxy-[1,3,5]triazin-2yl-amino)-methyl]-benzoic acid (213)

To a stirred solution at room temperature of 5 (300 mg, 0.73 mmol) in a mixture of MeOH/THF (10 ml/5 ml) was added an aqueous solution of KOH (10%, 5 ml). After 3 days, the reaction mixture was concentrated on the rotavap, diluted in water and acidified with 1N HCl until pH 5–6 in order to get a white precipitate. After 15 min, the suspension was filtered off and the cake was abundantly washed with water, and dried to afford the title compound 213 (282 mg, 0.72 mmol, 98% yield) as a white solid. MS: m/z=392.1 $[MH]^+$.

Step 2: N-(2-amino-phenyl)-4-{[6-(2-indanyl-amino)-4-methoxy-[1,3,5]-triazin-2-yl-amino]-methyl}-benzamide (214)

The title compound 214 was obtained from 213 in one step following the same procedure as Example 1, step 5. $^1H$ NMR (300 MHz, acetone-$d_6$+DMSO-$d_6$) δ (ppm): mixture of rotamers, 9.69–9.53 (m, 1H), AB system ($\delta_A$=8.04, $\delta_B$=7.52, $J_{AB}$=7.8 Hz, 4H), 7.80–7.60 (m, 1H), 7.45–7.10 (m, 6H), 7.01 (t, J=7.6 Hz, 1H), 6.88 (d, J=8.2 Hz, 1H), 6.68 (t, J=7.6 Hz, 1H), 4.92–4.60 (m, 5H), 3.90–3.78 (m, 3H), 3.35–3.22 (m, 2H), 3.02–2.83 (m, 2H). HRMS (calc.): 481.2226. (found): 481.2231.

Scheme 29

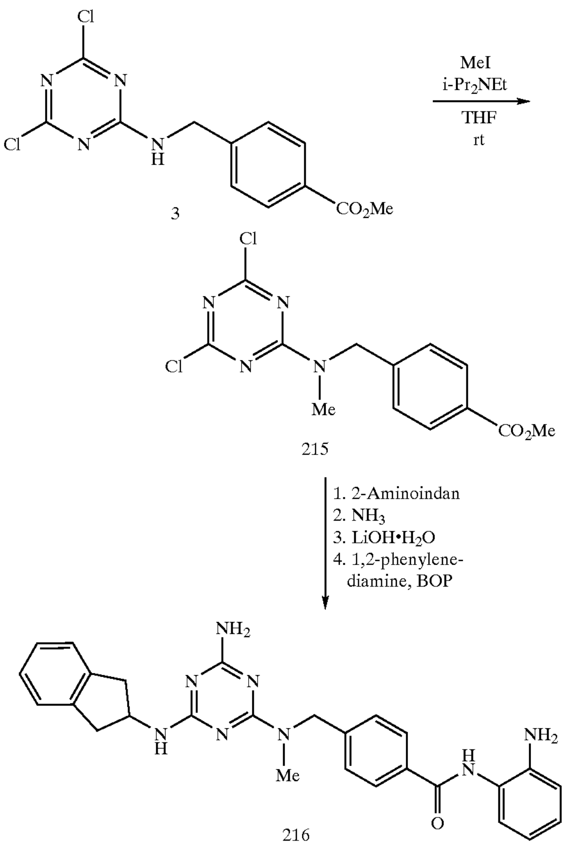

3

215

216
Example 140

Example 29

Step 1: Methyl 4-[(4,6-dichloro-[1,3,5]triazin-2-yl-N-methyl-amino)-methyl]-benzoic ester (216)

To a stirred suspension at room temperature of NaH (95%, 81 mg, 3.19 mmol) in anhydrous THF (10 ml) under nitrogen were successively added a solution of 3 (500 mg, 1.60 mmol) in anhydrous THF (10 ml) and MeI (298 μl, 4.79 mmol). After 16 h, the reaction mixture was poured into a saturated aqueous solution of $NH_4Cl$, and diluted with AcOEt. After separation, the organic layer was successively washed with sat. $NH_4Cl$, $H_2O$ and brine, dried over anhydrous $MgSO_4$, filtered and concentrated. The crude residue was then purified by flash chromatography on silica gel (AcOEt/hexane: 10/90→20/80) to afford the title compound 215 (200 mg, 0.61 mmol, 38% yield) as a white crystalline solid. $^1H$ NMR (300 MHz, $CDCl_3$) δ (ppm): AB system ($\delta_A$=8.04, $\delta_B$=7.31, $J_{AB}$=8.2 Hz, 4H), 4.93 (s, 2H), 3.93 (s, 3H), 3.18 (s, 3H).

Step 2: 4-([4-amino-6-(2-indanyl-amino)-[1,3,5]-triazin-2-yl-N-methyl-amino]-methyl-N-(2-amino-phenyl)-benzamide (216)

The title compound 216 from 215 in 4 steps was obtained following the same procedure as Example 1, Pathway B steps 2–5. $^1H$ NMR (300 MHz, acetone-$d_6$) δ (ppm): 9.11 (bs, 1H), 8.03 (d, J=8.0 Hz, 2H), 7.43 (bs, 2H), 7.33 (d, J=7.7 Hz, 1H),), 7.28–7.09 (m, 4H), 7.04 (td, J=7.6, 1.5 Hz, 1H), 6.90 (dd, J=8.0, 1.4 Hz, 1H), 6.71 (td, J=7.5, 1.3 Hz, 1H), 6.25–6.05 (m, 1H), 5.82 and 5.64 (2bs, 2H), 5.00–4.56 (m, 5H), 3.42–2.76 (m, 7H). HRMS (calc.): 480.2386. (found): 480.2377.

Scheme 30

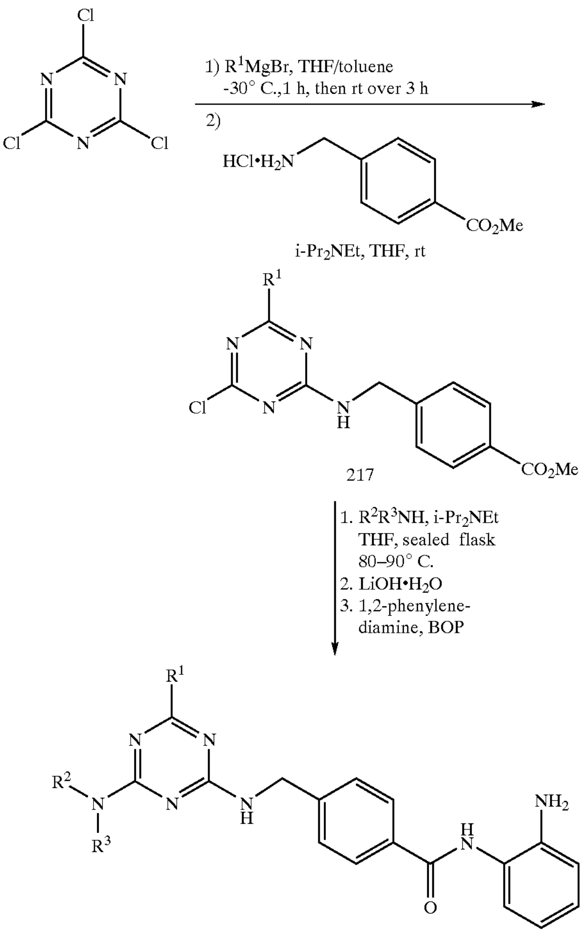

217

Example 141 218: $R^1$ = Me, $R^2R^3N$ = 2-indanyl-amino

Example 141

Step 1: Methyl 4-[(4-chloro-6-methyl-[1,3,5]triazin-2-yl-amino)-methyl]-benzoic ester (217)

To a stirred solution at −30° C. of cyanuric chloride 1 (2.00 g, 10.85 mmol) in anhydrous THF (100 ml) under nitrogen was slowly added a solution of MeMgBr (17 ml, 23.86 mmol, 1.4 M in anhydrous THF/toluene). After 1 h, the reaction mixture was allowed to warm to room temperature over 3 h. Then, methyl 4-(aminomethyl)benzoate.HCl 2 (2.08 g, 10.30 mmol) and i-$Pr_2NEt$ (3.78 ml, 21.69 mmol) were added, respectively. After 18 h, the reaction mixture was poured into a saturated aqueous solution of $NH_4Cl$, and diluted with AcOEt. After separation, the organic layer was successively washed with sat. $NH_4Cl$, $H_2O$ and brine, dried over anhydrous $MgSO_4$, filtered and concentrated. The crude residue was then purified by flash chromatography on silica gel (AcOEt/$CH_2Cl_2$: 10/90→15/85) to afford the title compound 217 (780 mg, 2.67 mmol, 25% yield) as a yellow powder. $^1H$ NMR (300 MHz, $CDCl_3$) δ (ppm): mixture of rotamers, 2 AB system ($\delta_A$=8.03, $\delta_{A'}$=8.02, $\delta_B$=7.39, $\delta_{B'}$=7.38, J=8.5 Hz, 4H), 6.28–6.08 (2 m, 1H), 4.76 and 4.74 (2d, J=6.3 Hz, 2H), 3.92 (s, 3H), 2.46 and 2.42 (2s, 3H).

Step 2: N-(2-amino-phenyl)-4-{[6-(2-indanyl-amino)-4-methyl-[1,3,5]-triazin-2-yl-amino]-methyl}benzamide (218)

The title compound 218 was obtained from 217 in 3 steps following the same procedure as Example 1, steps 3–5. $^{1}H$ NMR (300 MHz, acetone-$d_6$+ΣDMSO$d_6$) δ (ppm): mixture of rotamers, 9.62–9.50 (m, 1H), 8.04 (d, J=8.0 Hz, 2H), 7.68–7.37 (m, 3H), 7.33 (d, J=7.7 Hz, 1H), 7.28–7.07 (m, 5H), 7.02 (t, J=7.4 Hz, 1H), 6.89 (d, J=7.9 Hz, 1H), 6.69 (t, J=7.4 Hz, 1H), 4.92–4.60 (m, 5H), 3.35–3.10 (m, 2H), 3.02–2.82 (m, 2H), 2.25–2.12 (m, 3H).

Scheme 31

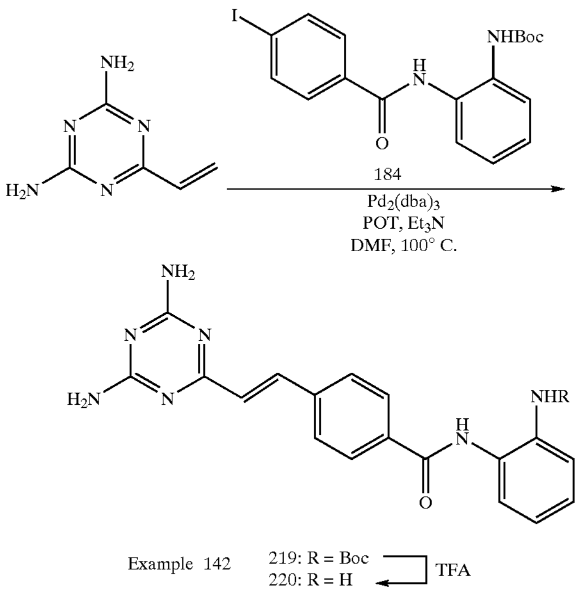

Example 142

Step 1: (2-{4-[2-(4,6-Diamino-[1,3,5]triazin-2-yl)-vinyl]-benzoylamino}-phenyl)-carbamic tert-butyl ester (219)

To a degazed solution of 184 (40 mg, 0.091 mmol) and 2-vinyl-4,6-diamino-1,3,5-triazine (11 mg, 0.083 mmol) in dry DMF (1 mL) was added tri-o-tolylphosphine (POT) (1.5 mg, 0.005 mmol) followed by $Et_3N$ (46 μL, 0.33 mmol) and tris(dibenzylideneacetone)dipalladium(0) (2 mg, 0.0025 mmol). The solution was heated at 100° C. for 16 h. Then, DMF was removed under reduced pressure. The reaction mixture was partitioned between AcOEt and a solution of sat. $NH_4Cl$. After separation, the organic layer was washed with brine, dried over anhydrous $Na_2SO_4$, filtered and concentrated. The crude residue was then purified by flash chromatography on silica gel ($MeOH/CH_2Cl_2$: 5/95) to afford the title compound 219 (25 mg, 0.056 mmol, 67% yield). $^{1}H$ NMR (300 MHz, Acetone-$d_6$) δ (ppm): 8.27 (s, 1H), 8.06 (d, J=8.1 Hz, 2H), 7.96 (d, J=15.9 Hz, 1H), 7.79 (d, J=8.1 Hz, 2H), 7.76–7.69 (m, 1H), 7.62–7.55 (m, 1H), 7.26–7.15 (m, 2H), 6.90 (d, J=15.9 Hz), 6.21 (s, 4H), 1.50 (s, 9H).

Step 2: N-(2-Amino-phenyl)-4-[2-(4,6-diamino-[1,3,5]triazin-2-yl)-vinyl]benzamide (220)

To a stirred solution at room temperature of 219 (25 mg, 0.056 mmol) in $CH_2Cl_2$ (1.5 mL) was added TFA (0.3 mL, 4.3 mmol). After 30 min, a solution of sat. $NaHCO_3$ was slowly added until pH 8 is reached, $CH_2Cl_2$ was removed under reduced pressure, AcOEt was added, and the phases were separated. The organic layer was washed with brine, dried over anhydrous $Na_2SO_4$, filtered and concentrated. The crude residue was purified by flash chromatography on silica gel ($MeOH/CH_2Cl_2$: 10/90) to afford the title compound 220 (19 mg, 0.054 mmol, 98% yield). $^{1}H$ NMR: (300 MHz, acetone-$d_6$) δ (ppm): 8.33, 8.13 (2d, J=7.5 Hz, 1H), 8.22 (d, J=15.9 Hz, 1H), 8.01 (d, J=8.1 Hz, 2H), 7.84 (d, J=8.1 Hz, 2H), 7.38–6.96 (m, 2H), 7.03 (d, J=15.9 Hz, 1H), 6.94–6.62 (m, 2H).

Scheme 32

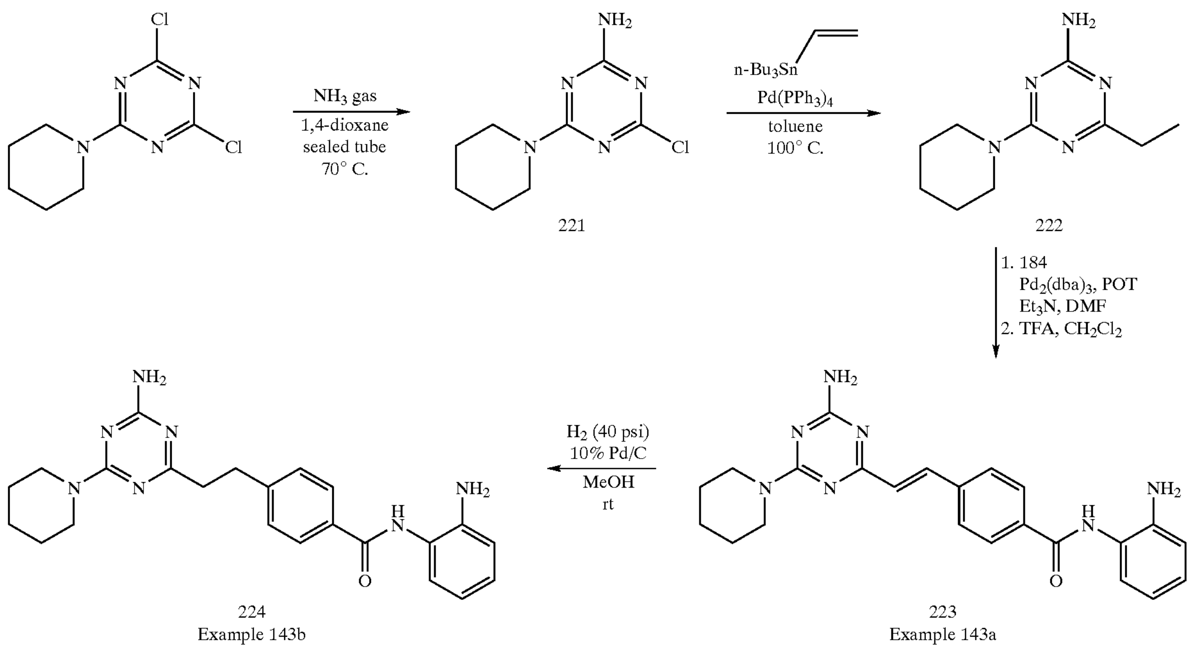

Example 143a

Step 1: 2-Amino-4-chloro-6-piperidin-1-yl-[1,3,5]triazin (221)

Ammonia was bubbled for 5 min in a solution of 2,4-dichloro-6-piperidin-1-yl-[1,3,5]triazine (500 mg, 2.15 mmol) in dry 1,4-dioxane (20 mL). The solution was heated at 70° C. for 16 h in a sealed tube. The reaction mixture was allowed to cool to room temperature, and partitioned between AcOEt and a solution of sat. $NH_4Cl$. After separation, the organic layer was washed with water and brine, dried over anhydrous $Na_2SO_4$, filtered and concentrated to afford the title compound 221 (453 mg, 2.12 mmol, 98% yield). LRMS: $[MH]^+$=214.1.

Step 2: 2-Amino 4-piperidin-1-yl-6-vinyl-[1,3,5]triazin (222)

To a solution of 221 (358 mg, 1.68 mmol) in dry toluene (7 mL) was added tributyl(vinyl)tin (514 μL, 1.76 mmol) followed by $Pd(PPh_3)_4$ (97 mg, 0.084 mmol) and the reaction mixture was heated at 100° C. for 16 h in a sealed tube. Then, the reaction mixture was allowed to cool to room temperature, concentrated, and purified directly by flash chromatography on silica gel (AcOEt/hexane: 10/90→30/70) to afford the title compound 222 (containing tributyltin chloride).

Steps 3: N-2-Amino-phenyl)-4-[2-(4-amino-6-piperidin-1-yl-[1,3,5]triazin-2-yl)-vinyl]-benzamide (223)

The title compound 223 was obtained from 222 in 2 steps following the same procedure as in scheme 31, steps 1 and 2. $^1H$ NMR: (300 MHz, DMSO-$d_6$) δ (ppm): 9.69 (s, 1H), 8.01 (d, J=7.5 Hz, 2H), 7.87 (d, J=16.0 Hz, 1H), 7.80 (d, J=7.5 Hz, 2H), 7.18 (d, J=7.5 Hz, 1H), 7.04–6.92 (m, 1H), 6.91 (d, J=16 Hz, 1H), 6.85–6.68 (m, 3H), 6.60 (t, J=7.2 Hz, 1H), 4.93 (s, 2H), 3.77 (s, 4H), 1.63 (s, 2H), 1.52 (s, 4H).

Example 143b

Step 4: N-(2-Amino-phenyl)-4-[2-(4-amino-6-piperidin-1-yl-[1,3,5]triazin-2-yl)-ethyl]benzamide (224)

To a solution of 223 (18 mg, 0.043 mmol) in MeOH (5 mL) was added 10% Pd/C (10 mg, 0.021 mmol). The reaction mixture was shaked under a pressure of $H_2$ (40 psi) at room temperature for 16 h using an hydrogenation apparatus. Then, the reaction mixture was purged with $N_2$, filtered through celite, and concentrated. The crude residue was then purified by flash chromatography on silica gel ($MeOH/CH_2Cl_2$: 2/98→44/96) to afford the title compound 224 (10 mg, 0.024 mmol, 56% yield). $^1H$ NMR (300 MHz, $CDCl_3$-$CD_3OD$) δ (ppm): 7.82 (d, J=8.1 Hz, 2H), 7.35 (d, J=8.1 Hz, 2H), 7.08 (t, J=7.0 Hz, 1H), 6.89–6.79 (m, 2H), 7.80–6.90 (m, 1H), 3.76 (s, 4H), 3.13 (t, J=8.1 Hz, 2H), 2.88 (t, J=8.1 Hz, 2H), 1.90–1.40 (m, 10H).

Scheme 33

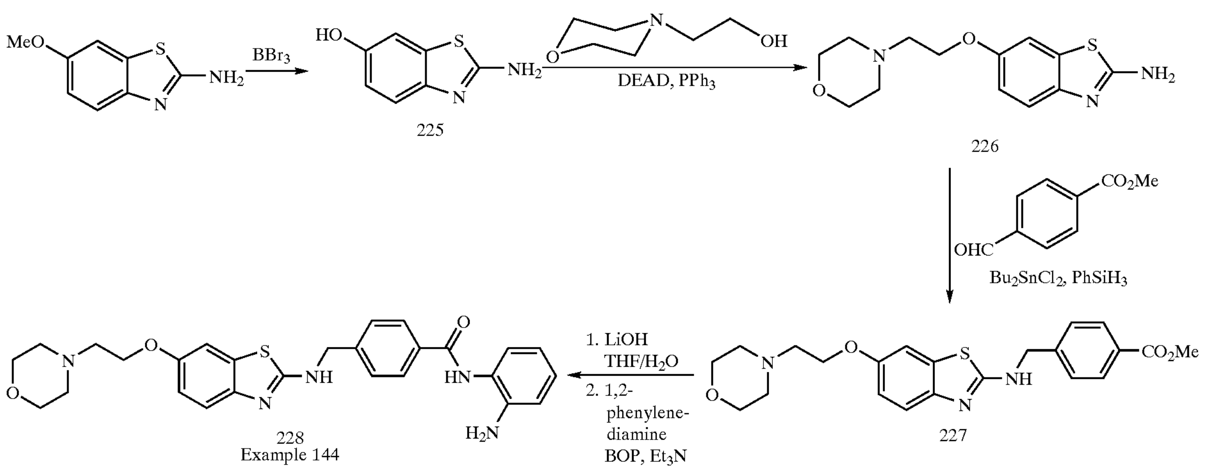

225

226

227

228

Example 144

Example 144

Step 1: 2-Amino-benzothiazol-6-ol (225):

A suspension of 2-amino-6-methoxybenzothiazole (5.00 g, 27.8 mmol) in dichloromethane (70 mL) was cooled to 0° C. under nitrogen and boron tribromide (3.93 mL, 41.6 mmol) was added dropwise. The light yellow mixture was stirred for 3 h, allowing to warm-up slowly from 0° C. to 10° C. The reaction was slowly quenched by dropwise addition of methanol and tafter stirring overnight at room temperature, the white solid was collected by filtration (6.04 g, 88% yield). This hydrobromic salt was dissolved in water, washed with ethyl acetate, and neutralized with a saturated aqueous solution of $NaHCO_3$. The resulting crystals were collected by filtration and dried in the oven at 135° C. for 1 h to afford the title compound 225 as colorless crystals (3.63 g, 79% yield). $^1H$ NMR: ($CD_3OD$) δ (ppm): 7.27 (d, J=8.8 Hz, 1H), 7.08 (d, J=2.2 Hz, 1H), 6.80 (dd, J=8.4, 2.2 Hz, 1H).

Step 2: 6-(2-Morpholin-4-yl-ethoxy)-benzothiazol-2-ylamine (226)

To a solution of benzothiazole 225 (3.62 g, 21.8 mmol) in THF at room temperature under nitrogen, were successively added 4-(2-hydroxyethyl)morpholine (3.17 mL, 26.1 mmol), triphenylphosphine (7.43 g, 28.3 mmol) followed by a dropwise addition of diethyl azodicarboxylate (4.46 mL, 28.3 mmol). The solution was stirred for 3.5 h and THF was partially removed in vacuo. The mixture was partitioned between ethyl acetate and $H_2O$. The combined organic layers were extracted with 1N HCl. The combined acidic extracts were neutralized using a saturated aqueous solution of $NaHCO_3$ and the precipitate was dissolved with ethyl acetate. These combined organic layers were washed with brine, dried over $MgSO_4$, and concentrated. The filtrate was concentrated to afford the title compound 226 (5.83 g, 96% yield) as a light yellow oil. $^1H$ NMR: (Acetone-$d_6$) δ (ppm): 7.37 (d, J=8.8 Hz, 1H), 7.34 (d, J=2.6 Hz, 1H), 6.94 (dd, J=8.8, 2.6 Hz, 1H), 6.60 (bs, 2H), 4.19 (t, J=6.2 Hz, 2H), 3.70–3.67 (m, 4H), 2.90 (s, 2H), 2.81 (t, J=6.2 Hz, 2H), 2.62–2.58 (m, 4H).

Step 3: 4-{[6-(2-Morpholin-4yl-ethoxy)-benzothiazol-2-ylamino]-methyl}-benzoic acid methyl ester (227):

To a round-bottom flask containing benzothiazole 226 (5.80 g, 20.8 mmol) was added methyl 4-formylbenzoate (5.11 g, 31.1 mmol), followed by THF (8 mL), dibutyltin dichloride (315 mg, 1.04 mmol) and dropwise addition of phenylsilane (3.24 mL, 31.1 mmol). The resulting mixture was stirred overnight at room temperature under nitrogen. The mixture was diluted in ethyl acetate and filtered. The filtrate was partitioned between ethyl acetate and water and the combined organic layers were washed with 1N HCl. The combined acidic layers were neutralized using a saturated aqueous solution of $NaHCO_3$ and the precipitate was extracted with ethyl acetate. The combined organic layers were washed with brine, dried over $MgSO_4$, and concentrated. The resulting crude was purified by flash chromatography using $MeOH/CHCl_3$(10:90) to afford 227 (3.69 g, 42% yield). $^1H$ NMR: (Acetone-$d_6$) δ (ppm): 8.04 (d, J=8.5 Hz, 2H), 7.65 (d, J=8.8 Hz, 2H), 7.41 (d, J=8.8 Hz, 1H), 7.34 (d, J=2.5 Hz, 1H), 6.94 (dd, J=8.5, 2.7 Hz, 1H), 4.50 (t, J=5.5 Hz, 2H), 3.86 (s, 3H).

Step 4: N-(2-Amino-phenyl)-4-{[6-(2-morpholin-4-ylethoxy)-benzothiazol-2-ylamino]methyl}-benzamide (228):

Following the procedure described in Example 1, step 4, 5 but substituting the previous compound for 6, the title compound 228 was obtained (958 mg, 46%) as a colorless solid. $^1H$ NMR: ($CD_3OD$) δ (ppm): 8.04 (d, J=8.2 Hz, 2H), 7.62 (d, J=8.5 Hz, 2H), 7.40 (d, J=8.8 Hz, 1H), 7.31 (d, J=2.5 Hz, 1H), 7.25 (d, J=7.4 Hz, 1H), 7.15 (t, J=7.4 Hz, 1H), 6.97 (dd, J=8.8, 2.5 Hz, 2H), 6.84 (t, J=7.4 Hz, 1H), 4.78 (s, 2H), 4.21 (t, J=5.2 Hz, 2H), 3.81–3.77 (m, 4H), 2.87 (t, J=5.5, 2H), 2.69–3.66 (m, 4H).

Example 145

Step 1: 4-[(5-Bromo-benzothiazol-2-ylamino)-methyl]-benzoic acid methyl ester (229):

Following the procedure described in Example 144, step 3, but substituting the 2-amino-6-bromobenzothiazole for 226, the title compound 229 was obtained in 56% yield. $^1H$ NMR: (DMSO-$d_6$) δ (ppm): 8.78 (t, J=5.9 Hz, 1H), 8.01 (d, J=8.2 Hz, 2H), 7.99 (s, 1H), 7.56 (d, J=8.2 Hz, 2H), 7.43–7.34 (m, 2H), 4.74 (d, J=5.9 Hz, 2H), 3.90 (s, 3H).

Step 2: 4-{[5-(3,4,5-Trimethoxy-phenyl)-benzothiazol-2-ylamino]-methyl}-benzoic acid methyl ester (230):

Following the procedure described in Example 15, step 1, but substituting 229 for 140, the title compound 230 was obtained in 44% yield as colorless crystals. $^1H$ NMR: (DMSO-$d_6$) δ (ppm): 8.73 (t, J=5.7 Hz, 1H), 8.11 (d, J=1.8 Hz, 1H), 8.02 (d, J=8.4 Hz, 2H), 7.63–7.57 (m, 3H), 7.48 (d, J=8.4 Hz, 1H), 6.97 (s, 2H), 4.77 (d, J=5.7 Hz, 2H), 3.92 (m, 6H), 3.90 (s, 3H), 3.74 (s, 3H).

Step 3: N-(2-Amino-phenyl)-4-{[5-(3,4,5-trimethoxy-phenyl)-benzothiazol-2-ylamino]-methyl}benzamide (231):

Following the procedure described in Example 1, step 4, 5 but substituting the previous compound for 6, the title compound 231 was obtained in 69% yield. $^1H$ NMR: (Acetone-$d_6$) δ (ppm): 8.31 (d, J=7.9 Hz, 2H), 8.20 (d, J=7.5 Hz, 1H), 8.13 (s, 1H), 7.73–7.58 (m, 3H), 7.63 (d, J=7.5 Hz, 2H), 7.48–7.43 (m, 2H), 7.05 (s, 2H), 4.98 (s, 2H), 4.00 (s, 6H), 3.84 (s, 3H).

Scheme 34

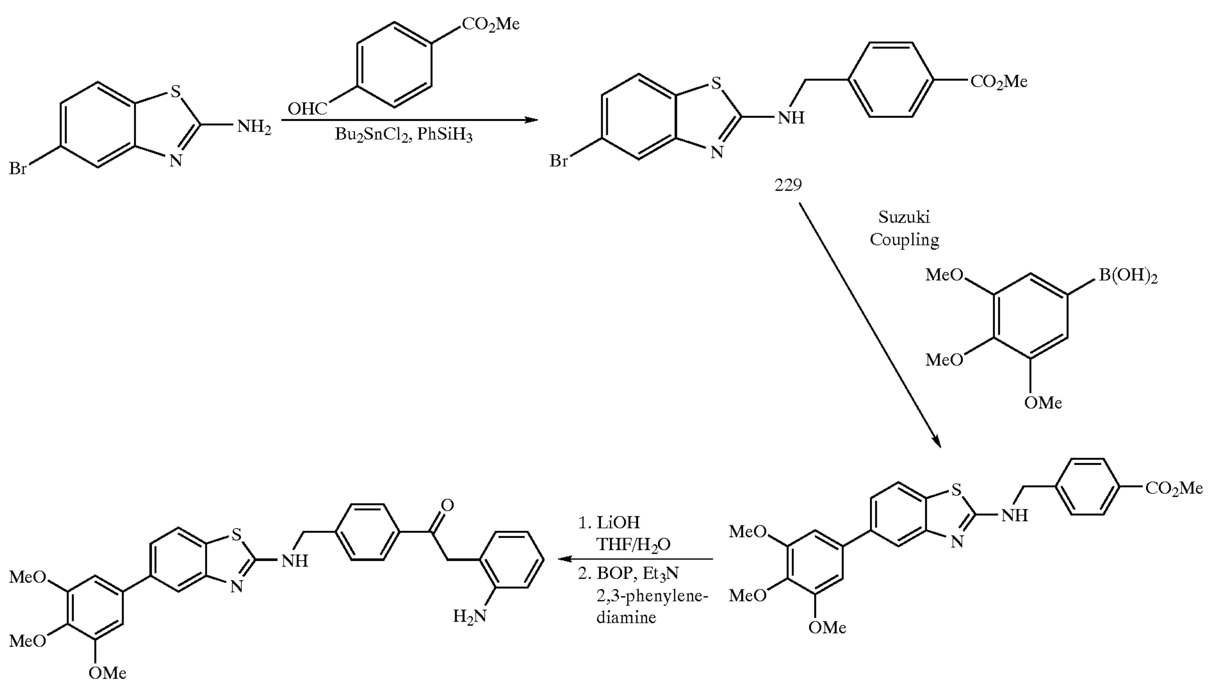

229

230

231

Example 145

Scheme 35

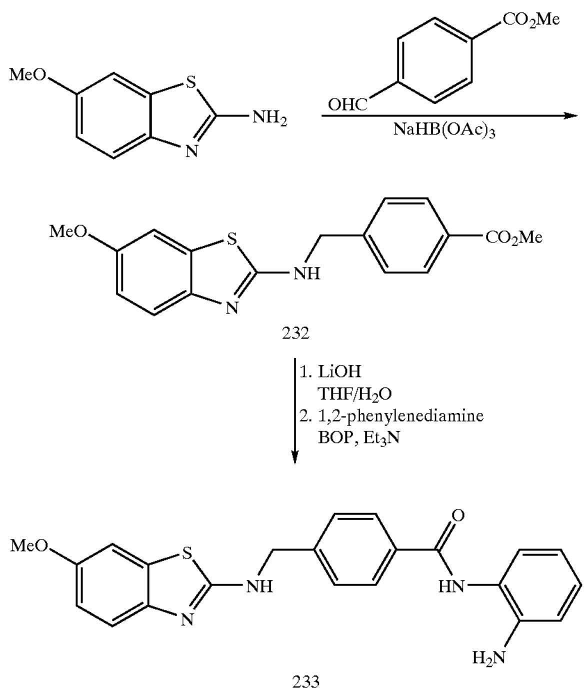

232

233
Example 146

Example 146

Step 1: 4-[(6-Methoxy-benzothiazol-2-ylamino)-methyl] benzoic acid methyl ester (232):

To a solution of 2-amino-6-methoxybenzothiazole (2.00 g, 11.1 mmol) in a mixture of dichloroethane (20 mL) and THF (20 mL), were successively added methyl 4-formylbenzoate (1.82 g, 11.1 mmol), sodium triacetoxy-borohydride (3.53 g, 16.7 mmol) and acetic acid (1.27 mL, 22.2 mmol). The mixture was stirred over 2 days and was quenched by adding aqueous saturated solution of $NaHCO_3$. The mixture was poured in a separating funnel containing water and was extracted with dichloromethane. The combined organic extracts were washed with brine, dried over $MgSO_4$ and concentrated in vacuo, The crude material was purified by flash chromatography using EtOAc/hexane (20:80 to 30:70) to afford the title compound 232 (1.85 g, 51% yield). $^1$H NMR: (Acetone-$d_6$) δ (ppm): 8.04 (d, J=8.5 Hz, 2H), 7.65 (d, J=8.8 Hz, 2H), 7.41 (d, J=8.8 Hz, 1H), 7.34 (d, J=2.5 Hz, 1H), 6.94 (dd, J=8.5, 2.7 Hz, 1H), 4.50 (t, J=5.5 Hz, 2H), 3.86 (s, 3H).

Step 2: N-(2-Amino-phenyl)-4-[(6-methoxy-benzothiazol-2-ylamino)-methyl]-benzamide(233):

Following the procedure described in Example 1, step 4, 5 but substituting the previous compound for 6, the title compound 233 was obtained in 19% yield as a light beige solid. $^1$H NMR: (DMSO-$d_6$) δ (ppm): 9.68 (s, 1H), 8.44 (t, J=5.8 Hz, 1H), 8.00 (d, J=8.2 Hz, 2H), 7.55 (d, J=8.2 Hz, 2H), 7.39 (d, J=2.7 Hz, 1H), 7.34 (d, J=8.8 Hz, 1H), 7.21 (d, J=6.6 Hz, 1H), 7.05 (t, J=6.3 Hz, 1H), 7.00 (d, J=1.4 Hz, 1H), 6.88 (dd, J=8.8, 2.7 Hz, 1H), 6.86 (dd, J=8.0, 1.4 Hz, 1H), 6.65 (td, J=7.4, 1.4 Hz, 1H), 4.95 (s, 2H), 4.70 (d, J=5.8 Hz, 2H), 3.79 (s, 3H).

Scheme 36

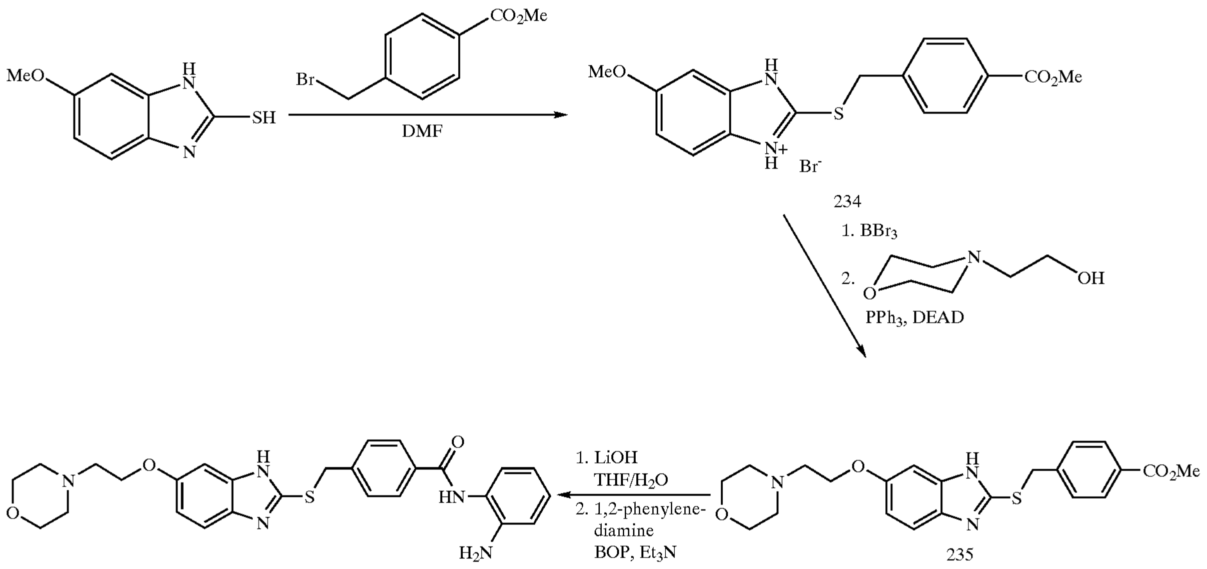

234

235

236
Example 147

Example 147

Step 1: 4-(6Methoxy-1H-benzoimidazol-2-ylsulfanylmethyl)-benzoic acid methyl ester hydrobromide (234):

To a solution of methyl 4-(bromomethyl)benzoate (2.51 g, 11.0 mmol) in DMF (50 mL) was added 5-methoxy-2benzimidazolethiol (1.98 g, 11.0 mmol). The mixture was stirred at room temperature for 24 h and the solvent was evaporated in vacuo. The residue was suspended in ethyl acetate and the hydrobromide salt was collected by filtration to afford the title compound 234 (4.10 g, 91% yield) as a colorless solid. $^1$H NMR: (DMSO-$d_6$) δ (ppm): 7.90 (d, J=8.2 Hz, 2H), 7.55 (d, J=8.2 Hz, 2H), 7.45 (d, J=8.2 Hz, 1H), 7.03 (s,1H), 6.94 (d, J=8.2 Hz,1H), 4.65 (s,2H), 3.82 (s,3H), 3.79 (s, 3H).

Step 2: 4-[6-(2-Morpholin-4-yl-ethoxy)-1H-benzoimidazol-2-ylsulfanylmethyl]-benzoic acid methyl ester (235):

Following the procedure described in Example 144, step 1, 2 but substituting the previous compound for 2-amino-6-methoxybenzothiazole, the title compound 235 was obtained in 37% yield. $^1$H NMR: ($CDCl_3$) δ (ppm): 8.04–8.00 (m, 2H), 7.77–7.72 (m, 1H), 7.69–7.59 (m, 1H), 7.56–7.49 (m, 2H), 6.96–6.90 (m, 1H), 4.68 (s, 2H), 4.31–4.16 (m, 4H), 3.97 (s, 3H), 3.98–3.91 (m, 2H), 3.82–3.72 (m, 2H), 2.75–2.47 (m, 4H).

Step 3: N-(2-Amino-phenyl)-4-[6-(2-morpholin-4-yl-ethoxy)-1H-benzoimidazol-2-ylsulfanylmethyl]-benzamide (236):

Following the procedure described in Example 1, step 4, 5 but substituting the previous compound for 6, the title compound 236 was obtained in 11% yield. $^1$H NMR: ($CD_3OD$) δ (ppm): 7.89 (d, J=8.2 Hz, 2H), 7.45 (d, J=8.2 Hz, 2H), 7.28 (d, J=8.5 Hz, 1H), 7.19–7.06 (m, 3H), 6.93–6.79 (m, 3H), 4.55 (s, 2H), 4.18 (t, J=6.3 Hz, 2H), 3.65–3.62 (m, 4H), 2.51 (t, J=6.6 Hz, 2H), 2.46–2.42 (m, 4H).

Scheme 37

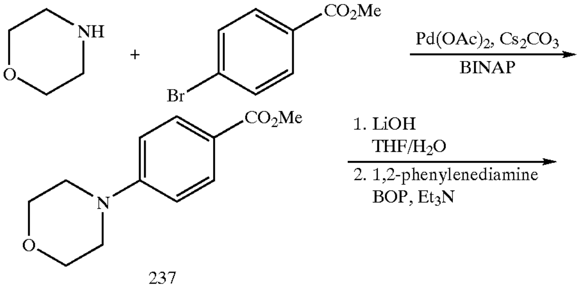

237

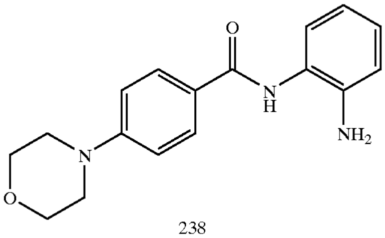

238
Example 148

Example 148

Step 1: 4-Morpholin-4-yl-benzoic acid methyl ester (237):

A flame-dried pressure vessel was charged with cesium carbonate (912 mg, 2.80 mmol) and toluene (8 mL) and the flasked was purged with nitrogen. Palladium acetate (9.0 mg, 0.004 mmol) and rac-2,2'-Bis(diphenylphosphino)-1,1'-binaphthyl (37 mg, 0.06 mmol). The mixture was degassed and heated at 100° C. for 18 h. It was allowed to cool to room temperature and was filtered through celite, rinsed with ethyl acetate and partitioned between ethyl acetate and water. The organic layer was washed with a saturated solution of $NaHCO_3$, brine, dried over $MgSO_4$ and concentrated in vacuo to afford the title compound 237 (443 mg, 100% yield). $^1$H NMR: ($CDCl_3$) δ (ppm): 8.02 (d, J=9.2 Hz, 2H), 6.95 (d, J=8.8 Hz, 2H), 3.95 (s, 4H), 3.92 (s, 3H), 3.38–3.35 (m, 4H).

Step 2: N-(2-Amino-phenyl)-4-morpholin-4-yl-benzamide (238):

Following the procedure described in Example 1, step 4, 5 but substituting the previous compound for 6, the title compound 238 was obtained in 33% yield. $^1$H NMR: (DMSO-$d_6$) δ (ppm): 7.20 (d, J=7.9 Hz, 1H), 7.07 (d, J=8.8 Hz, 2H), 7.01 (t, J=7.0 Hz, 1H), 6.83 (d, J=7.9 Hz, 1H), 6.65 (t, J=7.5 Hz, 1H), 4.90 (s, 2H), 3.81–3.79 (m, 4H), 3.32–3.28 (m, 4H).

Scheme 38

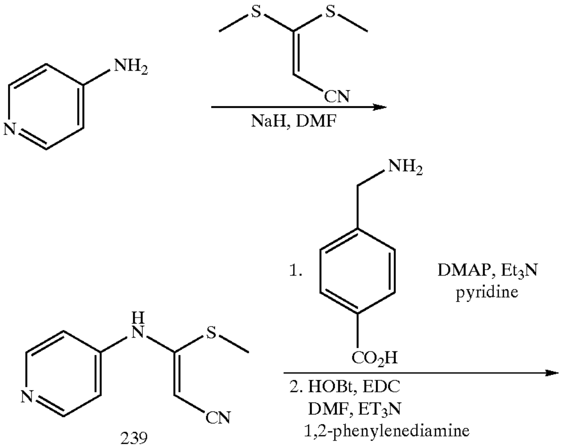

239

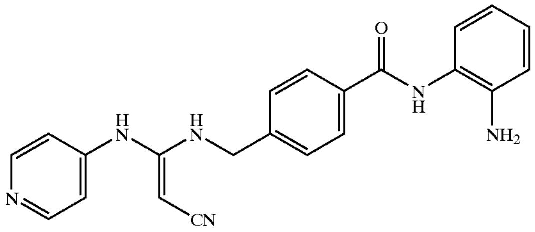

240
Example 149

Example 149

Step 1: 3-Methylsulfanyl-3-(pyridin-4-ylamino)-acrylonitrile (239)

To a solution of pyridin-4-ylamine (1.0 g, 11.0 mmol) and 3,3-Bis-Methylsulfanyl-acrylonitrile (2.05 g, 12.6 mmol) in DMF at room temperature, was added powdered 4A molecular sieves. The mixture was stirred for 1 hr. Subsequently the mixture was cooled to 0° C., 60% NaH dispersion in oil (0.92 g, 23.0 mmol) was added portionwise over 1 hr. and it was stirred at 0° C. for an additional 2 hrs. The cold bath was removed and the mixture was stirred at room temperature for 20 hrs. DMF was removed in vacuo and the crude was purified by column chromatography (gradient of EtOAc to 25% MeOH/EtOAc) to afford the desired product as an off-white solid (1.9 g, 89%).

Step 2: N-(2-Amino-phenyl)-4-{[2-cyano-1-(pyridin-4-ylamino)-vinylamino]-methyl}-benzamide (240)

To a mixture of 3-methylsulfanyl-3-(pyridin-4-ylamino)-acrylonitrile (0.2 g, 1.0 mmol), 4-aminomethyl-benzoic acid (0.173 g, 1.14 mmol), DMAP (1 mg) and $Et_3N$ (0.14 ml, 1.0 mmol) was added dry pyridine (0.5 ml). The resulting stirring mixture was heated to 55° C. for 4.5 hrs., additional $Et_3N$ (0.14 ml) was added and mixture was heated from 75° C. to 90° C. over a period of ~30 hrs. When the reaction was complete, pyridine was partially removed in vacuo and the crude was purified by column chromatography (gradient of EtOAc to 20% MeOH/EtOAc) to afford the desired product as an off-white solid (130 mg, 44%).

Following the procedure described in Example 1, step 4, 5 but substituting the previous compound for 6, the title compound 240 was obtained in 33% yield. $^1$H NMR: $^1$H NMR: (300 MHz, DMSO-$d_6$) δ (ppm): 9.69 (br, 2H), 8.48 (br, 3H), 8.03 (d, J=7.9 Hz, 2H), 7.51 (d, J=8.4 Hz, 2H), 7.29 (br, 2H), 7.23 (d, J=7.9 Hz, 1H), 7.03 (t, J=7.0 Hz, 1H), 6.84 (d, J=7.9 Hz, 1H), 6.65 (t, J=7.3 Hz, 1H), 4.96 (br, 2H), 4.62 (d, J=5.7 Hz, 2H).

Step 2: 4-{[2-Chloro-9-(2-methoxy-ethyl)-9H-purin-6-ylamino]-methyl]-benzoic acid methyl ester (242)

Following the procedure described in Example 144, step 2 but substituting the previous compound for 2-amino-6-methoxybenzothiazole, the title compound 242 was obtained in 41% yield.

Step 3: N-(2-Amino-phenyl)-4-{[2-chloro-9-(2-methoxy-ethyl)-9H-purin-6-ylamino]-methyl}-benzamide (243):

Following the procedure described in Example 1, step 4, 5 but substituting the previous compound for 6, the title compound 243 was obtained in 85% yield. $^1$H NMR ($CDCl_3$) δ (ppm): 9.64 (s, 1H), 8.94 (bs, 1H), 8.18 (s, 1H), 7.96 (d, J=7.8 Hz, 2H), 7.52 (d, J=7.8 Hz, 2H), 7.21 (d, J=7.7 Hz, 1H), 7,01 (dd, J=7.3, 8.0 Hz, 1H), 6.81 (d, J=8.0 Hz, 1H), 6.62 (dd, J=7.3, 7.7 Hz, 1H), 4.91 (bs, 2H), 4.78 (bs, 2H), 4.18 (m, 2H), 3.70 (m, 2H), 3.26 (s, 3H)

Scheme 39

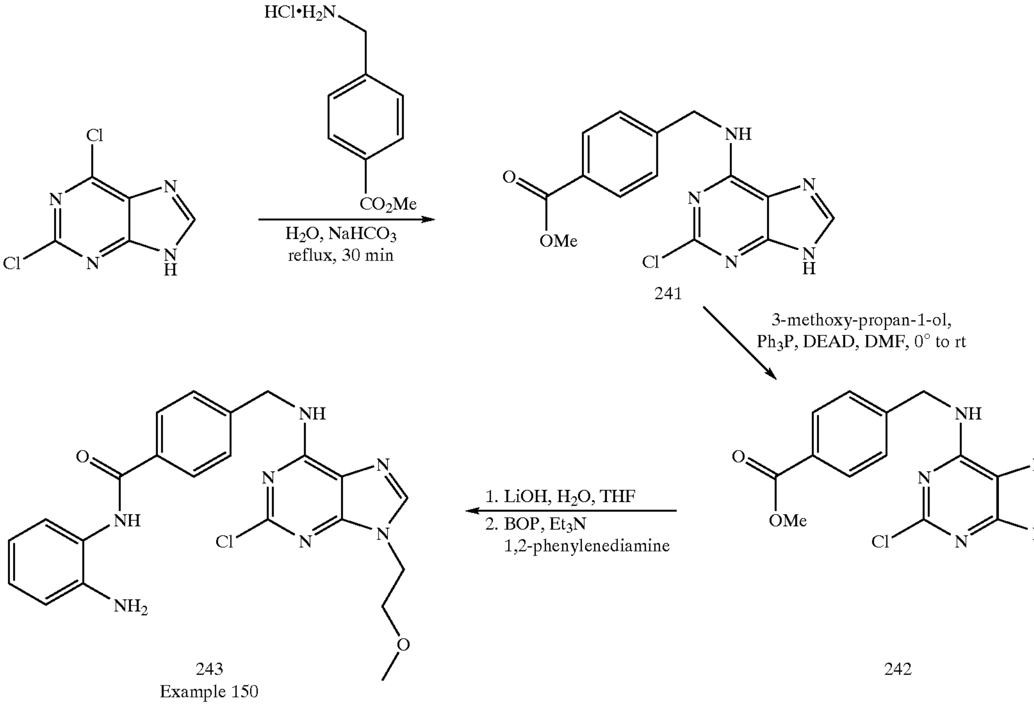

241

242

243
Example 150

Example 150

Step 1: 4-[(2-Chloro-9H-purin-6-ylamino)-methyl]-benzoic acid methyl ester (241)

A suspension of 2,6-dichloro-9H-purine (1 g, 5.29 mmol), 4-aminomethyl-benzoic acid methyl ester hydrochloride (1.2 equiv., 1.28 g) and $NaHCO_3$ (2.1 equiv., 935 mg) in water was heated at 100° C. The homogeneous solution thus formed was refluxed 30 min. The resulting white precipitate was filtered, washed with cold water and dried under vacuum giving the title compound 241 (1 g, 3.14 mmol, 60%). LRMS calc:317.7. found: 318.3 $(MH)^+$.

Scheme 40

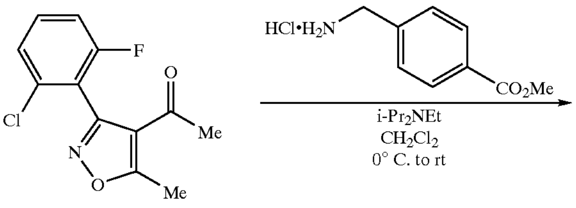

-continued

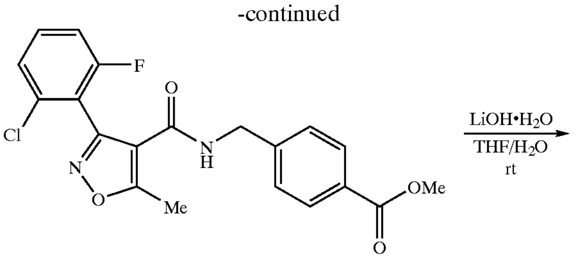

244

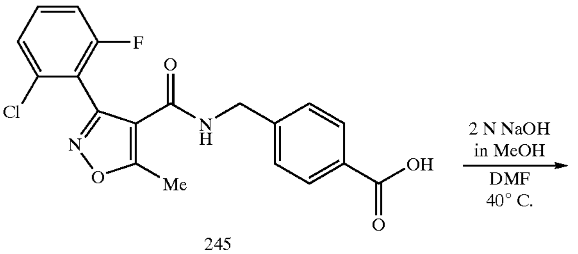

245

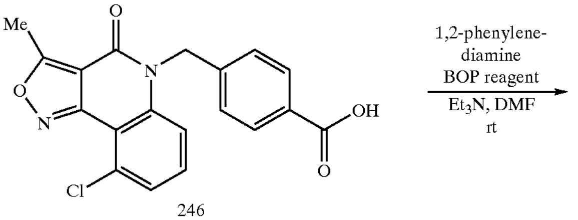

246

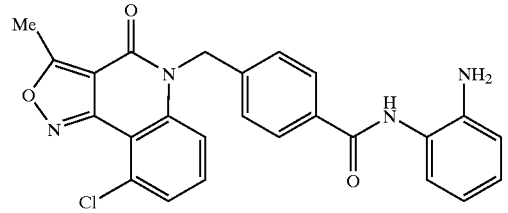

247
Example 151

Example 151

Step 1: Methyl-4-{[3-(2-chloro-6-fluoro-phenyl)-5-methyl-isoxazole-4-carbonyl]-amino-methyl}-benzoic acid ester (244)

To a stirred suspension at 0° C. of methyl 4-(aminomethyl)benzoate. HCl 2 (809 mg, 4.01 mmol) in anhydrous $CH_2Cl_2$ (25 ml) under nitrogen were successively added i-$Pr_2$NEt (1.91 ml, 10.95 mmol) and 3-(2-chloro-6-fluorophenyl)-5-methylisoxazole-4-carbonyl chloride (1.00 g, 3.65 mmol). After 45 min, the reaction mixture was allowed to warm up to room temperature for 3 h. Then, the reaction mixture was concentrated, diluted with AcOEt, and successively washed with sat. $NH_4Cl$, $H_2O$, sat. $NaHCO_3$, $H_2O$ and brine, dried over anhydrous $MgSO_4$, filtered and concentrated to afford the title compound 244 (1.50 g, quantitative yield) as a colorless sticky foam. $^1$H NMR (300 MHz, $CDCl_3$) δ (ppm): 7.93 (d, J=7.9 Hz, 2H), 7.46–7.35 (m, 1H), 7.29 (d, J=8.4 Hz, 1H), 7.15–7.05 (m, 3H), 5.49 (bs, 1H), 4.46 (d, J=5.7 Hz, 2H), 3.92 (s, 3H), 2.80 (s, 3H).

Step 2: 4-{[3-(2-Chloro-6-fluoro-phenyl)-5-methyl-isoxazole-4-carbonyl]-amino-methyl}-benzoic acid (245)

To a stirred solution at room temperature of 244 (1.45 g, 3.60 mmol) in THF (20 ml) was added a solution of $LiOH.H_2O$ (453 mg, 10.80 mmol) in water (20 ml). After 20 h, the reaction mixture was concentrated, diluted with water and acidified with 1N HCl until pH 6 in order to get a white precipitate. After 10 min, the suspension was filtered off and the cake was abundantly washed with water, and dried to afford the title compound 245 (1.23 g, 3.15 mmol, 88% yield) as a white solid. $^1$H NMR (300 MHz, DMSO-$d_6$) δ (ppm): 8.69 (t, J=5.9 Hz, 1H), 7.91 (d, J=7.9 Hz, 2H), 7.70–7.58 (m, 1H), 7.51 (d, J=7.9 Hz, 1H), 7.45–7.30 (m, 3H), 4.44 (d, J=5.7 Hz, 2H), 2.72 (s, 3H).

Step 3: 4-(9-Chloro-3-methyl-4-oxo-4H-isoxazolo[4,3-c]quinolin-5-ylmethyl)-benzoic acid (246)

To a stirred suspension at room temperature of 245 (795 mg, 2.05 mmol) in anhydrous DMF (10 ml) was added a solution of NaOH (409 mg, 10.22 mmol) in anhydrous MeOH (5.1 ml). Then, the reaction mixture was warmed up to 40° C. After 3 days, the reaction mixture was concentrated, diluted with water and acidified with 1N HCl until pH 5 in order to get a pale pinky precipitate. After 30 min, the suspension was filtered off and the cake was abundantly washed with water, and dried to afford the title compound 246 (679 mg, 1.84 mmol, 90% yield) as a pale pinky solid. $^1$H NMR (300 MHz, DMSO-$d_6$) δ (ppm): AB system ($\delta_A$=7.92, $\delta_B$=7.40, J=8.4 Hz, 4H), 7.56 (t, J=8.1 Hz, 1H), 7.47 (d, J=7.5 Hz, 1H), 7.31 (d, J=8.3 Hz, 1H), 5.59 (bs, 2H), 2.95 (s, 3H).

Step 4: N-(2-Amino-phenyl)-4-(9-chloro-3-methyl-4-oxo-4H-isoxazolo[4,3-c]quinolin-5-ylmethyl)-benzamide (247)

The title compound 247 was obtained from 246 in one step following the same procedure as Example 1, steps 5. $^1$H NMR (300 MHz, DMSO-$d_6$) δ (ppm): 9.65 (s, 1H), AB system ($\delta_A$=7.95, $\delta_B$=7.42, J=8.1 Hz, 4H), 7.58 (t, J=8.1 Hz, 1H), 7.48 (d, J=7.5 Hz, 1H), 7.35 (d, J=8.3 Hz, 1H), 7.17 (d, J=7.5 Hz, 1H), 7.00 (t, J=7.3 Hz, 1H), 6.80 (d, J=7.5 Hz, 1H), 6.62 (t, J=7.3 Hz, 1H), 5.61 (bs, 2H), 4.91 (s, 2H), 2.97 (s, 3H).

Scheme 41

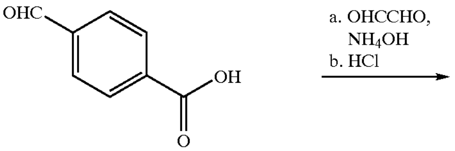

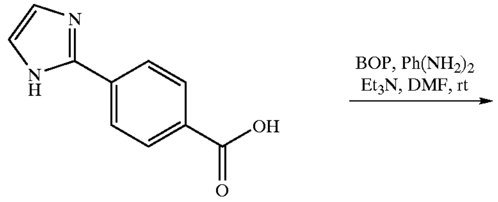

248

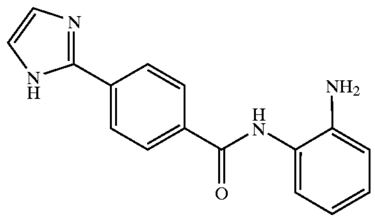

249
Example 152

Example 152

Step 1: 4-(1H-Imidazol-2-yl)-benzoic acid (248)

To a stirred solution of 4-formylbenzoic acid (2.00 g, 12.3 mmol) in ammonium hydroxide (9 ml) was added glyoxal (2.86 ml, 20.0 mmol). The reaction mixture was stirred 16 h at room temperature. 1N HCl was added to the reaction mixture to acidify to pH 5. The solvent was evaporated and the residue was triturated 30 min. in water (20 ml) and filtered to obtain the title compound 248 (2.08 g, 83%) as a white solid. LRMS: 188.1 (Calc.). 189.1 (found).

Step 2: N-(2-Amino-phenyl)-4-(1H-imidazol-2-yl)-benzamide (249)

The title compound 249 was obtained following the same procedure as Example 1, step 5. $^1$H NMR $CDCl_3$) δ (ppm): $^1$H NMR: (DMSO) δ (ppm): 9.72 (bs, 1H), 8.07 (s, 4H), 7.26 (s, 2H), 7.18 (d, J=7.9 Hz, 1H), 6.98 (dd, J=7.5, 7.5 Hz, 1H), 6.79 (d, J=7.9 Hz, 1H), 6.60 (dd, J=7.5, 7.5 Hz, 1H). MS: (calc.) 278.1. (obt.) 279.1 $(MH)^+$.

Step 2: 4-(4-Chloromethyl-thiazol-2-ylmethyl)-benzoic acid (251)

A solution of 250 (729 mg, 3.73 mmol) and 1,3-dichloroacetone (474 mg, 3.73 mmol) in THF (30 ml) was stirred at 40° C. during 48h. The solvent was evaporated then the residue was dissolved in ethyl acetate, washed with brine, dried over anhydrous $MgSO_4$, filtered and concentrated. The crude residue was purified by flash chromatography on silica gel (2–4% $MeOH/CH_2Cl_2$) to afford the title compound (827 mg, 83% yield) as a white solid. $^1$H NMR (DMSO) δ (ppm): 12.93 (bs, 1H), 7.91 (d, J=8.1 Hz, 2H), 7.63 (s, 1H), 7.46 (d, J=8.1 Hz, 2H), 4.78 (s, 2H), 4.42 (s, 2H).

Scheme 42

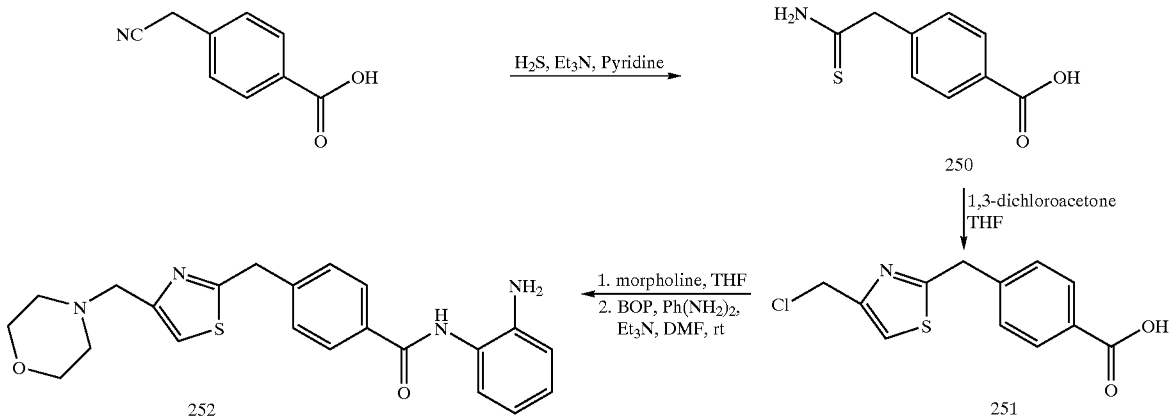

250

251

252

Example 153

Example 153

Step 1: 4-Thiocarbamoylmethyl-benzoic acid (250)

To a stirred suspension of 4-cyanomethyl-benzoic acid (1.65 g, 10.24 mmol) and $Et_3N$ (5 ml) in pyridine, $H_2S$ was bubbled during 3 h. The reaction mixture was stirred 16 h at room temperature. Water was then added to the reaction mixture which was agitated for 1 h before acidifying to pH 6 with 1M HCl. The solvent was evaporated and the residue was triturated 30 min. in water (20 ml) and filtered to obtain the title compound 250 (2.08 g, 83%) as a white solid. $^1$H NMR (DMSO) δ (ppm): 12.85 (bs, 1H), 9.53 (bs, 1H), 9.43 (bs, 1H), 7.88 (d, J=8.1 Hz, 2H), 7.44 (d, J=8.1 Hz, 2H), 3.88 (s, 2H).

Step 3: N-(2-Amino-phenyl)-4-(4-morpholin-4-ylmethyl-thiazol-2-ylmethyl)-benzamide (252)

$K_2CO_3$ (599 mg, 4.33 mmol) was added to a solution of 251 (527 mg, 1.97 mmol) and morpholine (189 □, 2.17 mmol) in THF (15 ml) was refluxed during 48h. The solvent was evaporated. The crude residue was purified by flash chromatography on silica gel (3–50% $MeOH/CH_2Cl_2$) to afford the title compound 252 (238 mg, 38% yield) as a pale yellow solid. LRMS: 318.2 (calc). 319.2 (found).

The title compound 252 was obtained following the same procedure as Example 1, step 5. 1H NMR (DMSO) δ (ppm): 9.63 (bs, 1H), 7.94 (d, J=8.1 Hz, 2H), 7.45 (d, J=8.1 Hz, 2H), 7.33 (s, 1H), 7.15 (d, J=8.1 Hz, 1H), 6.97 (dd, J=7.7, 7.7 Hz, 1H), 6.77 (d, J=7.3 Hz, 1H), 6.59 (dd, J=8.1, 8.1 Hz, 1H), 4.90 (bs, 2H), 4.40 (s, 2H), 3.59–3.56 (m, 6H), 2.44–2.38 (m, 4H). LRMS: 408.2 (calc). 409.2 (found).

Scheme 43

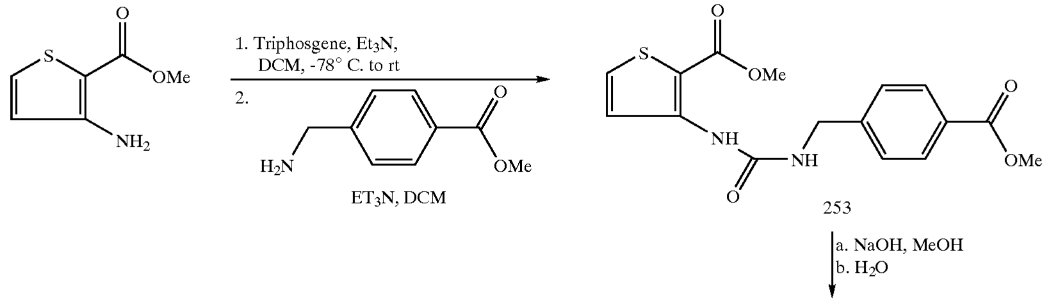

253

-continued

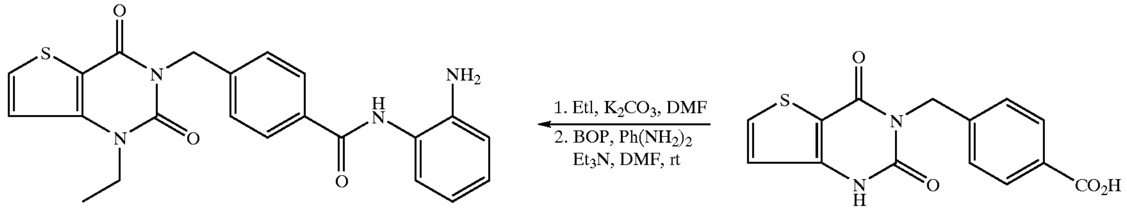

255
Example 154

254

Example 154

Step 1: Methyl 3-[3-(4-methoxycarbonyl-benzyl)-ureido]-thiophene-2-carboxylate (253)

The procedure described by Nakao (K. Nakao, R. Shimizu, H. Kubota, M. Yasuhara, Y. Hashimura, T. Suzuki, T. Fujita and H. Ohmizu; *Bioorg. Med. Chem.* 1998, 6, 849–868.) was followed to afford the title compound 253 (1.01 g, 91%) as a yellow solid. $^1$H NMR ($CDCl_3$) δ (ppm): 9.55 (bs, 1H), 8.00–7.97 (m, 3H), 7.42–7.37 (m, 3H), 5.45 (t, J=5.8 Hz, 1H), 4.52 (d, J=6.0 Hz, 2H), 3.91 (s, 3H), 3.82 (s, 3H).

Step 2: 4-(2,4-Dioxo-1,4-dihydro-2H-thieno[3,2-d]pyrimidin-3-ylmethyl)-benzoic acid (254)

To a suspension of 253 (422 mg, 1.21 mmol) in MeOH (15 ml) was added NaOH (145 mg, 3.63 mmol). The reaction mixture was heated at 60° C. during 16 h. Water (1 ml) was then added and the reaction mixture was stirred for 1 more hour. The solvent was evaporated and the residue was dissolved in water and acidified to pH 5 with HCl 1M. The precipitate was filtered to afford the desired compound 254 (348 mg, 95%) as a white solid. LRMS: 302.0 (Calc.). 303.0 (found).

Steps 3: N-(2-Amino-phenyl)-4-(1-ethyl-2,4-dioxo-1,4-dihydro-2H-thieno[3,2-d]pyrimidin-3-ylmethyl)-benzamide (255)

The title compound 255 was obtained as a yellow solid (73%) following the same procedure as Example 99, step 2, 3, then followed by Example 1, step 5. $^1$H NMR: (DMSO) δ (ppm): 9.61 (bs, 1H, NH), 8.22 (d, J=5.5 Hz, 1H, CH), 7.91 (d, J=8.2 Hz, 2H, CH), 7.43–7.40 (m, 3H, CH), 7.15 (d, J=7.4 Hz, 1H, CH), 6.96 (dd, J=7.6, 7.6 Hz, 1H, CH), 6.77 (d, J=7.1 Hz, 1H, CH), 6.59 (dd, J=7.4, 7.4 Hz, 1H, CH), 5.17 (s, 2H, $NCH_2$), 4.88 (bs, 2H, $NH_2$) 4.09 (q, J=7.0, 2H, $CH_2$), 1.22 (t, J=7.0, 3H, $CH_3$). LRMS: 420.1 (calc.). 421.0 (found).

-continued

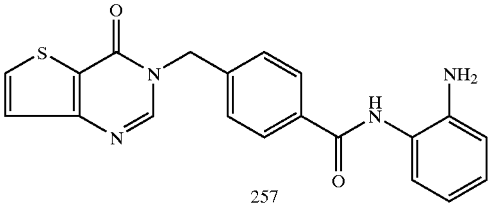

257
Example 155

Example 155

Step 1: 3Thieno[3,2-d]pyrimidin-4-one (256)

Methyl-3-amino-2-thiophene carboxylate (510 mg, 3.24 mmol) was dissolved in formamide (20 ml) and heated at 170° C. 16 h. The solvent was evaporated. The crude residue was then purified by flash chromatography on silica gel (2–4% MeOH/$CH_2Cl_2$) to afford the title compound 256 (157 mg, 32% yield). LRMS: 152.0 (Calc.). 152.9 (found).

Step 2: N-(2-Aminophenyl)-4-(4-oxo-4H-thieno[3,2-d]pyrimidin-3-ylmethyl)-benzamide (257)

Following the procedure described in Example 85, step 1 but substituting the previous compound for 119, followed by Example 1, step 4, 5, the title compound 257 was obtained in 41% yield. $^1$H NMR: (DMSO) δ (ppm): 9.61 (bs, 1H), 8.70 (s, 1H), 8.22 (dd, J=5.2, 0.5 Hz, 1H), 7.95 (d, J=8.2 Hz, 2H), 7.47 (d, J=8.5 Hz, 2H), 7.44 (dd, J=5.2, 0.6 Hz, 1H), 7.15 (d, J=7.7 Hz, 1H), 6.96 (dd, J=6.9, 6.9 Hz, 1H), 6.77 (d, J=7.1 Hz, 1H), 6.58 (dd, J=7.0, 7.0 Hz, 1H), 5.31 (s, 2H), 4.87 (bs, 2H). MS: 376.1 (calc.). 377.1 (found).

Scheme 44

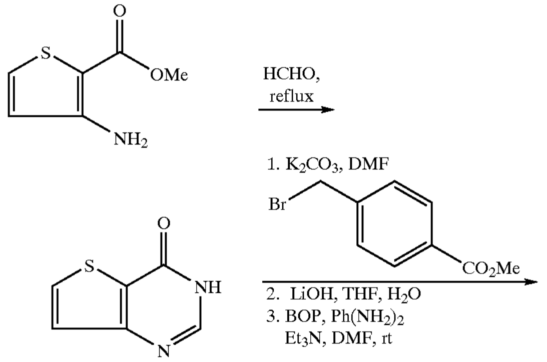

256

Scheme 45

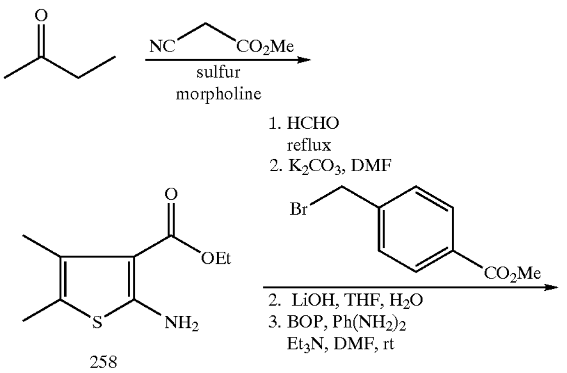

258

-continued

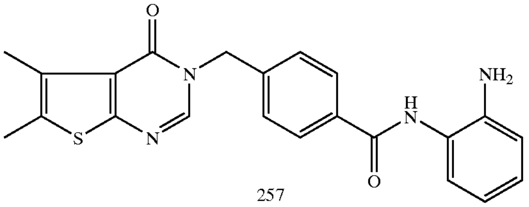

257
Example 155

Example 156

Step 1: Methyl 2-amino-4,5-dimethyl-thiophene-3-carboxylate (258)

The procedure described by Hozien (Z. A. Hozien, F. M. Atta, Kh. M. Hassan, A. A. Abdel-Wahab and S. A. Ahmed; *Synht Commun.* 1996, 26(20), 3733–3755.) was followed to afford the title compound 258 (1.44 g, 17%) as a yellow solid. LRMS: 197.1 (Calc.). 200.1 (found).

Steps 2: N-(2-Amino-phenyl)-4-(5,6-dimethyl-4-oxo-4H-thieno[2,3-]pyrimidin-3-ylmethyl)-benzamide (259)

Following the procedure described in Example 155, step 1, 2 but substituting 258 for 256, the title compound 259 was obtained as a white solid (55%). $^1$H NMR: (DMSO) δ (ppm): 9.61 (bs, 1H), 8.57 (s, 1H), 7.94 (d, J=8.0 Hz, 2H), 7.45 (d, J=7.7 Hz, 2H), 7.16 (d, J=7.7 Hz, 1H), 6.96 (dd, J=7.6, 7.6 Hz, 1H), 6.77 (d, J=8.0 Hz, 1H), 6.59 (dd, J=7.4, 7.4 Hz, 1H), 5.25 (s, 2H), 4.87 (bs, 2H), 2.39 (s, 3H), 2.37 (s, 3H). LRMS: 404.1 (calc). 405.0 (found).

Scheme 46

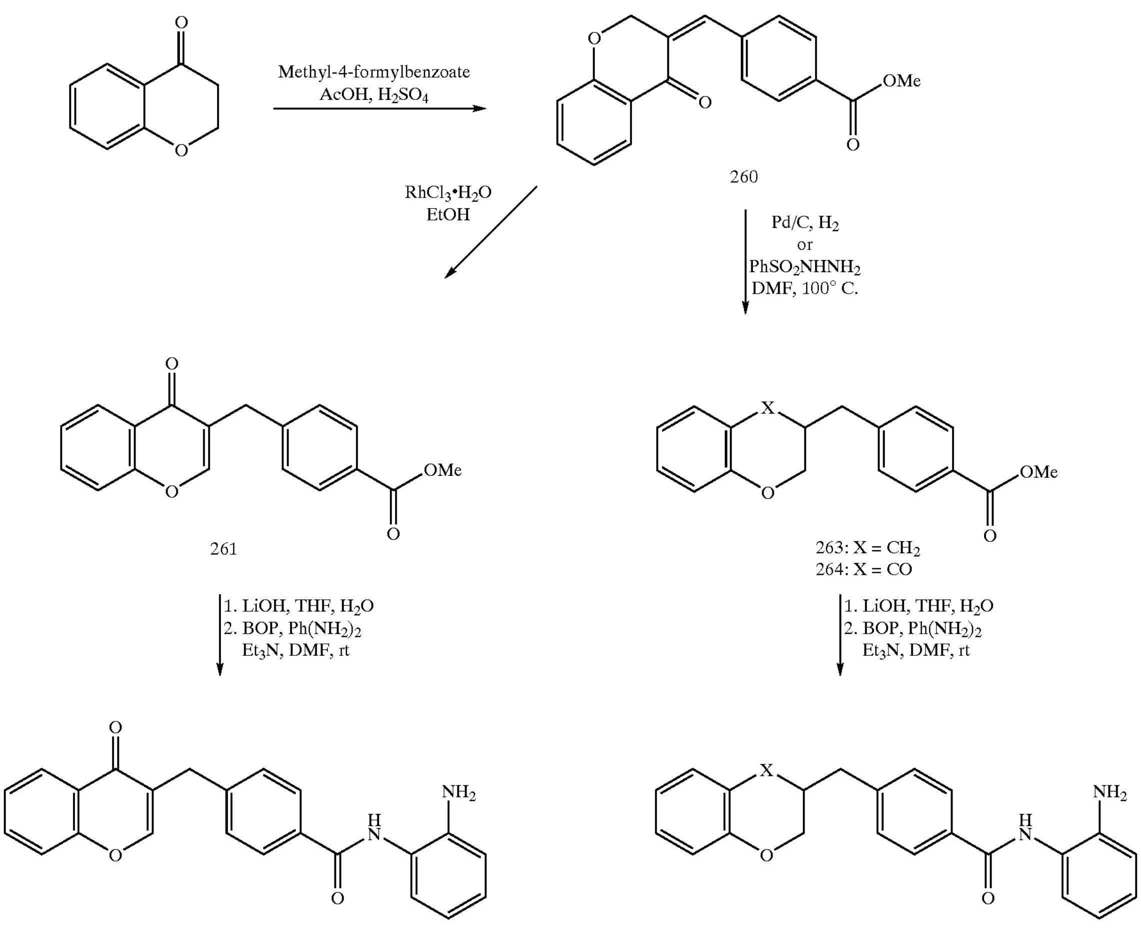

262
Example 157

Example 158 265: X = $CH_2$
Example 159 266: X = CO

Example 157

Step 1: Methyl 4(4-oxo-chroman-3-ylidenemethyl)-benzoate (260)

Concentrated $H_2SO_4$ (2 ml) was slowly added to a solution of 4-chromanone (2.00 g, 13.50 mmol) and methyl-4-formylbenzoate (2.11 g, 12.86 mmol) in glacial acetic acid. The reaction mixture was stirred 16 h at room temperature. The solvent was concentrated to half volume the resulting precipitate was filtered and rinsed with ethyl acetate to afford the title compound 260 (3.11 g, 82%) as a purple solid. $^1$H NMR: (DMSO) δ (ppm): 8.05 (d, J=8.2 Hz, 2H), 7.90 (d, J=7.6 Hz, 1 H), 7.79 (s, 1H), 7.64–7.59(m, 3H), 7.15 (dd, J=7.6, 7.6 Hz, 1H), 7.07 (d, J=8.2 Hz, 1H), 5.43 (s, 2H), 3.89 (s, 3H).

Step 2: Methyl-4-(4-oxo-4H-chromen-3-ylmethyl)-benzoate (261)

Water (0.2 ml) and $RhCl_3.H_2O$ (7 mg, 0.034 mmol) was added to a suspension of compound 260 (200 mg, 0.680 mmol) in EtOH (2 ml) and $CHCL_3$ (2 ml). The reaction mixture was stirred 16 h at 70° C. The reaction mixture was cooled down and diluted in ethyl acetate, washed with brine, dried over anhydrous $MgSO_4$, filtered and concentrated. The crude residue was then purified by flash chromatography on silica gel (0.5–1% $MeOH/CH_2Cl_2$) to afford the title compound 261 (118 mg, 59%) as a white solid. $^1$H NMR: (DMSO) δ (ppm): 8.45 (s, 1H), 8.03 (dd, J=7.9, 1.8 Hz, 1H), 7.87 (d, J=8.4 Hz, 2H), 7.83–7.77(m, 1H), 7.65 (d, J=8.3 Hz, 1H), 7.50–7.43 (m3, 1H), 3.82 (s, 3H), 3.80 (s, 2H).

Step 3: N-(2-Amino-phenyl)-4-(4-oxo-4H-chromen-3-ylmethyl)-benzamide (262)

The title compound 262 was obtained following the same procedure as Example 1, step 4, 5. $^1$H NMR: (DMSO) δ (ppm): 9.56 (bs, 1H), 8.45 (s, 1H), 8.04 (d, J=7.9 Hz, 1H), 7.88 (d, J=8.4 Hz, 2H), 7.80 (dd, J=7.5, 7.5 Hz, 1H), 7.65 (d, J=8.4 Hz, 1H), 7.51–7.42 (m, 3H), 7.14 (d, J=7.9 Hz, 1H), 6.96 (dd, J=7.3, 7.3 Hz, 1H), 6.76 (d, J=7.9 Hz, 1H), 6.58 (dd, J=7.3, 7.3 Hz, 1H), 4.86 (bs, 2H), 3.80 (s, 2H). LRMS: 370.1 (calc.). 371.1 (found).

Example 158

Step 2: Methyl 4-chroman-3-ylmethyl-benzoate (263)

Pd/C 10% was added to a suspension of 260 (200 mg, 0.68 mmol) in MeOH (40 ml) and DMA (10 ml) which was previously purged under vacuum. The reaction mixture was stirred during 4 h at room temperature. After evaporation of the MeOH, water was added to the oily residue and the precipitate obtained was filtered. The crude residue was then purified by flash chromatography on silica gel (5–8% AcOEt/Hex) to afford the title compound 263 (114 mg, 59%) as a white solid. LRMS: 282.1 (Calc.). 283.0 (found).

Step 3: N-(2-Amino-phenyl)-4-chroman-3-ylmethyl-benzamide (265)

The title compound 265 was obtained following the same procedure as Example 1, steps 4 and 5. $^1$H NMR: (acetone) δ (ppm): 9.06 (bs, 1H), 8.01 (d, J=7.9 Hz, 2H), 7.42 (d, J=8.4 Hz, 2H), 7.31 (d, J=7.9 Hz, 1H), 7.08–6.98 (m, 3H), 6.87 (d, J=7.5 Hz, 1H), 6.82–6.66 (m, 3H), 4.62 (s, 2H), 4.22–4.17 (m, 1H), 4.88–3.81 (m, 1H), 2.88–2.71 (m, 3H), 2.61–2.53 (m, 1H), 2.41–2.33 (m, 1H). LRMS: 358.2 (calc.). 359.1 (found).

Example 159

Step 2: Methyl 4-(4-oxo-chroman-3-ylmethyl)-benzoate (264)

A suspension of 260 (400 mg, 1.36 mmol) and benzenesulfonyl hydrazine (702 mg, 4.08 mmol) in DMF (7 ml) was stirred at 100° C. during 48 h. The solvent was evaporated and the residue was diluted in AcOEt, washed with $NH_4Cl$ sat., brine, dried over anhydrous $MgSO_4$, filtered and concentrated. The crude residue was then purified by flash chromatography on silica gel (5% AcOEt/HEx) to afford the title compound 264 (170 mg, 42%) as a white solid. LRMS: 296.1 (Calc.). 297.0 (found).

Step 3: N-(2-Amino-phenyl)-4-(4-oxo-chroman-3-ylmethyl)-benzamide (266)

The title compound 266 was obtained following the same procedure as Example 1, steps 4 and 5. $^1$H NMR: (acetone) δ (ppm): 9.62 (bs, 1H), 7.93 (d, J=7.9 Hz, 2H), 7.79 (d, J=7.9 Hz, 1H), 7.58 (dd, J=7.0, 7.0 Hz, 1H), 7.39 (d, J=7.9 Hz, 2H), 7.17–7.04 (m, 3H), 6.97 (dd, J=7.0, 7,0 Hz, 1H), 6.78 (d, J=7.9 Hz, 1H), 6.60 (dd, J=7.5, 7.5 Hz, 1H), 4.88 (s, 2H), 4.44–4.39 (m, 1H), 4.28–4.21 (m, 1H), 2.26–3.21 (m, 2H), 2.83–2.74 (m, 1H). LRMS: 372.1 (calc.). 372.1 (found).

Scheme 47

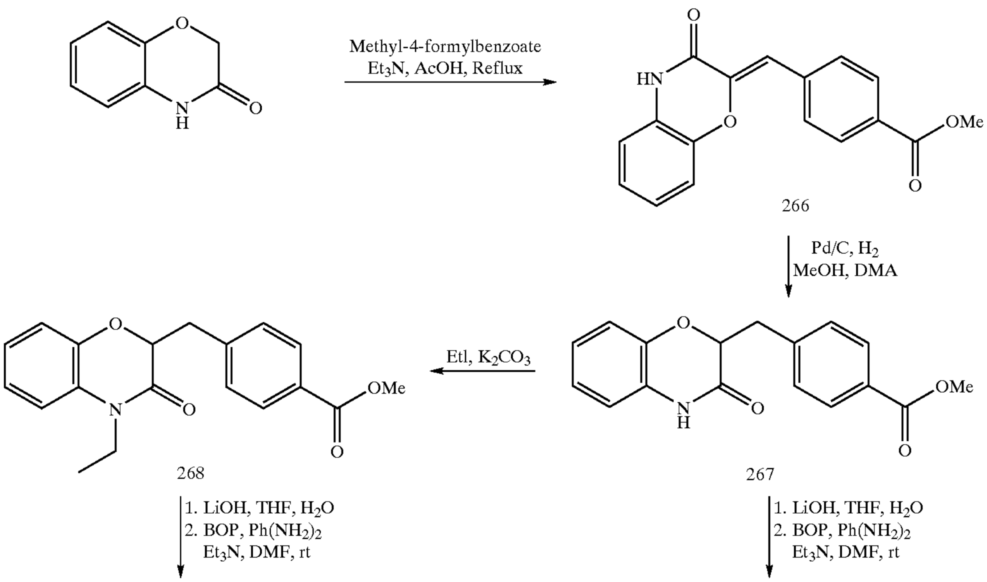

266

267

268

-continued

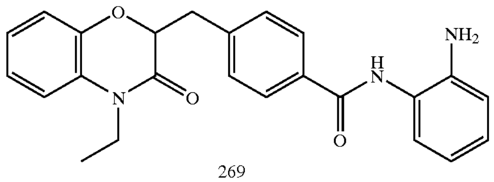

269
Example 160

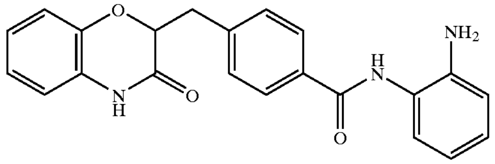

270
Example 161

Example 160

Step 1: Methyl 4-(3oxo-3,4-dihydro-2H-benzo[1,4]oxazin-2-ylmethyl)-benzoate (266)

$Et_3N$ (3.18 ml, 22.8 mmol) was added to a stirring solution of 2-H-1,4-benzoxazin-3-(4H)one (2.50 g, 16.8 mmol) and methyl 4-formylbenzoate (4.59 g, 27.5 mmol) in $Ac_2O$ (20 ml). The reaction mixture was refluxed 16 h. After this mixture was cooled for 3 days, the solid was filtered and rinsed with ethyl acetate to afford the title compound 266 (657 mg, 13%) as a yellow solid. LRMS: 295.1 (Calc.). 296.0 (found).

Step 2: Methyl 4-(3-oxo-3,4-dihydro-benzo[1.4]oxazin-2-ylidenemethyl)-benzoate (267)

The title compound 267 was obtained following the same procedure as Example 158, step 2. LRMS: 297.1 (Calc.). 298.1 (found).

Step 3: N-(2-Amino-phenyl)-4-(4-ethyl-3-oxo-3,4-dihydro-2 H-benzo[1,4]oxazin-2-ylmethyl)-benzamide (269)

The title compound 269 was obtained from 267 following the same procedure as Example 99, step 2, 3, then followed by Example 1, step 4, 5. $^{1}H$ NMR: (DMSO) δ (ppm): 9.61 (bs, 1H), 7.91 (d, J=7.9 Hz, 2H), 7.39 (d, J=7.9 Hz, 2H), 7.22 (d, J=7.9 Hz, 1H), 7.17 (d, J=7.5 Hz, 1H), 7.11–6.91 (m, 4H), 6.77 (d, J=7.0 Hz, 1H), 6.60 (dd, J=7.0, 7.0 Hz, 1H), 4.95–4.91 (m, 1H), 4.89 (bs, 2H), 3.95 (q, J=7.0 Hz, 2H), 3.28–3.22 (m, 1H), 3.17–2.89 (m, 1H), 1.16 (t, J=7.0 Hz, 3H). LRMS: 401.2 (calc.). 402.1 (obt.).

Example 161

Step 1: N-(2-Amino-phenyl)-4-(3-oxo-3,4-dihydro-2H-benzo[1,4]oxazin-2-ylmethyl)-benzamide (270)

The title compound 270 was obtained from 267 following the same procedure as Example 1, step 4, 5. $^{1}H$ NMR: (DMSO) δ (ppm): 10.74 (bs, 1H), 9.61 (bs, 1H), 7.91 (d, J=8.4 Hz, 2H), 7.41 (d, J=7.9 Hz, 2H), 7.17 (d, J=7.5 Hz, 1H), 6.99–6.85 (m, 5H), 6.78 (d, J=7.5 Hz, 1H), 6.60 (dd, J=7.0, 7.0 Hz, 1H), 4.92–4.89 (m, 3H), 3.29–3.23 (m, 1H), 3.15–3.07 (m, 1H). MS: (calc.) 373.1. (obt.) 374.1 $(MH)^+$.

Scheme 48

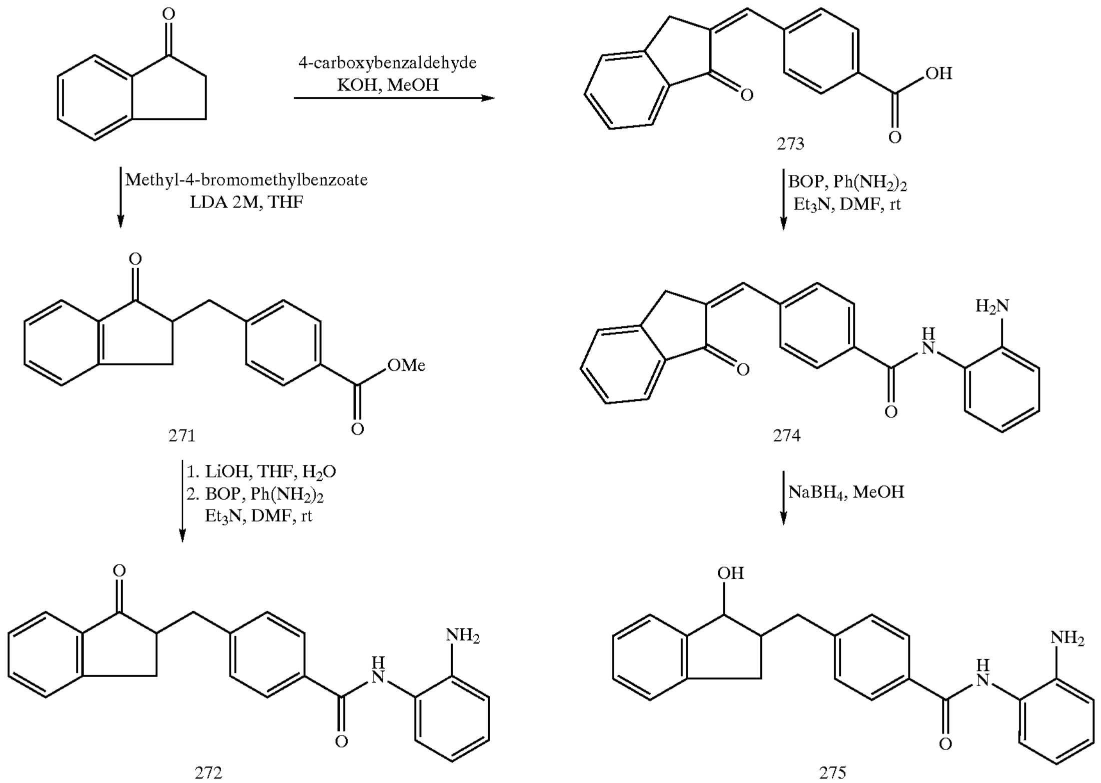

273

271

274

272
Example 162

275
Example 163

Example 162

Step 1: Methyl 4-(1-oxo-indan-2-ylmethyl)-benzoate (271)

A 2M LDA solution in THF (4.16 ml, 8.32 mmol) was added to a solution of indanone (1.00 g, 7.57 mmol) in THF (10 ml) at −60° C. The solution was slowly warmed to 0° C. during a period of 15 min. and was agitated for 15 more min. The reaction was then cooled to −78° C. and a solution of methyl-4-bromobenzoate (1.73 g, 7.57 mmol) was slowly added. The solution was slowly warmed to −20° C. and stirred during 4 hours. The reaction mixture was quenched with HCL 1M and the solvent was evaporated. The residue was diluted in ethyl acetate, washed with brine, dried over anhydrous $MgSO_4$, filtered and concentrated. The crude residue was then purified by flash chromatography on silica gel (5–20% AcOEt/HEx) to afford the title compound 271 (245 mg, 17%) as a white solid. LRMS: 280.1 (Calc.). 281.1 (found).

Step 2: N-(2-Amino-phenyl)-4-(1-oxo-indan-2-ylmethyl)-benzamide (272)

The title compound 272 was obtained following the same procedure as Example 1, step 4, 5. $^1$H NMR: (DMSO) δ (ppm): 9.59 (bs, 1H), 7.91 (d, J=7.6 Hz, 2H), 7.69–7.64 (m, 2H), 7.54 (d, J=7.6 Hz, 1H), 7.45–7.40 (m, 3H), 7.16 (d, J=8.2 Hz, 1H), 6.96 (dd, J=7.3, 7.3 Hz, 1H), 6.77 (d, J=8.2 Hz, 1H), 6.59 (dd, J=7.3, 7.3 Hz, 1H), 4.87 (bs, 2H), 3.23–3.14 (m, 3H), 2.85–2.81 (m, 2H). LRMS: 356.1 (calc.). 357.2 (found).

Example 163

Step 1: 4-(1Oxo-indan-2-ylidenemethyl)-benzoic acid (273)

To a suspension of indanone (2.00 g, 15.1 mmol) and 4carboxybenzaldehyde (1.89 g, 12.6 mmol) in EtOH (10 ml) was added KOH (1.77 g , 31.5 mmol) at 0° C. The reaction mixture was stirred 30 min at 0° C. then at room temperature for 16 h. The solvent was evaporated and the residue was dissolved in water, acidified to pH 5 with HCl 1 M. The precipitate was filtered and rinsed with water to afford the title compound 273 (2.27 g, 57%) as a yellow solid. LRMS: 264.1 (Calc.). 265.0 (found).

Step 2: N-(2-Amino-phenyl)-4-oxo-indan-2-ylidenemethyl)-benzamide (274)

The title compound 274 was obtained following the same procedure as Example 1, step 5. LRMS: 354.1 (Calc.). 355.0 (found).

Step 3: N-(2-Amino-phenyl)-4-(1-hydroxy-indan-2-ylmethyl)-benzamide (275)

To a suspension of 274 (300 mg, 0.85 mmol) in MeOH (8 ml) and water (1 ml) was added $NaBH_4$ (75 mg, 1.95 mmol). The reaction mixture was stirred at 50° C. 16 h and cooled down. Water was added to the solution and the precipitated was filtered and rinsed with cold water to afford the title compound 275 (224 mg, 74%) as a white solid. $^1$H NMR: (acetone) δ (ppm): 9.05 (bs, 1H), 8.00 (dd, J=8.2, 2.7 Hz, 2H), 7.47 (d, J=8.5 Hz, 1H), 7.43 (d, J=8.2 Hz, 1H), 7.38–7.30 (m, 2H), 7.22–7.12 (m, 3H), 7.01 (ddd, J=7.6, 7.6, 1.5 Hz, 1H), 6.87 (dd, J=8.0, 1.1 Hz, 1H), 6.68 (dd, J=7.6, 7.6 Hz, 1H), 4.98 (t, J=5.8 Hz, 0.4H), 4.89 (t, J=6.7 Hz, 0.6H), 4.63 (bs, 2H), 4.45 (d, J=6.9 Hz, 0.6H), 4.06 (d, J=6.0 Hz, 0.4H), 3.30–3.19 (m, 1H), 2.88–2.48 (m, 3H, $CH_2$). LRMS: 358.2 (calc.). 359.1 (found).

Scheme 49

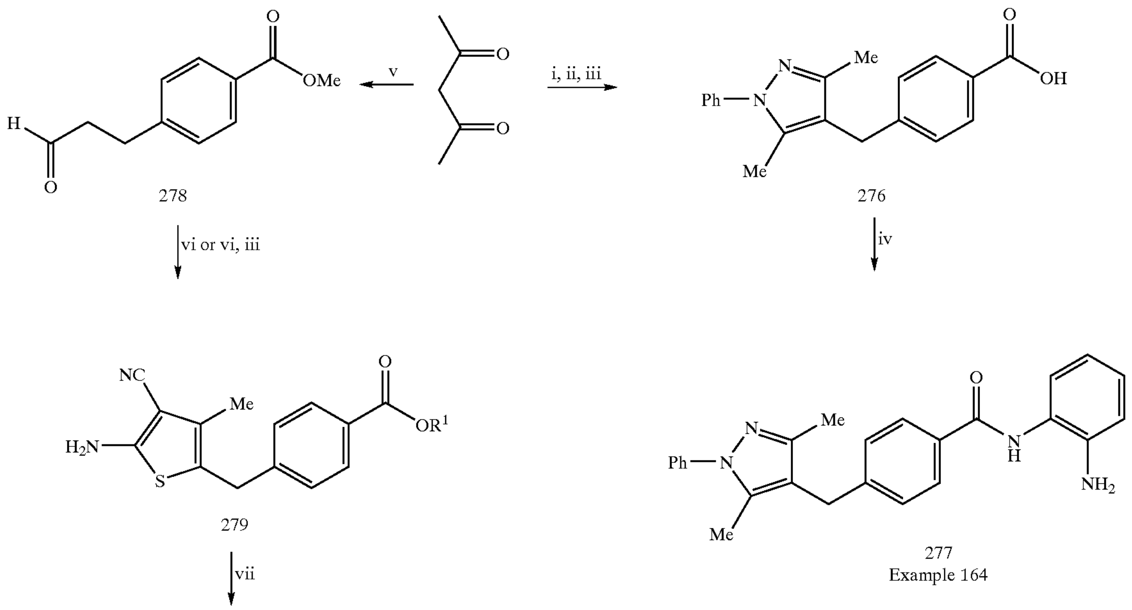

278

276

279

277
Example 164

-continued

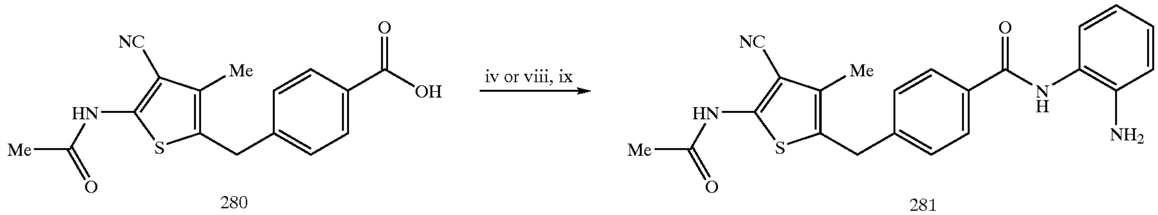

280

281
Example 165 i: $BrCH_2C_6H_4COOMe/MeONa/THF$;
ii: $PhNHNH_2$;
iii: NaOH, then HCl
iv: HOBt/EDC•HCl then 1,2-diaminobenzene;
v: $BrCH_2C_6H_4COOMe/MeONa/MeOH$, then HCl/AcOH;
vi: $CH_2(CN)_2/S_8/Et_2NH$(or $Et_3N$);
vii: AcCl, PhCOCl or PhNCO;
viii: 2-N-Bocamino aniline;
ix: TFA;

Example 164

Step 1 : 4-(3,5-Dimethyl-1-phenyl-1H-pyrazol-4-ylmethyl)-benzoic acid (276)

To a solution of NaH (60% in mineral oil, 250 mg, 6.3 mmol) at 0° C. acetyl acetone (0.646 ml, 6.3 mmol) was added followed by 4bromomethyl-benzoic acid methyl ester 2 (1.2 g, 5.2 mmol). The reaction mixture stirred 1 hour at room temperature and refluxed for 2 hours. Phenyl hydrazine (0.51 ml, 5.2 mmol) was added and the reaction mixture refluxed for an additional hour. THF was removed in vacuum and the oily residue was partitioned between water and ethyl acetate. Organic layer was separated, dried, evaporated and purify by chromatography on a silica gel column, eluent EtOAc-hexane (1:1) to produce an oily material (800 mg) which was treated with a solution of NaOH (0.8 g, 20 mmol) in 20 ml water for 1 hour at room temperature. The following steps, acidification with HCl (pH 6), extraction of the resultant emulsion with ethyl acetate, drying the extract with sodium sulfate, evaporation and column chromatography (eluent EtOAc-hexane, 1:1) afforded 390 mg of a mixture of 276 (the title compound) and 278 (molar ratio 1:2). $[M-1]^+$ 307.0 and 191.1. This mixture was taken for the next step as is.

Step 2. N-(2-Amino-phenyl)-4-(3,5-dimethyl-1H-pyrazol-4-ylmethyl)-benzamide (277)

Following a procedure analogous to that described in Example 92, step 2, but substituting 276 for 143, the title compound 277 was obtained in 25% yield (purified by chromatography using as eluent EtOAc-hexane, 1:1). $^1$H NMR: (300 MHz, DMSO-$d_6$, δ (ppm): 9.64 (s, 1H): 7.97 (d, J=7.6 Hz, 2H), 7.42–7.56 (m, 5H), 7.37 (d, J=8.2 Hz, 2H), 7.22 (d, J=7.6 Hz, 1H), 7.03 (t, J=7.6 Hz, 1H), 6.84 (d, J=8.2 Hz, 1H), 6.66 (t, J=7.6 Hz, 1H), 4.93 (s, 2H), 3.92 (s, 2H), 2.34 (s, 3H), 2.18 (s, 3H).

Example 165

Step 1: 4-(3-Oxo-butyl)-benzoic acid (278)

To a solution of acetyl acetone (5.0 ml, 49 mmol) at room temperature NaOMe (25% wt, 10.8 ml, 47.3 mmol) was added followed by 4-bromomethyl-benzoic acid methyl ester 2 (9.0 g, 39.3 mmol). The reaction mixture refluxed 3 hours, cooled to the room temperature and acidified with HCl (pH 1–2). Evaporation of the resultant solution yielded a residue, which was refluxed in a mixture of glacial AcOH (50 ml) and conc. HCl (25 ml) for 4 hours. Acids were removed in vacuum and the residue was triturated with water to form a crystalline material, which was collected by filtration and dried to afford 278 (6.72 g, 80% yield). [M−1] 191.1.

Step 2. 4-(5-Amino-4cyano-3-methyl-thiophen-2-ylmethyl)-benzoic acid 279

To a refluxing suspension of 4-(3-oxo-butyl)-benzoic acid 278 (700 mg, 3.65 mmol), malonodinitrile (241 mg, 3.65 mmol) and sulfur (130 mg, 3.65 mmol) in 20 ml EtOH, diethylamine (0.5 ml, 4.8 mmol) was added. The reaction mixture refluxed 1 hour, cooled to the room temperature, acidified with conc. HCl (pH 4–5) and evaporated to yield a solid residue. This material was partitioned between water and ethyl acetate, organic layer was separated, dried, evaporated and chromatographed on a silica gel column, eluent EtOAc-hexane, 1:1, to afford the title compound 279 (300 mg, 30% yield). $^1$H NMR: (300 MHz, DMSO-$d_6$, δ ppm): 7.87 (d, J=8.4 Hz, 2H), 7.29 (d, J=7.9 Hz, 2H), 6.98 (s, 2H), 3.92 (s, 2H), 2.03 (s, 3H).

Step 3. 4-(5Acetylamino-4-cyano-3methyl-thiophen-2-ylmethyl)-benzoic acid 280

To a solution of 4-(5-amino-4-cyano-3methyl-thiophen-2-ylmethyl)-benzoic acid 279 (230 mg, 0.86 mmol) in a solvent mixture acetone (5 ml)-dichloromethane (5 ml) at room temperature acetyl chloride (0.305 ml, 4.3 mmol) was added. After 2 hours of stirring at the same conditions a precipitate of the title compound 280 formed which was collected and dried (200 mg, 75% yield). [M−1] 313.1.

Step 4: N-(2-Amino-phenyl)-4-(5-acetylamino-4-cyano-3-methyl-thiophen-2-ylmethyl)-benzamide (281)

Following a procedure analogous to that described in Example 92, step 2, but substituting 280 for 143, the title compound 281 was obtained in 25% yield. 1H NMR (DMSO) δ (ppm): 9.61 (s, 1H); 7.91 (d, J=7.9 Hz, 2H), 7.34 (d, J=8.4 Hz, 2H), 7.15 (d, J=7.5 Hz, 1H), 6.96 (t, J=6.6 Hz, 1H), 6.77 (d, J=7.0 Hz, 1H), 6.59 (t, J=7.9 Hz, 1H), 4.89 (s, 2H), 4.10 (s, 2H), 2.19 (s, 3H), 2.16 (s, 3H). [M+1] 405.0.

Scheme 50

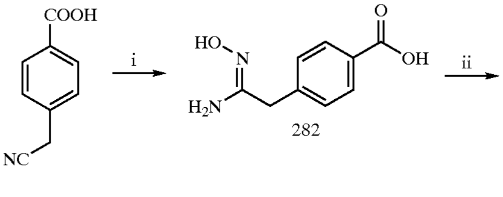

282

-continued

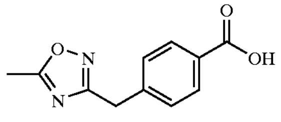

283

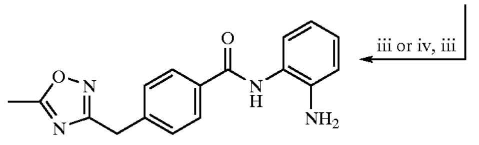

284

Example 166 i: $NH_2OH$/EtOH;

ii: RCOCl or $Ac_2O$/pyridine or $ClCH_2COCl$/toluene;

iii: HOBt/EDCxHCl then 1,2-diaminobenzene;

iv: morpholine or piperidine

Example 166

Step 1. 4-(N-Hydroxycarbamimidoylmethyl)-benzoic acid (282)

A suspension of 4-cyanomethyl benzoic acid (2.07 g, 12.86 mmol), $NH_2OH$.HCl (1.79 g, 25.71 mmol) and potassium hydroxide (2.16 g, 38.57 mmol) in 70 ml ethanol refluxed for 36 hours, poured into 100 ml water and acidified with conc. HCl (pH 5–6). EtOH was removed in vacuum and the remaining suspension was treated with another 100 ml water. A precipitate formed which was collected and dried to afford the title compound 282. [M+1]195.1.

Step 2. 4-(5-Methyl-[1,2,4]oxadiazol-3-ylmethyl)-benzoic acid (283)

A solution of 4-(N-hydroxycarbamimidoylmethyl)-benzoic acid 282 (388 mg, 2.0 mmol) in pyridine (8 ml) was treated with acetic anhydride (0.283 ml, 3.0 mmol). The resultant solution refluxed 6 hours, evaporated in vacuum and the remaining solid was triturated with water, collected by filtration, dried and purified by chromatography on a silica gel column, eluent EtOAc, EtOAc-MeOH (10:1) and finally EtOAc-MeOH (1:1), to produce 283 (164 mg, 38% yield). $[M-1]^-$ 217.1

Step 3. N-(2-Amino-phenyl)-4-(5-methyl-[1,2,4]oxadiazol-3-ylmethyl)-benzamide (284)

For the preparation of the title compound 284, a procedure analogous to that described in Example 92, step 2, but substituting 283 for 143, the title de compound 284 was obtained. $^1$H NMR: (DMSO) δ (ppm): 9.62 (s, 1H), 7.93 (d, J=7.9 Hz, 2H), 7.42 (d, J=8.4 Hz, 1H), 7.16 (d, J=7.5 Hz, 1H), 6.97 (t, J=7.9 Hz, 1H), 6.78 (d, J=7.5 Hz, 1H), 6.60 (t, J=7.9 Hz, 1H), 4.92 (s, 2H), 4.14 (s, 2H), 2.55 (s, 3H). $[M+1]^+$ 309.2

Scheme 51

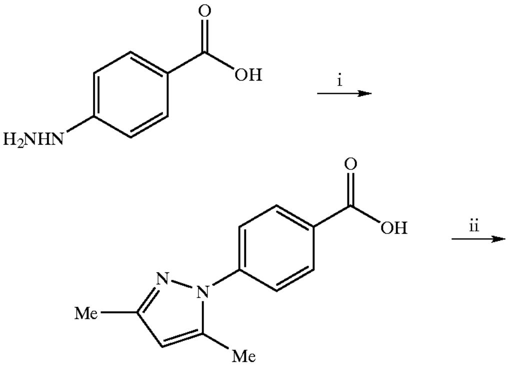

285

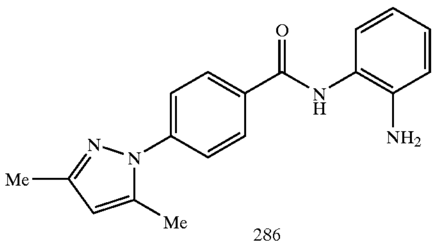

286

Example 167 i: Acetyl acetone/EtOH;

ii: HOBt/EDCxHCl then 1,2-diaminobenzene;

Example 167

Step 1: 4-(3,5-Dimethyl-pyrazol-1-yl)-benzoic acid (285)

A solution of 4-hydrazino-benzoic acid (0.60 g, 3.95 mmol) and acetyl acetone (0.405 ml, 3.95 mmol) in ethanol (20 ml) refluxed for 1 hour. Ethanol was removed in vacuum and the remaining solid was triturated with water and collected by filtration to produce 285 (0.71 mg, 83% yield). $[M-1]^-$ 215.1.

Step 2. N-(2-Amino-phenyl)-4-(3,5-dimethyl-pyrazol-1-yl)-benzamide (286)

For the preparation of the title compound 286, a procedure analogous to that described in Example 92, step 2, but substituting 285 for 143, the title compound 286 was obtained in 34% yield (purified by chromatography using as eluent $CH_2Cl_2$-methanol, 19:1). $^1$H NMR: (DMSO) δ (ppm): 9.73 (s, 1H); 8.09 (d, J=8.4 Hz, 2H), 7.64 (d, J=8.4 Hz, 2H), 7.17 (d, J=7.5 Hz, 1H), 6.98 (t, J=7.0 Hz, 1H), 6.78 (d, J=7.9 Hz, 1H), 6.60 (t, J=7.5 Hz, 1H), 6.13 (s, 1H), 4.92 (s, 2H), 2.37 (s, 3H), 2.20 (s, 3H). $[M+1]^+$ 303.3

Scheme 52

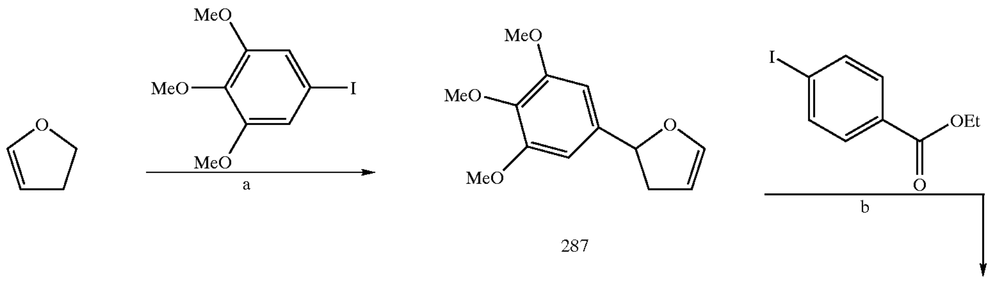

287

-continued

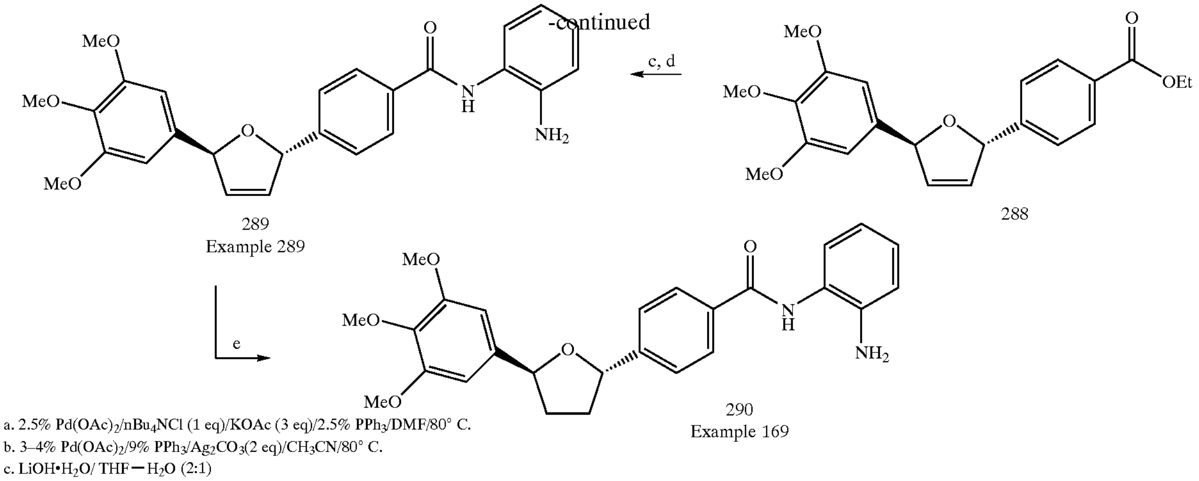

289
Example 289

288

290
Example 169 a. 2.5% $Pd(OAc)_2$/$nBu_4NCl$ (1 eq)/KOAc (3 eq)/2.5% $PPh_3$/DMF/80° C.
b. 3–4% $Pd(OAc)_2$/9% $PPh_3$/$Ag_2CO_3$(2 eq)/$CH_3CN$/80° C.
c. $LiOH{\cdot}H_2O$/ THF—$H_2O$ (2:1)
d. 1,2-phenylenediamine/BOP/$Et_3N$/DMF
e. $PtO_2$/$H_2$ (1 atm)/AcCOEt

Example 168

Step 1: 2-(3,4,5-Trimethoxy-phenyl)-2,3-dihydro-furan (287)

To a solution of 5-iodo-1,2,3-trimethoxybenzene (900 mg, 3.06 mmol) and 2,3-dihydrofuran (1.16 mL, 15.3 mmol) in dry DMF (8 mL) were added $PPh_3$ (20 mg, 0.077 mmol), KOAc (901 mg, 9.18 mmol), n-$Bu_4NCl$ (850 mg, 3.06 mmol) and $Pd(OAc)_2$ (17 mg, 0.077 mmol). The reaction mixture was stirred 18 h at 80° C. The reaction mixture was diluted with AcOEt and water. After separation, the organic layer was washed with brine, dried over anhydrous $Na_2SO_4$, filtered and concentrated. The crude residue was then purified by flash chromatography on silica gel (AcOEt/Hexane: 20/80) to afford the title compound 287 (311 mg, 1.32 mmol, 43% yield). $^1H$ NMR: (300 MHz, $CDCl_3$) δ (ppm): 6.59 (s, 2H), 6.45 (m, 1H), 5.45 (dd, J=10.5, 8.4 Hz, 1H), 4.97 (m, 1H), 3.87 (s, 6H), 3.84 (s, 3H), 3.06 (m, 1H), 2.62 (m, 1H).

Step 2: 4-[5-(3,4,5-Trimethoxy-phenyl)-2,5-dihydro-furan-2-yl]-benzoic acid ethyl ester (288)

To a solution of 287 (200 mg, 0.846 mmol) and 44odo-benzoic acid ethyl ester (468 mg, 1.69 mmol) in dry acetonitrile (4 mL) were added $PPh_3$ (20 mg, 0.076 mmol), $Ag_2CO_3$ (467 mg, 1.69 mmol) and $Pd(OAc)_2$ (7 mg, 0.03 mmol). The reaction mixture was stirred 18 h at 80° C. The reaction mixture was filtered through celite and washed with AcOEt. Water was added and the phases were separated. The organic layer was washed with brine, dried over anhydrous $Na_2SO_4$, filtered and concentrated. The crude residue was then purified by flash chromatography on silica gel (AcOEt/Hexane: 30/70) to afford the title compound 288 (280 mg, 0.728 mmol, 86% yield). $^1H$ NMR (300 MHz, $CDCl_3$) δ (ppm): 8.05 (d, J=7.5 Hz, 2H), 7.45 (d, J=7.5 Hz, 2H), 6.61 (s, 2H), 6.18–5.95 (m, 4H), 4.38 (q, J=7.0 Hz, 2H), 3.88 (s, 6H), 3.84 (s, 3H), 1.39 (t, J=7.0 Hz).

Step 3: N-(2-Amino-phenyl)-4-[5-(3,4,5-trimethoxy-phenyl)-2,5-dihydro-furan-2-yl]-benzamide (289)

Following a procedure analogous to that described in Example 1, step 4, 5, but substituting 288 for 6, the tile compound 289 was obtained in 48% yield. $^1H$ NMR (DMSO) δ (ppm): 8.00 (s, 1H), 7.91 (d, J=7.9 Hz, 2H), 7.48 (d, J=7.9 Hz, 2H), 7.33 (d, J=7.5 Hz, 1H), 7.09 (t, J=7.5 Hz, 1H), 6.92–6.82 (m, 2H), 6.61 (s, 2H), 6.14–5.99 (m, 4H), 3.89 (s, 6H), 3.84 (s, 3H).

Example 169

Step1: N-(2-Amino-phenyl)-4-[5-(3,4,5-trimethoxy-phenyl)-tetrahydro-furan-2-yl]-benzamide. (290)

To a degazed solution of 289 (43 mg, 0.096 mmol) in AcOEt (4 mL) was added $PtO_2$ (3 mg, 0.01 mmol) and the reaction mixture was stirred at room temperature under a 1 atm pressure of $H_2$ for 16 h. The reaction flask was purged with $N_2$ then the reaction mixture was filtered through celite, rinsed with MeOH and concentrated. The crude residue was purified three times by flash chromatography on silica gel (MeOH/DCM: 2/98, AcOEt/DCM: 30/70 and AcOEt/$CHCl_3$: 30/70) to afford the title compound 290 (10 mg, 0.22 mmol, 23% yield). $^1H$ NMR ($CDCl_3$) δ (ppm): 8.10 (s, 1H), 7.91 (d, J=8.0 Hz, 2H), 7.50 (d, J=8.0 Hz, 2H), 7.34 (d, J=7.5 Hz, 1H), 7.10 (t, J=7.5 Hz, 1H), 6.96–6.85 (m, 2H), 6.64 (s, 2H), 5.33 (t, J=7.0 Hz, 1H), 5.21 (t, J=7.0 Hz, 1H), 3.89 (s, 6H), 3.85 (s, 3H), 2.59–2.40 (m, 2H), 2.09–1.88 (m, 2H).

Scheme 53

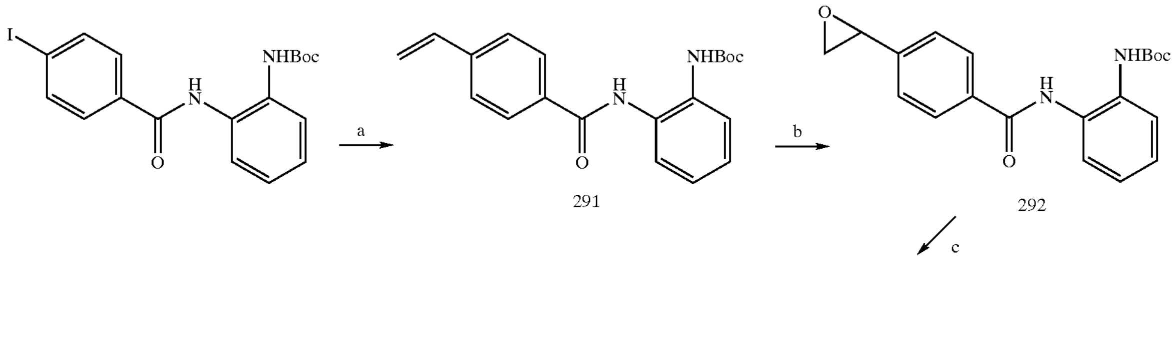

291

292

-continued

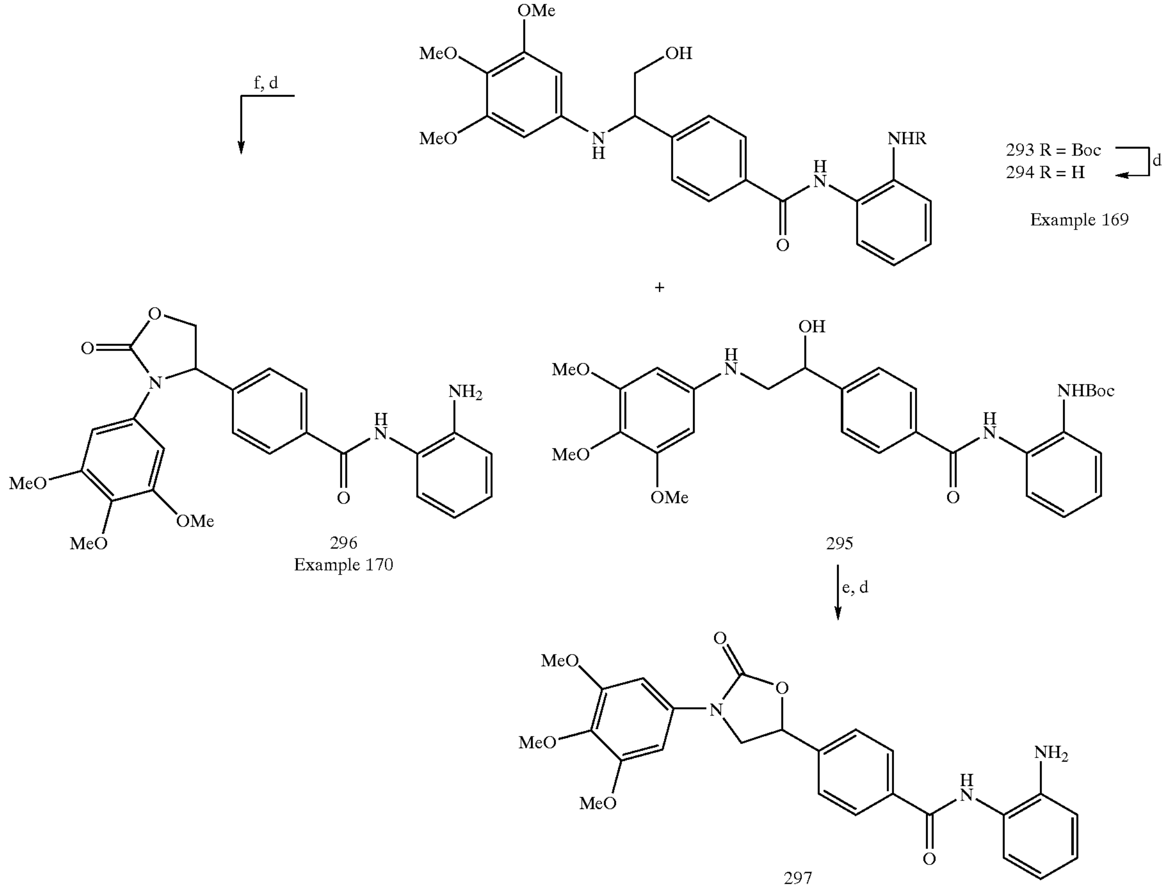

293 R = Boc
294 R = H

Example 169

+

296
Example 170

295

297
Example 171 a. Tributyl(vinyl)tin/Pd($PPh_3$)$_4$/Toluene/100° C.
b. m-CPBA/$CHCl_3$/r.t.
c. 3,4,5-trimethoxyaniline/$CoCl_2$/$CH_3CN$
d. TFA/DCM
e. 1,1′-carbonyldiimidazole/DCM/r.t.
f. 1,1′-carbonyldiimidazole/$Et_3N$/Toluene/THF/90° C.

Example 169

Step 1: [2-(4-Vinyl-benzoylamino)-phenyl]-carbamic acid tert-butyl ester (291)

Following a procedure analogous to that described in Example 143, step 2, but substituting 184 for 221, the title compound 291 was obtained in 90% yield as a dark yellow oil. $^1$H NMR: (300 MHz, $COCl_3$) δ (ppm): 9.18 (s, 1H), 7.94 (d, J=8.5 Hz, 2H), 7.77 (d, J=7.5 Hz, 1H), 7.49 (d, J=8.5 Hz, 2H), 7.30–7.10 (m, 3H), 6.89 (s, 1H), 6.77 (dd, J=17.4, 11.0 Hz, 1H), 5.87 (d, J=17.4 Hz, 1H), 5.39 (d, J=11.0 Hz, 1H), 1.52 (s, 9H).

Step 2: [2-(4-Oxiranyl-benzoylamino)-carbamic acid tert-butyl ester (292)

To a solution of 291 (4.1 g, 12.1 mmol) in dry $CHCl_3$ (60 mL) was added m-CPBA 70% (3.6 g, 14.5 mmol). The reaction mixture was stirred at room temperature for 5 h then additional m-CPBA (0.6 g, 2.4 mmol) was added and the stirring continued for 1 h. A further amount of m-CPBA (0.6 g, 2.4 mmol) was added and the reaction mixture was stirred for 16 h. Chloroform and a 10% solution of $NaHCO_3$ were added and the phases were separated. The organic layer was washed with water and brine, dried over anhydrous $Na_2SO_4$, filtered and concentrated. The crude residue was then purified by flash chromatography on silica gel (AcOEt/Hexane: 1/3) to afford the title compound 292 (2.86 g, 8.07 mmol, 66% yield). $^1$H NMR (300 MHz, $CDCl_3$) δ (ppm): 9.20 (s, 1H), 7.95 (d, J=8.1 Hz, 2H), 7.86–7.75 (m, 1H), 7.38 (d, J=8.1 Hz, 2H), 7.26–7.10 (m, 3H), 6.84–6.70 (m, 1H), 3.93 (t, J=3.0 Hz, 1H), 3.20 (t, J=5.0 Hz, 1H), 2.80 (dd, J=5.0, 3.0 Hz, 1H), 1.52 (s, 9H).

Step 3: (2-{4-[1-Hydroxy-2-(3,4,5-trimethoxy-phenylamino)-ethyl]-benzoylamino]-phenyl}-carbamic acid tert-butyl ester (295) and (2-{4-[2-Hydroxy-1-(3,4,5-trimethoxy-phenylamino)-ethyl]-benzoylamino}-phenyl)-carbamic acid tert-butyl ester (293)

To a stirred solution of $CoCl_2$ (8 mg, 0.06 mmol) in dry acetonitrile (10 mL) was added 292 (1 g, 2.8 mmol) followed by 3,4,5-trimethoxyaniline (516 mg, 2.8 mmol) and the reaction mixture was allowed to react for 16 h at room temperature then it was heated at 60° C. for 5 h. The reaction mixture was partitioned between AcOEt and water and the phases were separated. The organic layer was washed with brine, dried over anhydrous $Na_2SO_4$, filtered and concentrated. The crude residue was purified by flash chromatography on silica gel (AcOEt/Hexane: 1/1) to afford compounds 293 and 295 (combined: 1.07 g, 1.99 mmol, 71% yield, ratio 292/295=5/1) which can be separated by flash chromatography on silica gel (AcOEt/Hexane: 1/1). $^1$H NMR (300 MHz, $CDCl_3$) δ (ppm): Compound 292: 9.21 (s, 1H), 7.92 (d, J=8.1 Hz, 2H), 7.73 (d, J=6.6 Hz, 1H), 7.46 (d, J=8.1 Hz, 2H), 7.28–7.10 (m, 3H), 6.90 (s, 1H), 5.83 (s, 2H), 4.54–4.44 (m, 1H), 3.93 (dd, J=8.1, 3.9 Hz, 1H), 3.84–3.72 (m, 1H), 3.71 (s, 3H), 3.66 (s, 6H), 1.47 (s, 9H). Compound 295: 9.22 (s, 1H), 7.91 (d, J=8.1 Hz, 2H), 7.77 (d, J=7.2 Hz, 1H), 7.46 (d, J=8.1 Hz, 2H), 7.30–7.21 (m, 3H), 6.88 (s, 1H), 6.15 (s, 2H), 5.16–5.06 (m, 1H), 3.81 (s, 6H), 3.78 (s, 3H), 3.50–3.25 (m, 2H), 1.51 (s, 9H).

Step 4: N-(2-Amino-phenyl)-4-[2-hydroxy-1-(3,4,5-trimethoxy-phenylamino)-ethyl]-benzamide (294)

Following a procedure analogous to that described in Example 42, step 3, but substituting 293 for 46, the title compound 294 was obtained in 50% yield. $^1H$ NMR (DMSO) δ (ppm): 8.36 (s, 1H), 7.74 (d, J=6.9 Hz, 2H), 7.30 (d, J=7.8 Hz, 2H), 7.18 (d, J=6.9 Hz, 1H), 7.00 (t, J=7.2 Hz, 1H), 6.72 (m, 2H), 5.69 (s, 2H), 4.34 (m, 1H), 4.02–3.52 (m, 2H), 3.66 (s, 3H), 3.57 (s, 6H).

Example 170

Step 1: N-(2-Amino-phenyl)-4-[2-oxo-3-(3,4,5-trimethoxy-phenyl)-oxazolidin-4-yl]benzamide (296)

To a solution of 293 (200 mg, 0.372 mmol) in toluene (5 mL) and THF (1 mL) was added 1,1'-carbonyldiimidazole (72 mg, 0.45 mmol) followed by $Et_3N$ (156 μL, 1.12 mmol) and the mixture was stirred at room temperature for 5 h then at 90° C. for 48 h. The reaction mixture was diluted with AcOEt, a solution of sat. $NH_4Cl$ was added and the phases were separated. The organic layer was washed with brine, dried over anhydrous $Na_2SO_4$, filtered and concentrated. The crude residue was purified by flash chromatography on silica gel (DCM/AcOEt: 80/20) to afford the desired compound (120 mg, 0.21 mmol, 57% yield). $^1H$ NMR (DMSO) δ (ppm): 9.37 (s, 1H), 7.98 (d, J=8.1 Hz, 2H), 7.76 (d, J=7.5 Hz, 1H), 7.41 (d, J=8.1 Hz, 2H), 7.25–15 (m, 3H), 6.88 (s, 1H), 6.61 (s, 2H), 5.40 (dd, J=8.7, 6.0 Hz, 1H), 4.79 (t, J=8.7 Hz, 1H), 4.19 (dd, J=8.7, 6.0 1H), 3.75 (s, 3H), 3.72 (s, 6H), 1.47 (s, 9H).

Following a procedure analogous to that described in Example 42, step 3, but substituting the previous compound for 46, the title compound 296 was obtained in 81% yield. ). $^1H$ NMR (DMSO) δ (ppm): 8.03 (s, 1H), 7.91 (d, J=8.1 Hz, 2H), 7.41 (d, J=8.1 Hz, 2H), 7.30 (d, J=7.5 Hz, 1H), 7.07 (t, J=7.5 Hz, 1H), 6.82 (d, J=7.5 Hz, 2H), 6.61 (s, 2H), 5.40 (dd, J=8.7, 6.0 Hz, 1H), 4.78 (t, J=8.7 Hz, 1H), 4.18 (dd, J=8.7, 6.0 Hz, 1H), 3.75 (s, 3H), 3.71 (s, 6H).

Example 171

Step 1: N-(2-Amino-phenyl)-4-[2-oxo-3-(3,4,5-trimethoxy-phenyl)-oxazolidin-5-yl]-benzamide (297)

To a solution of 295 (130 mg, 0.242 mmol) in DCM (2 mL) was added 1,1'-carbonyidiimidazole (47 mg, 0.29 mmol) and the mixture was stirred at room temperature for 16 h. DCM was removed under reduced pressure, AcOEt and a solution of sat. $NH_4Cl$ were added and the phases were separated. The organic layer was washed with brine, dried over anhydrous $Na_2SO_4$, filtered and concentrated. The crude residue was purified by flash chromatography on silica gel (Hexane/AcOEt: 30/70) to afford the desired compound (80 mg, 0.14 mmol, 58% yield). $^1H$ NMR (DMSO) δ (ppm): 9.39 (s, 1H), 8.04 (d, J=8.1 Hz, 2H), 7.84 (d, J=7.5 Hz, 1H), 7.52 (d, J=8.1 Hz, 2H), 7.26–7.12 (m, 3H), 6.86–6.74 (m, 3H), 5.70 (t, J=8.4 Hz, 1H), 4.24 (t, J=8.7 Hz, 1H), 3.97–3.87 (m, 1H), 3.87 (s, 6H), 3.82 (s, 3H), 1.52 (s, 9H).

Following a procedure analogous to that described in Example 42, step 3, but substituting the previous compound for 46, the title compound 297 was obtained in 94% yield.). $^1H$ NMR (DMSO) δ (ppm); 8.38 (s, 1H), 7.97 (d, J=7.5 Hz, 2H), 7.47 (d, J=8.1 Hz, 2H), 7.35 (d, J=7.0 Hz, 1H), 7.08 (t, J=7.0 Hz, 1H), 6.97–6.87 (m, 2H), 6.79 (s, 2H), 5.66 (t, J=8.1 Hz, 1H), 4.41 (t, J=9.0 Hz, 1H), 3.91 (t, J=7.8 Hz, 1H), 3.86 (s, 6H), 3.82 (s, 3H).

Scheme 54

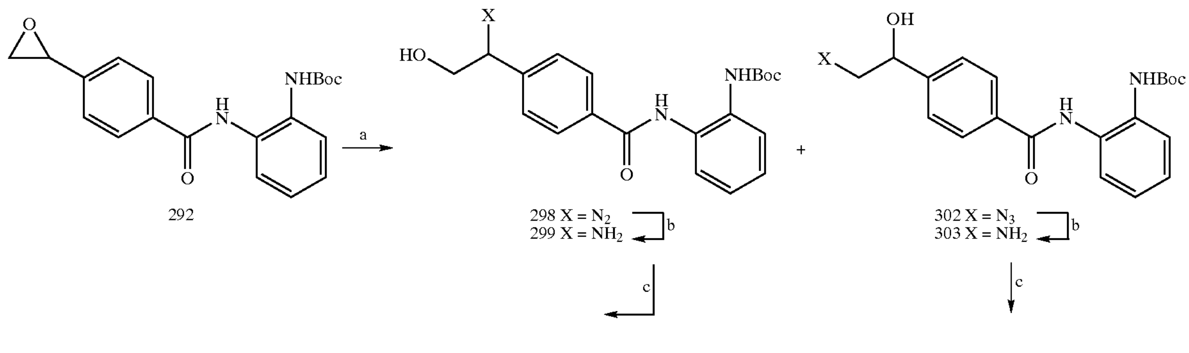

292

298 X = $N_2$
299 X = $NH_2$

302 X = $N_3$
303 X = $NH_2$

-continued
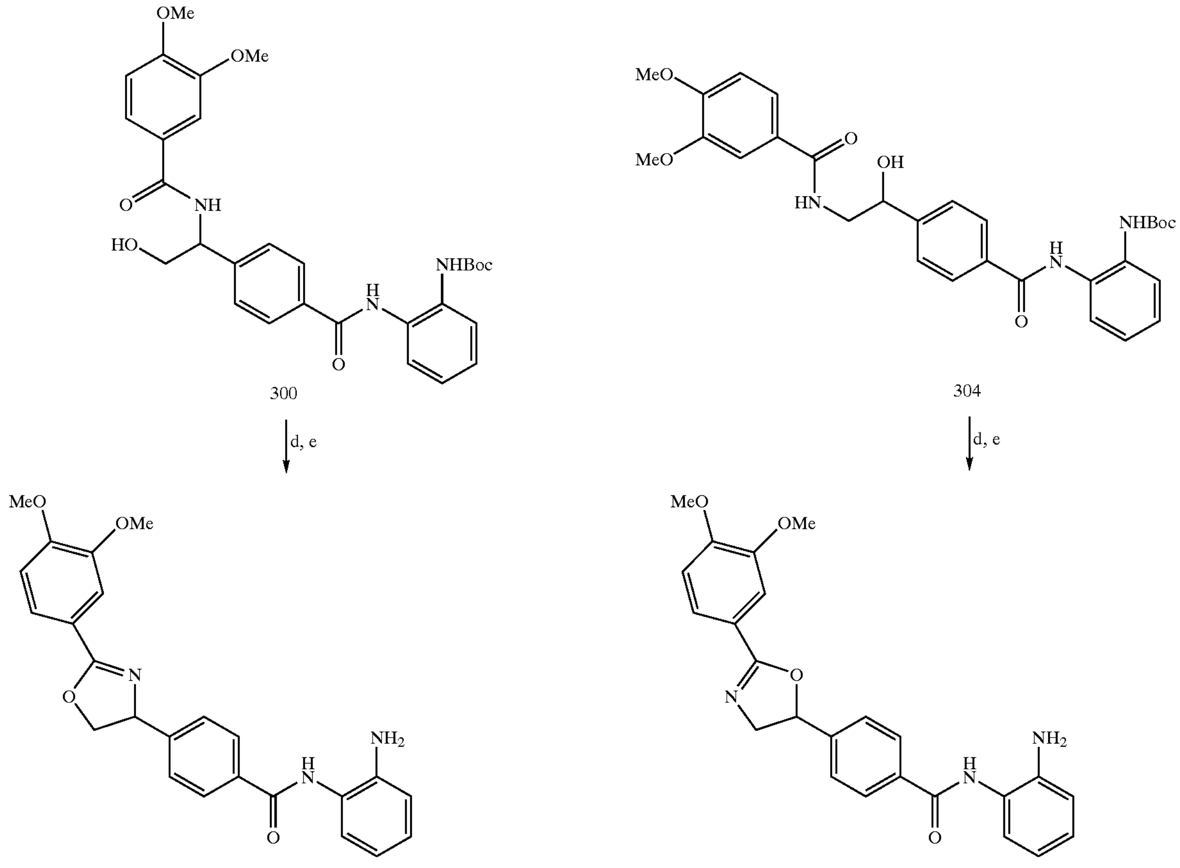
300
304
301
Example 172
305
Example 173
a. $CeCl_3$ heptahydrate/$NaN_3$/$CH_3CN$—$H_2O$ (9:1)/reflux
b. $H_2$/Pd/C (10%)/MeOH
c. 3,4-dimethoxybenzoyl chloride/$Et_3N$/DCM/-20° C. to r.t.
d. Burgess reagent/THF/70° C.
e. TFA/DCM
Scheme 55
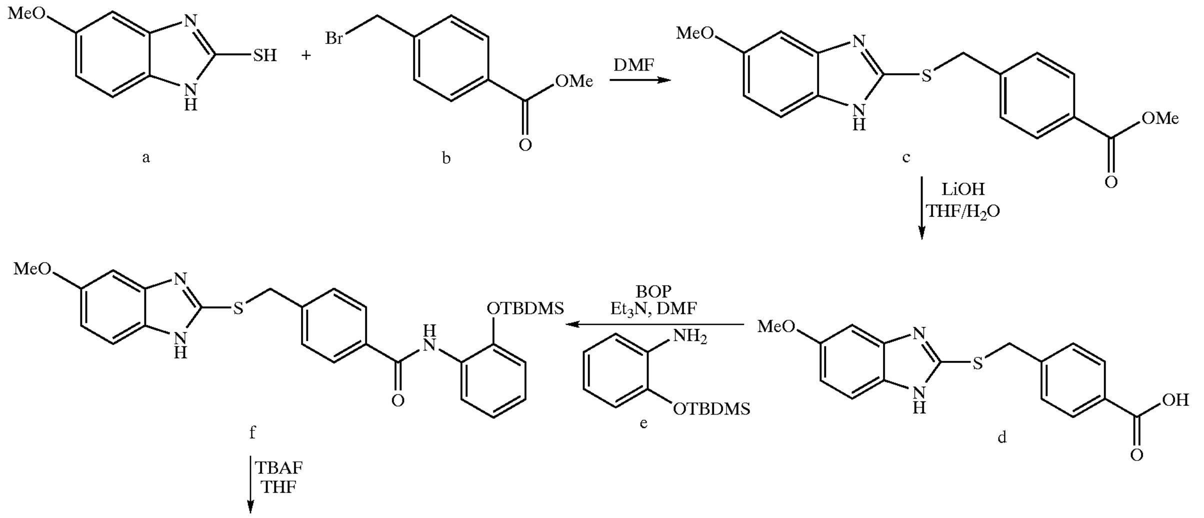
a b c d e f -continued

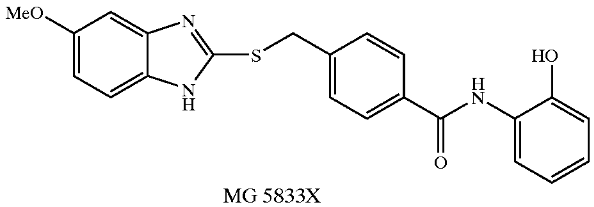

MG 5833X

Example 172

Step 1: {2-[4-(1-Azido-2-hydroxy-ethyl)-benzoylamino]-phenyl}-carbamic acid tert-butyl ester (298) and {2-[4-(2-Azido-1-hydroxy-ethyl)-benzoylamino]-phenyl}-carbamic acid tert-butyl ester (302)

To a solution of 292 (210 mg, 0.59 mmol) in acetonitrile (9 mL) and water (1 mL) was added $CeCl_3$ heptahydrate (110 mg, 0.296 mmol) followed by $NaN_3$ (42 mg, 0.65 mmol). The reaction mixture was refluxed for 3 h then acetonitrile was removed under reduced pressure. The residue was diluted with DCM, washed with brine, dried over anhydrous $Na_2SO_4$, filtered and concentrated. Purification by flash chromatography on silica gel (AcOEVHexane: 1/1) afforded a 1:1 mixture of title compounds 298 and 302 (combined: 187 mg, 0.47 mmol, 80% yield) which were separated by flash chromatography on silica gel (AcOEt/Hexane: 2/5). Compound 298: $^1$H NMR: (300 MHz, $CDCl_3$/$CD_3OD$) δ (ppm): 7.95 (d, J=8.1 Hz, 2H), 7.70–7.63 (m, 1H), 7.43 (d, J=8.1 Hz, 2H), 7.36–7.29 (m, 1H), 7.24–7.14 (m, 2H), 4.69 (dd, J=7.5, 4.8 Hz, 1H), 3.80–3.65 (m, 2H), 1.49 (s, 9H). Compound 302: $^1$H NMR: (300 MHz, $CDCl_3$) δ (ppm): 9.28 (s, 1H), 7.86 (d, J=8.4 Hz, 2H), 7.71 (d, J=7.5 Hz, 1H), 7.38 (d, J=8.4 Hz, 2H), 7.25–7.08 (m, 3H), 7.01 (s, 1H), 4.87 (dd, J=6.9, 5.1 Hz, 1H), 3.47–3.38 (m, 2H), 3.32–3.21 (bs, 1H), 1.50 (s, 9H).

Step 2: {2-[4-(1-Amino-2-hydroxy-ethyl)-benzoylamino]-phenyl}-carbamic acid tert-butyl ester (299)

To a solution of 298 (156 mg, 0.39 mmol) in MeOH (2 mL) was added Pd/C 10% (20 mg, 0.02 mmol). The reaction mixture was stirred under a 1 atm pressure of $H_2$ at room temperature for 16 h then it was purged with $N_2$. The palladium was removed by filtration through celite and the MeOH was evaporated under reduced pressure to afford the title compound 299 (88 mg, 0.24 mmol, 60% yield), which was used without purification. $^1$H NMR (300 MHz, $CDCl_3$) δ (ppm): 9.24 (s, 1H), 7.90 (d, J=7.8 Hz, 2H), 7.71 (d, J=6.6 Hz, 1H), 7.40 (d, J=7.8 Hz, 2H), 7.31–7.10 (m, 3H), 7.06–6.94 (m, 1H), 4.12 (dd, J=7.5, 4.5 Hz, 1H), 3.74 (dd, J=7.8, 5.4 Hz, 1H), 3.64–3.51 (m, 1H), 2.64 (s, 3H), 1.49 (s, 9H).

Step 3: (2-{4-[1-(3,4-Dimethoxy-benzoylamino)-2-hydroxy-ethyl]-benzoylamino}-phenyl)-carbamic acid tert-bytyl ester (300)

To a stirred solution of 299 (88 mg, 0.24 mmol) in dry DCM (2 mL) at −20° C. was added 3,4-dimethoxybenzoyl chloride (50 mg, 0.25 mmol) followed by $Et_3N$ (37 μL, 0.26 mmol). The reaction mixture was allowed to warm up to room temperature then was stirred for 48 h. A solution of sat. $NH_4Cl$ was added, followed by DCM and the phases were separated. The organic layer was washed with brine, dried over anhydrous $Na_2SO_4$, filtered and concentrated. The crude residue was purified by flash chromatography on silica gel (MeOH/DCM: 4/96) to afford title compound 300 (91 mg, 0.17 mmol, 71% yield). $^1$H NMR (300 MHz, $CDCl_3$) δ (ppm): 9.29 (s, 1H), 7.81 (d, J=8.1 Hz, 2H), 7.65–7.58 (m, 1H), 7.46 (m, 7H), 6.80 (d, J=8.1 Hz, 1H), 5.20–5.10 (m, 1H), 3.95–3.78 (m, 2H), 3.88 (s, 3H) 3.84 (s, 3H), 1.47 (s, 9H).

Step 4: N-(2-Amino-phenyl)-4-[2-(3,4- dimethoxy-phenyl)-4,5-dihydro-oxazol-4-yl]-benzamide (301)

To a solution of 300 (91 mg, 0.17 mmol) in dry THF (2 mL) was added the Burgess reagent (44 mg, 0.19 mmol) and the mixture was stirred at 70° C. for 2 h. The reaction mixture was partitioned between AcOEt and water and the phases were separated. The organic layer was washed with brine, dried over anhydrous $Na_2SO_4$, filtered and concentrated. The crude residue was purified by flash chromatography on silica gel (MeOH/DCM: 3/97) to afford the Boc-protected intermediate (75 mg, 0.14 mmol, 85% yield). $^1$H NMR ($CDCl_3$) δ (ppm): 9.31 (s, 1H), 7.94 (d, J=8.4 Hz, 2H), 7.72 (d, J=7.5 Hz, 1H), 7.66 (d, J=8.1 Hz, 1H), 7.61 (s, 1H), 7.39 (d, J=8.1 Hz, 2H), 7.27 (d, J=6.0 Hz, 1H), 7.23–7.08 (m, 3H), 6.93 (d, J=8.7 Hz, 1H), 5.43 (t, J=9.0 Hz, 1H), 4.84 (t, J=9.3 Hz, 1H), 4.26 (t, J=8.4 Hz, 1H), 3.95 (s, 3H), 3.94 (s, 3H), 1.50 (s, 9H).

Following a procedure analogous to that described in Example 42, step 3, but substituting the previous compound for 46, the title compound 301 was obtained in 82%. $^1$H NMR ($CDCl_3$) δ (ppm): 8.01 (s, 1H), 7.89 (d, J=7.9 Hz, 2H), 7.65 (dd, J=8.4, 1.5 Hz, 1H), 7.60 (d, J=1.5 Hz, 1H), 7.41 (d, J=7.9 Hz, 2H), 7.32 (d, J=7.9 Hz, 1H), 7.08 (t, J=6.6 Hz, 1H), 6.92 (d, J=8.4 Hz, 1H), 6.84 (d, J=7.9 Hz, 2H), 5.43 (dd, J=9.7, 8.4 Hz, 1H), 4.83 (dd, J=9.7, 8.4 Hz, 1H), 4.25 (t, J=8.1 Hz, 1H), 3.94 (s, 3H), 3.93 (s, 3H).

Example 173

Step 1: {2-[4-(2-Amino-1-hydroxy-ethyl)-benzoylamino]-phenyl}-carbamic acid tert-butyl ester (303)

The title compound 303 was obtained in 94% yield from 302 following the same procedure as in Example 172, step 2. The compound 303 was used directly for next step without purification.

Step 2: 2-{4-[2-(3,4-Dimethoxy-benzoylamino)-1-hydroxy-ethyl]-benzoylamino}-phenyl)-carbamic acid tert-butyl ester (304)

The title compound 304 was obtained in 40% yield from 303 and 3,4-dimethoxybenzoyl chloride following the same procedure as in Example 172, step 3. $^1$H NMR ($CDCl_3$) δ (ppm): 9.31 (s, 1H), 7.78 (d, J=8.1 Hz, 2H), 7.68 (d, J=6.9 Hz, 1H), 7.38 (d, J=1.8 Hz, 1H), 7.33 (d, J=8.1 Hz), 7.30–7.06 (m, 4H), 7.00–6.93 (m, 1H), 6.79 (d, J=8.4 Hz, 1H), 4.89–4.82 (m, 1H), 3.88 (s, 3H), 3.86 (s, 3H), 3.85–3.73 (m, 1H, 3.44–3.32 (m, 1H), 1.46 (s, 9H).

Step 3: N-(2-Amino-phenyl)-4-[2-(3,4-dimethoxy-phenyl)-4,5-dihydro-oxazol-5-yl]-benzamide (305)

Following a procedure analogous to that described in Example 172, step 4, 5, but substituting 304 for 300, the title compound 305 was obtained in 63%. $^1$H NMR ($CDCl_3$) δ (ppm): 8.02 (s, 1H), 7.93 (d, J=8.1 Hz, 2H), 7.63 (dd, J=8.4, 1.8 Hz, 1H), 7.60 (s, 1H), 7.44 (d, J=8.1 Hz, 2H), 7.33 (d, J=7.5 Hz, 1H), 7.09 (t, J=7.5 Hz, 1H), 6.91 (d, J=8.1 Hz, 1H), 6.85 (d, J=8.1 Hz, 2H), 5.74 (dd, J=10.0, 7.8 Hz, 1H), 4.51 (dd, J=14.5, 10.0 Hz, 1H), 4.00–3.90 (m, 7H).

Scheme 57

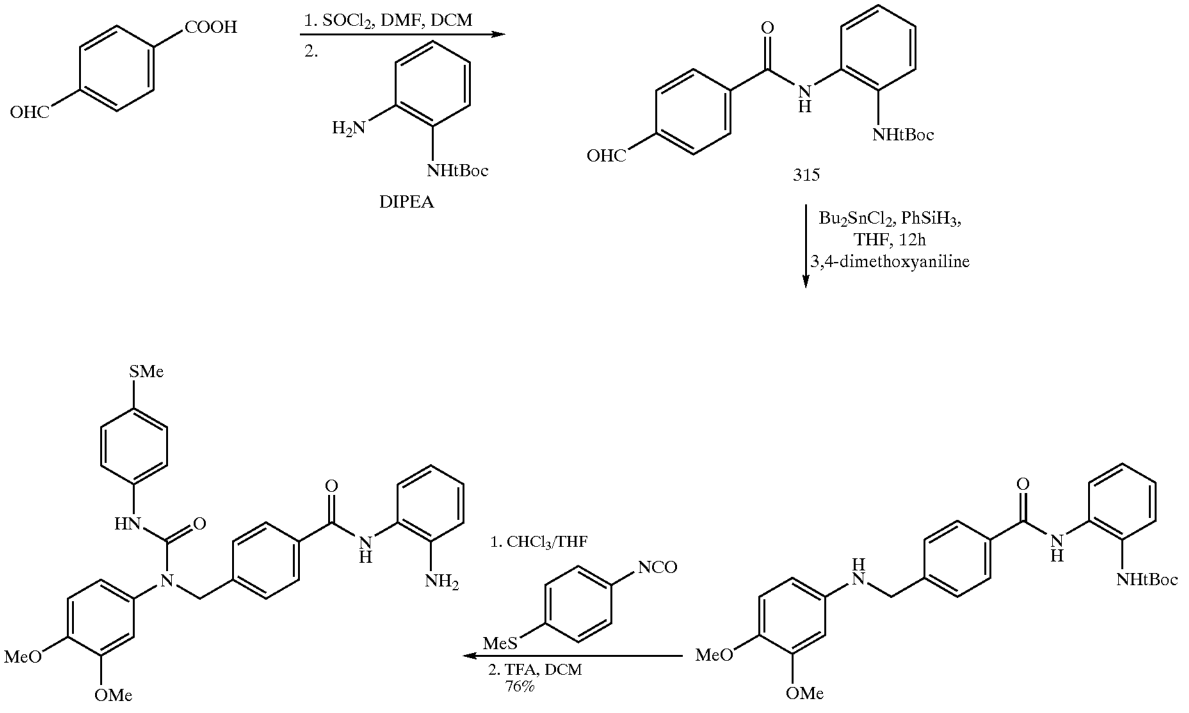

315, 316, 317

Example 178

Example 178

Step 1: [2-(4FORMYL-BENZOILAMINO)-PHENYL]-CARBAMIC ACID TERT-BUTYL ESTER (315)

To a suspension of 4-carboxybenzaldehyde (6 g, 40 mmol) in dichloromethane (10 mL) was added thionyl chloride (4.1 mL, 56 mmol, 1.4 eq), followed by DMF (1 mL) dropwise. The mixture was refluxed for 4 hours and excess of thionyl chloride and DMF were removed under reduced pressure. To a solution of (2-aminophenyl)-carbamic acid tert-butyl ester (8.32 g, 40 mmol, 1 eq) in dichloromethane (80 mL), stirred at 0° C., was added a suspension of 4-formyl benzoyl chloride in dichloromethane (20 mL), followed by diisopropyl ethylamine (3.61 mL, 20 mmol, 1 eq). The mixture was stirred for 30 minutes at 0° C. then at room temperature for 30 minutes. The crude residue was diluted with dichloromethane (300 mL) and washed with water. The combined organic layers were dried ($MgSO_4$), filtered and concentrated under vacuo. The crude residue was purified by column chromatography on silica gel (elution 20% ethyl acetate in hexane) to give 6.1 g (45% yield) of anilide 315. $^1$H NMR ($CDCl_3$): δ 10.18 (s, 1H), 9.64 (brs, 1H), 8.20 (d, J=7.9 Hz, 2H), 8.06 (d, J=7.9 Hz, 2H), 7.96 (d, J=7.9 Hz, 1H), 7.28–7.38 (m, 1H), 7.24 (d, J=4.4 Hz, 1H), 6.84 (s, 1H), 6.81 (d, J=8.8 Hz, 1H), 1.58 (s, 9H).

Step 2: (2-{4-[(3,4-Dimethoxyphenylamino)-Methyl]-Benzoylamino}-Phenyl)-Carbamic Acid Tert-Butyl Ester (316)

Following a procedure analogous to that described in Example 144, step 3, but substituting the previous compound for 226, the title compound 316 was obtained in quantitative yield. $^1$H NMR ($CDCl_3$): δ 9.21 (brs, 1H), 8.01 (d, J=7.9 Hz, 2H), 7.86 (d, J=7.0 Hz, 1H), 7.55 (d, J=8.3 Hz, 2H), 7.20–7.34 (m, 3H), 6.89 (brs, 1H), 6.81 (d, J=8.8 Hz, 1H), 6.37 (d, J=2.2 Hz, 1H), 6.23 (dd, J=2.6, 8.3 Hz, 1H), 4.45 (s, 2H), 3.89 (s, 3H), 3.88 (s, 3H), 1.58 (s, 9H).

Step 3: N-(2-Aminophenyl)-4-[1-(3,4-dimethoxyphenyl)-3-(4-methylsulfanylphenyl)-ureidomethyl]-benzamide 317

To a solution of anilide 316 (500 mg, 1.047 mmol) in chloroform/THF (1:1, 10 mL) was added isocyanate (169 μL, 1.205 mmol, 1.15 eq). The mixture was stirred overnight at room temperature under nitrogen and the crude residue was concentrated and purified by column chromatography on silica gel (elution 40% ethyl acetate in hexane) to give 606 mg (90% yield) of the desired compound. $^1$H NMR ($CDCl_3$): δ 9.25 (s, 1H), 7.96 (d, J=8.3 Hz, 2H), 7.85 (d, J=7.0 Hz, 1H), 7.44 (d, J=8.3 Hz, 2H), 7.20–7.36 (m, 6H), 6.93 (d, J=3.5 Hz, 1H), 6.90 (s, 1H), 6.75 (dd, J=2.2, 8.3 Hz, 1H), 6.68 (dd, J=2.6 Hz, 1H), 6.33 (s, 1H), 5.0 (s, 2H), 3.97 (s, 3H), 3.85 (s, 3H), 2.51 (s, 3H), 1.57 (s, 9H).

Following a procedure analogous to that described in Example 42, step 3, but substituting the previous compound for 46, the title compound 317 was obtained in 85% yield. $^1$H NMR (DMSO-$d_6$): δ 10.14 (brs, 1H), 7.99 (d, J=7.9 Hz, 2H), 7.93 (s, 1H), 7.49 (d, J=8.35 Hz, 4H), 7.39 (d, J=7.5 Hz, 1H), 7.10–7.30 (2m, 5H), 6.97 (dd, J=2.2, 8.35 Hz, 1H), 6.77 (dd, J=2.2, 8.35 Hz, 1H), 5.02 (s, 2H), 3.80 (s, 3H), 3.77 (s, 3H), 2.48 (s, 3H).

Scheme 58

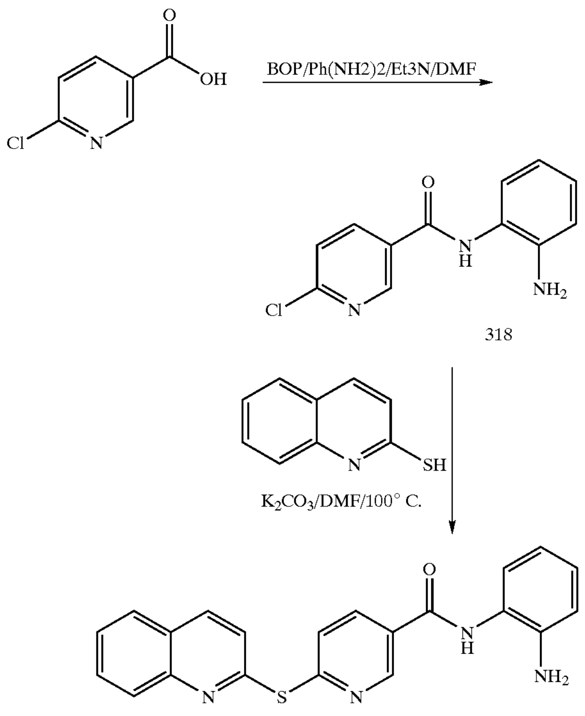

318

319
Example 179

Example 179

Step 1: N-(2-Amino-phenyl)-6-chloro-nicotinamide (318)

Following the procedure described in Example 42, step 2, the title compound 318 was obtained in 80% yield. LRMS=calc: 246.69. found: 247.7.

Step 2: N-(2-Amino-phenyl)-6-(quinolin-2-ylsulfanyl)-nicotinamide (319)

Following the procedure described in Example 45, step 1 but substituting 318 for 3,4,5-trimethoxybenzylamine, the tite compound 319 was obtained in 20% yield. $^1$H NMR: ($CD_3$OD-d6) δ (ppm): 9.08 (d, J=1.9 Hz, 1H), 8.35–8.25 (m, 2H), 7.99–7.56 (m, 7H), 7.23 (dd, J=1.2, 7.9 Hz, 1H), 7.12 (dd J=1.4, 7.9, 14.0 Hz, 1H), 6.93 (dd, J=1.2, 8.0 Hz, 1H), 6.79 (ddd, J=1.4, 7.7, 13.7 Hz, 1H).

Scheme 59

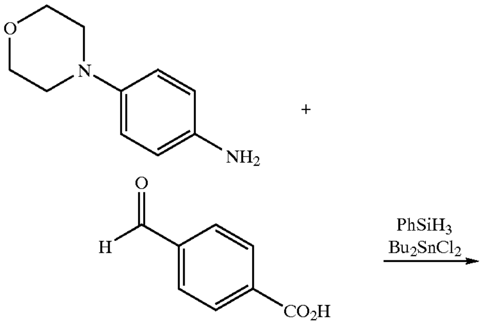

-continued

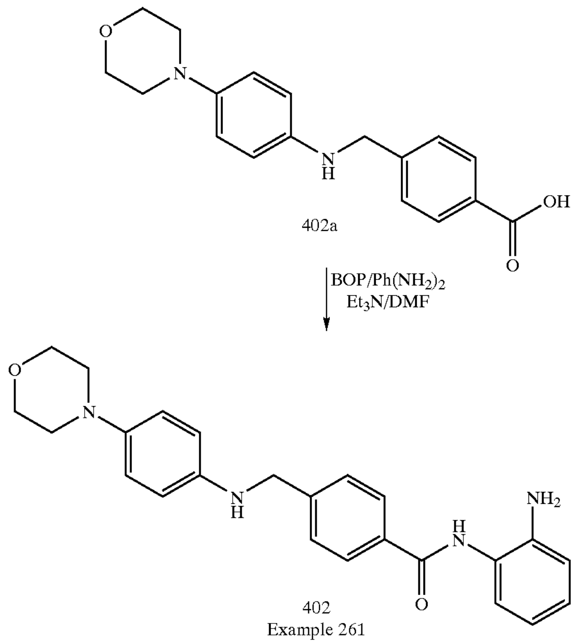

402a

402
Example 261

Example 261

Step 1: 4-[(4Morpholin-4-yl-phenylamino)-methyl]-benzoic acid (402a).

A suspension of 4-formylbenzoic acid (2.53 g; 16.8 mmol; 1 eq), 4-morpholinoaniline (3 g; 16.8 mmol; 1 eq) and $Bu_2SnCl_2$ (510 mg; 1.68 mmol; 0.1 eq) in dry THF (20 ml) was treated with $PhSiH_3$ (3.31 ml; 16.8 mmol; 1 eq) at room temperature for 12 h. The reaction was filtered and the solid product was washed with MeOH. The yield of the reaction was 5.25 g (99%). LRMS: calc 312.37. found: 313.2.

Step 2: N-(2-Amino-phenyl)-4-[(4-morpholin-4-yl-phenylamino)-methyl]-benzamide (402)

To a solution of acid 402a (2.61 g; 8.36 mmol; 1 eq), 1,2-phenylenediamine (903 mg; 8.36 mmol; 1 eq) and BOP (3.70 g; 8.36 mmol; 1 eq) in dry DMF (20 ml) was added $Et_3$N (4.64 ml; 33.4 mmol; 4 eq). After stirring overnight most of the DMF was removed under reduced pressure and chromatographed (Hex:EtAcO: 1:2/EtAcO). The crystal 402 was obtained in 70% (2.35 g). $^1$H-NMR (300.07 MHz, DMSO-d6) δ (ppm): 9.65 (s, 1H), 7.97 (d, J=7.9, 2H), 7.53 (d, J=7.9, 2H), 7.22 (d, J=7.5, 1H), 7.03 (dd, J=7.0, 7.5, 1H), 6.83 (d, J=7.9, 1H), 6.77 (d, J=8.8, 2H), 6.65 (dd, J=7.5, 7.0,1 H), 6.57 (d, J=8.8, 2H), 4.93 (bs, 2H), 4.36 (d, J=5.7, 2H), 3.75 (m, 4H), 2.93 (m, 4H). LRMS: calc 402.49. found: 403.4.

Scheme 60

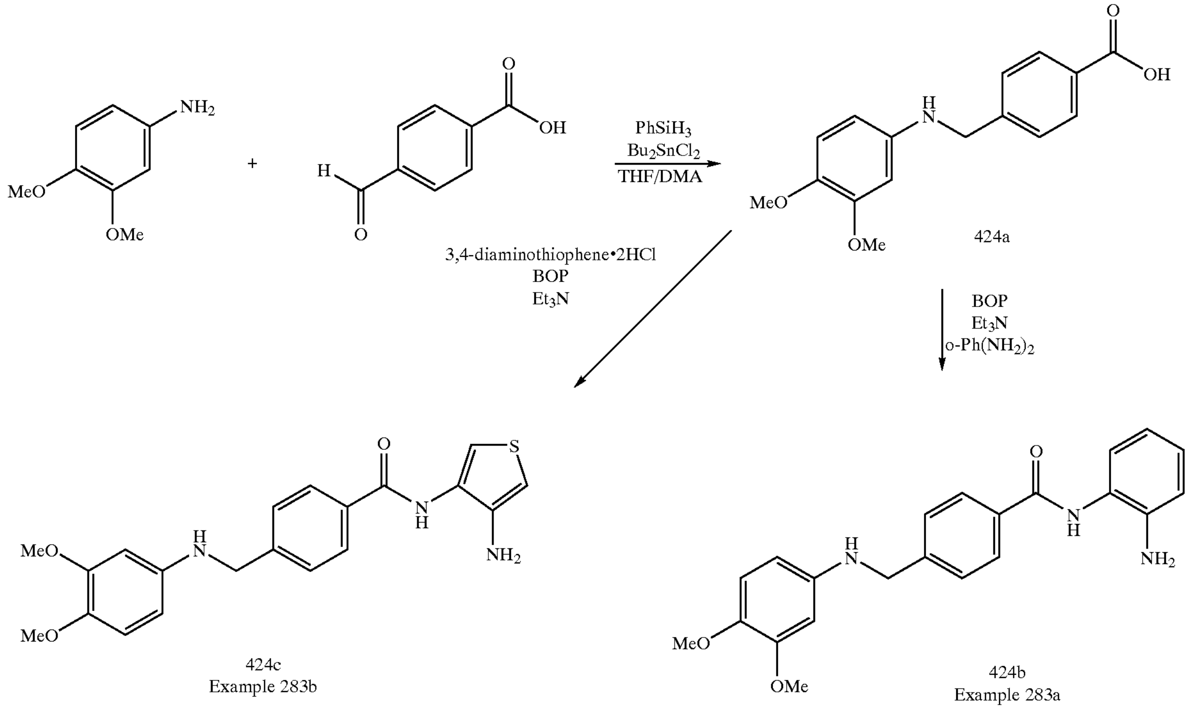

424a

424c
Example 283b

424b
Example 283a

Example 283a

Step 1. 4-[(3,4-Dimethoxyphenylamino)-methyl]-benzoic acid (424a)

In a 50 ml flask, a mixture of 4-aminoveratrole (1.53 g, 10 mmol), 4formyl-benzoic acid (1.50 g, 10 mmol), dibutyltin dichloride (304 mg, 1 mmol), phenylsilane (2.47 ml, 20 mmol) in anhydrous THF (10 mL) and DMA (10 ml) was stirred overnight. at room temperature. After solvents removal, the crude residue was dissolved in ethyl acetate (100 ml) and then washed with saturated aqueous solution of $NaHCO_3$ (50 mlx3). The combined aqueous layers were acidified with 6% of $NaHSO_4$ to pH=4. The resulting white suspension was filtrated and then the filter cake was washed with water (5 mlx3). The cake was dried over freeze dryer to afford acid (1.92 g, 67%) white solid product. LRMS=288 $(MH)^+$.

Step 2. N-(2-Aminophenyl)-4-[(3,4-dimethoxyphenyl-amino)-methyl]-benzamide (424b)

In a 150 ml flask, a mixture of acid (1.92 g, 6.69 mmol), benzotriazol-1-yloxy-tris(dimethylamino)phosphonium hexafluorophosphate (BOP, 3.26 g, 7.37 mmol), triethylamine (1.87 ml, 13.4 mmol), o-phenylenediamine (1.30 g, 12.02 mmol) in methylenechloride (67 ml) was stirred at rt for 2 h. After solvents removal, the crude residue was dissolved in EtOAc (100 ml) and then washed with $NaHCO_3$ saturated solution and brine 50 ml. The combined organic layers were dried over $Na_2SO_4$ and the filtrate was concentrated to dryness. The crude material was submitted to a chromatographic purification (column silica, 55%–70% EtOAc in 1% $Et_3N$ of hexanes) and then the all interested fractions were concentrated to dryness. The residue was suspended in minimum quantities of ethyl acetate and then filtered to afford final product (1.49 g, 59%). $^1H$ NMR (300 MHz, DMSO-$d_6$) δ (ppm): 9.65 (s, 1H), 7.98 (d, J=7.9 Hz, 2H), 7.54 (d, J=7.9 Hz, 2H), 7.22 (d, J=7.9 Hz, 1H), 7.02 (dd, J=7.9, 7.9 Hz, 1H), 6.83 (d, J=7.9 Hz, 1H), 6.72 (d, J=8.79 Hz, 1H), 6.45 (dd, J=7.5, 7.5 Hz, 1H), 6.39 (d, J=2.2 Hz, 1H), 6.01–6.08 (m, 2H), 4.94 (s, 2H, $NH_2$), 4.36 (d, J=6.16 Hz, 2H), 3.72 (s, 3H), 3.65 (s, 3H).

Example 283b

Step 1: N-(4-Aminothiophen-3-yl)-4-[(3,4-dimethoxyphenylamino)-methyl]-benzamide:

Acid 424a (1040 mg; 3.62 mmol); 3,4-diaminothiophene dihydrochloride (1017 mg; 5.44 mmol; 1.50 eq.) and BOP (1770 mg; 4.0 mmol; 1.1 eq.) were suspended in MeCN, treated with triethylamine (4 mL; 29 mmol) and stirred for 18 h at room temperature; concentrated and purified by chromatographic column on silica gel (elution 50% EtOAc in DCM) to render 527 mg (1.37 mmol; 38% yield) of compound 424c which was 90% pure. 1H-NMR (300.07 MHz; DMSO-d6) δ (ppm): 8.56 (s, 1H), 7.78 (d, J=7.9 Hz, 2H), 7.43 (d, J=3.5 Hz, 1H), 7.38 (d, J=7.9 Hz, 2H), 6.73 (d, J=8.8 Hz, 1H), 6.33 (d, J=3.5 Hz, 1H), 6.58 (d, J=2.6 Hz, 1H), 6.13 (dd, J=2.6, 8.3 Hz, 1H), 4.33 (s, 2H), 3.80 (s, 3H), 3.78 (s, 3H). LRMS: calc: 383.4642. found: 384.2 (M+H); 406.2 (M+Na) and 192.6 (M+2H)/2.

Scheme 61

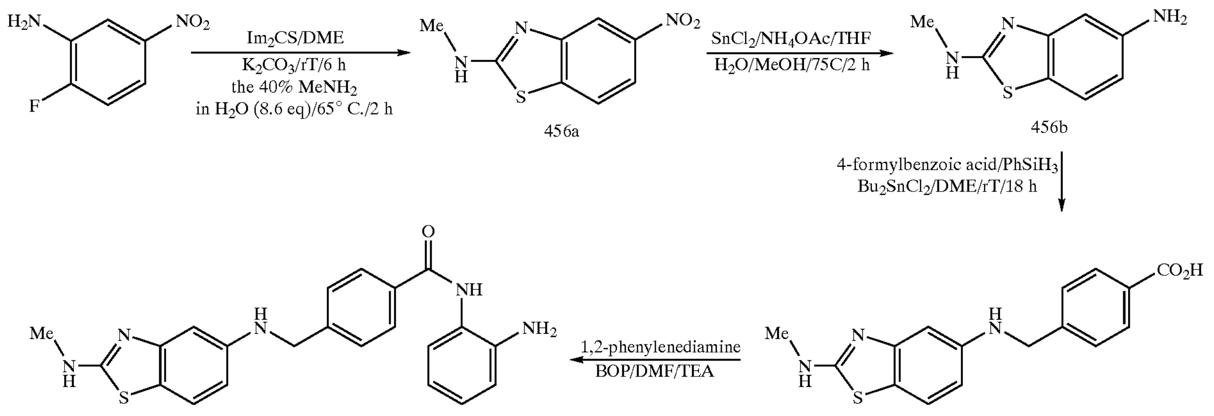

456
Example 315

Step 1: Methyl-(5-nitrobenzothiazol-2-yl)-amine (456a)

A mixture of 2-fluoro-5-nitroaniline (861 mg; 5.52 mmol; 1.02 eq); $Im_2CS$ (960.3 mg; 5.39 mmol) and dry $K_2CO_3$ (1.45 g) was suspended in dry DME (10 mL) and stirred under nitrogen for 90 min at room temperature. The yellow suspension was made fluid by diluting with DME (10 mL) followed by addition of 40% $MeNH_2$ in water (4.0 mL; 46.5 mmol; 8.6 eq). The system was heated up to 65C and stirred at this temperature for 3.5 h, cooled down, diluted with ethyl acetate and washed with saturated NaCl (×2). After conventional work-p procedures, the dark crude mixture was purified through chromatographic column on silica gel (elution 50% EtOAc in hexane, then 5% MeOH in DCM), to afford 836.8 mg (4.0 mmol; 72% yield) of compound 456a.

Step 2: N-Methyl-benzothiazole-2,5-diamine (456b)

A mixture of nitro compound 456a (593 mg; 2.83 mmol); $SnCl_2$ (4.02 g; 20.8 mmol; 7.35 eq) and $NH_4OAc$ (4.5 g) was suspended in THF:MeOH:$H_2O$=1:1:1 (60 mL) and stirred at 70° C. for 2 h, cooled down, diluted with ethyl acetate and successively washed with saturated $NaHCO_3$ and brine; dried ($MgSO_4$) filtered and concentrated. The residue (443 mg; 2.43 mmol; 87%) showed consistent spectrum and suitable purity degree for synthetic purposes, therefore was submitted to the next step without further purification.

Step 3: 4-[(2-Methylaminobenzothiazol-5-Ylamino)-Methyl]-Benzoic Acid (456c)

A solution of aniline 456b (509 mg; 2.8 mmol); 4-formylbenzoic acid (426 mg; 2.8 mmol) and $Bu_2SnCl_2$ (198 mg; 0.65 mmol; 23% mol) in DME (14 mL) was stirred at room temperature for 3 min and treated with neat $PhSiH_3$ (0.6 mL; 4.7 mmol; 1.7 mmol) and allowed to react for 18 h. After quenching the excess of silane with MeOH, the mixture was concentrated and purified by chromatographic column on silica gel (elution 5% MeOH in DCM) to give 729 mg (2.54 mmol; 91% yield) of acid 456c.

Step 4: N-(2-Aminophenyl)-4-[(2-methylamino-benzothiazol-5-ylamino)-methyl]-benzamide (456)

A mixture of acid 456c (729 mg; 2.54 mmol), 1,2-phenylenediamine (376 mg; 3.47 mmol; 1.36 eq) and BOP (1.43 g; 3.23 mmol; 1.27 eq) was dissolved in acetonitrile (15 mL), treated with triethylamine (3 mL) and stirred overnight. The reaction mixture was quenched with methanol, concentrated and purified by chromatographic column on silica gel (40% EtOAc in DCM) and the obtained material crystallized from DCM to give 358 mg (0.88 mmol; 35% yield) of pure compound 456. $^1$H-NMR (300 MHz; DMSO-d6) δ (ppm): 9.57 (s, 1H), 7.92 (d, J=7.9 Hz, 2H), 7.66 (d, J=4.8 Hz, 1H), 7.48 (d, J=8.3 Hz, 2H), 7.26 (d, J=8.3 Hz, 1H), 7.15 (d, J=7.9 Hz, 1H), 6.95 (t, J=7.5 Hz, 1H), 6.76 4.87 (bs, 2H), 6.58 (t, J=7.5 Hz, 1H), 6.54 (d, J=1.8 Hz, 1H), 6.13 (dd, J=1.8, 8.3 Hz, 1H), 6.27 (t, J=5.7 Hz, 1H), 4.87 (bs, 2H), 4.36 (d, J=5.7 Hz, 2H), 2.85 (d, J=4.8 Hz, 3H). LRMS: calc: 403.5008. found: 404.2(M+NH) and 202.6 (M+2H)/2.

Scheme 62

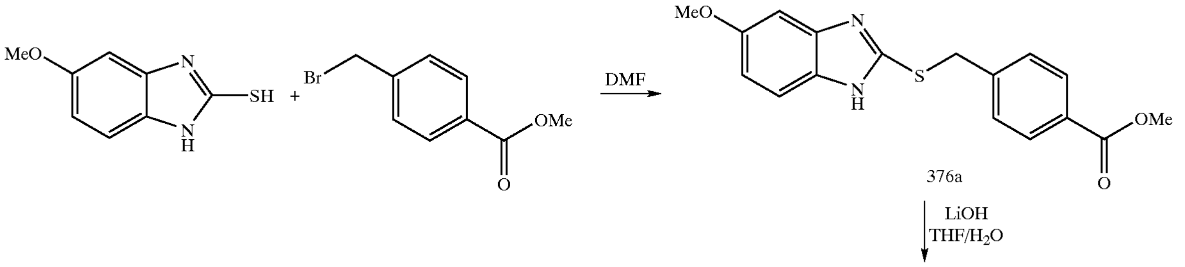

-continued

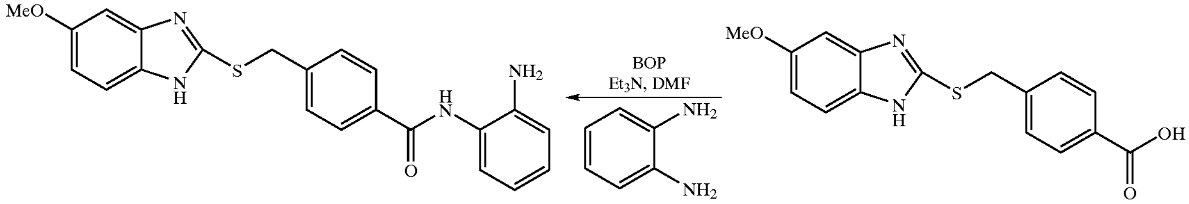

376
Example 235

376b

Example 235

Step 1: Methyl-4-(5-methoxy-1H-benzimidazol-2-yl-sulfanylmethyl)-benzoate (376a)

To a solution 5-methoxy-2-thiobenzimidazole (2.00 g, 11.1 mmol of in anhydrous DMF (40 ml) was added methyl-4bromomethyl)-benzoate (2.54 g, 11.1 mmol). The reaction mixture was stirred 16 h at room temperature. The DMF was evaporated and the residue was triturated in ethyl acetate during 30 min and then filtered and dried. The desired compound was isolated as the HBr salt: 98% yield, (4.44 g). $^1$H NMR: (DMSO) δ (ppm): 7.90 (d, J=8.8 Hz, 2H), 7.56–7.52 (m, 3H), 7.09 (d, J=2.2 Hz, 1H), 7.01 (dd, J=8.8, 2.2 Hz, 1H), 4.73 (s, 2H), 3.82 (s, 6H). MS: (calc.) 328.1. (obt.), 329.2 (MH)+.

Step 2: 4-(5-Methoxy-1H-benzimidazol-2-yl-sulfanylmethyl)-benzoic acid (376b)

A solution of LiOH.H2O (1.02 g, 24.4 mmol) in water (15 ml) was added to a suspension of 376a (3.99 g, 9.75 mmol of in THF (10 ml). The reaction mixture was stirred 16 h at room temperature. The reaction mixture was acidified with a solution of HCl 1 M to pH 4. The desired product was triturated 20 min. at 0° C. and then filtered and dried. Compound 376b was obtained as a white powder (100% yield, 3.05 g). $^1$H NMR: (DMSO) δ (ppm): 12.85 (bs, 1H), 7.86 (d, J=8.1 Hz, 2H), 7.53 (d, J=8.1 Hz, 2H), 7.35 (d, J=8.1 Hz, 1H), 6.97 (d, J=2.2 Hz, 1H), 6.76 (dd, J=8.8, 2.2 Hz, 1H), 4.60 (s, 2H), 3.82 (s, 3 H). MS: (calc.) 314.1. (obt.), 315.1 (MH)+.

Step 3: N-(2-Amino-phenyl)-4-(5-methoxy-1-H-benzimidazol-2-yl-sulfanylmethyl)-benzamide (376)

Following the procedure described in Example 1 step 5 but substituting 4-(5methoxy-1H-benzimidazol-2-yl-sulfanylmethyl)-benzoic acid 2 for 7 the title compound 376 was obtained as a white powder.: 36% yield (933 mg). $^1$H NMR: (DMSO) δ (ppm): 12.42 (bs, 1H), 9.57 (bs, 1H), 7.89 (d, J=8.1 Hz, 2H), 7.55 (d, J=8.1 Hz, 2H), 7.34 (d, J=8.8 Hz, 1H), 7.14 (d, J=7.3 Hz, 1H), 6.98–6.93 (m, 2H), 6.77–6.55 (m, 2H), 6.58 (dd, J=7.3, 7.3 Hz, 1H), 4.87 (s, 2H), 4.59 (s, 2H), 3.77 (s, 3 H). MS: (calc.) 404.1. (obt.), 405.4 (MH)+.

Examples 180–328

Examples 180 to 327 (compounds 320–468) were prepared using the same procedure as described for compound 126 to 319 in Example 85 to 179 (scheme 11 to 58).

Examples 329–344

Examples 329 to 344 (compounds 470–485) were prepared using the same procedure as described for compound 8 to 224 in Example 1 to 143 (scheme 1 to 32).

Scheme 63

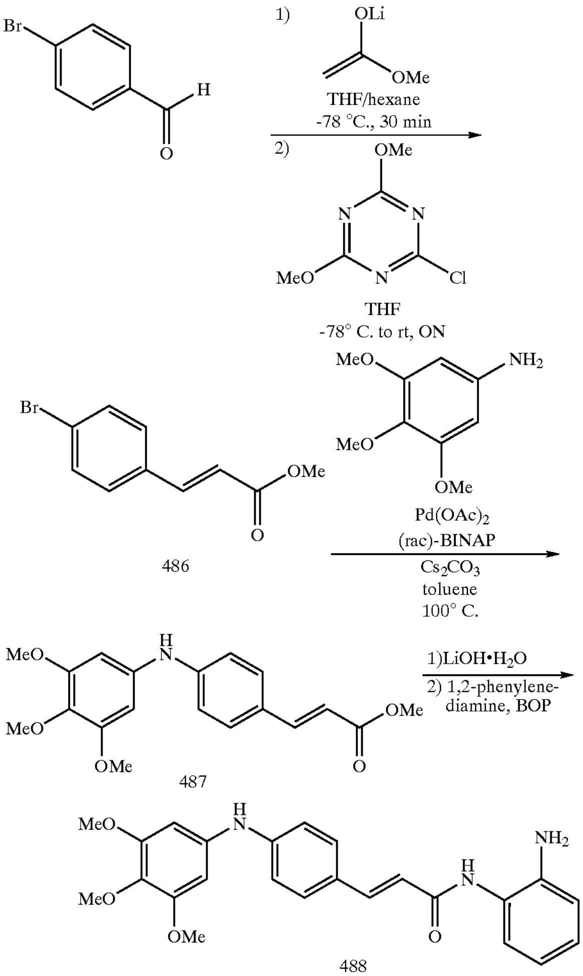

486

487

488
Example 345

Example 345

Step 1: Methyl 3-(4-bromo-phenyl)-acrylic ester (486)

To a solution of anhydrous i-$Pr_2$NH (758 $\mu$l, 5.40 mmol) in anhydrous THF (25 ml) stirred at 0° C. under nitrogen , was slowly added a solution of n-BuLi (2.22 ml, 5.54 mmol, 2.5 M in hexane). After 30 min, LDA was cooled to −78° C. and anhydrous methyl acetate (430 □, 5.40 mmol) was added dropewise. After 30 min, a solution of 4-bromobenzaldehyde (500 mg, 2.70 mmol) in anhydrous THF (10 ml) was slowly added. After 30 min, a solution of 2-chloro-4,6-dimethoxy-1,3,5-triazine (569 mg, 3.24 mmol)

in anhydrous THF (15 ml) was added. Then, the temperature was allowed to warm up to room temperature overnight. A suspension appeared. The reaction mixture was poured into a saturated aqueous solution of $NH_4Cl$, and diluted with AcOEt. After separation, the organic layer was successively washed with $H_2O$ and brine, dried over $MgSO_4$, filtered and concentrated. The crude product was purified by flash chromatography on silica gel (AcOEt/hexane: 10/90) to give the title product 486 (394 mg, 1.9 mmol, 61% yield) as a colorless crystalline solid. $^1$H NMR (300 MHz, $CDCl_3$) δ (ppm): 7.63 (d, J=16.2 Hz, 1H), AB system ($\delta_A$=7.53, $\delta_B$=7.39, J=8.4 Hz, 4H), 6.43 (d, J=15.8 Hz, 1H), 3.82 (s, 3H).

Step 2: Methyl 3-[4-(3,4,5-trimethoxy-phenylamino)-phenyl]-acrylic ester (487)

A mixture of $Cs_2CO_3$ (378 mg, 1.16 mmol), $Pd(OAc)_2$ (6 mg, 0.025 mmol), (rac)-BINAP (23 mg, 0.037 mmol), was purged with nitrogen for 10 min. 486 (200 mg, 0.83 mmol), 3,4,5-trimethoxyaniline (182 mg, 0.99 mmol), and anhydrous toluene (5 ml) were added, respectively. The reaction mixture was heated to 100° C. under nitrogen for 24 h. Then, it was allowed to cool to room temperature, diluted with AcOEt, and successively washed with a saturated aqueous solution $NaHCO_3$, $H_2O$, sat $NH_4Cl$, $H_2O$ and brine, dried over anhydrous $MgSO_4$, filtered and concentrated. The crude residue was then purified by flash chromatography on silica gel (AcOEt/hexane: 40/60) to afford the title compound 487 (280 mg, 0.82 mmol, 98% yield) as a yellow oil. $^1$H NMR (300 MHz, $CDCl_3$) δ (ppm): 7.64 (d, J=16.2 Hz, 1H), 7.43 (bd, J=7.9 Hz, 2H), 7.12–6.86 (m, 2H), 6.60–6.20 (m, 3H, included at 6.29, d, J=15.8 Hz), 3.84 (s, 9H), 3.80 (s, 3H).

Step 3: N-(2-Amino-phenyl)-3-[4-(3,4,5-trimethoxy-phenylamino)-phenyl]-acrylamide (488)

The title compound 488 was obtained from 487 in 2 steps following the same procedure as Example 1, steps 4 and 5. $^1$H NMR (300 MHz, DMSO-$d_6$) δ (ppm): 9.29 (s, 1H), 8.48 (s, 1H), 7.60–7.42 (m, 3H), 7.38 (d, J=7.5 Hz, 1H), 7.12 (d, J=8.4 Hz, 2H), 6.94 (t, J=7.5 Hz, 1H), 6.78 (d, J=7.9 Hz, 1H), 6.71 (d, J=15.8 Hz, 1H), 6.61 (t, J=7.1 Hz, 1H), 6.47 (s, 2H), 4.97 (s, 2H), 3.79 (s, 6H), 3.66 (s, 3H).

Scheme 64

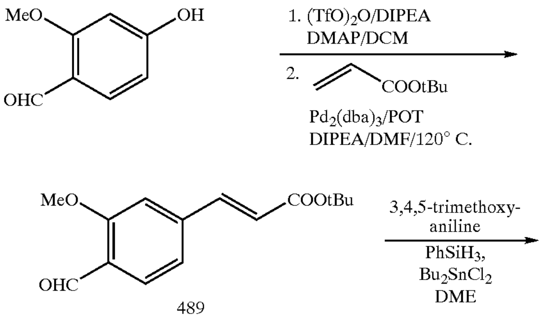

489

-continued

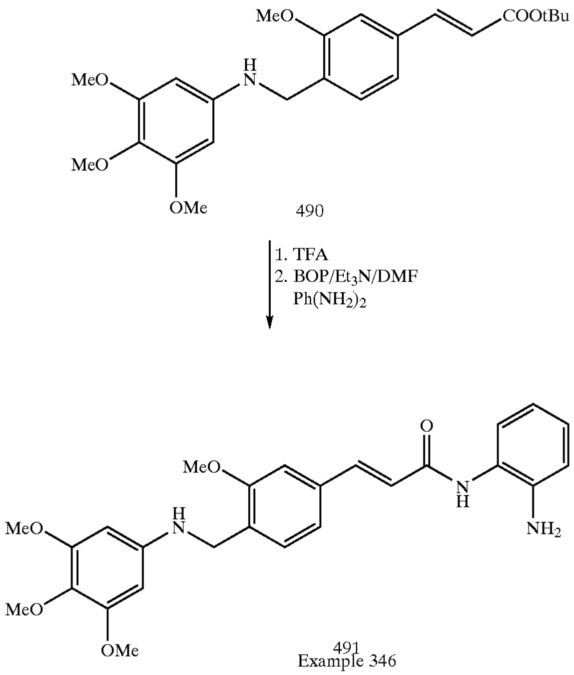

490

491
Example 346

Example 346

Step 1: 3-(4-Formyl-3-methoxy-phenyl)-acrylic acid tert-butyl ester 489

Following the procedure described in Example 53, step 1, but substituting 4 hydroxy-2-methoxybenzaldehyde for 84, followed by Example 42, step 2, but substituting the previous compound for 42, the title compound 489 was obtained in 29% yield. LRMS=calc: 262. found: 263.2. (M+$H^+$).

Step 2: 3-{3-Methoxy-4-[(3,4,5-trimethoxy-phenyllamino)-methyl]-phenyl}-acrylic acid tert-butyl ester 490

Following the procedure described in Example 144, step 3, but substituting 489 for 4-formylbenzaldehyde, the title compound 490 was obtained in 69% yield. LRMS=calc: 429. found: 430.5 (M+$H^+$).

Step 3: N-(2-Amino-phenyl)-3-{-methoxy-4-[(3,4,5-trimethoxy-phenylamino)-methyl]-phenyl}-acrylamide 491

Following the procedure described in Example 42, step 3, 4, but substituting 490 for 46, the title compound 491 was obtained in 67% yield. $^1$H NMR ($CDCl_3$), δ (ppm): 8.08 (s, 1H), 7.74 (d, J=15.4 Hz, 1H), 7.30 (m, 1H), 7.06 (m, 3H); 6.80 (m, 3H), 6.70 (d, J=15.4 Hz, 1H), 5.98 (s, 2H), 4.40 (s, 2H); 4.12 (bs, 3H), 3.94 (s, 3H), 3.84 (s, 3H), 3.77 (s, 6H).

Scheme 65

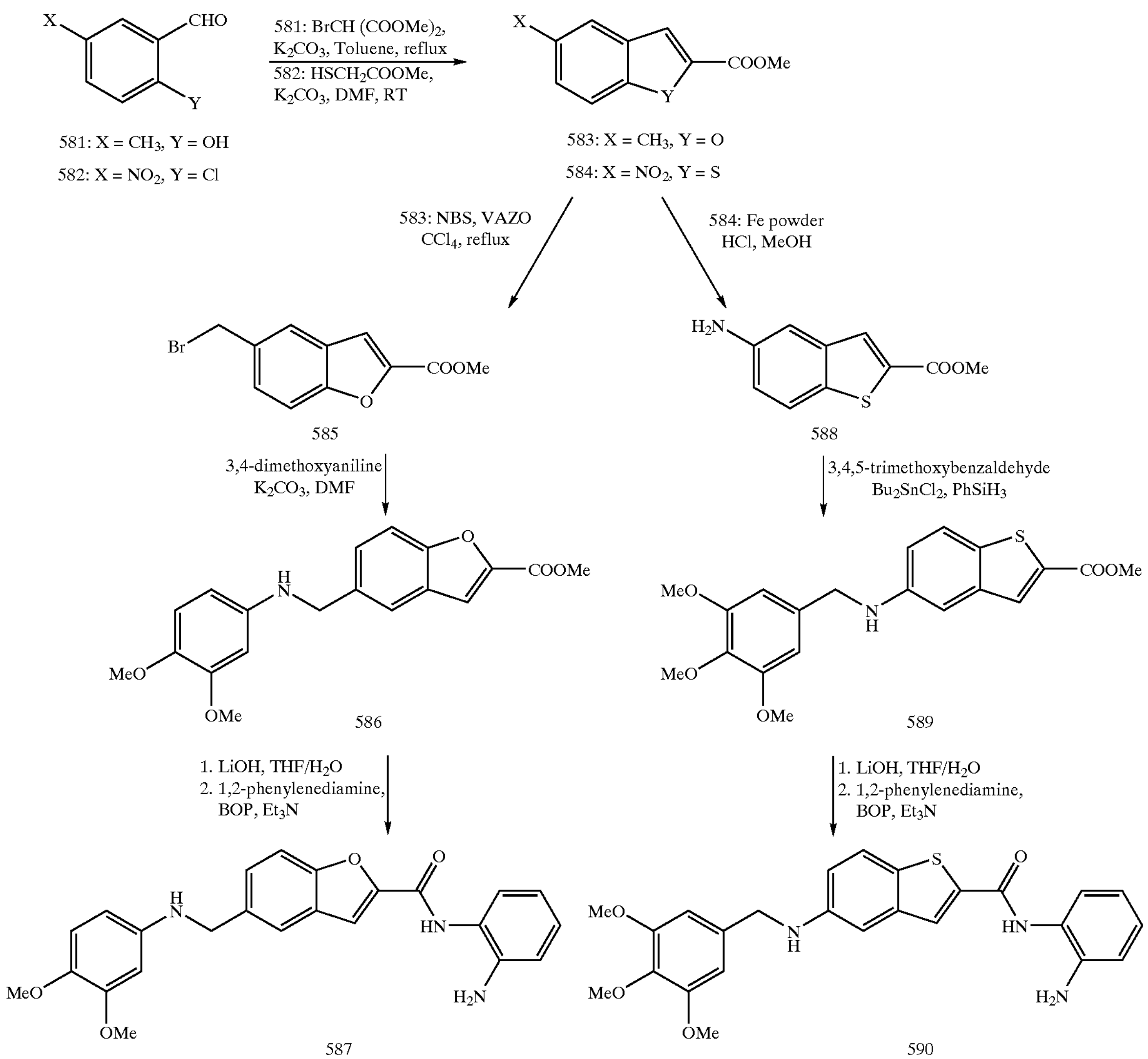

587
Example 436

590
Example 437

Example 436

Step 1: Methyl-5-methyl-benzofuran-2-carboxylate (583)

A stirring suspension of 5methylsalicylaldehyde (1.0 mg, 7.5 mmol), $K_2CO_3$ (1.55 g, 11.0 mmol), and $Bu_4NBr$ (322 mg, 1 mmol) in toluene (30 ml) was treated with dimethylbromomalo-nate (1.06 ml, 8.0 mmol). The suspension was heated to reflux with a Dean-Stark trap for 20 h. The brown suspension was cooled to 25° C. and concentrated in vacuo. The residue was taken in DCM and filtered. The filtrate was washed with $H_2O$, 1N NaOH and brine. The organic layer was dried over magnesium sulfate, filtered and concentrated. The crude residue was purified by column chromatography (10% ethyl acetate/hexane) to afford the title compound 583 (600 mg, 42% yield). LRMS: 190.2 (Calc.). 191.1 (found).

Step 2: Methyl-5-bromomethyl-benzofuran-2-carboxylate (585)

A mixture of 583 (500 mg, 2.63 mmol), Nbromosuccinimide (561 mg, 3.15 mmol) and 1,1'-azobis (cyclohexanecarbonitrile) (Vazo) (63 mg, 0.26 mmol) in 15 ml of $CCl_4$ was heated overnight under reflux. The mixture was cooled to room temperature, quenched by adding water and extracted with DCM. The organic layer was washed with brine and dried over $MgSO_4$, filtered and concentrated. The crude residue was purified by column chromatography (30% ethyl acetate/hexane) to afford the title compound 585 (680 mg, 96% yield). $^1$H NMR: ($CDCl_3$) δ (ppm): 7.79 (s, 1H), 7.70–7.52 (m, 3H), 4.69 (s, 2H), 4.06 (s, 3H), 3.72 (s, 2H). LRMS: 268.2 (Calc.). 269.1 (found).

Step 3: Methyl-5-[(3,4-dimethoxy-phenilamino)-methyl]-benzofuran-2-carboxylate (586)

Following the procedure described in Example 47, step 2, but substituting 585 for 63, the title compound 586 was obtained in 40% yield. LRMS: 341 (Calc.). 342.3 (found).

Step 4: 5-[(3,4-Dimethoxy-phenylamino)-methyl]-benzofuran-2-carboxylic acid (2-amino-phenyl)-amide (587)

Following the procedure described in Example 1, steps 4, 5, but substituting 585 for 6, the title compound 587 was obtained in 29% yield. $^1$H NMR: (DMSO) δ (ppm): 9.83 (s, 1H), 7.75 (s, 1H), 7.64 (s, 1H), 7.62 (d, J=8.0 Hz, 1H), 7.47 (d, J=9.0 Hz, 1H), 7.18 (d, J=8.0 Hz, 1H), 6.97 (t, J=7.5 Hz, 1H), 6.78 (d, J=8.0 Hz, 1H), 6.65 (d, J=8.5 Hz, 1H), 6.59 (t, J=7.5 Hz, 1H), 6.33 (s, 1H), 6.04 (d, J=8.0 Hz, 1H), 5,92 (d, J=5.5 Hz, 1H), 4.93 (s, 2H), 4.31 (d, J=5.5 Hz, 1H), 2.82 (s, 3H), 2.76 (s, 3H). LRMS: 417.46 (Calc.). 418.4 (found).

Example 437

Step 1: Methyl-5-nitro-benzo[b]thiophene-2-carboxylate (584)

A stirring suspension of 5-nitro-2-chlorobenzaldehyde (4.0 g, 21.6 mmol) in DMF (40 ml) at 5° C. was treated with $K_2CO_3$(3.52 g, 25.5 mmol) followed by methylglycolate (1.93 ml, 21.6 mmol). The resulting solution was warmed to 25° C. and stirred for 20 h. The solution was then poured into 250 ml of ice $H_2O$ and the white precipitate that formed was collected by filtration. Crystallization from EtOAc afforded fine pale orange needles of 584 (3.54 g, 69%). LRMS: 237.0 (Calc.). 238.1 (found). $^1$H NMR: (DMSO) δ (ppm): 9.00 (d, J=2.2 Hz, 1H), 8.45 (s, 1H), 8.39–8.30 (m, 2H), 3.93 (s, 3H).

Step 2: Methyl-5-amino-benzo[b]thiophene-2-carboxylate (588)

A suspension of 584 (3.52 g, 14.8 mmol) in methanol (100 ml) was treated with Fe powder (6.63 g, 118.7 mmol). The resulting suspension was heated to reflux, and 12M HCl (8.5 ml) was slowly added over 15 min. The resulting green dark suspension was refluxed for an additional 3 h, then cooled and concentrated. The residue was taken up in EtOAc and washed with saturated aqueous $NaHCO_3$, then brine, dried over $MgSO_4$, filtered and concentrated to afford (2.57 g, 84%). $^1$H NMR: (DMSO) δ (ppm): 7.92 (s, 1H), 7.65 (d, J=8.8 Hz, 1H), 7.05 (d, J=1.5 Hz, 1H), 6.88 (dd, J=1.8, 8.4 Hz, 1H), 5.27 (s, 2H), 3.85 (s, 3H). LRMS: 207.0 (Calc.). 208.1 (found).

Step 3: Methyl-5-(3,4,5-trimethoxy-benzylamino)-benzo[b]thiophene-2-carboxylate (589)

Following the procedure described in Example 144, step 3, but substituting 588 for 226, the title compound 589 was obtained in 68% yield. (DMSO) δ (ppm): 7.94 (s, 1H), 7.69 (d, J=8.8 Hz, 1H), 7.02–6.99 (m, 2H), 6.73 (s, 2H), 6.41 (t, J=5.7 Hz, 1H), 4.21 (d, J=5.9 Hz, 2H), 3.84 (s, 3H), 3.75 (s, 6H), 3.62 (s, 3H). LRMS: 387.1 (Calc.). 388.3 (found).

Step 4: 5-(3,4,5-Trimethoxy)-benzylamino)-benzo[b]thiophene-2-carboxylic acid (2-amino-phenyl)-amide (590)

Following the procedure described in Example 1, steps 4, 5, but substituting 589 for 6, the title compound 590 was obtained in % yield$^1$H NMR: (DMSO) δ (ppm): 7.79 (s, 1H), 7.60 (d, J=8.8 Hz, 1H), 7.00–6.95 (m, 2H), 6.74 (s, 2H), 4.32 (s, 2H), 3.80 (s, 6H), 3.73 (s, 3H).

Examples 347–425

Examples 347 to 425 (compounds 492–570) were prepared using the same procedure as described for compound 44 to 491 in Example 40 to 346 (scheme 3 to 64).

Example 426

Synthesis of N-(2-Amino-phenyl)-4-[(4-pyridin-3-pyrimidin-2-ylamino)-methyl]-benzamide Scheme 66

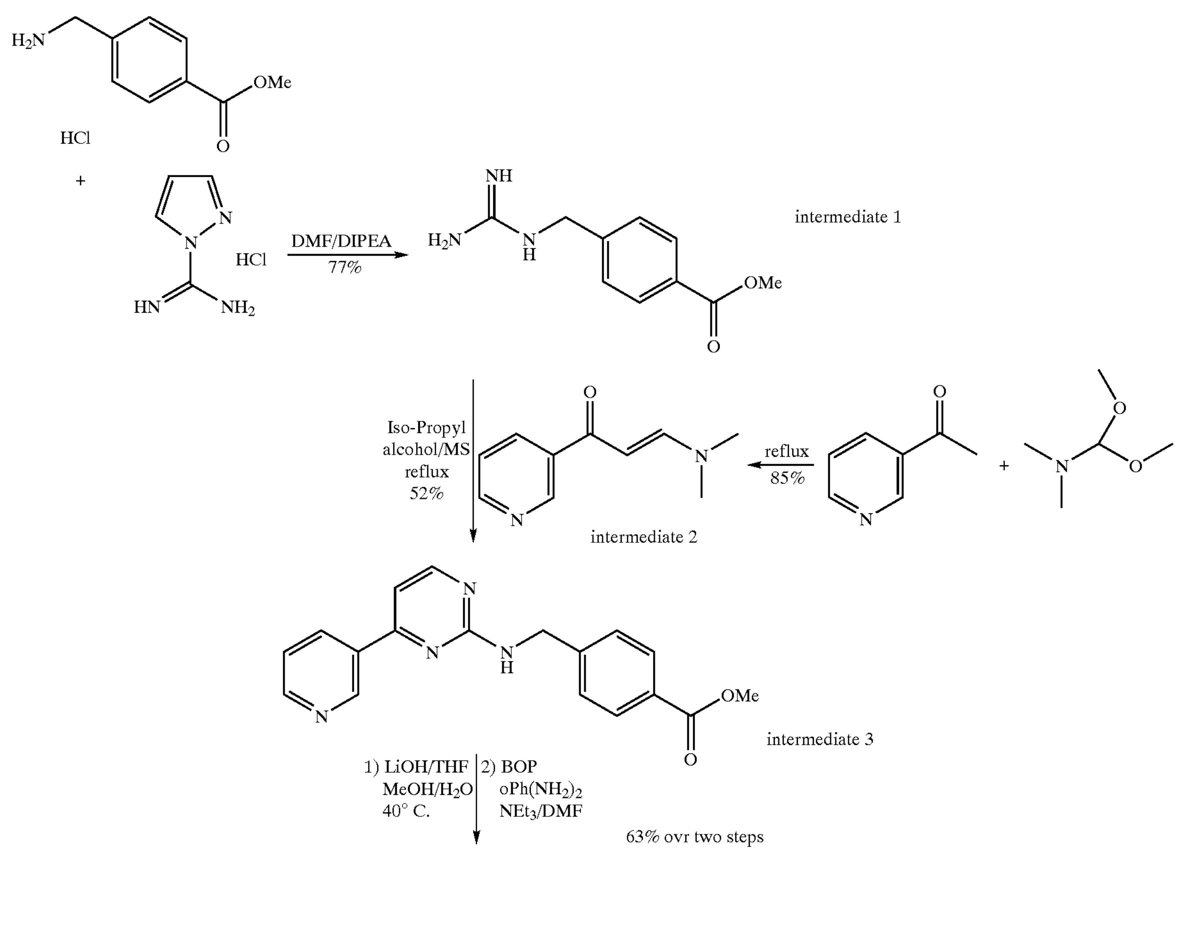

-continued

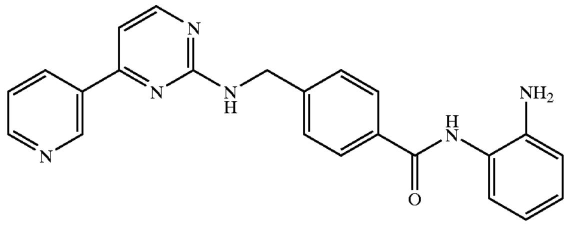

Step 1: Synthesis of 4-Guanidinomethyl-benzoic acid methyl ester Intermediate 1

The mixture of 4-Aminomethyl-benzoic acid methyl ester HCl (15.7 g, 77.8 mmol) in DMF (85.6 mL) and DIPEA (29.5 mL, 171.2 mmol) was stirred at rt for 10 min. Pyrazole-1-carboxamidine HCl (12.55 g, 85.6 mmol) was added to the reaction mixture and then stirred at rt for 4 h to give clear solution. The reaction mixture was evaporated to dryness under vacuum. Saturated $NaHCO_3$ solution (35 mL) was added to give nice suspension. The suspension was filtered and the filter cake was washed with cold water. The mother liquid was evaporated to dryness and then filtered. The two solids were combined and re-suspended over distilled $H_2O$ (50 ml). The filter cake was then washed with minimum quantities of cold $H_2O$ and ether to give 12.32 g white crystalline solid intermediate 1 (77% yield, M+1: 208 on MS).

Step 2: Synthesis of 3-Dimethylamino-1-pyridin-3-yl-propenone Intermediate 2

3-Acetyl-pyridine (30.0 g, 247.6 mmol) and DMF dimethyl acetal (65.8 mL, 495.2 mmol) were mixed together and then heated to reflux for 4 h. The reaction mixture was evaporated to dryness and then 50 mL diethyl ether was added to give brown suspension. The suspension was filtered to give 36.97 g orange color crystalline product (85% yield, M+1: 177 on MS).

Step 3: Synthesis of 4-[(4Pyridin-3-pyrimidin-2-ylamino)-methyl]benzoic acid methyl ester Intermediate 3

Intermediate 1 (0.394 g, 1.9 mmol) and intermediate 2 (0.402 g, 2.3 mmol) and molecular sieves (0.2 g, 4A, powder, >5 micron) were mixed with isopropyl alcohol (3.8 mL). The reaction mixture was heated to reflux for 5 h. MeOH (50 mL) was added and then heated to reflux. The cloudy solution was filtrated over a pad of celite. The mother liquid was evaporated to dryness and the residue was triturated with 3 mL EtOAc. The suspension was filtrated to give 0.317 g white crystalline solid Intermediate 3 (52%, M+1: 321 on MS).

Step 4: Synthesis of N-(2-Amino-phenyl)-4-[(4-pyrymidin-2-ylamino)-methyl]-benzamide Intermediate 3 (3.68 g, 11.5 mmol) was mixed with THF (23 mL), MeOH (23 mL) and $H_2O$ (11.5 mL) at rt. LiOH (1.06 g, 25.3 mmol) was added to reaction mixture. The resulting reaction mixture was warmed up to 40° C. overnight. HCl solution (12.8 mL, 2N) was added to adjust pH=3 when the mixture was cooled down to rt. The mixture was evaporated to dryness and then the solid was washed with minimum quantity of $H_2O$ upon filtration. The filter cake was dried over freeze dryer to give 3.44 g acid of the title compound (95%, M+1: 307 on MS).

Acid (3.39 g, 11.1 mmol) of the title compound, BOP (5.679 g, 12.84 mmol) and o-Ph$(NH_2)_2$ (2.314 g, 21.4 mmol) were dissolved in the mixture of DMF (107 mL) and $Et_3N$ (2.98 mL, 21.4 mmol). The reaction mixture was stirred at rt for 5 h and then evaporated to dryness. The residue was purified by flash column (pure EtOAc to 5% MeOH/EtOAc) and then interested fractions were concentrated. The final product was triturated with EtOAc to give 2.80 g of title product (66%, MS+1: 397 on MS). $^1$H NMR (400 MHz, DMSO-$D_6$) δ (ppm): 9.57 (s, 1H), 9.22 (s, 1H), 8.66 (d, J=3.5 Hz, 1H), 8.39 (d, J=5.1 Hz, 2H), 8.00 (t, J=6.5 Hz, 1H), 7.90 (d, J=8.2 Hz, 2H), 7.50 (m, 3H), 7.25 (d, J=5.1 Hz, 1H), 7.12 (d, J=7.4 Hz, 1H), 6.94 (dd, J=7.0, 7.8 Hz, 1H), 6.75 (d, J=8.2 Hz, 1H), 6.57 (dd, J=7.0, 7.8 Hz, 1H), 4.86 (s, 2H), 4.64 (d, J=5.9 Hz, 2H).

Assay Example 1

Inhibition of Histone Deacetylase Enzymatic Activity

1. Human HDAC-1

HDAC inhibitors were screened against a cloned recombinant human HDAC-1 enzyme expressed and purified from a Baculovirus insect cell expression system. For deacetylase assays, 20,000 cpm of the [$^3$H]-metabolically labeled acetylated histone substrate (M. Yoshida et al., *J. Biol. Chem.* 265(28): 17174–17179 (1990)) was incubated with 30 μg of the cloned recombinant hHDAC-1 for 10 minutes at 37° C. The reaction was stopped by adding acetic acid (0.04 M, final concentration) and HCl (250 mM, final concentration). The mixture was extracted with ethyl acetate and the released [$^3$]-acetic acid was quantified by scintillation counting. For inhibition studies, the enzyme was preincubated with compounds at 4° C. for 30 minutes prior to initiation of the enzymatic assay. $IC_{50}$ values for HOAC enzyme inhibitors were determined by performing dose response curves with individual compounds and determining the concentration of inhibitor producing fifty percent of the maximal inhibition. $IC_{50}$ values for representative compounds are presented in the third column of Table 5.

2. MTT Assay

HCT116 cells (2000/well) were plated into 96-well tissue culture plates one day before compound treatment. Compounds at various concentrations were added to the cells. The cells were incubated for 72 hours at 37° C. in 5% $CO_2$ incubator. MTT (3-[4,5-dimethylthiazol-2yl]-2,5 diphenyl tetrazolium bromide, Sigma) was added at a final concentration of 0.5 mg/ml and incubated with the cells for 4 hours before one volume of solubilization buffer (50% N,N-dimethylformamide, 20% SDS, pH 4.7) was added onto the cultured cells. After overnight incubation, solubilized dye was quantified by colorimetric reading at 570 nM using a reference at 630 nM using an MR700 plate reader (Dynatech Laboratories Inc.). OD values were converted to cell numbers according to a standard growth curve of the relevant cell line. The concentration which reduces cell numbers to 50% of that of solvent treated cells is determined as MTT $IC_{50}$. $IC_{50}$ values for representative compounds are presented in the fourth column of Table 5.

3. Histone H4 Acetylation in whole Cells by Immunoblots

T24 human bladder cancer cells growing in culture were incubated with HDAC inhibitors for 16 h. Histones were extracted from the cells after the culture period as described by M. Yoshida et al. (*J. Biol. Chem.* 265(28): 17174–17179 (1990)). 20 g of total histone protein was loaded onto SDS/PAGE and transferred to nitrocellulose membranes. Membranes were probed with polyclonal antibodies specific for acetylated histone H-4 (Upstate Biotech Inc.), followed by horse radish peroxidase conjugated secondary antibodies (Sigma). Enhanced Chemiluminescence (ECL) (Amersham) detection was performed using Kodak films (Eastman Kodak). Acetylated H-4 signal was quantified by densitometry. Representative data are presented in the fifth column of Table 5. Data are presented as the concentration effective for reducing the acetylated H-4 signal by 50% ($EC_{50}$).

TABLE 5

Inhibition of Histone Deacetylase

| Cpd | Structure | HumanHDAC-1 $IC_{50}$($\mu$M) | MTT(HCT116) $IC_{50}$($\mu$M) | H4Ac(T24) $EC_{50}$($\mu$M) |
|---|---|---|---|---|
| 8 | 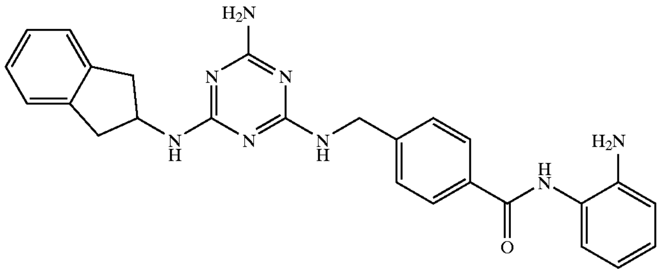 | 0.4 | 0.5 | 1 |
| 9 | 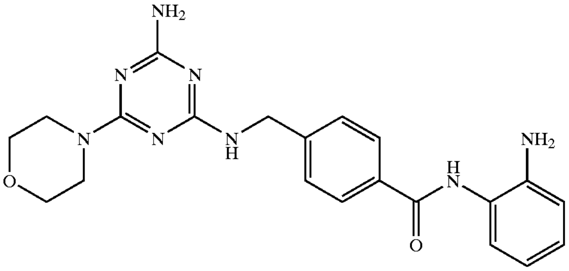 | 2 | 0.7 | 5 |
| 10 | 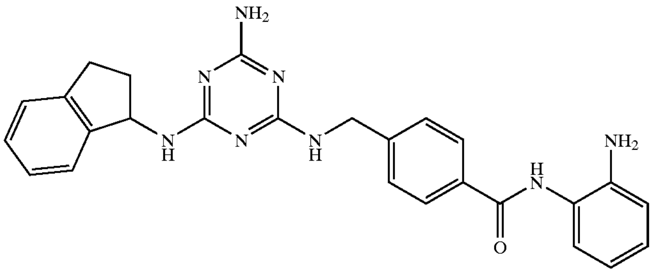 | 2 | 0.6 | 1 |
| 11 | 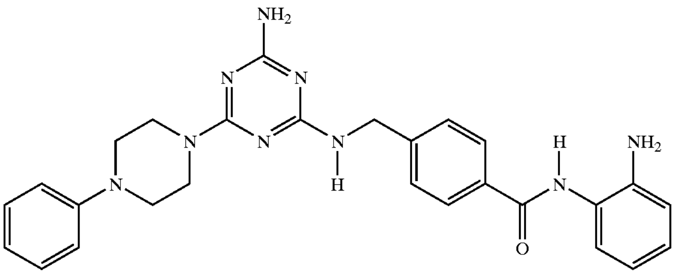 | 2 | 0.6 | 2 |

TABLE 5-continued
| Inhibition of Histone Deacetylase | | | | |
|---|---|---|---|---|
| 12 | 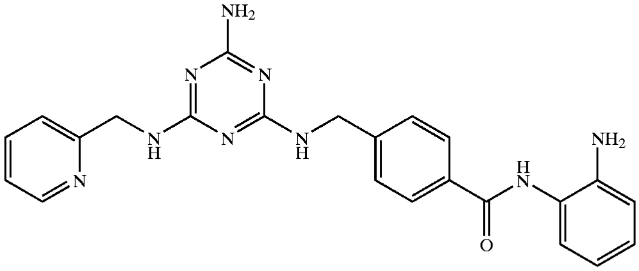 | 2 | 2 | 5 |
| 14 | 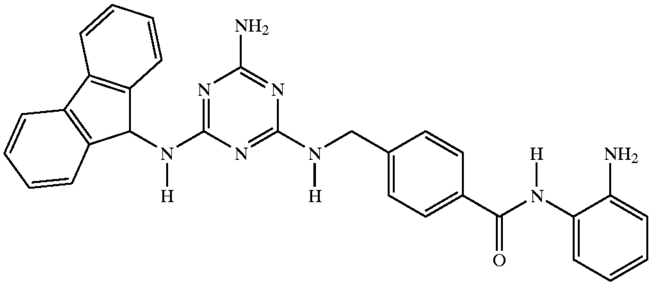 | 0.3 | 1 | 5 |
| 15 | 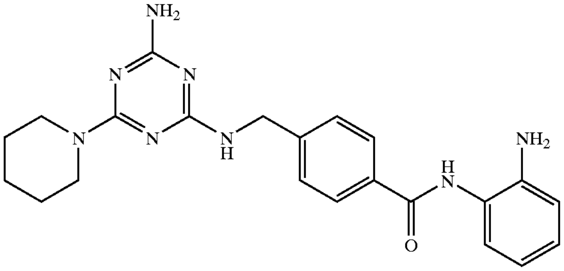 | 0.5 | 0.2 | 3 |
| 16 | 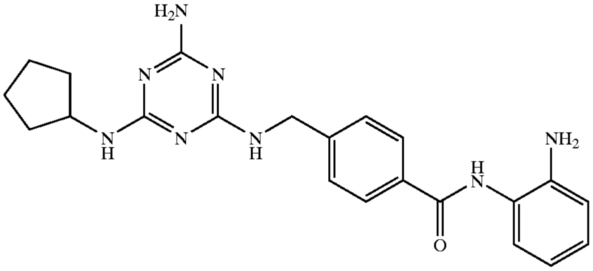 | 1 | 0.4 | 1 |
| 17 | 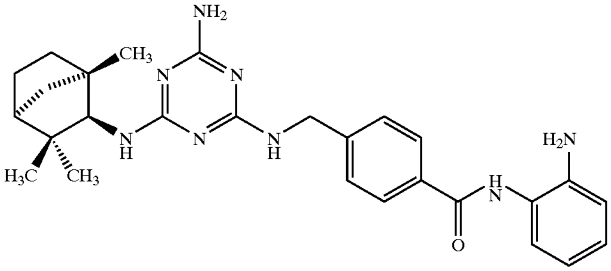 | 0.9 | 1 | 2 |

TABLE 5-continued
| | Inhibition of Histone Deacetylase | | | |
|---|---|---|---|---|
| 18 | 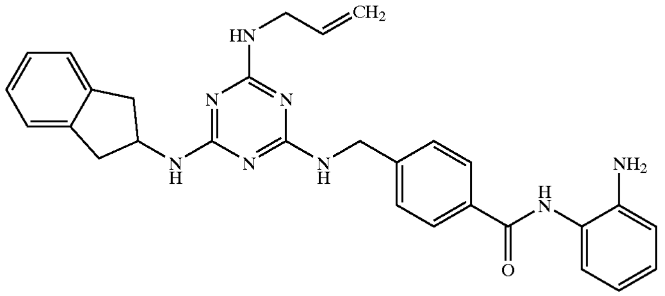 | 0.8 | 0.6 | 3 |
| 18b | 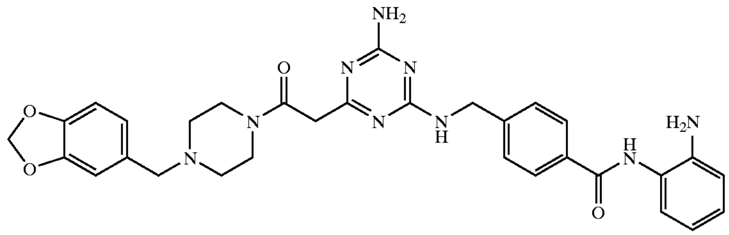 | 0.6 | 5 | 10 |
| 19 | 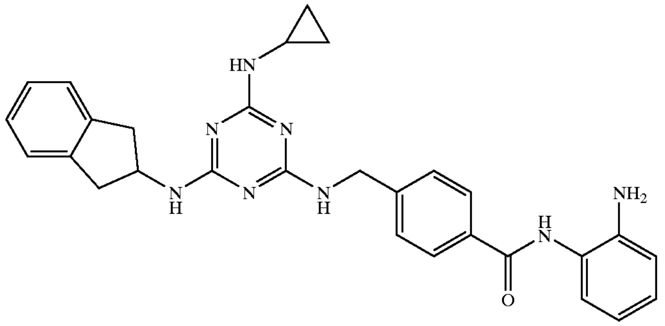 | 0.9 | 1 | 1 |
| 20 | 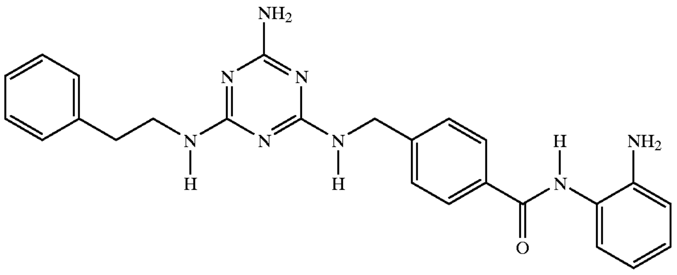 | 0.5 | 0.3 | 1 |
| 21 | 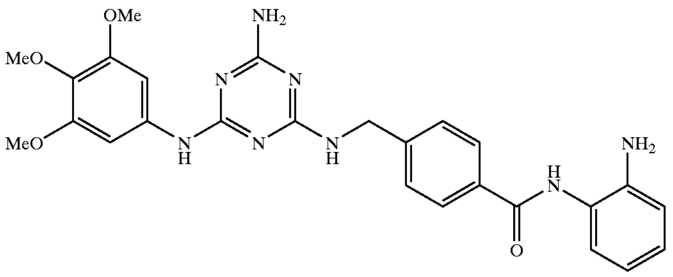 | 4 | 4 | 25 |

TABLE 5-continued
| Inhibition of Histone Deacetylase | | | | |
|---|---|---|---|---|
| 22 | 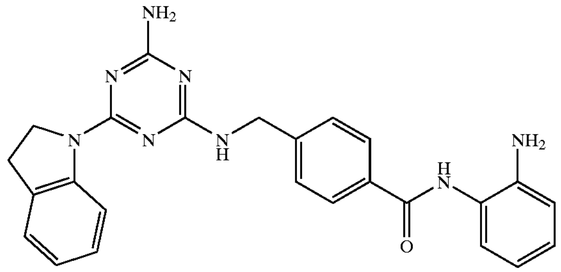 | 3 | 0.8 | 1 |
| 23 | 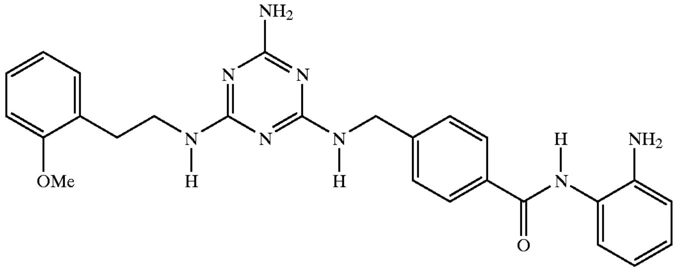 | 2 | 0.7 | 1 |
| 24 | 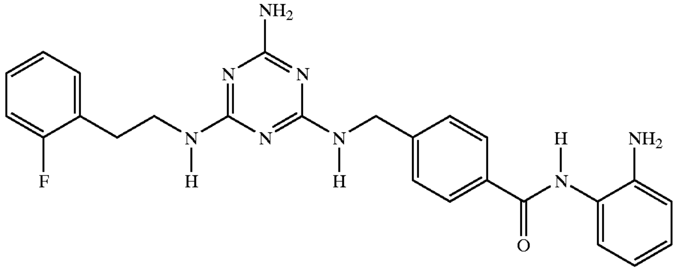 | 3 | 0.6 | 1 |
| 25 | 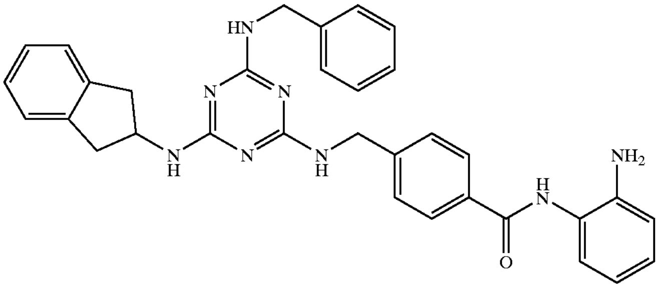 | 0.8 | 0.3 | 5 |
| 26 | 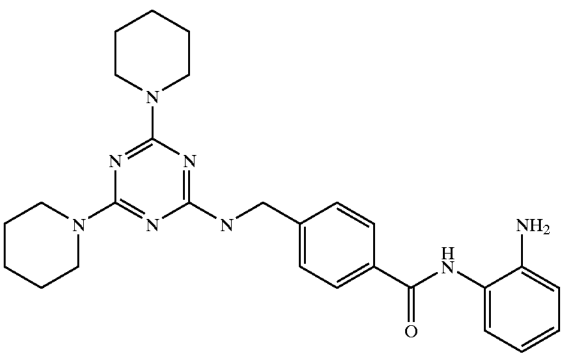 | 0.5 | 2 | na |

TABLE 5-continued
| Inhibition of Histone Deacetylase | | | | |
| --- | --- | --- | --- | --- |
| 27 | 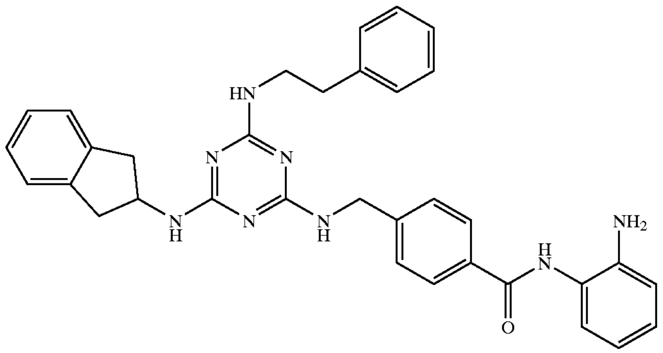 | 0.4 | 2 | na |
| 28 | 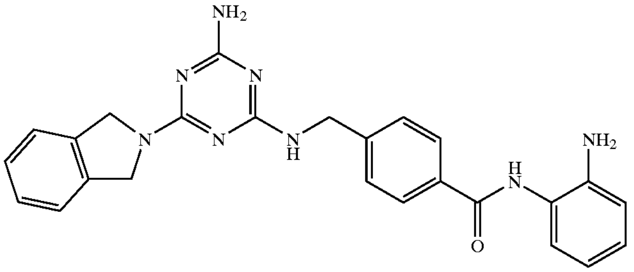 | 2 | 0.5 | 1 |
| 29 | 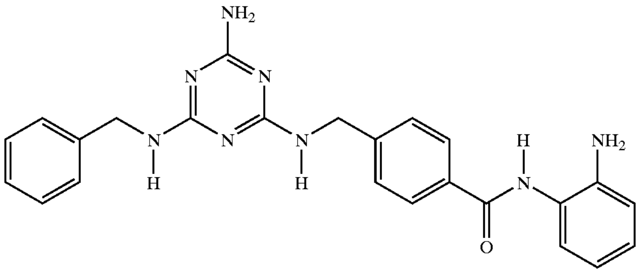 | 2 | 2 | 1 |
| 30 | 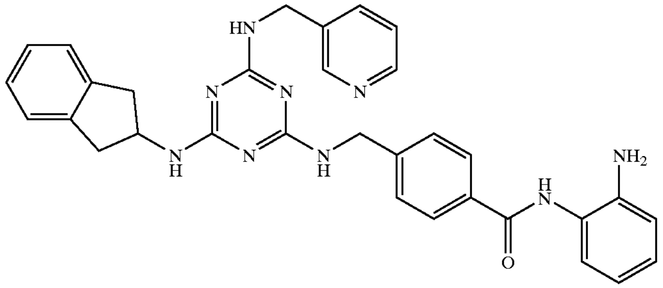 | 1 | 3 | 1 |
| 83 | 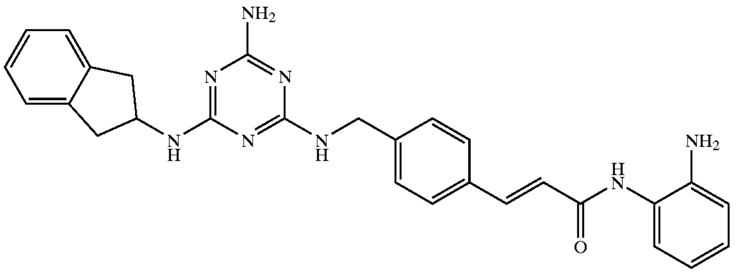 | 3 | 5 | 5 |
(na = not available; 99 = >25 $\mu$M)

TABLE 5-continued
Inhibition of Histone Deacetylase
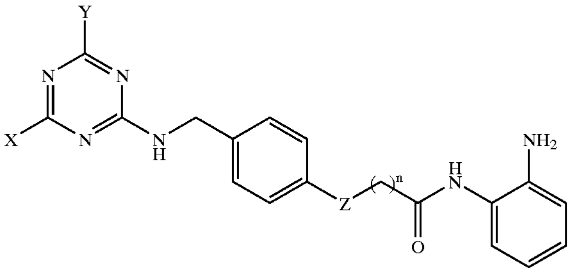
| Ex | Cpd | Structure | Human HDAC-1 $IC_{50}(\mu M)$ | MTT(HCT116) $IC_{50}(\mu M)$ | H4Ac(T24) $EC_{50}(\mu M)$ |
|---|---|---|---|---|---|
| 135 | 204 | 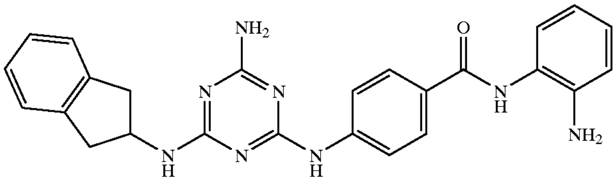 | 4 | na | 5 |
| 136 | 207 | 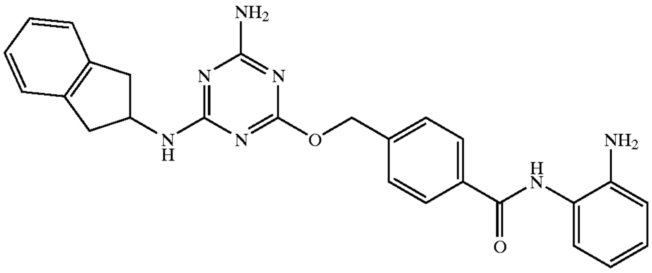 | 0.4 | 0.6 | 2 |
| 137 | 210 | 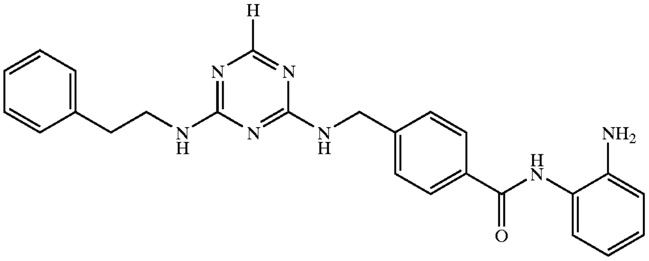 | 3 | 0.9 | 1 |
| 138 | 212 | 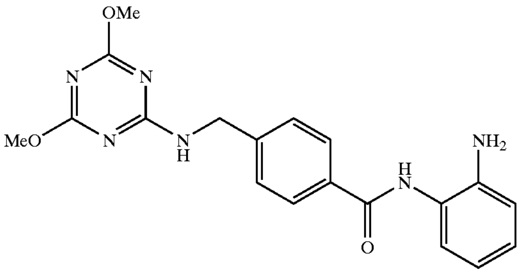 | 3 | 1 | 1 |

TABLE 5-continued
| Inhibition of Histone Deacetylase | | | | | |
|---|---|---|---|---|---|
| 139 | 214 | 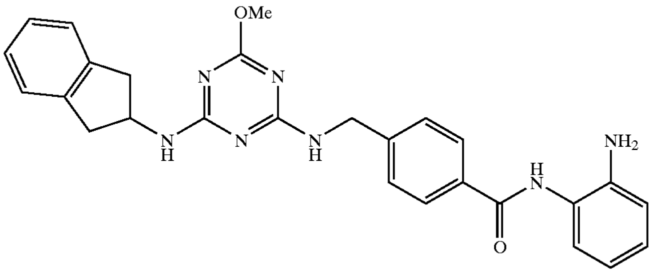 | 3 | 0.9 | 1 |
| 140 | 216 | 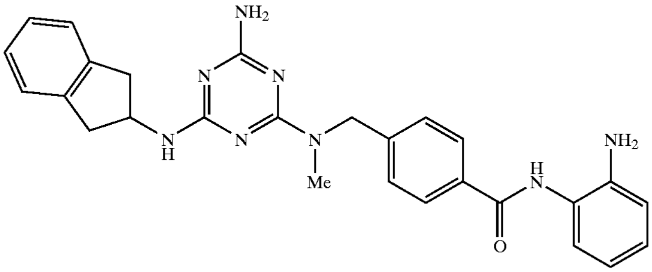 | 0.5 | 0.4 | 2 |
| 141 | 218 | 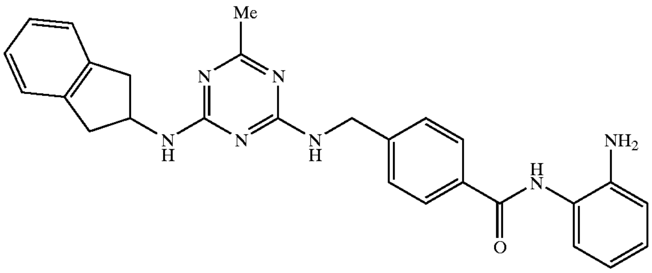 | 0.1 | 0.5 | na |
| 142 | 220 | 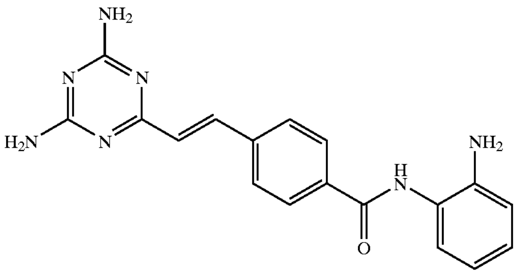 | 7 | 6 | na |
| 143a | 223 | 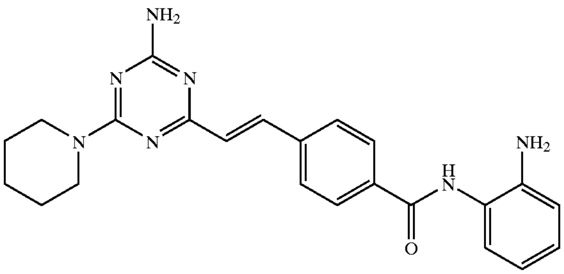 | 11 | 2 | na |

TABLE 5-continued
| Inhibition of Histone Deacetylase | | | | | |
|---|---|---|---|---|---|
| 143b | 224 | 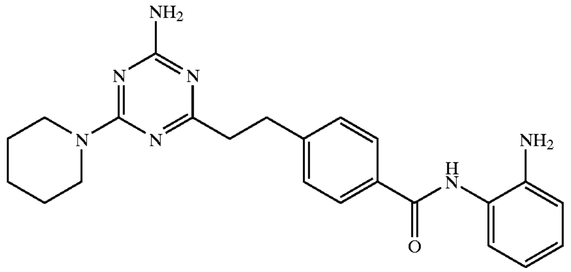 | 5 | 3 | na |
| 329 | 470 | 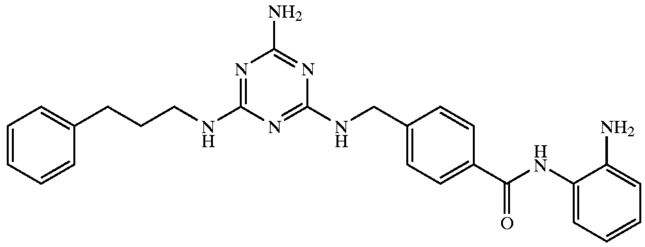 | 2 | 0.7 | 3 |
| 330 | 471 | 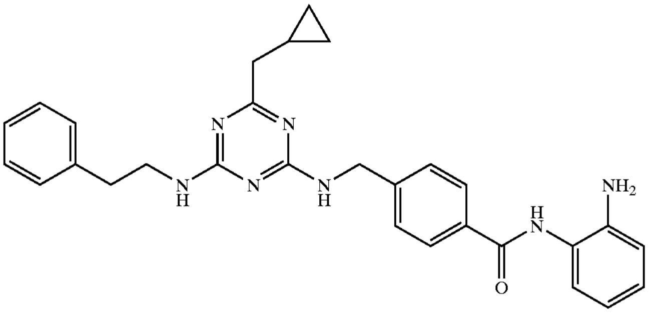 | 0.4 | 1 | 3 |
| 331 | 472 | 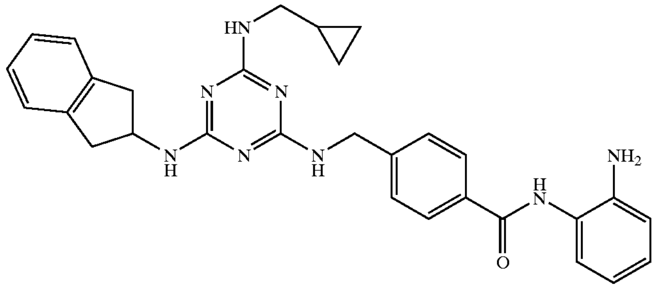 | 3 | 1 | 1 |
| 332 | 473 | 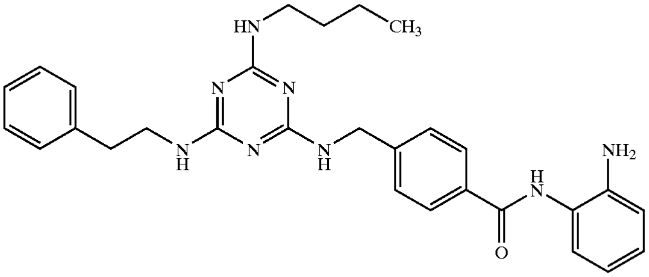 | 4 | 3 | na |

TABLE 5-continued
| Inhibition of Histone Deacetylase | | | | | |
|---|---|---|---|---|---|
| 333 | 474 | 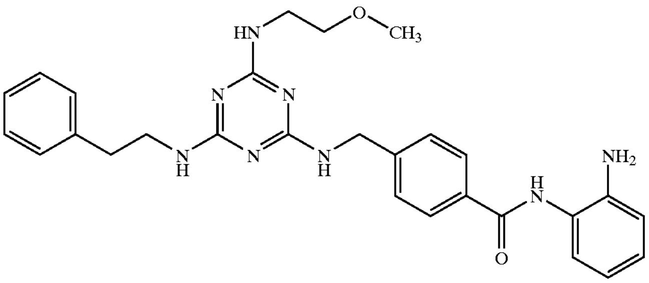 | 3 | 1 | 1 |
| 334 | 475 | 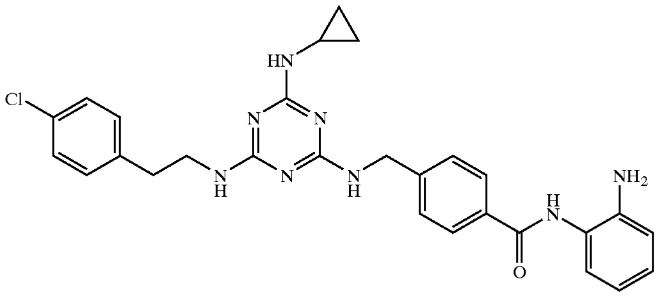 | 0.6 | 2 | na |
| 335 | 476 | 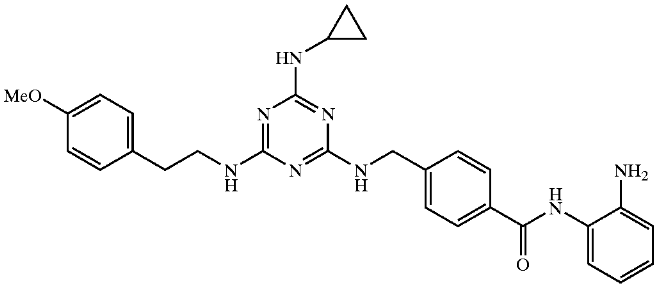 | 2 | 1 | 2 |
| 336 | 477 | 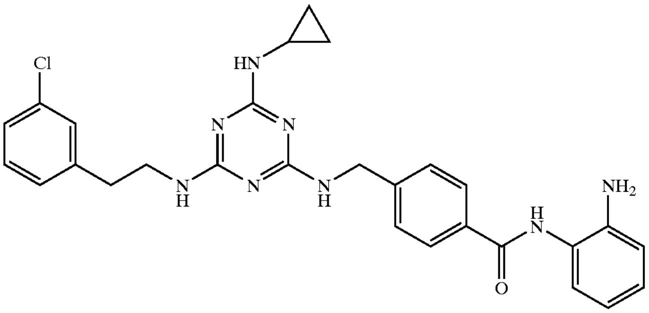 | 1 | 0.7 | na |
| 337 | 478 | 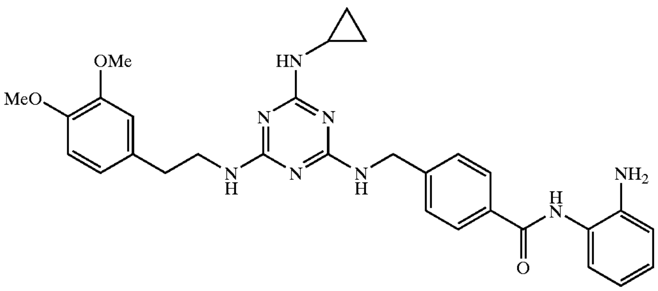 | 3 | 0.7 | na |

TABLE 5-continued
| Inhibition of Histone Deacetylase | | | | | |
|---|---|---|---|---|---|
| 338 | 479 | 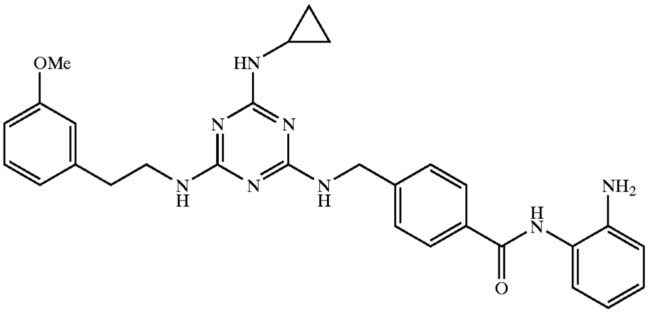 | 0.4 | 0.6 | na |
| 339 | 480 | 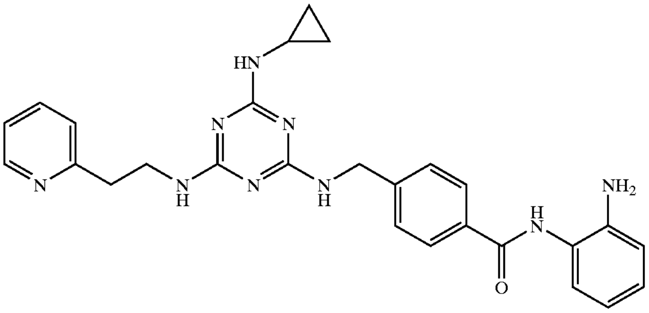 | 0.8 | 0.5 | na |
| 340 | 481 | 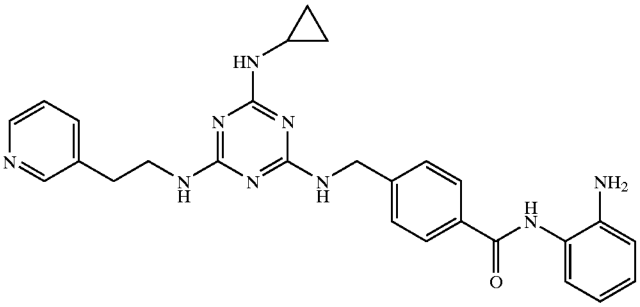 | 6 | 0.7 | na |
| 341 | 482 | 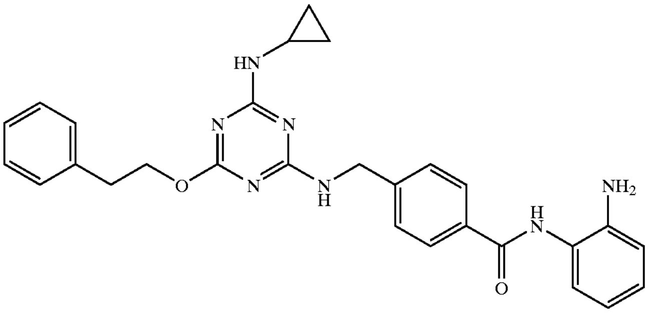 | 0.1 | 0.7 | na |
| 342 | 483 | 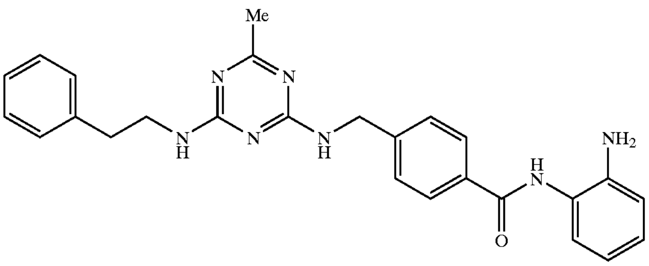 | 4 | na | na |

TABLE 5-continued
| Inhibition of Histone Deacetylase | | | | | |
|---|---|---|---|---|---|
| 343 | 484 | 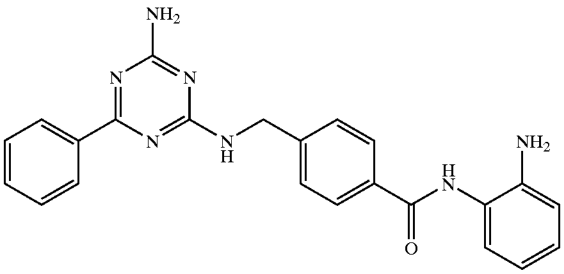 | 2 | 0.3 | na |
| 344 | 485 | 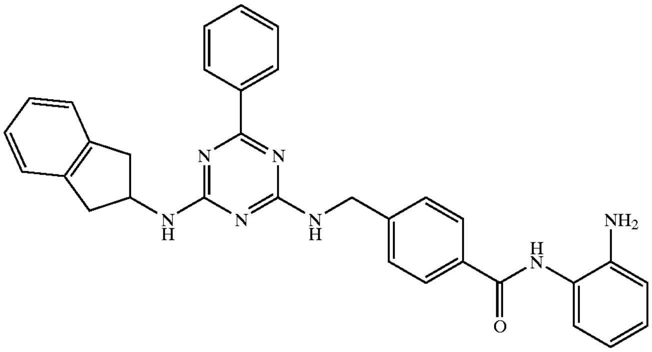 | 0.4 | 3 | na |
(na = nonavailable)
| Cpd | Structure | HumanHDAC-1 $IC_{50}(\mu M)$ | MTT(HCT116) $IC_{50}(\mu M)$ | H4Ac(T24) $EC_{50}(\mu M)$ |
|---|---|---|---|---|
| 51 | 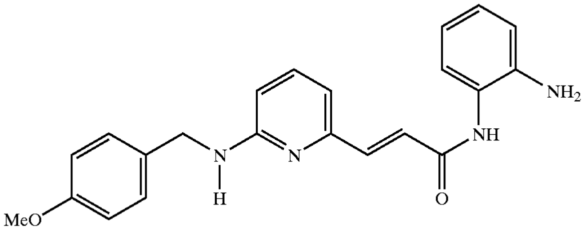 | 22 | 4 | na |
| 55b | 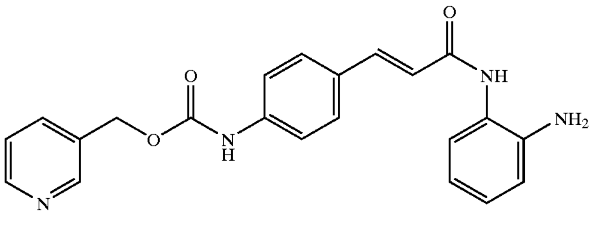 | 3 | 8 | 3 |
| 59 | 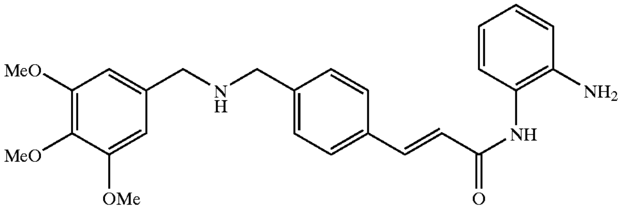 | 12 | 22 | na |

TABLE 5-continued
| Inhibition of Histone Deacetylase | | | | |
| --- | --- | --- | --- | --- |
| 61b | 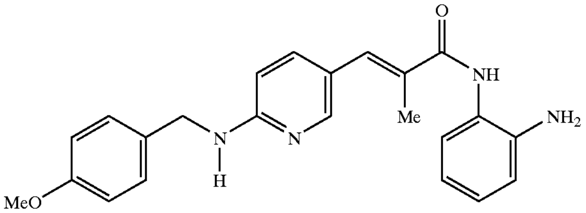 | 7 | 12 | na |
| 65 | 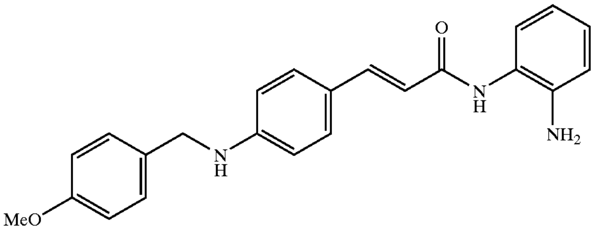 | 4 | 37 | na |
| 71 | 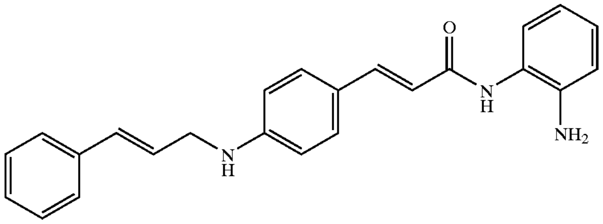 | 10 | 44 | na |
| 72 | 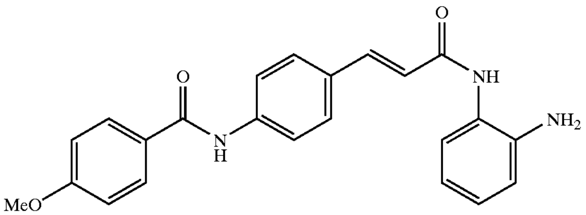 | 16 | 21 | na |
| 88 | 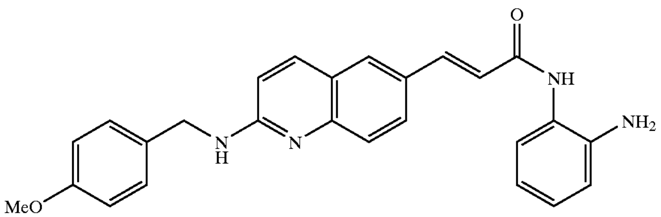 | na | >39 | na |
| 90 | 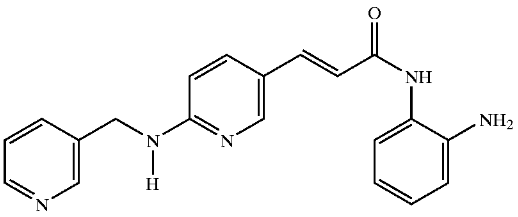 | 10 | 5 | 5 |

TABLE 5-continued
| Inhibition of Histone Deacetylase | | | | |
|---|---|---|---|---|
| 91 | 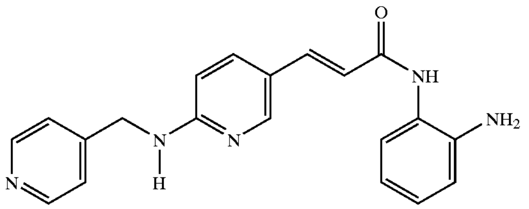 | 4 | 7 | 5 |
| 92 | 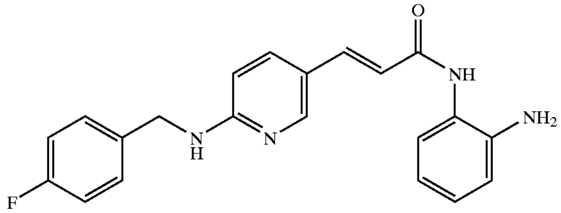 | 5 | 2 | 3 |
| 93 | 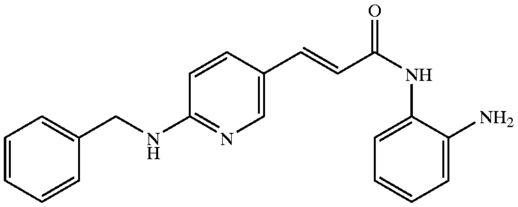 | 3 | 1 | 5 |
| 94 | 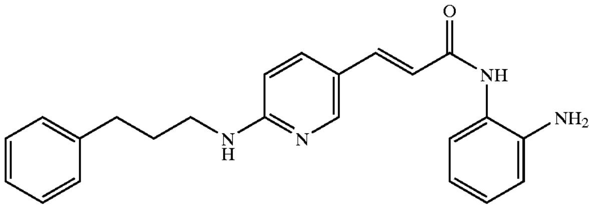 | 3 | 2 | 5 |
| 95 | 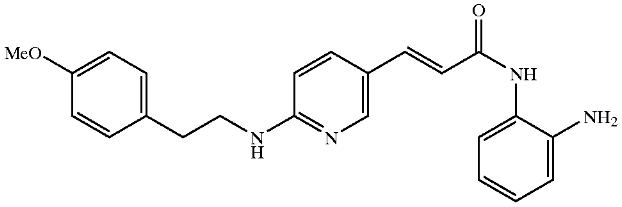 | 3 | 2 | 10 |
| 96 | 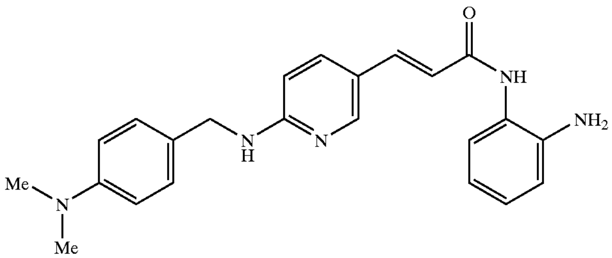 | 4 | 3 | 25 |
| 97 | 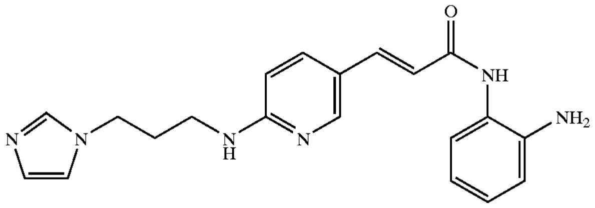 | 10 | 12 | na |

TABLE 5-continued
| Inhibition of Histone Deacetylase | | | | |
|---|---|---|---|---|
| 98 | 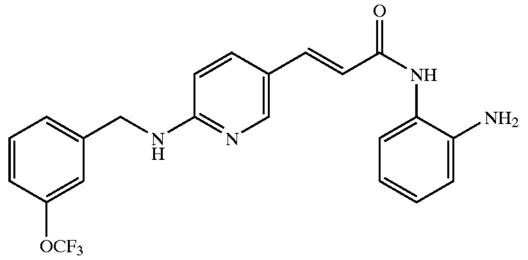 | 0.4 | 2 | 15 |
| 99 | 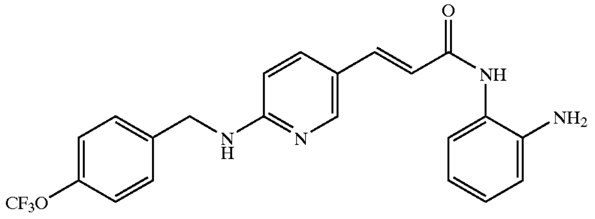 | 2 | 5 | 10 |
| 100 | 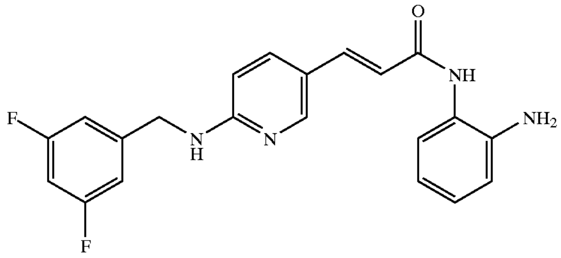 | 4 | 3 | 5 |
| 101 | 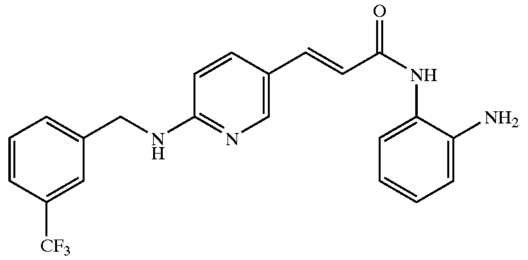 | 3 | 0.9 | 5 |
| 102 | 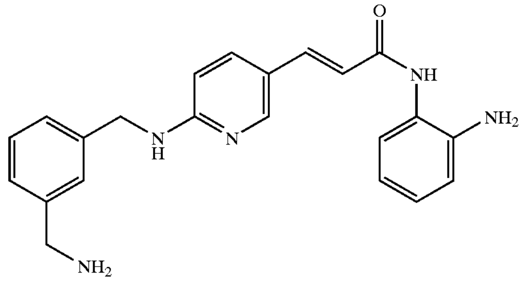 | 20 | 6 | na |
| 104 | 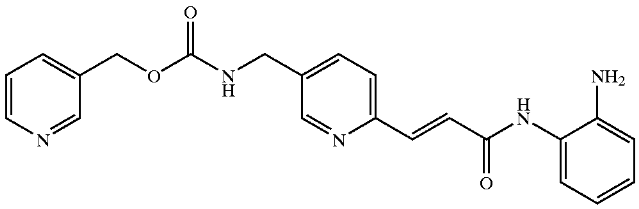 | 10 | 9 | 5 |

TABLE 5-continued
| Inhibition of Histone Deacetylase | | | | |
|---|---|---|---|---|
| 105 | 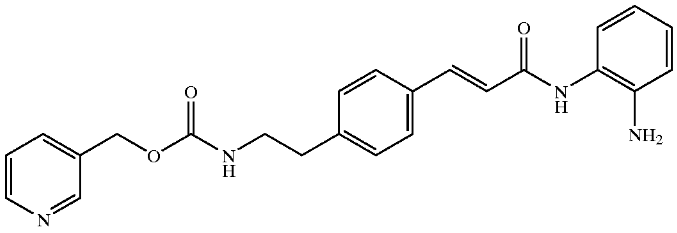 | 16 | 14 | na |
| 106 | 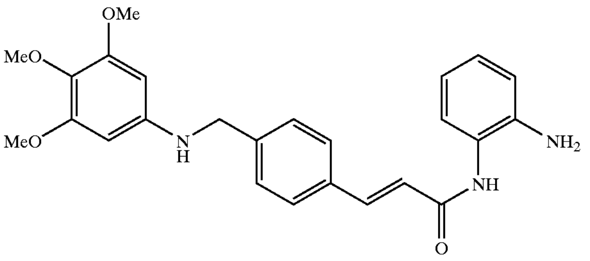 | 2 | 2 | 1 |
| 107 | 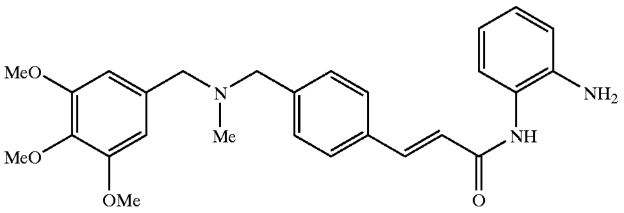 | 15 | 17 | na |
| 108 | 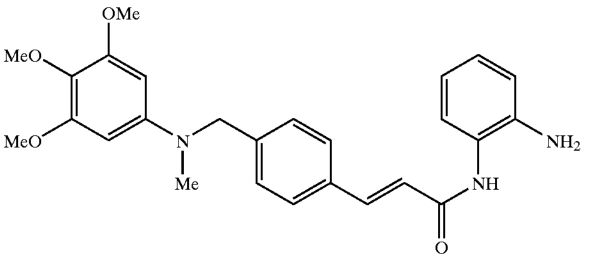 | 3 | 5 | 5 |
| 109 | 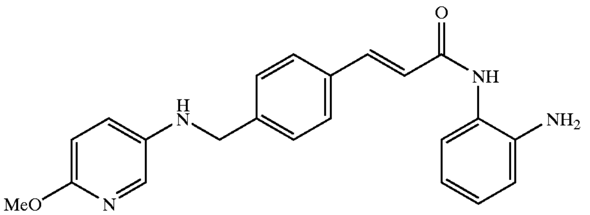 | 5 | 8 | 15 |
| 110 | 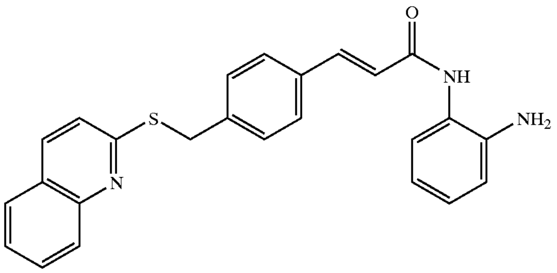 | 3 | 999 | na |

TABLE 5-continued
| Inhibition of Histone Deacetylase | | | | |
|---|---|---|---|---|
| 111 | 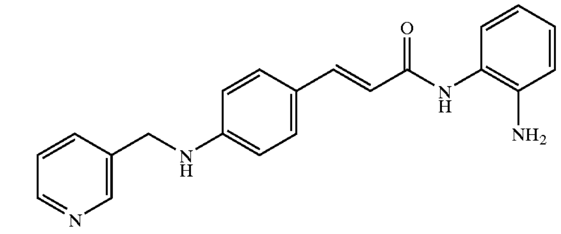 | 10 | 2 | 99 |
| 112 | 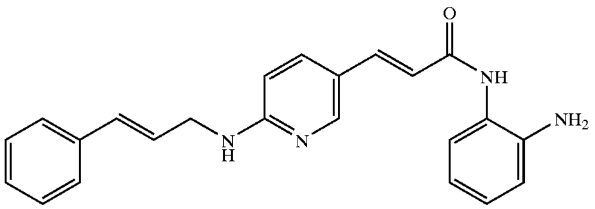 | 2 | 5 | 5 |
| 113 | 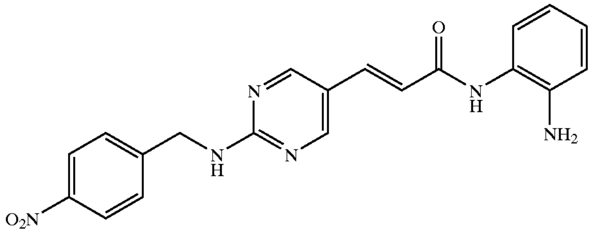 | | 0.3 | 5 |
| 114 | 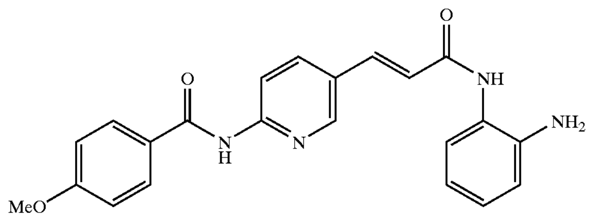 | 25 | 0.5 | 99 |
| 115 | 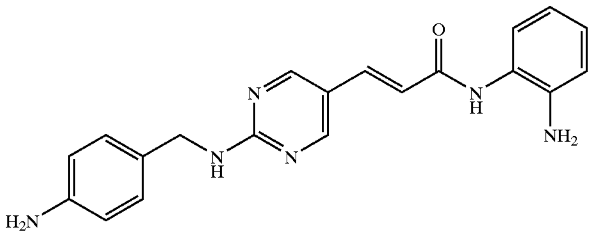 | 15 | 9 | na |
| 116 | 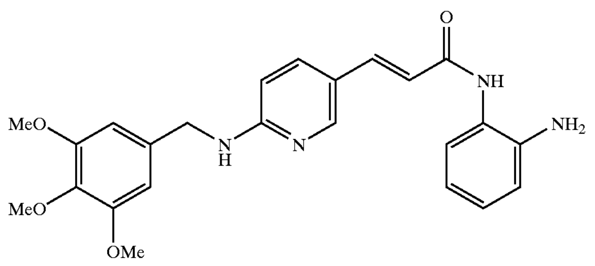 | 4 | 2 | 5 |

TABLE 5-continued
| Inhibition of Histone Deacetylase | | | | | |
|---|---|---|---|---|---|
| 117 | | 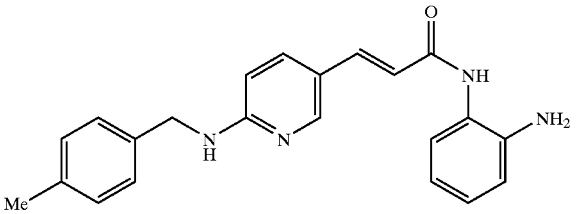 | 7 | 3 | na |
| 118 | | 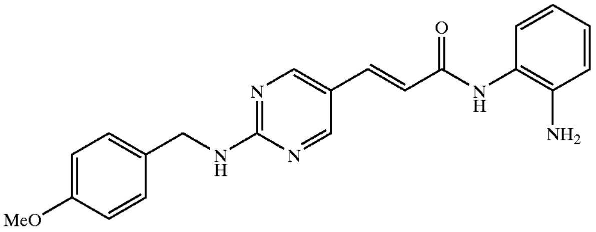 | 11 | 8 | na |
| Ex. | Cpd | Structure | HDAC-1 IC50(μM) | MTT(HCT116) IC50(μM) | H4Ac(T24) EC50(μM) |
| 338 | 481 | 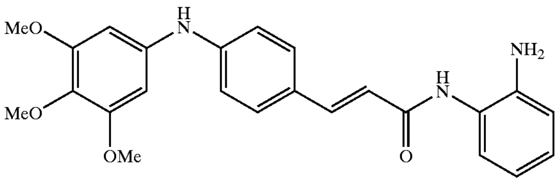 | 22 | 10 | — |
| 339 | 484 | 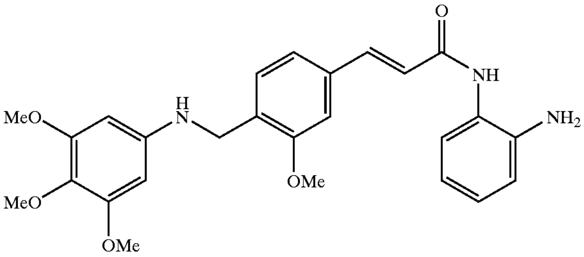 | 20 | 12 | — |
| 347 | 492 | 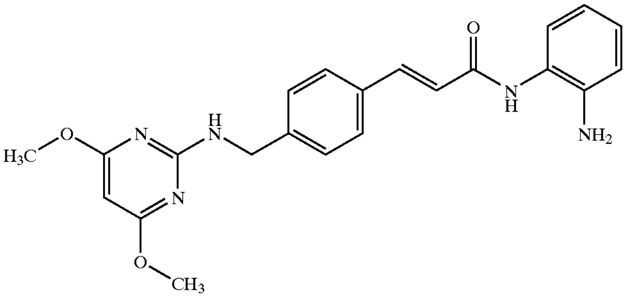 | 4 | 9 | 10 |

TABLE 5-continued
| Inhibition of Histone Deacetylase | | | | | |
|---|---|---|---|---|---|
| 348 | 493 | 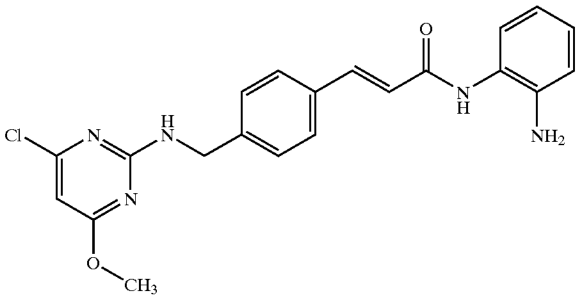 | 4 | 5 | — |
| 349 | 494 | 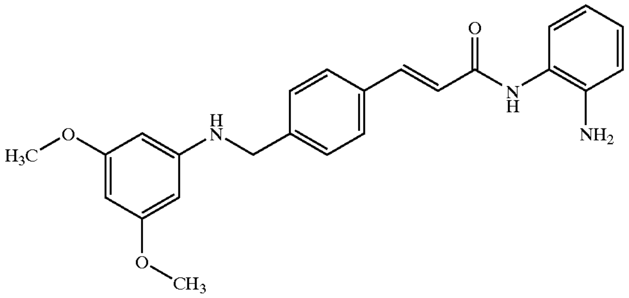 | 3 | 4 | — |
| 350 | 495 | 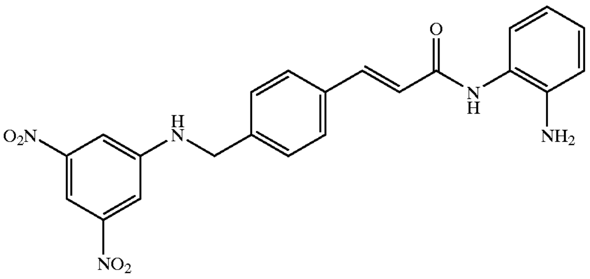 | 4 | 7 | — |
| 351 | 496 | 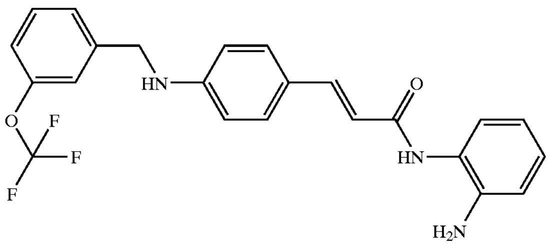 | 8 | 13 | — |
| 352 | 497 | 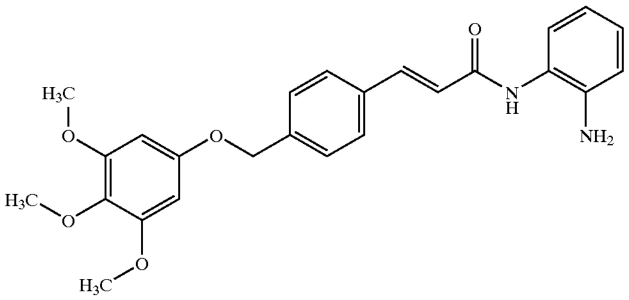 | 15 | 6 | — |

TABLE 5-continued
| Inhibition of Histone Deacetylase | | | | | |
|---|---|---|---|---|---|
| 353 | 498 | 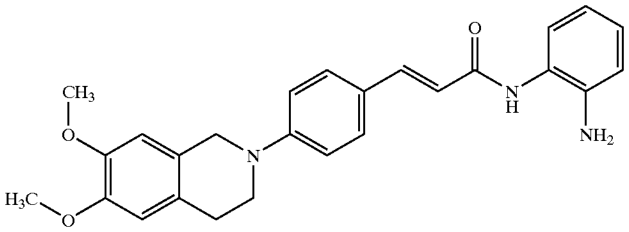 | >25 | — | — |
| 354 | 499 | 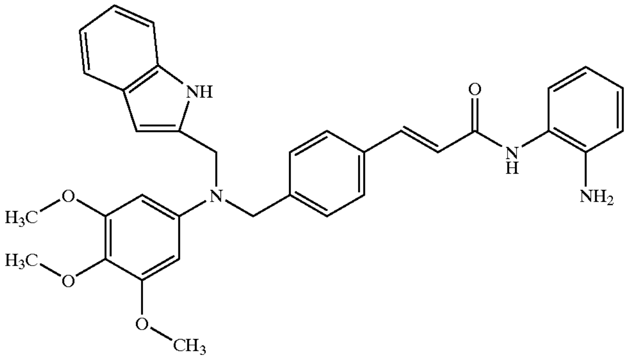 | >25 | 2 | >25 |
| 355 | 500 | 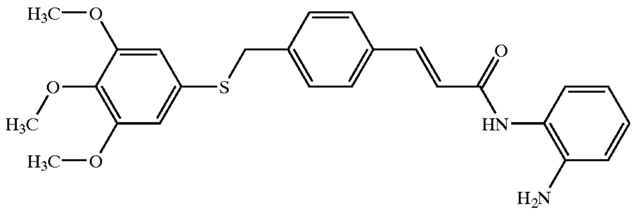 | 23 | 37 | — |
| 356 | 501 | 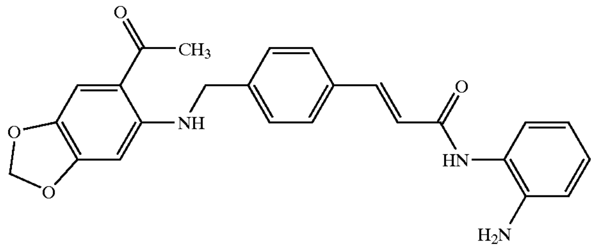 | 4 | 10 | — |
| 357 | 502 | 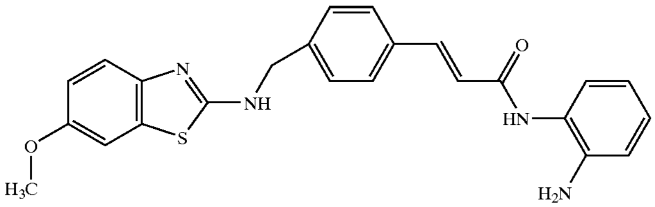 | 3 | >25 | — |
| 358 | 503 | 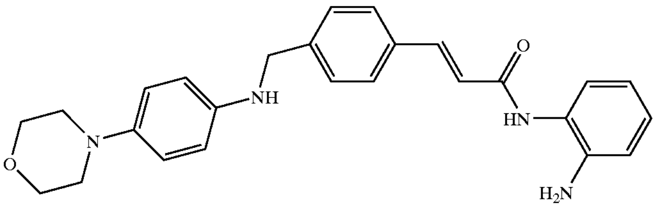 | 5 | >25 | — |

TABLE 5-continued
Inhibition of Histone Deacetylase
| | | | | | |
|---|---|---|---|---|---|
| 359 | 504 | 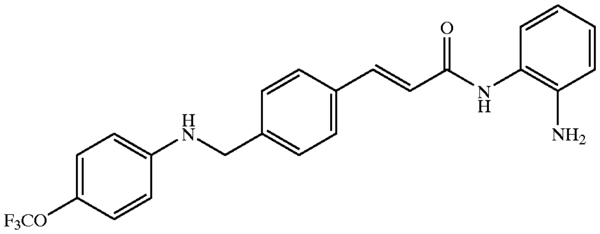 | 5 | >25 | — |
| 360 | 505 | 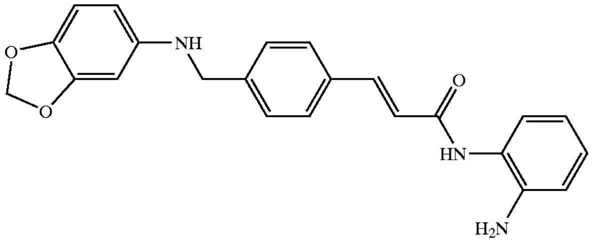 | 3 | 6 | — |
| 361 | 506 | 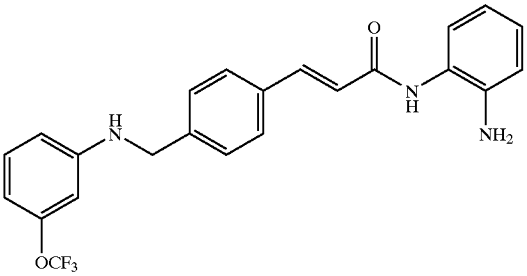 | 15 | 11 | — |
| 362 | 507 | 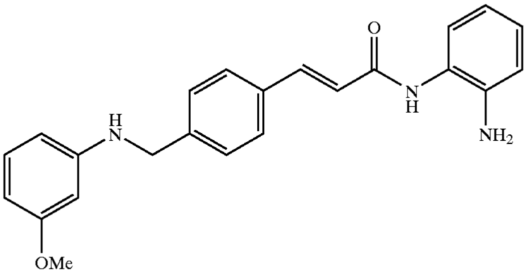 | 17 | 10 | — |
| 363 | 508 | 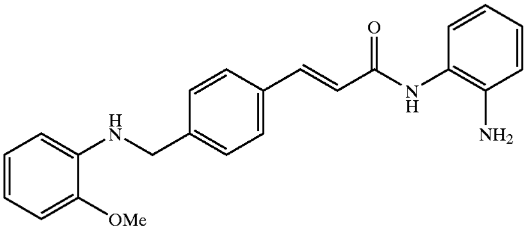 | 22 | 11 | — |
| 364 | 509 | 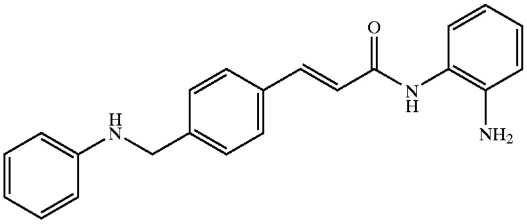 | 17 | 11 | — |

TABLE 5-continued
| Inhibition of Histone Deacetylase | | | | | |
|---|---|---|---|---|---|
| 365 | 510 | 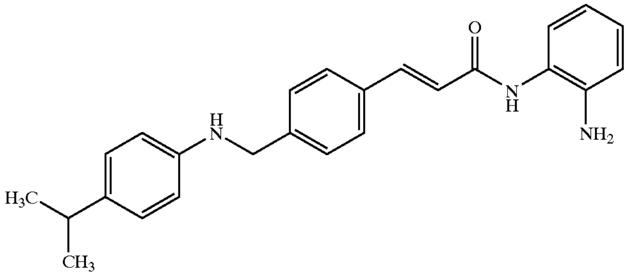 | 6 | 5 | — |
| 366 | 511 | 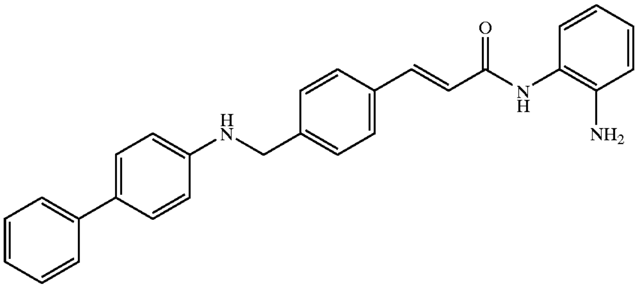 | 4 | >25 | — |
| 367 | 512 | 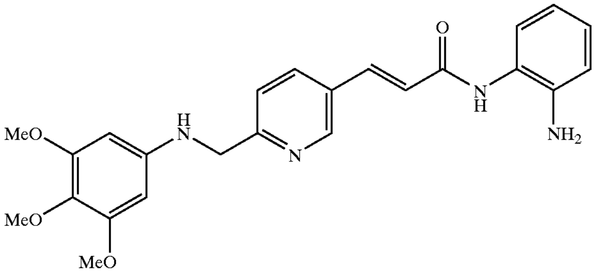 | 3 | 3 | 5 |
| 371 | 516 | 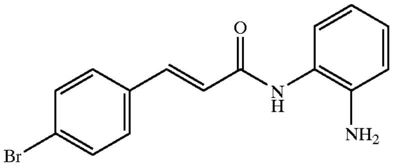 | 15 | 15 | — |
| 372 | 517 | 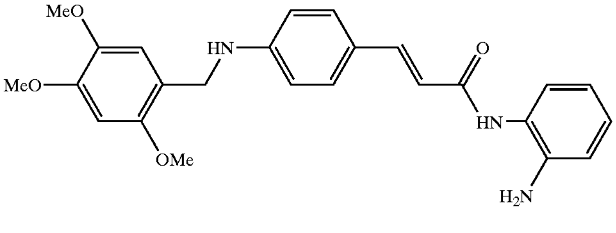 | 6 | 5 | — |
| 373 | 518 | 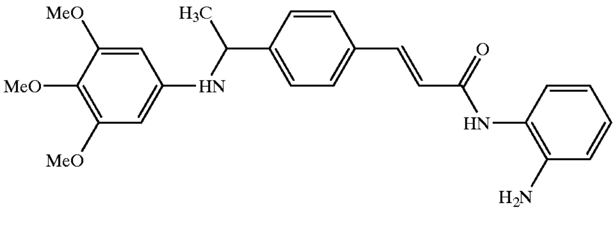 | 4 | 2 | 5 |

TABLE 5-continued
| Inhibition of Histone Deacetylase | | | | | |
|---|---|---|---|---|---|
| 374 | 519 | 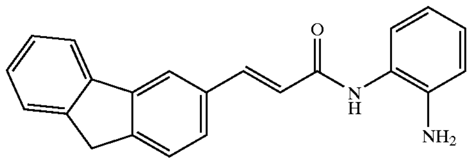 | 99 | 6 | — |
| 375 | 520 | 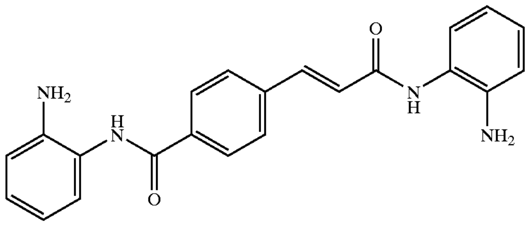 | 5 | 3 | — |
| 376 | 521 | 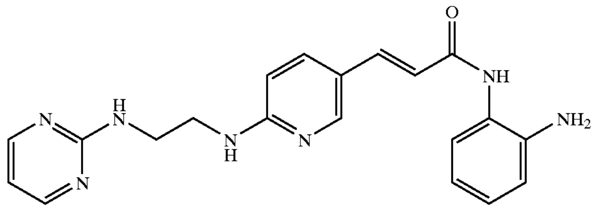 | 5 | 2 | 10 |
| 377 | 522 | 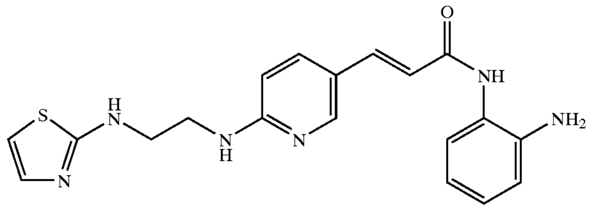 | 17 | 30 | — |
| 378 | 523 | 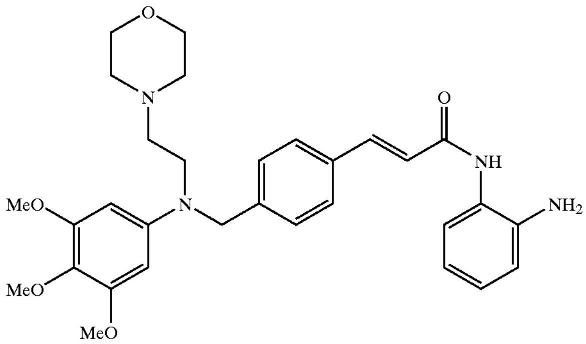 | 8 | 6 | 10 |
| 379 | 524 | 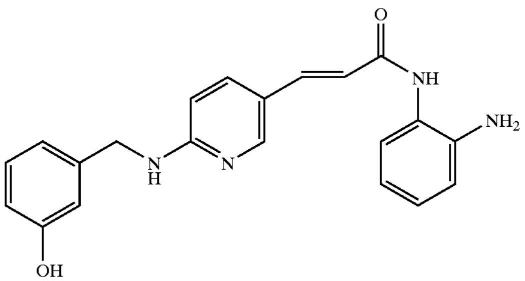 | 3 | 2 | 3 |

TABLE 5-continued
| Inhibition of Histone Deacetylase | | | | | |
|---|---|---|---|---|---|
| 380 | 525 | 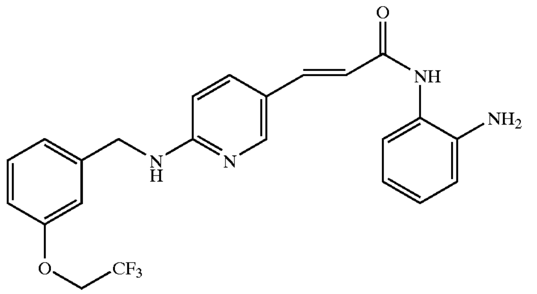 | 3 | 4 | 5 |
| 381 | 526 | 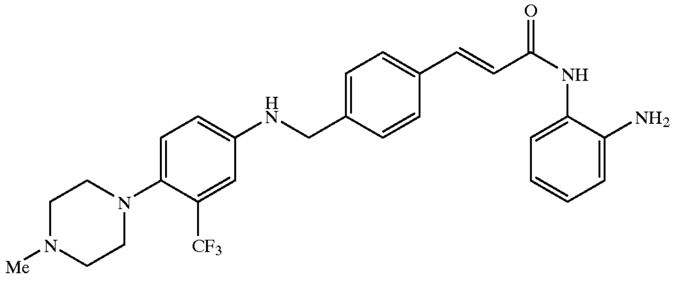 | 2 | 0.8 | 1 |
| 382 | 527 | 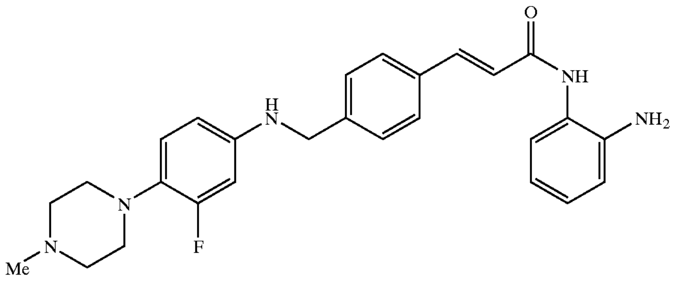 | 4 | 3 | — |
| 383 | 528 | 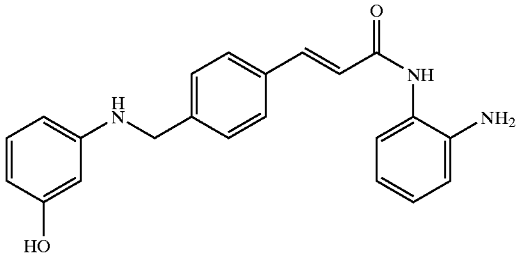 | 20 | 32 | — |
| 384 | 529 | 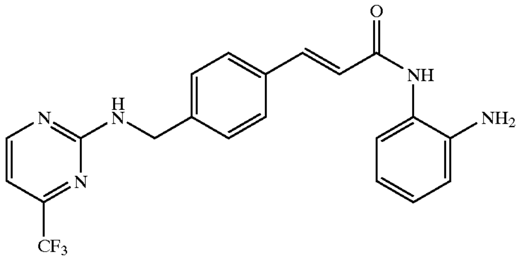 | 5 | 17 | — |

TABLE 5-continued
| Inhibition of Histone Deacetylase | | | | | |
|---|---|---|---|---|---|
| 385 | 530 | 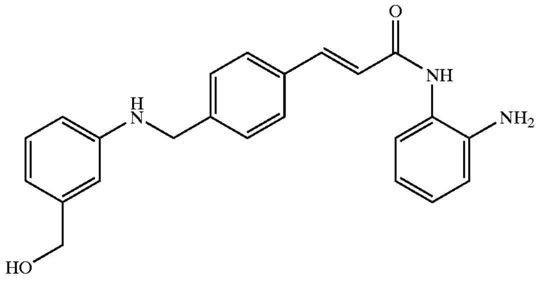 | 8 | 9 | — |
| 386 | 531 | 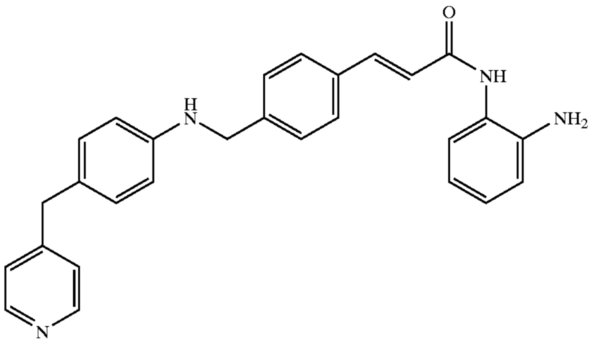 | 3 | 2 | 20 |
| 387 | 532 | 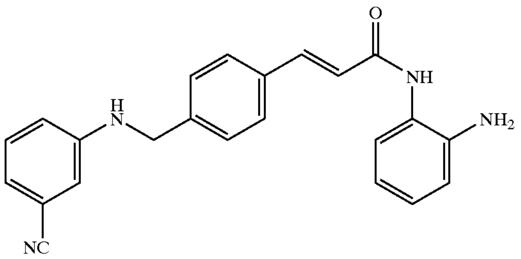 | 3 | 5 | — |
| 388 | 533 | 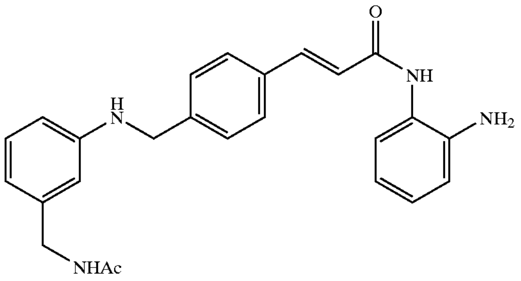 | 5 | 11 | — |
| 389 | 534 | 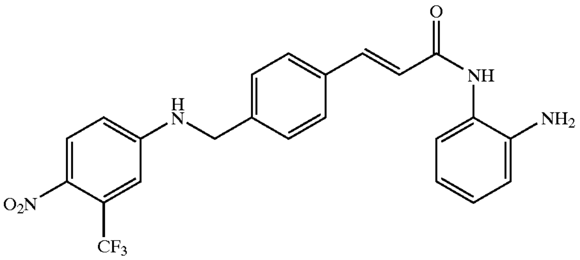 | 3 | 5 | — |

TABLE 5-continued
| Inhibition of Histone Deacetylase | | | | | |
|---|---|---|---|---|---|
| 390 | 535 | 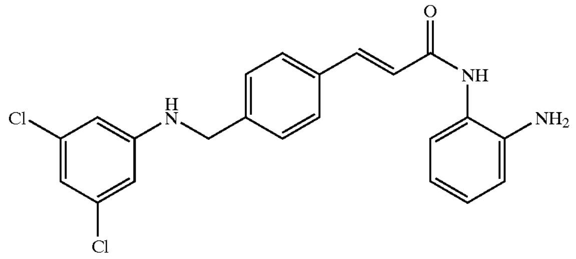 | 4 | 6 | — |
| 391 | 536 | 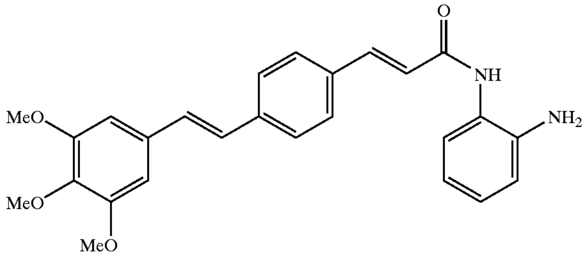 | 18 | 9 | — |
| 392 | 537 | 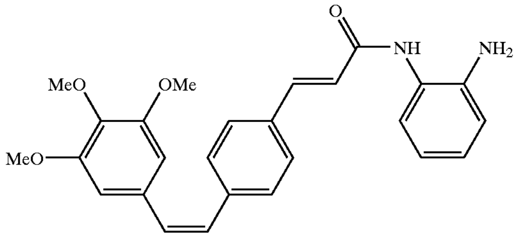 | 11 | 2 | >25 |
| 393 | 538 | 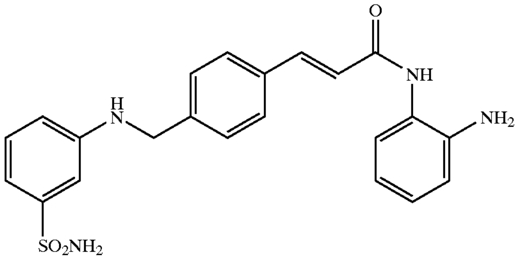 | 4 | 12 | — |
| 394 | 539 | 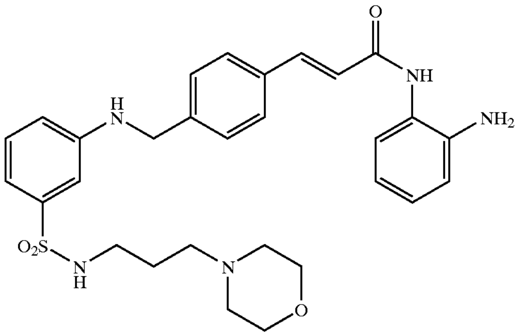 | 2 | 10 | — |

TABLE 5-continued
Inhibition of Histone Deacetylase
| | | | | | |
|---|---|---|---|---|---|
| 395 | 540 | 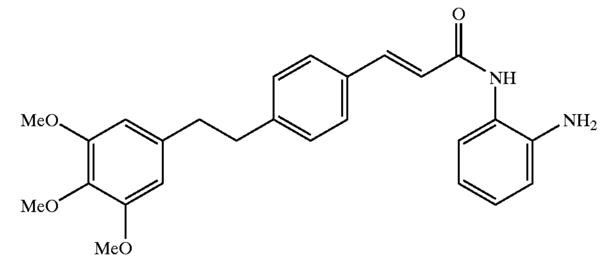 | 10 | 10 | — |
| 396 | 541 | 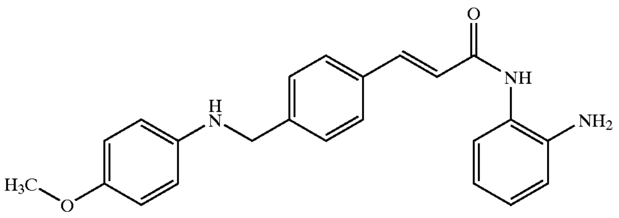 | 4 | 12 | — |
| 397 | 542 | 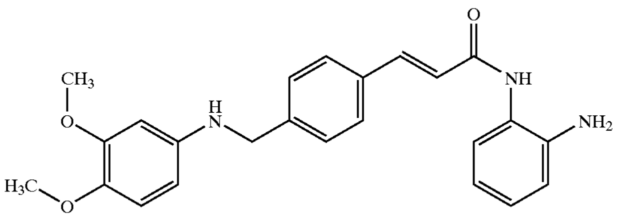 | 2 | 5 | 4 |
| 398 | 543 | 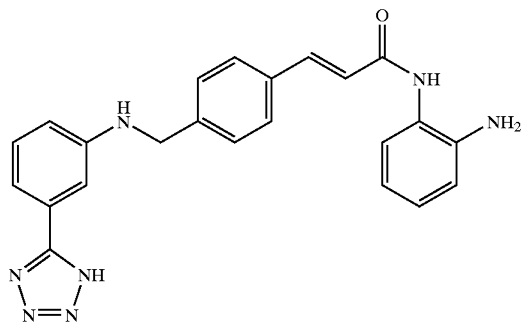 | 15 | >25 | — |
| 399 | 544 | 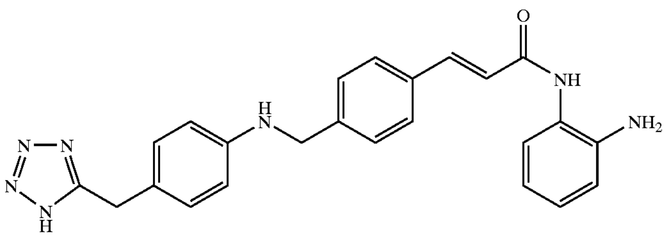 | 17 | 45 | — |
| 400 | 545 | 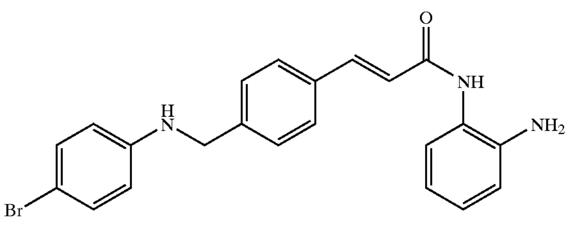 | 2 | 12 | — |

TABLE 5-continued
| Inhibition of Histone Deacetylase | | | | | |
|---|---|---|---|---|---|
| 401 | 546 | 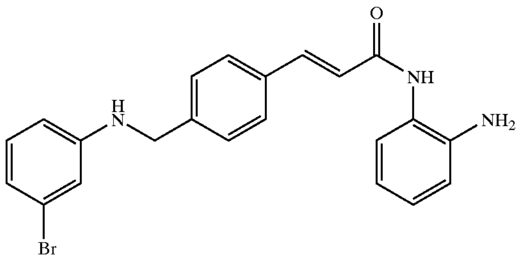 | 3 | 10 | — |
| 402 | 547 | 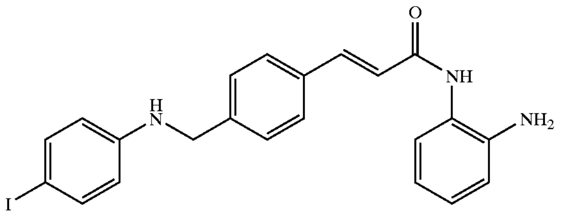 | 4 | 8 | — |
| 403 | 548 | 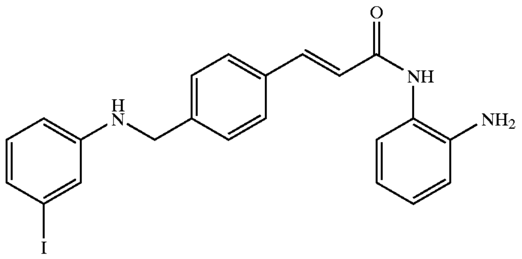 | 3 | 9 | — |
| 404 | 549 | 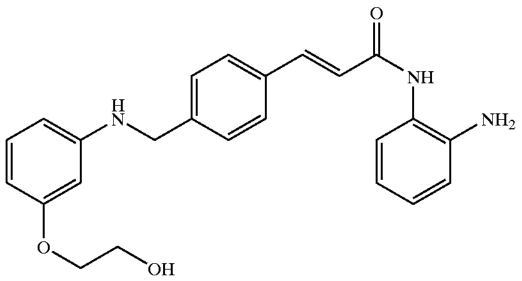 | 4 | 19 | — |
| 405 | 550 | 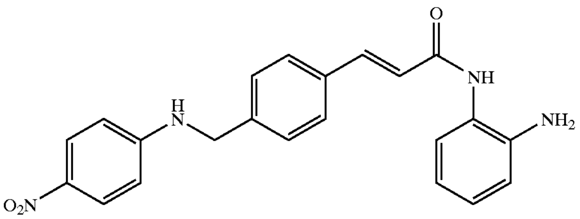 | 4 | 15 | — |
| 406 | 551 | 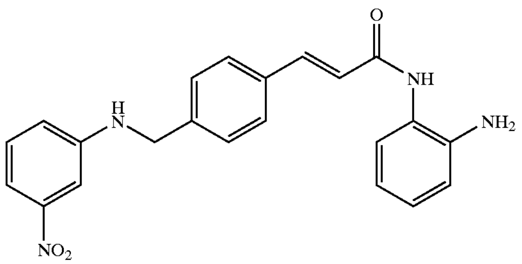 | 24 | 9 | — |

TABLE 5-continued
| Inhibition of Histone Deacetylase | | | | | |
|---|---|---|---|---|---|
| 407 | 552 | 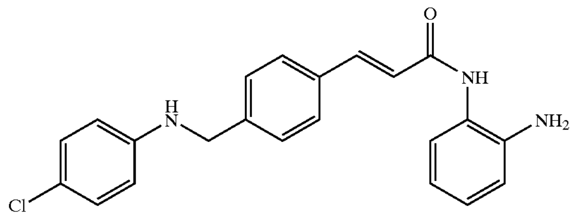 | 4 | 22 | — |
| 408 | 553 | 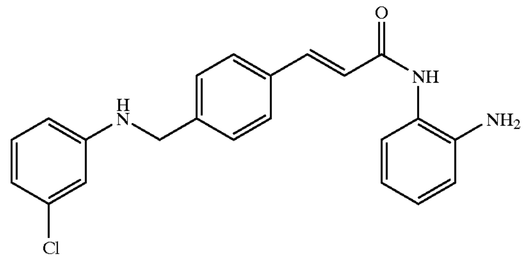 | 4 | 12 | — |
| 409 | 554 | 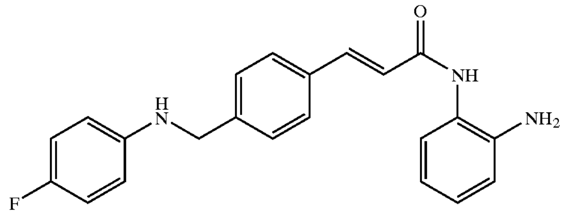 | 15 | 12 | — |
| 410 | 555 | 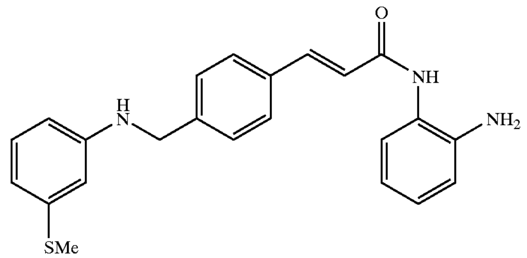 | 14 | 7 | — |
| 411 | 556 | 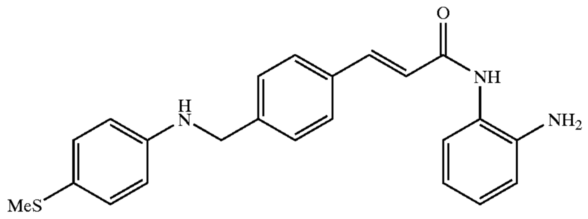 | 1 | 0.4 | 15 |
| 412 | 557 | 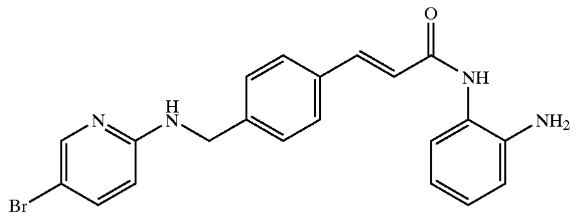 | 4 | 6 | — |

TABLE 5-continued
Inhibition of Histone Deacetylase
| | | | | | |
|---|---|---|---|---|---|
| 413 | 558 | 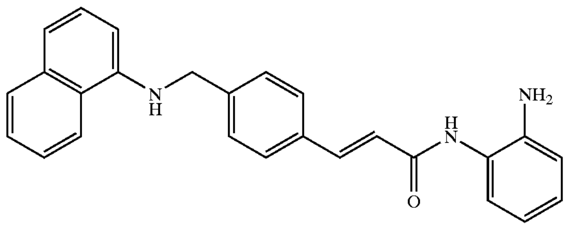 | 7 | 10 | — |
| 414 | 559 | 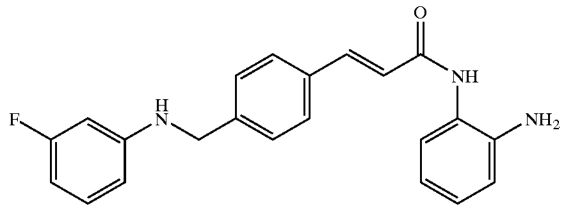 | 4 | 11 | — |
| 415 | 560 | 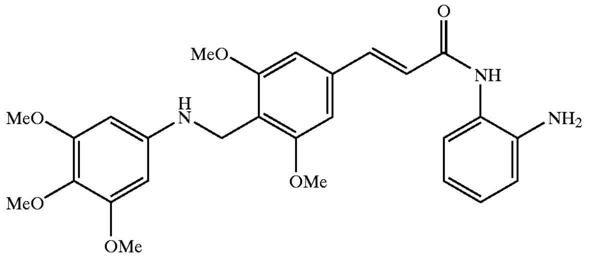 | 21 | 6 | — |
| 416 | 561 | 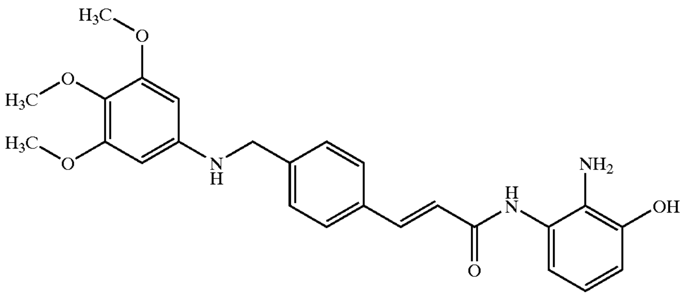 | >25 | >25 | — |
| 417 | 562 | 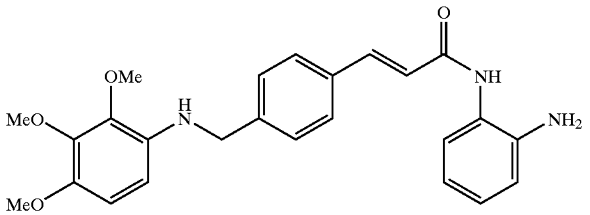 | 5 | 5 | — |
| 418 | 563 | 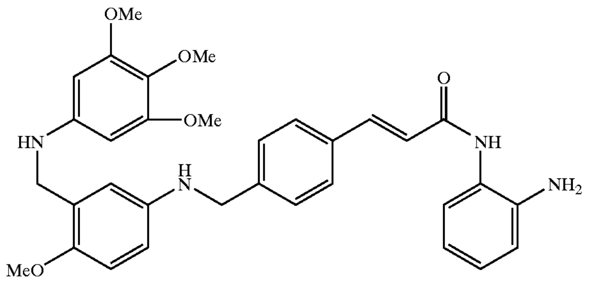 | 24 | 6 | — |

TABLE 5-continued
| Inhibition of Histone Deacetylase | | | | | |
|---|---|---|---|---|---|
| 419 | 564 | 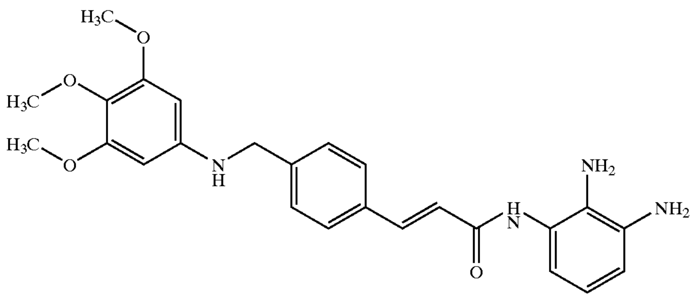 | >25 | >25 | — |
| 420 | 565 | 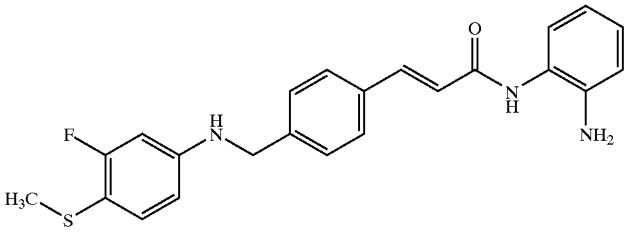 | 5 | 17 | — |
| 421 | 566 | 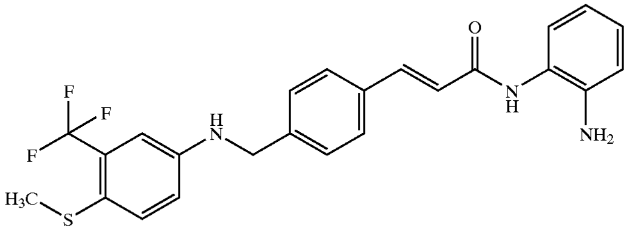 | 3 | 16 | — |
| 422 | 567 | 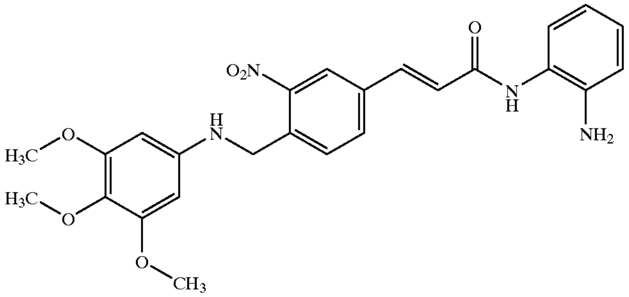 | 13 | 3 | — |
| 423 | 568 | 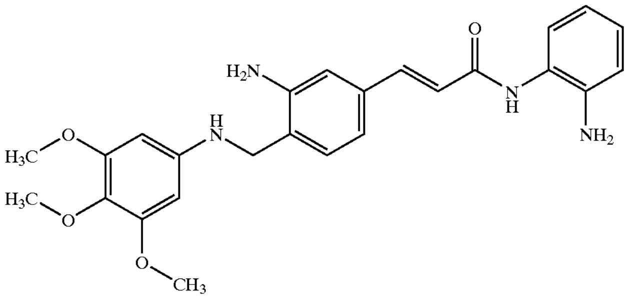 | >25 | 39 | — |

TABLE 5-continued
| Inhibition of Histone Deacetylase | | | | | |
|---|---|---|---|---|---|
| 424 | 569 | 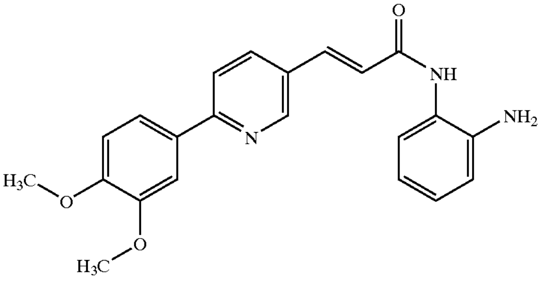 | 18 | 6 | — |
| 425 | 570 | 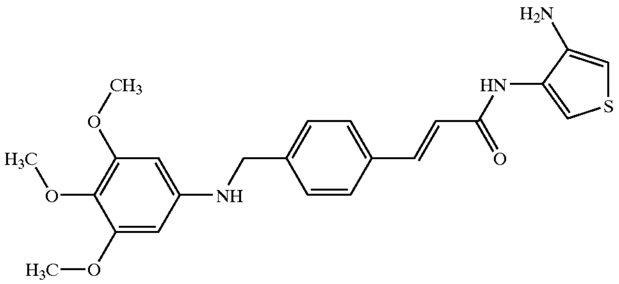 | 6 | 0.6 | 2 |
| Cpd | Structure | Human HDAC-1 $IC_{50}$ ($\mu$M) | MTT(HCT116) $IC_{50}$ ($\mu$M) | H4 Ac (T24) $EC_{50}$ ($\mu$M) |
|---|---|---|---|---|
| 87 | 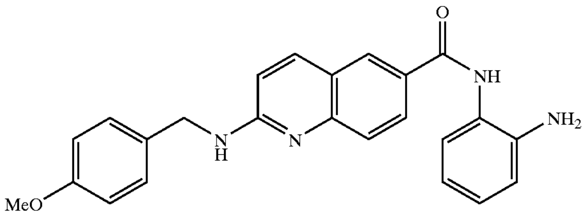 | 2 | 1 | 5 |
| 126 | 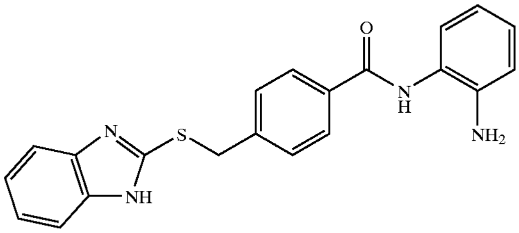 | 0.3 | 0.2 | 1 |
| 128 | 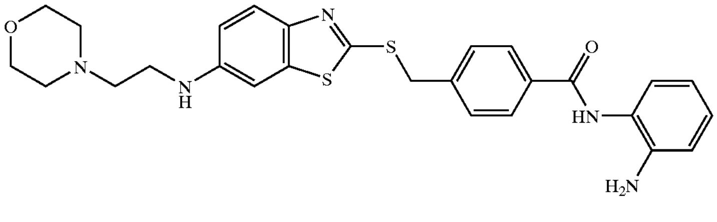 | 1 | 0.3 | 5 |
| 131 | 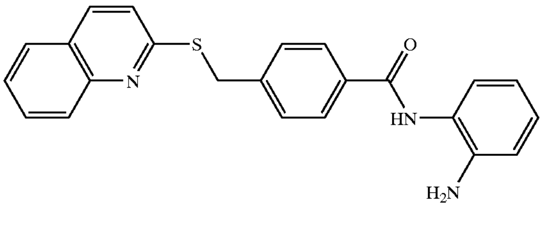 | 0.3 | 0.9 | 2 |

TABLE 5-continued
| Inhibition of Histone Deacetylase | | | | |
|---|---|---|---|---|
| 139 | 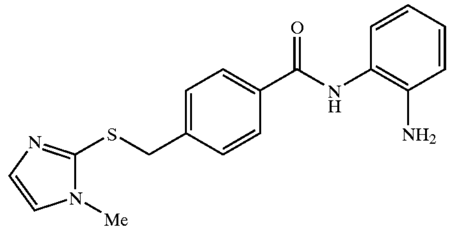 | 3 | 3 | 5 |
| 141 | 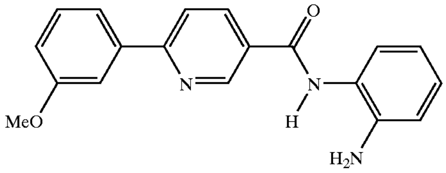 | 7 | 10 | na |
| 149 | 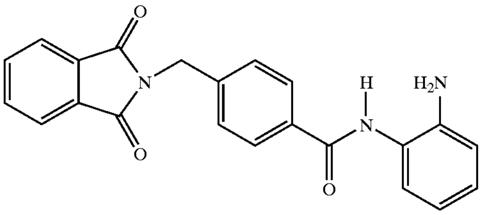 | 1 | 5 | 5 |
| 152 | 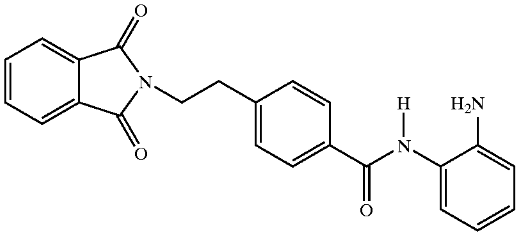 | 0.3 | 11 | na |
| 154 | 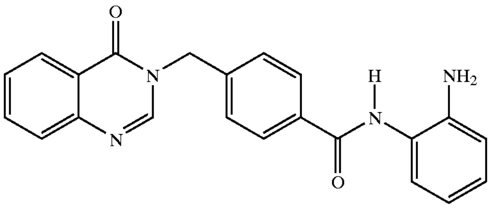 | 0.3 | 0.4 | <1 |
| 155 | 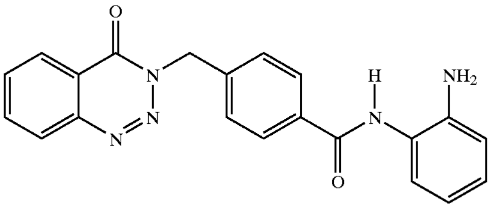 | 0.4 | 0.4 | 1 |
| 157 | 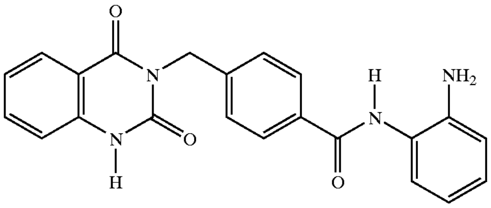 | 2 | 0.6 | 1 |

TABLE 5-continued
| Inhibition of Histone Deacetylase | | | | |
|---|---|---|---|---|
| 158 | 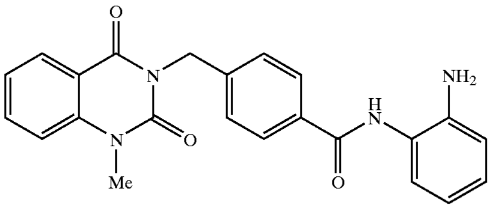 | 0.4 | 0.2 | 1 |
| 164 | 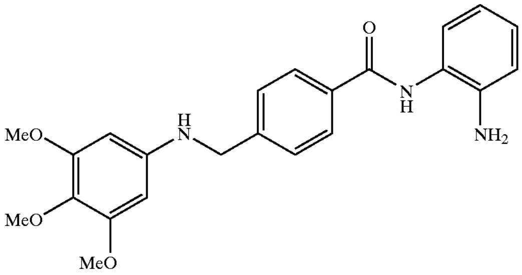 | 3 | 2 | 3 |
| 165 | 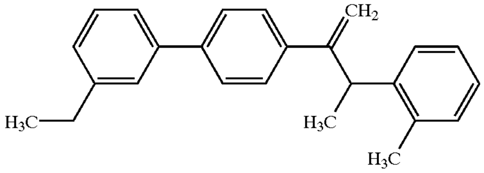 | 9 | 4 | 25 |
| 166 | 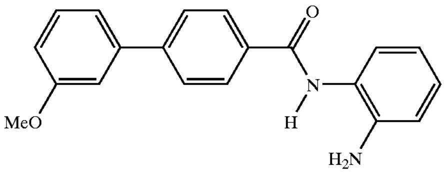 | 2 | 5 | 5 |
| 167 | 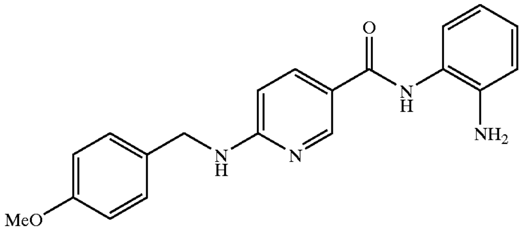 | 4 | 0.5 | 2 |
| 168 | 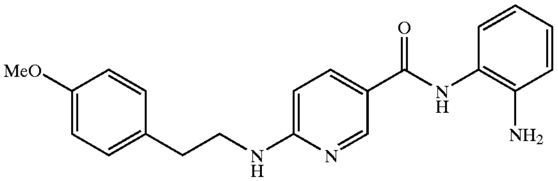 | 3 | 0.8 | 2 |

TABLE 5-continued
| Inhibition of Histone Deacetylase | | | | |
|---|---|---|---|---|
| 169 | 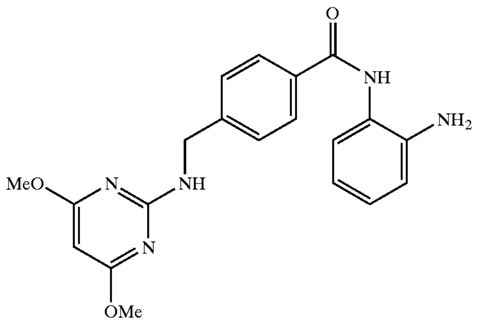 | 0.3 | 0.7 | 1 |
| 171 | 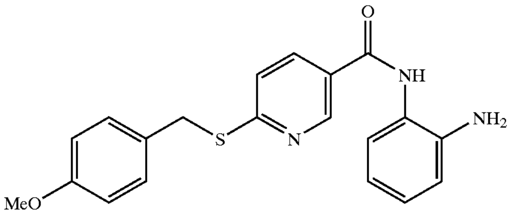 | 8 | 3 | 25 |
| 172 | 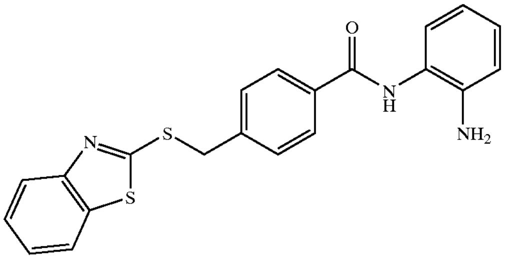 | 0.4 | 1 | 3 |
| 174 | 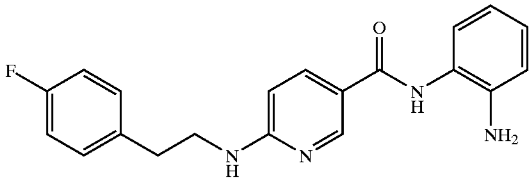 | 4 | 0.4 | 5 |
| 175 | 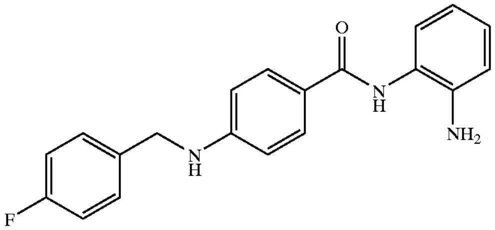 | 4 | 0.5 | 3 |
| 176 | 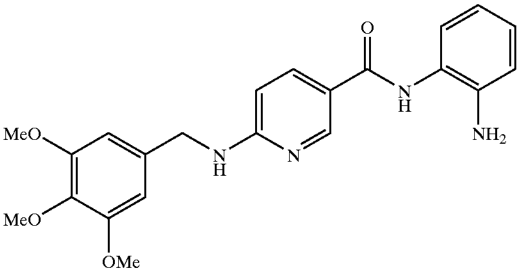 | 5 | 1 | 3 |

TABLE 5-continued
Inhibition of Histone Deacetylase
| Ex | Cpd | Structure | Human HDAC-1 $IC_{50}$ ($\mu M$) | MTT (HCT116) $IC_{50}$ ($\mu M$) | H4 Ac (T24) $EC_{50}$ ($\mu M$) |
|---|---|---|---|---|---|
| 177 | | 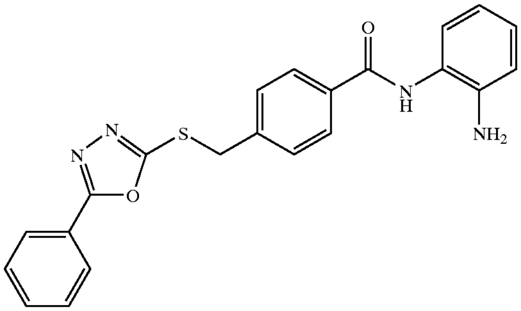 | 1 | 0.4 | 1 |
| 117 | 179 | 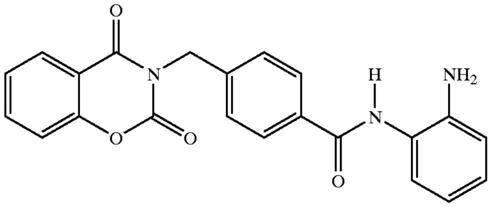 | 1 | 0.3 | 1 |
| 118 | 180 | 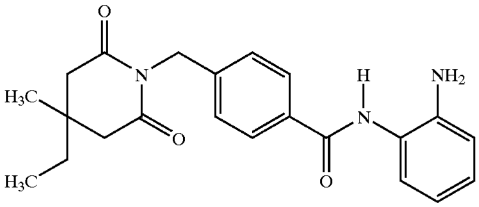 | 3 | 2 | 5 |
| 119 | 181 | 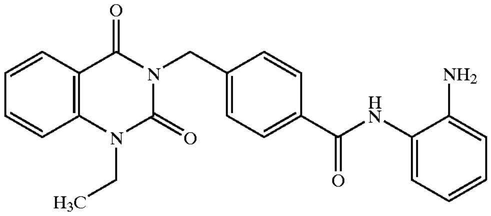 | 0.5 | 0.4 | 1 |
| 122 | 186 | 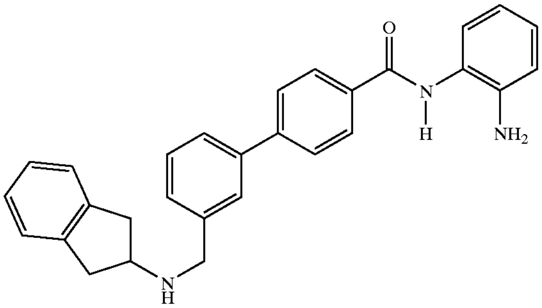 | 2 | 2 | 2 |

TABLE 5-continued
| Inhibition of Histone Deacetylase | | | | | |
|---|---|---|---|---|---|
| 123 | 187 | 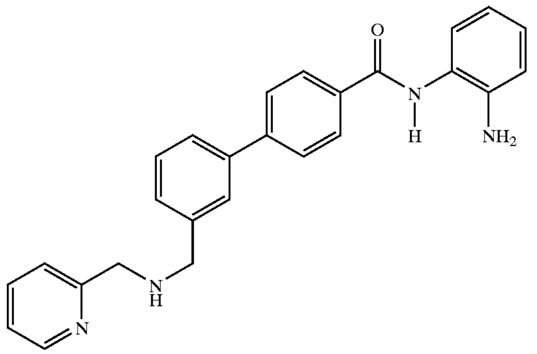 | 2 | 5 | 2 |
| 125 | 189 | 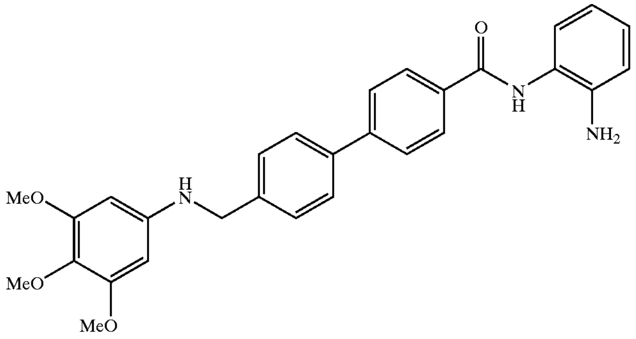 | 3 | 2 | 5 |
| 126 | 190 | 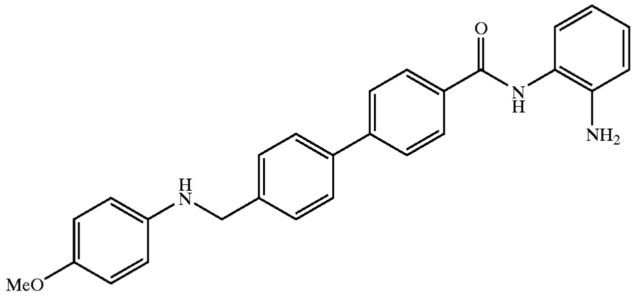 | 3 | 1 | >5 |
| 127 | 192 | 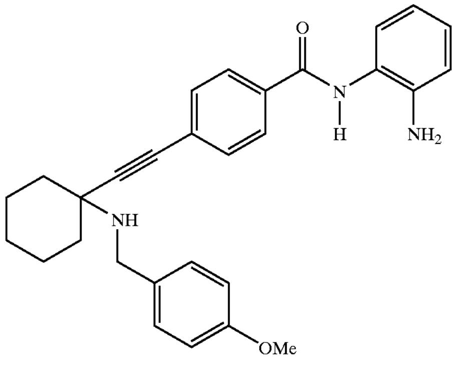 | 2 | 1 | 3 |

TABLE 5-continued
| Inhibition of Histone Deacetylase | | | | |
|---|---|---|---|---|
| 128 | 193 | 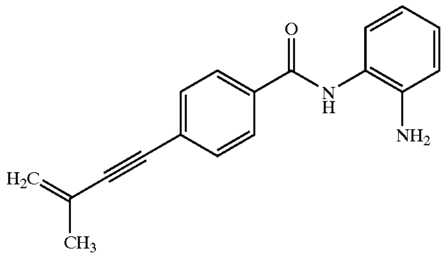 | 4 | 16 |
| 129 | 194 | 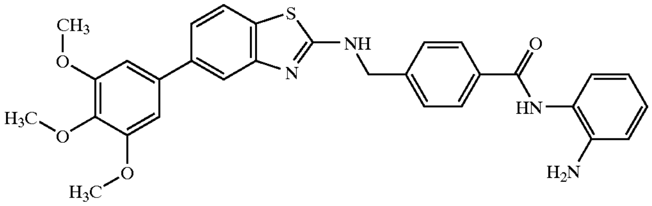 | 3 | 11 |
| 130 | 195 | 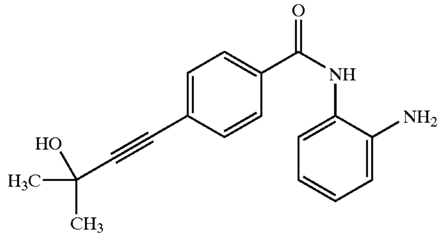 | 7 | 9 |
| 131 | 196 | 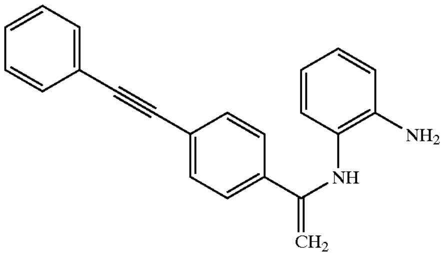 | 4 | 3 |
| 132 | 198 | 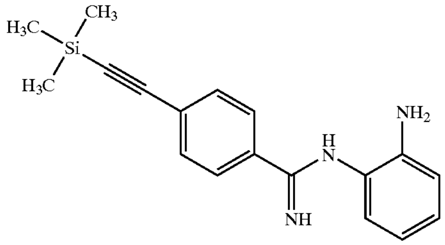 | 24 | 14 |
| 133 | 199 | 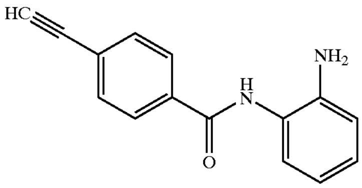 | 7 | 9 |

TABLE 5-continued
Inhibition of Histone Deacetylase
| | | | | | |
|---|---|---|---|---|---|
| 134 | 201 | 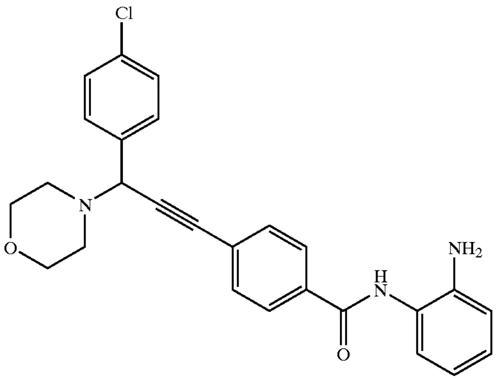 | 11 | 5 | |
| 144 | 228 | 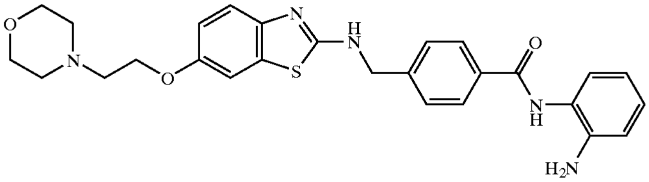 | 3 | 0.3 | 1 |
| 145 | 231 | 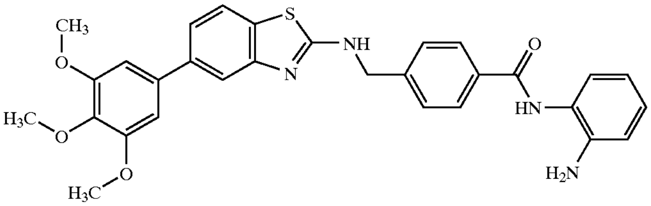 | 4 | 1 | 3 |
| 146 | 233 | 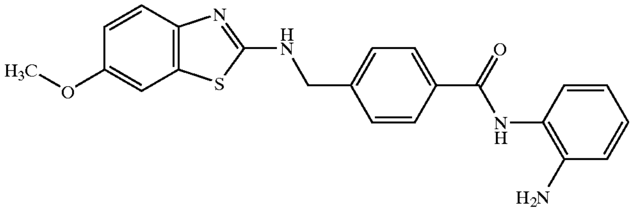 | 0.9 | 0.3 | 1 |
| 147 | 236 | 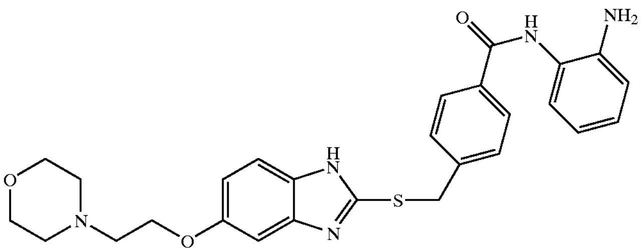 | 5 | 6 | |
| 148 | 238 | 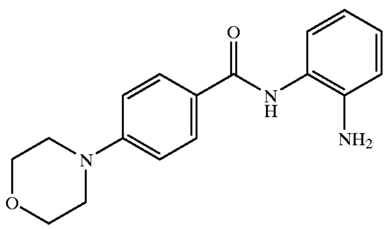 | 3 | 6 | |

TABLE 5-continued
| Inhibition of Histone Deacetylase | | | | | |
|---|---|---|---|---|---|
| 149 | 240 | 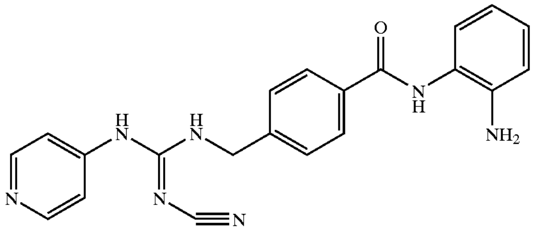 | 1.8 | 10 | |
| 150 | 243 | 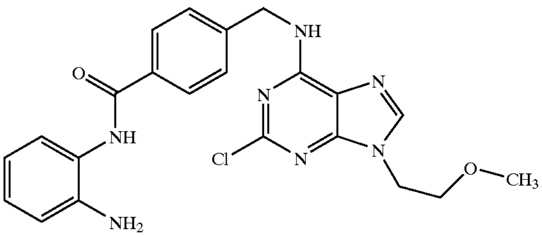 | 2 | 0.8 | 1 |
| 151 | 247 | 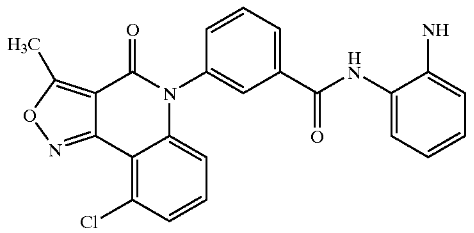 | 3 | 0.6 | 2 |
| 152 | 249 | 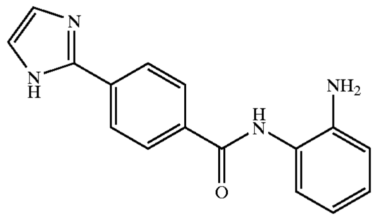 | 4 | 1 | 2 |
| 153 | 252 | 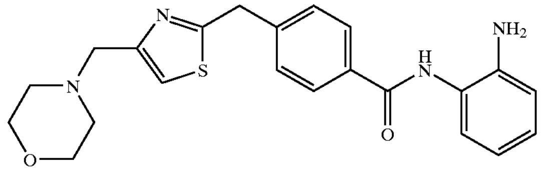 | 8 | 1 | 2 |
| 154 | 255 | 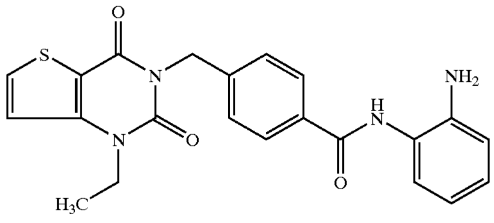 | 2 | 0.8 | 1 |
| 155 | 257 | 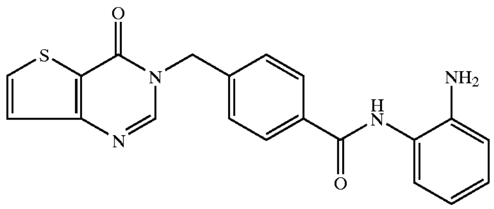 | 0.4 | 0.4 | 1 |

TABLE 5-continued
Inhibition of Histone Deacetylase
| | | | | | |
|---|---|---|---|---|---|
| 156 | 259 | 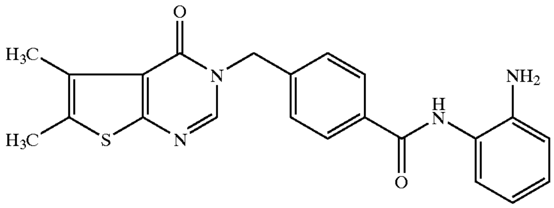 | 3 | 0.3 | 1 |
| 157 | 262 | 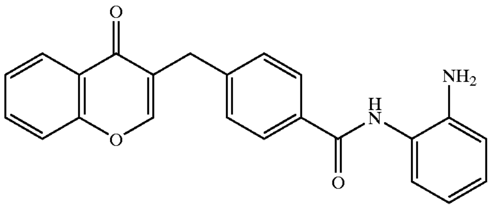 | 0.5 | 0.3 | 1 |
| 158 | 265 | 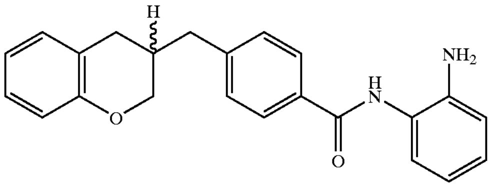 | 2 | 2 | 3 |
| 159 | 266 | 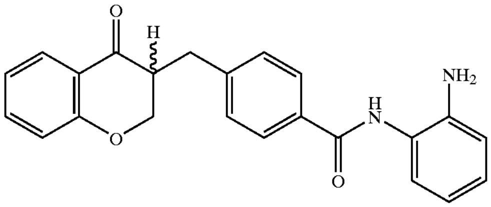 | 0.4 | 0.9 | 2 |
| 160 | 269 | 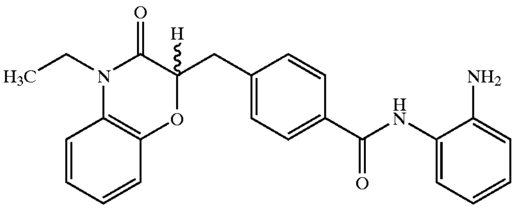 | 9 | 4 | |
| 161 | 270 | 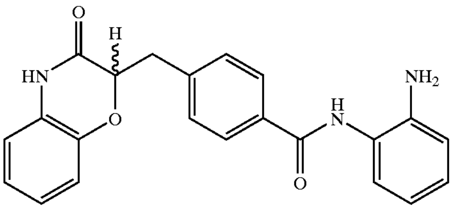 | 4 | 1 | 5 |
| 162 | 272 | 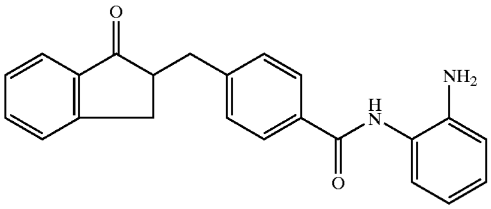 | 2 | 0.6 | <1 |

TABLE 5-continued
| Inhibition of Histone Deacetylase | | | | | |
|---|---|---|---|---|---|
| 163 | 275 | 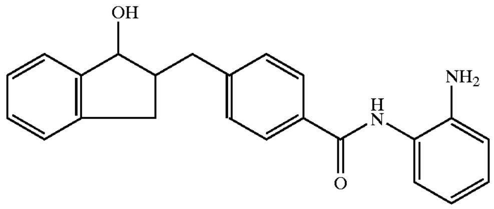 | 4 | 0.9 | 2 |
| 164 | 277 | 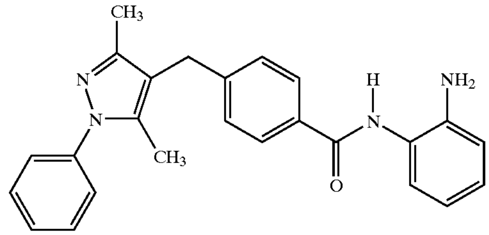 | 4 | 0.3 | 1 |
| 165 | 281 | 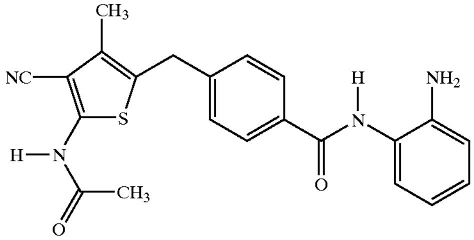 | 0.5 | 0.6 | 1 |
| 166 | 284 | 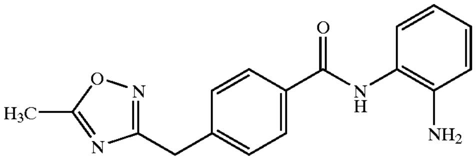 | 3 | 5 | |
| 167 | 286 | 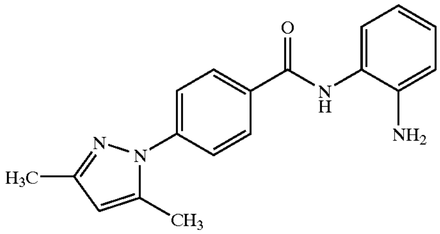 | 5 | 2 | |
| 168 | 289 | 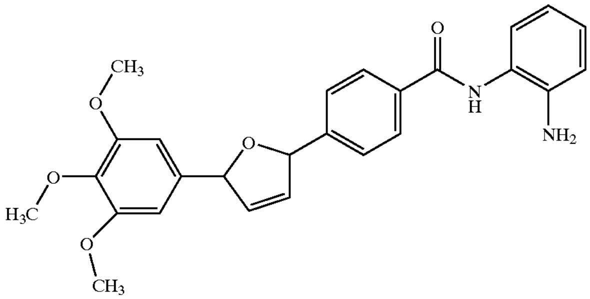 | 17 | 5 | |

TABLE 5-continued
| Inhibition of Histone Deacetylase | | | | | |
|---|---|---|---|---|---|
| 169 | 290 | 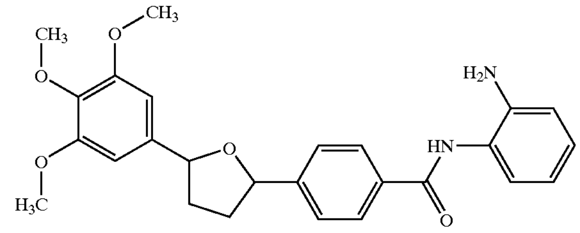 | 11 | 3 | |
| 170 | 296 | 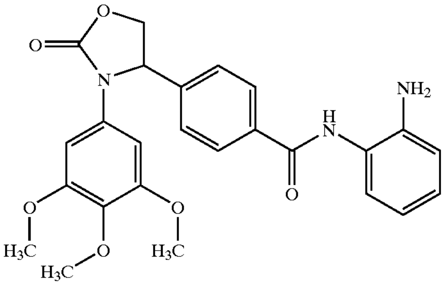 | 20 | 7 | |
| 171 | 297 | 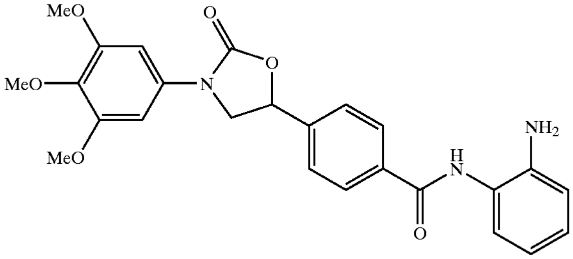 | 7 | 0.4 | 1 |
| 172 | 301 | 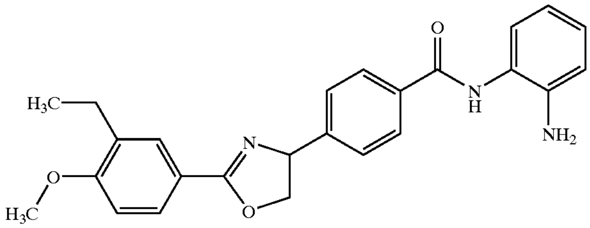 | 3 | 3 | |
| 173 | 305 | 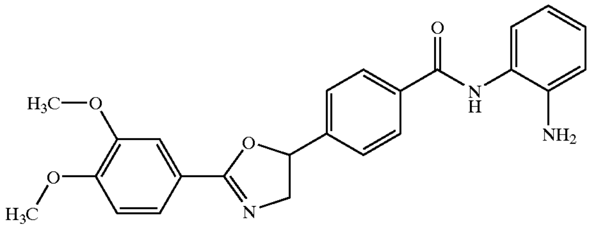 | 4 | 2 | |
| 174 | 311 | 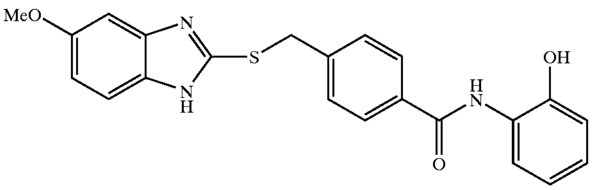 | 0.9 | 0.7 | 1 |

TABLE 5-continued
| Inhibition of Histone Deacetylase | | | | | |
|---|---|---|---|---|---|
| 178 | 317 | 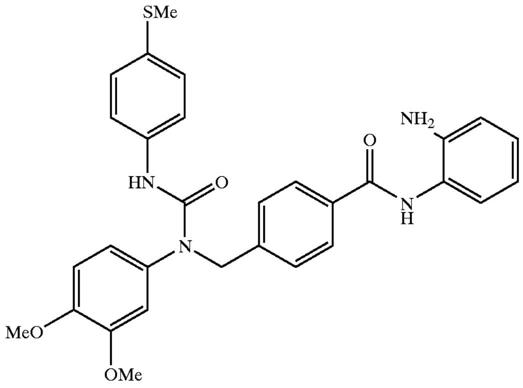 | 2 | 0.3 | 1 |
| 179 | 319 | 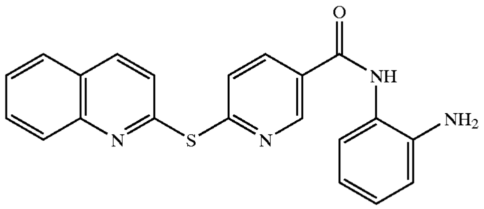 | 4 | 8 | |
| 180 | 320 | 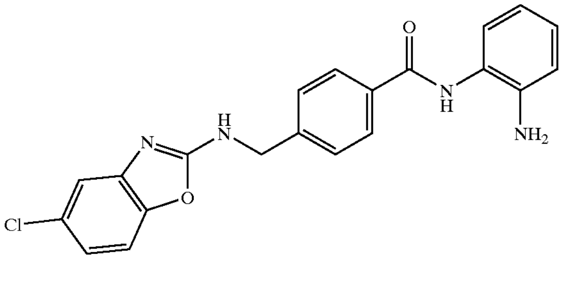 | 2 | | 1 |
| 181 | 321 | 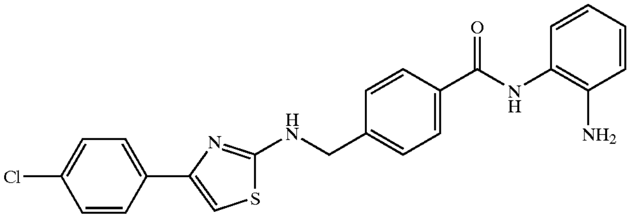 | 0.5 | 0.3 | 5 |
| 182 | 322 | 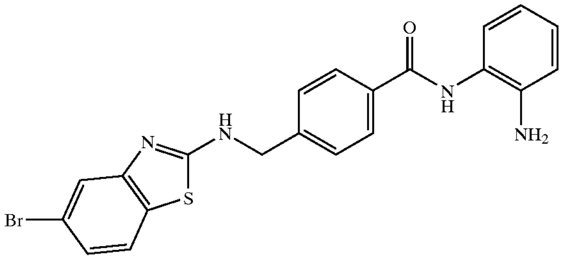 | 0.7 | 0.4 | 2 |

TABLE 5-continued
| Inhibition of Histone Deacetylase | | | | | |
|---|---|---|---|---|---|
| 183 | 323 | 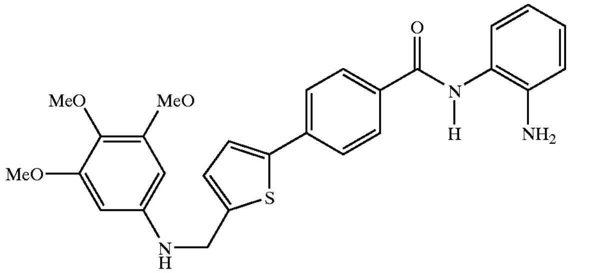 | 1 | 0.6 | 1 |
| 184 | 325 | 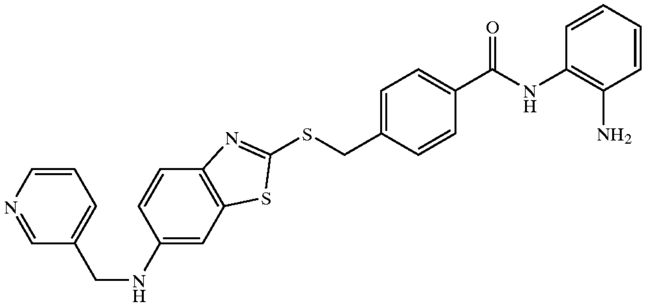 | 0.3 | 1 | 2 |
| 185 | 326 | 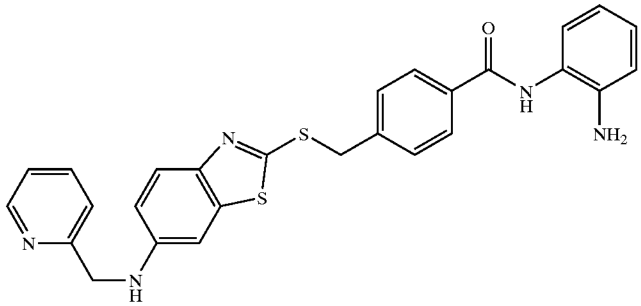 | 1 | 1 | 3 |
| 186 | 327 | 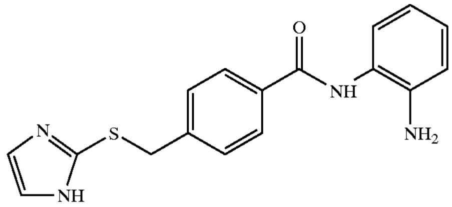 | 2 | 5 | 3 |
| 187 | 328 | 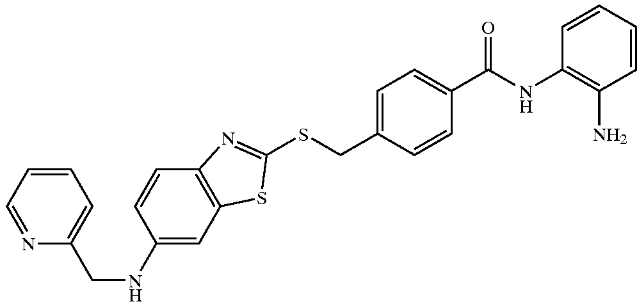 | 17 | 10 | |

TABLE 5-continued
| Inhibition of Histone Deacetylase | | | | | |
|---|---|---|---|---|---|
| 189 | 330 | 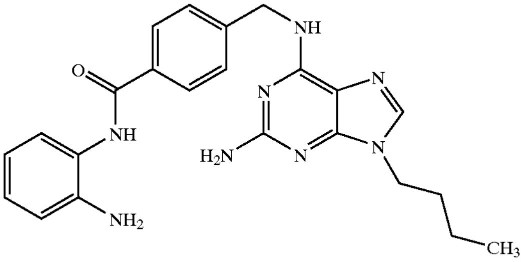 | 3 | 2 | 1 |
| 190 | 331 | 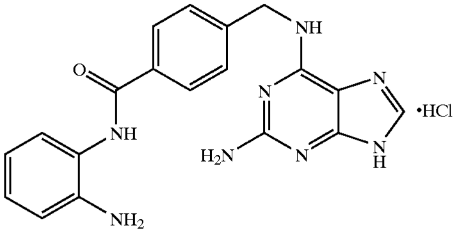 | 4 | 10 | |
| 191 | 332 | 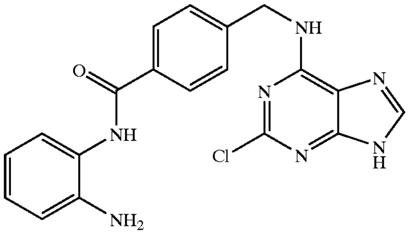 | 0.4 | 1 | 5 |
| 192 | 333 | 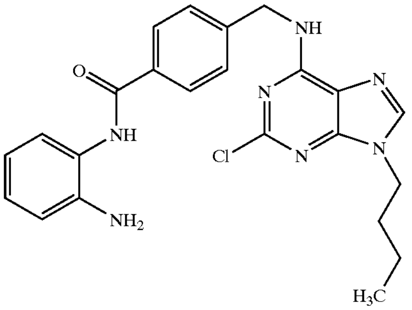 | 2 | 0.1 | 1 |
| 193 | 334 | 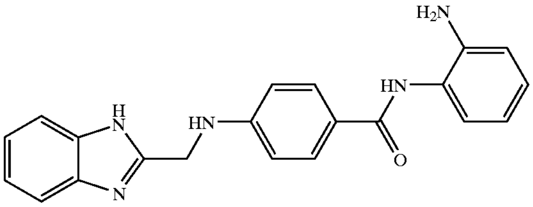 | 8 | 0.2 | 1 |
| 195 | 336 | 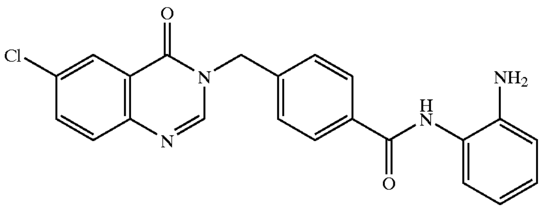 | 1 | 0.4 | <1 |

TABLE 5-continued
| Inhibition of Histone Deacetylase | | | | | |
|---|---|---|---|---|---|
| 196 | 337 | 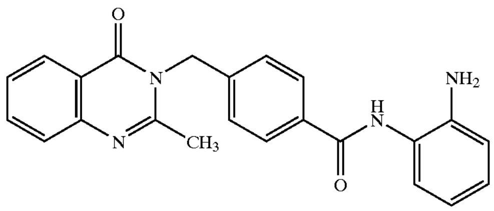 | 3 | 0.6 | 1 |
| 197 | 338 | 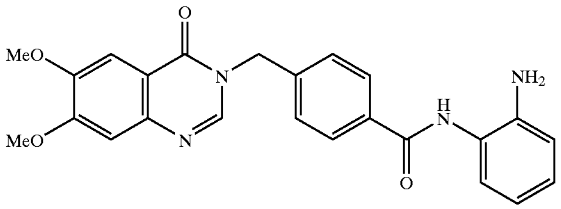 | 2 | 0.5 | 3 |
| 198 | 339 | 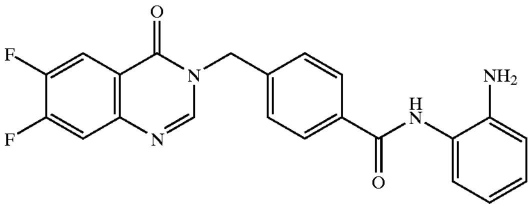 | 4 | 3 | |
| 199 | 340 | 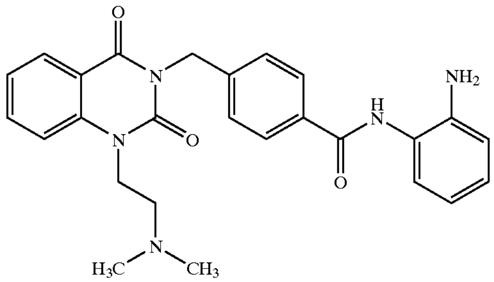 | 2 | 1 | 1 |
| 200 | 341 | 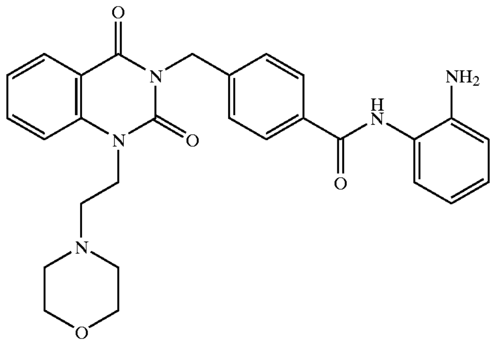 | 4 | 1 | 3 |
| 201 | 342 | 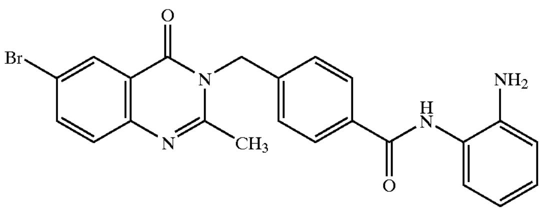 | 3 | 0.4 | 1 |

TABLE 5-continued
Inhibition of Histone Deacetylase
| | | | | | |
|---|---|---|---|---|---|
| 202 | 343 | 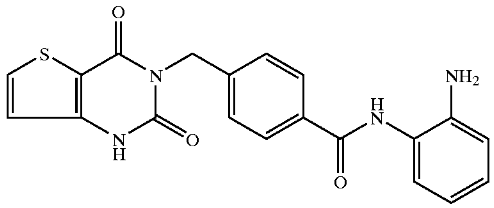 | 0.5 | 0.3 | 1 |
| 203 | 344 | 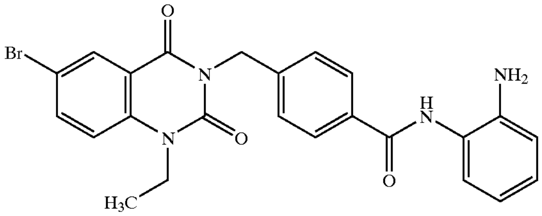 | 0.5 | 0.2 | 1 |
| 204 | 345 | 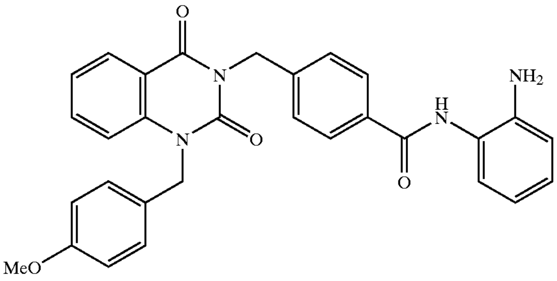 | 0.4 | 0.8 | 1 |
| 205 | 346 | 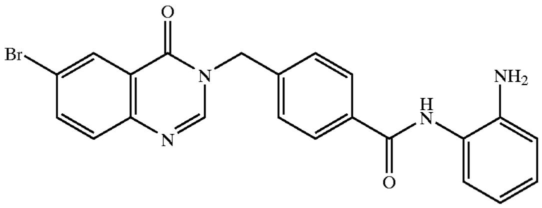 | 3 | 0.5 | <1 |
| 206 | 347 | 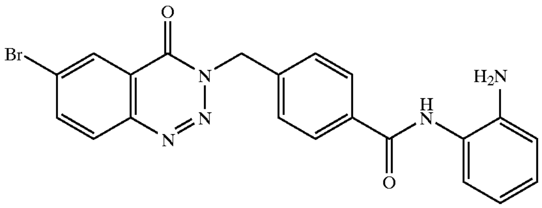 | 2 | 0.6 | 2 |
| 207 | 348 | 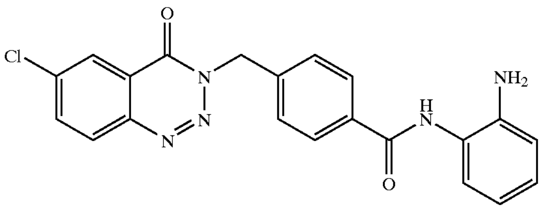 | 2 | 0.3 | 1 |

TABLE 5-continued
| Inhibition of Histone Deacetylase | | | | | |
|---|---|---|---|---|---|
| 208 | 349 | 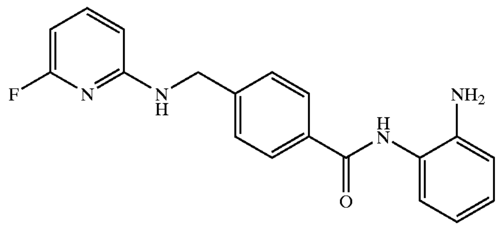 | 13 | 1 | 3 |
| 209 | 350 | 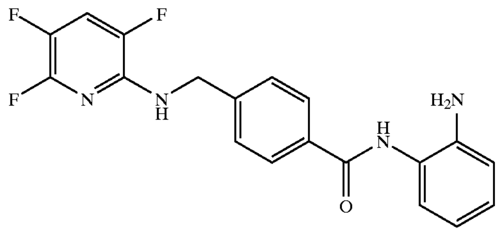 | 2 | 1 | 5 |
| 211 | 352 | 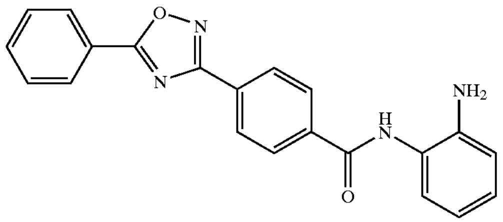 | 16 | 9 | |
| 212 | 353 | 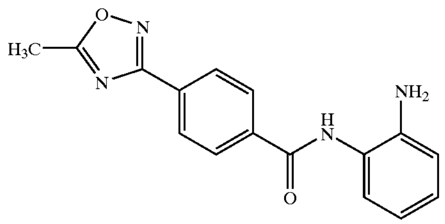 | 3 | 10 | |
| 213 | 354 | 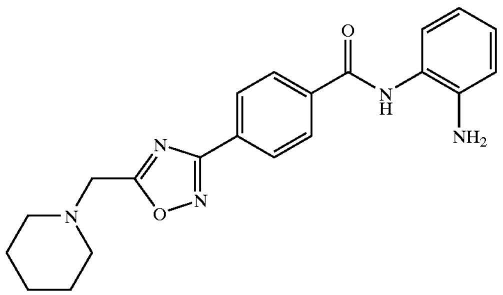 | 15 | 5 | |
| 214 | 355 | 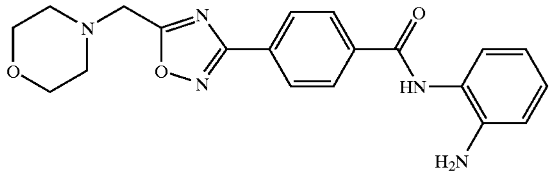 | 25 | 10 | |

TABLE 5-continued
| Inhibition of Histone Deacetylase | | | | | |
|---|---|---|---|---|---|
| 215 | 356 | 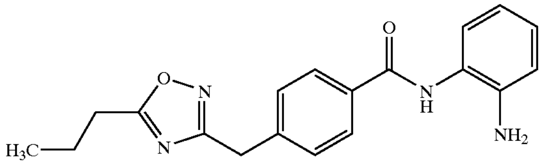 | 5 | 2 | |
| 216 | 357 | 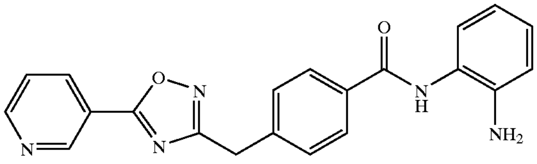 | 4 | 0.4 | 2 |
| 217 | 358 | 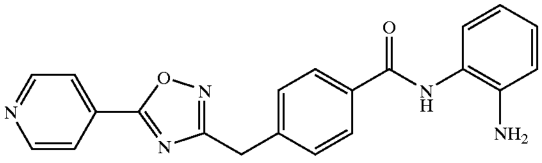 | 3 | 1 | 2 |
| 218 | 359 | 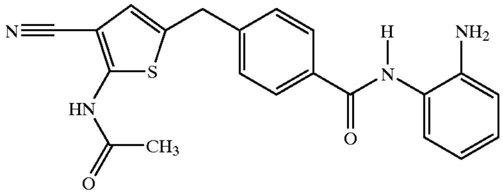 | 2 | 0.3 | 1 |
| 219 | 360 | 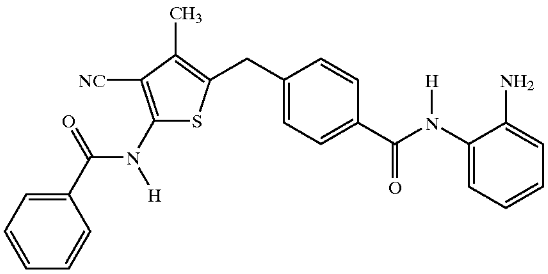 | 5 | 0.2 | 1 |
| 220 | 361 | 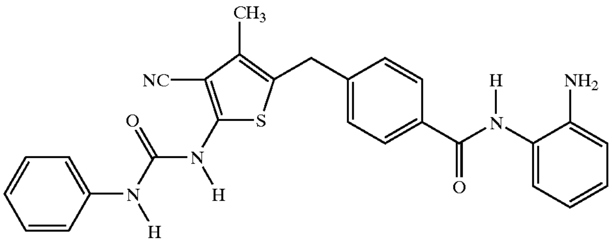 | 2 | 0.5 | 1 |
| 221 | 362 | 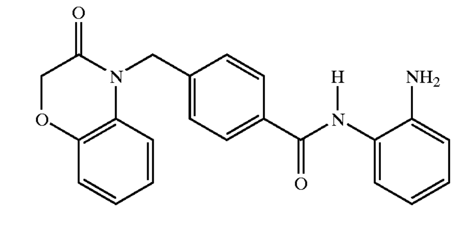 | 2 | 0.7 | 1 |

TABLE 5-continued
| Inhibition of Histone Deacetylase | | | | | |
|---|---|---|---|---|---|
| 222 | 363 | 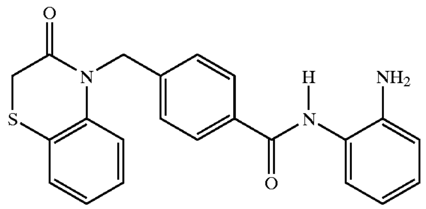 | 1 | 0.3 | 3 |
| 223 | 364 | 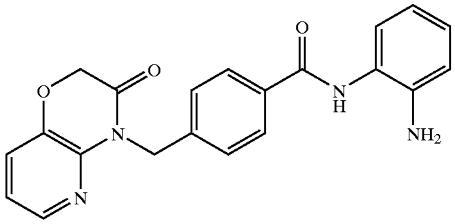 | 4 | 0.6 | |
| 224 | 365 | 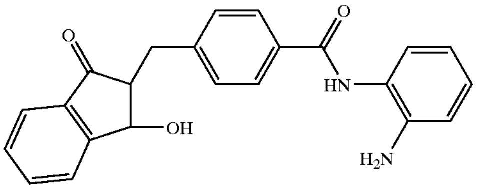 | 3 | 0.6 | 3 |
| 225 | 366 | 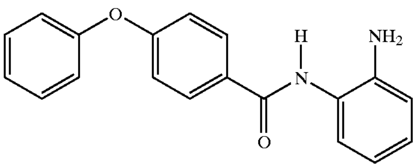 | 14 | 10 | |
| 226 | 367 | 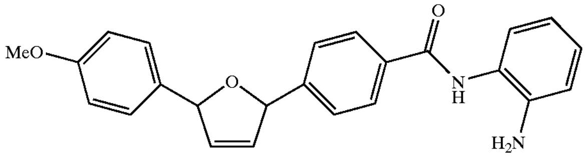 | 6 | 2 | 5 |
| 230 | 371 | 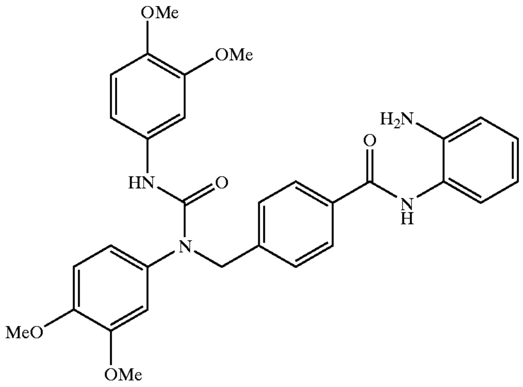 | 4 | 0.5 | 2 |

TABLE 5-continued
Inhibition of Histone Deacetylase
| | | | | | |
|---|---|---|---|---|---|
| 231 | 372 | 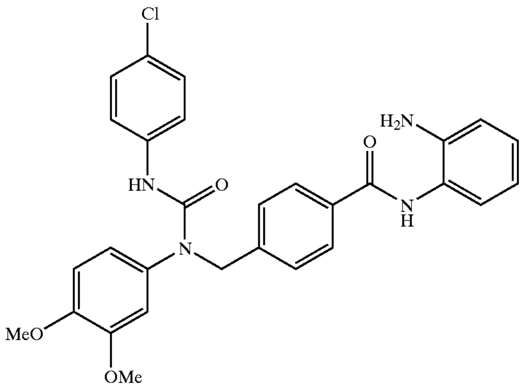 | 2 | 0.2 | 1 |
| 232 | 373 | 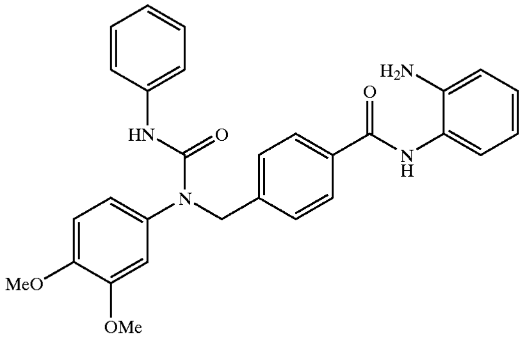 | 4 | 0.4 | 1 |
| 233 | 374 | 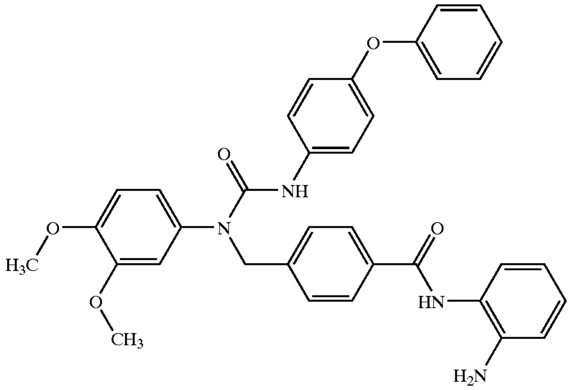 | 2.5 | 0.3 | 1 |
| 234 | 375 | 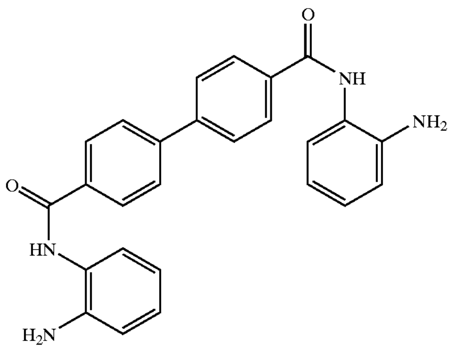 | 3 | 4 | 25 |

TABLE 5-continued
| Inhibition of Histone Deacetylase | | | | | |
|---|---|---|---|---|---|
| 235 | 376 | 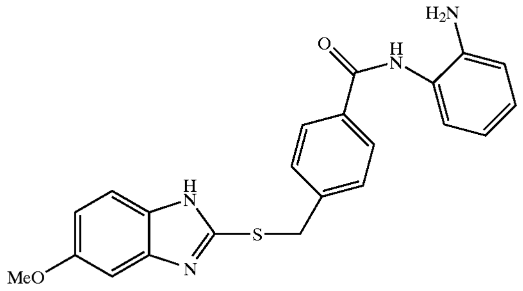 | 3 | 0.1 | 1 |
| 236 | 377 | 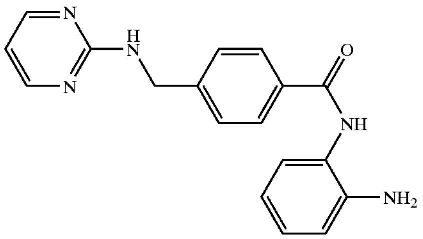 | 4 | 2 | 3 |
| 237 | 378 | 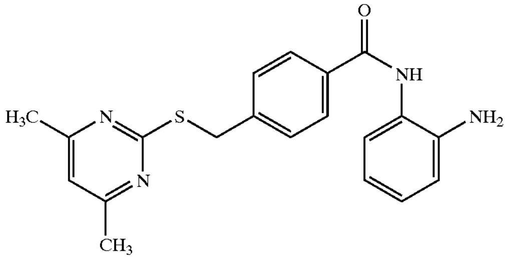 | 2 | 0.7 | 2 |
| 238 | 379 | 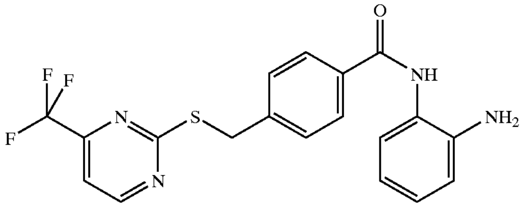 | 2 | 0.6 | 15 |
| 239 | 380 | 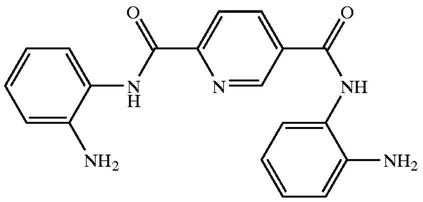 | 6 | 8 | |
| 240 | 381 | 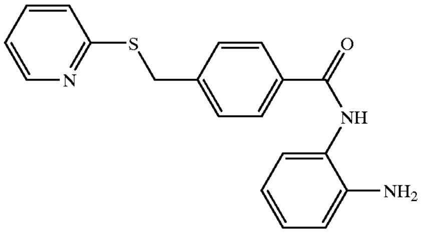 | 2 | 1 | 2 |

TABLE 5-continued
| Inhibition of Histone Deacetylase | | | | | |
|---|---|---|---|---|---|
| 241 | 382 | 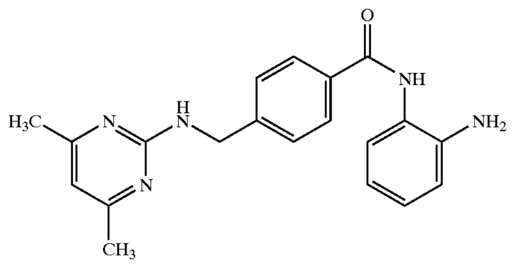 | 3 | 1 | 3 |
| 242 | 383 | 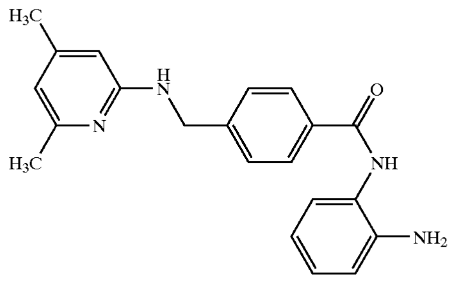 | 2 | 0.5 | 2 |
| 243 | 384 | 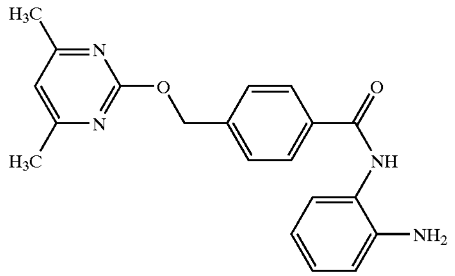 | 3 | 2 | 5 |
| 244 | 385 | 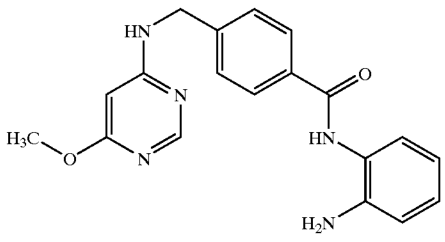 | 3 | 1 | 2 |
| 245 | 386 | 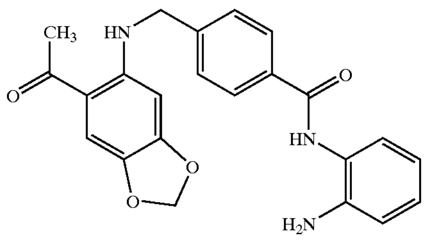 | 3 | 1 | 1 |

TABLE 5-continued
| Inhibition of Histone Deacetylase | | | | | |
|---|---|---|---|---|---|
| 246 | 387 | 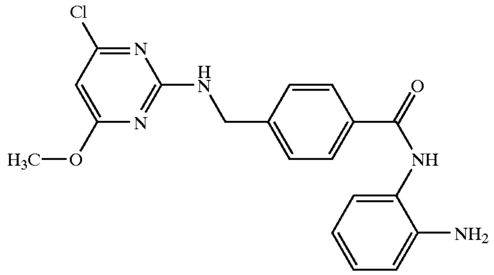 | 2 | 1 | 1 |
| 247 | 388 | 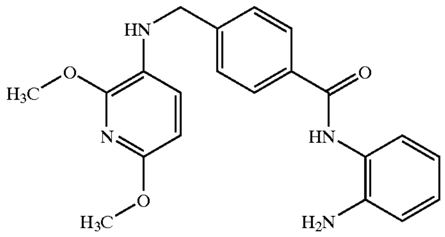 | 3 | 0.4 | 5 |
| 248 | 389 | 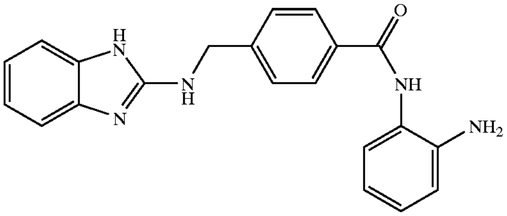 | 3 | 0.2 | 1 |
| 249 | 390 | 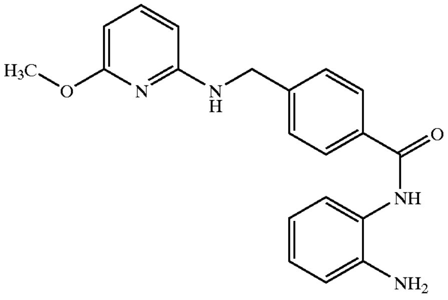 | 2 | 0.8 | 5 |
| 250 | 391 | 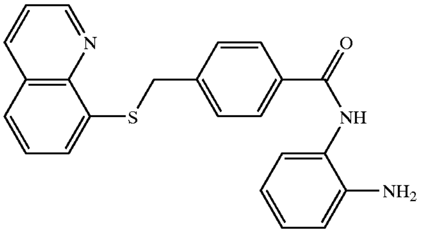 | 1 | 0.9 | 3 |

TABLE 5-continued
| Inhibition of Histone Deacetylase | | | | | |
|---|---|---|---|---|---|
| 251 | 392 | 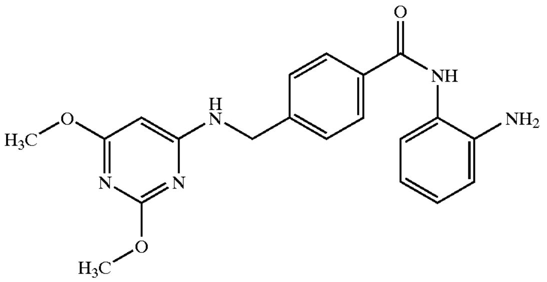 | 4 | 1 | 1 |
| 252 | 393 | 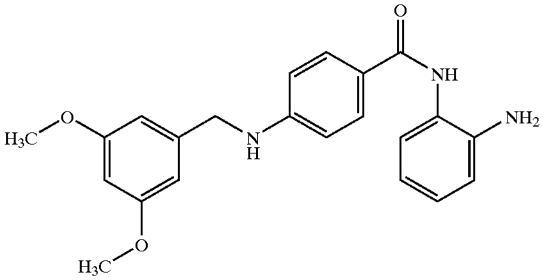 | 4 | 0.6 | 1 |
| 253 | 394 | 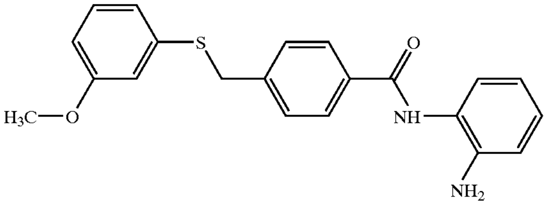 | 4 | 2 | 25 |
| 254 | 395 | 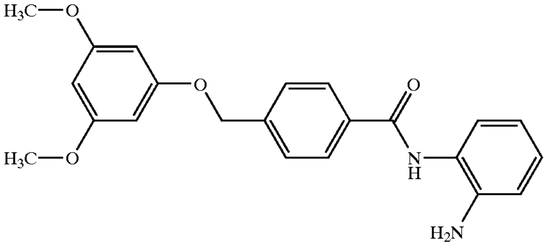 | 2 | 1 | 5 |
| 255 | 396 | 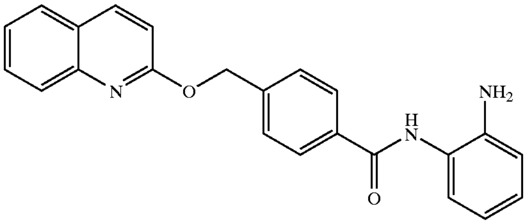 | 2 | 0.7 | 5 |
| 256 | 397 | 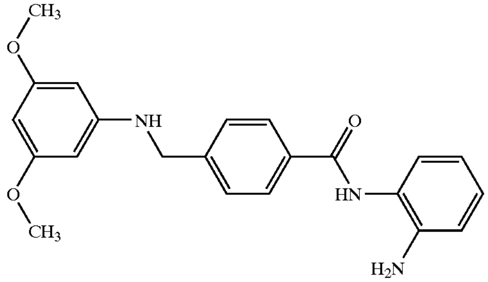 | 1 | 0.6 | 4 |

TABLE 5-continued
Inhibition of Histone Deacetylase
| | | | | | |
|---|---|---|---|---|---|
| 258 | 399 | 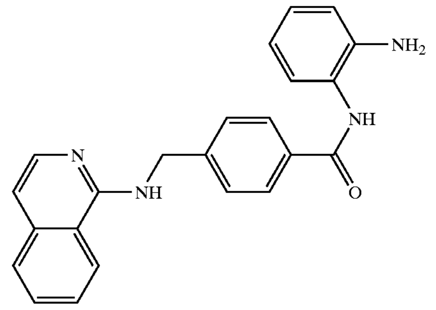 | 14 | 9 | |
| 259 | 400 | 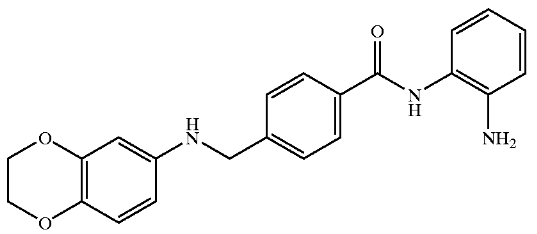 | 8 | 0.3 | 2 |
| 260 | 401 | 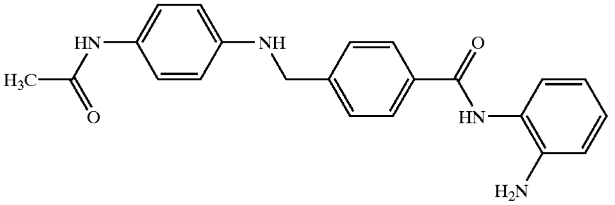 | 6 | 0.3 | 2 |
| 261 | 402 | 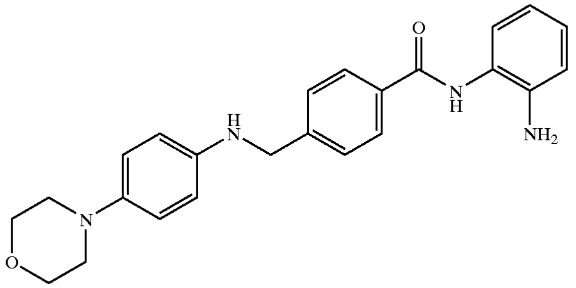 | 14 | 0.4 | 1 |
| 262 | 403 | 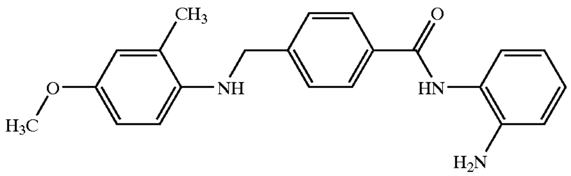 | 1 | 0.2 | 1 |
| 263 | 404 | 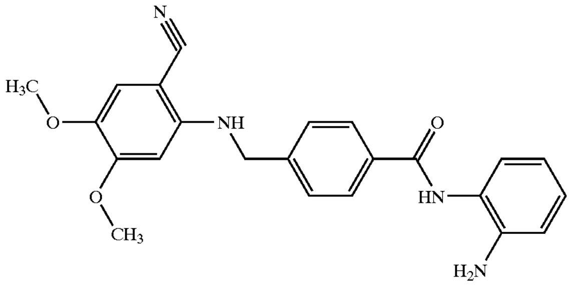 | 3 | 0.6 | 5 |

TABLE 5-continued
| Inhibition of Histone Deacetylase | | | | | |
|---|---|---|---|---|---|
| 264 | 405 | 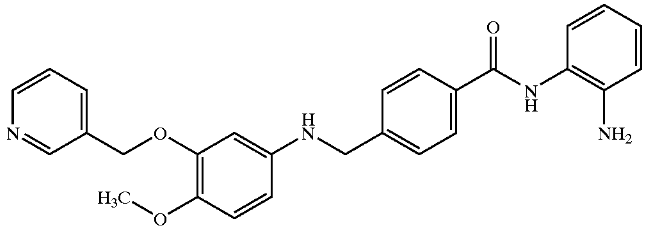 | 5 | 1 | 5 |
| 265 | 406 | 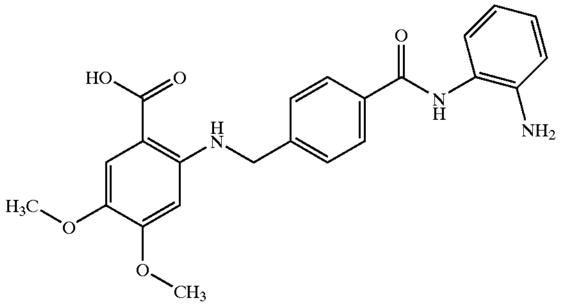 | 3 | 11 | |
| 266 | 407 | 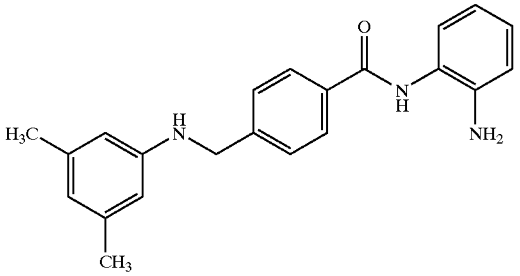 | 3 | 2 | |
| 267 | 408 | 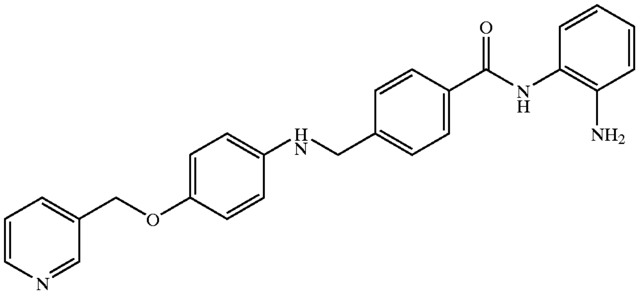 | 4 | 2 | |
| 268 | 409 | 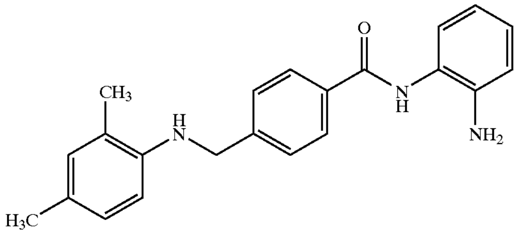 | 3 | 1 | 9999 |

TABLE 5-continued
Inhibition of Histone Deacetylase
| | | | | | |
|---|---|---|---|---|---|
| 269 | 410 | 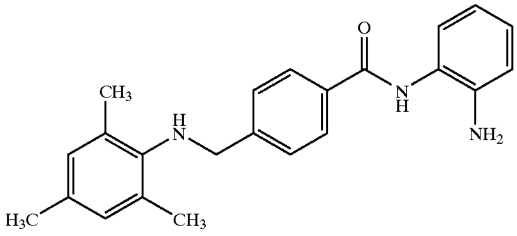 | 0.9 | 0.1 | >5 |
| 270 | 411 | 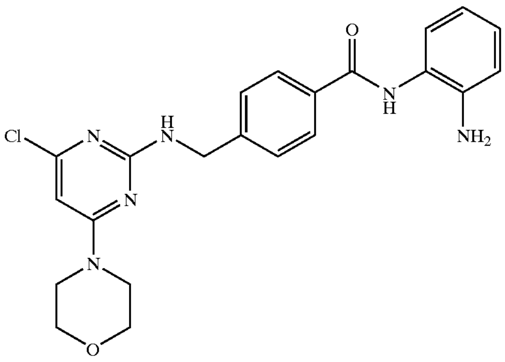 | 2 | | 1 |
| 271 | 412 | 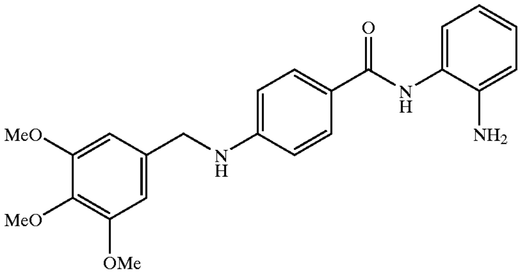 | 3 | 2 | 3 |
| 272 | 413 | 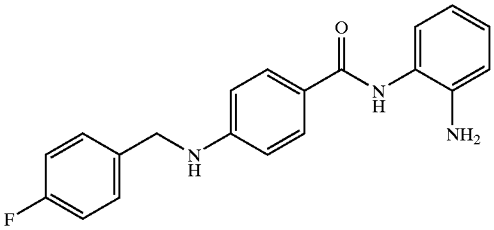 | 2 | 2 | 3 |
| 273 | 414 | 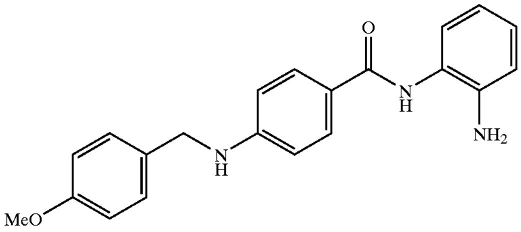 | 3 | 1 | 1 |

TABLE 5-continued
| Inhibition of Histone Deacetylase | | | | | |
|---|---|---|---|---|---|
| 274 | 415 | 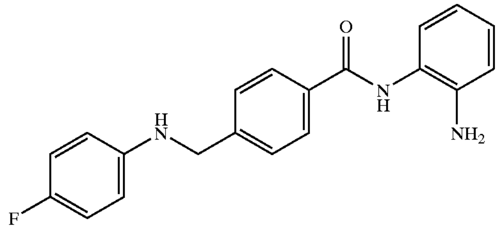 | 3 | 1 | 3 |
| 275 | 416 | 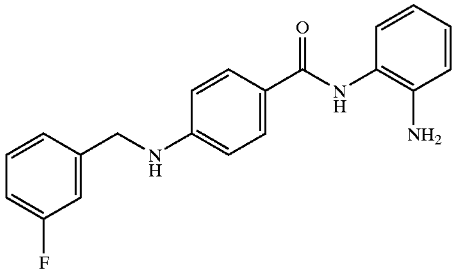 | 3 | 0.6 | 1 |
| 276 | 417 | 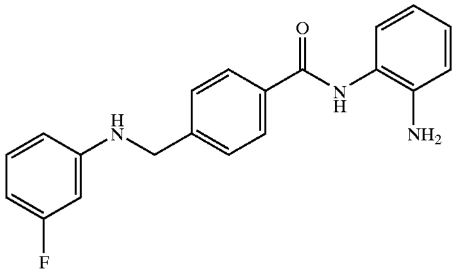 | 3 | 1 | 1 |
| 277 | 418 | 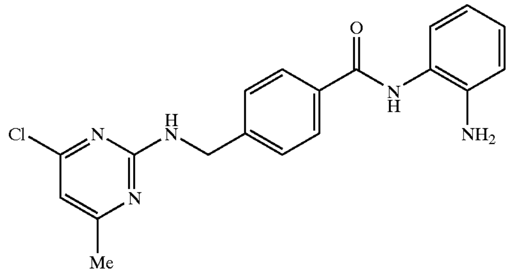 | 3 | 0.9 | 2 |
| 278 | 419 | 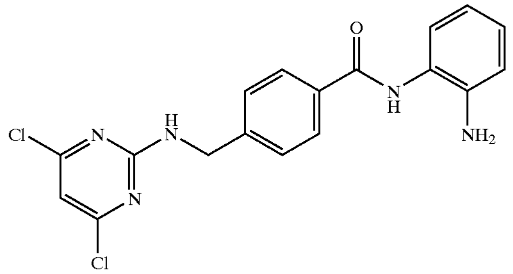 | 2 | 1 | 5 |

TABLE 5-continued
Inhibition of Histone Deacetylase
| | | | | | |
|---|---|---|---|---|---|
| 279 | 420 | 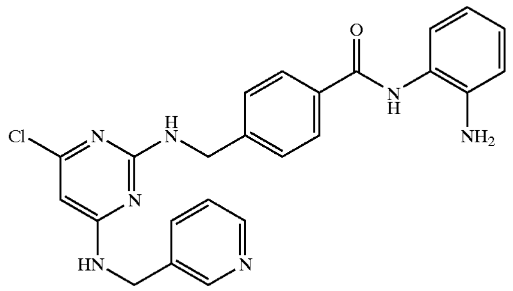 | 3 | 0.7 | 1 |
| 280 | 421 | 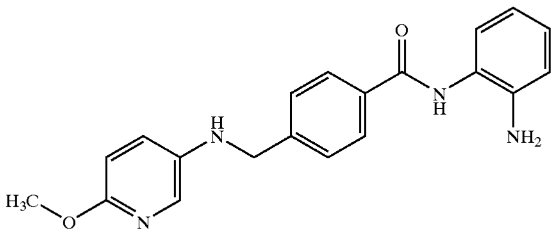 | 4 | 0.6 | 1 |
| 281 | 422 | 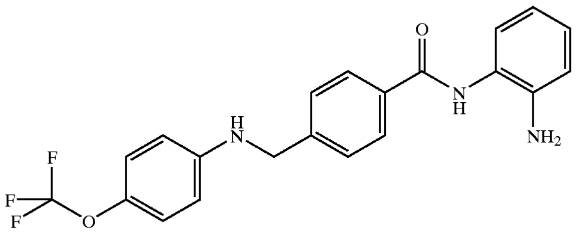 | <0.05 | 0.9 | 5 |
| 282 | 423 | 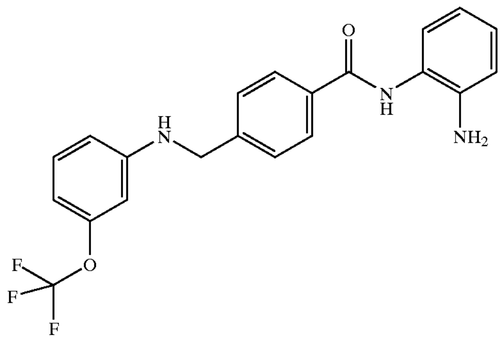 | 0.5 | 1 | 3 |
| 283a | 424b | 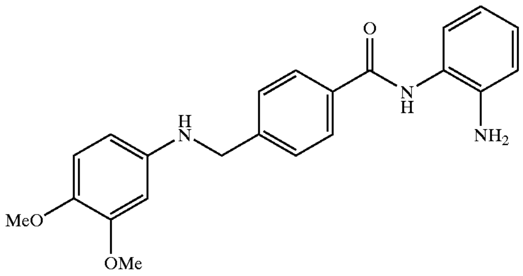 | 2 | 0.4 | 1 |

TABLE 5-continued
| Inhibition of Histone Deacetylase | | | | | |
|---|---|---|---|---|---|
| 283b | 424c | 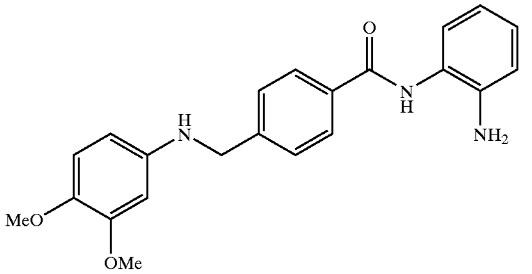 | 3 | 0.8 | 3 |
| 284 | 425 | 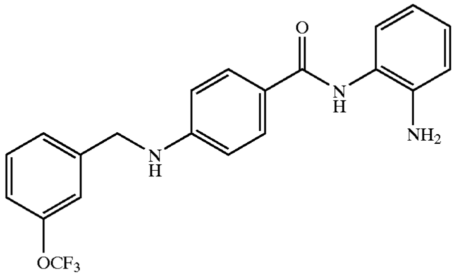 | 2 | 0.6 | 5 |
| 285 | 426 | 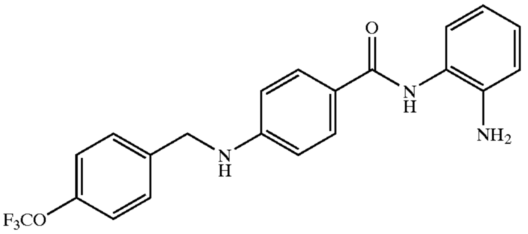 | 2 | 1 | 10 |
| 286 | 427 | 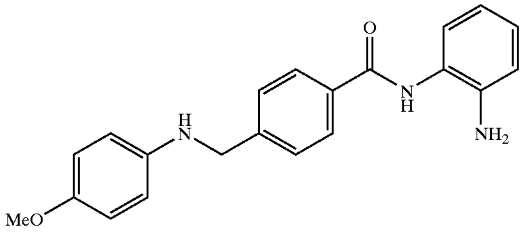 | 0.6 | 2 | 1 |
| 287 | 428 | 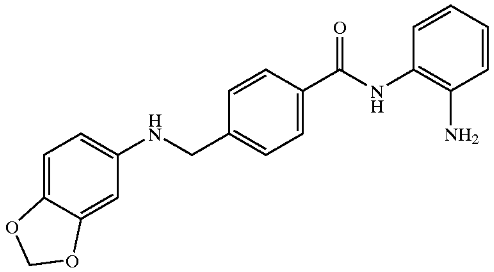 | 0.7 | 0.7 | 1 |
| 288 | 429 | 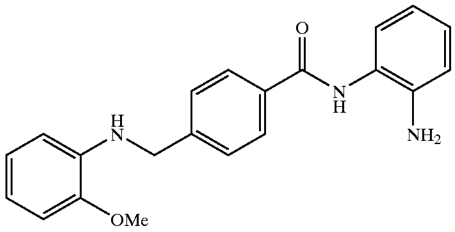 | 4 | 0.9 | 1 |

TABLE 5-continued
| Inhibition of Histone Deacetylase | | | | | |
|---|---|---|---|---|---|
| 289 | 430 | 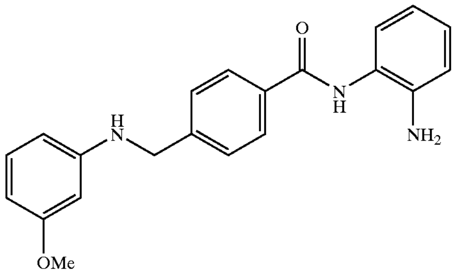 | 5 | 0.7 | 1 |
| 290 | 431 | 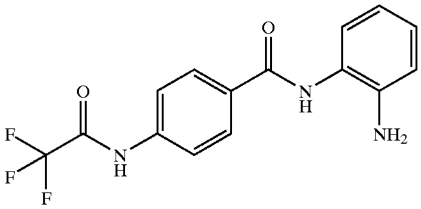 | 5 | 5 | |
| 291 | 432 | 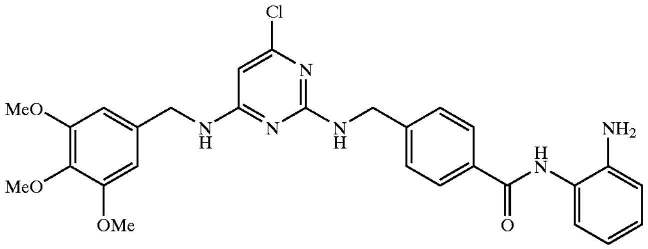 | 2 | 1 | 3 |
| 292 | 432 | 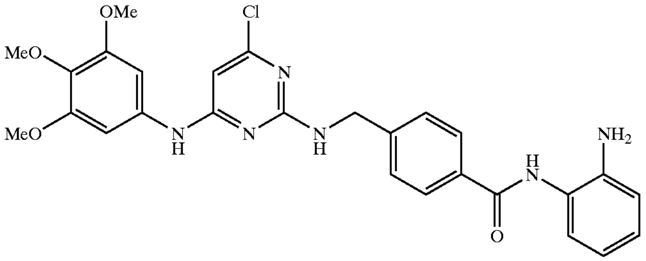 | 2 | 0.6 | 1 |
| 293 | 434 | 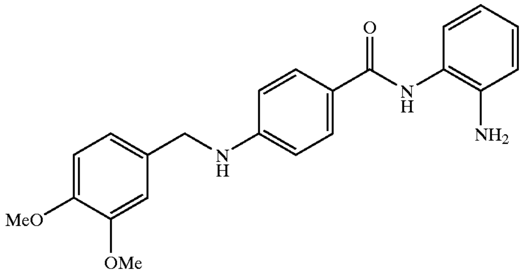 | 4 | 0.6 | 2 |
| 294 | 435 | 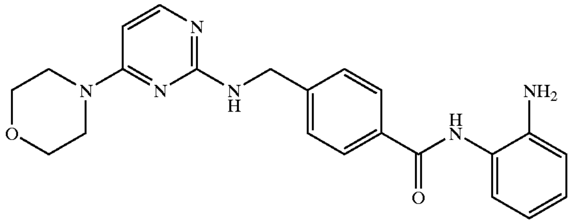 | 3 | 0.6 | 1 |

TABLE 5-continued
| Inhibition of Histone Deacetylase | | | | | |
|---|---|---|---|---|---|
| 295 | 436 | 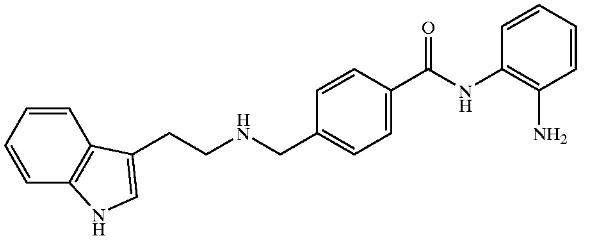 | 5 | 0.8 | 5 |
| 296 | 437 | 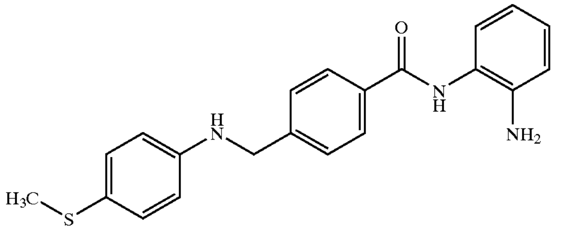 | 3 | 0.4 | 1 |
| 297 | 438 | 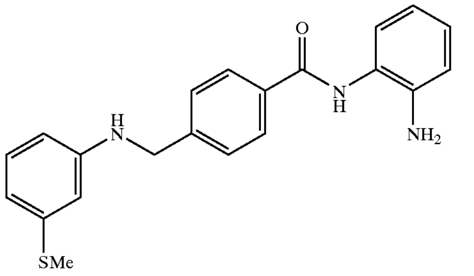 | 5 | 0.6 | 1 |
| 298 | 439 | 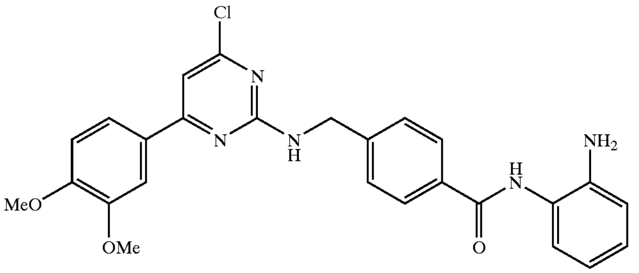 | 3 | 0.4 | 1 |
| 299 | 440 | 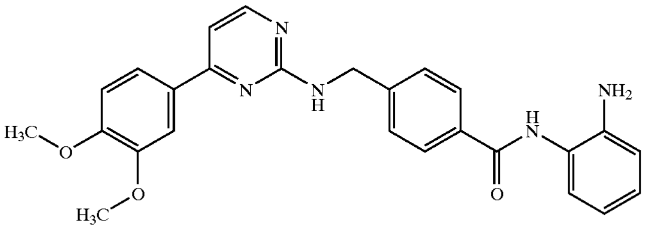 | 4 | 0.1 | 2 |

TABLE 5-continued
| Inhibition of Histone Deacetylase | | | | | |
|---|---|---|---|---|---|
| 300 | 441 | 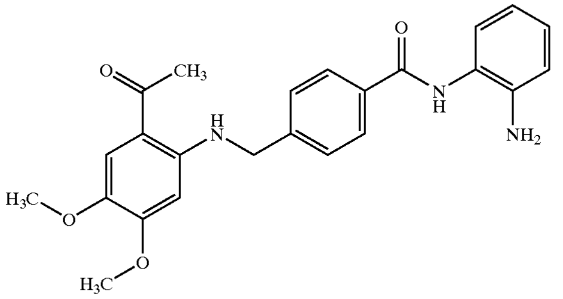 | 2 | 0.8 | 2 |
| 301 | 442 | 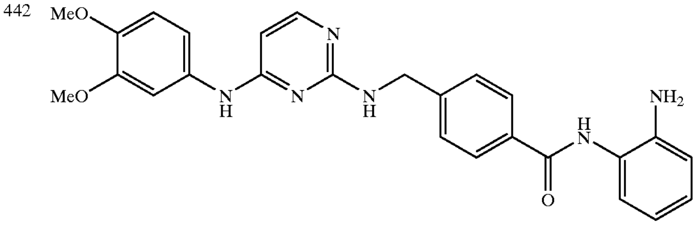 | 17 | 0.4 | 1 |
| 302 | 443 | 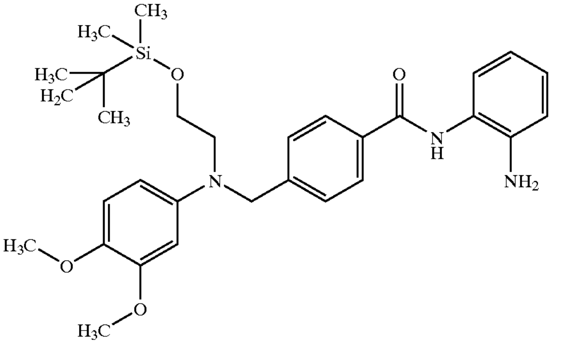 | | | |
| 303 | 444 | 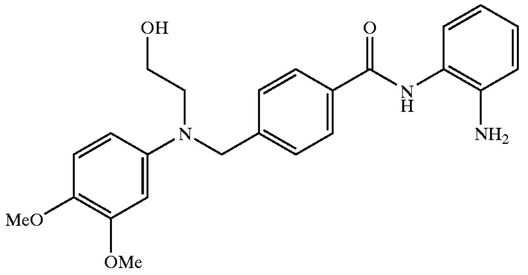 | | | |
| 304 | 445 | 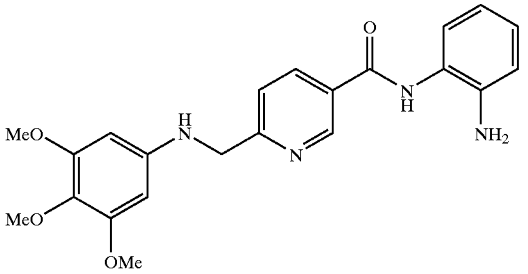 | 16 | 6 | |

TABLE 5-continued
Inhibition of Histone Deacetylase
| | | | | | |
|---|---|---|---|---|---|
| 305 | 446 | 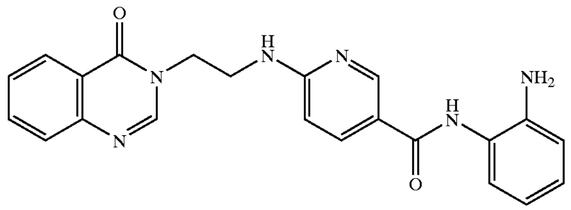 | 21 | 7 | |
| 307 | 448 | 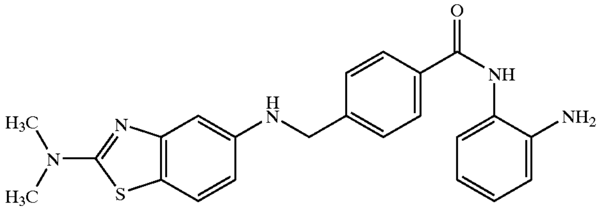 | 3 | 0.2 | 2 |
| 308 | 449 | 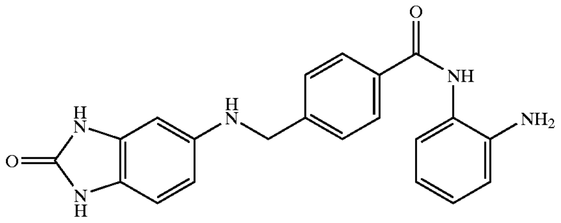 | 1 | 6 | |
| 309 | 450 | 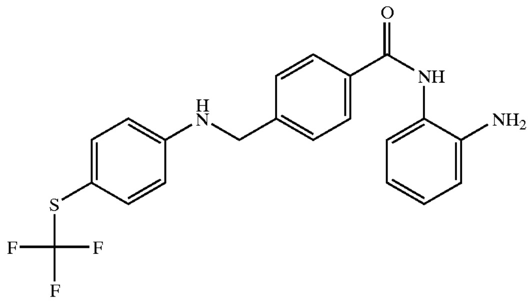 | 3 | 2 | |
| 310 | 451 | 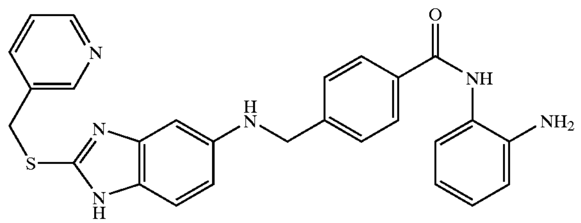 | 4 | 0.2 | 3 |
| 311 | 452 | 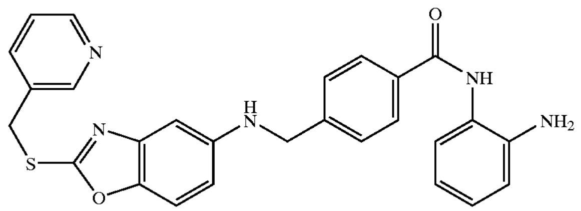 | 3 | 0.3 | 2 |

TABLE 5-continued
| Inhibition of Histone Deacetylase | | | | | |
|---|---|---|---|---|---|
| 312 | 453 | 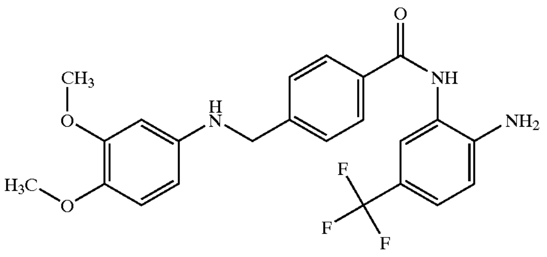 | 9999 | 37 | |
| 313 | 454 | 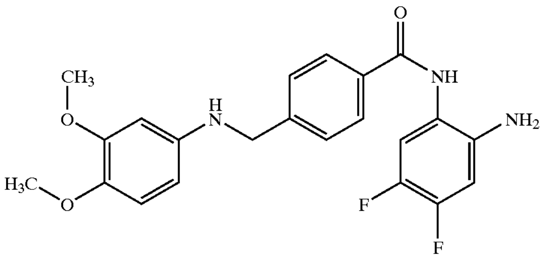 | 4 | 2 | 5 |
| 314 | 455 | 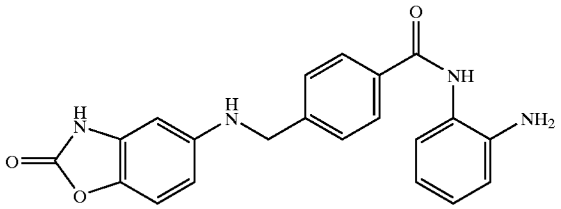 | 4 | 0.7 | 1 |
| 315 | 456 | 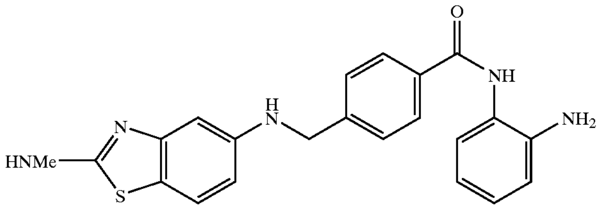 | 3 | 0.4 | 8888 |
| 316 | 457 | 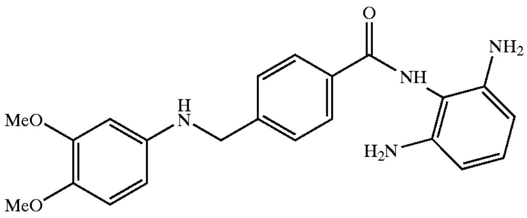 | 9999 | 9999 | |
| 317 | 458 | 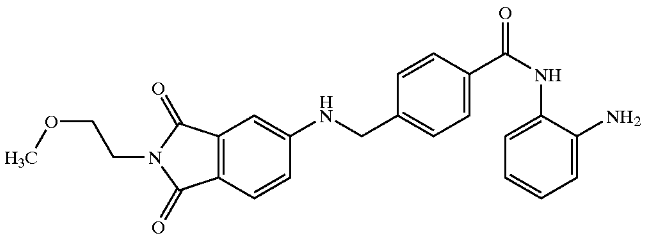 | 3 | 0.3 | 2 |

TABLE 5-continued
Inhibition of Histone Deacetylase
| | | | | | |
|---|---|---|---|---|---|
| 318 | 459 | 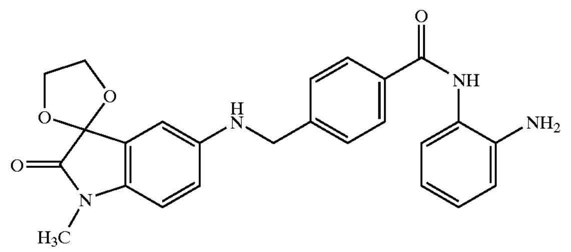 | 4 | 0.3 | 1 |
| 319 | 460 | 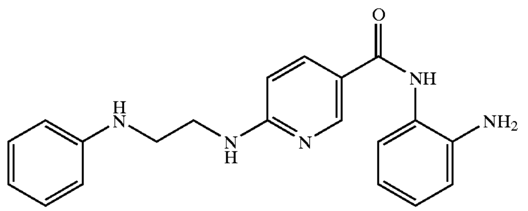 | 3 | 1 | 1 |
| 320 | 461 | 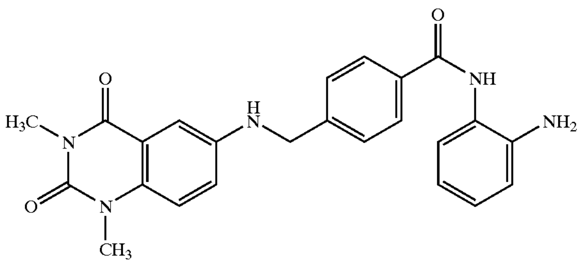 | 1.4 | 0.3 | 1 |
| 321 | 462 | 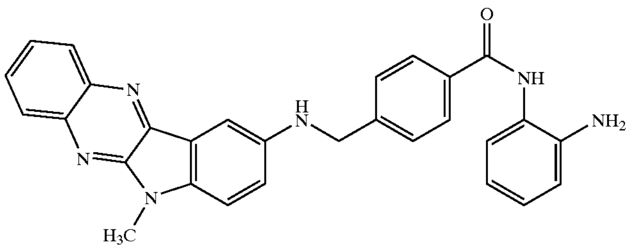 | 4 | 0.3 | 1 |
| 322 | 463 | 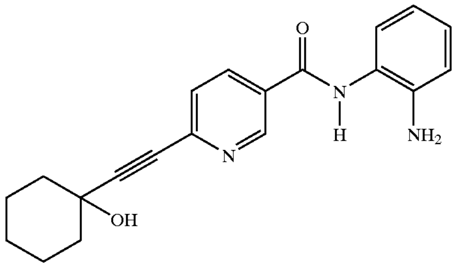 | 12 | 6 | |
| 323 | 464 | 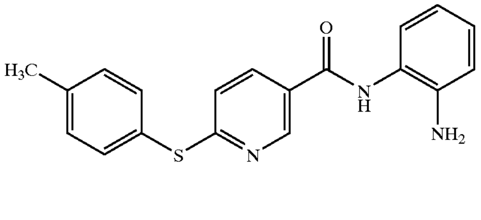 | 4 | 11 | |

TABLE 5-continued
| Inhibition of Histone Deacetylase | | | | | |
|---|---|---|---|---|---|
| 324 | 465 | 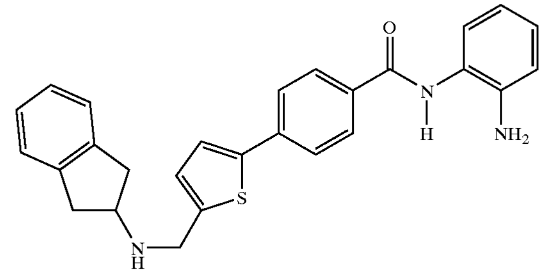 | 2 | 9999 | 9999 |
| 325 | 466 | 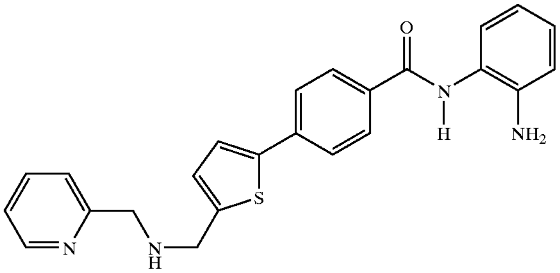 | 3 | 2 | 1 |
| 326 | 467 | 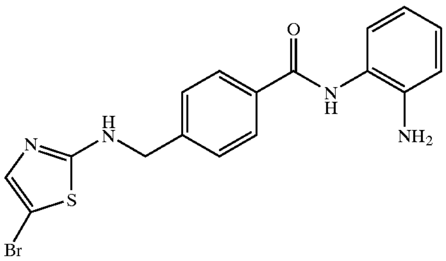 | 4 | 0.4 | 2 |
| 327 | 468 | 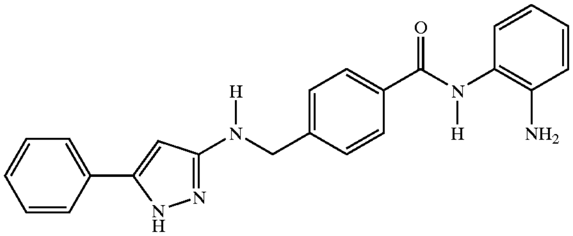 | 2 | 8 | <1 |
| 426 | 571 | 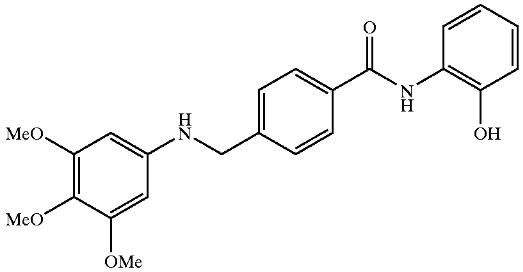 | 4 | 11 | |

TABLE 5-continued
| Inhibition of Histone Deacetylase | | | | | |
|---|---|---|---|---|---|
| 427 | 572 | 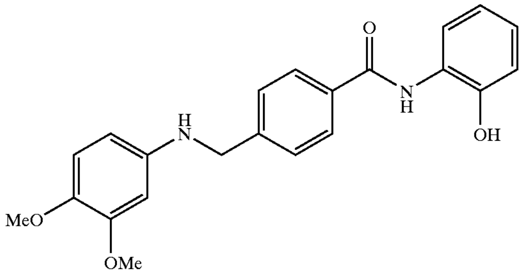 | 1.5 | 5 | 5 |
| 428 | 573 | 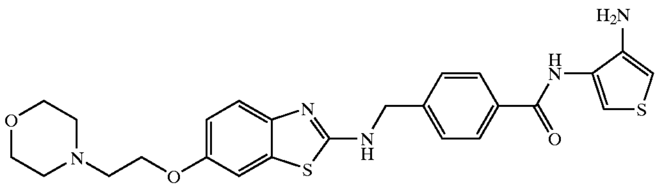 | 7 | 0.4 | 1 |
| 429 | 574 | 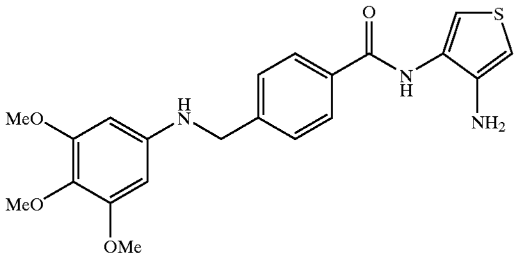 | 13 | 0.7 | 3 |
| 430 | 575 | 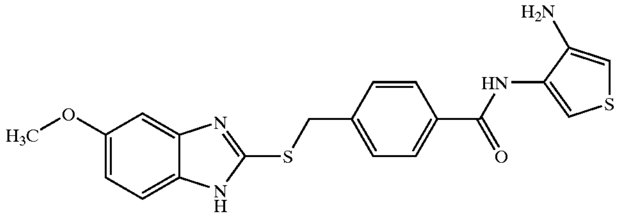 | 2 | 0.2 | 1 |
| 431 | 576 | 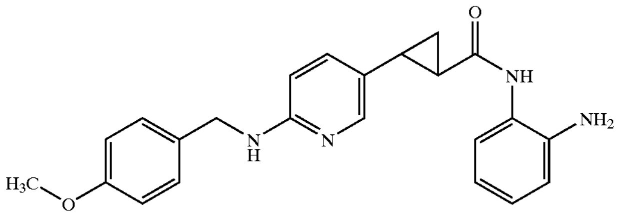 | 5 | 6 | |
| 432 | 577 | 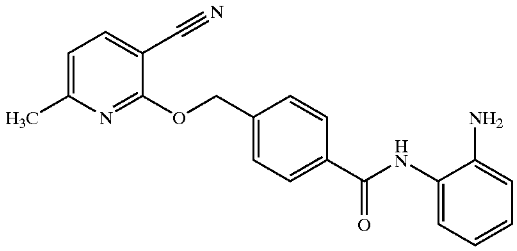 | 2 | 0.5 | 2 |

TABLE 5-continued
| Inhibition of Histone Deacetylase | | | | | |
|---|---|---|---|---|---|
| 433 | 578 | 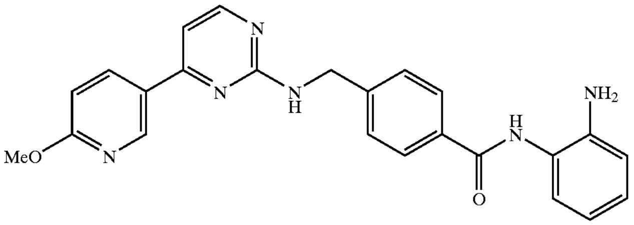 | 0.6 | 0.1 | 1 |
| 434 | 579 | 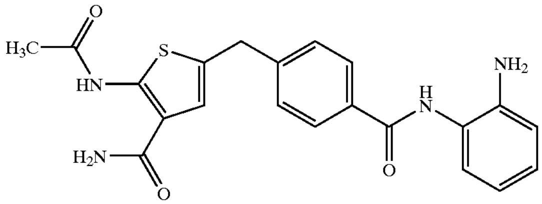 | 2 | 0.5 | 1 |
| 435 | 580 | 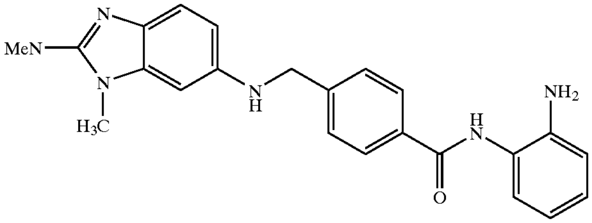 | 4 | 0.3 | <1 |
| 436 | 587 | 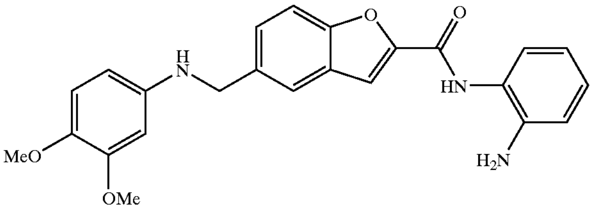 | 5 | 0.8 | 2 |
| 437 | 590 | 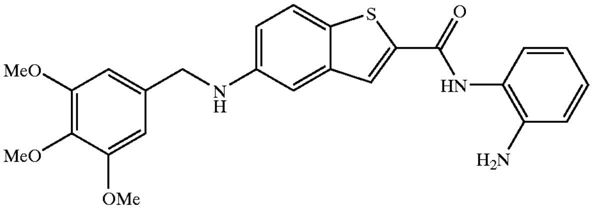 | 2 | 2 | 3 |
| 438 | 591 | 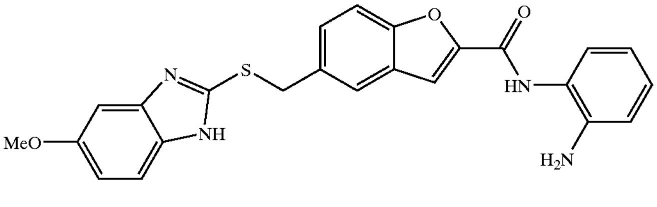 | 4 | 0.3 | <1 |
| 439 | 592 | 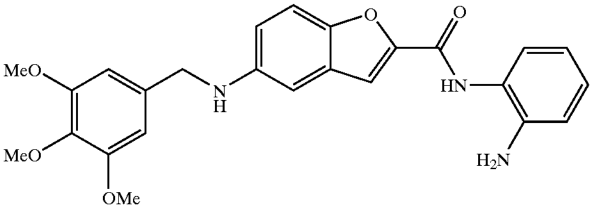 | 5 | 0.4 | <1 |

Assay Example 2

Antineoplastic Effects of Histone Deacetylase Inhibitors on Human Tumor Xenografts In Vivo Eight to ten week old female BALB/c nude mice (Taconic Labs, Great Barrington, N.Y.) were injected subcutaneously in the flank area with $2\times10^6$ preconditioned HCT116 human colorectal carcinoma cells. Preconditioning of these cells was done by a minimum of three consecutive tumor transplantations in the same strain of nude mice. Subsequently, tumor fragments of approximately 30 mgs were excised and implanted subcutaneously in mice, in the left flank area, under Forene anesthesia (Abbott Labs, Geneve, Switzerland). When the tumors reached a mean volume of 100 $mm^3$, the mice were treated intravenously, subcutaneously, or intraperitoneally by daily injection, with a solution of the histone deacetylase inhibitor in an appropriate vehicle, such as PBS, DMSO/water, or Tween 80/water, at a starting dose of 10 mg/kg. The optimal dose of the HDAC inhibitor was established by dose response experiments according to standard protocols. Tumor volume was calculated every second day post infusion according to standard methods (e.g., Meyer et al., *Int. J. Cancer* 43: 851–856 (1989)). Treatment with the HDAC inhibitors according to the invention caused a significant reduction in tumor weight and volume relative to controls treated with vehicle only (i.e., no HDAC inhibitor). In addition, the level of histone acetylation when measured was significantly elevated relative to controls. Data for selected compounds are presented in Table 6. FIG. 1 shows the full experimental results for compound 106, which inhibits tumor growth by 80%. FIGS. 2–10 show the results of additional compounds tested.

TABLE 6

Antitumor Activity in HCT 116 Colorectal Tumor Model In Vivo

| Compound | % Inhibition of Tumor Growth |
|---|---|
| 106 | 80[a] |
| 126 | 62[b] |
| 9 | 51[b] |
| 87 | 30[b] |
| 157 | 66[a] |
| 167 | 58[a] |
| 15 | 26[b] |
| 168 | 26[b] |
| 16 | 50[b] |
| 154 | 23[a] |
| 98 | 52[a] |

[a]20 mg/kg i.p.
[b]40 mg/kg i.p.

Assay Example 3

Combined Antineoplastic Effect of Histone Deacetylase Inhibitors and Histone Deacetylase Antisense Oligonucleotides on Tumor Cells In Vivo The purpose of this example is to illustrate the ability of the combined use of a histone deacetylase inhibitor of the invention and a histone deacetylase antisense oligonucleotide to enhance inhibition of tumor growth in a mammal. Preferably, the antisense oligonucleotide and the HDAC inhibitor inhibit the expression and activity of the same histone deacetylase.

As described in Example 126, mice bearing implanted HCT116 tumors (mean volume 100 $mm^3$) are treated daily with saline preparations containing from about 0.1 mg to about 30 mg per kg body weight of histone deacetylase antisense oligonucleotide. A second group of mice is treated daily with pharmaceutically acceptable preparations containing from about 0.01 mg to about 5 mg per kg body weight of HDAC inhibitor.

Some mice receive both the antisense oligonucleotide and the HDAC inhibitor. Of these mice, one group may receive the antisense oligonucleotide and the HDAC inhibitor simultaneously intravenously via the tail vein. Another group may receive the antisense oligonucleotide via the tail vein, and the HDAC inhibitor subcutaneously. Yet another group may receive both the antisense oligonucleotide and the HDAC inhibitor subcutaneously. Control groups of mice are similarly established which receive no treatment (e.g., saline only), a mismatch antisense oligonucleotide only, a control compound that does not inhibit histone deacetylase activity, and a mismatch antisense oligonucleotide with a control compound.

Tumor volume is measured with calipers. Treatment with the antisense oligonucleotide plus the histone deacetylase protein inhibitor according to the invention causes a significant reduction in tumor weight and volume relative to controls.

TABLE 7

Antineoplastic Effects Of Histone Deacetylase Inhibitors On Nude Mice Xenograft Models

| | % Inhibition Of Tumor Growth | | | | |
|---|---|---|---|---|---|
| cpd | A 549 (p.o.) | SW48 (p.o.) | A 549 (i.p.) | HCT 116 (i.p.) | SW 48 (i.p.) |
| 106 | 40% (70 mg/kg) | 16% (60 mg/kg) | — | — | — |
| 164 | 42% (70 mg/kg) | 62% (60 mg/kg) | — | 37% (20 mg/kg) | 99% (25 mg/kg) |
| 228 | 45% (70 mg/kg) | 25% (60 mg/kg) | 64% (20 mg/kg) | 45% (20 mg/kg) | 68% (20 mg/kg) |
| 424b | 67% (50 mg/kg) | 78% (30 mg/kg) | 60% (50 mg/kg) | 77% (75 mg/kg) | 68% (25 mg/kg) |

We claim:

1. A histone deacetylase inhibitor of formula (1):

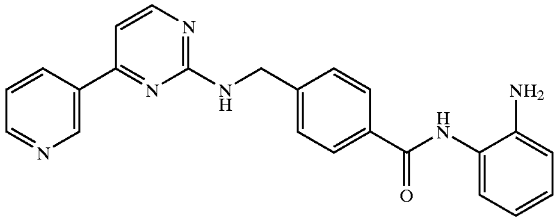

or a pharmaceutically acceptable salt thereof.

2. A composition comprising a compound according to claim 1 and a pharmaceutically acceptable carrier.

3. A method of inhibiting histone deacetylase in a cell, the method comprising contacting a cell with a compound according to claim 1, in an amount sufficient to inhibit histone deacetylase.

4. A method of inhibiting histone deacetylase in a cell, the method comprising contacting a cell with a composition according to claim 2, in an amount sufficient to inhibit histone deacetylase.

* * * * *